United States Patent
Min

(10) Patent No.: US 12,144,669 B2
(45) Date of Patent: Nov. 19, 2024

(54) SYSTEMS, DEVICES, AND METHODS FOR NON-INVASIVE IMAGE-BASED PLAQUE ANALYSIS AND RISK DETERMINATION

(71) Applicant: Cleerly, Inc., Denver, CO (US)

(72) Inventor: James K. Min, Denver, CO (US)

(73) Assignee: Cleerly, Inc., Denver, CO (US)

(*) Notice: Subject to any disclaimer, the term of this patent is extended or adjusted under 35 U.S.C. 154(b) by 0 days.

(21) Appl. No.: 18/444,367

(22) Filed: Feb. 16, 2024

(65) Prior Publication Data

US 2024/0188917 A1 Jun. 13, 2024

Related U.S. Application Data

(63) Continuation of application No. 18/508,098, filed on Nov. 13, 2023, which is a continuation-in-part of application No. 18/179,921, filed on Mar. 7, 2023.
(Continued)

(51) Int. Cl.
*A61B 6/00* (2024.01)
*A61B 6/03* (2006.01)
(Continued)

(52) U.S. Cl.
CPC ............ *A61B 6/5217* (2013.01); *A61B 6/032* (2013.01); *A61B 6/503* (2013.01); *A61B 6/504* (2013.01); *A61B 6/507* (2013.01); *A61B 6/5229* (2013.01); *G06T 7/0012* (2013.01); *G06T 7/62* (2017.01); *G06V 10/22* (2022.01); *G06V 10/26* (2022.01);
(Continued)

(58) Field of Classification Search
CPC ....... A61B 6/5217; A61B 6/032; A61B 6/503; A61B 6/504; A61B 6/507; A61B 6/5229; G06T 7/0012; G06T 7/62; G06T 2207/10081; G06T 2207/20076; G06T 2207/30048; G06T 2207/30104;
(Continued)

(56) References Cited

U.S. PATENT DOCUMENTS

| 4,945,478 A | 7/1990 | Merickel et al. |
| 5,056,130 A | 10/1991 | Engel |

(Continued)

FOREIGN PATENT DOCUMENTS

| AU | 2023200986 B2 | 2/2023 |
| CA | 2368390 C | 7/2010 |

(Continued)

OTHER PUBLICATIONS

US 11,791,027 B2, 10/2023, Buckler et al. (withdrawn)
(Continued)

*Primary Examiner* — Keith M Raymond
*Assistant Examiner* — Patrick M Mehl
(74) *Attorney, Agent, or Firm* — Perkins Coie LLP

(57) ABSTRACT

Various embodiments described herein relate to systems, devices, and methods for non-invasive image-based plaque analysis and risk determination. In particular, in some embodiments, the systems, devices, and methods described herein are related to analysis of one or more regions of plaque, such as for example coronary plaque, using non-invasively obtained images that can be analyzed using computer vision or machine learning to identify, diagnose, characterize, treat and/or track coronary artery disease.

18 Claims, 32 Drawing Sheets

Related U.S. Application Data

(60) Provisional application No. 63/478,084, filed on Dec. 30, 2022, provisional application No. 63/477,961, filed on Dec. 30, 2022, provisional application No. 63/478,076, filed on Dec. 30, 2022, provisional application No. 63/477,985, filed on Dec. 30, 2022, provisional application No. 63/477,640, filed on Dec. 29, 2022, provisional application No. 63/477,638, filed on Dec. 29, 2022, provisional application No. 63/477,656, filed on Dec. 29, 2022, provisional application No. 63/476,255, filed on Dec. 20, 2022, provisional application No. 63/476,245, filed on Dec. 20, 2022, provisional application No. 63/476,251, filed on Dec. 20, 2022, provisional application No. 63/386,376, filed on Dec. 7, 2022, provisional application No. 63/386,297, filed on Dec. 6, 2022, provisional application No. 63/385,472, filed on Nov. 30, 2022, provisional application No. 63/385,179, filed on Nov. 28, 2022, provisional application No. 63/383,904, filed on Nov. 15, 2022, provisional application No. 63/383,632, filed on Nov. 14, 2022, provisional application No. 63/381,210, filed on Oct. 27, 2022, provisional application No. 63/368,293, filed on Jul. 13, 2022, provisional application No. 63/365,381, filed on May 26, 2022, provisional application No. 63/364,084, filed on May 3, 2022, provisional application No. 63/364,078, filed on May 3, 2022, provisional application No. 63/362,856, filed on Apr. 12, 2022, provisional application No. 63/362,108, filed on Mar. 29, 2022, provisional application No. 63/269,136, filed on Mar. 10, 2022.

(51) Int. Cl.
    *A61B 6/50*     (2024.01)
    *G06T 7/00*     (2017.01)
    *G06T 7/62*     (2017.01)
    *G06V 10/22*     (2022.01)
    *G06V 10/26*     (2022.01)
    *G16H 30/40*     (2018.01)
    *G16H 50/20*     (2018.01)

(52) U.S. Cl.
    CPC ............ *G16H 30/40* (2018.01); *G16H 50/20* (2018.01); *G06T 2207/10081* (2013.01); *G06T 2207/20076* (2013.01); *G06T 2207/30048* (2013.01); *G06T 2207/30104* (2013.01); *G06V 2201/031* (2022.01)

(58) Field of Classification Search
    CPC .. G06V 10/22; G06V 10/26; G06V 2201/031; G16H 30/40; G16H 50/20
    See application file for complete search history.

(56) References Cited

U.S. PATENT DOCUMENTS

| | | |
|---|---|---|
| 5,722,408 A | 3/1998 | Dehner et al. |
| 5,891,030 A | 4/1999 | Johnson et al. |
| 6,047,080 A | 4/2000 | Chen et al. |
| 6,591,004 B1 | 7/2003 | VanEssen et al. |
| 6,993,382 B2 | 1/2006 | Casscells et al. |
| 7,535,986 B2 | 5/2009 | Hempel |
| 7,558,611 B2 | 7/2009 | Arnold et al. |
| 7,570,983 B2 | 8/2009 | Becker et al. |
| 7,711,165 B2 | 5/2010 | Lesage et al. |
| 7,715,626 B2 | 5/2010 | Florin et al. |
| 7,805,385 B2 | 9/2010 | Steck et al. |
| 7,813,549 B2 | 10/2010 | Buelow et al. |
| 7,840,062 B2 | 11/2010 | Boroczky et al. |
| 7,860,283 B2 | 12/2010 | Begelman et al. |
| 7,876,939 B2 | 1/2011 | Yankelevitz et al. |
| 7,899,764 B2 | 3/2011 | Martin et al. |
| 7,904,977 B1 | 3/2011 | Singh |
| 7,907,766 B2 | 3/2011 | Haas et al. |
| 7,912,528 B2 | 3/2011 | Krishnan et al. |
| 7,940,974 B2 | 5/2011 | Skinner et al. |
| 7,940,977 B2 | 5/2011 | Begelman et al. |
| 7,953,266 B2 | 5/2011 | Gulsun et al. |
| 7,993,274 B2 | 8/2011 | Pruvot et al. |
| 8,009,793 B2 | 8/2011 | Langheinrich et al. |
| 8,046,488 B2 | 10/2011 | Cherukuri et al. |
| 8,068,894 B2 | 11/2011 | Huizenga et al. |
| 8,107,695 B2 | 1/2012 | Wollenweber |
| 8,139,836 B2 | 3/2012 | Arnold et al. |
| 8,144,949 B2 | 3/2012 | Simon et al. |
| 8,200,466 B2 | 6/2012 | Spiker et al. |
| 8,386,188 B2 | 2/2013 | Taylor et al. |
| 8,494,244 B2 | 7/2013 | Dutta et al. |
| 8,526,699 B2 | 9/2013 | Mittal et al. |
| 8,582,854 B2 | 11/2013 | Zhang et al. |
| 8,605,979 B2 | 12/2013 | Arnold et al. |
| 8,660,326 B2 | 2/2014 | Ohayon et al. |
| 8,774,479 B2 | 7/2014 | Madabhushi et al. |
| 8,777,854 B2 | 7/2014 | Patwardhan et al. |
| 8,867,822 B2 | 10/2014 | Oh et al. |
| 8,885,905 B2 | 11/2014 | Dey et al. |
| 8,938,106 B2 | 1/2015 | Aulbach et al. |
| 9,008,392 B1 | 4/2015 | Bai et al. |
| 9,058,692 B1 | 6/2015 | Grady et al. |
| 9,070,214 B1 | 6/2015 | Grady et al. |
| 9,081,721 B1 | 7/2015 | Grady et al. |
| 9,129,417 B2 | 9/2015 | Zheng et al. |
| 9,155,512 B2 | 10/2015 | Choi et al. |
| 9,159,159 B2 | 10/2015 | Bai et al. |
| 9,195,801 B1 | 11/2015 | Sankaran et al. |
| 9,220,418 B2 | 12/2015 | Choi et al. |
| 9,220,419 B2 | 12/2015 | Choi et al. |
| 9,235,887 B2 | 1/2016 | Bucker et al. |
| 9,239,905 B1 | 1/2016 | Sankaran et al. |
| 9,280,639 B2 | 3/2016 | Sankaran et al. |
| 9,295,397 B2 | 3/2016 | Liu et al. |
| 9,295,429 B2 | 3/2016 | Ong et al. |
| 9,378,580 B2 | 6/2016 | Grady et al. |
| 9,430,827 B2 | 8/2016 | Kelm et al. |
| 9,538,925 B2 | 1/2017 | Sharma et al. |
| 9,610,272 B2 | 4/2017 | Soni |
| 9,642,586 B2 | 5/2017 | Kelm et al. |
| 9,649,171 B2 | 5/2017 | Sankaran et al. |
| 9,655,563 B2 | 5/2017 | Liu et al. |
| 9,679,374 B2 | 6/2017 | Choi |
| 9,700,219 B2 | 7/2017 | Sharma et al. |
| 9,715,562 B2 | 7/2017 | Goldstein |
| 9,721,340 B2 | 8/2017 | Gillies et al. |
| 9,761,004 B2 | 9/2017 | Mittal et al. |
| 9,767,557 B1 | 9/2017 | Gulsun et al. |
| 9,770,303 B2 | 9/2017 | Choi et al. |
| 9,785,748 B2 | 10/2017 | Koo et al. |
| 9,805,463 B2 | 10/2017 | Choi et al. |
| 9,805,470 B2 | 10/2017 | Bhatia et al. |
| 9,836,653 B2 | 12/2017 | Schnittman |
| 9,839,399 B2 | 12/2017 | Fonte et al. |
| 9,839,484 B2 | 12/2017 | Taylor |
| 9,881,372 B2 | 1/2018 | Gulsun et al. |
| 9,965,891 B2 | 5/2018 | Grady et al. |
| 10,010,255 B2 | 7/2018 | Fonte et al. |
| 10,078,124 B2 | 9/2018 | Horkay et al. |
| 10,082,553 B2 | 9/2018 | Boss |
| 10,170,206 B2 | 1/2019 | Koo et al. |
| 10,176,408 B2 | 1/2019 | Paik et al. |
| 10,354,360 B2 | 7/2019 | Sakamoto |
| 10,398,331 B2 | 9/2019 | Relan |
| 10,456,094 B2 | 10/2019 | Fonte et al. |
| 10,478,130 B2 | 11/2019 | Sharma et al. |
| 10,483,006 B2 | 11/2019 | Itu et al. |
| 10,492,755 B2 | 12/2019 | Lin |
| 10,498,755 B2 | 12/2019 | Harris |
| 10,517,677 B2 | 12/2019 | Sankaran et al. |

(56) References Cited

U.S. PATENT DOCUMENTS

| | | |
|---|---|---|
| 10,695,023 B2 | 6/2020 | Antoniades et al. |
| 10,740,880 B2 | 8/2020 | Paik et al. |
| 10,755,810 B2 | 8/2020 | Buckler et al. |
| 10,762,624 B2 | 9/2020 | Daughton et al. |
| 10,776,988 B2 | 9/2020 | Grady et al. |
| 10,813,612 B2 | 10/2020 | Min |
| 10,871,536 B2 | 12/2020 | Golden et al. |
| 10,939,828 B2 | 3/2021 | Fonte et al. |
| 10,939,960 B2 | 3/2021 | Choi et al. |
| 10,943,142 B2 | 3/2021 | Daughton et al. |
| 10,945,606 B2 | 3/2021 | Sanders et al. |
| 10,951,715 B2 | 3/2021 | Hart et al. |
| 10,964,071 B2 | 3/2021 | Grady et al. |
| 10,966,619 B2 | 4/2021 | Fonte et al. |
| 10,973,469 B2 | 4/2021 | Karimabadi |
| 10,973,583 B2 | 4/2021 | Taylor et al. |
| 10,978,210 B2 | 4/2021 | Grady et al. |
| 10,984,535 B2 | 4/2021 | Grady et al. |
| 10,987,010 B2 | 4/2021 | Grady et al. |
| 10,990,652 B2 | 4/2021 | Tayler et al. |
| 10,991,465 B2 | 4/2021 | Grady |
| 11,013,425 B2 | 5/2021 | Fonte et al. |
| 11,017,904 B2 | 5/2021 | Sankaran et al. |
| 11,033,332 B2 | 6/2021 | Taylor |
| 11,042,822 B2 | 6/2021 | Sankaran et al. |
| 11,071,501 B2 | 7/2021 | Buckler et al. |
| 11,083,524 B2 | 8/2021 | Taylor |
| 11,087,459 B2 | 8/2021 | Buckler et al. |
| 11,087,460 B2 | 8/2021 | Buckler et al. |
| 11,087,884 B2 | 8/2021 | Sankaran et al. |
| 11,090,118 B2 | 8/2021 | Taylor |
| 11,094,058 B2 | 8/2021 | Buclker et al. |
| 11,094,060 B1 | 8/2021 | Min et al. |
| 11,094,061 B1 | 9/2021 | Min et al. |
| 11,113,811 B2 | 9/2021 | Min et al. |
| 11,113,812 B2 | 9/2021 | Buckler et al. |
| 11,116,575 B2 | 9/2021 | Taylor |
| 11,120,312 B2 | 9/2021 | Buckler et al. |
| 11,120,549 B2 | 9/2021 | Min et al. |
| 11,120,550 B2 | 9/2021 | Min et al. |
| 11,120,893 B2 | 9/2021 | Choi et al. |
| 11,127,503 B2 | 9/2021 | Rabbat et al. |
| 11,132,796 B2 | 9/2021 | Min et al. |
| 11,135,012 B2 | 10/2021 | Taylor |
| 11,138,337 B2 | 10/2021 | Yousfi et al. |
| 11,154,361 B2 | 10/2021 | Taylor |
| 11,185,368 B2 | 11/2021 | Spilker et al. |
| 11,210,786 B2 | 12/2021 | Min et al. |
| 11,232,564 B2 | 1/2022 | Min et al. |
| 11,238,587 B2 | 2/2022 | Min et al. |
| 11,244,451 B1 | 2/2022 | Min et al. |
| 11,257,584 B2 | 2/2022 | Buckler et al. |
| 11,257,585 B2 | 2/2022 | Bhatia et al. |
| 11,276,170 B2 | 3/2022 | Min et al. |
| 11,288,799 B2 | 3/2022 | Min et al. |
| 11,288,813 B2 | 3/2022 | Grady et al. |
| 11,295,865 B2 | 4/2022 | Rabbat et al. |
| 11,298,187 B2 | 4/2022 | Taylor |
| 11,302,001 B2 | 4/2022 | Min et al. |
| 11,302,002 B2 | 4/2022 | Min et al. |
| 11,308,617 B2 | 4/2022 | Min et al. |
| 11,315,247 B2 | 4/2022 | Min et al. |
| 11,317,883 B2 | 5/2022 | Min et al. |
| 11,321,840 B2 | 5/2022 | Min et al. |
| 11,328,824 B2 | 5/2022 | Fonte |
| 11,341,644 B2 | 5/2022 | Min et al. |
| 11,350,899 B2 | 6/2022 | Min |
| 11,357,469 B2 | 6/2022 | Taylor et al. |
| 11,367,190 B2 | 6/2022 | Min et al. |
| 11,382,569 B2 | 7/2022 | Grady et al. |
| 11,398,029 B2 | 7/2022 | Grady et al. |
| 11,399,729 B2 | 8/2022 | Fonte et al. |
| 11,423,805 B2 | 8/2022 | Sankaran et al. |
| 11,424,036 B2 | 8/2022 | Fonte et al. |
| 11,424,038 B2 | 8/2022 | Grady et al. |
| 11,430,113 B2 | 8/2022 | Daughton et al. |
| 11,462,329 B2 | 10/2022 | Rabbat et al. |
| 11,482,339 B2 | 10/2022 | Koo et al. |
| 11,494,904 B2 | 11/2022 | Fonte et al. |
| 11,501,436 B2 | 11/2022 | Min et al. |
| 11,501,485 B2 | 11/2022 | Grady et al. |
| 11,504,019 B2 | 11/2022 | Fonte et al. |
| 11,508,063 B2 | 11/2022 | Buckler |
| 11,521,755 B2 | 12/2022 | Taylor et al. |
| 11,540,931 B2 | 1/2023 | Grady et al. |
| 11,547,367 B2 | 1/2023 | Taylor |
| 11,564,746 B2 | 1/2023 | Spilker et al. |
| 11,576,626 B2 | 2/2023 | Fonte et al. |
| 11,583,340 B2 | 2/2023 | Taylor |
| 11,589,924 B2 | 2/2023 | Passerini |
| 11,593,926 B2 | 2/2023 | Buckler et al. |
| 11,594,319 B2 | 2/2023 | Yousfi et al. |
| 11,605,466 B2 | 3/2023 | Grady et al. |
| 11,607,179 B2 | 3/2023 | Buckler et al. |
| 11,610,318 B2 | 3/2023 | Grady et al. |
| 11,617,620 B2 | 4/2023 | Tran et al. |
| 11,622,812 B2 | 4/2023 | Grady et al. |
| 11,638,609 B2 | 5/2023 | Sankaran et al. |
| 11,642,092 B1 | 5/2023 | Min |
| 11,642,171 B2 | 5/2023 | Jaquet et al. |
| 11,646,118 B2 | 5/2023 | Grady et al. |
| 11,653,833 B2 | 5/2023 | Sanders et al. |
| 11,657,486 B2 | 5/2023 | Buckler et al. |
| 11,660,058 B2 | 5/2023 | Min |
| 11,660,143 B2 | 5/2023 | Taylor et al. |
| 11,663,715 B2 | 5/2023 | Choi et al. |
| 11,730,437 B2 | 5/2023 | Min |
| 11,672,497 B2 | 6/2023 | Min |
| 11,676,359 B2 | 6/2023 | Buckler et al. |
| 11,678,937 B2 | 6/2023 | Choi et al. |
| 11,690,586 B2 | 7/2023 | Min |
| 11,696,735 B2 | 7/2023 | Buckler et al. |
| 11,701,175 B2 | 7/2023 | Bai et al. |
| 11,707,325 B2 | 7/2023 | Sankaran et al. |
| 11,715,187 B2 | 8/2023 | Buckler et al. |
| 11,715,198 B2 | 8/2023 | Kim et al. |
| 11,737,718 B2 | 8/2023 | Min |
| 11,751,826 B2 | 9/2023 | Min |
| 11,751,829 B2 | 9/2023 | Min |
| 11,751,830 B2 | 9/2023 | Min |
| 11,751,831 B2 | 9/2023 | Min |
| 11,759,161 B2 | 9/2023 | Min |
| 11,766,229 B2 | 9/2023 | Min |
| 11,766,230 B2 | 9/2023 | Min |
| 11,779,292 B2 | 10/2023 | Min |
| 11,832,982 B2 | 12/2023 | Min |
| 11,861,833 B2 | 1/2024 | Min |
| 11,896,415 B2 | 2/2024 | Min |
| 11,986,280 B2 | 5/2024 | Grady et al. |
| 11,992,293 B2 | 5/2024 | Fonte et al. |
| 11,996,182 B2 | 5/2024 | Lee et al. |
| 12,004,841 B2 | 6/2024 | Sanders et al. |
| 12,008,751 B2 | 6/2024 | Buckler et al. |
| 12,016,635 B2 | 6/2024 | Taylor |
| 12,020,432 B2 | 6/2024 | Ross et al. |
| 12,026,868 B2 | 7/2024 | Buckler et al. |
| 12,027,275 B2 | 7/2024 | Koo et al. |
| 12,029,494 B2 | 7/2024 | Taylor |
| 12,035,976 B2 | 7/2024 | Choi et al. |
| 12,039,765 B2 | 7/2024 | Buckler et al. |
| 12,045,983 B2 | 7/2024 | Buckler et al. |
| 12,046,367 B2 | 7/2024 | Yi et al. |
| 12,048,490 B2 | 7/2024 | Grady et al. |
| 12,051,497 B2 | 7/2024 | Grady et al. |
| 12,059,288 B2 | 8/2024 | Taylor et al. |
| 12,068,079 B2 | 8/2024 | Sankaran et al. |
| 12,073,561 B2 | 8/2024 | Buckler et al. |
| 12,073,943 B2 | 8/2024 | Yu et al. |
| 12,079,921 B2 | 9/2024 | Grady et al. |
| 12,079,988 B2 | 9/2024 | Guidry |
| 2001/0047137 A1 | 11/2001 | Moreno et al. |
| 2002/0172663 A1 | 11/2002 | Palasis |
| 2004/0101181 A1 | 5/2004 | Giger et al. |
| 2004/0133094 A1 | 7/2004 | Becker et al. |

(56) References Cited

U.S. PATENT DOCUMENTS

| | | |
|---|---|---|
| 2004/0133100 A1 | 7/2004 | Naghavi et al. |
| 2004/0136491 A1 | 7/2004 | Iatrou et al. |
| 2005/0043614 A1 | 2/2005 | Huizenga et al. |
| 2005/0110791 A1 | 5/2005 | Krishnamoorthy et al. |
| 2005/0118632 A1 | 6/2005 | Chen et al. |
| 2006/0036167 A1 | 2/2006 | Shina |
| 2006/0101075 A1 | 5/2006 | Lehel et al. |
| 2007/0018558 A1 | 1/2007 | Chua et al. |
| 2007/0019778 A1 | 1/2007 | Clouse et al. |
| 2007/0248250 A1 | 10/2007 | Gulsun et al. |
| 2007/0260141 A1 | 11/2007 | Margolis et al. |
| 2008/0058642 A1 | 3/2008 | Gould |
| 2008/0100621 A1 | 5/2008 | Aharon et al. |
| 2008/0103389 A1 | 5/2008 | Begelman et al. |
| 2008/0118131 A1 | 5/2008 | Skinner |
| 2008/0119713 A1 | 5/2008 | Le Nezet |
| 2008/0119734 A1 | 5/2008 | Pruvot et al. |
| 2008/0187199 A1 | 8/2008 | Gulsun et al. |
| 2008/0188962 A1 | 8/2008 | Suryanarayanan et al. |
| 2009/0012382 A1 | 1/2009 | Dutta et al. |
| 2009/0016588 A1 | 1/2009 | Slabaugh et al. |
| 2009/0129673 A1 | 5/2009 | Simon et al. |
| 2009/0264771 A1 | 10/2009 | Houben |
| 2009/0276161 A1 | 11/2009 | Cobain |
| 2009/0278846 A1 | 11/2009 | Gulsun et al. |
| 2009/0299645 A1 | 12/2009 | Colby |
| 2009/0307179 A1 | 12/2009 | Colby |
| 2010/0137711 A1 | 6/2010 | Hamilton et al. |
| 2010/0177945 A1 | 7/2010 | Moriya |
| 2010/0201786 A1 | 8/2010 | Schaefer et al. |
| 2010/0215225 A1 | 8/2010 | Kadomura et al. |
| 2010/0278405 A1 | 11/2010 | Kakadiaris et al. |
| 2010/0316274 A1 | 12/2010 | Langheinrich et al. |
| 2011/0026798 A1 | 2/2011 | Madabhushi et al. |
| 2011/0116697 A1 | 5/2011 | Dafni et al. |
| 2011/0206247 A1 | 8/2011 | Dachille et al. |
| 2011/0218427 A1 | 9/2011 | Kitamura |
| 2011/0229002 A1 | 9/2011 | Arnold et al. |
| 2011/0243412 A1 | 10/2011 | Grass |
| 2011/0245650 A1 | 10/2011 | Kerwin et al. |
| 2012/0041323 A1 | 2/2012 | Taylor et al. |
| 2012/0075638 A1 | 3/2012 | Rollins |
| 2012/0076377 A1 | 3/2012 | Dutta et al. |
| 2012/0128132 A1 | 5/2012 | Coolens et al. |
| 2012/0158432 A1 | 6/2012 | Jain |
| 2012/0243764 A1 | 9/2012 | Dey et al. |
| 2012/0263368 A1 | 10/2012 | Nakano et al. |
| 2013/0046168 A1 | 2/2013 | Sui |
| 2013/0066188 A1 | 3/2013 | Taerum et al. |
| 2013/0101187 A1 | 4/2013 | Sundar et al. |
| 2013/0190592 A1 | 7/2013 | Coppini et al. |
| 2013/0190595 A1 | 7/2013 | Oraevsky et al. |
| 2013/0202173 A1 | 8/2013 | Buckler et al. |
| 2013/0246034 A1 | 9/2013 | Sharma et al. |
| 2014/0058715 A1 | 2/2014 | Sharma et al. |
| 2014/0073976 A1 | 3/2014 | Fonte et al. |
| 2014/0114176 A1 | 4/2014 | Hirschenbain et al. |
| 2014/0306961 A1 | 10/2014 | Nagata |
| 2015/0016702 A1 | 1/2015 | Huizenga et al. |
| 2015/0065846 A1 | 3/2015 | Choi |
| 2015/0066818 A1 | 3/2015 | Choi et al. |
| 2015/0164342 A1 | 6/2015 | Choi et al. |
| 2015/0187025 A1 | 7/2015 | Wasserkrug et al. |
| 2015/0193944 A1 | 7/2015 | Lang et al. |
| 2016/0012614 A1 | 1/2016 | Goto |
| 2016/0066861 A1 | 3/2016 | Taylor |
| 2016/0078309 A1 | 3/2016 | Feldman |
| 2016/0104281 A1 | 4/2016 | Grady et al. |
| 2016/0203263 A1 | 7/2016 | Maier et al. |
| 2016/0239564 A1 | 8/2016 | Sohma |
| 2016/0292372 A1 | 10/2016 | Kamen et al. |
| 2016/0296288 A1 | 10/2016 | Sankaran et al. |
| 2016/0300350 A1 | 10/2016 | Choi et al. |
| 2016/0342765 A1 | 11/2016 | Sankaran et al. |
| 2016/0346043 A1 | 12/2016 | Jaquet et al. |
| 2016/0358333 A1 | 12/2016 | Lee et al. |
| 2017/0014034 A1 | 1/2017 | Koo et al. |
| 2017/0018081 A1 | 1/2017 | Taylor et al. |
| 2017/0046484 A1 | 2/2017 | Buckler et al. |
| 2017/0046839 A1* | 2/2017 | Paik .................. G06V 10/84 |
| 2017/0103525 A1 | 4/2017 | Hu et al. |
| 2017/0119333 A1 | 5/2017 | Zebaze et al. |
| 2017/0202621 A1 | 7/2017 | Taylor |
| 2017/0245821 A1 | 8/2017 | Itu et al. |
| 2017/0258433 A1 | 9/2017 | Gulsun et al. |
| 2017/0265831 A1 | 9/2017 | Sankaran et al. |
| 2017/0265832 A1 | 9/2017 | Antodiades |
| 2017/0337343 A1 | 11/2017 | Kakadiaris et al. |
| 2017/0340393 A1 | 11/2017 | Choi et al. |
| 2018/0078139 A1* | 3/2018 | Sanders ................. G16H 50/50 |
| 2018/0165811 A1 | 6/2018 | Flohr et al. |
| 2018/0179189 A1 | 6/2018 | MacPhee et al. |
| 2018/0225847 A1 | 8/2018 | Grady et al. |
| 2018/0330477 A1 | 11/2018 | Paik et al. |
| 2018/0336319 A1* | 11/2018 | Itu .................. G16B 25/10 |
| 2019/0021608 A1 | 1/2019 | Cope |
| 2019/0074082 A1 | 3/2019 | Buckler et al. |
| 2019/0110776 A1 | 4/2019 | Yu et al. |
| 2019/0159737 A1 | 5/2019 | Buckler et al. |
| 2019/0172197 A1 | 6/2019 | Buckler et al. |
| 2019/0174082 A1 | 6/2019 | Taruki et al. |
| 2019/0175130 A1 | 6/2019 | Raman et al. |
| 2019/0180153 A1 | 6/2019 | Buckler et al. |
| 2019/0180438 A1 | 6/2019 | Buckler et al. |
| 2019/0200881 A1 | 7/2019 | Grady et al. |
| 2019/0244347 A1 | 8/2019 | Buckler et al. |
| 2019/0244348 A1 | 8/2019 | Buckler et al. |
| 2019/0251713 A1 | 8/2019 | Chen et al. |
| 2019/0282211 A1 | 9/2019 | Merritt et al. |
| 2019/0318476 A1 | 10/2019 | Isgum et al. |
| 2019/0350538 A1 | 11/2019 | Wilson et al. |
| 2020/0069262 A1 | 3/2020 | Fonte et al. |
| 2020/0085501 A1 | 3/2020 | Sankaran et al. |
| 2020/0117851 A1 | 4/2020 | Grady et al. |
| 2020/0243076 A1 | 7/2020 | Kim |
| 2020/0273579 A1 | 8/2020 | Wright |
| 2020/0294659 A1 | 9/2020 | Gopinath |
| 2020/0320775 A1 | 10/2020 | Holladay et al. |
| 2020/0372701 A1 | 11/2020 | Grady et al. |
| 2020/0402234 A1 | 12/2020 | Daughton et al. |
| 2021/0007807 A1 | 1/2021 | Sankaran et al. |
| 2021/0030478 A1 | 2/2021 | Hart et al. |
| 2021/0035287 A1* | 2/2021 | Kim .................. G06N 3/08 |
| 2021/0035687 A1 | 2/2021 | Yi et al. |
| 2021/0042918 A1 | 2/2021 | Bucker |
| 2021/0042927 A1 | 2/2021 | Amis et al. |
| 2021/0074435 A1 | 3/2021 | Taylor et al. |
| 2021/0082579 A1 | 3/2021 | Grady et al. |
| 2021/0085397 A1 | 3/2021 | Passerini et al. |
| 2021/0090694 A1 | 3/2021 | Colley et al. |
| 2021/0093384 A1 | 4/2021 | Grady et al. |
| 2021/0151171 A1 | 5/2021 | Lee et al. |
| 2021/0153749 A1 | 5/2021 | Fonte et al. |
| 2021/0185131 A1 | 6/2021 | Hart et al. |
| 2021/0186448 A1 | 6/2021 | Min |
| 2021/0196391 A1 | 7/2021 | Taylor et al. |
| 2021/0201495 A1 | 7/2021 | Yu et al. |
| 2021/0202110 A1 | 7/2021 | Grady et al. |
| 2021/0209757 A1 | 7/2021 | Min |
| 2021/0210209 A1 | 7/2021 | Taylor et al. |
| 2021/0212565 A1 | 7/2021 | Gardner et al. |
| 2021/0217534 A1 | 7/2021 | Rabbat et al. |
| 2021/0228094 A1 | 7/2021 | Grady et al. |
| 2021/0241920 A1 | 8/2021 | Sankaran et al. |
| 2021/0244475 A1 | 8/2021 | Taylor |
| 2021/0267690 A1 | 9/2021 | Taylor |
| 2021/0272030 A1 | 9/2021 | Sankaran et al. |
| 2021/0282860 A1 | 9/2021 | Taylor |
| 2021/0312622 A1 | 10/2021 | Buckler et al. |
| 2021/0319558 A1 | 10/2021 | Min et al. |
| 2021/0335497 A1 | 10/2021 | Sankaran et al. |
| 2021/0338333 A1 | 11/2021 | Sankaran et al. |
| 2021/0358634 A1 | 11/2021 | Sankaran et al. |
| 2021/0358635 A1 | 11/2021 | Sankaran et al. |

(56) References Cited

U.S. PATENT DOCUMENTS

| | | |
|---|---|---|
| 2021/0374969 A1 | 12/2021 | Grady et al. |
| 2021/0375401 A1 | 12/2021 | Choi et al. |
| 2021/0375476 A1 | 12/2021 | Rabbat et al. |
| 2021/0390689 A1 | 12/2021 | Buckler et al. |
| 2021/0397746 A1 | 12/2021 | Yousfi et al. |
| 2022/0012865 A1 | 1/2022 | Buckler et al. |
| 2022/0012877 A1 | 1/2022 | Buckler et al. |
| 2022/0012878 A1* | 1/2022 | Aoyama ............... G06T 11/00 |
| 2022/0079540 A1 | 3/2022 | Sankaran et al. |
| 2022/0110687 A1 | 4/2022 | Spilker et al. |
| 2022/0139529 A1 | 5/2022 | Bhatia et al. |
| 2022/0172353 A1 | 6/2022 | Yi et al. |
| 2022/0211439 A1 | 7/2022 | Sankaran et al. |
| 2022/0230312 A1 | 7/2022 | Choi et al. |
| 2022/0241019 A1 | 8/2022 | Taylor |
| 2022/0265239 A1 | 8/2022 | Taylor et al. |
| 2022/0277443 A1 | 9/2022 | Min et al. |
| 2022/0322953 A1 | 10/2022 | Fonte et al. |
| 2022/0327701 A1 | 10/2022 | Grady et al. |
| 2022/0330902 A1 | 10/2022 | Forneris et al. |
| 2022/0335603 A1 | 10/2022 | Min |
| 2022/0335859 A1 | 10/2022 | Sankaran et al. |
| 2022/0359063 A1 | 11/2022 | Tombropoulos et al. |
| 2022/0366562 A1 | 11/2022 | Yu et al. |
| 2022/0367066 A1 | 11/2022 | Grady et al. |
| 2022/0383495 A1 | 12/2022 | Peterson et al. |
| 2022/0392065 A1 | 12/2022 | Min |
| 2022/0392070 A1 | 12/2022 | Buckler et al. |
| 2022/0398706 A1 | 12/2022 | Buckler et al. |
| 2022/0400963 A1 | 12/2022 | Buckler et al. |
| 2022/0406459 A1 | 12/2022 | Buckler et al. |
| 2022/0406470 A1 | 12/2022 | Fonte et al. |
| 2022/0409160 A1 | 12/2022 | Buckler et al. |
| 2022/0415519 A1 | 12/2022 | Buckler et al. |
| 2023/0005582 A1 | 1/2023 | Buckler et al. |
| 2023/0005583 A1 | 1/2023 | Buckler et al. |
| 2023/0005622 A1 | 1/2023 | Rabbat et al. |
| 2023/0016104 A1 | 1/2023 | Koo et al. |
| 2023/0033594 A1 | 2/2023 | Grade et al. |
| 2023/0055828 A1 | 2/2023 | Fonte et al. |
| 2023/0117134 A1 | 4/2023 | Clifton et al. |
| 2023/0124826 A1 | 4/2023 | Spilker et al. |
| 2023/0138144 A1 | 5/2023 | Min |
| 2023/0139102 A1 | 5/2023 | Taylor |
| 2023/0145596 A1 | 5/2023 | Min |
| 2023/0148977 A1 | 5/2023 | Fonte et al. |
| 2023/0154000 A1 | 5/2023 | Min |
| 2023/0154620 A1 | 5/2023 | Yi et al. |
| 2023/0165544 A1 | 6/2023 | Hahn, III et al. |
| 2023/0169702 A1 | 6/2023 | Hahn, III et al. |
| 2023/0172451 A1 | 6/2023 | Seo et al. |
| 2023/0196582 A1 | 6/2023 | Grady et al. |
| 2023/0197286 A1 | 6/2023 | Grady et al. |
| 2023/0207137 A1 | 6/2023 | Buckler et al. |
| 2023/0210602 A1 | 7/2023 | Sankaran et al. |
| 2023/0218346 A1 | 7/2023 | Tran et al. |
| 2023/0218347 A1 | 7/2023 | Taylor |
| 2023/0223148 A1 | 7/2023 | Grady et al. |
| 2023/0233261 A1 | 7/2023 | Jaquet et al. |
| 2023/0237654 A1 | 7/2023 | Min |
| 2023/0237759 A1 | 7/2023 | Buckler et al. |
| 2023/0240619 A1 | 8/2023 | Daughton et al. |
| 2023/0245775 A1 | 8/2023 | Buckler et al. |
| 2023/0248242 A1 | 8/2023 | Sanders et al. |
| 2023/0289963 A1 | 9/2023 | Min et al. |
| 2023/0298168 A1 | 9/2023 | Lee et al. |
| 2023/0301720 A1 | 9/2023 | Grady et al. |
| 2023/0301722 A1 | 9/2023 | Choi et al. |
| 2023/0310085 A1 | 10/2023 | Sankaran et al. |
| 2023/0326166 A1 | 10/2023 | Buckler et al. |
| 2024/0023918 A1 | 1/2024 | Min et al. |
| 2024/0057960 A1 | 2/2024 | Min et al. |
| 2024/0153229 A1 | 5/2024 | Buckler et al. |
| 2024/0153252 A1 | 5/2024 | Phillips et al. |
| 2024/0161295 A1 | 5/2024 | Buckler et al. |
| 2024/0161296 A1 | 5/2024 | Buckler et al. |
| 2024/0161297 A1 | 5/2024 | Buckler et al. |
| 2024/0202915 A1 | 6/2024 | Buckler et al. |
| 2024/0212143 A1 | 6/2024 | Buckler et al. |
| 2024/0259352 A1 | 8/2024 | Yousfi et al. |
| 2024/0274276 A1 | 8/2024 | Lee et al. |

FOREIGN PATENT DOCUMENTS

| | | |
|---|---|---|
| CA | 3238598 A1 | 5/2023 |
| CA | 3240201 A1 | 6/2023 |
| CA | 3017610 C | 4/2024 |
| CN | 112567378 A | 3/2021 |
| CN | 113439287 A | 9/2021 |
| CN | 117501379 A | 2/2024 |
| CN | 110914866 B | 4/2024 |
| CN | 117918872 A | 4/2024 |
| CN | 118077008 A | 5/2024 |
| CN | 118334070 A | 7/2024 |
| EP | 3185762 A1 | 7/2017 |
| EP | 3355762 A1 | 8/2018 |
| EP | 3 431 005 A1 | 1/2019 |
| EP | 3665702 A2 | 6/2020 |
| EP | 3846176 A1 | 7/2021 |
| EP | 3803687 A4 | 3/2022 |
| EP | 3899864 A4 | 8/2022 |
| EP | 4292098 A1 | 12/2023 |
| EP | 3516561 B1 | 3/2024 |
| EP | 4334941 A1 | 3/2024 |
| EP | 3326092 B1 | 4/2024 |
| EP | 4147632 B1 | 4/2024 |
| EP | 3912550 B1 | 6/2024 |
| EP | 4183344 A4 | 6/2024 |
| EP | 4377885 A1 | 6/2024 |
| EP | 3569150 B1 | 7/2024 |
| EP | 4404141 A2 | 7/2024 |
| EP | 3278254 B1 | 8/2024 |
| EP | 4418280 A2 | 8/2024 |
| FR | 2908976 A1 | 5/2008 |
| GB | 2618468 A | 11/2023 |
| JP | 2003-150703 | 5/2003 |
| JP | 2011-115481 | 6/2011 |
| JP | 2011-135938 | 7/2011 |
| JP | 5305821 B2 | 10/2013 |
| JP | 6203410 B2 | 9/2017 |
| JP | 2021-525929 A | 9/2021 |
| JP | 2022-123103 A | 8/2022 |
| JP | 7113916 B2 | 8/2022 |
| JP | 2022-543330 A | 10/2022 |
| JP | 2023-054309 A | 4/2023 |
| JP | 2023-093605 A | 7/2023 |
| JP | 2023-118960 A | 8/2023 |
| JP | 2024-506605 A | 2/2024 |
| JP | 2024-069343 A | 5/2024 |
| JP | 7483079 B2 | 5/2024 |
| JP | 7505093 B2 | 6/2024 |
| JP | 2024-528679 A | 7/2024 |
| JP | 2024-529232 A | 8/2024 |
| KR | 20210042267 A | 4/2021 |
| KR | 20210121062 A | 10/2021 |
| KR | 20220155828 A | 11/2022 |
| KR | 102491988 B1 | 1/2023 |
| KR | 20230069884 A | 5/2023 |
| KR | 20230146038 A | 10/2023 |
| KR | 20240054248 A | 4/2024 |
| KR | 20240064617 A1 | 5/2024 |
| KR | 102690881 B1 | 8/2024 |
| WO | WO 07/029129 | 3/2007 |
| WO | WO 09/105530 | 8/2009 |
| WO | WO 10/067276 | 6/2010 |
| WO | WO 14/107402 | 7/2014 |
| WO | WO 14/132829 | 9/2014 |
| WO | WO 15/095282 | 6/2015 |
| WO | WO 16/022533 | 2/2016 |
| WO | WO 16 /024128 | 2/2016 |
| WO | WO 17/011555 | 1/2017 |
| WO | WO 17/096407 | 6/2017 |
| WO | WO 17/106819 | 6/2017 |
| WO | WO 18/078395 | 5/2018 |

(56) References Cited

FOREIGN PATENT DOCUMENTS

| | | |
|---|---|---|
| WO | WO 19/033098 | 2/2019 |
| WO | WO 19/165432 | 8/2019 |
| WO | WO 19/242227 | 12/2019 |
| WO | 21/026125 | 2/2021 |
| WO | WO 21/141135 | 7/2021 |
| WO | 22/173534 | 8/2022 |
| WO | 22/261506 | 12/2022 |
| WO | 23/172273 | 9/2023 |
| WO | 24/102879 | 5/2024 |
| WO | 24/105483 | 5/2024 |
| WO | 24/105484 | 5/2024 |
| WO | 24/171153 | 8/2024 |

OTHER PUBLICATIONS

Yang et al. 2021 JACC Asia 1:37-48 (Year: 2021).*
Eskerud et al. 2021 IJC Heart & Vasculature 35:100831 9 pages (Year: 2021).*
Abbara et al., "SCCT Guidelines for the performance and acquisition of coronary computed tomographic angiography: A report of the society of Cardiovascular Computed Tomography Guidelines Committee: Endorsed by the North American Society for Cardiovascular Imaging (NASCI)." Journal of cardiovascular computed tomography 2016; 10(6):435-449.
Abdelrahman et al., Sep. 8, 2020, Coronary computed tomography angiography from clinical uses to emerging technologies, Journal of the American College of Cardiology, 76(10):1226-1243.
Ahmadi A. et al. "Do Plaques rapidly progress prior to myocardial infarction? The interplay between plaque vulnerability and progression." Circ Res. 2015; 117(1):99-104.
Achenbach et al. "Detection of calcified and noncalcified coronary atherosclerotic plaque by contrast-enhanced, submillimeter multidetector spiral computed tomography: a segment-based comparison with intravascular ultrasound." Circulation 2004; 109(1):14-17.
Ahmadi et al., "Association of Coronary Stenosis and Plaque Morphology with Fractional Flow Reserve and Outcomes." JAMA cardiology 2016; 1 (3):350-357. doi: 10.1001/jamacardio.2016.0263 [published Online First: Jul. 22, 2016].
Ahmadi et al., 2018, Lesion-Specific and Vessel-Related Determinants of Fractional Flow Reserve Beyond Coronary Artery Stenosis, JACCL Cardiovascular Imaging, 11(4):521-530.
Al'Aref et al. "Clinical Applications of machine learning in cardiovascular disease and its relevance to cardiac imaging." Eur Heart J. Jul. 27, 2018. [Epub ahead of print].
Al'Aref et al., "High-risk atherosclerotic plaque features for cardiovascular risk assessment in the Prospective Multicenter Imaging Study for Evaluation of Chest Pain trial", Cardiovascular Diagnosis and Therapy, vol. 9, No. 1, Feb. 2019. pp. 89-93.
Antonopoulos et al., "Detecting Human coronary inflammation by imaging perivascular fat", Sci. Transl. Med. 9, eaal2658 (2017) Jul. 12, 2017.
Arbab-Zadeh et al., "Contemporary Reviews in Cardiovascular Medicine, Acute Coronary Events", Amercan Heart Association, Inc., Circulation. 2012;125:1147-1156, Mar. 6, 2012, pp. 1147-1156.
Arbab-Zadeh, et al. "the myth of the vulnerable plaque: transitioning from a focus on individual lesions to atherosclerotic disease burden for coronary artery disease risk assessment." J Am Coll Cardiol. 2015;65: 846-855.
Bakhasi, et al. "Comparative Effectiveness of CT-Derived Atherosclerotic Plaque Metrics for Predicting Myocardial Ischemia." JACC Cardiovasc Imaging. Jul. 13, 2018. doi: 10.2013/j.jcmg.2018.05.019. [Epub ahead of print].
Baskaran et al., "Dense calcium and lesion-specific ischemia: A comparison of CCTA with fractional flow reserve", Atherosclerosis 260, 2017 pp. 163-168.
Benjamin, et al. "Heart Disease and Stroke Statistics—2018 Update: A Report From the American Heart Association." Circulation. 2018; 137: e67-e492.
Bergman "Using Multicoloured Halftsone Screens for Offset Print Quality Monitoring", Linköping Studies in Science and Technology; LiU-TEK-LIC-2005:02.
Blankstein R. et al. "Coronary CTA in the Evaluation of Stable Chest Pain: Clear Benefits, But Not for All." J Am Coll Cardiol 2017; 69 (14): 1771-73. doi: 10.1016/j.jacc.2017.02.011 [published Online First: Apr. 8, 2017].
Boogers, et al. "Automated Quantification of Coronary Plaque with Computed Tomography: Comparison with Intravascular Ultrasound using a Dedicated Registration Algorithm for Fusion-Based Quantification", Epub, (2012).
Boussoussou et al., 2023, The effect of patient and imaging characteristics on coronary CT angiography assessed perocoronary adipose tissue attenuation and gradient, Journal of Cardiovascular Computed Tomography, 17:34-42.
Budde et al., Sep. 15, 2021, CT-derived fractional flow reserve (FFRct) for functional coronary artery evaluation in the follow-up of patients after heart transplantation, European Radiology, https://doi.org/10/1007/s00330-0921-08246-5.
Budoff MJ, et al. "Diagnostic performance of 64-multidetector row coronary computed tomographic angiography for evaluation of coronary artery stenosis in individuals without know coronary artery disease: results from the prospective multicenter Accuracy (Assessment by Coronary Computed Tomography of Individuals Undergoing Invasive Coronary Angiography) trial." J Am Coll Cardiol 2008; 52(21): 1724-32.
Bzdok "Classical Statistics and Statistical Learning in Imaging Neuroscience." Front Neurosci. 2017; 11:543.
Calvert, et al. "Association between IVUS Findings and Adverse Outcomes in Patients with Coronary Artery Disease: the VIVA (VH-IVUS in Vulnerable Atherosclerosis) Study." JACC Cardiovasc Imaging. 2011;4: 894-901.
Celeng, et al. "Non-invasive and Invasive Imaging of Vulnerable Coronary Plaque." trends Cardiovasc Med. 2016;26-538-47.
Cerqueira et al. "Standardized myocardial segmentation and nomenclature for tomographic imaging of the heart. A statement for healthcare professionals from the Cardiac Imaging Committee of the Council on Clinical Cardiology of the American Heart Association." Int J Cardiovasc Imaging 2002; 18(1): 539-42.
Chang et al., "Coronary Atherosclerotic Precursors of Acute Coronary Syndromes", Journal of the American College of Cardiology, vol. 71, No. 22, Jun. 5, 2018. pp. 2511-2522.
Chang et al., "Selective Referral Using CCTA Versus Direct Referral for Individuals Referred to Invasive Coronary Angiography for Suspected CAD", JACC: Cardiovascular Imaging, vol. 12, No. 7, Jul. 2019. pp. 1303-1312.
Chrencik et al., Sep. 2019, Quantitative assessment of carotid plaque morphology (geometry and tissue composition) using computed tomography angiography, Journal of Vascular Surgery, 70(3):858-868.
Chung et al. "Image Segmentation Methods for Detecting Blood Vessels in Angiography", 2006 9th Int. Conf. Control, Automation, Robotics and Vision, Singapore, Dec. 5-8, 2006, ICARCV 2006, pp. 1424-1429.
Costopoulos, et al. "Intravascular Ultrasound and Optical Coherence Tomography Imaging of Coronary Atherosclerosis." Int J Cardiovasc Imaging. 2016;32: 189-200.
Cury et al., 2022, CAD-RADS™ 2.0—2022 coronary artery disease—reporting and data system an expert consensus document of the Society of Cardiovascular Computed Tomography (SCCT), the American College of Cardiology (ACC), the American College of Radiology (ACR) and the North America Society of Cardiovascular Imaging (NASCI), Journal of Cardiovascular Computed Tomography, https://doi.org/10.1016/j.jcct.2022.07.002.
Cury, et al. "CAD-RADS™ Coronary Artery Disease—Reporting and Data System. An Expert consensus documents of the Society of Cardiovascular Computed Tomography (SCCT), the American College of Radiology (ACR) and the North American Society for Cardiovascular Imaging (NASCI)." Endorsed by the American College of Cardiology. J Cardiovasc Compute Tomogr. 2016; 10: 269-81.
Danad et al. "Comparison of Coronary CT Angiography, SPECT, PET, and Hybrid Imaging for Diagnosis of Ischemic Heart Disease

(56) References Cited

OTHER PUBLICATIONS

Determined by Fractional Flow Reserve." JAMA Cardiol 2017; 2 (10): 1100-07. doi 10.1001/jamacardio.2017.2471 [published Online First: Aug. 17, 2017].

De Bruyne B. et al. "Fractional flow reserve-guided PCI for stable coronary artery disease." The NewEngland journal of medicine 2014; 371 (13): 1208-17. doi: 10.1056/NEJMoal408758 [published Online First: 2014/0902].

De Bruyne et al., Sep. 13, 2012, Fractional flow reserve-guided PCA versus medical therapy in stable coronary disease, The New England Journal of Medicine, 367(11):991-1001.

De Graaf, et al. "Automatic Quantification and Characterization of Coronary Atherosclerosis with Computed Tomography Coronary Angiography: Cross-Correlation with Intravascular Ultrasound Virtual Histology", *Int J Cardiovasc*, pp. 1177-1190, (2013).

De Graaf, et al. "Feasibility of an Automated Quantitative Computed Tomography Angiography-Derived Risk Stratification of Patients with Suspected CAD." *Am J Cardiol* (2014).

DeLong ER, et al. "Comparing the areas under two or more correlated receiver operating characteristic curves: a nonparametric approach." Biometrics 1988; 44 (3): 837-45. [published Online First: Sep. 1, 1988].

Dey et al., "Direct Quantitative In Vivo Comparison of Calcified Atherosclerotic Plaque on Vascular MRI and CT by Multimodality Image Registration" Journal of Magnetic Resonance Imaging 23:345-354 (2006).

Dey et al., 2018, Integrated prediction of lesion-specific ischemia from quantitative coronary CT Angiography using machine learning: a multicenter study, European Radiology, 28(6):2655-2664.

Dey, et al. "Comparison of Quantitative Atherosclerotic Plaque Burden from Coronary CT Angiography in Patients with First Acute Coronary Syndrome and Stable CAD" *J Cardiovasc Comput tomogr* (2014).

Dey, et al. "Non-Invasive Measurement of Coronary Plaque from Coronary CT Angiography and its Clinical Implication", *Expert Review of Cardiovascular Therapy* (2013).

Diaz-Zamudio, et al. "Automated Quantitative Plaque Burden from Coronary CT Angiography Non-Invasively Predicts Hemodynamic Significance by Using Fractional Flow Reserve in Intermediate Coronary Lesions." *Radiology* (2015).

Douglas et al., "Outcomes of Anatomical versus Functional Testing for Coronary Artery Disease", N Engl J Med. Apr. 2, 2015, p. 1291-1300.

Douglas et al., Aug. 2, 2016, 1-year outcomes of FFRCT-guided care in patients with suspected coronary disease, Journal of the American College of Cardiology, 68(5):435-445.

Driessen et al., "Adverse Plaque Characteristic Relate More Strongly With Hyperemic Fractional Flow Reserve and Instantaneous Wave-Free Ratio Than With Resting Instantaneous Wave-Free Ratio", JACC: Cardiovascular Imaging, 2019, in 11 pages.

Driessen et al., "Effect of Plaque Burden and Morphology on Myocardial Blood Flow and Fractional Flow Reserve", Journal of the American College of Cardiology, vol. 71, No. 5, 2018 p. 499-509.

Dwivedi et al., "Evaluation of Atherosclerotic Plaque in Non-invasive Coronary Imaging", Korean Circulation Journal, Feb. 2018. 48(2), pp. 124-133.

Ehara et al. "Spotty calcification typifies the culprit plaque in patients with acute myocardial infarction: an intravascular ultrasound study." Circulation 2004; 110(22): 3424-9.

Erickson BJ, et al. "Machine Learning for Medical Imaging." Radiographics 2017; 37(2) pp. 505-515.

Ferencik et al., "Use of High-Risk Coronary Atherosclerotic Plaque Detection for Risk Stratification of Patients With Stable Chest Pain", JAMA Cardiol, Feb. 2018 in 19 pages.

Ferencik, et al. "Computed Tomography-Based High-Risk Coronary Plaque Score to Predict ACS Among Patients with Acute Chest Pain" *Journal of Cardiovascular Computed Tomography*, (2015).

Fihn et al. "2012 ACCF/AHA/ACP/AATS/PCNA/SCAI/STS Guideline for the Diagnosis and the Management of Patients With Stable Ischemic Heart Disease: Executive Summary: A Report of the American College of Cardiology Foundation/American Heart Association Task Force on Practice Guidelines, and the American College of Physicians, American Association for Thoracic Surgery, Preventive Cardiovascular Nurses Association, Society for Cardiovascular Angiography and Interventions, and Society of Thoracic Surgeons." J Am Coll Cardio 2012;60(24):2564-603. doi: 10.1016/c.cacc.2012.07.012 [published Online First: Nov. 28, 2012].

Finh et al. "2014 ACC/AHA/AATS/PCNA/SCAI/STS focused update of the guideline for the diagnosis and management of patients with stable ischemic heart disease: a report of the American College of Cardiology/American Heart Association Task Force on Practice Guidelines, and the American Association for Thoracic Surgery, Preventive Cardiovascular Nurses Association, Society for Cardiovascular Angiography and Interventions, and Society of Thoracic Surgeons." Journal of the American College of Cardiology 2014;64 (18): 1929-49. doi:10.1016/j.jacc.2014.07.017 [published Online First: Aug. 1, 2014].

Friedman et al., "Additive logistic regression: a statistical view of boosting (With discussion and a rejoinder by the authors)." Ann Statist. 2000; 28(2) pp. 337-407.

Funama et al., Sep. 2017, Improved estimation of coronary plaque and luminal attenuation using a vendor-specific model-based iterative reconstruction algorithm in contrast-enhanced CT coronary angiography. Academic Radiology 24(9):1070-1078.

Gaemperli et al. "Cardiac hybrid imaging." Eur Heart J 2011; 32(17): 2100-8.

Gaur et al., "Coronary plaque quantification and fractional flow reserve by coronary computed tomography angiography identify ischaemia-causing lesions", European Heart Journal, 2016 pp. 1220-1227.

Goff, et al. "2013 ACC/AHA Guidelines on the Assessment of Cardiovascular Risk: a Report of the American College of Cardiology/American Heart Association Task Force on Practice Guidelines." J Am Coll Cardiol. 2014;63: 2935-59.

Gogas, et al. "Assessment of Coronary Atherosclerosis by IVUS and IVUS-based Imaging Modalities:Profession and Regression Studies, Tissue Composition and Beyond." Int J Cardiovasc Imaging. 2011;27: 225-37.

Goldstein et al., "Moving beyond regression techniques in cardiovascular risk prediction: applying machine learning to address analytic challenges." Eur Heart J. 2017; 38(23) pp. 1805-1814.

Greenwood et al. "Effect of Care Guided by Cardiovascular Magnetic Resonance, Myocardial Perfusion Scintigraphy, or NICE Guidelines on Subsequent Unnecessary Angiography Rates: The CE-MARC 2 Randomized Clinical Trial." JAMA 2016; 316(10): 1051-60. doi: 10.1001/jama.2016.12680 [published Online First: Aug. 30, 2016.

Gupta et al., Apr. 8, 2015, Moving beyond luminal stenosis: imaging strategies for stroke prevention in asymptomatic carotid stenosis, Cerebrovascular Diseases, 39:253-261.

Guyon et al., "An introduction to variable and feature selection." J Mach Learn Res. 2003; 3:1157-1182.

Hadamitzky et al., "Optimized Prognostic Score for Coronary Computed Tomographic Angiography", Journal of the American College of Cardiology, vol. 62, No. 5, 2013, pp. 468-476.

Hall et al., "Benchmarking attribute selection techniques for discrete clas data mining." IEEE Transaction on Knowledge and Data Engineering 2003; 15(6): pp. 1437-1447.

Hall et al., "The WEKA data mining software: an update." SIGKDD Explor News. 2009; 11(1) pp. 10-18.

Han et al. "Incremental role of resting myocardial computed tomography perfusion for predicting physiologically significant coronary artery disease: A machine learning approach." J Nucl Cardiol. 2018; 25(1) pp. 223-233.

Han et al., "Quantitative measurement of lipid rich plaque by coronary computed tomography angiography: A correlation of histology in sudden cardiac death", Atherosclerosis, 2018 pp. 426-433.

Hausleiter et al. "Estimated radiation dose associated with cardiac CT angiography." JAMA 2009; 301(5): 500-7.

Heo et al., "Optimal boundary detection method and window settings for coronary atherosclerotic plaque volume analysis in

(56) References Cited

OTHER PUBLICATIONS coronary computed tomography angiography: comparison with intravascular ultrasound", Eur Radiol, (2016) 26:31, pp. 3190-3198.
Hesse et al. "EANM/ESC procedural guidelines for myocardial perfusion imaging in nuclear cardiology." Eur J Nucl Med Mol Imaging 2005; 32 (7): 855-97. doi: 10.1007/s00259-005-1779-y.
Howard G. et al. "Cigarette smoking and progression of atherosclerosis: The Atherosclerosis Risk in Communities (AIRC) Study." JAMA 1998; 279(2) pp. 119-124.
Hundley WG et al. "Society for Cardiovascular Magnetic Resonance guidelines for reporting cardiovascular magnetic resonance examinations." J Cardiovasc Magn Reson 2009; 11:5.
Kanamori et al. "Robust Loss Functions for Boosting" Neural Computation. 2007; 19(8) pp. 2183-2244.
Kang et al., Apr. 2013, Automated Knowledge-Based Detection of Nonobstructive and Obstructive Arterial Lesions from Coronary CT Angiography. Medical Physics, 40(4):041912-1-041912-10.
Kang, et al. "Structured Learning Algorithm for Detection of Nonobstructive and Obstructive Coronary Plaque Lesions from Computed Tomography Angiography", *Journal of Medical Imaging*, (2015).
Kanitsar et al., 2002, CPR—curved planar reformation, IEEE Visualization, DOI: 10.1109/VISUAL.2002.1183754, 8 pp.
Karlof et al., 2019, Correlation of computed tomography with carotid plaque transcriptomes associates calcification with lesion-stabilization, atherosclerosis, 288:175-185.
Karlof et al., 2021, Carotid plaque phenotyping by correlating plaque morphology from computed tomography angiography with transcriptional profiling, Eur. J. Vas. Endovas. Surg., 62:716-726.
Kim et al., "Natural History of Diabetic Coronary Atherosclerosis by Quantitative Measurement of Serial Coronary Computed Tomographic Angiography", JACC: Cardiovascular Imaging, vol. 11, No. 10, 2018 pp. 1461-1471.
Klass O, et al. "Coronary plaque imaging with 256-slice multidetector computed tomography: interobserver variability of volumetric lesion parameters with semiautomatic plaque analysis software", *Int J Cardiovasc Imaging*, (2010). 26; pp. 711-720.
Klein et al. : Diagnostic quality of time-averaged ECG-Gated CT data, SPIE medical imaging, 2019.
Knuiman et al. "An Empirical comparison of multivariable methods for estimating risk of death from coronary heart disease." J. Cardiovasc Risk. 1997; 4(2): pp. 127-134.
Kolossvary, et al. "Radiomic Features are Superior to Conventional Quantitative Computed Tomographic Metrics to Identify Coronary Plaques with Napkin-Ring Sign." Circ Cardiovasc Imaging. 2017;10.
Koo BK, et al. "Diagnosis of ischemia-causing coronary stenoses by noninvasive fractional flow reserve computed from coronary computed tomographic angiograms. Results from the prospective multicenter Discovery-Flow (Diagnosis of Ischemia-Causes Stenoses Obtained via Noninvasive Fractional Flow Reserve) study." J Am Coll Cardiol 2011; 58 (19): 1989-97. doi: 10.1016/j.jacc.2011.06.066 [published Online First: Oct. 29, 2011].
Kramer et al. "Standardized cardiovascular magnetic resonance imaging (CMR) protocols, society for cardiovascular magnetic resonance: board of trustees task force on standardized protocols." J Cardiovasc Magn Reson 2008; 10:35. doi: 10.1186/1532-429X-10-35.
Kwan et al., "Bridging the gap for lipid lowering therapy: plaque regression, coronary computed tomographic angiography, and imaging-guided personalized medicine." Expert Rev Cardiovasc Ther. 2017; 15(7): pp. 547-558.
Kwee et al., Apr. 2010, Systematic review on the association between calcification in carotid plaques and clinical ischemic symptoms, Journal of Vascular Surgery, 51(4):1015-1025.
Lee et al., "Differences in Progression to Obstructive Lesions per High-Risk Plaque Features and Plaque Volumes With CCTA", JACC: Cardiovascular Imaging, 2019 in 9 pages.
Lee et al., "Identification of High-Risk Plaques Destined to Cause Acute Coronary Syndrome Using Coronary Computed Tomographic Angiography and Computational Fluid Dynamics", JACC: Cardiovascular Imaging, vol. 12, No. 6, Jun. 2019. pp. 1032-1043.
Lee et al., "Quantification of Coronary Atherosclerosis in the Assessment of Coronary Artery Disease." Circ Cardiovasc Imaging. 2018; 11(7): e007562.
Lee et al., Rationale and design of the Coronary Computed Tomographic Angiography for Selective Cardiac Catheterization: Relation to Cardiovascular Outcomes, Cost Effectiveness and Quality of Life (Conserve) trial:, Am Heart J, 2017; vol. 186, pp. 48-55.
Lee et al., "Rationale and design of the Progression of AtheRosclerotic PlAque Determined by Computed TomoGraphic Angiography Imaging (Paradigm) registry: A comprehensive exploration of plaque progression and its impact on clinical outcomes from a multicenter serial coronary computed tomographic angiography study", American Heart Journal, vol. 182. 2016 pp. 72-79.
Lee et al., "Reproducibility in the assessment of noncalcified coronary plaque with 256-slice multi-detector CT and automated plaque analysis software", Int J Cardiovasc Imaging; 2010; 26:237-244.
Lee et al., 2018, Effects of Statins on Coronary Atherosclerotic Plaques—The Paradigm (Progression of AtheRosclerotic PlAque Determined by Computed TomoGraphic Angiography Imaging) Study, JACC: Cardiovascular Imaging, 11(10):1475-1484.
Leipsic et al. "SCCT guidelines for the interpretation and reporting of coronary CT angiography: a report of the Society of Cardiovascular Computed Tomography Guidelines Committee" J Cardiovasc Comput Tomogr 2014; 8(5): 342-58.
Libby P. "Mechanisms of acute coronary syndromes and their implications for therapy." N Engl J Med. 2013; 368: 2004-13.
Lu et al., "Central Core Laboratory versus Site Interpretation of Coronary CT Angiography: Agreement and Association with Cardiovascular Events in the Promise Trial", Radiology: vol. 287, No. 1, Apr. 2018, pp. 87-95.
Lundberg, et al. "A Unified Approach to Interpreting Model Predictions." 31st Conference on Neural Information Processing Systems (NIPS 2017).
MacAlpin, Feb. 1980, Contribution of dynamic vascular wall thickening to luminal narrowing during coronary arterial constriction, Circulation, 60(2):296-301.
Mancio, Jennifer, et al. "Perivascular adipose tissue and coronary atherosclerosis." Hear 104.20 (2018): 1654-1662. (Year: 2018).
Maurovich-Horvat et al., 2014, Comprehensive plaque assessment by coronary CT angiography, Nature Reviews Cardiology, 11(7):390-402.
Maurovich-Horvat, et al. "Comprehensive Plaque Assessment by Coronary CT Angiography", Nature Reviews, (2014).
Maurovich-Horvat, et al. "The napkin-ring sign indicates advanced atherosclerotic lesions in coronary CT angiography.", JACC Cardiovasc Imaging 2012; 5(12): 1243-52.
Meijboom et al. "Diagnostic accuracy of 64-slice computed tomography coronary angiography: a prospective, multicenter, multivendor study." J Am Coll Cardiol 2008; 52 (25): 2135-44. doi: 10.1016/j.jacc.2008.08.058.
Melikian et al. "Fractional flow reserve and myocardial perfusion imaging in patients with angiographic multivessel coronary artery disease." JACC Cardiovasc Interv 2010; 3 (3): 307-14. doi: 10.1016/j.jcin.2009.12.010 [published Online First: Mar. 20, 2010].
Mettler et al. "Effective doses in radiology and diagnostic nuclear medicine: a catalog." Radiology 2008; 248(1): 254-63.
Michail et al., Jan. 2021, Feasibility and validity of computed tomography-derived fractional flow reserve in patients with severe aortic stenosis, Circ. Cardiovasc., Interv. 14:e009586.
Miller et al. "Diagnostic performance of coronary angiography by 61-row CT." N Engel J Med 2008; 359 (22): 2324-36. doi: 10.1056/NEJMoa0806576 [published Online First: Nov. 29, 2008].
Min et al. "Prognostic value of multidetector coronary computed tomographic angiography for predication of all-cause mortality" J Am Coll Cardio 2007; 50(12): 1161-70.
Min et al., "Atherosclerosis, Stenosis, and Ischemia", JACC: Cardiovascular Imaging, vol. 11, No. 4, Apr. 2018. pp. 531-533.
Min et al., "Diagnostic accuracy of fractional flow reserve from anatomic CT angiography." JAMA 2012; 038 (12): 1237-45. doi: 10.1001/2012.jama.11274 [published Online First: Aug. 28, 2012].

(56) References Cited

OTHER PUBLICATIONS

Min et al., "The Immediate Effects of Statins on Coronary Atherosclerosis", JACC: Cardiovascular Imaging, vol. 11, No. 6, Jun. 2018. pp. 839-841.

Min et al., 2022, Coronary CTA plaque volume severity stages according to invasive coronary angiography and FFR, Journal of Cardiovascular Computed Tomography, https://doi.org/10.1016/j.jcct.2002.03.001.

Min, "Atherosclerotic plaque characterization: a need for a paradigm shift for prediction of risk", European Heart Journal-Cardiovascular Imaging, Oct. 2017. pp. 1340-1341.

Min, "Chess and Coronary Artery Ischemia: Clinical Implications of Machine-Learning Applications", Circulation: Cardiovascular Imaging, 2018 in 4 pages.

Min, et al. "Rationale and Design of the Confirm (Coronary CT Angiography Evaluation for Clinical Outcomes: An International Multicenter) Registry." J Cardiovasc Comput Tomogr. 2011;5: 84-92.

Mintz GS. "Intravascular Imaging of Coronary Calcification and its Clinical Implications." JACC Cardiovasc Imaging. 2015;8: 461-471.

Montalescot et al. "2013 ESC guidelines on the management of stable coronary artery disease: the Task Force on the management of stable coronary artery disease of the European Society of Cardiology." Eur Heart J 2013;34(35: 2949-3003. doi: 10.1093/eurheartj/eht296 [published Online First: Sep. 3, 2013].

Motoyama et al. "Atherosclerotic plaque characterization by 0.5-mm-slice multislice computed tomographic imaging." Circ J 2009; 71(3): 363-6.

Motoyama et al. "Computed tomographic angiography characteristics of atherosclerotic plaques subsequently resulting in acute coronary syndrome." J Am Coll Cardiol 2009; 54(1): 49-57.

Motoyama et al. "Multislice computed tomographic characteristics of coronary lesions in acute coronary syndromes." J Am Coll Cardiol 2007; 50(4): 319-26.

Motwani et al., "Machine learning for prediction of all-cause mortality in patients with suspected coronary artery disease: a 5-year multicentre prospective registry analysis", European Heart Journal, 2017, pp. 500-507.

Murgia et al., Aug. 2020, Plaque imaging volume analysis: technique and application, Cardiovasc Diagn Ther, 10(4):1032-1047.

Naghavi, et al. From Vulnerable Plaque to Vulnerable Patient: a call for new definitions and risk assessment strategies: Part I. Circulation. 2003; 108: 1664-72.

Nair, et al. "Automated Coronary Plaque Characterisation with intravascular ultrasound backscatter: ex vivo validation." EuroIntervention. 2007; 3: 113-20.

Nakanishi R. et al. "Plaque progression assessed by a novel semi-automated quantitative plaque software on coronary computed tomography angiography between diabetes and non-diabetes patients: A propensity-score matching study." Atherosclerosis 2016; 255 pp. 73-79.

Nakazato et al., "Additive diagnostic value of atherosclerotic plaque characteristics to non-invasive FFR for identification of lesions causing ischaemia: results from a prospective international multicentre trial", http://www.pcronline.com/eurointervention/ahead_of_print/201509-02/ in 9 pages.

Nakazato et al., "Aggregate Plaque volume by Coronary Computed Tomography Angiography Is Superior and Incremental to Luminal Narrowing for Diagnosis of Ischemic Lesions of Intermediate Stenosis Severity", Journal of the American College of Cardiology, vol. 62, No. 5, 2013 pp. 460-467.

Nakazato et al., "Atherosclerotic plaque characterization by CT angiography for identification of high-risk coronary artery lesions: a comparison to optical coherence tomography", European Heart Journal —Cardiovascular Imaging, vol. 16, 2015. pp. 373-379.

Nakazato et al., "Quantification and characterisation of coronary artery plaque volume and adverse plaque features by coronary computed tomographic angiography: a direct comparison to intravascular ultrasound", Eur Radiol (2013) 23, pp. 2109-2117.

Nakazato et al., "Relationship of low- and high-density lipoproteins to coronary artery plaque composition by CT angiography", Journal of Cardiovascular Computed Tomography 7, 2013, pp. 83-90.

Narula et al., 2021, SCCT 2021 expert consensus document of coronary computed tomographic angiography: a report of the Society of Cardiovascular Computed Tomography, Journal of Cardiovascular Computed Tomography.

Neglia et al. "Detection of significant coronary artery disease by noninvasive anatomical and functional imaging." Circ Cardiovasc Imaging 2015; 8 (3) doi: 10.1161/CIRCIMAGING.114.002179 [published Online First: Feb. 26, 2015].

Newby et al., "Coronary CT Angiography and 5-Year Risk of Myocardial Infarction", The New England Journal of Medicine, Aug. 25, 2018, pp. 924-933.

Newby et al., "CT coronary angiography in patients with suspected angina due to coronary heart disease (SCOT-HEART): an open-label, parallel-group, multicentre trial", www.thelancet.com, vol. 385. Jun. 13, 2015, pp. 2383-2391.

Nicholls et al. "Intravascular ultrasound-derived measures of coronary atherosclerotic plaque burden and clinical outcome." J Am Coll Cardiol. 2010; 55(21): pp. 2399-2407.

Nicholls, et al. "Effect of Evolocumab on Coronary Plaque Composition." J Am Coll Cardiol. 2018;72: 2012-2021.

Norgaard et al., 2020, Clinical outcomes following real-world computed tomography angiography-derived factional flow reserve testing in chronic coronary syndrome patients with calcification, European Heart Journal—Cardiovascular Imaging, doi:10.1093/ehjc/jeaa173.

Norgaard et al., Apr. 1, 2014, Diagnostic performance of noninvasive fractional flow reserve derived from coronary computed tomography angiography in suspected coronary artery disease, Journal of the American College of Cardiology, 63(12):1145-1155.

Obaid, D.R., et al. "Atherosclerotic Plaque Composition and Classification Identified by Coronary Computed Tomography: Assessment of CT-Generated Plaque Maps Compared with Virtual Histology Intravascular Ultrasound and Histology." Circulation: Cardiovascular Imaging 6.5 (2013): 655-664. (Year: 2013).

Obaid, Daniel R., et al. "Coronary CT angiography features of ruptured and high-risk atherosclerotic plaques: correlation with intra-vascular ultrasound." Journal of Cardiovascular Computed Tomography 11.6 (2017): 455-461. (Year: 2017).

Oikonomou et al., Aug. 28, 2018, Non-invasive detection of coronary inflammation using computed tomography7 and prediction of residual cardiovascular risk (the CRIPS CT study): a post-hoc analysis of prospective outcome data, The Lancet, 382(10151):929-939.

Okubo, Ryo, et al. "Pericoronary adipose tissue ratio is a stronger associated factor of plaque vulnerability than epicardial adipose tissue on coronary computed tomography angiography." Heart and vessels 32.7 (2017): 813-822. (Year: 2017).

Otsuka et al. "Napkin-ring sign on coronary CT angiography for the prediction of acute coronary syndrome." JACC Cardiovasc Imaging 2013; 6(4): 448-57.

Ovrehus et al., "CT-based total vessel plaque analyses improves prediction of hemodynamic significance lesions as assessed by fractional flow reserve in patients with stable angina pectoris", Journal of Cardiovascular Computed Tomography 12, 2018 pp. 344-349.

Ovrehus, et al. "Reproducibility of Semi-Automatic Coronary Plaque Quantification in Coronary CT Angiography with Sub-mSv Radiation Dose." *J Cardiovasc Comput Tomogr*, (2016).

Papadopoulou et al., 2013, Reproducibility of CT Angiography Data Analysis Using Semiautomated Plaque Quantification Software: Implications for the Design of Longitudinal Studies, Int J Cardiovasc Imaging, 29:1095-1104.

Papadopoulou, et al. "Detection and Quantification of Coronary Atherosclerotic plaque by 64-slice multidetector CT: A systematic head-to-head comparison with intravascular ultrasound." Atherosclerosis. 2011;219: 163-70.

Park et al., "Atherosclerotic Plaque Characteristics by CT Angiography Identify Coronary Lesions That Cause Ischemia", JACC: Cardiovascular Imaging, vol. 8, No. 1, 2015 in 10 pages.

(56) References Cited

OTHER PUBLICATIONS

Park, et al. "Clinical Feasibility of 3D Automated Coronary Atherosclerotic Plaque Quantification Algorithm on Coronary Computed Tomography Angiography: Comparison with Intravascular Ultrasound" European Radiology (2015), 25: 3073-3083.

Park, et al. "Visual-functional Mismatch between Coronary Angiography and Fractional Flow Reserve." JACC Cardiovasc Interv. 2012; 5: 1029-36.

Patel et al., 2019, 1-year impact on medical practice and clinical outcomes of FFRCT, JACC: Cardiovascular Imaging, https://doi.org/10., 1016/j.jcmg.2019.03.003, 9 pp.

Pavlou et al., "A note on obtaining correct marginal predictions from a random intercepts model for binary outcomes." BMC Med Res Methodol 2015; 15:59. doi: 10.1186/s12874-015-004606 [published Online First: Aug. 6, 2015].

Pedregosa, et al. "Scikit-learn: Machine Learning in Python." Journal of Machine Learning Research, 2011;12: 2825-2830.

Picano et al. "The appropriate and justified use of medical radiation in cardiovascular imaging: a position document of the ESC Associations of Cardiovascular Imaging, Percutaneous Cardiovascular Interventions and Electrophysiology." Eur Heart J 2014; 35(10): 665-72.

Puchner et al., Mar. 2015, High-Risk Coronary Plaque at Coronary CT Angiography is Associated with NAFLD, Independent of Coronary Plaque and Stenosis Burden, J Cardiovasc Comput Tomogr., 274(3):693-701.

Puchner, et al. "High-Risk Plaque Detected on Coronary CT Angiography Predicts Acute Coronary Syndrome Independent of Significant Stenosis in Patients with Acute Chest Pain" *J Am Coll Cardiol* 2014.

Raff, et al. "SCCT guidelines for the interpretation and reporting of coronary computed tomographic angiography" *J Cardiovasc Comput Tomogr* 2009: 3(2): 122-36.

Rehani et al. "ICRP Publication 117. Radiological protection in fluoroscopically guided procedures performed outside the imaging department." Ann ICRP 2010; 40(6): 1-102.

Rizvi et al., "Diffuse coronary artery disease among other atherosclerotic plaque characteristics by coronary computed tomography angiography for predicting coronary vessel-specific ischemia by fractional flow reserve", Atherosclerosis 258, 2017 pp. 145-151.

Rizvi et al., "Rationale and Design of the Credence Trial: computed Tomographic evaluation of atherosclerotic Determinants of myocardial Ischemia", BMC Cardiovascular Disorders, 2016, in 10 pages.

Roy-Cardinal et al. "Intravascular Ultrasound Image Segmentation: A Three-Dimensional Fast-Marching Method Based on Grey Level Distributions", IEEE Transactions on Medical Imaging, vol. 25, No. 5, May 2006.

Rozie et al., 2009, Atherosclerotic plaque volume and composition in symptomatic carotid arteries assess with the multidetector CT angiography; relationship with severity of stenosis and cardiovascular risk factors, Eur Radiol, 19:2294-2301.

Sabir, A et al. Measuring Noncalcified Coronary Atherosclerotic Plaque Using Voxel Analysis with MDCT Angiography: Phantom Validation: American Journal of Roentgenology, Apr. 2008; vol. 190, No. 4, pp. 242-246.

Samady H. et al. "Coronary artery wall shear is associated with progression and transformation of atherosclerotic plaque and arterial remodeling in patients with coronary artery disease." American Heart Association Circulation, vol. 124, Issue 7, Aug. 16, 2011, pp. 779-788.

Schinkel et al. "Noninvasive evaluation of ischaemic heart disease: myocardial perfusion imaging or stress echocardiography?" European Heart Journal (2003) 24, 789-800.

Schlett et al. "How to assess non-calcified plaque in CT angiography: delineation methods affect diagnostic accuracy of low-attenuation plaque by CT for lipid-core plaque in history." Euro Heart J Cardiovasc Imaging 2013; 14(11): 1099-105.

Schuurman, et al. "Prognostic Value of Intravascular Ultrasound in Patients with Coronary Artery Disease." J Am Coll Cardiol. 2018;72: 2003-2011.

Seghier et al., "Lesion identification using unified segmentation-normalisation models and fuzzy clustering" NeuroImage 40(2008) 1253-1266.

Seifarth, et al. "Histopathological Correlates of the Napkin-Ring Sign Plaque in Coronary CT Angiography." Send to Atherosclerosis. 2012;224: 90-6.

Sharma et al., "Stress Testing Versus CT Angiography in Patients With Diabetes and Suspected Coronary Artery Disease", Journal of the American College of Cardiology, vol. 73, No. 8, 2019 pp. 893-902.

Shaw et al. "Optimal medical therapy with or without percutaneous coronary intervention to reduce ischemic burden: results from the Clinical Outcomes Utilizing Revascularization and Aggressive Drug Evaluation (Courage) trail nuclear substudy." Circulation 2008; 117 (10): 1283-91. doi: 10.116/CIRCULATIONAHA.107.743963.

Shaw et al. "Why all the focus on cardiac imaging?" JAAC Cardiovasc Imaging 2010; 3(7): 789-94 doi: 10.16/j.jcmg.2010.05.004.

Sheahan et al., Feb. 2018, Atherosclerotic plaque tissue: noninvasive quantitative assessment of characteristics with software-aided measurements from conventional CT angiography, Radiology, 286(2):622-631.

Shin S. et al., "Impact of Intensive LDL Cholesterol Lowering on Coronary Artery Atherosclerosis Progression: A Serial CT Angiography Study." JACC Cardiovasc Imaging. 2017; 10(4) pp. 437-446.

Siasos, et al. "Local Low Shear Stress and Endothelial Dysfunction in Patients with Nonobstructive Coronary Atherosclerosis." J Am Coll Cardiol. 2018;71: 2092-2102.

Song et al. "Comparison of machine learning techniques with classical statistical models in predicting health outcomes." Stud Health Technol Inform. 2004; 107(Pt 1) pp. 736-740.

Staruch, et al. "Automated Quantitative Plaque Analysis for Discrimination of Coronary Chronic Total Occlusion and Subtotal Occlusion in Computed Tomography Angiography", *J Thoracic Imaging*, (2016).

Stone, et al. "A prospective natural-history study of coronary atherosclerosis." N Engl J Med 2011; 364(3): 226-35.

Stuijfzand, et al. "Stress Myocardial Perfusion Imaging vs Coronary Computed Tomographic Angiography for Diagnosis of Invasive Vessel-Specific Coronary Physiology Predictive Modeling Results From the Computed Tomographic Evaluation of Atherosclerotic Determinants of Myocardial Ischemia (Credence) Trial", JAMA Cardiology, doi: 10.1001/jamacardio.2020.3409, Aug. 19, 2020.

Sun et al., Mar. 2017, Carotid plaque lipid content and fibrous cap status predict systemic cv outcomes, JACC: Cardiovascular Imaging, 10(3):241-249.

Sun, et al. "Diagnostic Value of Multislice Computed Tomography Angiography in Coronary Artery Disease: a Meta-Analysis." Eur J Radiol. 2006;60: 279-86.

Taylor et al., "Patient-Specific Modeling of Cardiovascular Mechanics", Annu. Rev. Biomed. Eng. 2009.11:109-139.

Thim, et al. "Unreliable Assessment of Necrotic Core by Virtual Histology Intravascular Ultrasound in Porcine Coronary Artery Disease." Circ Cardiovasc Imaging. 2010;3: 384-91.

Thygesen, et al. "Third Universal Definition of Myocardial Infarction." Glob Heart. 2013;7: 275-95.

Tian, et al. "Distinct Morphological Features of Ruptured Culprit Plaque for Acute Coronary Events Compared to those with Silent Rupture and Thin-Cap Fibroatheroma: a Combined Optical Coherence Tomography and Intravascular Ultrasound Study." J Am Coll Cardiol. 2014;63: 2209-16.

Tilkemeier et al., "American Society of Nuclear Cardiology information statement: Standardized reporting matrix for radionuclide myocardial perfusion imaging." J Nucl Cardiol 2006; 13 (6): e157-71. doi: 10.1016/j.nuclcard.2006.08.014.

Tomey MI, et al. "Advances in the understanding of plaque composition and treatment options: year in review." J Am Coll Cardio. 2014; 63(16) pp. 1604-1616.

Tonino et al., "Angiographic versus functional severity of coronary artery stenoses in the FAME study fractional flow reserve versus

(56) References Cited

OTHER PUBLICATIONS angiography in multivessel evaluation." Journal of the American College of Cardiology 2010; 55 (25): 2816-21. doi: 10.1016/j.jacc. 2009.11-096 [published Online First: Jun. 29, 2010].

Tonino et al., Jan. 15, 2009, Fractional flow reserve versus angiography for guiding percutaneous coronary interventions, The New England Journal of Medicine, 360(3):213-224.

U.S. Food and Drug Administration, Nov. 5, 2019, K190868 501(k) Summary, 10 pp.

U.S. Food and Drug Administration, Oct. 2, 2020, K202280 501(k) Summary, 9 pp.

Van Ooijen, et al. "Coronary Artery Imaging with Multidetector CT: Visualization Issues" *RadioGraphics*, vol. 23. (2003).

Van Rosendael et al., "Maximization of the usage of coronary CTA derived plaque information using a machine learning based algorithm to improve risk stratification; insights from the Confirm registry", Journal of Cardiovascular Computed Tomography 12, 2018, pp. 204-209.

Van Rosendael et al., "Quantitative Evaluation of High-Risk Coronary Plaque by Coronary CTA and Subsequent Acute Coronary Events", JACC: Cardiovascular Imaging, vol. 12, No. 8, Aug. 2019. pp. 1568-1571.

Versteylen MO, et al. "Additive value of semiautomated quantification of coronary artery disease using cardiac computed tomographic angiography to predict future acute coronary syndrome." J Am Coll Cardiol. 2013; 61(22): pp. 2296-2305.

Virmani, et al. "Atherosclerotic plaque progression and vulnerability to rupture: angiogenesis as a source of intraplaque hemorrhage." Arterioscler Thromb Vasc Biol. 2005; 25: 2054-61.

Virmani, et al. "Lessons from sudden coronary death: a comprehensive morphological classification scheme for atherosclerotic lesions." Arterioscler Thromb Vasc Biol. 2000;20: 1262-75.

Virmani, et al. "Pathology of the Vulnerable Plaque." J Am Coll Cardiol. 2006; 47: C13-8.

Wei, et al. "Computerized Detection of Noncalcified Plaques in Coronary CT Angiography: Evaluation of Topological Soft Gradient Prescreening Method and Luminal Analysis" *Med Phys*, (2014).

Weir-MacCall et al., "Impact of Non-obstructive left main disease on the progression of coronary artery disease: A Paradigm substudy", Journal of Cardiovascular Computed Tomography 12, 2018, pp. 231-237.

Weisenfeld et al. "Automatic Segmentation of Newborn Brain MRI", NIH PA Author Manuscript 2010.

Williams et al. "Use of Coronary Computed Tomographic Angiography to Guide Management of Patients with Coronary Disease." Journal of American College of Cardiology 2016; 67 (15) : 1759-68. doi: 10.1016/J.Jacc.2016.02.026 [published Online First: Apr. 16, 2016].

Williams et al., "Coronary Artery Plaque Characteristics Associated With Adverse Outcomes in the SCOT-HEART Study", Journal of the American College of Cardiology, vol. 73, No. 3, Jan. 29, 2019. pp. 291-301.

Wilson et al. "Prediction of coronary heart disease using risk factor categories" Circulation 1998; 97(18) pp. 1837-1847.

Wintermark et al., May 2008, High-resolution CT imaging of carotid artery atherosclerotic plaques, Am J Neuroradiol, 29:875-882.

Won et al., "Longitudinal assessment of coronary plaque volume change related to glycemic status using serial coronary computed tomography angiography: A Computed TomoGraphic Angiography Imaging) substudy", Journal of Cardiovascular Computed Tomography 13, 2019 pp. 142-147.

Won et al., "Longitudinal quantitative assessment of coronary plaque progression related to body mass index using serial coronary computed tomography angiography, European Heart Journal—Cardiovascular Imaging", 2019 pp. 591-599.

Wu et al., Jun. 11, 2018, Group normalization, arXiv:1803.08494v3, [cs.CV], 10 pp.

Xu et al., Aug. 2023, Elixr: Towards a general purpose X-ray artificial intelligence system through alignment of large language models and radiology vision encoders, arXiv.2308.01317 [cs.CV], 54 pp.

Yang, et al. "Automatic centerline extraction of coronary arteries in coronary computed tomographic angiography" *The International Journal of Cardiovascular Imaging*, 28:921-933. (2012).

Yokoya K, et al. "Process of progression of coronary artery lesions from mild or moderate stenosis to moderate or severe stenosis: A study based on four serial coronary arteriograms per year." Circulation 1999; 100(9):903-909.

Zeb I et al. "Effect of statin treatment on coronary plaque progression—a serial coronary CT angiography study." Atherosclerosis. 2013; 231(2):198-204.

Zhao Z., et al. "Dynamic nature of nonculprit coronary artery lesion morphology in STEMI: a serial IVUS analysis from Horizons-AMI trial." JACC Cardiovasc Imaging, 2013; 6(1):86-95.

Zreik et al., Dec. 10, 2018, A recurrent CNN for automatic detection and classification of coronary artery plaque and stenosis in coronary CT angiography, arXiv:1803/04360v4, 11 pp.

International Search Report and Written Opinion for Application No. PCT/US20/15035 dated Apr. 14, 2020, in 20 pages.

International Preliminary Report on Patentability for Application No. PCT/US2020/015035 dated Jul. 27, 2021, in 7 pages.

International Search Report and Written Opinion for Application No. PCT/US2021/012218 dated Mar. 17, 2021, in 11 pages.

International Search Report and Written Opinion for Application No. PCT/US2021/037919 dated Oct. 6, 2021, in 12 pages.

International Search Report and Written Opinion for Application No. PCT/US22/40816 dated Mar. 1, 2023, in 16 pages.

International Search Report and Written Opinion for Application No. PCT/US23/63972 dated Aug. 9, 2023, in 17 pages.

Benjamin, Mina M., Rabbat, Mark G., "Machine learning-based advances in coronary computed tomography angiography," Editorial, Quantitative Imaging in Medicine and Sugery, vol. 11, No. Jun. 6, 2021, http://dx.doi.org/10.21037/qims-21-99.

Ferencik, et al. "Computed Tomography-Based High-Risk Coronary Plaque Score to Predict Acute Coronary Syndrome Among Patients with Acute Chest Pain—Results from the Romicat II Trial" J Cardiovascular Comput Tomogr., 2015 ; 9(6): 538-545. doi:10.1016/j.jcct.2015.07.003.

Hampe, N., Van Velzen, S. G., Aben, J., Collet, C., & Igum, I. (2023). Deep Learning-Based Prediction of Fractional Flow Reserve along the Coronary Artery. ArXiv. /abs/2308.04923.

Job, Mark, Section 510(k) premarket notification of intent to market device "Plaque View, Model No. CSPV-001A" as filed and Review, K043111, Department of Health & Human Services, Food and Drug Administration, Nov. 18, 2004, 5 pages, Silver Springs, Maryland.

Rongero, Jeff D., Section 510(k) premarket notification of intent to market device "Vessel Analysis and Autoplaque for ORS Visual" as filed and Review, K122429, Department of Health & Human Services, Food and Drug Administration, Nov. 28, 2012, 11 pages, Silver Springs, Maryland.

Smith, John, Section 510(k) premarket notification of intent to market device "Adjunctive cardiovascular status indicator" as filed and Review, K231335, Department of Health & Human Services, Food and Drug Administration, Sep. 8, 2023, 9 pages, Silver Springs, Maryland.

Smith, John, Section 510(k) premarket notification of intent to market device "Picture archiving and communications system" as filed and Review, K190868, Department of Health & Human Services, Food and Drug Administration, Nov. 5, 2019, 10 pages, Silver Springs, Maryland.

Smith, John, Section 510(k) premarket notification of intent to market device "Picture archiving and communications system" as filed and Review, K202280, Department of Health & Human Services, Food and Drug Administration, Oct. 2, 2020, 9 pages, Silver Springs, Maryland.

Won, Philip, Section 510(k) premarket notification of intent to market device "Medical image management and processing system" as filed and Review, K212758, Department of Health & Human Services, Food and Drug Administration, May 19, 2023, 9 pages, Silver Springs, Maryland.

(56) References Cited

OTHER PUBLICATIONS

M. Zreik, N. Lessmann, R. W. van Hamersvelt, et al., "Deep learning analysis of the myocardium in coronary CT angiography for identification of patients with functionally significant coronary artery stenosis," Medical Image Analysis 44, 72-85 (2018).

M. Zreik, R. W. van Hamersvelt, N. Khalili, et al., "Deep Learning Analysis of Coronary Arteries in Cardiac CT Angiography for Detection of Patients Requiring Invasive Coronary Angiography," IEEE Transactions on Medical Imaging 39, 1545-1557 (2020).

\* cited by examiner

SYSTEMS, DEVICES, AND METHODS FOR NON-INVASIVE IMAGE-BASED PLAQUE ANALYSIS AND RISK DETERMINATION

PRIORITY AND RELATED APPLICATIONS

This application is a continuation of U.S. application Ser. No. 18/508,098, filed Nov. 13, 2023, which is a continuation-in-part of U.S. application Ser. No. 18/179,921, filed Mar. 7, 2023, and also claims the benefit of priority to:
  U.S. Provisional Application No. 63/385,179, filed Nov. 28, 2022;
  U.S. Provisional Application No. 63/476,255, filed Dec. 20, 2022;
  U.S. Provisional Application No. 63/477,640, filed Dec. 29, 2022;
  U.S. Provisional Application No. 63/477,638, filed Dec. 29, 2022;
  U.S. Provisional Application No. 63/477,985, filed Dec. 30, 2022;
  U.S. Provisional Application No. 63/477,961, filed Dec. 30, 2022;
  U.S. Provisional Application No. 63/478,076, filed Dec. 30, 2022;
  U.S. Provisional Application No. 63/478,084, filed Dec. 30, 2022;
  U.S. Provisional Application No. 63/383,632, filed Nov. 14, 2022;
  U.S. Provisional Application No. 63/383,904, filed Nov. 15, 2022;
  U.S. Provisional Application No. 63/386,297, filed Dec. 6, 2022;
  U.S. Provisional Application No. 63/476,251, filed Dec. 20, 2022;
  U.S. Provisional Application No. 63/476,245, filed Dec. 20, 2022;
  U.S. Provisional Application No. 63/477,656, filed Dec. 29, 2022;
  U.S. Provisional Application No. 63/385,472, filed Nov. 30, 2022; and
  U.S. Provisional Application No. 63/386,376, filed Dec. 7, 2022.

This application is also related to U.S. Pat. No. 10,813,612, filed Jan. 23, 2020, U.S. Pat. No. 11,501,436, filed Jan. 5, 2021, and U.S. Pat. No. 11,302,001, filed Aug. 4, 2021, and U.S. application Ser. No. 17/820,439, filed Aug. 17, 2022, and U.S. application Ser. No. 18/179,921, filed Mar. 7, 2023, and each of the above-listed patents and applications is incorporated by reference herein in its entirety. Any and all applications for which a foreign or domestic priority claim is identified in the Application Data Sheet as filed with the present application are hereby incorporated by reference under 37 CFR 1.57.

BACKGROUND

The present application relates to non-invasive image-based plaque analysis and risk determination.

SUMMARY

Various embodiments described herein relate to systems, devices, and methods for non-invasive image-based plaque analysis and risk determination. In particular, in some embodiments, the systems, devices, and methods described herein are related to analysis of one or more regions of plaque, such as for example coronary plaque, using non-invasively obtained images that can be analyzed using computer vision or machine learning to identify, diagnose, characterize, treat and/or track coronary artery disease.

BRIEF DESCRIPTION OF THE DRAWINGS

A better understanding of the devices and methods described herein will be appreciated upon reference to the following description in conjunction with the accompanying drawings.

DETAILED DESCRIPTION

Figure 1:
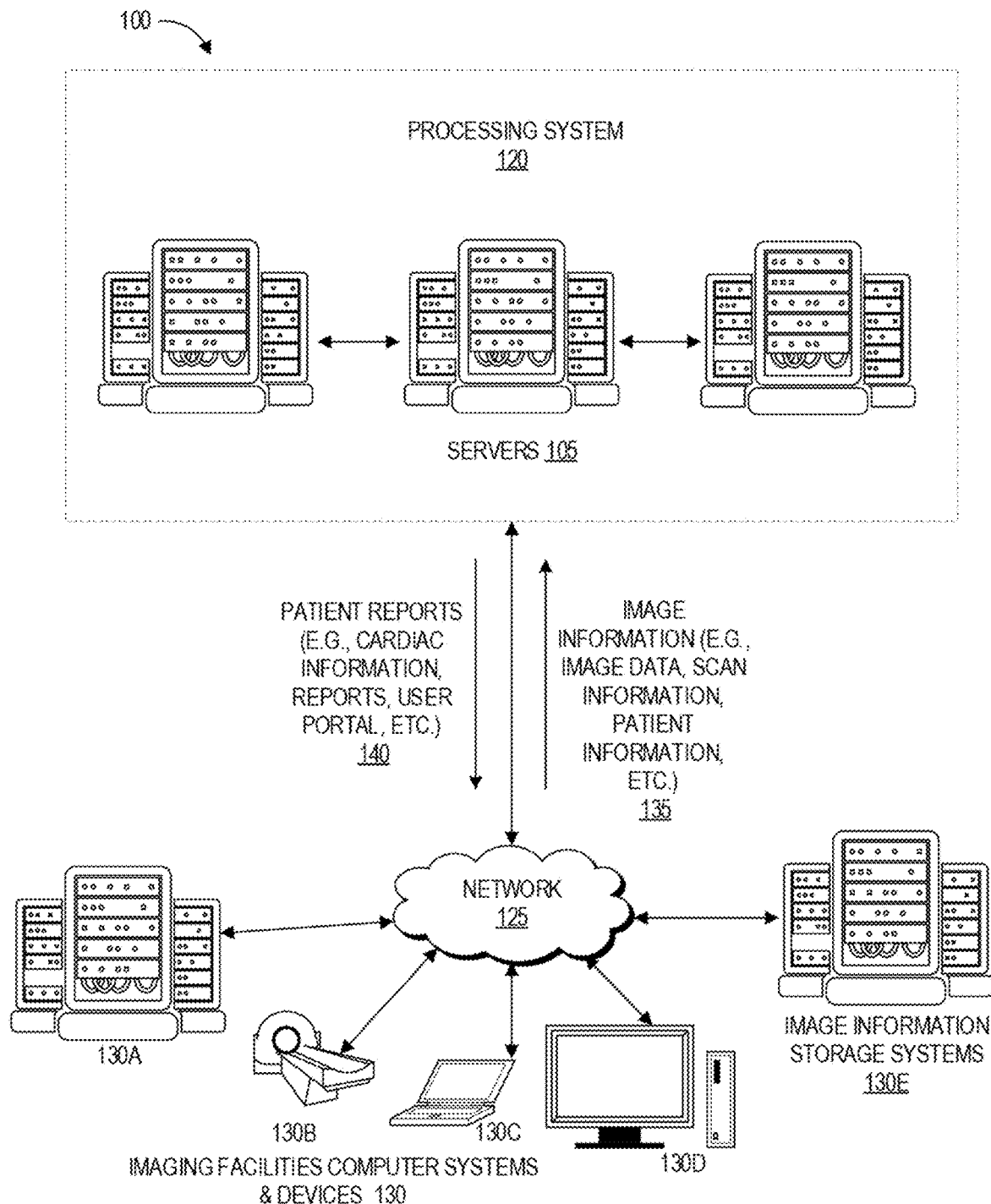
FIG. 1 depicts a schematic of an example of an embodiment of a system 100 that includes a processing system configured to characterize coronary plaque.

Although several embodiments, examples, and illustrations are disclosed below, it will be understood by those of ordinary skill in the art that the inventions described herein extend beyond the specifically disclosed embodiments, examples, and illustrations and includes other uses of the inventions and obvious modifications and equivalents thereof. Embodiments of the inventions are described with reference to the accompanying figures, wherein like numerals refer to like elements throughout. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Disclosed herein are systems, devices, and methods for non-invasive image-based plaque analysis and risk determination. In particular, in some embodiments, the systems, devices, and methods described herein are related to analysis of one or more regions of plaque, such as for example coronary plaque, based on one or more distances, volumes, shapes, morphologies, embeddedness, and/or axes (or dimension) measurements. "Plaque" or "a region of plaque" or "one or more regions of plaque" may be referred to simply as "plaque" for ease of reference unless otherwise indicated, explicitly or by context. For example, in some embodiments, the systems, devices, and methods described herein are related to plaque analysis based on one or more of distance between plaque and a vessel wall, distance between plaque and a lumen wall, length along longitudinal axis of plaque, length along latitudinal axis of plaque, volume of low density non-calcified plaque, volume of total plaque, a ratio(s) between volume of low density non-calcified plaque and volume of total plaque, embeddedness of low density non-calcified plaque, and/or the like. In some embodiments, the systems, devices, and methods described herein are configured to determine a risk of coronary artery disease (CAD), such as for example myocardial infarction (MI), based on one or more plaque analyses described herein. In some embodiments, the systems, devices, and methods described herein are configured to generate a proposed treatment and/or graphical representation based on the determined risk of CAD and/or one or more plaque analyses described herein.

Also disclosed herein are systems, methods, and devices for cardiovascular risk and/or state assessment using image-based analyses. In particular, in some embodiments, the systems, devices, and methods are related to cardiovascular risk and/or disease state assessment using image-based analysis of vessel surface and/or coordinates of features. In some embodiments, assessment of cardiovascular risk and/or disease state generated using the systems, methods, and devices herein can be utilized to diagnose and/or generate a proposed treatment for a patient.

Also disclosed herein are systems, methods, and devices for cardiovascular risk and/or state assessment using image-based analyses, where in some embodiments, the systems, devices, and methods are related to cardiovascular risk and/or disease state assessment using image-based analysis of vessel surface and/or coordinates of features. In some embodiments, assessment of cardiovascular risk and/or disease state generated using the systems, methods, and devices herein can be utilized to diagnose and/or generate a proposed treatment for a patient.

Also disclosed herein are systems, methods, and devices for cardiovascular risk and/or state assessment using image-based analyses, where in some embodiments the systems, devices, and methods are related to cardiovascular risk and/or disease and/or state assessment using modified and/or normalized image analysis-based plaque parameters. In some embodiments, assessment of cardiovascular risk and/or disease and/or state generated using the systems, methods, and devices herein can be utilized to diagnose and/or generate a proposed treatment for a patient.

Also disclosed herein are systems, methods, and devices for generation of a patient-specific report on the risk and/or state assessment, diagnosis, and/or treatment of cardiovascular disease, including for example coronary artery disease (CAD). In particular, in some embodiments, the systems, devices, and methods are configured to generate an immersive patient-specific report on the patient's cardiovascular disease risk, state, diagnosis, and/or treatment. In some embodiments, the systems, devices, and methods are configured to generate an immersive patient-specific report based at least in part on image-based analysis, for example of one or more plaque and/or vessel parameters. In some embodiments, the systems, devices, and methods are configured to view the patient's cardiovascular disease state or risk from a point of view within one or more arteries of the patient. In some embodiments, the systems, devices, and methods are configured to graphically view and/or track actual or hypothetical progression of the patient's cardiovascular disease state or risk based on actual or proposed treatment from a point of view within one or more arteries of the patient.

Also disclosed herein are systems, methods, and devices for cardiovascular risk and/or state assessment using image-based analyses, wherein in some embodiments the systems, devices, and methods are related to cardiovascular risk and/or disease and/or state assessment using normalized image analysis-based plaque parameters. In some embodiments, assessment of cardiovascular risk and/or disease and/or state generated using the systems, methods, and devices herein can be utilized to diagnose and/or generate a proposed treatment for a patient.

Also disclosed herein are systems, devices, and methods for non-invasive image-based determination of fractional flow reserve (FFR) and/or ischemia. In particular, in some embodiments, the systems, devices, and methods are related to FFR and/or ischemia analysis of arteries, such as coronary, aortic, and/or carotid arteries using one or more image analysis techniques. For example, in some embodiments, the systems, methods, and devices can be configured to derive one or more stenosis and/or normal measurements from a medical image, which can be obtained non-invasively, and use the same to derive an assessment of FFR and/or ischemia. In some embodiments, the systems, methods, and devices can be configured to apply one or more allometric scaling laws to one or more stenosis and/or normal measurements to derive and/or generate an assessment of FFR and/or ischemia.

Coronary heart disease affects over 17.6 million Americans. The current trend in treating cardiovascular health issues is generally two-fold. First, physicians generally review a patient's cardiovascular health from a macro level, for example, by analyzing the biochemistry or blood content or biomarkers of a patient to determine whether there are high levels of cholesterol elements in the bloodstream of a patient. In response to high levels of cholesterol, some physicians will prescribe one or more drugs, such as statins, as part of a treatment plan in order to decrease what is perceived as high levels of cholesterol elements in the bloodstream of the patient.

The second general trend for currently treating cardiovascular health issues involves physicians evaluating a patient's cardiovascular health through the use of angiography to identify large blockages in various arteries of a patient. In response to finding large blockages in various arteries, physicians in some cases will perform an angioplasty procedure wherein a balloon catheter is guided to the point of narrowing in the vessel. After properly positioned, the balloon is inflated to compress or flatten the plaque or fatty matter into the artery wall and/or to stretch the artery open to increase the flow of blood through the vessel and/or to the heart. In some cases, the balloon is used to position and expand a stent within the vessel to compress the plaque and/or maintain the opening of the vessel to allow more blood to flow. About 500,000 heart stent procedures are performed each year in the United States.

However, a recent federally funded $100 million study calls into question whether the current trends in treating cardiovascular disease are the most effective treatment for all types of patients. The recent study involved over 5,000 patients with moderate to severe stable heart disease from 320 sites in 37 countries and provided new evidence showing that stents and bypass surgical procedures are likely no more effective than drugs combined with lifestyle changes for people with stable heart disease. Accordingly, it may be more advantageous for patients with stable heart disease to forgo invasive surgical procedures, such as angioplasty and/or heart bypass, and instead be prescribed heart medicines, such as statins, and certain lifestyle changes, such as regular exercise. This new treatment regimen could affect thousands of patients worldwide. Of the estimated 500,000 heart stent procedures performed annually in the United States, it is estimated that a fifth of those are for people with stable heart disease. It is further estimated that 25% of the estimated 100,000 people with stable heart disease, or roughly 23,000 people, are individuals that do not experience any chest pain. Accordingly, over 20,000 patients annually could potentially forgo invasive surgical procedures or the complications resulting from such procedures.

To determine whether a patient should forego invasive surgical procedures and opt instead for a drug regimen and/or to generate a more effective treatment plan, it can be important to more fully understand the cardiovascular disease of a patient. Specifically, it can be advantageous to better understand the arterial vessel health of a patient. For example, it is helpful to understand whether plaque build-up in a patient is mostly fatty matter build-up or mostly calcified matter build-up, because the former situation may warrant treatment with heart medicines, such as statins, whereas in the latter situation a patient should be subject to further periodic monitoring without prescribing heart medicine or implanting any stents. However, if the plaque build-up is significant enough to cause severe stenosis or narrowing of the arterial vessel such that blood flow to heart muscle might be blocked, then an invasive angioplasty procedure to implant a stent may likely be required because heart attack or sudden cardiac death (SCD) could occur in such patients without the implantation of a stent to enlarge the vessel opening. Sudden cardiac death is one of the largest causes of natural death in the United States, accounting for approximately 325,000 adult deaths per year and responsible for nearly half of all deaths from cardiovascular disease. For males, SCD is twice as common as compared to females. In general, SCD strikes people in the mid-30 to mid-40 age range. In over 50% of cases, sudden cardiac arrest occurs with no warning signs.

With respect to the millions suffering from heart disease, there is a need to better understand the overall health of the artery vessels within a patient beyond just knowing the blood chemistry or content of the blood flowing through such artery vessels. For example, in some embodiments of systems, devices, and methods disclosed herein, arteries with "good" or stable plaque or plaque comprising hardened calcified content are considered non-life threatening to patients whereas arteries containing "bad" or unstable plaque or plaque comprising fatty material are considered more life threatening because such bad plaque may rupture within arteries thereby releasing such fatty material into the arteries. Such a fatty material release in the blood stream can cause inflammation that may result in a blood clot. A blood clot within an artery can prevent blood from traveling to heart muscle thereby causing a heart attack or other cardiac event. Further, in some instances, it is generally more difficult for blood to flow through fatty plaque buildup than it is for blood to flow through calcified plaque build-up. Therefore, there is a need for better understanding and analysis of the arterial vessel walls of a patient.

Further, while blood tests and drug treatment regimens are helpful in reducing cardiovascular health issues and mitigating against cardiovascular events (for example, heart attacks), such treatment methodologies are not complete or perfect in that such treatments can misidentify and/or fail to pinpoint or diagnose significant cardiovascular risk areas. For example, the mere analysis of the blood chemistry of a patient will not likely identify that a patient has artery vessels having significant amounts of fatty deposit material bad plaque buildup along a vessel wall. Similarly, an angiogram, while helpful in identifying areas of stenosis or vessel narrowing, may not be able to clearly identify areas of the artery vessel wall where there is significant buildup of bad plaque. Such areas of buildup of bad plaque within an artery vessel wall can be indicators of a patient at high risk of suffering a cardiovascular event, such as a heart attack. In certain circumstances, areas where there exist areas of bad plaque can lead to a rupture wherein there is a release of the fatty materials into the bloodstream of the artery, which in turn can cause a clot to develop in the artery. A blood clot in the artery can cause a stoppage of blood flow to the heart tissue, which can result in a heart attack. Accordingly, there is a need for new technology for analyzing artery vessel walls and/or identifying areas within artery vessel walls that comprise a buildup of plaque whether it be bad or otherwise.

In some embodiments, the systems, devices, and methods described herein are configured to utilize non-invasive medical imaging technologies, such as a CT image or CCTA for example, which can be inputted into a computer system configured to automatically and/or dynamically analyze the medical image to identify one or more coronary arteries and/or plaque within the same. For example, in some embodiments, the system can be configured to utilize one or more machine learning and/or artificial intelligence algorithms to automatically and/or dynamically analyze a medical image to identify, quantify, and/or classify one or more coronary arteries and/or plaque. In some embodiments, the system can be further configured to utilize the identified, quantified, and/or classified one or more coronary arteries and/or plaque to generate a treatment plan, track disease progression, and/or a patient-specific medical report, for example using one or more artificial intelligence and/or machine learning algorithms. In some embodiments, the system can be further configured to dynamically and/or automatically generate a visualization of the identified, quantified, and/or classified one or more coronary arteries and/or plaque, for example in the form of a graphical user interface. Further, in some embodiments, to calibrate medical images obtained from different medical imaging scanners and/or different scan parameters or environments, the system can be configured to utilize a normalization device comprising one or more compartments of one or more materials.

As will be discussed in further detail, the systems, devices, and methods described herein allow for automatic and/or dynamic quantified analysis of various parameters relating to plaque, cardiovascular arteries, and/or other structures. More specifically, in some embodiments described herein, a medical image of a patient, such as a coronary CT image or CCTA, can be taken at a medical facility. Rather than having a physician eyeball or make a general assessment of the patient, the medical image is transmitted to a backend main server in some embodiments that is configured to conduct one or more analyses thereof in a reproducible manner. As such, in some embodiments, the systems, methods, and devices described herein can provide a quantified measurement of one or more features of a coronary CT image using automated and/or dynamic processes. For example, in some embodiments, the main server system can be configured to identify one or more vessels, plaque, fat, and/or one or more measurements thereof from a medical image. Based on the identified features, in some embodiments, the system can be configured to generate one or more quantified measurements from a raw medical image, such as for example radiodensity of one or more regions of plaque, identification of stable plaque and/or unstable plaque, volumes thereof, surface areas thereof, geometric shapes, heterogeneity thereof, and/or the like. In some embodiments, the system can also generate one or more quantified measurements of vessels from the raw medical image, such as for example diameter, volume, morphology, and/or the like. Based on the identified features and/or quantified measurements, in some embodiments, the system can be configured to generate a risk and/or disease state assessment and/or track the progression of a plaque-based disease or condition, such as for example atherosclerosis, stenosis, and/or ischemia, using raw medical images. Further, in some embodiments, the system can be configured to generate a visualization of GUI of one or more identified features and/or quantified measurements, such as a quantized color mapping of different features. In some embodiments, the systems, devices, and methods described herein are configured to utilize medical image-based processing to assess for a subject his or her risk of a cardiovascular event, major adverse cardiovascular event (MACE), rapid plaque progression, and/or non-response to medication. In particular, in some embodiments, the system can be configured to automatically and/or dynamically assess such health risk of a subject by analyzing only non-invasively obtained medical images. In some embodiments, one or more of the processes can be automated using an artificial intelligence (AI) and/or machine learning (ML) algorithm. In some embodiments, one or more of the processes described herein can be performed within minutes in a reproducible manner. This is stark contrast to existing measures today which do not produce reproducible prognosis or assessment, take extensive amounts of time, and/or require invasive procedures. In some embodiments, the systems, methods, and devices described herein comprise and/or are configured to utilize any one or more of such techniques described in US Patent Application Publication No. US 2021/0319558, which is incorporated herein by reference in its entirety.

As such, in some embodiments, the systems, devices, and methods described herein are able to provide physicians and/or patients specific quantified and/or measured data relating to a patient's plaque and/or ischemia that do not exist today. In some embodiments, such detailed level of quantified plaque parameters from image processing and downstream analytical results can provide more accurate and useful tools for assessing the health and/or risk of patients in completely novel ways.

Disclosed are methods for identification of high-risk plaques using volumetric characterization of coronary plaque and perivascular adipose tissue data by computed tomography (CT) scanning. The volumetric characterization of the coronary plaque and perivascular adipose tissue allows for determination of the inflammatory status of the plaque by CT scanning. This is of use in the diagnosis, prognosis and treatment of coronary artery disease. While certain example embodiments are shown by way of example in the drawings and will herein be described in detail, these embodiments are capable of various modifications and alternative forms. There is no intent to limit example embodiments to the particular forms disclosed, but on the contrary, example embodiments are to cover all modifications, equivalents, and alternatives falling within the scope of example embodiments.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes all combinations of one or more of the associated listed items.

The terminology used herein is for the purpose of describing embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof. In this specification, the term "and/or" picks out each individual item as well as all combinations of them.

Unless otherwise defined, all terms (including technical and scientific terms) used herein have the same meaning as commonly understood by one of ordinary skill in the art to which example embodiments belongs. It will be further understood that terms, such as those defined in commonly used dictionaries, should be interpreted as having a meaning that is consistent with their meaning in the context of the relevant art and should not be interpreted in an idealized or overly formal sense unless expressly so defined herein. It should also be noted that in some alternative implementations, the functions/acts noted may occur out of the order noted in the figures. For example, two figures shown in succession may in fact be executed concurrently or may sometimes be executed in the reverse order, depending upon the functionality/acts involved.

In the drawings, the dimensions of layers and regions are exaggerated for clarity of illustration. It will also be understood that when a layer (or tissue) is referred to as being "on" another layer or tissue, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being 'between' two layers, it can be the only layer between the two layers, or one or more intervening layers may also be present. Like reference numerals refer to like elements throughout.

Overview of Example Processing System to Characterize Coronary Plaque

This disclosure includes methods and systems of using data generated from images collected by scanning a patient's arteries to identify coronary artery plaques that are at higher risk of causing future heart attack or acute coronary syndrome. In particular, the characteristics of perivascular coronary fat, coronary plaque, and/or the coronary lumen, and the relationship of the characteristics of perivascular coronary fat, coronary plaque, and/or the coronary lumen are discussed to determine ways for identifying the coronary plaque that is more susceptible to implication in future ACS, heart attack and death. The images used to generate the image data may be CT images, CCTA images, or images generated using any applicable technology that can depict the relative densities of the coronary plaque, perivascular fat, and coronary lumen. For example, CCTA images may be used to generate two-dimensional (2D) or volumetric (three-dimensional (3-D)) image data, and this image data may be analyzed to determine certain characteristics that are associated with the radiodensities of the coronary plaque, perivascular fat, and/or coronary lumen. In some implementations, the Hounsfield scale is used to provide a measure of the radiodensity of these features. A Hounsfield unit, as is known, represents an arbitrary unit of x-ray attenuation used for CT scans. Each pixel (2D) or voxel (3D) of a feature in the image data may be assigned a radiodensity value on the Hounsfield scale, and then these values characterizing the features may be analyzed.

In various embodiments, processing of image information may include: (1) determining scan parameters (for example, mA (milliampere), kvP (peak kilovoltage)); (2) determining the scan image quality (e.g., noise, signal-to-noise ratio, contrast-to-noise ratio); (3) measuring scan-specific coronary artery lumen densities (e.g., from a point distal to a coronary artery wall to a point proximal to the coronary artery wall to distal to the coronary artery, and from a central location of the coronary artery to an outer location (e.g., outer relative to radial distance from the coronary artery): (4) measuring scan-specific plaque densities (e.g., from central to outer, abruptness of change within a plaque from high-to-low or low-to-high) as a function of their 3D shape; and (5) measuring scan-specific perivascular coronary fat densities (from close to the artery to far from the artery) as a function of its 3D shape.

From these measurements, which are agnostic to any commonly known features of ischemia-causing atherosclerosis, we can determine several characteristics, including but not limited to:

1. A ratio of lumen attenuation to plaque attenuation, wherein the volumetric model of scan-specific attenuation density gradients within the lumen adjusts for reduced luminal density across plaque lesions that are more functionally significant in terms of risk value
2. A ratio of plaque attenuation to fat attenuation, wherein plaques with high radiodensities are considered to present a lower risk, even within a subset of plaques considered "calcified," where there can be a gradation of densities (for example, 130 to 4000 HU) and risk is considered to be reduced as density increases.
3. A ratio of lumen attenuation/plaque attenuation/fat attenuation
4. A ratio of #1-3 as a function of 3D shape of atherosclerosis, which can include a 3D texture analysis of the plaque
5. The 3D volumetric shape and path of the lumen along with its attenuation density from the beginning to the end of the lumen.
6. The totality of plaque and plaque types before and after any given plaque to further inform its risk.

7. Determination of "higher plaque risks" by "subtracting" calcified (high-density) plaques to obtain a better absolute measure of high risk plaques (lower-density plaques). In other words, this particular embodiment involves identifying calcified plaque and excluding it from further analysis of plaque for the purpose of identifying high risk plaques.

Other characteristics can also be determined.

The above listed characteristics/metrics, and others, can be analyzed together to assess the risk of the plaque being implicated in future heart attack, ACS, ischemia or death. This can be done through development and/or validation of a traditional risk score or through machine learning methods. Factors for analysis from the metrics, that are likely to be associated with heart attack, ACS, ischemia or death, may include: (1) a ratio of [bright lumen: dark plaque]; (2) a ratio of [dark plaque:light fat]; (3) a ratio of [bright lumen:dark plaque: light fat]; and (4) a low ratio of [dark lumen:dark myocardium in 1 vessel area]/[lumen: myocardium in another vessel area]. Some improvements in the disclosed methods and systems include: (1) using numerical values from ratios of [lumen:plaque], [plaque:fat] and [lumen:plaque:fat] instead of using qualitative definitions of atherosclerotic features; (2) using a scan-specific [lumen:plaque attenuation] ratio to characterize plaque; (3) using a scan-specific [plaque:fat attenuation] ratio to characterize plaque; (4) using ratios of [lumen:plaque:fat circumferential] to characterize plaque; and (5) integration of plaque volume and type before and after as a contributor to risk for any given individual plaque.

Atherosclerotic plaque features may change over time with medical treatment (colchicine and statin medications) and while some of these medications may retard progression of plaque, they also have very important roles in promoting the change in plaque. While statin medications may have reduced the overall progression of plaque they may also have actually resulted in an increased progression of calcified plaque and a reduction of non-calcified plaque. This change will be associated with a reduction in heart attack or ACS or death, and the disclosed methods can be used to monitor the effects of medical therapy on plaque risk over time. Also, this method can also be used to identify individuals whose atherosclerotic plaque features or [lumen:plaque]/[plaque:fat]/[lumen:plaque:fat] ratios indicate that they are susceptible to rapid progression or malignant transformation of disease. In addition, these methods can be applied to single plaques or to a patient-basis wherein whole-heart atherosclerosis tracking can be used to monitor risk to the patient for experiencing heart attack (rather than trying to identify any specific plaque as being causal for future heart attack). Tracking can be done by automated co-registration processes of image data associated with a patient over a period of time.

FIG. 1 depicts a schematic of an example of an embodiment of a system 100 that includes a processing system 120 configured to characterize coronary plaque. The processing system 120 include one or more servers (or computers) 105 each configured with one or more processors. The processing system 120 includes non-transitory computer memory components for storing data and non-transitory computer memory components for storing instructions that are executed by the one or more processors data communication interfaces, the instructions configuring the one or more processors to perform methods of analyzing image information. A more detailed example of a server/computer 105 is described in reference to FIG. 9.

The system 100 also includes a network. The processing system 120 is in communication with the network 125. The network 125 may include, as at least a portion of the network 125, the Internet, a wide area network (WAN), a wireless network, or the like. In some embodiments, the processing system 120 is part of a "cloud" implementation, which can be located anywhere that is in communication with the network 125. In some embodiments, the processing system 120 is located in the same geographic proximity as an imaging facility that images and stores patient image data. In other embodiments, the processing system 120 is located remotely from where the patient image data is generated or stored.

FIG. 1 also illustrates in system 100 various computer systems and devices 130 (e.g., of an imaging facility) that are related to generating patient image data and that are also connected to the network 125. One or more of the devices 130 may be at an imaging facility that generates images of a patient's arteries, a medical facility (e.g., a hospital, doctor's office, etc.) or may be the personal computing device of a patient or care provider. For example, as illustrated in FIG. 1, an imaging facility server (or computer) 130A may be connected to the network 125. Also, in this example, a scanner 130B in an imaging facility maybe connected to the network 125. One or more other computer devices may also be connected to the network 125. For example, a laptop 130C, a personal computer 130D, and/or and an image information storage system 130E may also be connected to the network 125, and communicate with the processing system 120, and each other, via the network 125.

In some examples, the scanner 130B can be a computed tomography (CT) scanner that uses a rotating X-ray tube and a row of detectors to measure X-ray attenuations by different tissues in the body and form a corresponding image. In another example, a scanner 130B can use a spinning tube ("spiral CT") in which an entire X-ray tube and detectors are spun around a central axis of the area being scanned. In another example, the scanner 130B can utilize electron beam tomography (EBT). In another example, the scanner 130B can be a dual source CT scanner with a two X-ray tube system. The methods and systems described herein can also use images from other CT scanners. In some examples, the scanner 130B is a photon counting CT scanner, a spectral CT scanner, or a dual energy CT scanner. A photon counting CT scanner, a spectral CT scanner, or a dual energy CT scanner can help provide more detailed higher resolution images that better show small blood vessels, plaque, and other vascular pathologies, and allow for the determination of absolute material densities over relative densities. In general, a photon counting CT scanner uses an X-ray detector to count photons and quantifies the energy, determining the count of the number of photons in several discrete energy bins, resulting in higher contrast-to-noise ratio, and improved spatial resolution and spectral imaging compared to conventional CT scanners. Each registered photon is assigned to a specific bin depending on its energy, such that each pixel measures a histogram of the incident X-ray spectrum. This spectral information provides several advantages, First, it can be used to quantitatively determine the material composition of each pixel in the reconstructed CT image, as opposed to the estimated average linear attenuation coefficient obtained in a conventional CT scan. The spectral/energy information can be used to remove beam hardening artifacts that occur higher linear attenuation of many materials that shifts mean energy of the X-ray spectrum towards higher energies. Also, use of more than two energy bins allows discrimination between objects (bone, calcifications, contrast agents, tissue, etc.). In some embodiments, images generated using a photon counting CT scanner allows assessment of plaques at different monochromatic energies as well as different polychromatic spectra (e.g., 100 kvp, 120 kvp, 140 kvp, etc.), and this can change definition of non-calcified and calcified plaques compared to conventional CT scanners. A spectral CT scanner uses different X-ray wavelengths (or energies) to produce a CT scan. A dual energy CT scanner uses separate X-ray energies to detect two different energy ranges. In an example, a dual energy CT scanner (also known as spectral CT) can use an X-ray detector with separate layers to detect two different energy ranges ('dual layer'). In another example, a dual energy CT scanner can use a single scanner to scan twice using two different energy levels (e.g., electronic kVp switching). Images can be formed from combining the images detected at each different energy level, or the images may be used separately to assess a medical condition of a patient. In addition to providing absolute material densities, a photon counting CT scanner also allows for evaluation of images that are "monochromatic" as opposed to the typical CT, which is polychromatic spectra of light. As noted above, features (e.g., low density non-calcified plaque, calcified plaque, non-calcified plaque) that are depicted images formed using a photon counting CT scanner, a spectral CT scanner, or a dual energy CT scanner may have different radiodensities than those depicted in images formed from a conventional CT scanner, that is, such images may affect or change the definition of calcified and non-calcified plaque. However, radiodensities of calcified and non-calcified plaque, or other features depicted in images formed from a photon counting CT scanner, a spectral CT scanner, or a dual energy CT scanner, can be normalized to correspond to densities of conventional CT scanners and to the densities disclosed herein. Accordingly, the radiodensities disclosed herein can be directly correlated to radiodensities of images generated with a photon counting CT scanner, a spectral CT scanner, or a dual energy CT scanner such that the systems and methods, analysis, plaque densities etc. disclosed herein are directly applicable to images formed from a photon counting CT scanner, a spectral CT scanner, or a dual energy CT scanner, and are directly applicable to images formed from a photon counting CT scanner, a spectral CT scanner, or a dual energy CT scanner that are normalized to equivalent conventional CT scanner radiodensities.

The information communicated from the devices 130 to the processing system 120 via the network 125 may include image information 135. In various embodiments, the image information 135 may include 2D or 3D image data of a patient, scan information related to the image data, patient information, and other imagery or image related information that relates to a patient. For example, the image information may include patient information including (one or more) characteristics of a patient, for example, age, gender, body mass index (BMI), medication, blood pressure, heart rate, height, weight, race, whether the patient is a smoker or non-smoker, body habitus (for example, the "physique" or "body type" which may be based on a wide range of factors), medical history, diabetes, hypertension, prior coronary artery disease (CAD), dietary habits, drug history, family history of disease, information relating to other previously collected image information, exercise habits, drinking habits, lifestyle information, lab results and the like. In some embodiments, the image information includes identification information of the patient, for example, patient's name, patient's address, driver's license number, Social Security number, or indicia of another patient identification. Once the processing system 120 analyzes the image information 135, information relating to a patient 140 may be communicated from the processing system 120 to a device 130 via the network 125. The patient information 140 may include for example, a patient report. Also, the patient information 140 may include a variety of patient information which is available from a patient portal, which may be accessed by one of the devices 130.

In some embodiments, image information comprising a plurality of images of a patient's coronary arteries and patient information/characteristics may be provided from one or more of the devices 130 to the one or more servers 105 of the processing system 120 via a network 125. The processing system 120 is configured to generate coronary artery information using the plurality of images of the patient's coronary arteries to generate two-dimensional and/or three-dimensional data representations of the patient's coronary arteries. Then, the processing system 120 analyzes the data representations to generate patient reports documenting a patient's health conditions and risks related to coronary plaque. The patient reports may include images and graphical depictions of the patient's arteries in the types of coronary plaque in or near the coronary arteries. Using machine learning techniques or other artificial intelligent techniques, the data representations of the patient's coronary arteries may be compared to other patients' data representations (e.g., that are stored in a database) to determine additional information about the patient's health. For example, based on certain plaque conditions of the patient's coronary arteries, the likelihood of a patient having a heart attack or other adverse coronary effect can be determined. Also, for example, additional information about the patient's risk of CAD may also be determined.

Figure 2:
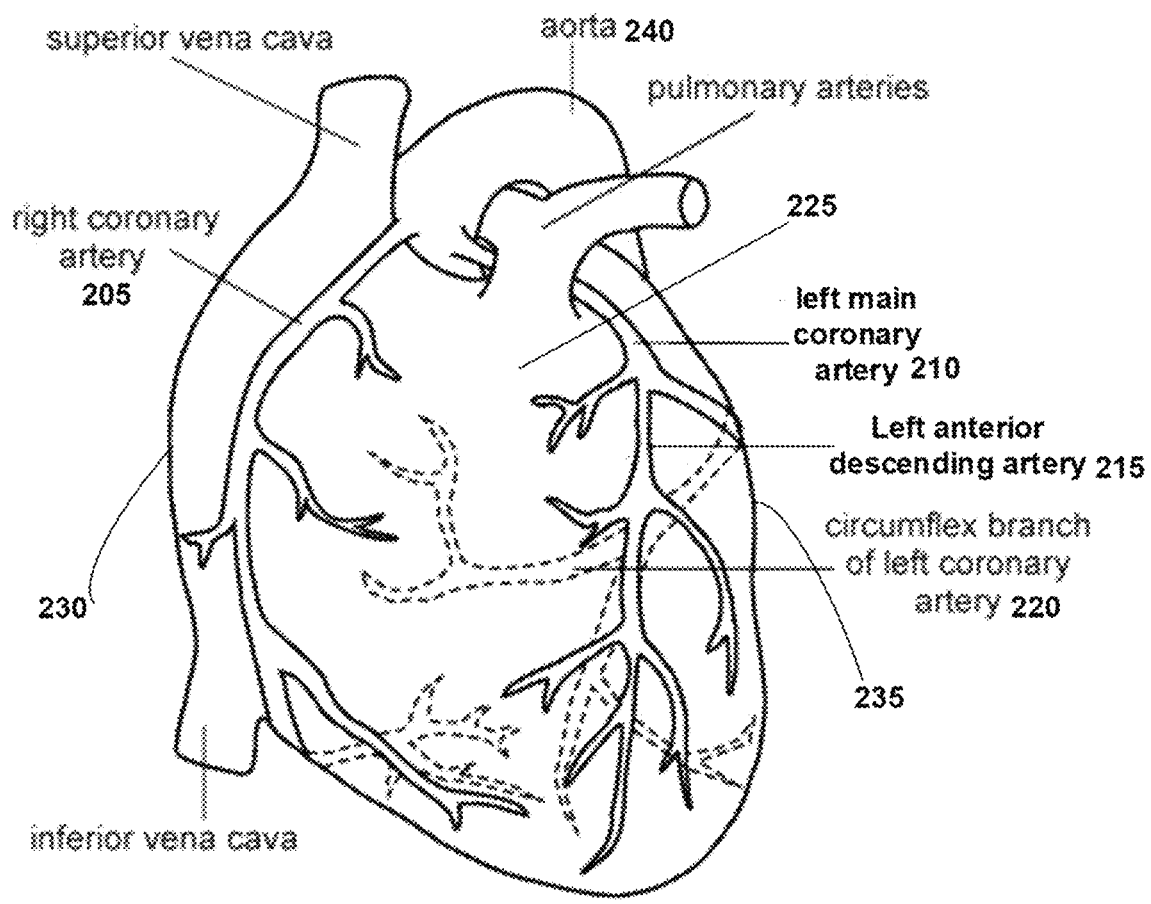
FIG. 2 is a schematic illustrating an example of a heart muscle and its coronary arteries.

FIG. 2 is a schematic illustrating an example of a heart muscle 225 and its coronary arteries. The coronary vasculature includes a complex network of vessels ranging from large arteries to arterioles, capillaries, venules, veins, etc. FIG. 1 depicts a model 220 of a portion of the coronary vasculature that circulates blood to and within the heart and includes an aorta 240 that supplies blood to a plurality of coronary arteries, for example, a left anterior descending (LAD) artery 215, a left circumflex (LCX) artery 220, and a right coronary (RCA) artery 230, described further below. Coronary arteries supply blood to the heart muscle 225. Like all other tissues in the body, the heart muscle 225 needs oxygen-rich blood to function. Also, oxygen-depleted blood must be carried away. The coronary arteries wrap around the outside of the heart muscle 225. Small branches dive into the heart muscle 225 to bring it blood. The examples of methods and systems described herein may be used to determine information relating to blood flowing through the coronary arteries in any vessels extending therefrom. In particular, the described examples of methods and systems may be used to determine various information relating to one or more portions of a coronary artery where plaque has formed which is then used to determine risks associated with such plaque, for example, whether a plaque formation is a risk to cause an adverse event to a patient.

The right side 230 of the heart 225 is depicted on the left side of FIG. 2 (relative to the page) and the left side 235 of the heart is depicted on the right side of FIG. 2. The coronary arteries include the right coronary artery (RCA) 205 which extends from the aorta 240 downward along the right side 230 of the heart 225, and the left main coronary artery (LMCA) 210 which extends from the aorta 240 downward on the left side 235 of the heart 225. The RCA 205 supplies blood to the right ventricle, the right atrium, and the SA (sinoatrial) and AV (atrioventricular) nodes, which regulate the heart rhythm. The RCA 205 divides into smaller branches, including the right posterior descending artery and the acute marginal artery. Together with the left anterior descending artery 215, the RCA 205 helps supply blood to the middle or septum of the heart.

The LMCA 210 branches into two arteries, the anterior interventricular branch of the left coronary artery, also known as the left anterior descending (LAD) artery 215 and the circumflex branch of the left coronary artery 220. The LAD artery 215 supplies blood to the front of the left side of the heart. Occlusion of the LAD artery 215 is often called the widow-maker infarction. The circumflex branch of the left coronary artery 220 encircles the heart muscle. The circumflex branch of the left coronary artery 220 supplies blood to the outer side and back of the heart, following the left part of the coronary sulcus, running first to the left and then to the right, reaching nearly as far as the posterior longitudinal sulcus.

Figure 3:
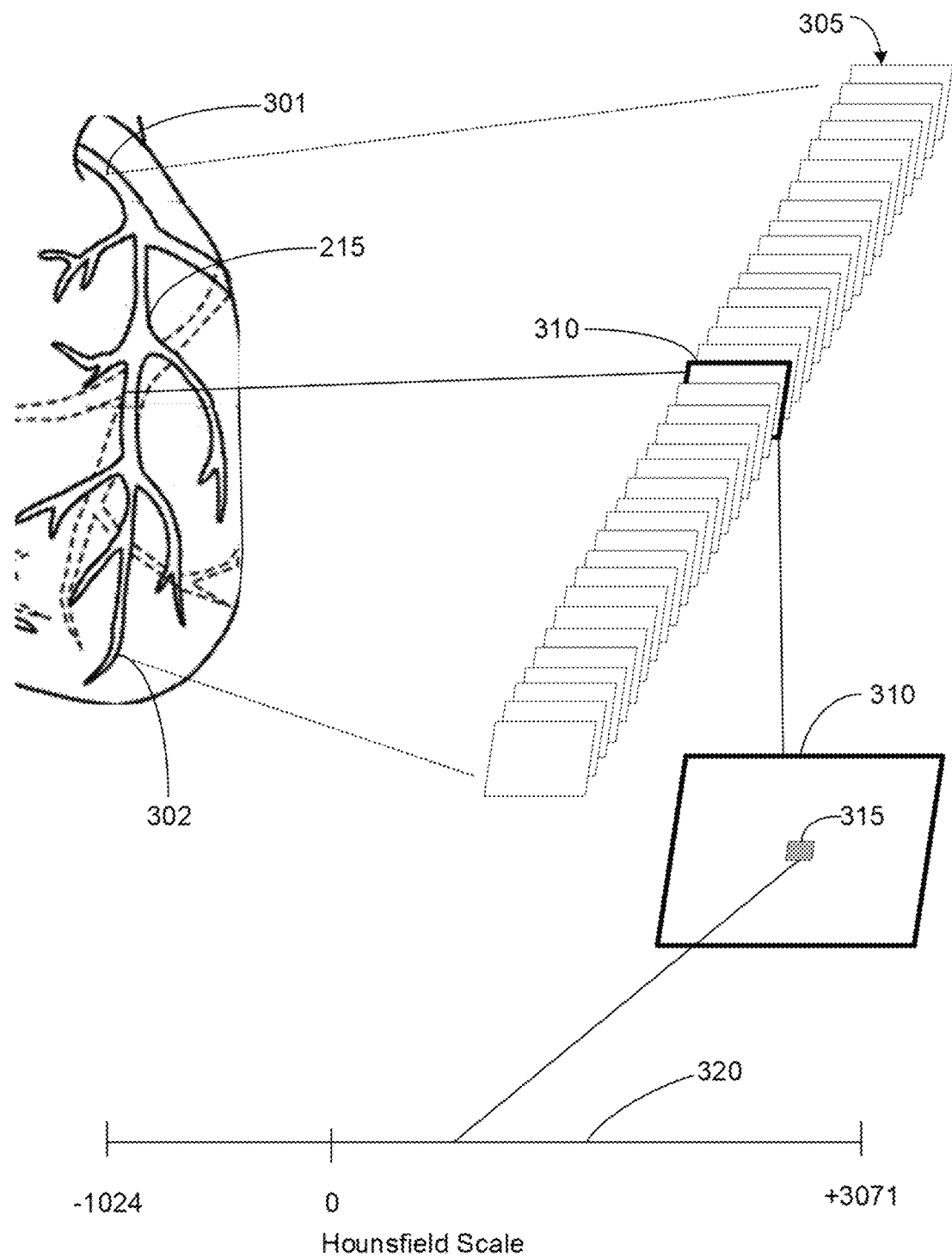
FIG. 3 illustrates an example of a set of images generated from scanning along a coronary artery, including a selected image of a portion of a coronary artery, and how image data may correspond to a value on the Hounsfield Scale.

FIG. 3 illustrates an example of a set of images generated from scanning along a coronary artery, including a selected image of a portion of a coronary artery, and how image data may correspond to a value on the Hounsfield Scale. As discussed in reference to FIG. 1, in addition to obtaining image data, scan information including metrics related to the image data, and patient information including characteristics of the patient may also be collected.

A portion of a heart 225, the LMCA 210, and the LAD artery 215 is illustrated in the example of FIG. 3. A set of images 305 can be collected along portions of the LMCA 210 and the LAD artery 215, in this example from a first point 301 on the LMCA 210 to a second point 302 on the LAD artery 215. In some examples, the image data may be obtained using noninvasive imaging methods. For example, CCTA image data can be generated using a scanner to create images of the heart in the coronary arteries and other vessels extending therefrom. Collected CCTA image data may be subsequently used to generate three-dimensional image models of the features contained in the CCTA image data (for example, the right coronary artery 205, the left main coronary artery 210, the left anterior descending artery 215, the circumflex branch of the left coronary artery 220, the aorta 240, and other vessels related to the heart that appear in the image data.

In various embodiments, different imaging methods may be used to collect the image data. For example, ultrasound or magnetic resonance imaging (MRI) may be used. In some embodiments, the imaging methods involve using a contrast agent to help identify structures of the coronary arteries, the contrast agent being injected into the patient prior to the imaging procedure. The various imaging methods may each have their own advantages and disadvantages of usage, including resolution and suitability of imaging the coronary arteries. Imaging methods which may be used to collect image data of the coronary arteries are constantly improving as improvements to the hardware (e.g., sensors and emitters) and software are made. The disclosed systems and methods contemplate using CCTA image data and/or any other type of image data that can provide or be converted into a representative 3D depiction of the coronary arteries, plaque contained within the coronary arteries, and perivascular fat located in proximity to the coronary arteries containing the plaque such that attenuation or radiodensity values of the coronary arteries, plaque, and/or perivascular fat can be obtained.

Referring still to FIG. 3, a particular image 310 of the image data 305 is shown, which represents an image of a portion of the left anterior descending artery 215. The image 310 includes image information, the smallest point of the information manipulated by a system referred to herein generally as a pixel, for example pixel 315 of image 310. The resolution of the imaging system used to capture the image data will affect the size of the smallest feature that can be discerned in an image. In addition, subsequent manipulation of the image may affect the dimensions of a pixel. As one example, the image 310 in a digital format, may contain 4000 pixels in each horizontal row, and 3000 pixels in each vertical column. Pixel 315, and each of the pixels in image data 310 and in the image data 305, can be associated with a radiodensity value that corresponds to the density of the pixel in the image. Illustratively shown in FIG. 3 is mapping pixel 315 to a point on the Hounsfield scale 320. The Hounsfield scale 320 is a quantitative scale for describing radiodensity. The Hounsfield unit scale linear transformation of the original linear attenuation coefficient measurement into one in which the radiodensity of distilled water at standard pressure and temperature is defined as zero Hounsfield units (HU), while the radiodensity of air at standard pressure and temperature is defined as ~1000 HU. Although FIG. 3 illustrates an example of mapping pixel 315 of image 310 to a point on the Hounsfield scale 320, such an association of a pixel to a radiodensity value can also be done with 3D data. For example, after the image data 305 is used to generate a three-dimensional representation of the coronary arteries.

Once the data has been obtained and rendered into a three-dimensional representation, various processes can be performed on the data to identify areas of analysis. For example, a three-dimensional depiction of a coronary artery may be segmented to define a plurality of portions of the artery and identified as such in the data. In some embodiments, the data may be filtered (e.g., smoothed) by various methods to remove anomalies that are the result of scanning or other various errors. Various known methods for segmenting and smoothing the 3D data may be used, and therefore for brevity of the disclosure will not be discussed in any further detail herein.

Figure 4A:
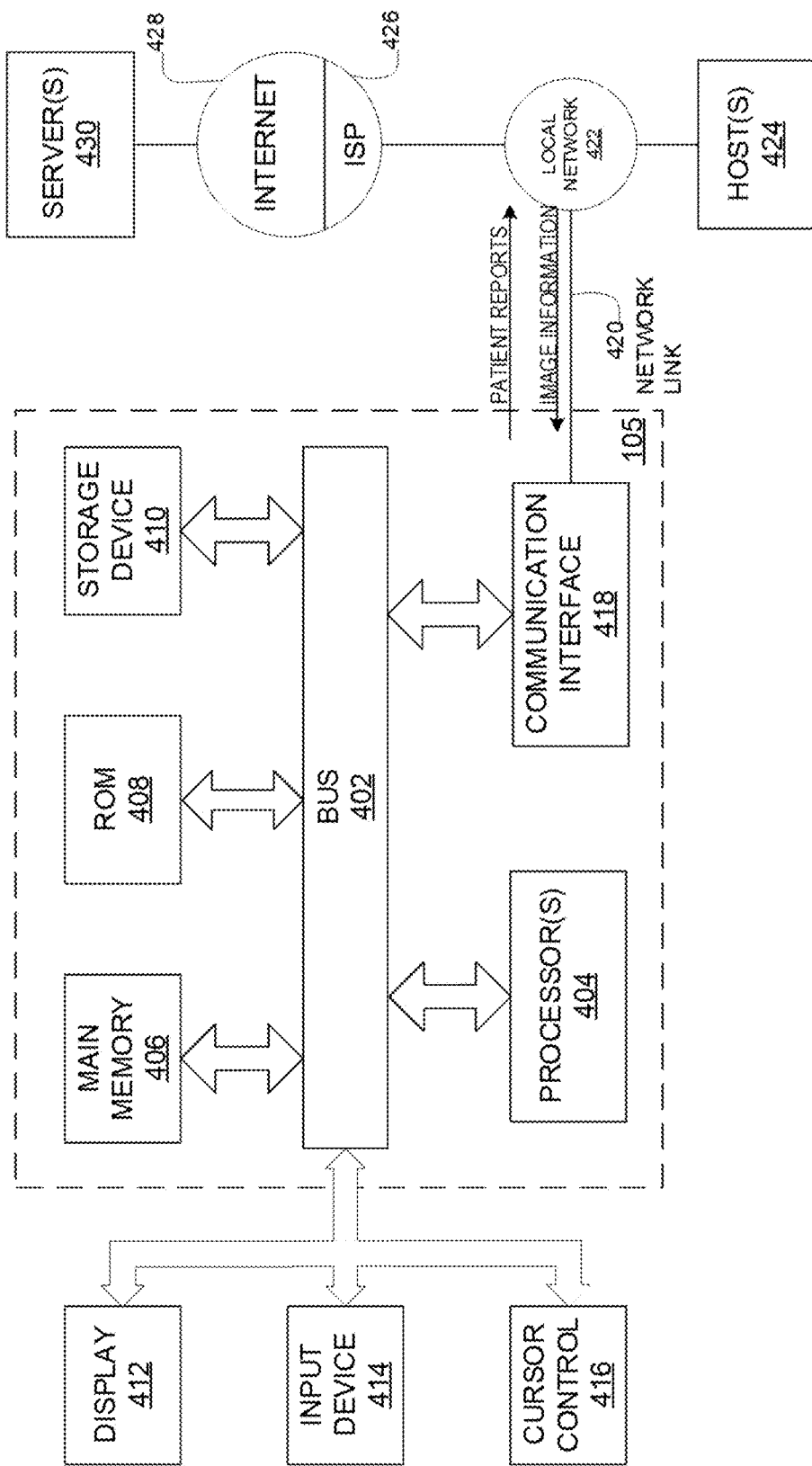
FIG. 4A is a block diagram that illustrates a computer system upon which various embodiments may be implemented.

FIG. 4A is a block diagram that illustrates a computer system 400 upon which various embodiments may be implemented. Computer system 400 includes a bus 402 or other communication mechanism for communicating information, and a hardware processor, or multiple processors, 404 coupled with bus 402 for processing information. Hardware processor(s) 404 may be, for example, one or more general purpose microprocessors.

Computer system 400 also includes a main memory 406, such as a random access memory (RAM), cache and/or other dynamic storage devices, coupled to bus 402 for storing information and instructions to be executed by processor 404. Main memory 406 also may be used for storing temporary variables or other intermediate information during execution of instructions to be executed by processor 404. Such instructions, when stored in storage media accessible to processor 404, render computer system 400 into a special-purpose machine that is customized to perform the operations specified in the instructions. The main memory 406 may, for example, include instructions that analyze image information to determine characteristics of coronary features (e.g., plaque, perivascular fat and coronary arteries) to produce patient reports containing information that characterizes aspects of the patient's health relating to their coronary arteries. For example, one or more metrics may be determined, the metrics including one or more of a slope/gradient of a feature, a maximum density, minimum density, a ratio of a slope of one feature to the slope of another feature, a ratio of a maximum density of one feature to the maximum density of another feature, a ratio of a minimum density of a feature to the minimum density of the same feature, or a ratio of the minimum density of a feature to the maximum density of another feature.

Computer system 400 further includes a read only memory (ROM) 408 or other static storage device coupled to bus 402 for storing static information and instructions for processor 404. A storage device 410, such as a magnetic disk, optical disk, or USB thumb drive (Flash drive), etc., is provided and coupled to bus 402 for storing information and instructions.

Computer system 400 may be coupled via bus 402 to a display 412, such as a cathode ray tube (CRT) or LCD display (or touch screen), for displaying information to a computer user. An input device 414, including alphanumeric and other keys, is coupled to bus 402 for communicating information and command selections to processor 404. Another type of user input device is cursor control 416, such as a mouse, a trackball, or cursor direction keys for communicating direction information and command selections to processor 404 and for controlling cursor movement on display 412. This input device typically has two degrees of freedom in two axes, a first axis (e.g., x) and a second axis (e.g., y), that allows the device to specify positions in a plane. In some embodiments, the same direction information and command selections as cursor control may be implemented via receiving touches on a touch screen without a cursor.

Computing system 400 may include a user interface module to implement a GUI that may be stored in a mass storage device as computer executable program instructions that are executed by the computing device(s). Computer system 400 may further, as described below, implement the techniques described herein using customized hard-wired logic, one or more ASICs or FPGAs, firmware and/or program logic which in combination with the computer system causes or programs computer system 400 to be a special-purpose machine. According to one embodiment, the techniques herein are performed by computer system 400 in response to processor(s) 404 executing one or more sequences of one or more computer readable program instructions contained in main memory 406. Such instructions may be read into main memory 406 from another storage medium, such as storage device 410. Execution of the sequences of instructions contained in main memory 406 causes processor(s) 404 to perform the process steps described herein. In alternative embodiments, hard-wired circuitry may be used in place of or in combination with software instructions.

Various forms of computer readable storage media may be involved in carrying one or more sequences of one or more computer readable program instructions to processor 404 for execution. For example, the instructions may initially be carried on a magnetic disk or solid state drive of a remote computer. The remote computer can load the instructions into its dynamic memory and send the instructions over a telephone line using a modem. A modem local to computer system 400 can receive the data on the telephone line and use an infra-red transmitter to convert the data to an infra-red signal. An infra-red detector can receive the data carried in the infra-red signal and appropriate circuitry can place the data on bus 402. Bus 402 carries the data to main memory 406, from which processor 404 retrieves and executes the instructions. The instructions received by main memory 406 may optionally be stored on storage device 410 either before or after execution by processor 404.

Computer system 400 also includes a communication interface 418 coupled to bus 402. Communication interface 418 provides a two-way data communication coupling to a network link 420 that is connected to a local network 422. For example, communication interface 418 may be an integrated services digital network (ISDN) card, cable modem, satellite modem, or a modem to provide a data communication connection to a corresponding type of telephone line. As another example, communication interface 418 may be a local area network (LAN) card to provide a data communication connection to a compatible LAN (or WAN component to communicate with a WAN). Wireless links may also be implemented. In any such implementation, communication interface 418 sends and receives electrical, electromagnetic or optical signals that carry digital data streams representing various types of information.

Network link 420 typically provides data communication through one or more networks to other data devices. For example, network link 420 may provide a connection through local network 422 to a host computer 424 or to data equipment operated by an Internet Service Provider (ISP) 426. ISP 426 in turn provides data communication services through the worldwide packet data communication network now commonly referred to as the "Internet" 428. Local network 422 and Internet 428 both use electrical, electromagnetic or optical signals that carry digital data streams. The signals through the various networks and the signals on network link 420 and through communication interface 418, which carry the digital data to and from computer system 400, are example forms of transmission media.

Computer system 400 can send messages and receive data, including program code, through the network(s), network link 420 and communication interface 418. In the Internet example, a server 430 might transmit a requested code for an application program through Internet 428, ISP 426, local network 422 and communication interface 418.

The received code may be executed by processor 404 as it is received, and/or stored in storage device 410, or other non-volatile storage for later execution.

Accordingly, in an embodiment, the computer system 105 comprises a non-transitory computer storage medium storage device 410 configured to at least store image information of patients. The computer system 105 can also include non-transitory computer storage medium storage that stores instructions for the one or more processors 404 to execute a process (e.g., a method) for characterization of coronary plaque tissue data and perivascular tissue data using image data gathered from a computed tomography (CT) scan along a blood vessel, the image information including radiodensity values of coronary plaque and perivascular tissue located adjacent to the coronary plaque. Executing the instructions, the one or more processors 404 can quantify, in the image data, the radiodensity in regions of coronary plaque, quantify in the image data, radiodensity in at least one region of corresponding perivascular tissue adjacent to the coronary plaque, determine gradients of the quantified radiodensity values within the coronary plaque and the quantified radiodensity values within the corresponding perivascular tissue, determine a ratio of the quantified radiodensity values within the coronary plaque and the corresponding perivascular tissue, and characterizing the coronary plaque by analyzing one or more of the gradients of the quantified radiodensity values in the coronary plaque and the corresponding perivascular tissue, or the ratio of the coronary plaque radiodensity values and the radiodensity values of the corresponding perivascular tissue.

Various embodiments of the present disclosure may be a system, a method, and/or a computer program product at any possible technical detail level of integration. The computer program product may include a computer readable storage medium (or mediums) having computer readable program instructions thereon for causing a processor to carry out aspects of the present disclosure. For example, the functionality described herein may be performed as software instructions are executed by, and/or in response to software instructions being executed by, one or more hardware processors and/or any other suitable computing devices. The software instructions and/or other executable code may be read from a computer readable storage medium (or mediums).

The computer readable storage medium can be a tangible device that can retain and store data and/or instructions for use by an instruction execution device. The computer readable storage medium may be, for example, but is not limited to, an electronic storage device (including any volatile and/or non-volatile electronic storage devices), a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a solid state drive, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions (as also referred to herein as, for example, "code," "instructions," "module," "application," "software application," and/or the like) for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. Computer readable program instructions may be callable from other instructions or from itself, and/or may be invoked in response to detected events or interrupts. Computer readable program instructions configured for execution on computing devices may be provided on a computer readable storage medium, and/or as a digital download (and may be originally stored in a compressed or installable format that requires installation, decompression or decryption prior to execution) that may then be stored on a computer readable storage medium. Such computer readable program instructions may be stored, partially or fully, on a memory device (e.g., a computer readable storage medium) of the executing computing device, for execution by the computing device. The computer readable program instructions may execute entirely on a user's computer (e.g., the executing computing device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart(s) and/or block diagram(s) block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks. For example, the instructions may initially be carried on a magnetic disk or solid state drive of a remote computer. The remote computer may load the instructions and/or modules into its dynamic memory and send the instructions over a telephone, cable, or optical line using a modem. A modem local to a server computing system may receive the data on the telephone/cable/optical line and use a converter device including the appropriate circuitry to place the data on a bus. The bus may carry the data to a memory, from which a processor may retrieve and execute the instructions. The instructions received by the memory may optionally be stored on a storage device (e.g., a solid state drive) either before or after execution by the computer processor.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. In addition, certain blocks may be omitted in some implementations. The methods and processes described herein are also not limited to any particular sequence, and the blocks or states relating thereto can be performed in other sequences that are appropriate.

Figure 4B:
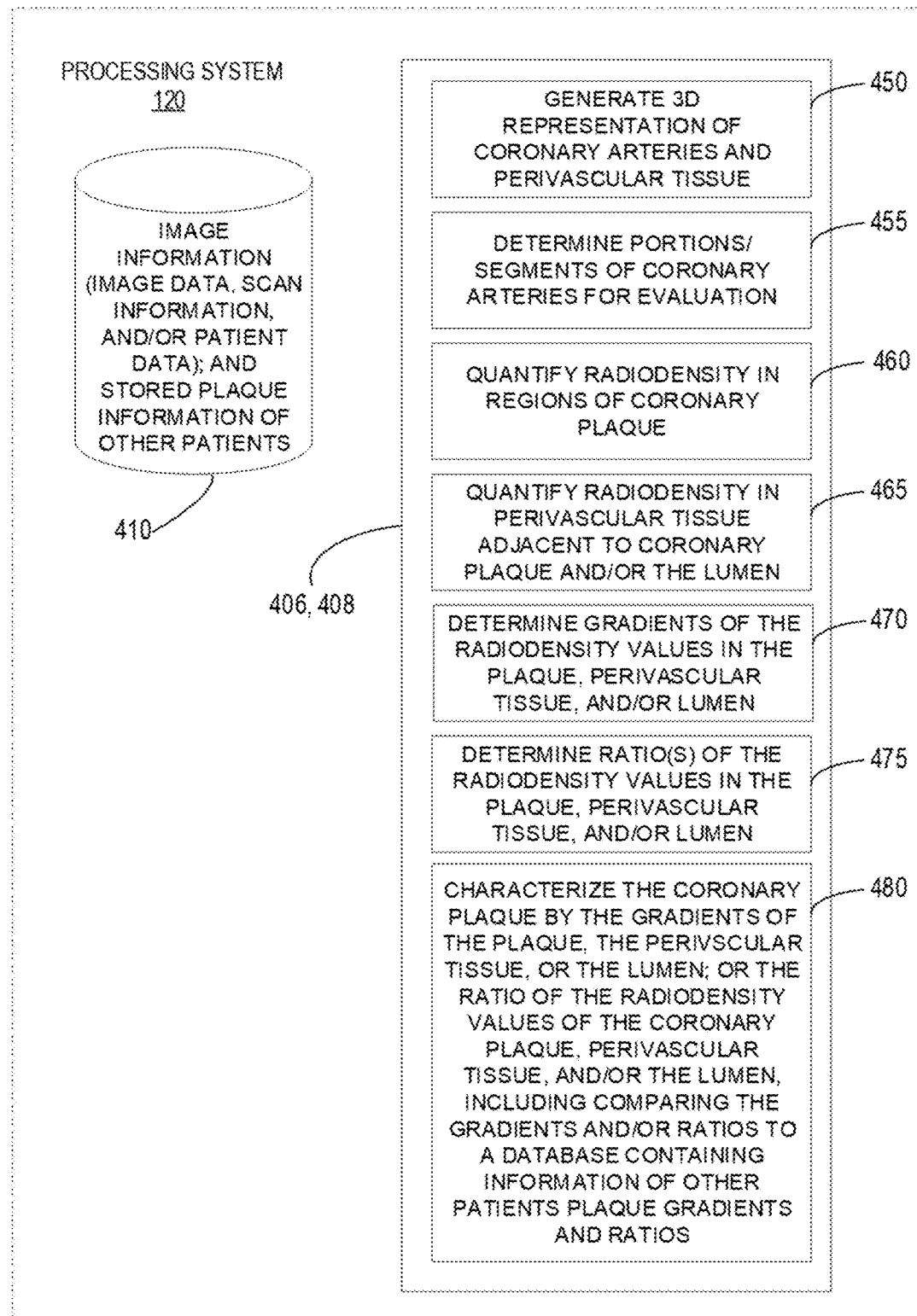
FIG. 4B is a block diagram that illustrates computer modules in a computer system 400 which may implement various embodiments.

FIG. 4B is a block diagram that illustrates examples of representative instructions which may be executed by one or more computer hardware processors in one or more computer modules in a representative processing system (computer system) 120 which may implement various embodiments described herein. As illustrated in FIG. 1, the processing system 120 can be implemented in one computer (for example, a server) or in 2 or more computers (two or more servers). Although the instructions are represented in FIG. 4B as being in seven modules 450, 455, 460, 465, 470, 475, 480, in various implementations the executable instructions may be in fewer modules, including a single module, or more modules.

The processing system 120 includes image information stored on a storage device 410, which may come from the network 125 illustrated in FIG. 1. The image information may include image data, scan information, and/or patient data. In this example, the storage device 410 also includes stored plaque information of other patients. For example, the stored plaque information of other patients may be stored in a database on the storage device 410. In other examples, stored plaque information of other patients is stored on a storage device that is in communication with processing system 120. The other patients' stored plaque information may be a collection of information from one, dozens, hundreds, thousands, tens of thousands, hundreds of thousands, or millions of patients, or more.

The information for each patient may include characterizations of that patient's plaque, such as densities and density gradients of the patient's plaque, and the location of the plaque relative to the perivascular tissue near or adjacent to the plaque. The information for each patient may include patient information. For example, the information may include one or more of sex, age, BMI (body mass index), medication, blood pressure, heart rate, weight, height, race, body habitus, smoking history, history or diagnosis of diabetes, history or diagnosis of hypertension, prior coronary artery disease, family history of coronary artery disease and/or other diseases, or one or more lab results (e.g., blood test results). The information for each patient may include scan information. For example, the information may include one or more of contrast-to-noise ratio, signal-to-noise ratio, tube current, tube voltage, contrast type, contrast volume, flow rate, flow duration, slice thickness, slice spacing, pitch, vasodilator, beta blockers, recon option whether it's iterative or filter back projection, recon type whether it's standard or high resolution, display field-of-view, rotation speed, gating whether it's perspective triggering or retrospective gating, stents, heart rate, or blood pressure. The information for each patient may also include cardiac information. For example, the information may include characterizations of plaque including one or more of density, volume, geometry (shape), location, remodeling, baseline anatomy (for diameter, length), compartments (inner, outer, within), stenosis (diameter, area), myocardial mass, plaque volume, and/or plaque composition, texture, or uniformity.

The processing system 120 also includes memory 406, 408, which may be main memory of the processing system or read only memory (ROM). The memory 406, 408 stores instructions executable by one or more computer hardware processors 404 (groups of which referred to herein as "modules") to characterize coronary plaque. The memory 406, 408 will be collectively referred to, in reference to this diagram, as memory 406 for the sake of brevity. Examples of the functionality that is performed by the executable instructions are described below.

Memory 406 includes module 450 that generates, from the image data stored on the storage device 410, 2-D or 3-D representations of the coronary arteries, including plaque, and perivascular tissue that is located adjacent to or in proximity of the coronary arteries in the plaque. The generation of the 2-D or 3-D representations of the coronary arteries may be done from a series of images 305 (e.g., CCTA images) is described above in reference to FIG. 3. Once the representation of the coronary arteries are generated, different portions or segments of the coronary arteries can be identified for evaluation. For example, portions of interest of the right coronary artery 205, the left anterior descending artery 215, or the circumflex branch of the left coronary artery 220 may be identified as areas of analysis (areas of interest) based on input from a user, or based on a feature determined from the representation of the coronary artery (plaque).

In module 460, the one or more computer hardware processors quantify radiodensity in regions of coronary plaque. For example, the radiodensity in regions of coronary plaque are set to a value on the Hounsfield scale. In module 465, the one or more computer hardware processors quantify radiodensity of perivascular tissue that is adjacent to the coronary plaque, and quantify radiodensity value of the lumen of the vessel of interest. In module 470, the one or more computer hardware processors determine gradients of the radiodensity values of the plaque the perivascular tissue and/or the lumen. In module 475, the one or more computer hardware processors determine one or more ratios of the radiodensity values in the plaque, perivascular tissue, and/or the lumen. Next, in module 480, the one or more computer hardware processors characterize the coronary plaque using the gradients of the plaque, the perivascular tissue, and/or the lumen, and/or characterize ratio of the radiodensity values of the coronary plaque to perivascular tissue and/or the lumen including comparing the gradients and or ratios to a database containing information of other patients' plaque gradients and ratios. For example, the gradients and/or the ratios are compared to patient data that stored on storage device 410. Determining gradients and ratios of the plaque the perivascular tissue and the lumen are described in more detail with reference to FIGS. 6-12.

Figure 5A:
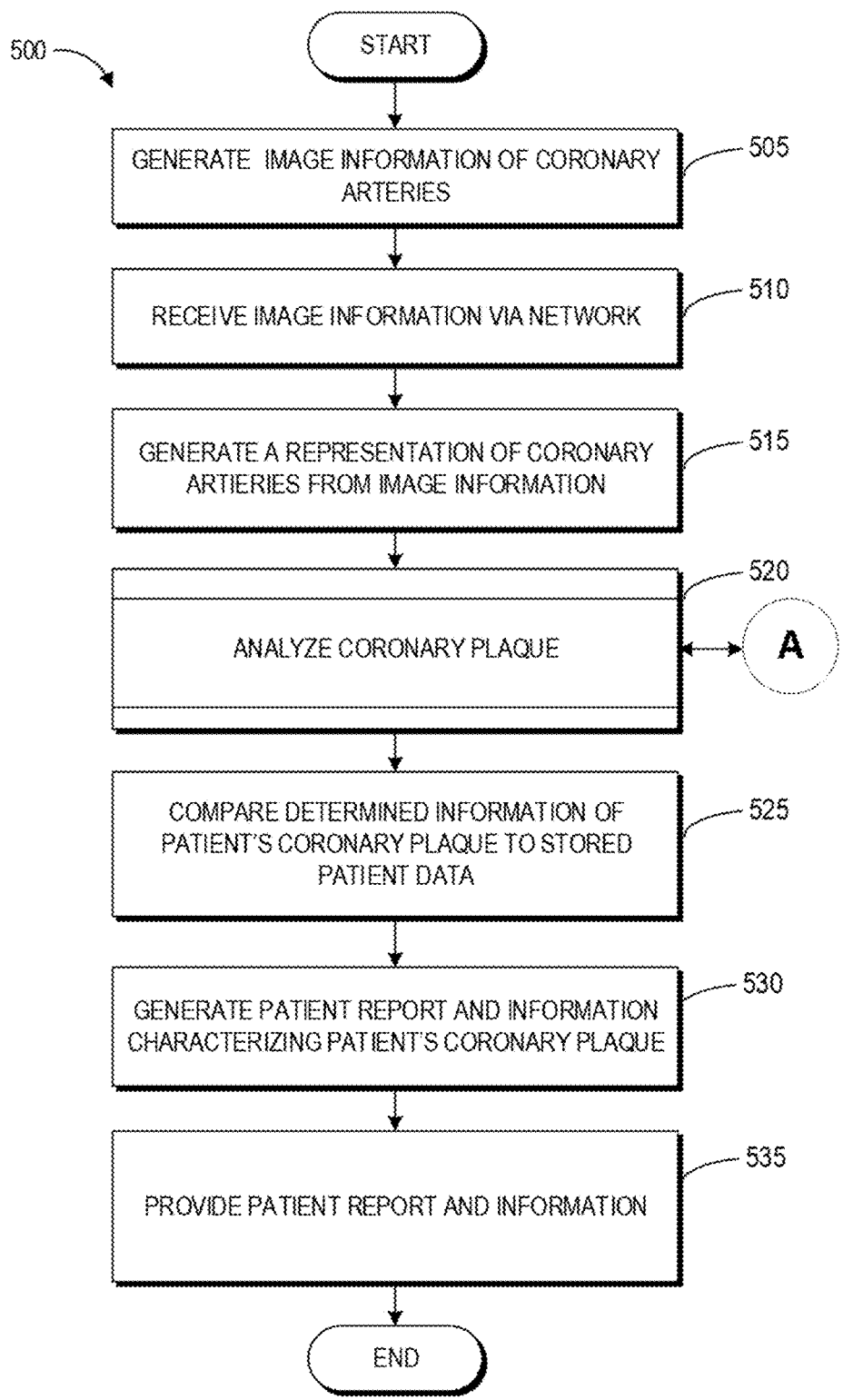
FIG. 5A illustrates an example of a flowchart of a process for analyzing coronary plaque.

FIG. 5A illustrates an example of a flowchart of a process 500 for analyzing coronary plaque. At block 505, the process 500 generates image information including image data relating to coronary arteries. In various embodiments, this may be done by a scanner 130B (FIG. 1). At block 510, a processing system may receive image information via a network 125 (FIG. 1), the image information including the image data. At block 515, the process 500 generates a 3D representation of the coronary arteries including perivascular fat and plaque on the processing system. The functionality of blocks 505, 510, and 515, can be performed, for example, using various scanning techniques (e.g., CCTA) to generate image data, communication techniques to transfer data over the network, and processing techniques to generate the 3D representation of the coronary arteries from the image data.

Figure 5B:
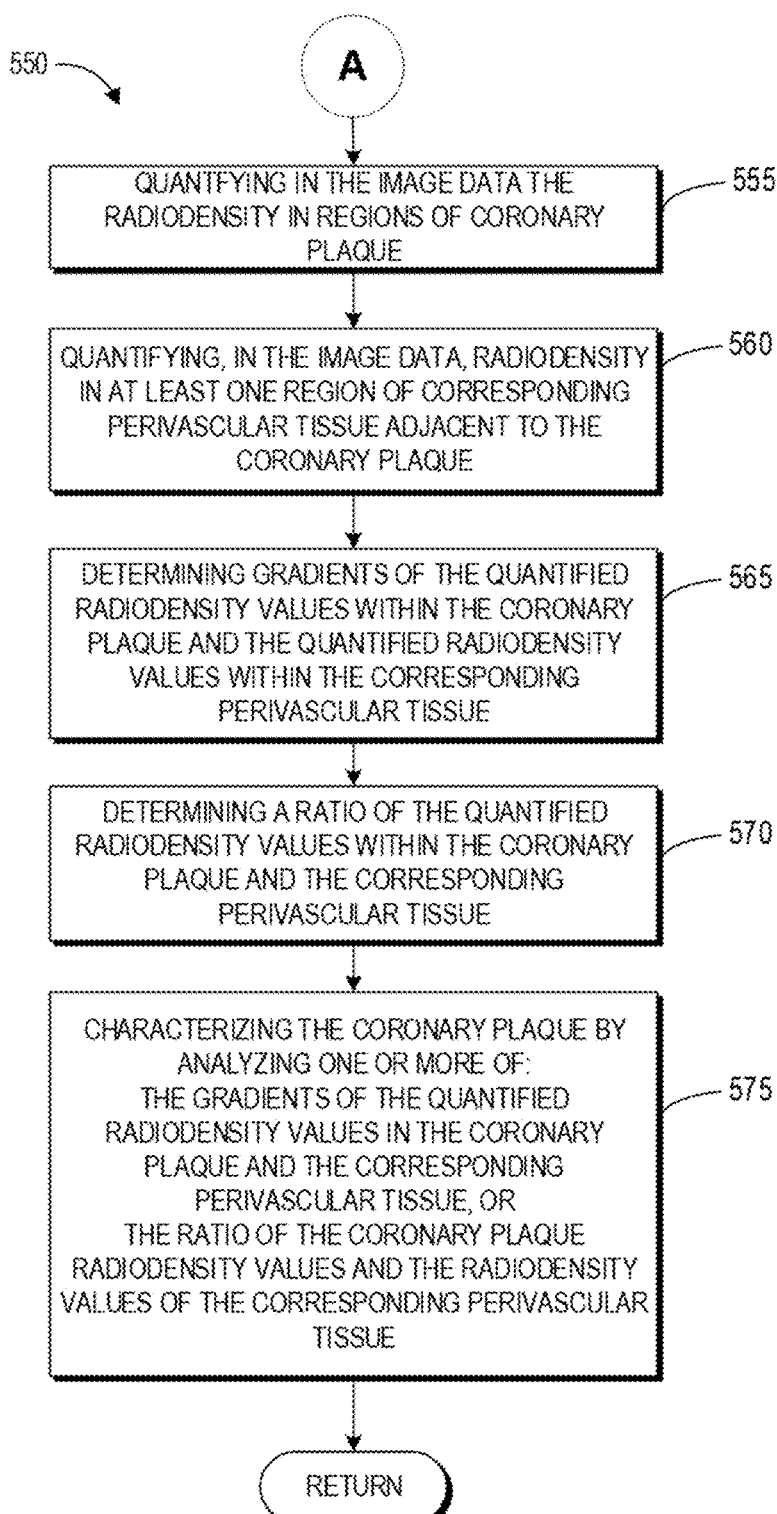
FIG. 5B illustrates an example of a flowchart that expands on a portion of the flowchart in FIG. 5A for determining characteristics of coronary plaque.

At block 520, the processing system performs a portion of the process 500 to analyze the coronary plaque, which is described in further detail in reference to process 550 of FIG. 5B. Additional details of this process to analyze the coronary plaque in reference to FIGS. 6-12.

FIG. 5B illustrates an example of a flowchart that expands on a portion of the flowchart in FIG. 5A for determining characteristics of coronary plaque. Referring now to FIG. 5B, at block 555, process 550 can utilize the one or more processors 404 to quantify the radiodensity in regions of coronary plaque. At block 560, the process 550 can utilize the one or more processors 404 to quantify, in the image data, radiodensity in at least one region of corresponding perivascular tissue, meaning perivascular tissue that is adjacent to the coronary plaque. At block 565, the process 550 determines gradients of the quantified radiodensity values within the coronary plaque and the quantified radiodensity values within the corresponding perivascular tissue. The one or more processors 404 can be the means to determine these gradients. At block 570, the process 550 may determine a ratio of the quantified radiodensity values within the coronary plaque and the corresponding perivascular tissue. For example, the perivascular tissue that is adjacent to the coronary plaque. The one or more processors 404 can determine these ratios. At block 575, process 550 can utilize the one or more processors 404 to characterize the coronary plaque by analyzing one or more of the gradients of the quantified radiodensity values in the coronary plaque and the corresponding perivascular tissue, or the ratio of the coronary plaque radiodensity values and the radiodensity values of the corresponding perivascular tissue. The process 550 can then return to process 500 as illustrated by the circle A.

Referring again to FIG. 5A, at block 525, the process 500 may compare determined information of a particular patient's coronary plaque to stored patient data, for example patient data stored on storage device 410. An example of the coronary plaque information of a particular patient that can be compared to stored patient data. To better understand the patient's coronary plaque information, and/or to help determine the particular patient's coronary plaque information, one or more of the scan information may be used. Also, when comparing a particular patient's coronary plaque information to previously stored coronary plaque information, one or more characteristics of the patient may be compared, including, for example, one or more of the characteristics of a patient. In some examples, the coronary plaque information of the patient being examined may be compared to or analyzed in reference to a patient who has one or more of the same or similar patient characteristics. For example, the patient being examined may be compared to a patient that has the same or similar characteristics of sex, age, BMI, medication, blood pressure, heart rate, weight, height, race, body habitus, smoking, diabetes, hypertension, prior coronary artery disease, family history, and lab results. Such comparisons can be done through various means, for example machine learning and/or artificial intelligence techniques. In some examples, neural network is used to compare a patient's coronary artery information to numerous (e.g., 10,000+) other patients' coronary artery information. For such patients that have similar patient information and similar cardiac information, risk assessments of the plaque of the patient being examined may be determined.

Figure 6:
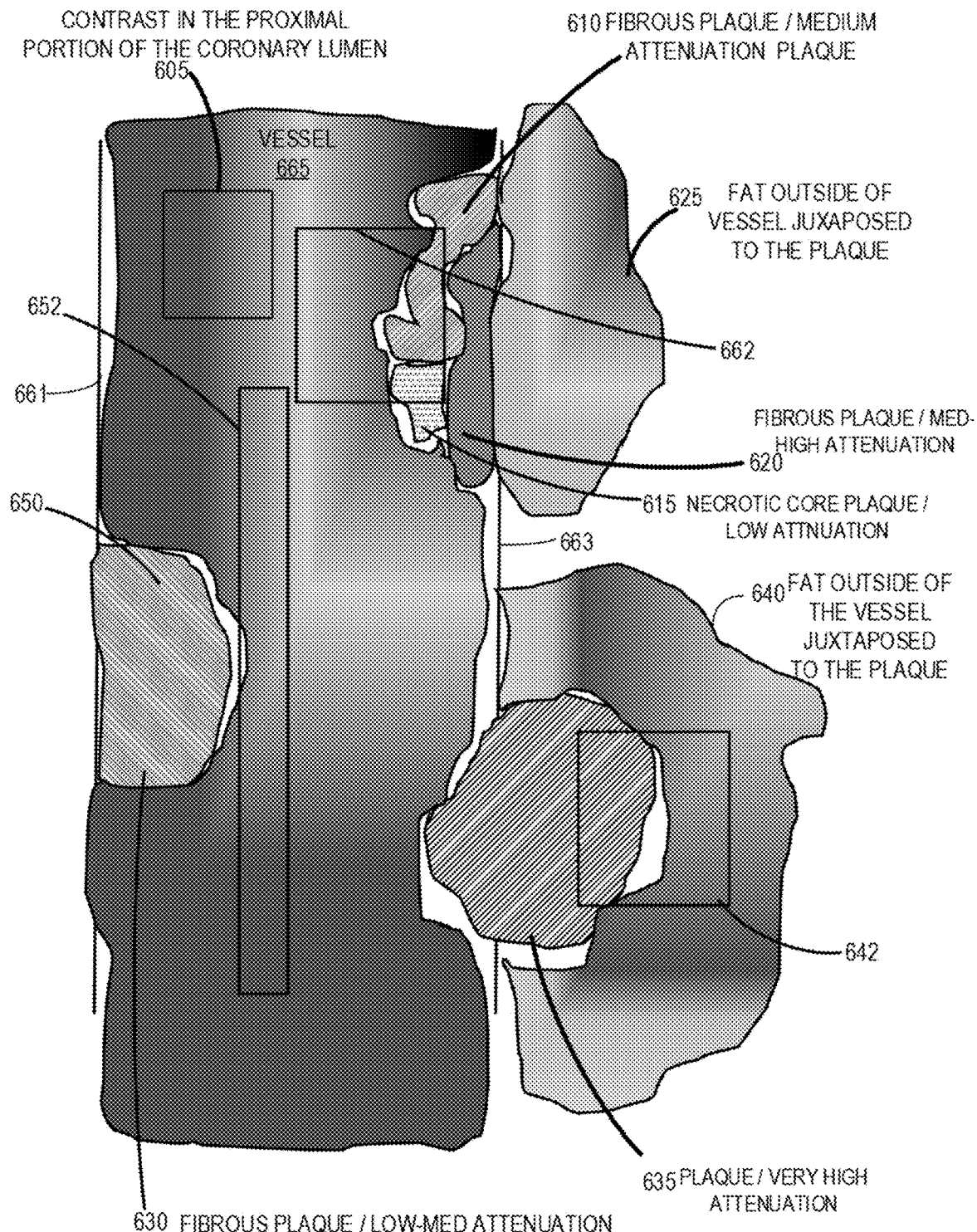
FIG. 6 illustrates a representation of image data depicting an example of a portion of a coronary artery (sometimes referred to herein as a "vessel" for ease of reference).

FIG. 6 illustrates an example of an area, indicated by box 605, where contrast attenuation patterns in a proximal portion of the coronary lumen can be analyzed, box 605 extending from a central area of the vessel 665 towards the vessel wall 661. FIG. 6 illustrates another example of an area, indicated by box 652, where contrast attenuation patterns in a portion of the coronary lumen of vessel 665 can be analyzed, box 652 extending longitudinally relative to vessel 665 from a central area of the vessel 665 towards the vessel wall 661. FIG. 6 further illustrates an example of an area, indicated by box 662, where contrast attenuation patterns of a portion of the lumen, a portion of fibrous plaque 610 and plaque 620 can be analyzed, box 662 thus covering a portion of the vessel 665 and a portion of fibrous plaque 610 and plaque 620. FIG. 6 further illustrates an example of an area indicated by box 642, where contrast attenuation patterns of a portion of plaque 635 and a portion of fat 640 positioned adjacent to plaque 635 can be analyzed, box 642 extending over a portion of plaque 635 and a portion of fat 640. Information determined by analyzing various aspects of the density of coronary artery features (e.g., the lumen, the plaque, and/or the perivascular fat) can be combined with other information to determine characteristics of a patient's arteries. In some examples, the determined information may include for any of the lumen, plaque or perivascular fat, one or more of a slope/gradient of a feature, a maximum density, a minimum density, a ratio of a slope of the density of one feature to the slope of the density of another feature, a ratio of a maximum density of one feature to the maximum density of another feature, a ratio of a minimum density of a feature to the minimum density of the same feature, a directionality of the density ratios, e.g., a density ratio between features facing one way or direction and features facing in an opposite direction (for example, the radiodensity ratio of features facing inwards towards the myocardium and features facing outwards toward the pericardium), or a ratio of the minimum density of a feature to the maximum density of another feature. Such determined information may indicate distinct differences in risks of plaque in a patient. In some examples, determined information (for example as listed above) may be used with a percentage diameter of stenosis to determine characteristics of a patient's arteries.

Still referring to FIG. 6, in an example of the directionality of radiodensity ratios, the density of a portion of the necrotic core plaque 615 to the density of a portion of the vessel 665 (e.g., plaque:vessel inward facing ratio) can be determined and may indicate a certain risk of plaque. In another example of the directionality of radiodensity ratios, the density of a portion of a portion of the vessel 665 to the density of the necrotic core plaque 615 (e.g., vessel:plaque outward facing) can be determined and may indicate a certain risk of plaque. In another example, the density ratio of the necrotic core plaque 615 to the density of a portion of the vessel 665 (e.g., plaque:vessel inward facing ratio) can be compared to the density ratio of the necrotic core plaque 615 to the fibrous plaque 620 (e.g., plaque:plaque outward facing) may indicate a certain risk of plaque. In other examples, features that are adjacently positioned can be used to determine inward and/or outward directional radiodensity values that may be used to indicate a risk associated with plaque. Such ratios may provide distinct differences in risk of plaque. Various embodiments of directional radiodensity values and/or directional radiodensity ratios can be included with any of the other information described herein to indicates plaque risk.

The size of a compartment may be used to also indicate a risk associated with plaque. For example, determination of risk associated with a plaque may be based at least partially on the size of the compartments, such that the ratio of the of the radiodensities affects the determination of risk and the function of the size of the compartments can also affect the determination of risk. While the presence of plaque in a patient where the ratio of plaque:fat may indicate a high risk plaque, if there is only a small amount of plaque (e.g., a small compartment of plaque), it would be of risk than if there was a larger compartment of the same plaque with the same radiodensity ratio of plaque to fat. In one implementation, the size (e.g., a volume) of the compartment a feature (e.g., of lumen, plaque, perivascular tissue (fat), and myocardium) can be determined, and a radiodensity ratio can also be determined, and then the ratio can be weighted based on the size of the compartment. For example, a large compartment can increase the weight of a ratio to make the ratio more indicative of a risk associated with the plaque. Similarly, a small compartment can decrease the weight of a ratio to make the ratio less indicative of a risk associated with the plaque. In an implementation, only the compartment size of the plaque is used to weight (or adjust) the ratio. In an implementation, the compartment size of both of the features that are used in the radiodensity ratio can be used to weight the ratio to determine a resulting risk. In an implementation, the compartment size of one of plaque, lumen, perivascular tissue, or myocardium is used to weight (or adjust) the risk associated with the radiodensity ratio. In an implementation, the compartment size of more than one of plaque, lumen, perivascular tissue, or myocardium is used to weight the risk associated with the radiodensity ratio. Various embodiments of determining plaque risk using compartment size can be included with any of the other information described herein to indicate plaque risk.

Figure 7:
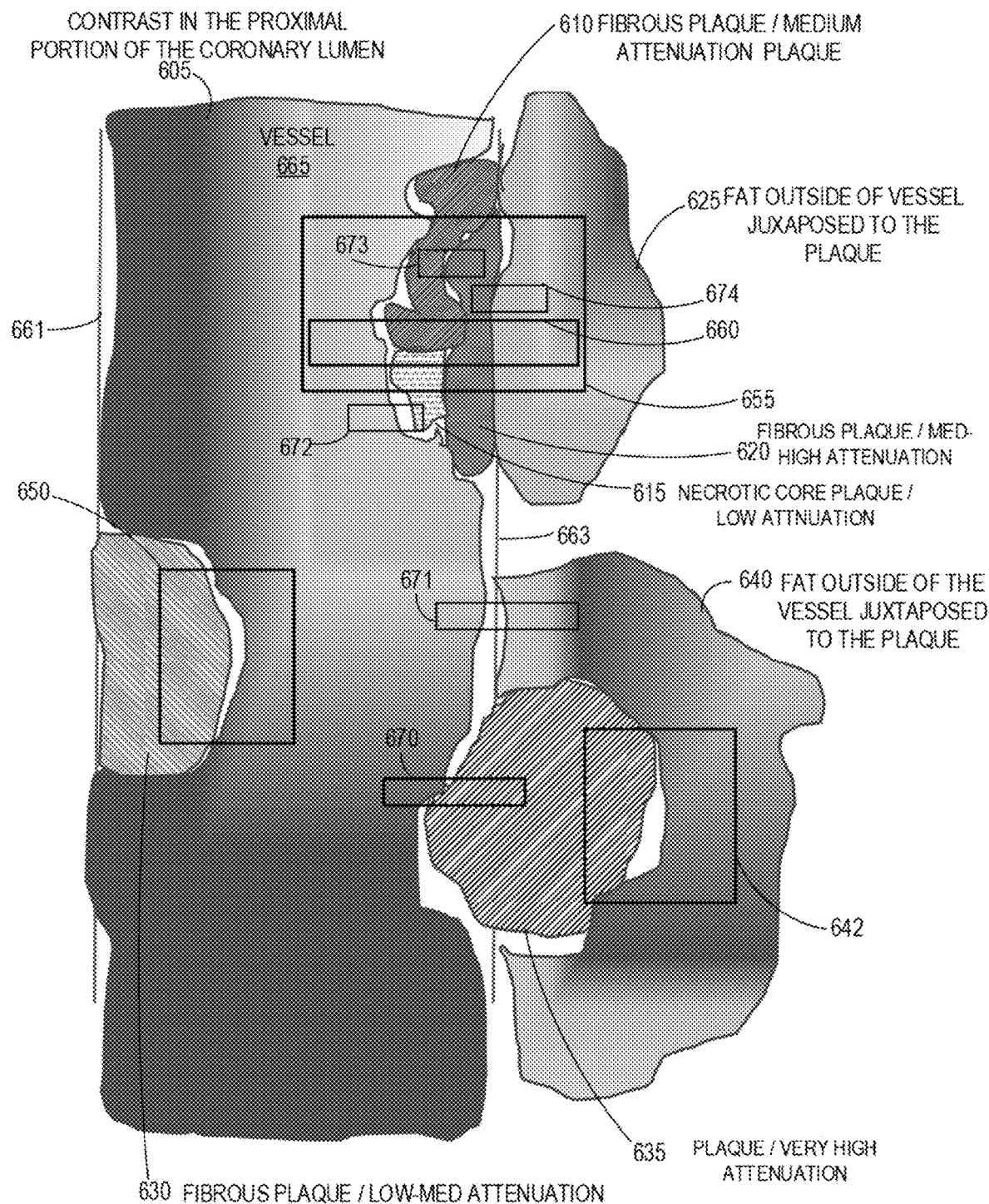
FIG. 7 illustrates the same vessel and features of plaque and fat as illustrated in FIG. 6 and further illustrates additional examples of areas of an artery, and the plaque and/or perivascular fat that is near an artery, that may be analyzed to determine characteristics of a patient's arteries.

FIG. 7 illustrates the same vessel 665 and features of plaque and fat as illustrated in FIG. 6 and further illustrates additional examples of areas of an artery, and plaque and/or perivascular fat near the artery, that may be analyzed to determine characteristics of a patient's arteries. Such areas are indicated in FIG. 7 by rectangular boxes, similar to the illustrations in FIG. 6. Although particular locations of the rectangular boxes are illustrated in FIG. 6 and FIG. 7, these are only examples of areas that may be analyzed. In one example, FIG. 7 illustrates box 660 which includes a portion of the vessel 665, a portion of necrotic core plaque 615, a portion of fibrous plaque 610, a portion of plaque 620, and a portion of fat 625. In another example, FIG. 7 illustrates box 655 which includes a portion of the vessel 665, a portion of the fibers plaque 610 a portion of the plaque 620 the portion of the necrotic core plaque 615, and a portion of fat 625. Box 655 may, in some cases, illustrate the general area for analysis due to the existence of 3 different types of plaque 610, 615, 620, and adjacently disposed fat 625. Particular portions of a general area for analysis may be analyzed to better understand the characteristics formed by adjacent features. For example, FIG. 7 illustrates the general area 665 containing box 660 (described above), box 673, which extends across a portion of fibrous plaque 610 and plaque 620, and box 674 which extends across a portion of plaque 620 and perivascular fat 625. As another example, FIG. 7 also illustrates another box 672 that extends across a portion of the vessel 655 and necrotic core plaque 615. As a further example, FIG. 7 illustrates box 671 that extends across a portion of the vessel 665 and fat 640 juxtaposed to the vessel 665. As a further example, FIG. 7 illustrates box 670 that extends across a portion of the vessel 665 and plaque 635. As indicated above, characteristics of a patient's arteries that can be analyzed based on these features can include but are not limited to:

1. A ratio of lumen attenuation to plaque attenuation, wherein the volumetric model of scan-specific attenuation density gradients within the lumen adjusts for reduced luminal density across plaque lesions that are more functionally significant in terms of risk value.
2. A ratio of plaque attenuation to fat attenuation, wherein plaques with high radiodensities are considered to present a lower risk, even within a subset of plaques considered "calcified," where there can be a gradation of densities (for example, 130 to 4000 HU) and risk is considered to be reduced as density increases.
3. A ratio of lumen attenuation/plaque attenuation/fat attenuation.
4. A ratio of #1-3 as a function of 3D shape of atherosclerosis, which can include a 3D texture analysis of the plaque.
5. The 3D volumetric shape and path of the lumen along with its attenuation density from the beginning to the end of the lumen.
6. The totality of plaque and plaque types before and after any given plaque to further inform its risk.
7. Determination of "higher plaque risks" by "subtracting" calcified (high-density) plaques to obtain a better absolute measure of high risk plaques (lower-density plaques). In other words, this particular embodiment involves identifying calcified plaque and excluding it from further analysis of plaque for the purpose of identifying high risk plaques.

In some embodiments, the systems, devices, and methods described herein can automatically and/or dynamically perform quantified analysis of various parameters relating to plaque, cardiovascular arteries, and/or other structures. For example, rather than having a physician eyeball or make a general assessment of the patient, a medical image can be transmitted to a backend main server in some embodiments that is configured to conduct such analyses, which advantageously can be performed in a consistent, objective, and/or reproducible manner. In some embodiments, the systems, methods, and devices described herein can provide a quantified measurement of one or more features of a coronary CT image using automated and/or dynamic processes. For example, in some embodiments, the main server system can be configured to identify one or more vessels, plaque, and/or fat from a medical image. Based on the identified features, in some embodiments, the system can be configured to generate one or more quantified measurements from a raw medical image, such as for example density and/or radiodensity of one or more regions of plaque, identification of stable plaque and/or unstable plaque, perivascular fat, pericoronary adipose tissue (PCAT), fat attenuation index (FAI), volumes thereof, surface areas thereof, geometric shapes, heterogeneity thereof, and/or the like. In some embodiments, the system can also generate one or more quantified measurements of vessels from the raw medical image, such as for example diameter, volume, morphology, and/or the like.

Based on the identified features and/or quantified measurements, in some embodiments, the system can be configured to generate a risk assessment and/or track the progression of a plaque-based disease or condition, such as for example atherosclerosis, stenosis, ischemia, myocardial infarction, and/or major adverse cardiovascular event (MACE), using raw medical images. As described further herein, in some embodiments the system can perform risk assessment and/or tracking the progression of a plaque-based disease based on other patients' information. For example, by comparing or evaluating features in a patient's medical images and patient information (e.g., age, gender, BMI, medication, blood pressure, heart rate, height, weight, race, whether the patient is a smoker or non-smoker, medical history, family history of disease, etc.) to features in other patients' medical images and their associated patient information including their outcome after a period of time.

Further, in some embodiments, the system can be configured to generate a visualization of GUI of one or more identified features and/or quantified measurements, such as a quantized color mapping of different features. In some embodiments, the systems, devices, and methods described herein are configured to utilize medical image-based processing to assess for a subject his or her risk of a cardiovascular event, major adverse cardiovascular event (MACE), rapid plaque progression, and/or response to non-response to medication and/or lifestyle change and/or other treatment and/or invasive procedure. In particular, in some embodiments, the system can be configured to automatically and/or dynamically assess such health risk of a subject by analyzing only non-invasively obtained medical images. In some embodiments, one or more of the processes can be automated using an artificial intelligence (AI) and/or machine learning (ML) algorithm. In some embodiments, one or more of the processes described herein can be performed within minutes in a reproducible manner. This is stark contrast to existing measures today which do not produce reproducible prognosis or assessment, take extensive amounts of time, and/or require invasive procedures.

In some embodiments, image information comprising a plurality of images of a patient's coronary arteries and patient information/characteristics may be provided from one or more of the devices to the one or more servers of the processing system via a network. The processing system is configured to generate coronary artery information using the plurality of images of the patient's coronary arteries to generate two-dimensional and/or three-dimensional data representations of the patient's coronary arteries. Then, the processing system analyzes the data representations to generate patient reports documenting a patient's health conditions and risks related to coronary plaque. The patient reports may include images and graphical depictions of the patient's arteries in the types of coronary plaque in or near the coronary arteries. Using machine learning techniques or other artificial intelligent techniques, the data representations of the patient's coronary arteries may be compared to other patients' data representations (e.g., that are stored in a database) to determine additional information about the patient's health. In some embodiments, the artificial intelligence can be trained using a dataset of other patients' data representations to identify correlations in data. For example, based on certain plaque conditions of the patient's coronary arteries, the likelihood of a patient having a heart attack or other adverse coronary effect can be determined. Also, for example, additional information about the patient's risk of CAD may also be determined.

In some embodiments, the coronary plaque information of a patient being examined may be compared to or analyzed in reference to a patient who has one or more of the same or similar patient characteristics. For example, the patient being examined may be compared to a patient that has the same or similar characteristics of sex, age, BMI, medication, blood pressure, heart rate, weight, height, race, body habitus, smoking, diabetes, hypertension, prior coronary artery disease, family history, and lab results. Such comparisons can be done through various means, for example machine learning and/or artificial intelligence techniques. In some examples, neural network is used to compare a patient's coronary artery information to numerous (e.g., 10,000+) other patients' coronary artery information. For such patients that have similar patient information and similar cardiac information, risk assessments of the plaque of the patient being examined may be determined.

In some embodiments, Deep Learning (DL) methods, machine learning (ML) methods, and artificial intelligence (AI) methods can be used to analyze image information. In an example, this analysis can comprise image segmentation, feature extraction, and classification. In some embodiments, ML methods can comprise image feature extraction and image-based learning from raw data. In some embodiments, the ML method can receive an input of a large training set to learn to ignore variations that could otherwise skew the results of the method. In some embodiments, DL can comprise a Neural Network (NN) with three or more layers that can improve the accuracy of determinations. Advantageously, in some embodiments, DL can obviate the need for pre-processing data and, instead, process raw data. For example, while a human may input a hierarchy of important features of coronary image information for a ML algorithm to make determinations, DL algorithms can determine which features are important and use these features to make determinations. Advantageously, in some embodiments, a DL algorithm can adjust itself for accuracy and precision. In some embodiments, ML and DL algorithms can perform supervised learning, unsupervised learning, and reinforcement learning.

In some embodiments, NN approaches, including convolutional neural networks (CNN) and recurrent convolutional neural networks (RCNN), among others, can be used to analyze information in a manner similar to high-level cognitive functions of a human mind. In some embodiments, a NN approach can comprise training an object recognition system numerous medical images in order to teach it patterns in the images that correlate with particular labels. In some embodiments, a CNN can comprise a NN where the nodes of each layer are clustered, the clusters overlap, and each cluster feeds data to multiple nodes of the next layer. In some embodiments, a RCNN can comprise a CNN where recurrent connections are incorporated in each convolutional layer. Advantageously, in some embodiments, the recurrent connections can make object recognition a dynamic process despite the fact that the input is static.

In some embodiments, the vessel identification algorithm, coronary artery identification algorithm, and/or plaque identification algorithm can be trained on a plurality of medical images wherein one or more vessels, coronary arteries, and/or regions of plaque are pre-identified. Based on such training, for example by use of a CNN in some embodiments, the system can be configured to automatically and/or dynamically identify from raw medical images the presence and/or parameters of vessels, coronary arteries, and/or plaque. In some embodiments, the system can be configured to utilize one or more AI and/or ML algorithms to identify and/or analyze vessels or plaque, derive one or more quantification metrics and/or classifications, and/or generate a treatment plan. In some embodiments, the system can be configured to utilize an AI and/or ML algorithm to identify areas in an artery that exhibit plaque buildup within, along, inside and/or outside the arteries. In some embodiments, input to the AI and/or ML algorithms can include images of a patient and patient information (or characteristics), for example, one or more of age, gender, body mass index (BMI), medication, blood pressure, heart rate, height, weight, race, whether the patient is a smoker or non-smoker, body habitus (for example, the "physique" or "body type" which may be based on a wide range of factors), medical history, diabetes, hypertension, prior coronary artery disease (CAD), dietary habits, drug history, family history of disease, information relating to other previously collected image information, exercise habits, drinking habits, lifestyle information, or lab results, and the like. In an example where a NN is used, the NN can be trained using information from a plurality of patients, where the information for each patient can include medical images and one or more patient characteristics.

In some embodiments, the system can be configured to utilize one or more AI and/or ML algorithms to automatically and/or dynamically identify one or more regions of plaque using image processing. For example, in some embodiments, the one or more AI and/or ML algorithms can be trained using a CNN on a set of medical images on which regions of plaque have been identified, thereby allowing the AI and/or ML algorithm automatically identify regions of plaque directly from a medical image. In some embodiments, the system can be configured to identify a vessel wall and a lumen wall for each of the identified coronary arteries in the medical image. In some embodiments, the system is then configured to determine the volume in between the vessel wall and the lumen wall as plaque. In some embodiments, the system can be configured to identify regions of plaque based on the radiodensity values typically associated with plaque, for example by setting a predetermined threshold or range of radiodensity values that are typically associated with plaque with or without normalizing using a normalization device.

In some embodiments, the one or more vascular morphology parameters and/or plaque parameters can comprise quantified parameters derived from the medical image. For example, in some embodiments, the system can be configured to utilize an AI and/or ML algorithm or other algorithm to determine one or more vascular morphology parameters and/or plaque parameters. As another example, in some embodiments, the system can be configured to determine one or more vascular morphology parameters, such as classification of arterial remodeling due to plaque, which can further include positive arterial remodeling, negative arterial remodeling, and/or intermediate arterial remodeling. In some embodiments, the classification of arterial remodeling is determined based on a ratio of the largest vessel diameter at a region of plaque to a normal reference vessel diameter of the same region which can be retrieved from a normal database. In some embodiments, the system can be configured to classify arterial remodeling as positive when the ratio of the largest vessel diameter at a region of plaque to a normal reference vessel diameter of the same region is more than 1.1. In some embodiments, the system can be configured to classify arterial remodeling as negative when the ratio of the largest vessel diameter at a region of plaque to a normal reference vessel diameter is less than 0.95. In some embodiments, the system can be configured to classify arterial remodeling as intermediate when the ratio of the largest vessel diameter at a region of plaque to a normal reference vessel diameter is between 0.95 and 1.1.

In some embodiments, the system is configured to classify atherosclerosis of a subject based on the quantified atherosclerosis as one or more of high risk, medium risk, or low risk. In some embodiments, the system is configured to classify atherosclerosis of a subject based on the quantified atherosclerosis using an AI, ML, and/or other algorithm. In some embodiments, the system is configured to classify atherosclerosis of a subject by combining and/or weighting one or more of a ratio of volume of surface area, volume, heterogeneity index, and radiodensity of the one or more regions of plaque.

In some embodiments, the system can be configured to identify one or more regions of fat, such as epicardial fat, in the medical image, for example using one or more AI and/or ML algorithms to automatically and/or dynamically identify one or more regions of fat. In some embodiments, the one or more AI and/or ML algorithms can be trained using a CNN on a set of medical images on which regions of fat have been identified, thereby allowing the AI and/or ML algorithm automatically identify regions of fat directly from a medical image. In some embodiments, the system can be configured to identify regions of fat based on the radiodensity values typically associated with fat, for example by setting a predetermined threshold or range of radiodensity values that are typically associated with fat with or without normalizing using a normalization device.

In some embodiments, the system is configured to utilize an AI, ML, and/or other algorithm to characterize the change in calcium score based on one or more plaque parameters derived from a medical image. For example, in some embodiments, the system can be configured to utilize an AI and/or ML algorithm that is trained using a CNN and/or using a dataset of known medical images with identified plaque parameters combined with calcium scores. In some embodiments, the system can be configured to characterize a change in calcium score by accessing known datasets of the same stored in a database. For example, the known dataset may include datasets of changes in calcium scores and/or medical images and/or plaque parameters derived therefrom of other subjects in the past. In some embodiments, the system can be configured to characterize a change in calcium score and/or determine a cause thereof on a vessel-by-vessel basis, segment-by-segment basis, plaque-by-plaque basis, and/or a subject basis.

In some embodiments, the systems disclosed herein can be used to dynamically and automatically determine a necessary stent type, length, diameter, gauge, strength, and/or any other stent parameter for a particular patient based on processing of the medical image data, for example using AI, ML, and/or other algorithms.

In some embodiments, the system can be configured to utilize an AI and/or ML algorithm to generate the patient-specific report. In some embodiments, the patient-specific report can include a document, AR experience, VR experience, video, and/or audio component.

Figure 8A:
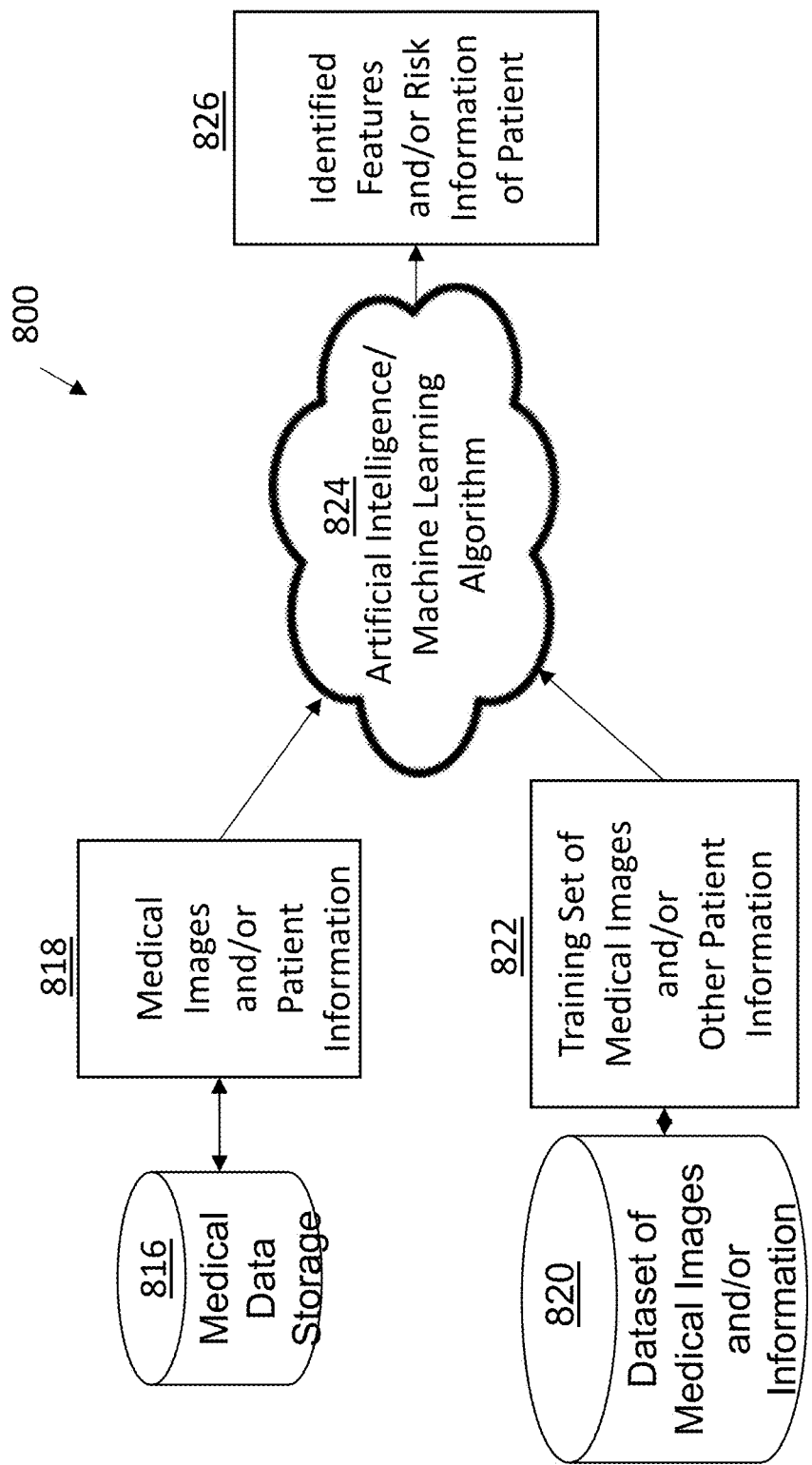
FIG. 8A is a block diagram that illustrates an example process of identifying features of medical images using artificial intelligence or machine learning.

FIG. 8A is a block diagram that illustrates an example of a system and/or process 800 (both referred to here as a "system" for ease of reference) for identifying features and/or risk information of a patient using AI/ML based on non-invasively obtained medical images of the patient and/or patient information. A current patient's medical data including images and/or patient information is first obtained and electronically stored on medical data storage 816 (e.g., cloud storage, hard disk, etc.). The system 800 obtains medical images and/or patient information 818 from the medical data storage 816 and preprocess it, if necessary, for example to re-format it as necessary for further processing. The system 800 can also obtain a training set of medical images and/or patient information 822 from a stored dataset 820 of medical images and/or information of other patients (e.g., hundreds, thousands, tens of thousands, or hundreds of thousands or more of other patients). The medical images and information of other patients can be used to train the AI/ML algorithm 824 prior to processing the medical images and/or patient information 818 of the current patient, as described in further detail in reference to FIGS. 8C and 8D. In some embodiments, the AI/ML algorithm 824 can include one or more NN's, for example, as described in reference to the example NN illustrated in FIG. 8B. The ML/AI 824 processes the medical images and/or patient information 818 of the current patient and generates outputs of identified features and/or risk information 826 of the current patient.

Figure 8B:
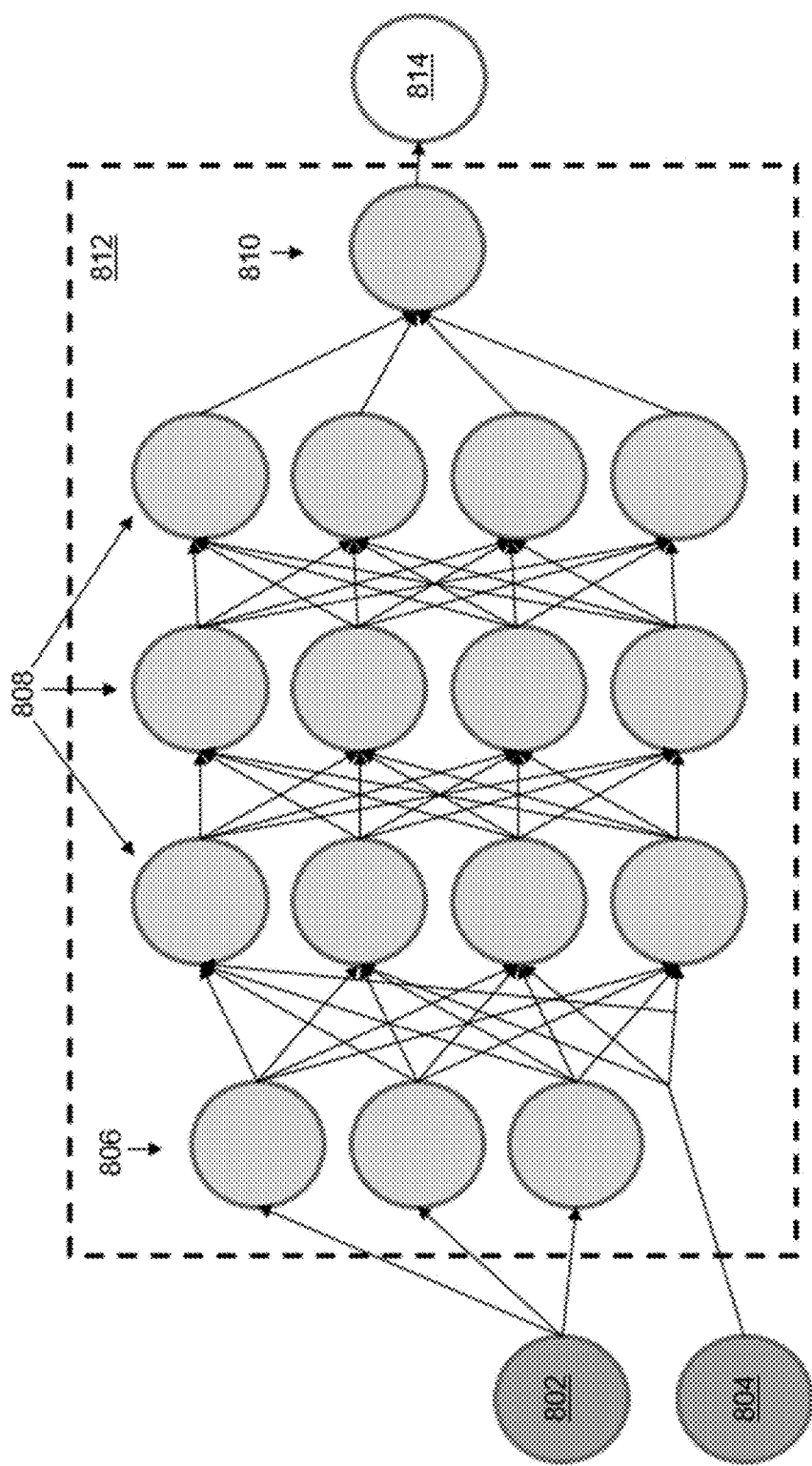
FIG. 8B is a schematic illustrating an example neural network that makes determinations about characteristics of a patient based on medical images.

FIG. 8B is a schematic illustrating an example of a NN 812 that makes determinations 814 about characteristics of a (current) patient based on inputs that include medical images 802. In some embodiments, the NN 812 can be configured to receive other inputs 804. In some embodiments, the other inputs 804 can be medical images of other patients. In some embodiments, the other inputs 804 can be medical history of other patients. In some embodiments, the other inputs 804 can be medical history of the (current) patient. The NN 812 can include an input layer 806. In some embodiments, the NN 812 can be configured to present the training pattern to the input layer 806. In some embodiments, the NN 812 can include one or more hidden layers 808. In some embodiments, the input layer 806 can provide signals to the hidden layers 808, and the hidden layers 808 can receive signals from the input layer 806. In some embodiments, the hidden layers 808 can pass signals to the output layer 810. In some embodiments, one or more hidden layers 808 may be configured as convolutional layers (comprising neurons/nodes connected by weights, the weights corresponding to the strength of the connection between neurons), pooling layers, fully connected layers and/or normalization layers. In some embodiments, the NN 812 may be configured with pooling layers that combine outputs of neuron clusters at one layer into a single neuron in the next layer. In some embodiments, max pooling and/or average pooling may be utilized. In some embodiments, max pooling may utilize the maximum value from each of a cluster of neurons at the prior layer. In some embodiments, back propagation may be utilized, and the corresponding neural network weights may be adjusted to minimize or reduce the error. In some embodiments, the loss function may comprise the Binary Cross Entropy loss function.

In some embodiments, the NN 812 can include an output layer 810. In some embodiments, the output layer 810 can receive signals from the hidden layers 808. In some embodiments, the output layer can generate determinations 814. In some embodiments, the NN 812 can make determinations 814 about characteristics of the patient. In some embodiments, the determinations 814 can include a characterized set of plaque. In some embodiments, the determinations 814 can include a patient's risk of CAD.

Figure 8C:
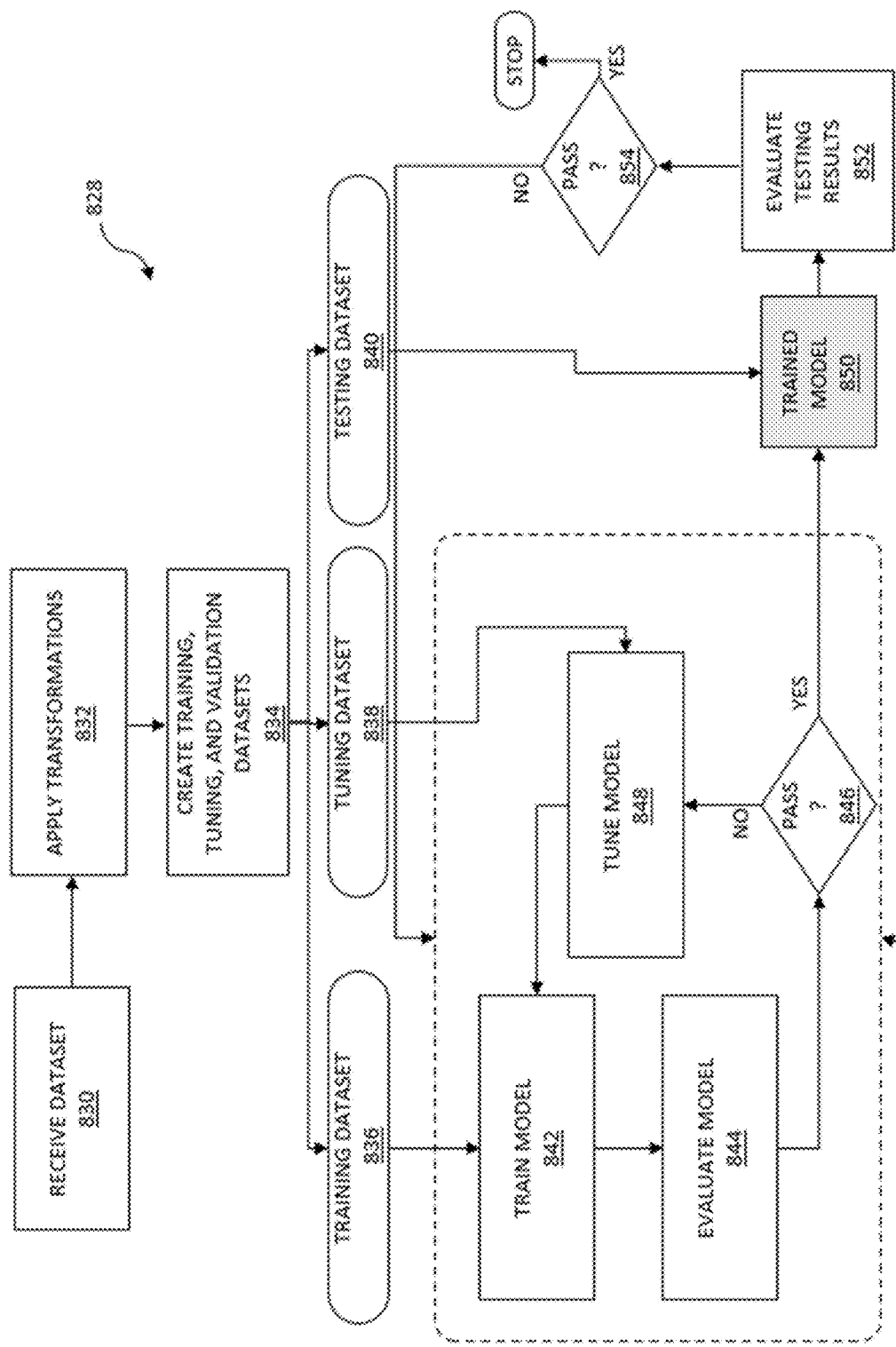
FIG. 8C depicts a flow chart for training an artificial intelligence or machine learning model according to some embodiments.

FIG. 8C depicts an example of a process in a flow diagram for training an artificial intelligence or machine learning model. The process 828 can be performed on a computing system. Various embodiments of such a process for training an AI or ML model may include additional features, and/or may exclude certain illustrated features (for example, when a transformed dataset is accessed such that "apply transformations" in block 832 does not need to be performed.)

As illustrated in the example of FIG. 8C, at block 830 the system receives a dataset that includes patient health information which can include medical images, user surveys, historical test results, genetic information, and/or other patient information (e.g., height, weight, age, etc.). The dataset can also include non-health information, for example, employment information, income information, transportation information, housing information, distances to pharmacies, and/or distances to healthcare providers.

At block 832, one or more transformations may be performed on the data. In an example, data may require transformations to conform to expected input formats to conform with expected formatting, e.g., date formatting, units (e.g., pounds vs kilograms, Celsius vs Fahrenheit, inches vs centimeters, etc.), address conventions, be of a consistent format, and the like. In some embodiments, addresses can be converted, or altered, to be of a consistent format and/or to conform to standards published by the United States Postal Service or a similar postal authority. In some embodiments, the data may undergo conversions to prepare it for use in training an AI or ML algorithm, for example, categorical data may be encoded in a particular manner. In some embodiments, nominal data may be encoded using one-hot encoding, binary encoding, feature hashing, or other suitable encoding methods. In some embodiments, ordinal data may be encoded using ordinal encoding, polynomial encoding, Helmert encoding, and so forth. In some embodiments, numerical data may be normalized, for example by scaling data to a maximum of 1 and a minimum of 0 or −1. These are merely examples, and the skilled artisan will readily appreciate that other transformations are possible.

At block 834, the system may create, from the received dataset, training, tuning, and testing/validation datasets. In some embodiments, the training dataset 836 may be used during training to determine features for forming a predictive model. In some embodiments, the tuning dataset 838 may be used to select final models and to prevent or correct overfitting that may occur during training with the training dataset 836, as the trained model should be generally applicable to a broad spectrum of patients. In some embodiments, the testing dataset 840 may be used after training and tuning to evaluate the model. For example, in some embodiments, the testing dataset 840 may be used to check if the model is overfitted to the training dataset. In some embodiments, the system, in training loop 856, may train the model at block 842 using the training dataset 836. In some embodiments, training may be conducted in a supervised, unsupervised, or partially supervised manner. At 844, in some embodiments, the system may evaluate the model according to one or more evaluation criteria. For example, in some embodiments, the evaluation may include determining how often the model determines reasonable scores for a patient's risk of CAD. At 846, in some embodiments, the system may determine if the model meets the one or more evaluation criteria. In some embodiments, if the model fails evaluation, the system may, at 848, tune the model using the tuning dataset 838, repeating the training 842 and evaluation 844 until the model passes the evaluation at 846. In some embodiments, once the model passes the evaluation at 846, the system may exit the model training loop 856. In some embodiments, the testing dataset 836 may be run through the trained model 842 and, at block 844, the system may evaluate the results. In some embodiments, if the evaluation fails, at block 846, the system may reenter training loop 856 for additional training and tuning. If the model passes, the system may stop the training process, resulting in a trained model 850. In some embodiments, the training process may be modified. For example, in some embodiments, the system may not use a tuning dataset 838. In some embodiments, the model may not use a testing dataset 840.

While described above with respect to determining risk scores for CAD, a model can be trained for use in a wide variety of problems.

Figure 8D:
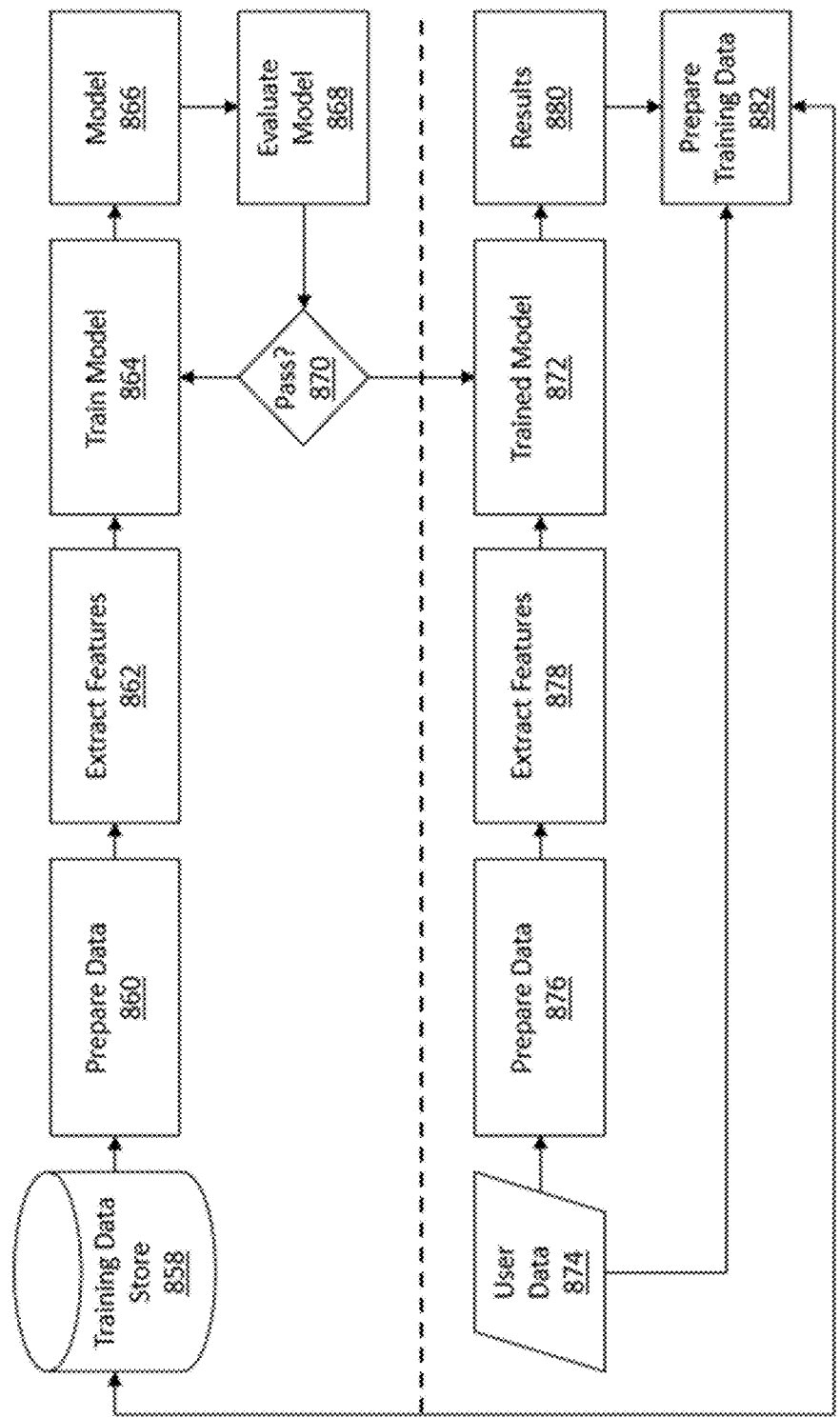
FIG. 8D illustrates an example of training and using an AI/ML model according to some embodiments.

FIG. 8D illustrates an example of a process for training and using an AI/ML model. In some embodiments, the process of FIG. 8D can be used for various purposes, e.g., to determine risk scores of CAD for a patient or to characterize plaque. In some embodiments, training data store 858 can store data for training a model. For example, in some embodiments, training data store 858 can store a patient's medical images, as well as information about patient's health, age, socioeconomic status, employment status, housing arrangements, transportation, and so forth. In some embodiments, the training data can be annotated to include information about user outcomes. For example, in some embodiments, the user outcomes can indicate whether a user had to miss work due to illness, was hospitalized, visited an emergency room, visited an urgent care facility, and so forth. In some embodiments, the training data can indicate whether a user received medication to treat an illness at home, treatments delivered at a hospital or other healthcare facility, did not receive any treatment, and so forth. At block 860, in some embodiments, a system can be configured to prepare the training data if it was not previously prepared for use in training a model. In some embodiments, as described briefly above, preparing the training data can include performing one or more normalization procedures, standardization procedures, and so forth, such as converting units (e.g., between Fahrenheit and Celsius, between inches and centimeters, between pounds and kilograms), converting dates to a standard format, converting times to a standard format, and so forth. In some embodiments, similar treatments or symptoms may be described or coded differently by different healthcare providers. In some embodiments, different providers may use different coding schemes. In some embodiments, even within a particular coding scheme, providers may select different codes to indicate similar information. In some embodiments, a large number of similar codes can lead to variances in coding. Thus, in some embodiments, a code can be changed to another related code. In some embodiments, certain codes can be excluded if they are not relevant to the issue that the model is intended to address. In some embodiments, it can be desirable to exclude certain data as additional data can consume additional computing resources and it can take longer to train a model. However, in some embodiments, exclusions may not be desirable as there can be a risk of excluding a factor that actually is relevant to the patient's risk. In some embodiments, data preparation at block 860 can include modifying or removing coding data, treatment data, and so forth. At block 862, the system can extract features from the training data and, at block 864, can train the model using the training data to produce model 866. At block 868, in some embodiments, the system can evaluate the model to determine if it passes one or more criteria. In some embodiments, at decision point 870, if the model fails, the system can perform additional training. In some embodiments, if, at decision point 870, the model passes, the system can make available trained model 872, which can be the model 872 after training is complete.

In some embodiments, the trained model 872 can be used to evaluate a particular user. The user data 874 can relate to a specific user for whom the outputs of the trained model 872 are desired. At block 876, the system can prepare the data, for example as described above in relations to the stored training data. In some embodiments, at block 878, the system can extract features from the prepared user data. In some embodiments, the system can be configured to feed the extracted features to the trained model 872 to produce results 880. The results 880 can be used to, for example, to determine a risk level associated with the user and/or to determine one or more risk sub-scores for the user.

In some embodiments, the user data 874, the results 880, and other information about the user (e.g., information about the user's outcomes after either receiving or not receiving treatment for plaque-based disease) can be used to train the model. At block 882, in some embodiments, the system can user prepare the user data 874 and the results 880 for use in training. In some embodiments, preparing the data can include, for example, anonymizing the data. For example, in some embodiments, any information about the patient's name, social security number, or other information that could personally identify the patient can be removed. In some embodiments, the system can anonymize the user data 874 in part by altering the user's birthday, for example retaining only the year the user was born (as age is often an important factor in evaluating ask) or the year and month the user was born. In some embodiments, the system can store the prepared data in training data store 858. In some embodiments, the prepared data can be stored, additionally or alternatively, in another database or data store. In some embodiments, the system can retrain the model on periodically, continuously, or whenever an operator indicates to the system that the model should be retrained. Thus, in some embodiments, the trained model 872 can evolve over time, which can result in, for example, improved risk evaluation over time as the model is trained on additional data.

Figure 9:
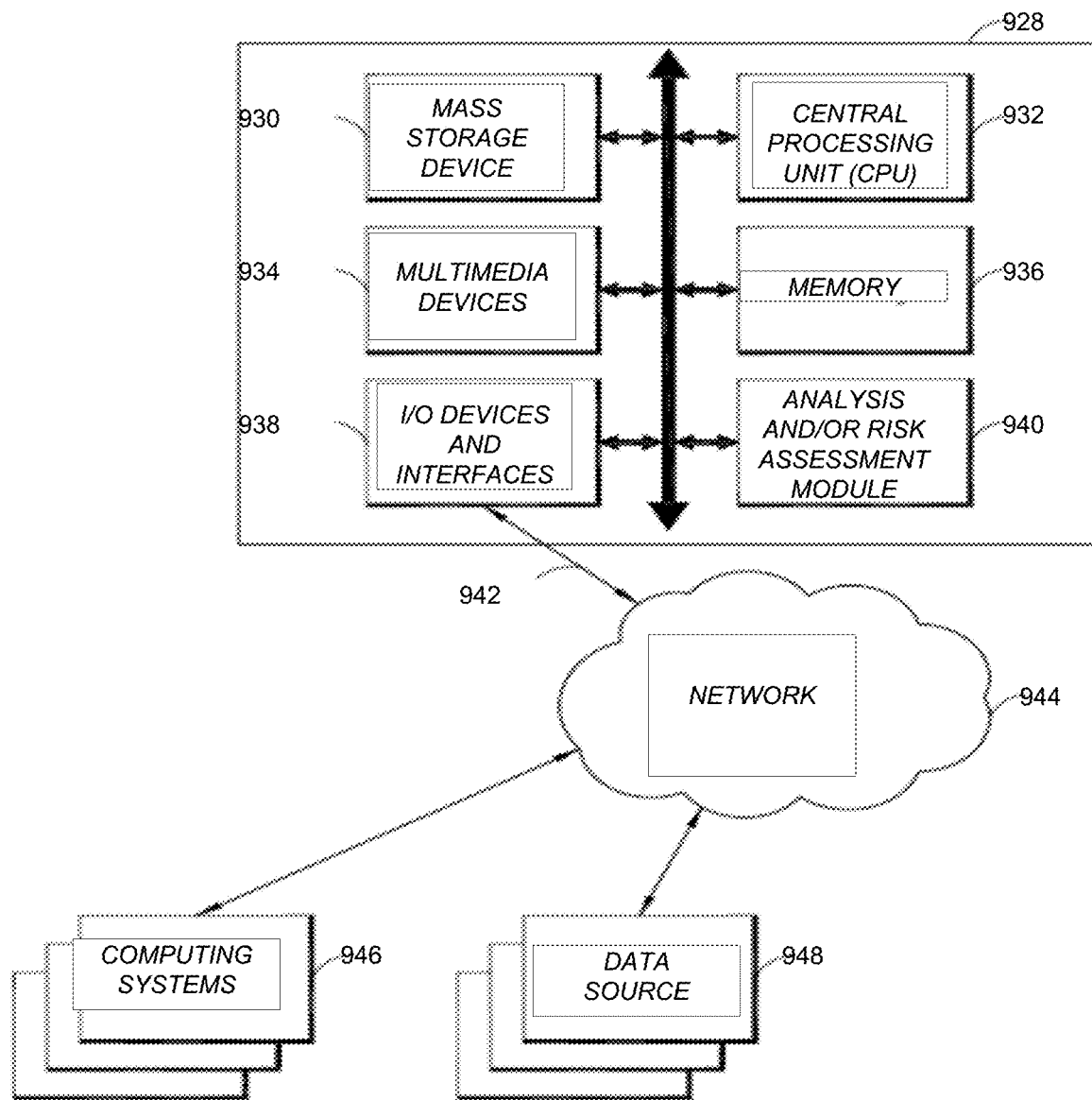
FIG. 9 is a block diagram depicting an embodiment(s) of a computer hardware system configured to run software for implementing one or more embodiments of systems, devices, and methods described herein.

In some embodiments, the systems, processes, and methods described herein are implemented using a computing system, such as the one illustrated in FIG. 9. The example computer system 928 is in communication with one or more computing systems 946 and/or one or more data sources 948 via one or more networks 944. While FIG. 9 illustrates an embodiment of a computing system 928, it is recognized that the functionality provided for in the components and modules of computer system 928 can be combined into fewer components and modules, or further separated into additional components and modules.

The computer system 928 can comprise a plaque analysis and/or risk assessment module 940 that carries out the functions, methods, acts, and/or processes described herein. The plaque analysis and/or risk assessment module 940 executed on the computer system 928 by a central processing unit 932 discussed further below.

In general the word "module," as used herein, refers to logic embodied in hardware or firmware or to a collection of software instructions, having entry and exit points. Modules are written in a program language, such as JAVA, C, or C++, or the like. Software modules can be compiled or linked into an executable program, installed in a dynamic link library, or can be written in an interpreted language such as BASIC, PERL, LAU, PHP or Python and any such languages. Software modules can be called from other modules or from themselves, and/or can be invoked in response to detected events or interruptions. Modules implemented in hardware include connected logic units such as gates and flip-flops, and/or can include programmable units, such as programmable gate arrays or processors.

Generally, the modules described herein refer to logical modules that can be combined with other modules or divided into sub-modules despite their physical organization or storage. The modules are executed by one or more computing systems, and can be stored on or within any suitable computer readable medium, or implemented in-whole or in-part within special designed hardware or firmware. Not all calculations, analysis, and/or optimization require the use of computer systems, though any of the above-described methods, calculations, processes, or analyses can be facilitated through the use of computers. Further, in some embodiments, process blocks described herein can be altered, rearranged, combined, and/or omitted.

The computer system 928 includes one or more processing units (CPU) 932, which can comprise a microprocessor. The computer system 928 further includes a physical memory 936, such as random access memory (RAM) for temporary storage of information, a read only memory (ROM) for permanent storage of information, and a mass storage device 930, such as a backing store, hard drive, rotating magnetic disks, solid state disks (SSD), flash memory, phase-change memory (PCM), 3D XPoint memory, diskette, or optical media storage device. Alternatively, the mass storage device can be implemented in an array of servers. Typically, the components of the computer system 928 are connected to the computer using a standards based bus system. The bus system can be implemented using various protocols, such as Peripheral Component Interconnect (PCI), Micro Channel, SCSI, Industrial Standard Architecture (ISA) and Extended ISA (EISA) architectures.

The computer system 928 includes one or more input/output (I/O) devices and interfaces 938, such as a keyboard, mouse, touch pad, and printer. The I/O devices and interfaces 938 can include one or more display devices, such as a monitor, which allows the visual presentation of data to a user. More particularly, a display device provides for the presentation of GUIs as application software data, and multi-media presentations, for example. The I/O devices and interfaces 938 can also provide a communications interface to various external devices. The computer system 928 can comprise one or more multi-media devices 934, such as speakers, video cards, graphics accelerators, and microphones, for example.

The computer system 928 can run on a variety of computing devices, such as a server, a Windows server, a Structure Query Language server, a Unix Server, a personal computer, a laptop computer, and so forth. In other embodiments, the computer system 928 can run on a cluster computer system, a mainframe computer system and/or other computing system suitable for controlling and/or communicating with large databases, performing high volume transaction processing, and generating reports from large databases. The computing system 928 is generally controlled and coordinated by an operating system software, such as z/OS, Windows, Linux, UNIX, BSD, PHP, SunOS, Solaris, MacOS, ICloud services or other compatible operating systems, including proprietary operating systems. Operating systems control and schedule computer processes for execution, perform memory management, provide file system, networking, and I/O services, and provide a user interface, such as a graphical user interface (GUI), among other things.

The computer system 928 illustrated in FIG. 9 is coupled to a network 944, such as a LAN, WAN, or the Internet via a communication link 942 (wired, wireless, or a combination thereof). Network 944 communicates with various computing devices and/or other electronic devices. Network 944 is communicating with one or more computing systems 946 and one or more data sources 948. The plaque analysis and/or risk assessment module 940 can access or can be accessed by computing systems 946 and/or data sources 948 through a web-enabled user access point. Connections can be a direct physical connection, a virtual connection, and other connection type. The web-enabled user access point can comprise a browser module that uses text, graphics, audio, video, and other media to present data and to allow interaction with data via the network 944.

The output module can be implemented as a combination of an all-points addressable display such as a cathode ray tube (CRT), a liquid crystal display (LCD), a plasma display, or other types and/or combinations of displays. The output module can be implemented to communicate with input devices 938 and they also include software with the appropriate interfaces which allow a user to access data through the use of stylized screen elements, such as menus, windows, dialogue boxes, tool bars, and controls (for example, radio buttons, check boxes, sliding scales, and so forth). Furthermore, the output module can communicate with a set of input and output devices to receive signals from the user.

The computing system 928 can include one or more internal and/or external data sources (for example, data sources 948). In some embodiments, one or more of the data repositories and the data sources described above can be implemented using a relational database, such as DB2, Sybase, Oracle, CodeBase, and Microsoft® SQL Server as well as other types of databases such as a flat-file database, an entity relationship database, and object-oriented database, and/or a record-based database.

The computer system 928 can also access one or more databases 948. The databases 948 can be stored in a database or data repository. The computer system 928 can access the one or more databases 948 through a network 944 or can directly access the database or data repository through I/O devices and interfaces 938. The data repository storing the one or more databases 948 can reside within the computer system 928.

In some embodiments including any of the embodiments disclosed herein (above or below) one or more features of the systems, methods, and devices described herein can utilize a URL and/or cookies, for example for storing and/or transmitting data or user information. A Uniform Resource Locator (URL) can include a web address and/or a reference to a web resource that is stored on a database and/or a server. The URL can specify the location of the resource on a computer and/or a computer network. The URL can include a mechanism to retrieve the network resource. The source of the network resource can receive a URL, identify the location of the web resource, and transmit the web resource back to the requestor. A URL can be converted to an IP address, and a Domain Name System (DNS) can look up the URL and its corresponding IP address. URLs can be references to web pages, file transfers, emails, database accesses, and other applications. The URLs can include a sequence of characters that identify a path, domain name, a file extension, a host name, a query, a fragment, scheme, a protocol identifier, a port number, a username, a password, a flag, an object, a resource name and/or the like. The systems disclosed herein can generate, receive, transmit, apply, parse, serialize, render, and/or perform an action on a URL.

A cookie, also referred to as an HTTP cookie, a web cookie, an internet cookie, and a browser cookie, can include data sent from a website and/or stored on a user's computer. This data can be stored by a user's web browser while the user is browsing. The cookies can include useful information for websites to remember prior browsing information, such as a shopping cart on an online store, clicking of buttons, login information, and/or records of web pages or network resources visited in the past. Cookies can also include information that the user enters, such as names, addresses, passwords, credit card information, etc. Cookies can also perform computer functions. For example, authentication cookies can be used by applications (for example, a web browser) to identify whether the user is already logged in (for example, to a web site). The cookie data can be encrypted to provide security for the consumer. Tracking cookies can be used to compile historical browsing histories of individuals. Systems disclosed herein can generate and use cookies to access data of an individual. Systems can also generate and use JSON web tokens to store authenticity information, HTTP authentication as authentication protocols, IP addresses to track session or identity information, URLs, and the like.

Image-Based Risk Assessment of Ischemia

Various embodiments described herein relate to systems, devices, and methods for non-invasive image-based risk assessment of ischemia. In particular, in some embodiments, the systems, devices, and methods described herein are related to facilitating risk assessment of an ischemic lesion based at least in part on non-invasive medical image analysis of myocardium subtended by the ischemic lesion. In some embodiments, the systems, devices, and methods described herein use the amount of myocardium subtended and the position on the artery tree to determine a risk level. In some embodiments, the systems, devices, and methods described herein determine that the higher the ischemic lesion is on the artery tree, the more myocardium the ischemic lesion will subtend. In some embodiments, the systems, devices, and methods described herein determine that the lower the ischemic lesion is on the artery tree, the less myocardium the ischemic lesion will subtend. In some embodiments, the systems, devices, and methods described herein determine that a higher amount of subtended myocardium results in a higher risk. In some embodiments, the systems, devices, and methods described herein determine that a lower amount of subtended myocardium results in a lower risk. In some embodiments, the systems, devices, and methods described herein generate a graphical representation of the risk level. In some embodiments, the graphical representation is a caricature of the heart. In some embodiments, the graphical representation is a display of the volume of myocardium subtended or not subtended by a specific ischemic lesion. In some embodiments, the systems, devices, and methods described herein can be repeated for different ischemic lesions and displayed together in a single graphical representation. In some embodiments, the user can select one ischemic lesion, which will then highlight or show in a different color the portion of the myocardium subtended by that ischemic lesion. In some embodiments, the systems, devices, and methods described herein can generate a myocardial perfusion map representing perfusion of blood through the myocardium subtended by the ischemic lesion. In some embodiments, the systems, devices, and methods described herein can be used to determine the risk of an ischemic lesion.

Generally speaking, ischemia can refer to a condition in which blood flow and/or oxygen is restricted or reduced in a part of the body. For example, myocardial ischemia can refer to restricted or reduced flow of blood from coronary arteries to the myocardium. Within the coronary arteries, ischemia may be present in one or coronary arteries and/or one or more lesions within one or more coronary arteries. While the presence of ischemia anywhere can be considered a problem, the location or lesion in which ischemia is present can dictate the seriousness or magnitude of the disease. For example, an ischemic lesion may appear anywhere along the coronary artery tree. However, for two equally ischemic lesions, an ischemic lesion appearing higher in the coronary artery tree can be considered more problematic and/or higher risk compared to an ischemic lesion appearing lower in the coronary artery tree. This can be because an ischemic lesion appearing higher in the coronary artery tree, compared to an equally ischemic lesion appearing lower in the coronary artery tree, can affect more downstream coronary arteries and/or myocardium. In other words, an ischemic lesion that feeds into more branches within the coronary artery tree is likely to have an effect on more myocardial mass compared to an equally ischemic lesion that feeds into fewer branches within the coronary artery tree. As such, the location of an ischemic lesion within an artery tree, such as a coronary artery tree, can be important to assess the risk and/or likelihood of the ischemic lesion leading to a major adverse event, such as for example a major adverse cardiovascular event (MACE). For such reasons, the location of an ischemic lesion within an artery tree may have a significant impact in addition to how ischemic a lesion is. However, existing technologies do not determine and/or provide the magnitude of an ischemic lesion based on its location within an artery tree and/or downstream tissue that is affected by the ischemic lesion. Some embodiments of the systems, methods, and devices herein address this technical shortcoming. For example, in some embodiments, the systems, methods, and devices are configured to determine how much tissue is affected by an ischemic lesion and/or generate a visualization thereof to help determine the seriousness, magnitude, and/or potential risk of a major adverse event arising due to the ischemic lesion. In particular, in some embodiments, the systems, devices, and methods are configured to analyze one or more coronary arteries to determine the presence of ischemia and/or determine the myocardium subtended by a particular ischemic lesion, which can be used in turn to determine a risk of MACE for the subject based on that ischemic lesion. In some embodiments, the systems, methods, and devices can be configured to generate a visual and/or graphical representation of myocardium subtended by an ischemic lesion to provide a clinician and/or subject with visual graphic that shows risk associated with the ischemic lesion.

Figure 10:
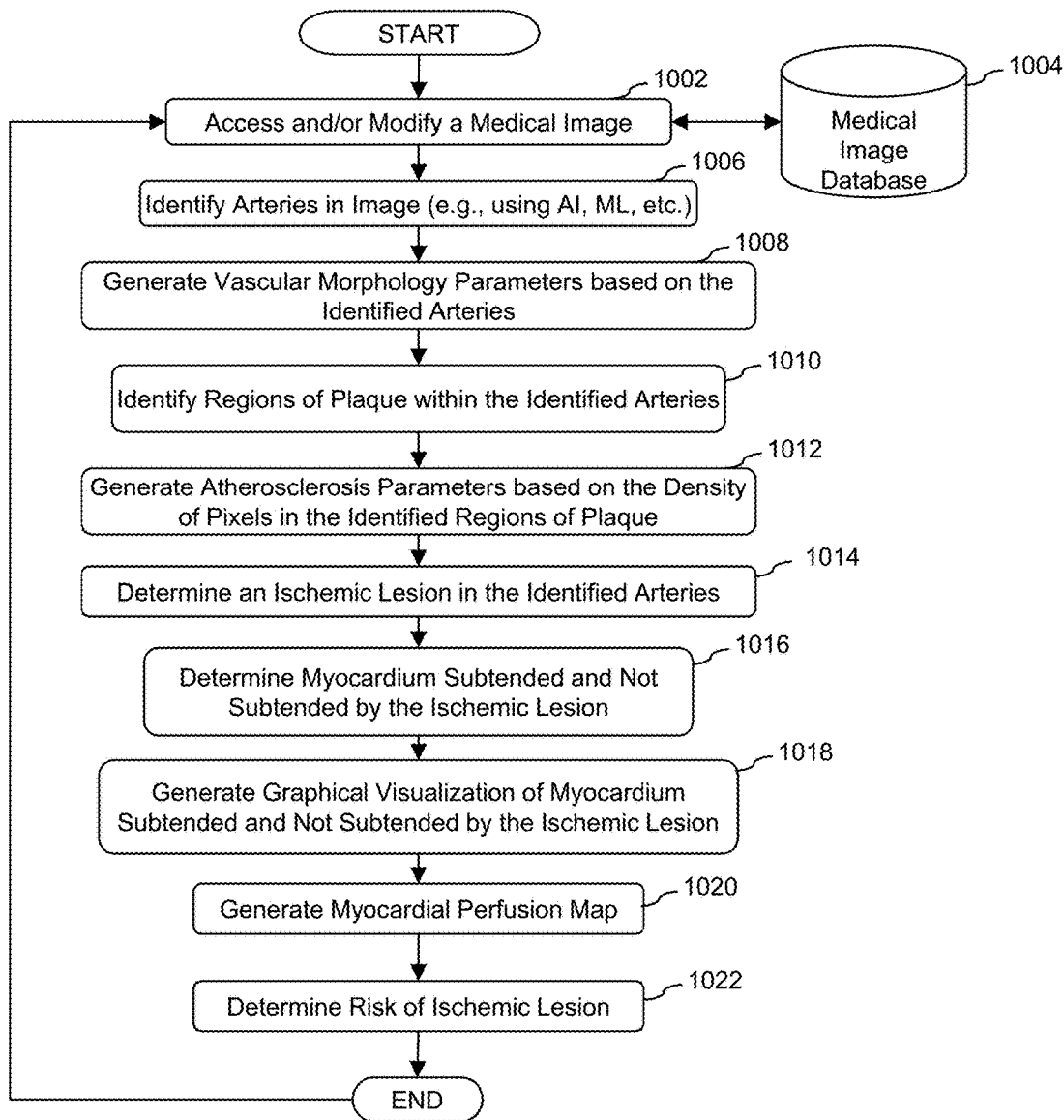
FIG. 10 is a flowchart illustrating an example embodiment(s) of systems, devices, and methods for non-invasive image-based risk assessment of ischemia.

FIG. 10 is a flowchart illustrating an example embodiment(s) of systems, devices, and methods for non-invasive image-based risk assessment of ischemia. As illustrated in FIG. 10, in some embodiments, the system can be configured to access and/or modify one or more medical images at block 1002. In some embodiments, the medical image can include one or more arteries, such as coronary, carotid, and/or other arteries of a subject. In some embodiments, the one or more coronary arteries comprise one or more of left main (LM), ramus intermedius (RI), left anterior descending (LAD), diagonal 1 (D1), diagonal 2 (D2), left circumflex (Cx), obtuse marginal 1 (OM1), obtuse marginal 2 (OM2), left posterior descending artery (L-PDA), left posterolateral branch (L-PLB), right coronary artery (RCA), right posterior descending artery (R-PDA), or right posterolateral branch (R-PLB). In some embodiments, the medical image can be stored in a medical image database 1004. In some embodiments, the medical image database 1004 can be locally accessible by the system and/or can be located remotely and accessible through a network connection. The medical image can comprise an image obtain using one or more modalities such as for example, CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the medical image comprises one or more of a contrast-enhanced CT image, non-contrast CT image, MR image, and/or an image obtained using any of the modalities described above.

In some embodiments, the system can be configured to automatically and/or dynamically perform one or more analyses of the medical image as discussed herein. For example, in some embodiments, at block 1006, the system can be configured to identify one or more vessels, such as of one or more arteries. The one or more arteries can include coronary arteries, carotid arteries, aorta, renal artery, lower extremity artery, upper extremity artery, and/or cerebral artery, amongst others. In some embodiments, the system can be configured to utilize one or more AI and/or ML algorithms to automatically and/or dynamically identify one or more arteries or coronary arteries using image processing. For example, in some embodiments, the one or more AI and/or ML algorithms can be trained using a Convolutional Neural Network (CNN) on a set of medical images on which arteries or coronary arteries have been identified, thereby allowing the AI and/or ML algorithm automatically identify arteries or coronary arteries directly from a medical image. In some embodiments, the arteries or coronary arteries are identified by size and/or location.

In some embodiments, at block 1008, the system can be configured to identify one or more regions of plaque in the medical image. In some embodiments, the system can be configured to utilize one or more AI and/or ML algorithms to automatically and/or dynamically identify one or more regions of plaque using image processing. For example, in some embodiments, the one or more AI and/or ML algorithms can be trained using a Convolutional Neural Network (CNN) on a set of medical images on which regions of plaque have been identified, thereby allowing the AI and/or ML algorithm automatically identify regions of plaque directly from a medical image. In some embodiments, the system is configured to identify vessel and lumen walls and classify everything in between the vessel and lumen walls as plaque.

In some embodiments, at block 1010, the system can be configured to analyze and/or characterize one or more regions of plaque based on density. For example, in some embodiments, the system can be configured to analyze and/or characterize one or more regions of plaque based on absolute density and/or relative density and/or radiodensity. In some embodiments, the volume of the one or more regions of plaque is determined based at least in part on analyzing density of one or more pixels corresponding to the one or more regions of plaque in the medical image. In some embodiments, low density non-calcified plaque corresponds to one or more pixels with a radiodensity value between about −189 and about 30 Hounsfield units. In some embodiments, non-calcified plaque corresponds to one or more pixels with a radiodensity value between about 190 and about 350 Hounsfield units. calcified plaque corresponds to one or more pixels with a radiodensity value between about 351 and 2500 Hounsfield units. In some embodiments, the system can be configured to classify a region of plaque as one of low density non-calcified plaque, non-calcified plaque, and calcified plaque, using any one or more processes and/or features described herein.

In some embodiments, at block 1012, the system can be configured to analyze and/or characterize one or more regions of plaque based on one or more distances. For example, as described herein, in some embodiments, the system can be configured to determine a distance between a low density non-calcified plaque and lumen wall and/or vessel wall. In some embodiments, proximity of a low density non-calcified plaque to the lumen wall can be indicative of a high-risk plaque and/or CAD. Conversely, in some embodiments, a position of a low density non-calcified plaque far from the lumen wall can be indicative of less risk. In some embodiments, the system can be configured to utilize one or more predetermined thresholds in determining the risk factor associated with the proximity of low density non-calcified plaque with the vessel wall and/or lumen wall. In some embodiments, the system can be configured to utilize one or more image processing algorithms to automatically and/or dynamically determine one or more distances to and/or from one or more regions of plaque.

In some embodiments, at block 1012, the system can be configured to analyze and/or characterize one or more regions of plaque based on morphology or shape and/or one or more axes measurements of low density non-calcified plaque. As described herein, in some embodiments, the system can be configured to determine the length of one or more axes of a low density non-calcified plaque, such as for example a major axis of a longitudinal cross section and/or a major and/or minor axis of a latitudinal cross section of a low density non-calcified plaque. In some embodiments, the system can be configured to utilize the one more axes measurements to determine a morphology and/or shape of a low density non-calcified plaque. In some embodiments, the system can be configured to utilize one or more image processing algorithms to automatically and/or dynamically determine one or more axes measurements of one or more regions of plaque.

In some embodiments, the system can be configured to utilize one or more AI and/or ML algorithms to automatically and/or dynamically classify the shape of one or more regions of plaque using image processing. For example, in some embodiments, the one or more AI and/or ML algorithms can be trained using a Convolutional Neural Network (CNN) on a set of medical images on which the shape of regions of plaque have been identified, thereby allowing the AI and/or ML algorithm automatically identify the shape or morphology of a region of plaque directly from a medical image. In some embodiments, the system can be configured to classify the shape or morphology of a region of plaque as one or more of crescent, lobular, round, or bean-shaped. In some embodiments, round and/or bean-shaped plaques can be associated with high risk, while crescent and/or lobular-shaped plaques can be associated with low risk of CAD.

In some embodiments, at block 1012, the system can be configured to analyze and/or characterize one or more regions of plaque based on one or more sizes and/or volumes. For example, in some embodiments, the system can be configured to determine a size and/or volume of plaque based at least in part on one or more axes measurements described herein. In some embodiments, the system can be configured to determine the size and/or volume of a region of plaque directly from analysis of a three-dimensional image scan. In some embodiments, the system can be configured to determine the size and/or volume of total plaque, low-density non-calcified plaque, non-calcified plaque, calcified plaque, and/or a ratio between two of the aforementioned volumes or sizes. In some embodiments, a high total plaque volume and/or high low-density non-calcified plaque and/or non-calcified plaque volume can be associated with high risk of CAD. In some embodiments, a high ratio of low-density non-calcified plaque volume to total plaque volume and/or a high ratio of non-calcified plaque volume to total plaque volume can be associated with high risk of CAD. In some embodiments, a high calcified plaque volume and/or high ratio of calcified plaque volume to total plaque volume can be associated with low risk of CAD. In some embodiments, the system can be configured to utilize one or more predetermined threshold values for determining the risk of CAD based on plaque volume, size, or one or more ratios thereof. In some embodiments, the system can be configured to utilize one or more image processing algorithms to automatically and/or dynamically determine the size and/or volume of one or more regions of plaque.

In some embodiments, at block 1012, the system can be configured to analyze and/or characterize plaque based on embeddedness. For example, in some embodiments, the system can be configured to determine how embedded or surrounded a low density non-calcified plaque is by non-calcified plaque or calcified plaque. In some embodiments, the system can be configured to analyze the embeddedness of low density non-calcified plaque based on the degree by which it is surrounded by other types of plaque. In some embodiments, a higher embeddedness of a low density non-calcified plaque can be indicative of high risk of CAD. For example, in some embodiments, a low density non-calcified plaque that is surrounded by 270 degrees or more by non-calcified plaque can be associated with high risk of CAD. In some embodiments, the system can be configured to utilize one or more image processing algorithms to automatically and/or dynamically determine the embeddedness of one or more regions of plaque.

In some embodiments, at block 1014, the system can be configured to determine an ischemic lesion in the plurality of vessels based at least in part on the plurality of plaque parameters. In some embodiments, the plurality of plaque parameters comprises one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, or low-density plaque volume. In some embodiments, the ischemic lesion in the plurality of vessels is determined by a machine learning algorithm. In some embodiments, the machine learning algorithm is trained based at least in part on a dataset comprising the plurality of plaque parameters and presence of ischemia derived using invasive fractional flow reserve. In some embodiments, the machine learning algorithm is trained based at least in part on a dataset comprising the plurality of plaque parameters and presence of ischemia derived using one or more of CT fractional flow reserve, computational fractional flow reserve, virtual fractional flow reserve, vessel fractional flow reserve, or quantitative flow ratio.

In some embodiments, at block 1016, the system can be configured to determine myocardium subtended by the ischemic lesion and myocardium not subtended by the ischemic lesion based at least in part on mapping of the plurality of vessels. In some embodiments, if the ischemic lesion appears higher up in the artery tree, the system can determine that the vessel that includes the ischemic lesion will subtend more myocardium, and therefore be related to higher risk. In some embodiments, if the ischemic lesion appears lower in the artery tree, the system can determine that the vessel that includes the ischemic lesion will subtend less myocardium and be related to lower risk. In some embodiments, an ischemic lesion being higher up in the artery tree means the ischemic lesion feeds into more branches of the artery tree. In some embodiments, an ischemic lesion being lower in the artery tree means the ischemic lesion feeds into fewer branches of the artery tree. In some embodiments, the system can be configured to generate an assessment of risk of coronary artery disease (CAD) or major adverse cardiovascular event (MACE) of the subject based at least in part on the myocardium subtended by the ischemic lesion. In some embodiments, the system can be configured to generate a graphical representation of the assessment of risk of CAD or MACE. In some embodiments, the system can be configured to generate a recommended treatment for the subject based at least in part on the assessment of risk of CAD or MACE.

In some embodiments, at block 1018, the system can be configured to generate a graphical visualization of the myocardium subtended by the ischemic lesion and/or the myocardium not subtended by the ischemic lesion. In some embodiments, the graphical visualization comprises a graphical representation of the myocardium. In some embodiments, the graphical visualization comprises a representation of volume of the myocardium subtended by the ischemic lesion. In some embodiments, the graphical visualization comprises a representation of volume of the myocardium subtended by the ischemic lesion and a representation of volume of the myocardium not subtended by the ischemic lesion. In some embodiments, the graphical visualization comprises a caricature of the myocardium subtended by the ischemic lesion. In some embodiments, the graphical visualization comprises a caricature of the myocardium subtended by the ischemic lesion and the myocardium not subtended by the ischemic lesion. In some embodiments, the graphical visualization comprises a caricature of the heart. In some embodiments, the graphical visualization comprises a display of the volume of myocardium subtended or not subtended by a specific ischemic lesion. In some embodiments, the system herein can be repeated for different ischemic lesions and be shown together in a single graphical representation. In some embodiments, the user can select one ischemic lesion, which will then highlight or show in a different color the portion of the myocardium subtended by that ischemic lesion.

In some embodiments, at block 1020, the system can be configured to generate a myocardial perfusion map representing perfusion of blood through the myocardium subtended by the ischemic lesion. In some embodiments, the system can be configured to generate an overlap of the myocardial perfusion map with the graphical visualization of the myocardium subtended by the ischemic lesion. In some embodiments, the myocardial perfusion map is configured to be used to determine presence of a perfusion defect in the myocardium subtended by the ischemic lesion. In some embodiments, the perfusion defect appearing smaller than the myocardium subtended by the ischemic lesion is indicative of collateral vessels providing blood to the myocardium subtended by the ischemic lesion. In some embodiments, the perfusion defect appearing larger than the myocardium subtended by the ischemic lesion is indicative of additional disease.

In some embodiments, at block 1022, the system can be configured to determine the risk of the ischemic lesion to the subject. In some embodiments, the graphical visualization of the myocardium subtended by the ischemic lesion compared to the myocardium not subtended by the ischemic lesion is configured to be utilized to determine risk of the ischemic lesion to the subject. In some embodiments, a higher amount of myocardium subtended by the ischemic lesion is indicative of higher risk compared to a lower amount of myocardium subtended by the ischemic lesion. In some embodiments, having more myocardium subtended in vessels higher up in a vessel tree results in a higher risk. In some embodiments, the determination of risk is presented as a displayed number. In some embodiments, the graphical visualization comprises a caricature of the heart. In some embodiments, the graphical visualization comprises a display of the volume of myocardium subtended or not subtended by a specific ischemic lesion. In some embodiments, the system herein can be repeated for different ischemic lesions and be shown together in a single graphical representation. In some embodiments, the user can select one ischemic lesion, which will then highlight or show in a different color the portion of the myocardium subtended by that ischemic lesion.

The computer system 902 of FIG. 9, and in some instances, the analysis and/or risk assessment module 940, can be configured to carry out the functions, methods, acts, and/or processes for image-based risk assessment of ischemia described herein, such as those described above with reference to FIG. 10.

The following are non-limiting examples of certain embodiments of systems and methods for image-based risk assessment of ischemia. Other embodiments may include one or more other features, or different features, that are discussed herein.

Embodiment 1: A computer-implemented method of facilitating risk assessment of an ischemic lesion based at least in part on non-invasive medical image analysis of myocardium subtended by the ischemic lesion, the method comprising: accessing, by a computer system, a medical image of a subject, wherein the medical image of the subject is obtained non-invasively; analyzing, by the computer system, the medical image of the subject to map a plurality of vessels, the plurality of vessels comprising one or more regions of plaque; identifying, by the computer system, the one or more regions of plaque within the plurality of vessels; analyzing, by the computer system, the one or more regions of plaque to generate a plurality of plaque parameters, the plurality of plaque parameters comprising density and volume of the one or more regions of plaque; determining, by the computer system, an ischemic lesion in the plurality of vessels based at least in part on the plurality of plaque parameters; determining, by the computer system, myocardium subtended by the ischemic lesion and myocardium not subtended by the ischemic lesion based at least in part on mapping of the plurality of vessels; and generating, by the computer system, a graphical visualization of the myocardium subtended by the ischemic lesion and the myocardium not subtended by the ischemic lesion, wherein the graphical visualization of the myocardium subtended by the ischemic lesion compared to the myocardium not subtended by the ischemic lesion is configured to be utilized to determine risk of the ischemic lesion to the subject, wherein a higher amount of myocardium subtended by the ischemic lesion is indicative of higher risk compared to a lower amount of myocardium subtended by the ischemic lesion, wherein the computer system comprises a computer processor and an electronic storage medium.

Embodiment 2: The computer-implemented method of Embodiment 1, wherein the graphical visualization comprises a graphical representation of the myocardium.

Embodiment 3: The computer-implemented method of Embodiment 1, wherein the graphical visualization comprises a representation of volume of the myocardium subtended by the ischemic lesion.

Embodiment 4: The computer-implemented method of Embodiment 1, wherein the graphical visualization comprises a representation of volume of the myocardium subtended by the ischemic lesion and a representation of volume of the myocardium not subtended by the ischemic lesion.

Embodiment 5: The computer-implemented method of Embodiment 1, wherein the graphical visualization comprises a caricature of the myocardium subtended by the ischemic lesion.

Embodiment 6: The computer-implemented method of Embodiment 1, wherein the graphical visualization comprises a caricature of the myocardium subtended by the ischemic lesion and the myocardium not subtended by the ischemic lesion.

Embodiment 7: The computer-implemented method of Embodiment 1, wherein the plurality of plaque parameters comprises stenosis.

Embodiment 8: The computer-implemented method of Embodiment 1, wherein the volume of the one or more regions of plaque comprises one or more of volume of total plaque, volume of low density non-calcified plaque, volume of non-calcified plaque, or volume of calcified plaque.

Embodiment 9: The computer-implemented method of Embodiment 8, wherein the volume of the one or more regions of plaque is determined based at least in part on analyzing density of one or more pixels corresponding to the one or more regions of plaque in the medical image.

Embodiment 10: The computer-implemented method of Embodiment 9, wherein the density comprises material density.

Embodiment 11: The computer-implemented method of Embodiment 9, wherein the density comprises radiodensity.

Embodiment 12: The computer-implemented method of Embodiment 11, wherein low density non-calcified plaque corresponds to one or more pixels with a radiodensity value between about −189 and about 30 Hounsfield units.

Embodiment 13: The computer-implemented method of Embodiment 11, wherein non-calcified plaque corresponds to one or more pixels with a radiodensity value between about 190 and about 350 Hounsfield units.

Embodiment 14: The computer-implemented method of Embodiment 11, wherein calcified plaque corresponds to one or more pixels with a radiodensity value between about 351 and 2500 Hounsfield units.

Embodiment 15: The computer-implemented method of Embodiment 1, wherein the medical image comprises a Computed Tomography (CT) image.

Embodiment 16: The computer-implemented method of Embodiment 1, wherein the medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 17: The computer-implemented method of Embodiment 1, wherein the plurality of plaque parameters comprises one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, or low-density plaque volume.

Embodiment 18: The computer-implemented method of Embodiment 1, wherein the plurality of vessels comprises one or more coronary arteries.

Embodiment 19: The computer-implemented method of Embodiment 18, wherein the one or more coronary arteries comprise one or more of left main (LM), ramus intermedius (RI), left anterior descending (LAD), diagonal 1 (D1), diagonal 2 (D2), left circumflex (Cx), obtuse marginal 1 (OM1), obtuse marginal 2 (OM2), left posterior descending artery (L-PDA), left posterolateral branch (L-PLB), right coronary artery (RCA), right posterior descending artery (R-PDA), or right posterolateral branch (R-PLB).

Embodiment 20: The computer-implemented method of Embodiment 1, wherein the ischemic lesion in the plurality of vessels is determined by a machine learning algorithm.

Embodiment 21: The computer-implemented method of Embodiment 20, wherein the machine learning algorithm is trained based at least in part on a dataset comprising the plurality of plaque parameters and presence of ischemia derived using invasive fractional flow reserve.

Embodiment 22: The computer-implemented method of Embodiment 20, wherein the machine learning algorithm is trained based at least in part on a dataset comprising the plurality of plaque parameters and presence of ischemia derived using one or more of CT fractional flow reserve, computational fractional flow reserve, virtual fractional flow reserve, vessel fractional flow reserve, or quantitative flow ratio.

Embodiment 23: The computer-implemented method of Embodiment 1, further comprising generating, by the computer system, an assessment of risk of coronary artery disease (CAD) or major adverse cardiovascular event (MACE) of the subject based at least in part on the myocardium subtended by the ischemic lesion.

Embodiment 24: The computer-implemented method of Embodiment 23, further comprising generating, by the computer system, a graphical representation of the assessment of risk of CAD or MACE.

Embodiment 25: The computer-implemented method of Embodiment 23, further comprising generating, by the computer system, a recommended treatment for the subject based at least in part on the assessment of risk of CAD or MACE.

Embodiment 26: The computer-implemented method of Embodiment 1, further comprising generating, by the computer system, a myocardial perfusion map representing perfusion of blood through the myocardium subtended by the ischemic lesion.

Embodiment 27: The computer-implemented method of Embodiment 26, further comprising generating, by the computer system, an overlap of the myocardial perfusion map with the graphical visualization of the myocardium subtended by the ischemic lesion.

Embodiment 28: The computer-implemented method of Embodiment 26, wherein the myocardial perfusion map is configured to be used to determine presence of a perfusion defect in the myocardium subtended by the ischemic lesion.

Embodiment 29: The computer-implemented method of Embodiment 28, wherein the perfusion defect appearing smaller than the myocardium subtended by the ischemic lesion is indicative of collateral vessels providing blood to the myocardium subtended by the ischemic lesion.

Embodiment 30: The computer-implemented method of Embodiment 28, wherein the perfusion defect appearing larger than the myocardium subtended by the ischemic lesion is indicative of additional disease.

Embodiment 31: A non-transitory computer readable medium configured for facilitating risk assessment of an ischemic lesion based at least in part on non-invasive medical image analysis of myocardium subtended by the ischemic lesion, the computer readable medium having program instructions for causing a hardware processor to perform a method of: accessing, by a computer system, a medical image of a subject, wherein the medical image of the subject is obtained non-invasively; analyzing, by the computer system, the medical image of the subject to map a plurality of vessels, the plurality of vessels comprising one or more regions of plaque; identifying, by the computer system, the one or more regions of plaque within the plurality of vessels; analyzing, by the computer system, the one or more regions of plaque to generate a plurality of plaque parameters, the plurality of plaque parameters comprising density and volume of the one or more regions of plaque; determining, by the computer system, an ischemic lesion in the plurality of vessels based at least in part on the plurality of plaque parameters; determining, by the computer system, myocardium subtended by the ischemic lesion and myocardium not subtended by the ischemic lesion based at least in part on mapping of the plurality of vessels; and generating, by the computer system, a graphical visualization of the myocardium subtended by the ischemic lesion and the myocardium not subtended by the ischemic lesion, wherein the graphical visualization of the myocardium subtended by the ischemic lesion compared to the myocardium not subtended by the ischemic lesion is configured to be utilized to determine risk of the ischemic lesion to the subject, wherein a higher amount of myocardium subtended by the ischemic lesion is indicative of higher risk compared to a lower amount of myocardium subtended by the ischemic lesion, wherein the computer system comprises a computer processor and an electronic storage medium.

Embodiment 32: The non-transitory computer readable medium configured as in Embodiment 31, wherein the graphical visualization comprises a graphical representation of the myocardium.

Embodiment 33: The non-transitory computer readable medium configured as in Embodiment 31, wherein the graphical visualization comprises a representation of volume of the myocardium subtended by the ischemic lesion.

Embodiment 34: The non-transitory computer readable medium configured as in Embodiment 31, wherein the graphical visualization comprises a representation of volume of the myocardium subtended by the ischemic lesion and a representation of volume of the myocardium not subtended by the ischemic lesion.

Embodiment 35: The non-transitory computer readable medium configured as in Embodiment 31, wherein the graphical visualization comprises a caricature of the myocardium subtended by the ischemic lesion.

Embodiment 36: The non-transitory computer readable medium configured as in Embodiment 31, wherein the graphical visualization comprises a caricature of the myocardium subtended by the ischemic lesion and the myocardium not subtended by the ischemic lesion.

Embodiment 37: The non-transitory computer readable medium configured as in Embodiment 31, wherein the plurality of plaque parameters comprises stenosis.

Embodiment 38: The non-transitory computer readable medium configured as in Embodiment 31, wherein the volume of the one or more regions of plaque comprises one or more of volume of total plaque, volume of low density non-calcified plaque, volume of non-calcified plaque, or volume of calcified plaque.

Embodiment 39: The non-transitory computer readable medium configured as in Embodiment 38, wherein the volume of the one or more regions of plaque is determined based at least in part on analyzing density of one or more pixels corresponding to the one or more regions of plaque in the medical image.

Embodiment 40: The non-transitory computer readable medium configured as in Embodiment 39, wherein the density comprises material density.

Embodiment 41: The non-transitory computer readable medium configured as in Embodiment 39, wherein the density comprises radiodensity.

Embodiment 42: The non-transitory computer readable medium configured as in Embodiment 41, wherein low density non-calcified plaque corresponds to one or more pixels with a radiodensity value between about −189 and about 30 Hounsfield units.

Embodiment 43: The non-transitory computer readable medium configured as in Embodiment 41, wherein non-calcified plaque corresponds to one or more pixels with a radiodensity value between about 190 and about 350 Hounsfield units.

Embodiment 44: The non-transitory computer readable medium configured as in Embodiment 41, wherein calcified plaque corresponds to one or more pixels with a radiodensity value between about 351 and 2500 Hounsfield units.

Embodiment 45: The non-transitory computer readable medium configured as in Embodiment 31, wherein the medical image comprises a Computed Tomography (CT) image.

Embodiment 46: The non-transitory computer readable medium configured as in Embodiment 31, wherein the medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 47: The non-transitory computer readable medium configured as in Embodiment 31, wherein the plurality of plaque parameters comprises one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, or low-density plaque volume.

Embodiment 48: The non-transitory computer readable medium configured as in Embodiment 31, wherein the plurality of vessels comprises one or more coronary arteries.

Embodiment 49: The non-transitory computer readable medium configured as in Embodiment 48, wherein the one or more coronary arteries comprise one or more of left main (LM), ramus intermedius (RI), left anterior descending (LAD), diagonal 1 (D1), diagonal 2 (D2), left circumflex (Cx), obtuse marginal 1 (OM1), obtuse marginal 2 (OM2), left posterior descending artery (L-PDA), left posterolateral branch (L-PLB), right coronary artery (RCA), right posterior descending artery (R-PDA), or right posterolateral branch (R-PLB).

Embodiment 50: The non-transitory computer readable medium configured as in Embodiment 31, wherein the ischemic lesion in the plurality of vessels is determined by a machine learning algorithm.

Embodiment 51: The non-transitory computer readable medium configured as in Embodiment 50, wherein the machine learning algorithm is trained based at least in part on a dataset comprising the plurality of plaque parameters and presence of ischemia derived using invasive fractional flow reserve.

Embodiment 52: The non-transitory computer readable medium configured as in Embodiment 50, wherein the machine learning algorithm is trained based at least in part on a dataset comprising the plurality of plaque parameters and presence of ischemia derived using one or more of CT fractional flow reserve, computational fractional flow reserve, virtual fractional flow reserve, vessel fractional flow reserve, or quantitative flow ratio.

Embodiment 53: The non-transitory computer readable medium configured as in Embodiment 31, further comprising generating, by the computer system, an assessment of risk of coronary artery disease (CAD) or major adverse cardiovascular event (MACE) of the subject based at least in part on the myocardium subtended by the ischemic lesion.

Embodiment 54: The non-transitory computer readable medium configured as in Embodiment 53, further comprising generating, by the computer system, a graphical representation of the assessment of risk of CAD or MACE.

Embodiment 55: The non-transitory computer readable medium configured as in Embodiment 53, further comprising generating, by the computer system, a recommended treatment for the subject based at least in part on the assessment of risk of CAD or MACE.

Embodiment 56: The non-transitory computer readable medium configured as in Embodiment 31, further comprising generating, by the computer system, a myocardial perfusion map representing perfusion of blood through the myocardium subtended by the ischemic lesion.

Embodiment 57: The non-transitory computer readable medium configured as in Embodiment 56, further comprising generating, by the computer system, an overlap of the myocardial perfusion map with the graphical visualization of the myocardium subtended by the ischemic lesion.

Embodiment 58: The non-transitory computer readable medium configured as in Embodiment 56, wherein the myocardial perfusion map is configured to be used to determine presence of a perfusion defect in the myocardium subtended by the ischemic lesion.

Embodiment 59: The non-transitory computer readable medium configured as in Embodiment 58, wherein the perfusion defect appearing smaller than the myocardium subtended by the ischemic lesion is indicative of collateral vessels providing blood to the myocardium subtended by the ischemic lesion.

Embodiment 60: The non-transitory computer readable medium configured as in Embodiment 58, wherein the perfusion defect appearing larger than the myocardium subtended by the ischemic lesion is indicative of additional disease.

Embodiment 61: A system comprising: accessing, by a computer system, a medical image of a subject, wherein the medical image of the subject is obtained non-invasively;

analyzing, by the computer system, the medical image of the subject to map a plurality of vessels, the plurality of vessels comprising one or more regions of plaque; identifying, by the computer system, the one or more regions of plaque within the plurality of vessels; analyzing, by the computer system, the one or more regions of plaque to generate a plurality of plaque parameters, the plurality of plaque parameters comprising density and volume of the one or more regions of plaque; determining, by the computer system, an ischemic lesion in the plurality of vessels based at least in part on the plurality of plaque parameters; determining, by the computer system, myocardium subtended by the ischemic lesion and myocardium not subtended by the ischemic lesion based at least in part on mapping of the plurality of vessels; and generating, by the computer system, a graphical visualization of the myocardium subtended by the ischemic lesion and the myocardium not subtended by the ischemic lesion, wherein the graphical visualization of the myocardium subtended by the ischemic lesion compared to the myocardium not subtended by the ischemic lesion is configured to be utilized to determine risk of the ischemic lesion to the subject, wherein a higher amount of myocardium subtended by the ischemic lesion is indicative of higher risk compared to a lower amount of myocardium subtended by the ischemic lesion, wherein the computer system comprises a computer processor and an electronic storage medium.

Embodiment 62: The system of Embodiment 61, wherein the graphical visualization comprises a graphical representation of the myocardium.

Embodiment 63: The system of Embodiment 61, wherein the graphical visualization comprises a representation of volume of the myocardium subtended by the ischemic lesion.

Embodiment 64: The system of Embodiment 61, wherein the graphical visualization comprises a representation of volume of the myocardium subtended by the ischemic lesion and a representation of volume of the myocardium not subtended by the ischemic lesion.

Embodiment 65: The system of Embodiment 61, wherein the graphical visualization comprises a caricature of the myocardium subtended by the ischemic lesion.

Embodiment 66: The system of Embodiment 61, wherein the graphical visualization comprises a caricature of the myocardium subtended by the ischemic lesion and the myocardium not subtended by the ischemic lesion.

Embodiment 67: The system of Embodiment 61, wherein the plurality of plaque parameters comprises stenosis.

Embodiment 68: The system of Embodiment 61, wherein the volume of the one or more regions of plaque comprises one or more of volume of total plaque, volume of low density non-calcified plaque, volume of non-calcified plaque, or volume of calcified plaque.

Embodiment 69: The system of Embodiment 68, wherein the volume of the one or more regions of plaque is determined based at least in part on analyzing density of one or more pixels corresponding to the one or more regions of plaque in the medical image.

Embodiment 70: The system of Embodiment 69, wherein the density comprises material density.

Embodiment 71: The system of Embodiment 69, wherein the density comprises radiodensity.

Embodiment 72: The system of Embodiment 71, wherein low density non-calcified plaque corresponds to one or more pixels with a radiodensity value between about −189 and about 30 Hounsfield units.

Embodiment 73: The system of Embodiment 71, wherein non-calcified plaque corresponds to one or more pixels with a radiodensity value between about 190 and about 350 Hounsfield units.

Embodiment 74: The system of Embodiment 71, wherein calcified plaque corresponds to one or more pixels with a radiodensity value between about 351 and 2500 Hounsfield units.

Embodiment 75: The system of Embodiment 61, wherein the medical image comprises a Computed Tomography (CT) image.

Embodiment 76: The system of Embodiment 61, wherein the medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 77: The system of Embodiment 61, wherein the plurality of plaque parameters comprises one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, or low-density plaque volume.

Embodiment 78: The system of Embodiment 61, wherein the plurality of vessels comprises one or more coronary arteries.

Embodiment 79: The system of Embodiment 78, wherein the one or more coronary arteries comprise one or more of left main (LM), ramus intermedius (RI), left anterior descending (LAD), diagonal 1 (D1), diagonal 2 (D2), left circumflex (Cx), obtuse marginal 1 (OM1), obtuse marginal 2 (OM2), left posterior descending artery (L-PDA), left posterolateral branch (L-PLB), right coronary artery (RCA), right posterior descending artery (R-PDA), or right posterolateral branch (R-PLB).

Embodiment 80: The system of Embodiment 61, wherein the ischemic lesion in the plurality of vessels is determined by a machine learning algorithm.

Embodiment 81: The system of Embodiment 80, wherein the machine learning algorithm is trained based at least in part on a dataset comprising the plurality of plaque parameters and presence of ischemia derived using invasive fractional flow reserve.

Embodiment 82: The system of Embodiment 80, wherein the machine learning algorithm is trained based at least in part on a dataset comprising the plurality of plaque parameters and presence of ischemia derived using one or more of CT fractional flow reserve, computational fractional flow reserve, virtual fractional flow reserve, vessel fractional flow reserve, or quantitative flow ratio.

Embodiment 83: The system of Embodiment 61, further comprising generating, by the computer system, an assessment of risk of coronary artery disease (CAD) or major adverse cardiovascular event (MACE) of the subject based at least in part on the myocardium subtended by the ischemic lesion.

Embodiment 84: The system of Embodiment 83, further comprising generating, by the computer system, a graphical representation of the assessment of risk of CAD or MACE.

Embodiment 85: The system of Embodiment 83, further comprising generating, by the computer system, a recommended treatment for the subject based at least in part on the assessment of risk of CAD or MACE.

Embodiment 86: The system of Embodiment 61, further comprising generating, by the computer system, a myocardial perfusion map representing perfusion of blood through the myocardium subtended by the ischemic lesion.

Embodiment 87: The system of Embodiment 86, further comprising generating, by the computer system, an overlap of the myocardial perfusion map with the graphical visualization of the myocardium subtended by the ischemic lesion.

Embodiment 88: The system of Embodiment 86, wherein the myocardial perfusion map is configured to be used to determine presence of a perfusion defect in the myocardium subtended by the ischemic lesion.

Embodiment 89: The system of Embodiment 88, wherein the perfusion defect appearing smaller than the myocardium subtended by the ischemic lesion is indicative of collateral vessels providing blood to the myocardium subtended by the ischemic lesion.

Embodiment 90: The system of Embodiment 88, wherein the perfusion defect appearing larger than the myocardium subtended by the ischemic lesion is indicative of additional disease.

Determination of Ischemia Based on Image-Based Analysis of Stenosis

Disclosed herein are systems, devices, and methods for determination of ischemia based on image-based analysis of stenosis. In particular, in some embodiments, the systems, devices, and methods described herein are related to determining the severity of stenoses and using that data to determine the likelihood of ischemia. A percentage of stenosis, or the percentage to which a vessel has narrowed, can be correlated with the likelihood of ischemia, or a restriction of blood flow. In some embodiments, the percentage of stenosis is determined by measuring the plaque in a vessel. In some embodiments, the systems, devices, and methods described herein determine the percentages of multiple stenosis (i.e., two or more stenoses) on a vessel to determine the likelihood of ischemia. In some embodiments, the likelihood of ischemia is used to determine whether to measure the fractional flow reserve (FFR) of the patient.

Figure 11:
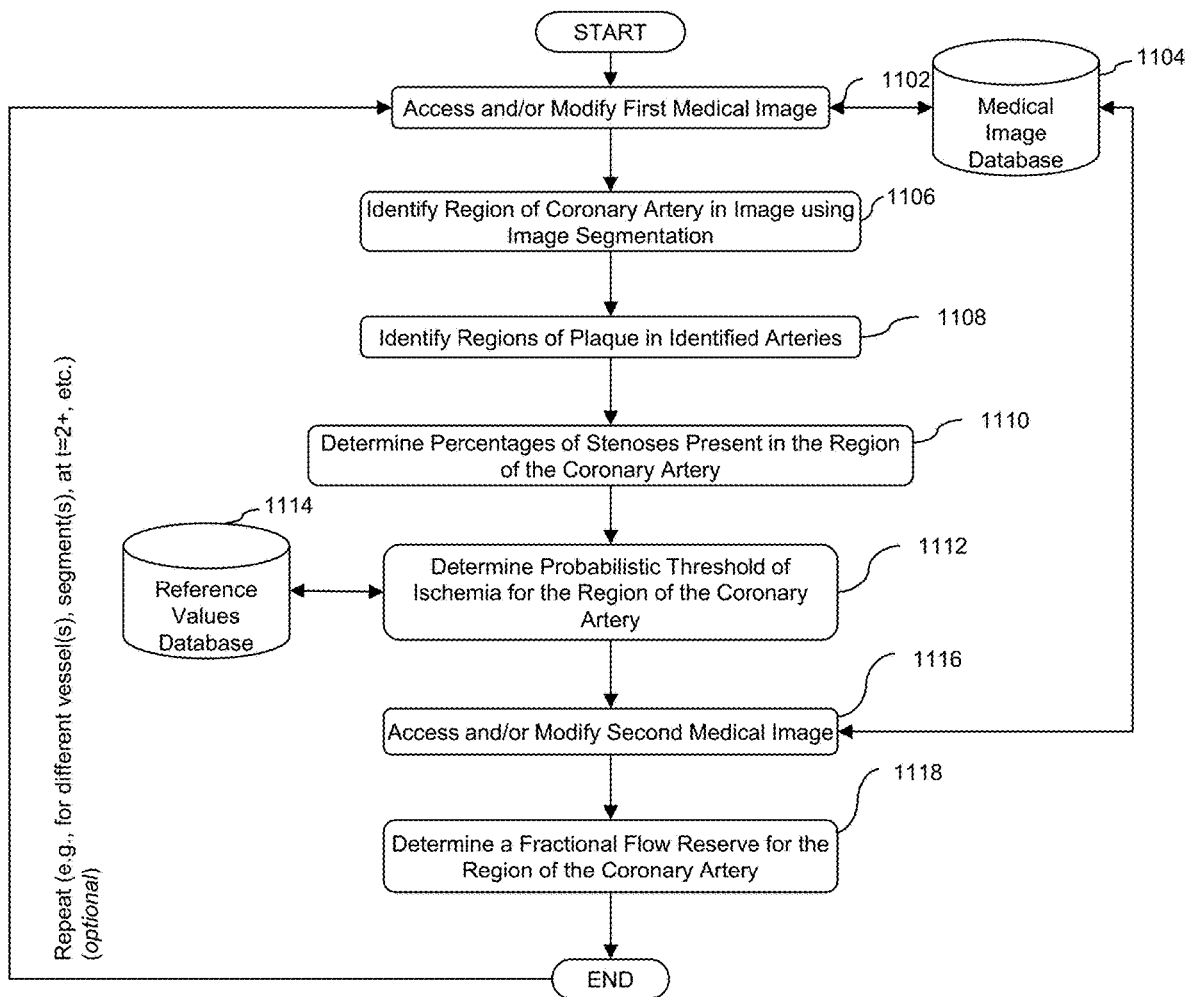
FIG. 11 is a flowchart illustrating an example embodiment(s) of systems, devices, and methods for determination of ischemia based on image-based analysis of stenosis.

FIG. 11 is a flowchart illustrating an example embodiment(s) of systems, devices, and methods for determination of ischemia based on image-based analysis of stenosis. As illustrated in FIG. 11, in some embodiments, the system can be configured to access and/or modify one or more first medical images at block 1102. In some embodiments, the first medical image can include one or more arteries, such as coronary, carotid, and/or other arteries of a subject. In some embodiments, the first medical image can be stored in a medical image database 1104. In some embodiments, the medical image database 1104 can be locally accessible by the system and/or can be located remotely and accessible through a network connection. The first medical image can comprise an image obtained using one or more modalities such as for example, CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the first medical image comprises one or more of a contrast-enhanced CT image, non-contrast CT image, MR image, and/or an image obtained using any of the modalities described above. In some embodiments, the first medical image(s) can be modified, for example using one or more image processing techniques to enhance image quality, change contrast, and/or identify a region of interest.

In some embodiments, the system can be configured to automatically and/or dynamically perform one or more analyses of the first medical image as discussed herein. For example, in some embodiments, at block 1106, the system can be configured to identify one or more vessels, such as of one or more arteries. The one or more arteries can include coronary arteries, carotid arteries, aorta, renal artery, lower extremity artery, upper extremity artery, and/or cerebral artery, amongst others. In some embodiments, the system can be configured to utilize image segmentation to identify a region of a coronary artery. In some embodiments, the system can be configured to utilize one or more AI and/or ML algorithms to automatically and/or dynamically identify one or more arteries or coronary arteries using image processing. For example, in some embodiments, the one or more AI and/or ML algorithms can be trained using a Convolutional Neural Network (CNN) on a set of medical images on which arteries or coronary arteries have been identified, thereby allowing the AI and/or ML algorithm automatically identify arteries or coronary arteries directly from a medical image. In some embodiments, the arteries or coronary arteries are identified by size and/or location.

In some embodiments, at block 1108, the system can be configured to identify one or more regions of plaque in the first medical image. In some embodiments, the system can be configured to utilize one or more AI and/or ML algorithms to automatically and/or dynamically identify one or more regions of plaque using image processing. For example, in some embodiments, the one or more AI and/or ML algorithms can be trained using a Convolutional Neural Network (CNN) on a set of medical images on which regions of plaque have been identified, thereby allowing the AI and/or ML algorithm automatically identify regions of plaque directly from a medical image. In some embodiments, the system is configured to identify vessel and lumen walls and classify everything in between the vessel and lumen walls as plaque.

In some embodiments, at block 1108, the system can be configured to analyze and/or characterize one or more regions of plaque based on density. For example, in some embodiments, the system can be configured to analyze and/or characterize one or more regions of plaque based on absolute density and/or relative density and/or radiodensity and/or material density. In some embodiments, the system can be configured to classify a region of plaque as one of low density non-calcified plaque, non-calcified plaque, and calcified plaque, using any one or more processes and/or features described herein.

In some embodiments, at block 1108, the system can be configured to analyze and/or characterize one or more regions of plaque based on one or more distances. For example, as described herein, in some embodiments, the system can be configured to determine a distance between a low density non-calcified plaque and lumen wall and/or vessel wall. In some embodiments, proximity of a low density non-calcified plaque to the lumen wall can be indicative of a high-risk plaque and/or CAD. Conversely, in some embodiments, a position of a low density non-calcified plaque far from the lumen wall can be indicative of less risk. In some embodiments, the system can be configured to utilize one or more predetermined thresholds in determining the risk factor associated with the proximity of low density non-calcified plaque with the vessel wall and/or lumen wall. In some embodiments, the system can be configured to utilize one or more image processing algorithms to automatically and/or dynamically determine one or more distances to and/or from one or more regions of plaque. In some embodiments, regions of plaque are identified at least in part based on the density of one or more pixels in the first medical image.

In some embodiments, at block 1108, the system can be configured to analyze and/or characterize one or more regions of plaque based on morphology or shape and/or one or more axes measurements of low density non-calcified plaque. As described herein, in some embodiments, the system can be configured to determine the length of one or more axes of a low density non-calcified plaque, such as for example a major axis of a longitudinal cross section and/or a major and/or minor axis of a latitudinal cross section of a low density non-calcified plaque. In some embodiments, the system can be configured to utilize the one more axes measurements to determine a morphology and/or shape of a low density non-calcified plaque. In some embodiments, the system can be configured to utilize one or more image processing algorithms to automatically and/or dynamically determine one or more axes measurements of one or more regions of plaque.

In some embodiments, the system can be configured to utilize one or more AI and/or ML algorithms to automatically and/or dynamically classify the shape of one or more regions of plaque using image processing. For example, in some embodiments, the one or more AI and/or ML algorithms can be trained using a Convolutional Neural Network (CNN) on a set of medical images on which the shape of regions of plaque have been identified, thereby allowing the AI and/or ML algorithm automatically identify the shape or morphology of a region of plaque directly from a medical image. In some embodiments, the system can be configured to classify the shape or morphology of a region of plaque as one or more of crescent, lobular, round, or bean-shaped. In some embodiments, round and/or bean-shaped plaques can be associated with high risk, while crescent and/or lobular-shaped plaques can be associated with low risk of CAD.

In some embodiments, at block 1108, the system can be configured to analyze and/or characterize one or more regions of plaque based on one or more sizes and/or volumes. For example, in some embodiments, the system can be configured to determine a size and/or volume of plaque based at least in part on one or more axes measurements described herein. In some embodiments, the system can be configured to determine the size and/or volume of a region of plaque directly from analysis of a three-dimensional image scan. In some embodiments, the system can be configured to determine the size and/or volume of total plaque, low-density non-calcified plaque, non-calcified plaque, calcified plaque, and/or a ratio between two of the aforementioned volumes or sizes. In some embodiments, a high total plaque volume and/or high low-density non-calcified plaque and/or non-calcified plaque volume can be associated with high risk of CAD. In some embodiments, a high ratio of low-density non-calcified plaque volume to total plaque volume and/or a high ratio of non-calcified plaque volume to total plaque volume can be associated with high risk of CAD. In some embodiments, a high calcified plaque volume and/or high ratio of calcified plaque volume to total plaque volume can be associated with low risk of CAD. In some embodiments, the system can be configured to utilize one or more predetermined threshold values for determining the risk of CAD based on plaque volume, size, or one or more ratios thereof. In some embodiments, the system can be configured to utilize one or more image processing algorithms to automatically and/or dynamically determine the size and/or volume of one or more regions of plaque.

In some embodiments, at block 1108, the system can be configured to analyze and/or characterize plaque based on embeddedness. For example, in some embodiments, the system can be configured to determined how embedded or surrounded a low density non-calcified plaque is by non-calcified plaque or calcified plaque. In some embodiments, the system can be configured to analyze the embeddedness of low density non-calcified plaque based on the degree by which it is surrounded by other types of plaque. In some embodiments, a higher embeddedness of a low density non-calcified plaque can be indicative of high risk of CAD. For example, in some embodiments, a low density non-calcified plaque that is surrounded by 270 degrees or more by non-calcified plaque can be associated with high risk of CAD. In some embodiments, the system can be configured to utilize one or more image processing algorithms to automatically and/or dynamically determine the embeddedness of one or more regions of plaque.

In some embodiments, at block 1110, the system can be configured to determine a percentage of one or more stenoses present in the region of the coronary artery arising from the one or more regions of plaque. In some embodiments, the percentage of one or more stenoses is determined based at least in part on interpolating a lumen volume or diameter of the region of the coronary artery without the one or more regions of plaque. In some embodiments, the percentage of one or more stenoses is determined by determining the dimensions of a coronary artery in the first medical image. In some embodiments, the percentage of one or more stenoses is determined by comparing the dimensions of a coronary artery in the first medical image with the dimensions of a reference coronary artery. In some embodiments, the reference coronary artery is from the patient at another point in time. In some embodiments, the reference coronary artery is from a reference database.

In some embodiments, at block 1112, the system can be configured to determine a probabilistic threshold of ischemia for the identified region of the coronary artery. In some embodiments, the probabilistic threshold of ischemia for the region of the coronary artery is based at least in part on the percentage of the one or more stenoses present in the region of the coronary artery. In some embodiments, the probabilistic threshold of ischemia for the region of the coronary artery is based at least in part on a plurality of reference values of percentages of stenoses with known presence or absence of ischemia derived from a plurality of other subjects from a reference values database 1114. In some embodiments, the probabilistic threshold of ischemia comprises a statistical likelihood of the region of the coronary artery being ischemic. In some embodiments, the probabilistic threshold of ischemia for the region of the coronary artery being higher than a predetermined threshold is indicative of a need for further assessment of ischemia for the subject. In some embodiments, the probabilistic threshold of ischemia for the region of the coronary artery is determined using a machine learning algorithm trained on the plurality of reference values of percentages of stenoses with known presence or absence of ischemia derived from the plurality of other subjects. In some embodiments, the probabilistic threshold of ischemia for the region of the coronary artery is determined based at least in part on the percentages of all stenoses identified in the region of the coronary artery. In some embodiments, the probabilistic threshold of ischemia for the region of the coronary artery is determined based at least in part on a weighted measure of the percentages of all stenoses identified in the region of the coronary artery. In some embodiments, the probabilistic threshold of ischemia for the region of the coronary artery is determined by calculating the volume of the region of the coronary artery with the stenoses. In some embodiments, the probabilistic threshold of ischemia for the region of the coronary artery is determined by adding together the sizes of the stenoses. In some embodiments, the probabilistic threshold of ischemia for the region of the coronary artery is determined by determining the distances between the stenoses. In some embodiments, the probabilistic threshold of ischemia for the region of the coronary artery is determined by calculating the blood flow in the region of the coronary artery with the stenoses. In some embodiments, the probabilistic threshold of ischemia for the region of the coronary artery comprises a binary output. In some embodiments, the probabilistic threshold of ischemia for the region of the coronary artery comprises an output on a continuous scale.

In some embodiments, the system can be configured to determine that further analysis for ischemia and/or fractional flow reserve (FFR) is warranted and/or required based on the determined probabilistic threshold of ischemia. For example, in some embodiments, if the probabilistic threshold of ischemia is determined to be high or higher than a predetermined threshold based on plaque and/or stenoses, then the system can be configured to determine that further analysis of ischemia and/or FFR is warranted and/or required for the subject. As part of performing further analysis, for example in some embodiments, at block 1116, the system can be configured to access and/or modify one or more second medical images. In some embodiments, the second medical image can include one or more arteries, such as coronary, carotid, and/or other arteries of a subject. In some embodiments, the second medical image is configured to be used to determine a fractional flow reserve for a region of a coronary artery. In some embodiments, the second medical image can be stored in a medical image database 1104. In some embodiments, the medical image database 1104 can be locally accessible by the system and/or can be located remotely and accessible through a network connection. The second medical image can comprise an image obtained using one or more modalities such as for example, CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the second medical image comprises one or more of a contrast-enhanced CT image, non-contrast CT image, MR image, and/or an image obtained using any of the modalities described above. In some embodiments, the second medical image can be the same as the first medical image; in other words, in some embodiments, further analysis for ischemia, such as FFR, can be performed on the same image that was analyzed for plaque, stenosis, and/or probabilistic threshold of ischemia. In some embodiments, the second medical image is different from the first medical image. For example, in some embodiments, the second medical image for further ischemia analysis can comprise a different resolution, quality, contrast, region of interest, and/or the like compared to the first medical image. As such, in some embodiments, the first medical image and/or analysis thereof can be used as a gatekeeper to determine if further analysis of ischemia and/or a different medical image acquisition is required. In some embodiments, the second medical image is modified for analysis for example using one or more image processing techniques to enhance image quality, change contrast, and/or identify a region of interest.

In some embodiments, at block 11, the system can be configured to determine a fractional flow reserve for the region of the coronary artery using the one or more second medical images and/or first medical images. In some embodiments, the systems, devices, and methods determine a fractional flow reserve for the region of the coronary artery when the probabilistic threshold of ischemia for the region of the coronary artery is higher than the predetermined threshold. In some embodiments, determining the fractional flow reserve comprises determining, by the computer system, the fractional flow reserve for the region of the coronary artery using computational fluid dynamics. In some embodiments, the computational fluid dynamics analysis is conducted on the one or more second medical images and/or first medical images. In some embodiments, the fractional flow reserve is determined based on one or more of invasive fractional flow reserve, computed tomography (CT) fractional flow reserve, computational fractional flow reserve, virtual fractional flow reserve, vessel fractional flow reserve, or quantitative flow ratio. In some embodiments, the further assessment of ischemia for the subject comprises invasive fractional flow reserve. In some embodiments, the further assessment of ischemia for the subject comprises computed tomography (CT) fractional flow reserve. In some embodiments, the further assessment of ischemia for the subject comprises one or more of CT fractional flow reserve, computational fractional flow reserve, virtual fractional flow reserve, vessel fractional flow reserve, or quantitative flow ratio.

In some embodiments, the system can be configured to repeat one or more processes described in relation to blocks 1102-118, for example for one or more other vessels, segment, regions of plaque, different subjects, and/or for the same subject at a different time. As such, in some embodiments, the system can provide for longitudinal disease tracking and/or personalized treatment for a subject.

The computer system 902 of FIG. 9, and in some instances, the analysis and/or risk assessment module 940, can be configured to carry out the functions, methods, acts, and/or processes for determination of ischemia based on image-based analysis of stenosis described herein, such as those described above with reference to FIG. 11.

The following are non-limiting examples of certain embodiments of systems and methods for determination of ischemia based on image-based analysis of stenosis. Other embodiments may include one or more other features, or different features, that are discussed herein.

Embodiment 1: A computer-implemented method of determining a probabilistic threshold of ischemia for a coronary artery based at least in part on a stenosis percentage generated from image-based analysis, the method comprising: accessing, by a computer system, a first medical image of a subject, the first medical image comprising a region of a coronary artery of the subject; analyzing, by the computer system, the first medical image to identify the region of the coronary artery using image segmentation; identifying, by the computer system, one or more regions of plaque within the region of the coronary artery, wherein the one or more regions of plaque are identified based at least in part on density of one or more pixels in the first medical image corresponding to the one or more regions of plaque; determining, by the computer system, a percentage of one or more stenoses present in the region of the coronary artery arising from the one or more regions of plaque, wherein the percentage of one or more stenoses is determined based at least in part on interpolating a lumen volume or diameter of the region of the coronary artery without the one or more regions of plaque; and determining, by the computer system, a probabilistic threshold of ischemia for the region of the coronary artery based at least in part on the percentage of the one or more stenoses present in the region of the coronary artery and a plurality of reference values of percentages of stenoses with known presence or absence of ischemia derived from a plurality of other subjects, wherein the probabilistic threshold of ischemia comprises a statistical likelihood of the region of the coronary artery being ischemic, wherein the probabilistic threshold of ischemia for the region of the coronary artery being higher than a predetermined threshold is indicative of a need for further assessment of ischemia for the subject, wherein the computer system comprises a computer processor and an electronic storage medium.

Embodiment 2: The computer-implemented method of Embodiment 1, further comprising determining a fractional flow reserve for the region of the coronary artery when the probabilistic threshold of ischemia for the region of the coronary artery is higher than the predetermined threshold.

Embodiment 3: The computer-implemented method of Embodiment 2, wherein determining the fractional flow reserve comprises: accessing, by the computer system, a second medical image, the second medical image comprising the region of a coronary artery of the subject; and determining, by the computer system, the fractional flow reserve for the region of the coronary artery using computational fluid dynamics.

Embodiment 4: The computer-implemented method of Embodiment 2, wherein the fractional flow reserve is determined based on one or more of invasive fractional flow reserve, computed tomography (CT) fractional flow reserve, computational fractional flow reserve, virtual fractional flow reserve, vessel fractional flow reserve, or quantitative flow ratio.

Embodiment 5: The computer-implemented method of Embodiment 1, wherein the further assessment of ischemia for the subject comprises invasive fractional flow reserve.

Embodiment 6: The computer-implemented method of Embodiment 1, wherein the further assessment of ischemia for the subject comprises computed tomography (CT) fractional flow reserve.

Embodiment 7: The computer-implemented method of Embodiment 1, wherein the further assessment of ischemia for the subject comprises one or more of CT fractional flow reserve, computational fractional flow reserve, virtual fractional flow reserve, vessel fractional flow reserve, or quantitative flow ratio.

Embodiment 8: The computer-implemented method of Embodiment 1, wherein the probabilistic threshold of ischemia for the region of the coronary artery is determined using a machine learning algorithm trained on the plurality of reference values of percentages of stenoses with known presence or absence of ischemia derived from the plurality of other subjects.

Embodiment 9: The computer-implemented method of Embodiment 8, wherein the presence or absence of ischemia is derived from the plurality of other subjects using one or more of invasive fractional flow reserve, CT fractional flow reserve, computational fractional flow reserve, virtual fractional flow reserve, vessel fractional flow reserve, or quantitative flow ratio.

Embodiment 10: The computer-implemented method of Embodiment 1, wherein the probabilistic threshold of ischemia for the region of the coronary artery is determined based at least in part on the percentages of all stenoses identified in the region of the coronary artery.

Embodiment 11: The computer-implemented method of Embodiment 1, wherein the probabilistic threshold of ischemia for the region of the coronary artery is determined based at least in part on a weighted measure of the percentages of all stenoses identified in the region of the coronary artery.

Embodiment 12: The computer-implemented method of Embodiment 1, wherein the probabilistic threshold of ischemia for the region of the coronary artery comprises a binary output.

Embodiment 13: The computer-implemented method of Embodiment 1, wherein the probabilistic threshold of ischemia for the region of the coronary artery comprises an output on a continuous scale.

Embodiment 14: The computer-implemented method of Embodiment 1, wherein the density comprises radiodensity.

Embodiment 15: The computer-implemented method of Embodiment 1, wherein the density comprises material density.

Embodiment 16: The computer-implemented method of Embodiment 1, wherein the first medical image is obtained using CT.

Embodiment 17: The computer-implemented method of Embodiment 1, wherein the first medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 18: A non-transitory computer readable medium configured for determining a probabilistic threshold of ischemia for a coronary artery based at least in part on a stenosis percentage generated from image-based analysis, the computer readable medium having program instructions for causing a hardware processor to perform a method of: accessing a first medical image of a subject, the first medical image comprising a region of a coronary artery of the subject; analyzing the first medical image to identify the region of the coronary artery using image segmentation; identifying one or more regions of plaque within the region of the coronary artery, wherein the one or more regions of plaque are identified based at least in part on density of one or more pixels in the first medical image corresponding to the one or more regions of plaque; determining a percentage of one or more stenoses present in the region of the coronary artery arising from the one or more regions of plaque, wherein the percentage of one or more stenoses is determined based at least in part on interpolating a lumen volume or diameter of the region of the coronary artery without the one or more regions of plaque; and determining a probabilistic threshold of ischemia for the region of the coronary artery based at least in part on the percentage of the one or more stenoses present in the region of the coronary artery and a plurality of reference values of percentages of stenoses with known presence or absence of ischemia derived from a plurality of other subjects, wherein the probabilistic threshold of ischemia comprises a statistical likelihood of the region of the coronary artery being ischemic, wherein the probabilistic threshold of ischemia for the region of the coronary artery being higher than a predetermined threshold is indicative of a need for further assessment of ischemia for the subject.

Embodiment 19: The non-transitory computer readable medium configured as in Embodiment 18, further comprising determining a fractional flow reserve for the region of the coronary artery when the probabilistic threshold of ischemia for the region of the coronary artery is higher than the predetermined threshold.

Embodiment 20: The non-transitory computer readable medium configured as in Embodiment 19, wherein determining the fractional flow reserve comprises: accessing a second medical image, the second medical image comprising the region of a coronary artery of the subject; and determining the fractional flow reserve for the region of the coronary artery using computational fluid dynamics.

Embodiment 21: The non-transitory computer readable medium configured as in Embodiment 19, wherein the fractional flow reserve is determined based on one or more of invasive fractional flow reserve, computed tomography (CT) fractional flow reserve, computational fractional flow reserve, virtual fractional flow reserve, vessel fractional flow reserve, or quantitative flow ratio.

Embodiment 22: The non-transitory computer readable medium configured as in Embodiment 18, wherein the further assessment of ischemia for the subject comprises invasive fractional flow reserve.

Embodiment 23: The non-transitory computer readable medium configured as in Embodiment 18, wherein the further assessment of ischemia for the subject comprises computed tomography (CT) fractional flow reserve.

Embodiment 24: The non-transitory computer readable medium configured as in Embodiment 18, wherein the further assessment of ischemia for the subject comprises one or more of CT fractional flow reserve, computational fractional flow reserve, virtual fractional flow reserve, vessel fractional flow reserve, or quantitative flow ratio.

Embodiment 25: The non-transitory computer readable medium configured as in Embodiment 18, wherein the probabilistic threshold of ischemia for the region of the coronary artery is determined using a machine learning algorithm trained on the plurality of reference values of percentages of stenoses with known presence or absence of ischemia derived from the plurality of other subjects.

Embodiment 26: The non-transitory computer readable medium configured as in Embodiment 25, wherein the presence or absence of ischemia is derived from the plurality of other subjects using one or more of invasive fractional flow reserve, CT fractional flow reserve, computational fractional flow reserve, virtual fractional flow reserve, vessel fractional flow reserve, or quantitative flow ratio.

Embodiment 27: The non-transitory computer readable medium configured as in Embodiment 18, wherein the probabilistic threshold of ischemia for the region of the coronary artery is determined based at least in part on the percentages of all stenoses identified in the region of the coronary artery.

Embodiment 28: The non-transitory computer readable medium configured as in Embodiment 18, wherein the probabilistic threshold of ischemia for the region of the coronary artery is determined based at least in part on a weighted measure of the percentages of all stenoses identified in the region of the coronary artery.

Embodiment 29: The non-transitory computer readable medium configured as in Embodiment 18, wherein the probabilistic threshold of ischemia for the region of the coronary artery comprises a binary output.

Embodiment 30: The non-transitory computer readable medium configured as in Embodiment 18, wherein the probabilistic threshold of ischemia for the region of the coronary artery comprises an output on a continuous scale.

Embodiment 31: The non-transitory computer readable medium configured as in Embodiment 18, wherein the density comprises radiodensity.

Embodiment 32: The non-transitory computer readable medium configured as in Embodiment 18, wherein the density comprises material density.

Embodiment 33: The non-transitory computer readable medium configured as in Embodiment 18, wherein the first medical image is obtained using CT.

Embodiment 34: The non-transitory computer readable medium configured as in Embodiment 18, wherein the first medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 35: A system comprising: accessing, by a computer system, a first medical image of a subject, the first medical image comprising a region of a coronary artery of the subject; analyzing, by the computer system, the first medical image to identify the region of the coronary artery using image segmentation; identifying, by the computer system, one or more regions of plaque within the region of the coronary artery, wherein the one or more regions of plaque are identified based at least in part on density of one or more pixels in the first medical image corresponding to the one or more regions of plaque; determining, by the computer system, a percentage of one or more stenoses present in the region of the coronary artery arising from the one or more regions of plaque, wherein the percentage of one or more stenoses is determined based at least in part on interpolating a lumen volume or diameter of the region of the coronary artery without the one or more regions of plaque; and determining, by the computer system, a probabilistic threshold of ischemia for the region of the coronary artery based at least in part on the percentage of the one or more stenoses present in the region of the coronary artery and a plurality of reference values of percentages of stenoses with known presence or absence of ischemia derived from a plurality of other subjects, wherein the probabilistic threshold of ischemia comprises a statistical likelihood of the region of the coronary artery being ischemic, wherein the probabilistic threshold of ischemia for the region of the coronary artery being higher than a predetermined threshold is indicative of a need for further assessment of ischemia for the subject, wherein the computer system comprises a computer processor and an electronic storage medium.

Embodiment 36: The system of Embodiment 35, further comprising determining a fractional flow reserve for the region of the coronary artery when the probabilistic threshold of ischemia for the region of the coronary artery is higher than the predetermined threshold.

Embodiment 37: The system of Embodiment 36, wherein determining the fractional flow reserve comprises: accessing, by the computer system, a second medical image, the second medical image comprising the region of a coronary artery of the subject; and determining, by the computer system, the fractional flow reserve for the region of the coronary artery using computational fluid dynamics.

Embodiment 38: The system of Embodiment 36, wherein the fractional flow reserve is determined based on one or more of invasive fractional flow reserve, computed tomography (CT) fractional flow reserve, computational fractional flow reserve, virtual fractional flow reserve, vessel fractional flow reserve, or quantitative flow ratio.

Embodiment 39: The system of Embodiment 35, wherein the further assessment of ischemia for the subject comprises invasive fractional flow reserve.

Embodiment 40: The system of Embodiment 35, wherein the further assessment of ischemia for the subject comprises computed tomography (CT) fractional flow reserve.

Embodiment 41: The system of Embodiment 35, wherein the further assessment of ischemia for the subject comprises one or more of CT fractional flow reserve, computational fractional flow reserve, virtual fractional flow reserve, vessel fractional flow reserve, or quantitative flow ratio.

Embodiment 42: The system of Embodiment 35, wherein the probabilistic threshold of ischemia for the region of the coronary artery is determined using a machine learning algorithm trained on the plurality of reference values of percentages of stenoses with known presence or absence of ischemia derived from the plurality of other subjects.

Embodiment 43: The system of Embodiment 35, wherein the presence or absence of ischemia is derived from the plurality of other subjects using one or more of invasive fractional flow reserve, CT fractional flow reserve, computational fractional flow reserve, virtual fractional flow reserve, vessel fractional flow reserve, or quantitative flow ratio.

Embodiment 44: The system of Embodiment 35, wherein the probabilistic threshold of ischemia for the region of the coronary artery is determined based at least in part on the percentages of all stenoses identified in the region of the coronary artery.

Embodiment 45: The system of Embodiment 35, wherein the probabilistic threshold of ischemia for the region of the coronary artery is determined based at least in part on a weighted measure of the percentages of all stenoses identified in the region of the coronary artery.

Embodiment 46: The system of Embodiment 35, wherein the probabilistic threshold of ischemia for the region of the coronary artery comprises a binary output.

Embodiment 47: The system of Embodiment 35, wherein the probabilistic threshold of ischemia for the region of the coronary artery comprises an output on a continuous scale.

Embodiment 48: The system of Embodiment 35, wherein the density comprises radiodensity.

Embodiment 49: The system of Embodiment 35, wherein the density comprises material density.

Embodiment 50: The system of Embodiment 35, wherein the first medical image is obtained using CT.

Embodiment 51: The system of Embodiment 35, wherein the first medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Multivariable Image-Based Analysis of Ischemia

Disclosed herein are systems, devices, and methods for multivariable image-based analysis of ischemia Various embodiments described herein relate to systems, devices, and methods for multivariable image-based analysis of ischemia. In particular, in some embodiments, the systems, devices, and methods described herein are related to determination of one or more variables for a plurality of vessels, such as for each of a first coronary artery and a second coronary artery. In some embodiments, the variables are determined based on a medical image of a patient, such as a noninvasively obtained medical images. The variables for the plurality of variables can be analyzed, for example, using a machine learning algorithm, to determine the presence of ischemia within one of the vessels. That is, determination of the presence of ischemia can be made for one of the vessels based on an analysis of variable determined from more than one (e.g., two, three, or more vessels). This can be advantageous because the effects of disease, such as coronary artery disease, are often diffuse across several vessels. For example, stenosis within one vessel can impact blood flow within a different vessel. In some embodiments, the analyses described herein account for the diffuse nature of the effects of disease by determining ischemia within one vessel based on analysis of variable determined for a plurality of vessels. In some embodiments, the systems, devices, and methods described herein are configured to determine a risk of coronary artery disease (CAD), such as for example myocardial infarction (MI), based on one or more plaque analyses described herein. In some embodiments, the systems, devices, and methods described herein are configured to generate a proposed treatment and/or graphical representation based on the determined risk of CAD and/or one or more plaque analyses described herein.

In some embodiments, it can be difficult or impossible to determine a fractional flow reserve (FFR) measurement for a vessel by only pinpointing a specific stenosis within the vessel. This can be because the diffuseness of the disease across the length of the vessel or within a network of vessels can contribute to the ischemia of a single vessel. For example, the totality of plaque across or along a vessel or throughout a plurality of vessels as well as the vessel morphology along or across the vessel or throughout the plurality of vessels all contributes to the presence of ischemia. As described in this application, a more accurate determination of the presence of ischemia can be made using mixed effects modeling based on variables determined across or along a vessel and/or throughout a plurality of vessels in a vascular network. For example, determination or measurement of a single stenosis alone may be insufficient to determine the FFR value of that vessel. Rather, it may be needed to know all the stenoses within the vessel, including the location, the vascular morphology, the lumen volume, the vessel volume, as well as similar parameters of other vessels or arteries in the network.

Previous approaches to determining the presence of ischemia have focused on determination of specific instances of stenosis, without regard for the diffuse impact of disease spread throughout the vascular network. As recognized herein, however, interactivity between all of the variables across location, geography, vessel territory, distal, proximal, bifurcation, trifurcation, lumen volume, etc., all impact the presence of ischemia.

For example, stenosis in one vessel can cause blood flow to increase in a vessel that has less stenosis. Thus, when determining the presence of ischemia, it can be important to consider the effects caused in neighboring vessels.

As a more specific example, in some embodiments, one or more of a plurality of parameters can be determined for one or more territories or one or more lesions of two or more vessels. These parameters can include one or more of the following, among others: lesion length, remodeling index, plaque slice percentage, stenosis area percentage, presence of low density plaque, stenosis diameter percentage, presence of positive remodeling, reference diameter after stenosis, reference diameter before stenosis, vessel length, lumen volume, number of CTO, vessel volume, number of stenosis, total plaque volume, number of mild stenosis, low density plaque volume, etc. These parameters can be determined, in some embodiments, based on one or more medical images (e.g., non-invasively obtained medical images) of a patient, for example, using machine learning, artificial intelligence, or other image-based recognition techniques. Then, for one of the vessels, the presence of ischemia can be determined, for example, using a machine learning algorithm, based on the plurality of vessels determined for the that vessel as well as one or more other vessels, such as one or more neighboring vessels. This is because the measures from one vessel or vessel territory could be used to inform the probability of ischemia in another vessel.

In some embodiments, per lesion level data could also be used. In some embodiments, the principles can be applied with even more granularity, for example, with slight axial slice specific data. In some embodiments, a stenosis can be considered a two-dimensional measurement, for example, a percent of narrowing within a two-dimensional slice. However, stenosis is generally a three-dimensional in nature, so it may be advantageous to analyze stenosis in a three-dimensional manner, for example along a length of the vessel. For example, variable can be determined for each a plurality of two-dimensional slices and variables determined from each slice can be analyzed together to gain an understanding of the three-dimensional topology across the length of the vessel. In some embodiments, instead of analyzing segment level data based on a plurality of cross-sections amalgamated and analyzed together (like a loaf of bread), it may be advantageous to analyze the slices individually (e.g., slice level data) and apply a machine learning algorithm that determines how the three-dimensional topology influences ischemia.

As described previously, it is more than a single stenosis that contributes to the determination of ischemia, but other parameter as well, such as other stenoses within that vessel and other vascular morphology parameters. Moreover, it is not only parameters from one vessel because that vessel is informed by other vessels.

Figure 12:
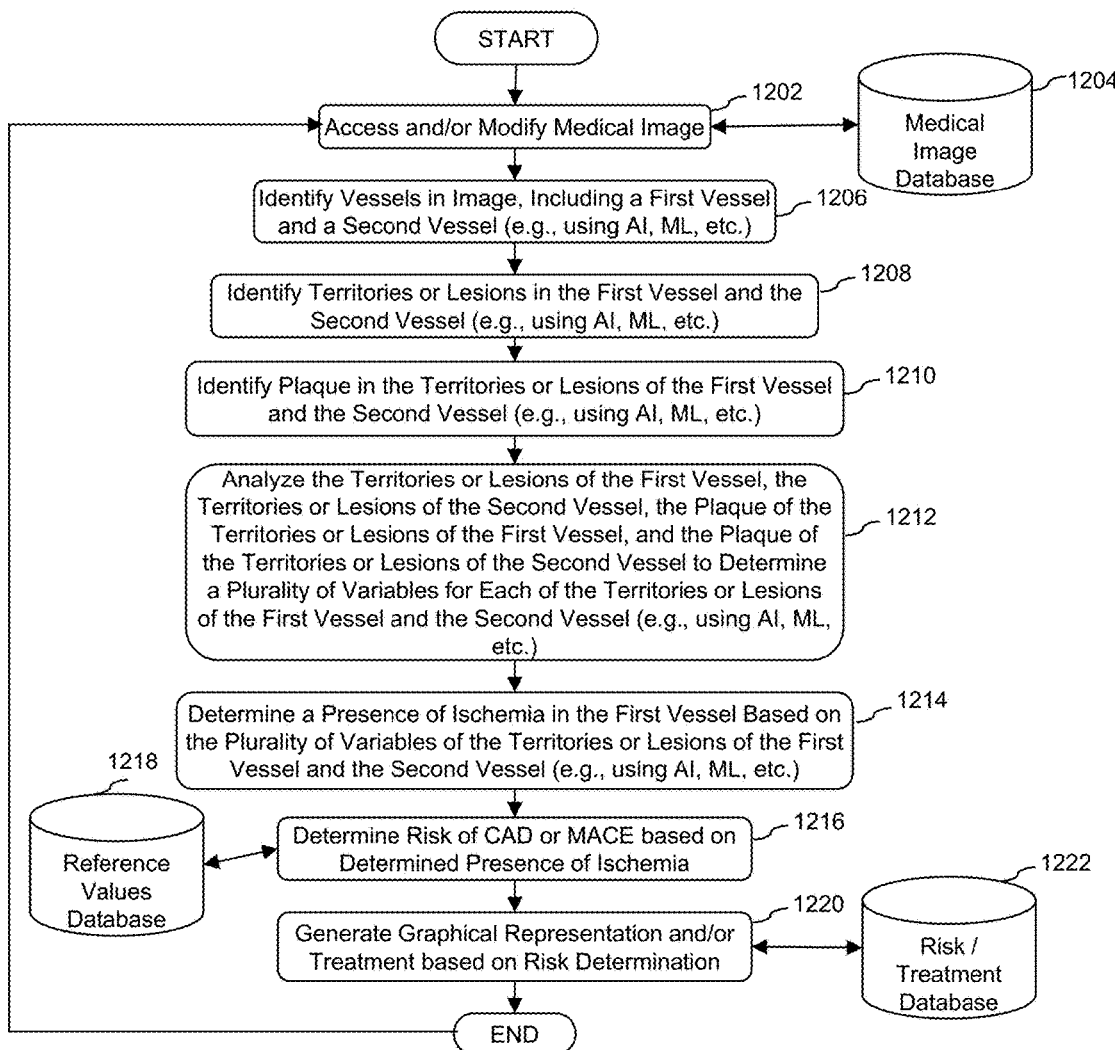
FIG. 12 is a flowchart illustrating an example embodiment(s) of systems, devices, and methods for multivariable image-based analysis of ischemia.

FIG. 12 is a flowchart illustrating an example embodiment(s) of systems, devices, and methods for multivariable analysis of ischemia. As illustrated in FIG. 12, in some embodiments, the system can be configured to access and/or modify one or more medical images at block 1202. In some embodiments, the medical image can include one or more arteries, such as coronary, carotid, and/or other arteries of a subject. In some embodiments, the medical image can be stored in a medical image database 1204. In some embodiments, the medical image database 1204 can be locally accessible by the system and/or can be located remotely and accessible through a network connection. The medical image can comprise an image obtain using one or more modalities such as for example, CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the medical image comprises one or more of a contrast-enhanced CT image, non-contrast CT image, MR image, and/or an image obtained using any of the modalities described above.

In some embodiments, the system can be configured to automatically and/or dynamically perform one or more analyses of the medical image as discussed herein. For example, in some embodiments, at block 1206, the system can be configured to identify one or more vessels, such as of one or more arteries. As shown in FIG. 12, in some embodiments, the system can identify at least two vessels (e.g., a first vessel and a second vessel) within the image. In some embodiments, greater numbers of vessels, for example, three, four, five, six, seven, eight, or more vessels can be identified. As described herein, more than one of the plurality of vessels can be analyzed to determine the presence of ischemia within one of the identified vessels. The one or more arteries can include coronary arteries, carotid arteries, aorta, renal artery, lower extremity artery, upper extremity artery, and/or cerebral artery, amongst others. In some embodiments, the one or more coronary arteries comprise one or more of left main (LM), ramus intermedius (RI), left anterior descending (LAD), diagonal 1 (D1), diagonal 2 (D2), left circumflex (Cx), obtuse marginal 1 (OM1), obtuse marginal 2 (OM2), left posterior descending artery (L-PDA), left posterolateral branch (L-PLB), right coronary artery (RCA), right posterior descending artery (R-PDA), or right posterolateral branch (R-PLB).

In some embodiments, the system can be configured to utilize one or more AI and/or ML algorithms to automatically and/or dynamically identify one or more arteries or coronary arteries using image processing. For example, in some embodiments, the one or more AI and/or ML algorithms can be trained using a Convolutional Neural Network (CNN) on a set of medical images on which arteries or coronary arteries have been identified, thereby allowing the AI and/or ML algorithm automatically identify arteries or coronary arteries directly from a medical image. In some embodiments, the arteries or coronary arteries are identified by size and/or location.

In some embodiments, at block 1208, the system can be configured to identify one or more territories or lesions within the plurality of vessels, for example, within the first vessel and the second vessel. In some embodiments, a territory can include a portion, subsection, or portion of a length of a vessel. For example, a territory can be 1%, 5%, 10%, 20%, 25%, or 50% of a length of the vessel, or any other percentage length of the vessel up to and including the entire length of the vessel.

In some embodiments, at block 1210, the system can be configured to identify one or more regions of plaque in the medical image, for example, regions of plaque associated with the identified territories or lesion of the first and second vessels. In some embodiments, the system can be configured to utilize one or more AI and/or ML algorithms to automatically and/or dynamically identify one or more regions of plaque using image processing. For example, in some embodiments, the one or more AI and/or ML algorithms can be trained using a Convolutional Neural Network (CNN) on a set of medical images on which regions of plaque have been identified, thereby allowing the AI and/or ML algorithm automatically identify regions of plaque directly from a medical image. In some embodiments, the system is configured to identify vessel and lumen walls and classify everything in between the vessel and lumen walls as plaque.

In some embodiments, the system can be configured to analyze and/or characterize one or more regions of plaque based on density. For example, in some embodiments, the system can be configured to analyze and/or characterize one or more regions of plaque based on absolute density and/or relative density and/or radiodensity. In some embodiments, the system can be configured to classify a region of plaque as one of low density non-calcified plaque, non-calcified plaque, and calcified plaque, using any one or more processes and/or features described herein.

In some embodiments, the system can be configured to analyze and/or characterize one or more regions of plaque based on one or more distances. For example, as described herein, in some embodiments, the system can be configured to determine a distance between a low density non-calcified plaque and lumen wall and/or vessel wall. In some embodiments, proximity of a low density non-calcified plaque to the lumen wall can be indicative of a high-risk plaque and/or CAD. Conversely, in some embodiments, a position of a low density non-calcified plaque far from the lumen wall can be indicative of less risk. In some embodiments, the system can be configured to utilize one or more predetermined thresholds in determining the risk factor associated with the proximity of low density non-calcified plaque with the vessel wall and/or lumen wall. In some embodiments, the system can be configured to utilize one or more image processing algorithms to automatically and/or dynamically determine one or more distances to and/or from one or more regions of plaque.

In some embodiments, the system can be configured to analyze and/or characterize one or more regions of plaque based on morphology or shape and/or one or more axes measurements of low density non-calcified plaque. In some embodiments, the system can be configured to determine the length of one or more axes of a low density non-calcified plaque, such as for example a major axis of a longitudinal cross section and/or a major and/or minor axis of a latitudinal cross section of a low density non-calcified plaque. In some embodiments, the system can be configured to utilize the one more axes measurements to determine a morphology and/or shape of a low density non-calcified plaque. In some embodiments, the system can be configured to utilize one or more image processing algorithms to automatically and/or dynamically determine one or more axes measurements of one or more regions of plaque.

In some embodiments, the system can be configured to utilize one or more AI and/or ML algorithms to automatically and/or dynamically classify the shape of one or more regions of plaque using image processing. For example, in some embodiments, the one or more AI and/or ML algorithms can be trained using a Convolutional Neural Network (CNN) on a set of medical images on which the shape of regions of plaque have been identified, thereby allowing the AI and/or ML algorithm automatically identify the shape or morphology of a region of plaque directly from a medical image. In some embodiments, the system can be configured to classify the shape or morphology of a region of plaque as one or more of crescent, lobular, round, or bean-shaped. In some embodiments, round and/or bean-shaped plaques can be associated with high risk, while crescent and/or lobular-shaped plaques can be associated with low risk of CAD.

In some embodiments, the system can be configured to analyze and/or characterize one or more regions of plaque based on one or more sizes and/or volumes. For example, in some embodiments, the system can be configured to determine a size and/or volume of plaque based at least in part on one or more axes measurements described herein. In some embodiments, the system can be configured to determine the size and/or volume of a region of plaque directly from analysis of a three-dimensional image scan. In some embodiments, the system can be configured to determine the size and/or volume of total plaque, low-density non-calcified plaque, non-calcified plaque, calcified plaque, and/or a ratio between two of the aforementioned volumes or sizes. In some embodiments, a high total plaque volume and/or high low-density non-calcified plaque and/or non-calcified plaque volume can be associated with high risk of CAD. In some embodiments, a high ratio of low-density non-calcified plaque volume to total plaque volume and/or a high ratio of non-calcified plaque volume to total plaque volume can be associated with high risk of CAD. In some embodiments, a high calcified plaque volume and/or high ratio of calcified plaque volume to total plaque volume can be associated with low risk of CAD. In some embodiments, the system can be configured to utilize one or more predetermined threshold values for determining the risk of CAD based on plaque volume, size, or one or more ratios thereof. In some embodiments, the system can be configured to utilize one or more image processing algorithms to automatically and/or dynamically determine the size and/or volume of one or more regions of plaque.

In some embodiments, the system can be configured to analyze and/or characterize plaque based on embeddedness. For example, in some embodiments, the system can be configured to determined how embedded or surrounded a low density non-calcified plaque is by non-calcified plaque or calcified plaque. In some embodiments, the system can be configured to analyze the embeddedness of low density non-calcified plaque based on the degree by which it is surrounded by other types of plaque. In some embodiments, a higher embeddedness of a low density non-calcified plaque can be indicative of high risk of CAD. For example, in some embodiments, a low density non-calcified plaque that is surrounded by 270 degrees or more by non-calcified plaque can be associated with high risk of CAD. In some embodiments, the system can be configured to utilize one or more image processing algorithms to automatically and/or dynamically determine the embeddedness of one or more regions of plaque.

In some embodiments, at block 1212, the system can be configured to analyze the territories or lesions of the first vessel, the territories or lesions of the second vessel, the plaque of the territories or lesions of the first vessel, and the plaque of the territories or lesions of the second vessel to determine a plurality of variables for each of the territories or lesions of the first vessel and the second vessel. In some embodiments, the plurality of variables comprise stenosis.

In some embodiments the plurality of variables comprise volume of plaque. In some embodiments, the volume of plaque comprises one or more of volume of total plaque, volume of low density non-calcified plaque, volume of non-calcified plaque, or volume of calcified plaque. In some embodiments, the volume of plaque is determined based at least in part on analyzing density of one or more pixels corresponding to plaque in the medical image. In some embodiments, the density comprises material density. In some embodiments, the density comprises radiodensity. For example, in some embodiments, the system can be configured to characterize a particular region of plaque as low density non-calcified plaque when the radiodensity of an image pixel or voxel corresponding to that region of plaque is between about −189 and about 30 Hounsfield units (HU). In some embodiments, the system can be configured to characterize a particular region of plaque as non-calcified plaque when the radiodensity of an image pixel or voxel corresponding to that region of plaque is between about 31 and about 350 HU. In some embodiments, the system can be configured to characterize a particular region of plaque as calcified plaque when the radiodensity of an image pixel or voxel corresponding to that region of plaque is between about 351 and about 2500 HU. In some embodiments, the lower and/or upper Hounsfield unit boundary threshold for determining whether a plaque corresponds to one or more of low density non-calcified plaque, non-calcified plaque, and/ or calcified plaque can be about −1000 HU, about −900 HU, about −800 HU, about −700 HU, about −600 HU, about −500 HU, about −400 HU, about −300 HU, about −200 HU, about −190 HU, about −180 HU, about −170 HU, about −160 HU, about −150 HU, about −140 HU, about −130 HU, about −120 HU, about −110 HU, about −100 HU, about −90 HU, about −80 HU, about −70 HU, about −60 HU, about −50 HU, about −40 HU, about −30 HU, about −20 HU, about −10 HU, about 0 HU, about 10 HU, about 20 HU, about 30 HU, about 40 HU, about 50 HU, about 60 HU, about 70 HU, about 80 HU, about 90 HU, about 100 HU, about 110 HU, about 120 HU, about 130 HU, about 140 HU, about 150 HU, about 160 HU, about 170 HU, about 180 HU, about 190 HU, about 200 HU, about 210 HU, about 220 HU, about 230 HU, about 240 HU, about 250 HU, about 260 HU, about 270 HU, about 280 HU, about 290 HU, about 300 HU, about 310 HU, about 320 HU, about 330 HU, about 340 HU, about 350 HU, about 360 HU, about 370 HU, about 380 HU, about 390 HU, about 400 HU, about 410 HU, about 420 HU, about 430 HU, about 440 HU, about 450 HU, about 460 HU, about 470 HU, about 480 HU, about 490 HU, about 500 HU, about 510 HU, about 520 HU, about 530 HU, about 540 HU, about 550 HU, about 560 HU, about 570 HU, about 580 HU, about 590 HU, about 600 HU, about 700 HU, about 800 HU, about 900 HU, about 1000 HU, about 1100 HU, about 1200 HU, about 1300 HU, about 1400 HU, about 1500 HU, about 1600 HU, about 1700 HU, about 1800 HU, about 1900 HU, about 2000 HU, about 2100 HU, about 2200 HU, about 2300 HU, about 2400 HU, about 2500 HU, about 2600 HU, about 2700 HU, about 2800 HU, about 2900 HU, about 3000 HU, about 3100 HU, about 3200 HU, about 3300 HU, about 3400 HU, about 3500 HU, and/or about 4000 HU.

In some embodiments, at block 1214, the system can be configured to determine a presence of ischemia for one of the vessels, for example, the first vessel, based on the plurality of vessels determined for each of a plurality of vessels, for example, for the first vessel and the second vessel. For example, in some embodiments, a machine learning algorithm can be applied to the pluralities of vessels to determine the presence of ischemia. In some embodiments, the machine learning algorithm is trained based at least in part on a dataset comprising the plurality of variables and presence of ischemia derived using one or more of CT fractional flow reserve, computational fractional flow reserve, virtual fractional flow reserve, vessel fractional flow reserve, or quantitative flow ratio.

In some embodiments, at block 1216 the system can be configured to determine a risk of CAD or MI based on one or more plaque analyses described herein, for example in relation to one or more of blocks 1202-1216. In some embodiments, the system can be configured to utilize some or all of the plaque analyses results. In some embodiments, the system can be configured to generate a weighted measure of some or all of the plaque analyses described herein in determining a risk of CAD. In some embodiments, the system can be configured to refer to one or more reference values of one or more plaque analyses results in determining risk of CAD. For example, in some embodiments, the one or more reference values can comprise one or more values derived from a population with varying states of risks of CAD, wherein the one or more values can comprise one or more of one or more distances to and/or from a low density non-calcified plaque, one or more axes measurements, morphology classification, size and/or volume, and/or embeddedness of low density non-calcified plaque. In some embodiments, the one or more reference values can be stored on a reference values database 1218, which can be locally accessible by the system and/or can be located remotely and accessible through a network connection.

In some embodiments, at block 120, the system can be configured to generate a graphical representation of the analyses results, determined risk of CAD, and/or proposed treatment for the subject. In some embodiments, the analyses results can be displayed on a vessel, lesion, and/or subject basis. In some embodiments, the proposed treatment can include, for example, medical treatment such as statins, interventional treatment such as stent implantation, and/or lifestyle treatment such as exercise or diet. In some embodiments, in determining the risk or state of cardiovascular disease or health and/or treatment, the system can access a plaque risk/treatment database 1222, which can be locally accessible by the system and/or can be located remotely and accessible through a network connection. In some embodiments, the plaque risk/treatment database 1222 can include reference points or data that relate one or more treatment to cardiovascular disease risk or state determined based on one or more reference plaque analyses values.

In some embodiments, the system can be configured to repeat one or more processes described in relation to blocks 1202-1220, for example for one or more other vessels, segment, regions of plaque, different subjects, and/or for the same subject at a different time.

The computer system 902 of FIG. 9, and in some instances, the analysis and/or risk assessment module 940, can be configured to carry out the functions, methods, acts, and/or processes for multivariable image-based analysis of ischemia described herein, such as those described above with reference to FIG. 12.

The following are non-limiting examples of certain embodiments of systems and methods for multivariable image-based analysis of ischemia. Other embodiments may include one or more other features, or different features, that are discussed herein.

Embodiment 1: A computer-implemented method of determining presence of vessel-specific ischemia based at least in part on a plurality of variables derived from non-invasive medical image analysis, the method comprising: accessing, by a computer system, a medical image of a subject, wherein the medical image of the subject is obtained non-invasively; analyzing, by the computer system, the medical image of the subject to identify a plurality of vessels, the plurality of vessels comprising a first vessel and a second vessel; identifying, by the computer system, one or more territories in the first vessel and one or more territories in the second vessel; identifying, by the computer system, one or more regions of plaque within the one or more territories in the first vessel and the one or more territories in the second vessel; analyzing, by the computer system, the one or more territories in the first vessel, the one or more territories in the second vessel, the one or more regions of plaque within the one or more territories in the first vessel, and the one or more regions of plaque within the one or more territories in the second vessel to determine a plurality of variables for each of the one or more territories in the first vessel and the one or more territories in the second vessel; and applying, by the computer system, a machine learning algorithm to determine a presence of ischemia in the first vessel based at least in part on the plurality of variables determined for the one or more territories in the first vessel and the plurality of variables determined for the one or more territories in the second vessel, wherein the computer system comprises a computer processor and an electronic storage medium.

Embodiment 2: The computer-implemented method of Embodiment 1, wherein the plurality of variables comprises stenosis.

Embodiment 3: The computer-implemented method of Embodiment 1, wherein the plurality of variables comprises volume of plaque.

Embodiment 4: The computer-implemented method of Embodiment 3, wherein the volume of plaque comprises one or more of volume of total plaque, volume of low density non-calcified plaque, volume of non-calcified plaque, or volume of calcified plaque.

Embodiment 5: The computer-implemented method of Embodiment 4, wherein the volume of plaque is determined based at least in part on analyzing density of one or more pixels corresponding to plaque in the medical image.

Embodiment 6: The computer-implemented method of Embodiment 5, wherein the density comprises material density.

Embodiment 7: The computer-implemented method of Embodiment 5, wherein the density comprises radiodensity.

Embodiment 8: The computer-implemented method of Embodiment 7, wherein low density non-calcified plaque corresponds to one or more pixels with a radiodensity value between about −189 and about 30 Hounsfield units.

Embodiment 9: The computer-implemented method of Embodiment 7, wherein non-calcified plaque corresponds to one or more pixels with a radiodensity value between about 31 and about 189 Hounsfield units.

Embodiment 10: The computer-implemented method of Embodiment 7, wherein non-calcified plaque corresponds to one or more pixels with a radiodensity value between about 190 and about 350 Hounsfield units.

Embodiment 11: The computer-implemented method of Embodiment 7, wherein calcified plaque corresponds to one or more pixels with a radiodensity value between about 351 and 2500 Hounsfield units.

Embodiment 12: The computer-implemented method of Embodiment 1, wherein the medical image comprises a Computed Tomography (CT) image.

Embodiment 13: The computer-implemented method of Embodiment 1, wherein the medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 14: The computer-implemented method of Embodiment 1, wherein the plurality of variables comprises one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, or low-density plaque volume.

Embodiment 15: The computer-implemented method of Embodiment 1, wherein the plurality of vessels comprises one or more coronary arteries.

Embodiment 16: The computer-implemented method of Embodiment 15, wherein the one or more coronary arteries comprise one or more of left main (LM), ramus intermedius (RI), left anterior descending (LAD), diagonal 1 (D1), diagonal 2 (D2), left circumflex (Cx), obtuse marginal 1 (OM1), obtuse marginal 2 (OM2), left posterior descending artery (L-PDA), left posterolateral branch (L-PLB), right coronary artery (RCA), right posterior descending artery (R-PDA), or right posterolateral branch (R-PLB).

Embodiment 17: The computer-implemented method of Embodiment 1, wherein the machine learning algorithm is trained based at least in part on a dataset comprising the plurality of variables and presence of ischemia derived using invasive fractional flow reserve.

Embodiment 18: The computer-implemented method of Embodiment 1, wherein the machine learning algorithm is trained based at least in part on a dataset comprising the plurality of variables and presence of ischemia derived using one or more of CT fractional flow reserve, computational fractional flow reserve, virtual fractional flow reserve, vessel fractional flow reserve, or quantitative flow ratio.

Embodiment 19: The computer-implemented method of Embodiment 1, further comprising generating, by the computer system, an assessment of risk of coronary artery disease (CAD) or major adverse cardiovascular event (MACE) of the subject based at least in part on the determination of presence of ischemia in the first vessel.

Embodiment 20: The computer-implemented method of Embodiment 19, further comprising generating, by the computer system, a graphical representation of the generated assessment of risk of CAD or MACE.

Embodiment 21: The computer-implemented method of Embodiment 19, further comprising generating, by the computer system, a recommended treatment for the subject based at least in part on the generated assessment of risk of CAD or MACE.

Embodiment 22: A computer-implemented method of determining presence of vessel-specific ischemia based at least in part on a plurality of variables derived from non-invasive medical image analysis, the method comprising: accessing, by a computer system, a medical image of a subject, wherein the medical image of the subject is obtained non-invasively; analyzing, by the computer system, the medical image of the subject to identify a plurality of vessels, the plurality of vessels comprising a first vessel and a second vessel; identifying, by the computer system, one or more lesions in the first vessel and one or more lesions in the second vessel; identifying, by the computer system, one or more regions of plaque within the one or more lesions in the first vessel and one or more regions of plaque within the one or more lesions in the second vessel; analyzing, by the computer system, the one or more lesions in the first vessel, the one or more lesions in the second vessel, the one or more regions of plaque within the one or more lesions in the first vessel, and the one or more regions of plaque within the one or more lesions in the second vessel to determine a plurality of variables for each of the one or more lesions in the first vessel and the one or more lesions in the second vessel; and applying, by the computer system, a machine learning algorithm to determine a presence of ischemia in the first vessel based at least in part on the plurality of variables determined for the one or more lesions in the first vessel and the plurality of variables determined for the one or more lesions in the second vessel, wherein the computer system comprises a computer processor and an electronic storage medium.

Embodiment 23: The computer-implemented method of Embodiment 22, wherein the plurality of variables comprises stenosis.

Embodiment 24: The computer-implemented method of Embodiment 22, wherein the plurality of variables comprises volume of plaque.

Embodiment 25: The computer-implemented method of Embodiment 24, wherein the volume of plaque comprises one or more of volume of total plaque, volume of low density non-calcified plaque, volume of non-calcified plaque, or volume of calcified plaque.

Embodiment 26: The computer-implemented method of Embodiment 25, wherein the volume of plaque is determined based at least in part on analyzing density of one or more pixels corresponding to plaque in the medical image.

Embodiment 27: The computer-implemented method of Embodiment 26, wherein the density comprises material density.

Embodiment 28: The computer-implemented method of Embodiment 26, wherein the density comprises radiodensity.

Embodiment 29: The computer-implemented method of Embodiment 28, wherein low density non-calcified plaque corresponds to one or more pixels with a radiodensity value between about −189 and about 30 Hounsfield units.

Embodiment 30: The computer-implemented method of Embodiment 28, wherein low density non-calcified plaque corresponds to one or more pixels with a radiodensity value between about 31 and about 189 Hounsfield units.

Embodiment 31: The computer-implemented method of Embodiment 28, wherein non-calcified plaque corresponds to one or more pixels with a radiodensity value between about 190 and about 350 Hounsfield units.

Embodiment 32: The computer-implemented method of Embodiment 28, wherein calcified plaque corresponds to one or more pixels with a radiodensity value between about 351 and 2500 Hounsfield units.

Embodiment 33: The computer-implemented method of Embodiment 22, wherein the medical image comprises a Computed Tomography (CT) image.

Embodiment 34: The computer-implemented method of Embodiment 22, wherein the medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 35: The computer-implemented method of Embodiment 22, wherein the plurality of variables comprises one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, or low-density plaque volume.

Embodiment 36: The computer-implemented method of Embodiment 22, wherein the plurality of vessels comprises one or more coronary arteries.

Embodiment 37: The computer-implemented method of Embodiment 36, wherein the one or more coronary arteries comprise one or more of left main (LM), ramus intermedius (RI), left anterior descending (LAD), diagonal 1 (D1), diagonal 2 (D2), left circumflex (Cx), obtuse marginal 1 (OM1), obtuse marginal 2 (OM2), left posterior descending artery (L-PDA), left posterolateral branch (L-PLB), right coronary artery (RCA), right posterior descending artery (R-PDA), or right posterolateral branch (R-PLB).

Embodiment 38: The computer-implemented method of Embodiment 22, wherein the machine learning algorithm is trained based at least in part on a dataset comprising the plurality of variables and presence of ischemia derived using invasive fractional flow reserve.

Embodiment 39: The computer-implemented method of Embodiment 22, wherein the machine learning algorithm is trained based at least in part on a dataset comprising the plurality of variables and presence of ischemia derived using one or more of CT fractional flow reserve, computational fractional flow reserve, virtual fractional flow reserve, vessel fractional flow reserve, or quantitative flow ratio.

Embodiment 40: The computer-implemented method of Embodiment 22, further comprising generating, by the computer system, an assessment of risk of coronary artery disease (CAD) or major adverse cardiovascular event (MACE) of the subject based at least in part on the determination of presence of ischemia in the first vessel.

Embodiment 41: The computer-implemented method of Embodiment 40, further comprising generating, by the computer system, a graphical representation of the generated assessment of risk of CAD or MACE.

Embodiment 42: The computer-implemented method of Embodiment 40, further comprising generating, by the computer system, a recommended treatment for the subject based at least in part on the generated assessment of risk of CAD or MACE.

Embodiment 43: A system for determining presence of vessel-specific ischemia based at least in part on a plurality of variables derived from non-invasive medical image analysis, the comprising: a non-transitory computer storage medium configured to at least store computer-executable instructions; and one or more computer hardware processors in communication with the first non-transitory computer storage medium, the one or more computer hardware processors configured to execute the computer-executable instructions to at least: access a medical image of a subject, wherein the medical image of the subject is obtained non-invasively; analyze the medical image of the subject to identify a plurality of vessels, the plurality of vessels comprising a first vessel and a second vessel; identify one or more territories in the first vessel and one or more territories in the second vessel; identify one or more regions of plaque within the one or more territories in the first vessel and the one or more territories in the second vessel; analyze the one or more territories in the first vessel, the one or more territories in the second vessel, the one or more regions of plaque within the one or more territories in the first vessel, and the one or more regions of plaque within the one or more territories in the second vessel to determine a plurality of variables for each of the one or more territories in the first vessel and the one or more territories in the second vessel; and apply a machine learning algorithm to determine a presence of ischemia in the first vessel based at least in part on the plurality of variables determined for the one or more territories in the first vessel and the plurality of variables determined for the one or more territories in the second vessel.

Embodiment 44: The system of Embodiment 43, wherein the plurality of variables comprises stenosis.

Embodiment 45: The system of Embodiment 43, wherein the plurality of variables comprises volume of plaque.

Embodiment 46: The system of Embodiment 45, wherein the volume of plaque comprises one or more of volume of total plaque, volume of low density non-calcified plaque, volume of non-calcified plaque, or volume of calcified plaque.

Embodiment 47: The system of Embodiment 46, wherein the volume of plaque is determined based at least in part on analyzing density of one or more pixels corresponding to plaque in the medical image.

Embodiment 48: The system of Embodiment 47, wherein the density comprises material density.

Embodiment 49: The system of Embodiment 47, wherein the density comprises radiodensity.

Embodiment 50: The system of Embodiment 49, wherein low density non-calcified plaque corresponds to one or more pixels with a radiodensity value between about −189 and about 30 Hounsfield units.

Embodiment 51: The system of Embodiment 49, wherein non-calcified plaque corresponds to one or more pixels with a radiodensity value between about 31 and about 189 Hounsfield units.

Embodiment 52: The system of Embodiment 49, wherein non-calcified plaque corresponds to one or more pixels with a radiodensity value between about 190 and about 350 Hounsfield units.

Embodiment 53: The system of Embodiment 49, wherein calcified plaque corresponds to one or more pixels with a radiodensity value between about 351 and 2500 Hounsfield units.

Embodiment 54: The system of Embodiment 43, wherein the medical image comprises a Computed Tomography (CT) image.

Embodiment 55: The system of Embodiment 43, wherein the medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 56: The system method of Embodiment 43, wherein the plurality of variables comprises one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, or low-density plaque volume.

Embodiment 57: The system of Embodiment 43, wherein the plurality of vessels comprises one or more coronary arteries.

Embodiment 58: The system of Embodiment 57, wherein the one or more coronary arteries comprise one or more of left main (LM), ramus intermedius (RI), left anterior descending (LAD), diagonal 1 (D1), diagonal 2 (D2), left circumflex (Cx), obtuse marginal 1 (OM1), obtuse marginal 2 (OM2), left posterior descending artery (L-PDA), left posterolateral branch (L-PLB), right coronary artery (RCA), right posterior descending artery (R-PDA), or right posterolateral branch (R-PLB).

Embodiment 59: The system of Embodiment 43, wherein the machine learning algorithm is trained based at least in part on a dataset comprising the plurality of variables and presence of ischemia derived using invasive fractional flow reserve.

Embodiment 60: The system of Embodiment 43, wherein the machine learning algorithm is trained based at least in part on a dataset comprising the plurality of variables and presence of ischemia derived using one or more of CT fractional flow reserve, computational fractional flow reserve, virtual fractional flow reserve, vessel fractional flow reserve, or quantitative flow ratio.

Embodiment 61: The system of Embodiment 43, wherein the processor is further configured to generate an assessment of risk of coronary artery disease (CAD) or major adverse cardiovascular event (MACE) of the subject based at least in part on the determination of presence of ischemia in the first vessel.

Embodiment 62: The system of Embodiment 61, wherein the processor is further configured to generate a graphical representation of the generated assessment of risk of CAD or MACE.

Embodiment 63: The system of Embodiment 61, wherein the processor is further configured to generate recommended treatment for the subject based at least in part on the generated assessment of risk of CAD or MACE.

Embodiment 64: A system for determining presence of vessel-specific ischemia based at least in part on a plurality of variables derived from non-invasive medical image analysis, the comprising: a non-transitory computer storage medium configured to at least store computer-executable instructions; and one or more computer hardware processors in communication with the first non-transitory computer storage medium, the one or more computer hardware processors configured to execute the computer-executable instructions to at least: identify one or more lesions in the first vessel and one or more lesions in the second vessel; identify one or more regions of plaque within the one or more lesions in the first vessel and one or more regions of plaque within the one or more lesions in the second vessel; analyze the one or more lesions in the first vessel, the one or more lesions in the second vessel, the one or more regions of plaque within the one or more lesions in the first vessel, and the one or more regions of plaque within the one or more lesions in the second vessel to determine a plurality of variables for each of the one or more lesions in the first vessel and the one or more lesions in the second vessel; and apply a machine learning algorithm to determine a presence of ischemia in the first vessel based at least in part on the plurality of variables determined for the one or more lesions in the first vessel and the plurality of variables determined for the one or more lesions in the second vessel.

Embodiment 65: The system of Embodiment 64, wherein the plurality of variables comprises stenosis.

Embodiment 66: The system of Embodiment 64, wherein the plurality of variables comprises volume of plaque.

Embodiment 67: The system of Embodiment 66, wherein the volume of plaque comprises one or more of volume of total plaque, volume of low density non-calcified plaque, volume of non-calcified plaque, or volume of calcified plaque.

Embodiment 68: The system of Embodiment 67, wherein the volume of plaque is determined based at least in part on analyzing density of one or more pixels corresponding to plaque in the medical image.

Embodiment 69: The system of Embodiment 67, wherein the density comprises material density.

Embodiment 70: The system of Embodiment 67, wherein the density comprises radiodensity.

Embodiment 71: The system of Embodiment 70, wherein low density non-calcified plaque corresponds to one or more pixels with a radiodensity value between about −189 and about 30 Hounsfield units.

Embodiment 72: The system of Embodiment 70, wherein low density non-calcified plaque corresponds to one or more pixels with a radiodensity value between about 31 and about 189 Hounsfield units.

Embodiment 73: The system of Embodiment 70, wherein non-calcified plaque corresponds to one or more pixels with a radiodensity value between about 190 and about 350 Hounsfield units.

Embodiment 74: The system of Embodiment 70, wherein calcified plaque corresponds to one or more pixels with a radiodensity value between about 351 and 2500 Hounsfield units.

Embodiment 75: The system of Embodiment 64, wherein the medical image comprises a Computed Tomography (CT) image.

Embodiment 76: The system of Embodiment 64, wherein the medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 77: The system of Embodiment 64, wherein the plurality of variables comprises one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, or low-density plaque volume.

Embodiment 78: The system of Embodiment 64, wherein the plurality of vessels comprises one or more coronary arteries.

Embodiment 79: The system of Embodiment 78, wherein the one or more coronary arteries comprise one or more of left main (LM), ramus intermedius (RI), left anterior descending (LAD), diagonal 1 (D1), diagonal 2 (D2), left circumflex (Cx), obtuse marginal 1 (OM1), obtuse marginal 2 (OM2), left posterior descending artery (L-PDA), left posterolateral branch (L-PLB), right coronary artery (RCA), right posterior descending artery (R-PDA), or right posterolateral branch (R-PLB).

Embodiment 80: The system of Embodiment 64, wherein the machine learning algorithm is trained based at least in part on a dataset comprising the plurality of variables and presence of ischemia derived using invasive fractional flow reserve.

Embodiment 81: The system of Embodiment 64, wherein the machine learning algorithm is trained based at least in part on a dataset comprising the plurality of variables and presence of ischemia derived using one or more of CT fractional flow reserve, computational fractional flow reserve, virtual fractional flow reserve, vessel fractional flow reserve, or quantitative flow ratio.

Embodiment 82: The system of Embodiment 64, wherein the processor is further configured to generate an assessment of risk of coronary artery disease (CAD) or major adverse cardiovascular event (MACE) of the subject based at least in part on the determination of presence of ischemia in the first vessel.

Embodiment 83: The system of Embodiment 82, wherein the processor is further configured to generate a graphical representation of the generated assessment of risk of CAD or MACE.

Embodiment 84: The system of Embodiment 82, wherein the processor is further configured to generate a recommended treatment for the subject based at least in part on the generated assessment of risk of CAD or MACE.

Embodiment 85: A non-transitory computer readable medium configured for determining presence of vessel-specific ischemia based at least in part on a plurality of variables derived from non-invasive medical image analysis, the computer readable medium having program instructions for causing a hardware processor to perform a method of: accessing a medical image of a subject, wherein the medical image of the subject is obtained non-invasively; analyzing the medical image of the subject to identify a plurality of vessels, the plurality of vessels comprising a first vessel and a second vessel; identifying one or more territories in the first vessel and one or more territories in the second vessel; identifying one or more regions of plaque within the one or more territories in the first vessel and the one or more territories in the second vessel; analyzing the one or more territories in the first vessel, the one or more territories in the second vessel, the one or more regions of plaque within the one or more territories in the first vessel, and the one or more regions of plaque within the one or more territories in the second vessel to determine a plurality of variables for each of the one or more territories in the first vessel and the one or more territories in the second vessel; and applying a machine learning algorithm to determine a presence of ischemia in the first vessel based at least in part on the plurality of variables determined for the one or more territories in the first vessel and the plurality of variables determined for the one or more territories in the second vessel.

Embodiment 86: The non-transitory computer readable medium of Embodiment 85, wherein the plurality of variables comprises stenosis.

Embodiment 87: The non-transitory computer readable medium of Embodiment 85, wherein the plurality of variables comprises volume of plaque.

Embodiment 88: The non-transitory computer readable medium of Embodiment 87, wherein the volume of plaque comprises one or more of volume of total plaque, volume of low density non-calcified plaque, volume of non-calcified plaque, or volume of calcified plaque.

Embodiment 89: The non-transitory computer readable medium of Embodiment 88, wherein the volume of plaque is determined based at least in part on analyzing density of one or more pixels corresponding to plaque in the medical image.

Embodiment 90: The non-transitory computer readable medium of Embodiment 89, wherein the density comprises material density.

Embodiment 91: The non-transitory computer readable medium of Embodiment 89, wherein the density comprises radiodensity.

Embodiment 92: The non-transitory computer readable medium of Embodiment 91, wherein low density non-calcified plaque corresponds to one or more pixels with a radiodensity value between about 189 and about 30 Hounsfield units.

Embodiment 93: The non-transitory computer readable medium of Embodiment 91, wherein non-calcified plaque corresponds to one or more pixels with a radiodensity value between about 31 and about 189 Hounsfield units.

Embodiment 94: The non-transitory computer readable medium of Embodiment 91, wherein non-calcified plaque corresponds to one or more pixels with a radiodensity value between about 190 and about 350 Hounsfield units.

Embodiment 95: The non-transitory computer readable medium of Embodiment 91, wherein calcified plaque corresponds to one or more pixels with a radiodensity value between about 351 and 2500 Hounsfield units.

Embodiment 96: The non-transitory computer readable medium of Embodiment 85, wherein the medical image comprises a Computed Tomography (CT) image.

Embodiment 97: The non-transitory computer readable medium of Embodiment 85, wherein the medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 98: The non-transitory computer readable medium of Embodiment 85, wherein the plurality of variables comprises one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, or low-density plaque volume.

Embodiment 99: The non-transitory computer readable medium of Embodiment 85, wherein the plurality of vessels comprises one or more coronary arteries.

Embodiment 100: The non-transitory computer readable medium of Embodiment 99, wherein the one or more coronary arteries comprise one or more of left main (LM), ramus intermedius (RI), left anterior descending (LAD), diagonal 1 (D1), diagonal 2 (D2), left circumflex (Cx), obtuse marginal 1 (OM1), obtuse marginal 2 (OM2), left posterior descending artery (L-PDA), left posterolateral branch (L-PLB), right coronary artery (RCA), right posterior descending artery (R-PDA), or right posterolateral branch (R-PLB).

Embodiment 101: The non-transitory computer readable medium of Embodiment 85, wherein the machine learning algorithm is trained based at least in part on a dataset comprising the plurality of variables and presence of ischemia derived using invasive fractional flow reserve.

Embodiment 102: The non-transitory computer readable medium of Embodiment 85, wherein the machine learning algorithm is trained based at least in part on a dataset comprising the plurality of variables and presence of ischemia derived using one or more of CT fractional flow reserve, computational fractional flow reserve, virtual fractional flow reserve, vessel fractional flow reserve, or quantitative flow ratio.

Embodiment 103: The non-transitory computer readable medium of Embodiment 85, wherein the method further comprises generating, by the computer system, an assessment of risk of coronary artery disease (CAD) or major adverse cardiovascular event (MACE) of the subject based at least in part on the determination of presence of ischemia in the first vessel.

Embodiment 104: The non-transitory computer readable medium of Embodiment 103, wherein the method further comprises generating, by the computer system, a graphical representation of the generated assessment of risk of CAD or MACE.

Embodiment 105: The non-transitory computer readable medium of Embodiment 103, wherein the method further comprises generating, by the computer system, a recommended treatment for the subject based at least in part on the generated assessment of risk of CAD or MACE.

Embodiment 106: A non-transitory computer readable medium configured for determining presence of vessel-specific ischemia based at least in part on a plurality of variables derived from non-invasive medical image analysis, the computer readable medium having program instructions for causing a hardware processor to perform a method of: accessing a medical image of a subject, wherein the medical image of the subject is obtained non-invasively; analyzing the medical image of the subject to identify a plurality of vessels, the plurality of vessels comprising a first vessel and a second vessel; identifying one or more lesions in the first vessel and one or more lesions in the second vessel; identifying one or more regions of plaque within the one or more lesions in the first vessel and one or more regions of plaque within the one or more lesions in the second vessel; analyzing the one or more lesions in the first vessel, the one or more lesions in the second vessel, the one or more regions of plaque within the one or more lesions in the first vessel, and the one or more regions of plaque within the one or more lesions in the second vessel to determine a plurality of variables for each of the one or more lesions in the first vessel and the one or more lesions in the second vessel; and applying a machine learning algorithm to determine a presence of ischemia in the first vessel based at least in part on the plurality of variables determined for the one or more lesions in the first vessel and the plurality of variables determined for the one or more lesions in the second vessel.

Embodiment 107: The non-transitory computer readable medium of Embodiment 106, wherein the plurality of variables comprises stenosis.

Embodiment 108: The non-transitory computer readable medium of Embodiment 106, wherein the plurality of variables comprises volume of plaque.

Embodiment 109: The non-transitory computer readable medium of Embodiment 108, wherein the volume of plaque comprises one or more of volume of total plaque, volume of low density non-calcified plaque, volume of non-calcified plaque, or volume of calcified plaque.

Embodiment 110: The non-transitory computer readable medium of Embodiment 109, wherein the volume of plaque is determined based at least in part on analyzing density of one or more pixels corresponding to plaque in the medical image.

Embodiment 111: The non-transitory computer readable medium of Embodiment 109, wherein the density comprises material density.

Embodiment 112: The non-transitory computer readable medium of Embodiment 109, wherein the density comprises radiodensity.

Embodiment 113: The non-transitory computer readable medium of Embodiment 112, wherein low density non-calcified plaque corresponds to one or more pixels with a radiodensity value between about −189 and about 30 Hounsfield units.

Embodiment 114: The non-transitory computer readable medium of Embodiment 112, wherein low density non-calcified plaque corresponds to one or more pixels with a radiodensity value between about 31 and about 189 Hounsfield units.

Embodiment 115: The non-transitory computer readable medium of Embodiment 112, wherein non-calcified plaque corresponds to one or more pixels with a radiodensity value between about 190 and about 350 Hounsfield units.

Embodiment 116: The non-transitory computer readable medium of Embodiment 112, wherein calcified plaque corresponds to one or more pixels with a radiodensity value between about 351 and 2500 Hounsfield units.

Embodiment 117: The non-transitory computer readable medium of Embodiment 109, wherein the medical image comprises a Computed Tomography (CT) image.

Embodiment 118: The non-transitory computer readable medium of Embodiment 109, wherein the medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 119: The non-transitory computer readable medium of Embodiment 109, wherein the plurality of variables comprises one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, or low-density plaque volume.

Embodiment 120: The non-transitory computer readable medium of Embodiment 109, wherein the plurality of vessels comprises one or more coronary arteries.

Embodiment 121: The non-transitory computer readable medium of Embodiment 120, wherein the one or more coronary arteries comprise one or more of left main (LM), ramus intermedius (RI), left anterior descending (LAD), diagonal 1 (D1), diagonal 2 (D2), left circumflex (Cx), obtuse marginal 1 (OM1), obtuse marginal 2 (OM2), left posterior descending artery (L-PDA), left posterolateral branch (L-PLB), right coronary artery (RCA), right posterior descending artery (R-PDA), or right posterolateral branch (R-PLB).

Embodiment 122: The non-transitory computer readable medium of Embodiment 109, wherein the machine learning algorithm is trained based at least in part on a dataset comprising the plurality of variables and presence of ischemia derived using invasive fractional flow reserve.

Embodiment 123: The non-transitory computer readable medium of Embodiment 109, wherein the machine learning algorithm is trained based at least in part on a dataset comprising the plurality of variables and presence of ischemia derived using one or more of CT fractional flow reserve, computational fractional flow reserve, virtual fractional flow reserve, vessel fractional flow reserve, or quantitative flow ratio.

Embodiment 124: The non-transitory computer readable medium of Embodiment 109, wherein the method further comprises generating, by the computer system, an assessment of risk of coronary artery disease (CAD) or major adverse cardiovascular event (MACE) of the subject based at least in part on the determination of presence of ischemia in the first vessel.

Embodiment 125: The non-transitory computer readable medium of Embodiment 124, wherein the method further comprises generating, by the computer system, a graphical representation of the generated assessment of risk of CAD or MACE.

Embodiment 126: The non-transitory computer readable medium of Embodiment 124, wherein the method further comprises generating, by the computer system, a recommended treatment for the subject based at least in part on the generated assessment of risk of CAD or MACE.

Image-Based Analysis for Determination of Cardiac Catheterization

Disclosed herein are systems, devices, and methods for image-based analysis for determination of cardiac catheterization. In particular, in some embodiments, the systems, devices, and methods described herein analyze one or more medical images (e.g., noninvasively obtained medical images) of a patient identify one or more vessels (e.g., coronary arteries) within the image and one or more regions of plaque associated with the vessels. The systems, devices, and methods can further analyze the identified one or more vessels and the identified one or more regions of plaque to generate a plurality of image-derived variables associated therewith. The plurality of variables can include one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, or low-density plaque volume.

The devices, systems, and methods can further include applying a machine learning algorithm to determine risk of coronary artery disease (CAD) or major adverse cardiovascular event (MACE) for the patient based at least in part on the plurality of variables. In some embodiments, the machine learning algorithm can be trained based at least in part on the variables derived from medical images of other subjects with known risk of CAD or MACE. The devices, systems, and methods can then further include determining a need for cardiac catheterization for the patient based at least in part on the determined risk of CAD or MACE. In some embodiments, a risk stratification (e.g., low, intermediate, or high) can be determined. In some embodiments, the need for catheterization is determined based on the risk of CAD or MACE being above a predetermined threshold is indicative of a need for cardiac catheterization. In some embodiments, the devices, systems and methods can further generate a graphical representation of the determined need for cardiac catheterization for the patient. In some embodiments, In some embodiments, the devices systems and methods can further determine a type of cardiac catheterization for the patient based at least in part on the determined risk of CAD or MACE and the plurality variables. The type of cardiac catheterization can include one or more of coronary angiography, right heart catheterization, coronary catheterization, placement of a pacemaker or defibrillator, valve assessment, pulmonary angiography, shunt evaluation, ventriculography, percutaneous aortic valve replacement, balloon septostomy, stenting, or alcohol septal ablation. In some embodiments, the type of cardiac catheterization for the patient can be determined using a machine learning algorithm trained based at least in part on the plurality of image-derived variables derived from medical images of other subjects with known risk of CAD or MACE and with known types of cardiac catheterization.

In some embodiments, the cardiac catheterization can be used for one or more of coronary angiography, right heart catheterization, coronary catheterization, placement of a pacemaker or defibrillator, valve assessment, pulmonary angiography, shunt evaluation, ventriculography, percutaneous aortic valve replacement, balloon septostomy, stenting, or alcohol septal ablation.

In some embodiments, the systems, devices, and methods for determination of cardiac catheterization can be useful in determining whether a patient can safely be discharged, or whether the patient should be sent to a catheterization lab or emergency room.

Figure 13:
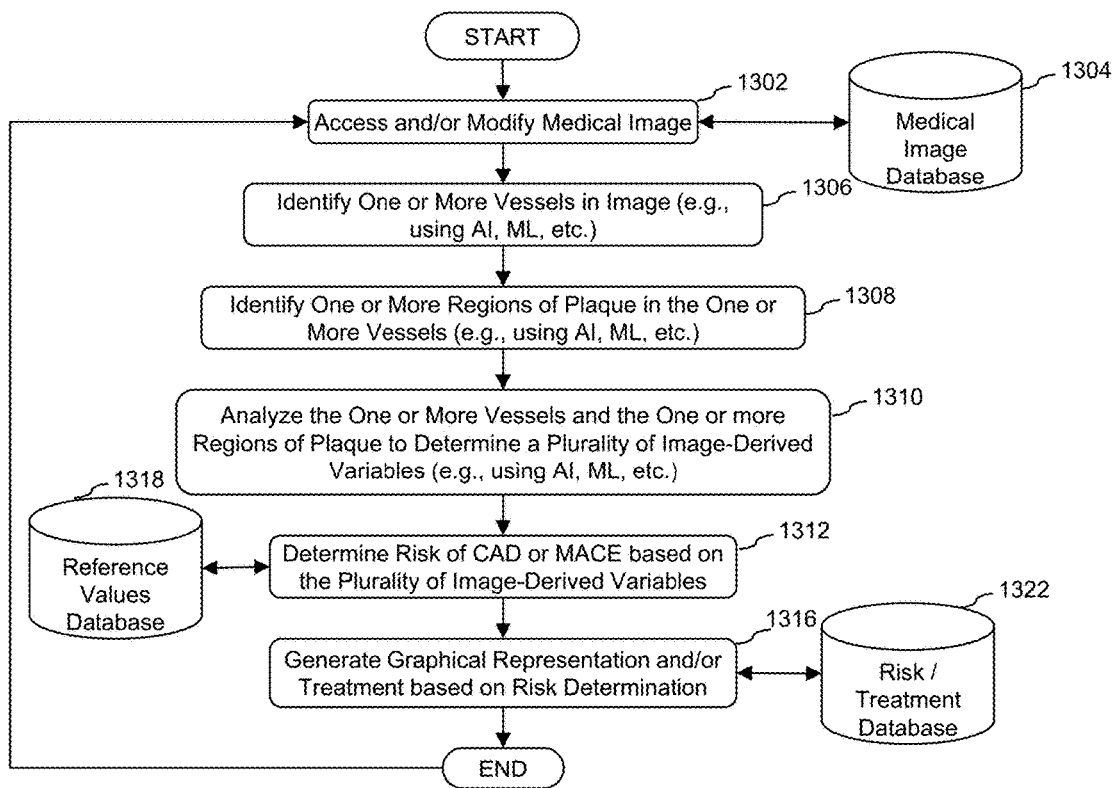
FIG. 13 is a flowchart illustrating an example embodiment(s) of systems, devices, and methods for image-based analysis for determination of cardiac catheterization.

FIG. 13 is a flowchart illustrating an example embodiment(s) of systems, devices, and methods for determination of cardiac catheterization. As illustrated in FIG. 13, in some embodiments, the system can be configured to access and/or modify one or more medical images at block 1302. In some embodiments, the medical image can include one or more arteries, such as coronary, carotid, and/or other arteries of a subject. In some embodiments, the medical image can be stored in a medical image database 1304. In some embodiments, the medical image database 1304 can be locally accessible by the system and/or can be located remotely and accessible through a network connection. The medical image can comprise an image obtain using one or more modalities such as for example, CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the medical image comprises one or more of a contrast-enhanced CT image, non-contrast CT image, MR image, and/or an image obtained using any of the modalities described above.

In some embodiments, the system can be configured to automatically and/or dynamically perform one or more analyses of the medical image as discussed herein. For example, in some embodiments, at block 1306, the system can be configured to identify one or more vessels, such as of one or more arteries. The one or more arteries can include coronary arteries, carotid arteries, aorta, renal artery, lower extremity artery, upper extremity artery, and/or cerebral artery, amongst others. In some embodiments, the one or more coronary arteries comprise one or more of left main (LM), ramus intermedius (RI), left anterior descending (LAD), diagonal 1 (D1), diagonal 2 (D2), left circumflex (Cx), obtuse marginal 1 (OM1), obtuse marginal 2 (OM2), left posterior descending artery (L-PDA), left posterolateral branch (L-PLB), right coronary artery (RCA), right posterior descending artery (R-PDA), or right posterolateral branch (R-PLB).

In some embodiments, the system can be configured to utilize one or more AI and/or ML algorithms to automatically and/or dynamically identify one or more arteries or coronary arteries using image processing. For example, in some embodiments, the one or more AI and/or ML algorithms can be trained using a Convolutional Neural Network (CNN) on a set of medical images on which arteries or coronary arteries have been identified, thereby allowing the AI and/or ML algorithm automatically identify arteries or coronary arteries directly from a medical image. In some embodiments, the arteries or coronary arteries are identified by size and/or location.

In some embodiments, at block 1308, the system can be configured to identify one or more regions of plaque in the medical image. In some embodiments, the system can be configured to utilize one or more AI and/or ML algorithms to automatically and/or dynamically identify one or more regions of plaque using image processing. For example, in some embodiments, the one or more AI and/or ML algorithms can be trained using a Convolutional Neural Network (CNN) on a set of medical images on which regions of plaque have been identified, thereby allowing the AI and/or ML algorithm automatically identify regions of plaque directly from a medical image. In some embodiments, the system is configured to identify vessel and lumen walls and classify everything in between the vessel and lumen walls as plaque.

In some embodiments, the system can be configured to analyze and/or characterize one or more regions of plaque based on density. For example, in some embodiments, the system can be configured to analyze and/or characterize one or more regions of plaque based on absolute density and/or relative density and/or radiodensity. In some embodiments, the system can be configured to classify a region of plaque as one of low density non-calcified plaque, non-calcified plaque, and calcified plaque, using any one or more processes and/or features described herein.

In some embodiments, the system can be configured to analyze and/or characterize one or more regions of plaque based on one or more distances. For example, as described herein, in some embodiments, the system can be configured to determine a distance between a low density non-calcified plaque and lumen wall and/or vessel wall. In some embodiments, proximity of a low density non-calcified plaque to the lumen wall can be indicative of a high-risk plaque and/or CAD. Conversely, in some embodiments, a position of a low density non-calcified plaque far from the lumen wall can be indicative of less risk. In some embodiments, the system can be configured to utilize one or more predetermined thresholds in determining the risk factor associated with the proximity of low density non-calcified plaque with the vessel wall and/or lumen wall. In some embodiments, the system can be configured to utilize one or more image processing algorithms to automatically and/or dynamically determine one or more distances to and/or from one or more regions of plaque.

In some embodiments, the system can be configured to analyze and/or characterize one or more regions of plaque based on morphology or shape and/or one or more axes measurements of low density non-calcified plaque. In some embodiments, the system can be configured to determine the length of one or more axes of a low density non-calcified plaque, such as for example a major axis of a longitudinal cross section and/or a major and/or minor axis of a latitudinal cross section of a low density non-calcified plaque. In some embodiments, the system can be configured to utilize the one more axes measurements to determine a morphology and/or shape of a low density non-calcified plaque. In some embodiments, the system can be configured to utilize one or more image processing algorithms to automatically and/or dynamically determine one or more axes measurements of one or more regions of plaque.

In some embodiments, the system can be configured to utilize one or more AI and/or ML algorithms to automatically and/or dynamically classify the shape of one or more regions of plaque using image processing. For example, in some embodiments, the one or more AI and/or ML algorithms can be trained using a Convolutional Neural Network (CNN) on a set of medical images on which the shape of regions of plaque have been identified, thereby allowing the AI and/or ML algorithm automatically identify the shape or morphology of a region of plaque directly from a medical image. In some embodiments, the system can be configured to classify the shape or morphology of a region of plaque as one or more of crescent, lobular, round, or bean-shaped. In some embodiments, round and/or bean-shaped plaques can be associated with high risk, while crescent and/or lobular-shaped plaques can be associated with low risk of CAD.

In some embodiments, the system can be configured to analyze and/or characterize one or more regions of plaque based on one or more sizes and/or volumes. For example, in some embodiments, the system can be configured to determine a size and/or volume of plaque based at least in part on one or more axes measurements described herein. In some embodiments, the system can be configured to determine the size and/or volume of a region of plaque directly from analysis of a three-dimensional image scan. In some embodiments, the system can be configured to determine the size and/or volume of total plaque, low-density non-calcified plaque, non-calcified plaque, calcified plaque, and/or a ratio between two of the aforementioned volumes or sizes. In some embodiments, a high total plaque volume and/or high low-density non-calcified plaque and/or non-calcified plaque volume can be associated with high risk of CAD. In some embodiments, a high ratio of low-density non-calcified plaque volume to total plaque volume and/or a high ratio of non-calcified plaque volume to total plaque volume can be associated with high risk of CAD. In some embodiments, a high calcified plaque volume and/or high ratio of calcified plaque volume to total plaque volume can be associated with low risk of CAD. In some embodiments, the system can be configured to utilize one or more predetermined threshold values for determining the risk of CAD based on plaque volume, size, or one or more ratios thereof. In some embodiments, the system can be configured to utilize one or more image processing algorithms to automatically and/or dynamically determine the size and/or volume of one or more regions of plaque.

In some embodiments, the system can be configured to analyze and/or characterize plaque based on embeddedness. For example, in some embodiments, the system can be configured to determined how embedded or surrounded a low density non-calcified plaque is by non-calcified plaque or calcified plaque. In some embodiments, the system can be configured to analyze the embeddedness of low density non-calcified plaque based on the degree by which it is surrounded by other types of plaque. In some embodiments, a higher embeddedness of a low density non-calcified plaque can be indicative of high risk of CAD. For example, in some embodiments, a low density non-calcified plaque that is surrounded by 270 degrees or more by non-calcified plaque can be associated with high risk of CAD. In some embodiments, the system can be configured to utilize one or more image processing algorithms to automatically and/or dynamically determine the embeddedness of one or more regions of plaque.

In some embodiments, at block 1310, the system can be configured to analyze the one or more vessels and the one or more regions of plaque to determine a plurality of variables. In some embodiments, the plurality of image-derived variables can include one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, or low-density plaque volume.

In some embodiments the plurality of variables can comprise volume of plaque. In some embodiments, the volume of plaque comprises one or more of volume of total plaque, volume of low density non-calcified plaque, volume of non-calcified plaque, or volume of calcified plaque. In some embodiments, the volume of plaque is determined based at least in part on analyzing density of one or more pixels corresponding to plaque in the medical image. In some embodiments, the density comprises material density. In some embodiments, the density comprises radiodensity. For example, in some embodiments, the system can be configured to characterize a particular region of plaque as low density non-calcified plaque when the radiodensity of an image pixel or voxel corresponding to that region of plaque is between about −189 and about 30 Hounsfield units (HU).

In some embodiments, the system can be configured to characterize a particular region of plaque as non-calcified plaque when the radiodensity of an image pixel or voxel corresponding to that region of plaque is between about 31 and about 350 HU. In some embodiments, the system can be configured to characterize a particular region of plaque as calcified plaque when the radiodensity of an image pixel or voxel corresponding to that region of plaque is between about 351 and about 2500 HU. In some embodiments, the lower and/or upper Hounsfield unit boundary threshold for determining whether a plaque corresponds to one or more of low density non-calcified plaque, non-calcified plaque, and/or calcified plaque can be about −1000 HU, about −900 HU, about −800 HU, about −700 HU, about −600 HU, about −500 HU, about −400 HU, about −300 HU, about −200 HU, about −190 HU, about −180 HU, about −170 HU, about −160 HU, about −150 HU, about −140 HU, about −130 HU, about −120 HU, about −110 HU, about −100 HU, about −90 HU, about −80 HU, about −70 HU, about −60 HU, about −50 HU, about −40 HU, about −30 HU, about −20 HU, about −10 HU, about 0 HU, about 10 HU, about 20 HU, about 30 HU, about 40 HU, about 50 HU, about 60 HU, about 70 HU, about 80 HU, about 90 HU, about 100 HU, about 110 HU, about 120 HU, about 130 HU, about 140 HU, about 150 HU, about 160 HU, about 170 HU, about 180 HU, about 190 HU, about 200 HU, about 210 HU, about 220 HU, about 230 HU, about 240 HU, about 250 HU, about 260 HU, about 270 HU, about 280 HU, about 290 HU, about 300 HU, about 310 HU, about 320 HU, about 330 HU, about 340 HU, about 350 HU, about 360 HU, about 370 HU, about 380 HU, about 390 HU, about 400 HU, about 410 HU, about 420 HU, about 430 HU, about 440 HU, about 450 HU, about 460 HU, about 470 HU, about 480 HU, about 490 HU, about 500 HU, about 510 HU, about 520 HU, about 530 HU, about 540 HU, about 550 HU, about 560 HU, about 570 HU, about 580 HU, about 590 HU, about 600 HU, about 700 HU, about 800 HU, about 900 HU, about 1000 HU, about 1100 HU, about 1200 HU, about 1300 HU, about 1400 HU, about 1500 HU, about 1600 HU, about 1700 HU, about 1800 HU, about 1900 HU, about 2000 HU, about 2100 HU, about 2200 HU, about 2300 HU, about 2400 HU, about 2500 HU, about 2600 HU, about 2700 HU, about 2800 HU, about 2900 HU, about 3000 HU, about 3100 HU, about 3200 HU, about 3300 HU, about 3400 HU, about 3500 HU, and/or about 4000 HU.

In some embodiments, at block 1312, the system can be configured to determine a risk of CAD or MI based on one or more plaque analyses described herein, for example in relation to one or more of blocks 1302-1310. In some embodiments, the system can be configured to utilize some or all of the plaque analyses results. In some embodiments, the system can be configured to generate a weighted measure of some or all of the plaque analyses described herein in determining a risk of CAD. In some embodiments, the system can be configured to refer to one or more reference values of one or more plaque analyses results in determining risk of CAD. For example, in some embodiments, the one or more reference values can comprise one or more values derived from a population with varying states of risks of CAD, wherein the one or more values can comprise one or more of one or more distances to and/or from a low density non-calcified plaque, one or more axes measurements, morphology classification, size and/or volume, and/or embeddedness of low density non-calcified plaque. In some embodiments, the one or more reference values can be stored on a reference values database 1318, which can be locally accessible by the system and/or can be located remotely and accessible through a network connection. In some embodiments, the risk of CAD or MACE is determined as one of low, medium, or high.

In some embodiments, at block 1316, the system can be configured to generate a graphical representation of the analyses results, determined risk of CAD, and/or proposed treatment for the subject. In some embodiments, the analyses results can be displayed on a vessel, lesion, and/or subject basis. In some embodiments, the proposed treatment can include, for example, medical treatment such as statins, interventional treatment such as stent implantation, and/or lifestyle treatment such as exercise or dict. In some embodiments, in determining the risk or state of cardiovascular disease or health and/or treatment, the system can access a plaque risk/treatment database 1322, which can be locally accessible by the system and/or can be located remotely and accessible through a network connection. In some embodiments, the plaque risk/treatment database 1322 can include reference points or data that relate one or more treatment to cardiovascular disease risk or state determined based on one or more reference plaque analyses values.

In some embodiments, the system can further be configured to determine a type of cardiac catheterization for the patient based at least in part on the determined risk of CAD or MACE and the plurality of image-derived variables. The type of cardiac catheterization can include one or more of coronary angiography, right heart catheterization, coronary catheterization, placement of a pacemaker or defibrillator, valve assessment, pulmonary angiography, shunt evaluation, ventriculography, percutaneous aortic valve replacement, balloon septostomy, stenting, or alcohol septal ablation. In some embodiments, the type of cardiac catheterization for the patient can be determined using a machine learning algorithm trained based at least in part on the plurality of image-derived variables derived from medical images of other subjects with known risk of CAD or MACE and with known types of cardiac catheterization. In some embodiments, the cardiac catheterization is configured to be used for one or more of coronary angiography, right heart catheterization, coronary catheterization, placement of a pacemaker or defibrillator, valve assessment, pulmonary angiography, shunt evaluation, ventriculography, percutaneous aortic valve replacement, balloon septostomy, stenting, or alcohol septal ablation In some embodiments, the system can be configured to repeat one or more processes described in relation to blocks 1302-1322, for example for one or more other vessels, segment, regions of plaque, different subjects, and/or for the same subject at a different time.

The computer system 902 of FIG. 9, and in some instances, the analysis and/or risk assessment module 940, can be configured to carry out the functions, methods, acts, and/or processes for Image-Based Analysis for determination of cardiac catheterization described herein, such as those described above with reference to FIG. 13.

The following are non-limiting examples of certain embodiments of systems and methods for determination of cardiac catheterization. Other embodiments may include one or more other features, or different features, that are discussed herein.

Embodiment 1: A computer-implemented method of guiding therapeutic decision-making to determine a need for cardiac catheterization for a patient based at least in part on automated analysis of one or more medical images, the method comprising: accessing, by the computer system, one or more medical images of a patient, the one or more medical images comprising a representation of a portion of one or more coronary arteries; analyzing, by the computer system, the one or more medical images to identify one or more coronary arteries, the one or more coronary arteries comprising one or more regions of plaque; analyzing, by the computer system, the identified one or more coronary arteries and the one or more regions of plaque to generate a plurality of image-derived variables, the plurality of image-derived variables comprising one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, or low-density plaque volume; applying, by the computer system, a machine learning algorithm to determine risk of coronary artery disease (CAD) or major adverse cardiovascular event (MACE) for the patient based at least in part on the plurality of image-derived variables, wherein the machine learning algorithm is trained based at least in part on the plurality of image-derived variables derived from medical images of other subjects with known risk of CAD or MACE; and determining, by the computer system, a need for cardiac catheterization for the patient based at least in part on the determined risk of CAD or MACE, wherein risk of CAD or MACE above a predetermined threshold is indicative of a need for cardiac catheterization, wherein the computer system comprises a computer processor and an electronic storage medium.

Embodiment 2: The computer-implemented method of Embodiment 1, further comprising determining, by the computer system, a type of cardiac catheterization for the patient based at least in part on the determined risk of CAD or MACE and the plurality of image-derived variables, the type of cardiac catheterization comprising one or more of coronary angiography, right heart catheterization, coronary catheterization, placement of a pacemaker or defibrillator, valve assessment, pulmonary angiography, shunt evaluation, ventriculography, percutaneous aortic valve replacement, balloon septostomy, stenting, or alcohol septal ablation.

Embodiment 3: The computer-implemented method of Embodiment 2, wherein the type of cardiac catheterization for the patient is determined using a machine learning algorithm trained based at least in part on the plurality of image-derived variables derived from medical images of other subjects with known risk of CAD or MACE and with known types of cardiac catheterization.

Embodiment 4: The computer-implemented method of Embodiment 2, further comprising causing, by the computer system, generation of a graphical representation of the determined type of cardiac catheterization for the patient.

Embodiment 5: The computer-implemented method of Embodiment 1, further comprising causing, by the computer system, generation of a graphical representation of the determined need for cardiac catheterization for the patient.

Embodiment 6: The computer-implemented method of Embodiment 1, wherein cardiac catheterization is configured to be used for one or more of coronary angiography, right heart catheterization, coronary catheterization, placement of a pacemaker or defibrillator, valve assessment, pulmonary angiography, shunt evaluation, ventriculography, percutaneous aortic valve replacement, balloon septostomy, stenting, or alcohol septal ablation.

Embodiment 7: The computer-implemented method of Embodiment 1, further comprising generating, by the computer system, a weighted measure of the plurality of image-derived variables, wherein the risk of CAD or MACE for the subject is determined based at least in part on the weighted measure of the plurality of image-derived variables.

Embodiment 8: The computer-implemented method of Embodiment 1, wherein the risk of CAD or MACE is determined as one of low, medium, or high.

Embodiment 9: The computer-implemented method of Embodiment 1, further comprising generating a ranking of need for cardiac catheterization for the patient among other patients based at least in part on the determined risk of CAD or MACE for the patient.

Embodiment 10: The computer-implemented method of Embodiment 1, wherein the one or more medical images comprises a Computed Tomography (CT) image.

Embodiment 11: The computer-implemented method of Embodiment 1, wherein one or more of the one or more medical images is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 12: A computer-implemented method of guiding therapeutic decision-making to determine a need for cardiac catheterization for a patient based at least in part on automated analysis of one or more medical images, the method comprising: accessing, by the computer system, one or more medical images of a patient, the one or more medical images comprising a representation of a portion of one or more coronary arteries; analyzing, by the computer system, the one or more medical images to identify one or more coronary arteries, the one or more coronary arteries comprising one or more regions of plaque; analyzing, by the computer system, the identified one or more coronary arteries and the one or more regions of plaque to generate a plurality of image-derived variables, the plurality of image-derived variables comprising one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, or low-density plaque volume; applying, by the computer system, a machine learning algorithm to determine a need for cardiac catheterization for the patient based at least in part on the plurality of image-derived variables, wherein the machine learning algorithm is trained based at least in part on the plurality of image-derived variables derived from medical images of other subjects with known risk of coronary artery disease (CAD) or major adverse cardiovascular event (MACE); and generating, by the computer system, a graphical representation of the determined need for cardiac catheterization for the patient, wherein the computer system comprises a computer processor and an electronic storage medium.

Embodiment 13: The computer-implemented method of Embodiment 12, further comprising determining, by the computer system, a type of cardiac catheterization for the patient based at least in part on the plurality of image-derived variables, the type of cardiac catheterization comprising one or more of coronary angiography, right heart catheterization, coronary catheterization, placement of a pacemaker or defibrillator, valve assessment, pulmonary angiography, shunt evaluation, ventriculography, percutaneous aortic valve replacement, balloon septostomy, stenting, or alcohol septal ablation.

Embodiment 14: The computer-implemented method of Embodiment 13, wherein the type of cardiac catheterization for the patient is determined using a machine learning algorithm trained based at least in part on the plurality of image-derived variables derived from medical images of other subjects with known types of cardiac catheterization.

Embodiment 15: The computer-implemented method of Embodiment 13, further comprising causing, by the computer system, generation of a graphical representation of the determined type of cardiac catheterization for the patient.

Embodiment 16: The computer-implemented method of Embodiment 12, wherein cardiac catheterization is configured to be used for one or more of coronary angiography, right heart catheterization, coronary catheterization, placement of a pacemaker or defibrillator, valve assessment, pulmonary angiography, shunt evaluation, ventriculography, percutaneous aortic valve replacement, balloon septostomy, stenting, or alcohol septal ablation.

Embodiment 17: The computer-implemented method of Embodiment 12, further comprising generating, by the computer system, a weighted measure of the plurality of image-derived variables, wherein the need for cardiac catheterization for the patient is determined based at least in part on the weighted measure of the plurality of image-derived variables.

Embodiment 18: The computer-implemented method of Embodiment 12, wherein the need for cardiac catheterization for the patient is determined as one of low, medium, or high.

Embodiment 19: The computer-implemented method of Embodiment 12, further comprising generating a ranking of need for cardiac catheterization for the patient among other patients based at least in part on the determined need for cardiac catheterization for the patient.

Embodiment 20: The computer-implemented method of Embodiment 12, wherein the one or more medical images comprises a Computed Tomography (CT) image.

Embodiment 21: The computer-implemented method of Embodiment 12, wherein one or more of the one or more medical images is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 22: A system for guiding therapeutic decision-making to determine a need for cardiac catheterization for a patient based at least in part on automated analysis of one or more medical images, the system comprising: a non-transitory computer storage medium configured to at least store computer-executable instructions; and one or more computer hardware processors in communication with the first non-transitory computer storage medium, the one or more computer hardware processors configured to execute the computer-executable instructions to at least: access or more medical images of a patient, the one or more medical images comprising a representation of a portion of one or more coronary arteries; analyze the one or more medical images to identify one or more coronary arteries, the one or more coronary arteries comprising one or more regions of plaque; analyze the identified one or more coronary arteries and the one or more regions of plaque to generate a plurality of image-derived variables, the plurality of image-derived variables comprising one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, or low-density plaque volume; apply a machine learning algorithm to determine risk of coronary artery disease (CAD) or major adverse cardiovascular event (MACE) for the patient based at least in part on the plurality of image-derived variables, wherein the machine learning algorithm is trained based at least in part on the plurality of image-derived variables derived from medical images of other subjects with known risk of CAD or MACE; and determine a need for cardiac catheterization for the patient based at least in part on the determined risk of CAD or MACE, wherein risk of CAD or MACE above a predetermined threshold is indicative of a need for cardiac catheterization.

Embodiment 23: The system of Embodiment 22, wherein the processor is further configured to determine a type of cardiac catheterization for the patient based at least in part on the determined risk of CAD or MACE and the plurality of image-derived variables, the type of cardiac catheterization comprising one or more of coronary angiography, right heart catheterization, coronary catheterization, placement of a pacemaker or defibrillator, valve assessment, pulmonary angiography, shunt evaluation, ventriculography, percutaneous aortic valve replacement, balloon septostomy, stenting, or alcohol septal ablation.

Embodiment 24: The system of Embodiment 23, wherein the type of cardiac catheterization for the patient is determined using a machine learning algorithm trained based at least in part on the plurality of image-derived variables derived from medical images of other subjects with known risk of CAD or MACE and with known types of cardiac catheterization.

Embodiment 25: The system of Embodiment 23, wherein the processor is further configured to generate a graphical representation of the determined type of cardiac catheterization for the patient.

Embodiment 26: The system of Embodiment 22, wherein the processor is further configured to cause a graphical representation of the determined need for cardiac catheterization for the patient.

Embodiment 27: The system of Embodiment 22, wherein cardiac catheterization is configured to be used for one or more of coronary angiography, right heart catheterization, coronary catheterization, placement of a pacemaker or defibrillator, valve assessment, pulmonary angiography, shunt evaluation, ventriculography, percutaneous aortic valve replacement, balloon septostomy, stenting, or alcohol septal ablation.

Embodiment 28: The system of Embodiment 22, wherein the processor is further configured to generate a weighted measure of the plurality of image-derived variables, wherein the risk of CAD or MACE for the subject is determined based at least in part on the weighted measure of the plurality of image-derived variables.

Embodiment 29: The system of Embodiment 22, wherein the risk of CAD or MACE is determined as one of low, medium, or high.

Embodiment 30: The system of Embodiment 22, wherein the processor is further configured to generate a ranking of need for cardiac catheterization for the patient among other patients based at least in part on the determined risk of CAD or MACE for the patient.

Embodiment 31: The system of Embodiment 22, wherein the one or more medical images comprises a Computed Tomography (CT) image.

Embodiment 32: The system of Embodiment 22, wherein one or more of the one or more medical images is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 33: A system for guiding therapeutic decision-making to determine a need for cardiac catheterization for a patient based at least in part on automated analysis of one or more medical images, the system comprising: a non-transitory computer storage medium configured to at least store computer-executable instructions; and one or more computer hardware processors in communication with the first non-transitory computer storage medium, the one or more computer hardware processors configured to execute the computer-executable instructions to at least: access one or more medical images of a patient, the one or more medical images comprising a representation of a portion of one or more coronary arteries; analyze the one or more medical images to identify one or more coronary arteries, the one or more coronary arteries comprising one or more regions of plaque; analyze the identified one or more coronary arteries and the one or more regions of plaque to generate a plurality of image-derived variables, the plurality of image-derived variables comprising one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, or low-density plaque volume; apply a machine learning algorithm to determine a need for cardiac catheterization for the patient based at least in part on the plurality of image-derived variables, wherein the machine learning algorithm is trained based at least in part on the plurality of image-derived variables derived from medical images of other subjects with known risk of coronary artery disease (CAD) or major adverse cardiovascular event (MACE); and generate a graphical representation of the determined need for cardiac catheterization for the patient.

Embodiment 34: The system of Embodiment 33, wherein the processor is further configured to determine a type of cardiac catheterization for the patient based at least in part on the plurality of image-derived variables, the type of cardiac catheterization comprising one or more of coronary angiography, right heart catheterization, coronary catheterization, placement of a pacemaker or defibrillator, valve assessment, pulmonary angiography, shunt evaluation, ventriculography, percutaneous aortic valve replacement, balloon septostomy, stenting, or alcohol septal ablation.

Embodiment 35: The system of Embodiment 34, wherein the type of cardiac catheterization for the patient is determined using a machine learning algorithm trained based at least in part on the plurality of image-derived variables derived from medical images of other subjects with known types of cardiac catheterization.

Embodiment 36: The system of Embodiment 34, wherein the processor is further configured to cause generation of a graphical representation of the determined type of cardiac catheterization for the patient.

Embodiment 37: The system of Embodiment 33, wherein cardiac catheterization is configured to be used for one or more of coronary angiography, right heart catheterization, coronary catheterization, placement of a pacemaker or defibrillator, valve assessment, pulmonary angiography, shunt evaluation, ventriculography, percutaneous aortic valve replacement, balloon septostomy, stenting, or alcohol septal ablation.

Embodiment 38: The system of Embodiment 33, wherein the processor is further configured to generate a weighted measure of the plurality of image-derived variables, wherein the need for cardiac catheterization for the patient is determined based at least in part on the weighted measure of the plurality of image-derived variables.

Embodiment 39: The system of Embodiment 33, wherein the need for cardiac catheterization for the patient is determined as one of low, medium, or high.

Embodiment 40: The system of Embodiment 33, wherein the processor is further configured to generate a ranking of need for cardiac catheterization for the patient among other patients based at least in part on the determined need for cardiac catheterization for the patient.

Embodiment 41: The system of Embodiment 33, wherein the one or more medical images comprises a Computed Tomography (CT) image.

Embodiment 42: The system of Embodiment 33, wherein one or more of the one or more medical images is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 43: A non-transitory computer readable medium configured for determining presence of vessel-specific ischemia based at least in part on a plurality of variables derived from non-invasive medical image analysis, the computer readable medium having program instructions for causing a hardware processor to perform a method of: accessing one or more medical images of a patient, the one or more medical images comprising a representation of a portion of one or more coronary arteries; analyzing the one or more medical images to identify one or more coronary arteries, the one or more coronary arteries comprising one or more regions of plaque; analyzing the identified one or more coronary arteries and the one or more regions of plaque to generate a plurality of image-derived variables, the plurality of image-derived variables comprising one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, or low-density plaque volume; applying a machine learning algorithm to determine risk of coronary artery disease (CAD) or major adverse cardiovascular event (MACE) for the patient based at least in part on the plurality of image-derived variables, wherein the machine learning algorithm is trained based at least in part on the plurality of image-derived variables derived from medical images of other subjects with known risk of CAD or MACE; and determining a need for cardiac catheterization for the patient based at least in part on the determined risk of CAD or MACE, wherein risk of CAD or MACE above a predetermined threshold is indicative of a need for cardiac catheterization.

Embodiment 44: The non-transitory computer readable medium of Embodiment 43, wherein the method further comprises determining a type of cardiac catheterization for the patient based at least in part on the determined risk of CAD or MACE and the plurality of image-derived variables, the type of cardiac catheterization comprising one or more of coronary angiography, right heart catheterization, coronary catheterization, placement of a pacemaker or defibrillator, valve assessment, pulmonary angiography, shunt evaluation, ventriculography, percutaneous aortic valve replacement, balloon septostomy, stenting, or alcohol septal ablation.

Embodiment 45: The non-transitory computer readable medium of Embodiment 44, wherein the type of cardiac catheterization for the patient is determined using a machine learning algorithm trained based at least in part on the plurality of image-derived variables derived from medical images of other subjects with known risk of CAD or MACE and with known types of cardiac catheterization.

Embodiment 46: The non-transitory computer readable medium of Embodiment 44, wherein the method further comprises causing generation of a graphical representation of the determined type of cardiac catheterization for the patient.

Embodiment 47: The non-transitory computer readable medium of Embodiment 43, wherein the method further comprises causing generation of a graphical representation of the determined need for cardiac catheterization for the patient.

Embodiment 48: The non-transitory computer readable medium of Embodiment 43, wherein cardiac catheterization is configured to be used for one or more of coronary angiography, right heart catheterization, coronary catheterization, placement of a pacemaker or defibrillator, valve assessment, pulmonary angiography, shunt evaluation, ventriculography, percutaneous aortic valve replacement, balloon septostomy, stenting, or alcohol septal ablation.

Embodiment 49: The non-transitory computer readable medium of Embodiment 43 wherein the method further comprises generating a weighted measure of the plurality of image-derived variables, wherein the risk of CAD or MACE for the subject is determined based at least in part on the weighted measure of the plurality of image-derived variables.

Embodiment 50: The non-transitory computer readable medium of Embodiment 43, wherein the risk of CAD or MACE is determined as one of low, medium, or high.

Embodiment 51: The non-transitory computer readable medium of Embodiment 43, wherein the method further comprises generating a ranking of need for cardiac catheterization for the patient among other patients based at least in part on the determined risk of CAD or MACE for the patient.

Embodiment 52: The non-transitory computer readable medium of Embodiment 43, wherein the one or more medical images comprises a Computed Tomography (CT) image.

Embodiment 53: The non-transitory computer readable medium of Embodiment 43, wherein one or more of the one or more medical images is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 54: A non-transitory computer readable medium configured for determining presence of vessel-specific ischemia based at least in part on a plurality of variables derived from non-invasive medical image analysis, the computer readable medium having program instructions for causing a hardware processor to perform a method of: accessing one or more medical images of a patient, the one or more medical images comprising a representation of a portion of one or more coronary arteries; analyzing the one or more medical images to identify one or more coronary arteries, the one or more coronary arteries comprising one or more regions of plaque; analyzing the identified one or more coronary arteries and the one or more regions of plaque to generate a plurality of image-derived variables, the plurality of image-derived variables comprising one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, or low-density plaque volume; applying a machine learning algorithm to determine a need for cardiac catheterization for the patient based at least in part on the plurality of image-derived variables, wherein the machine learning algorithm is trained based at least in part on the plurality of image-derived variables derived from medical images of other subjects with known risk of coronary artery disease (CAD) or major adverse cardiovascular event (MACE); and generating a graphical representation of the determined need for cardiac catheterization for the patient.

Embodiment 55: The non-transitory computer readable medium of Embodiment 54, wherein the method further comprises determining a type of cardiac catheterization for the patient based at least in part on the plurality of image-derived variables, the type of cardiac catheterization comprising one or more of coronary angiography, right heart catheterization, coronary catheterization, placement of a pacemaker or defibrillator, valve assessment, pulmonary angiography, shunt evaluation, ventriculography, percutaneous aortic valve replacement, balloon septostomy, stenting, or alcohol septal ablation.

Embodiment 56: The non-transitory computer readable medium of Embodiment 55, wherein the type of cardiac catheterization for the patient is determined using a machine learning algorithm trained based at least in part on the plurality of image-derived variables derived from medical images of other subjects with known types of cardiac catheterization.

Embodiment 57: The non-transitory computer readable medium of Embodiment 55 wherein the method further comprises causing generation of a graphical representation of the determined type of cardiac catheterization for the patient.

Embodiment 58: The non-transitory computer readable medium of Embodiment 54, wherein cardiac catheterization is configured to be used for one or more of coronary angiography, right heart catheterization, coronary catheterization, placement of a pacemaker or defibrillator, valve assessment, pulmonary angiography, shunt evaluation, ventriculography, percutaneous aortic valve replacement, balloon septostomy, stenting, or alcohol septal ablation.

Embodiment 59: The non-transitory computer readable medium of Embodiment 54, wherein the method further comprises generating a weighted measure of the plurality of image-derived variables, wherein the need for cardiac catheterization for the patient is determined based at least in part on the weighted measure of the plurality of image-derived variables.

Embodiment 60: The non-transitory computer readable medium of Embodiment 54, wherein the need for cardiac catheterization for the patient is determined as one of low, medium, or high.

Embodiment 61: The non-transitory computer readable medium of Embodiment 54, wherein the method further comprises generating a ranking of need for cardiac catheterization for the patient among other patients based at least in part on the determined need for cardiac catheterization for the patient.

Embodiment 62: The non-transitory computer readable medium of Embodiment 54, wherein the one or more medical images comprises a Computed Tomography (CT) image.

Embodiment 63: The non-transitory computer readable medium of Embodiment 54, wherein one or more of the one or more medical images is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Patient-Specific Atherosclerosis Treatment Based on Computational Modeling

Various embodiments described herein relate to systems, devices, and methods for patient-specific atherosclerosis treatment based on computational modeling. In some embodiments, the systems, devices, and methods utilize an image-based analysis, wherein an image of the patient (e.g., a CT scan or other non-invasive medical image) is analyzed and modified to determine a patient's risk of a risk of coronary artery disease (CAD), such as for example myocardial infarction (MI), and to evaluate the outcome of potential treatment options. For example, a medical image of the patient can be analyzed by a computer system that identifies vessels and regions of plaque in the image. The computer system can further determine vascular morphology parameters associated with the vessels and atherosclerosis parameters associated with the regions of plaque. A baseline risk based on the analysis of the image can be established. One or more computer models can be generated and applied to the image to (i) computationally reduce one or more of the regions of plaque (e.g., as a possible outcome of treatment) and/or (ii) computationally transform one or more of the regions of plaque from one type of plaque to another type of plaque (e.g., as another possible outcome of treatment). One or more predicted risks can be generated from the computer models and the systems, devices, and methods can be configured to generate a graphical representation that illustrates the baseline risk and predicted risk as a way to visualize and evaluate the effects of the proposed treatments.

In some embodiments, the systems, devices, and methods described herein are configured to generate a first computational model of the one or more regions of plaque, such as for example coronary plaque, in which one or more regions of plaque, such as for example coronary plaque, is computationally reduced. In some embodiments, the systems, devices, and methods described herein are configured to determine a first predicted risk of coronary artery disease (CAD), such as for example myocardial infarction (MI), based on one or more plaque analyses described herein of the first computational model. In some embodiments, the systems, devices, and methods described herein are configured to generate a graphical representation based on the first predicted risk of CAD and/or one or more plaque analyses described herein.

In some embodiments, the systems, devices, and methods described herein are configured to generate a second computational model of the one or more regions of plaque, such as for example coronary plaque, in which one or more regions of plaque, such as for example coronary plaque, is computationally transformed such that one or more regions of low density non-calcified plaque is transformed to non-calcified plaque or calcified plaque. In some embodiments, the systems, devices, and methods described herein are configured to generate a second computational model of the one or more regions of plaque, such as for example coronary plaque, in which one or more regions of plaque, such as for example coronary plaque, is computationally transformed such that one or more regions of non-calcified plaque is transformed into to calcified plaque. In some embodiments, the systems, devices, and methods described herein are configured to determine a second predicted risk of coronary artery disease (CAD), such as for example myocardial infarction (MI), based on one or more plaque analyses described herein of the second computational model. In some embodiments, the systems, devices, and methods described herein are configured to generate a graphical representation based on the second predicted risk of CAD and/or one or more plaque analyses described herein.

In some embodiments, the systems, devices, and methods described herein are configured to generate a graphical representation based on the first baseline risk, the first predicted risk, and the second predicted risk of coronary artery disease (CAD), such as for example myocardial infarction (MI). In some embodiments, the systems, devices, and methods described herein are configured to facilitate determination of a patient-specific treatment for coronary artery disease (CAD), such as for example myocardial infarction (MI), for the patient based on the first baseline risk, the first predicted risk, and the second predicted risk of coronary artery disease (CAD), such as for example myocardial infarction (MI). In some embodiments, this treatment comprises stent implantation. In some embodiments, this treatment comprises medication or lifestyle treatment.

In some embodiments, the one or more arteries comprise one or more coronary arteries. In some embodiments, the one or more arteries comprise one or more coronary arteries, carotid arteries, aorta, upper extremity arteries, or lower extremity arteries. In some embodiments, the artery disease comprises coronary artery disease (CAD). In some embodiments, the artery disease comprises one or more major adverse cardiovascular events (MACE) or myocardial infarction. In some embodiments, the first baseline risk of artery disease is generated based at least in part on the machine learning algorithm. In some embodiments, the artery disease comprises ischemia. In some embodiments, the first baseline risk of artery disease is generated based at least in part on the machine learning algorithm. In some embodiments, the first baseline risk of artery disease is generated based at least in part on one or more of invasive fractional flow reserve, CT fractional flow reserve, computational fractional flow reserve, virtual fractional flow reserve, vessel fractional flow reserve, or quantitative flow ratio. In some embodiments, the method further comprises: accessing, by the computer system, a second baseline risk of artery disease derived at the second point in time; and generating, by the computer system, a comparison of the second baseline risk of artery disease and one or more of the first predicted risk of artery disease and the second predicted risk of artery disease, wherein the comparison is configured to facilitate reevaluation of the determined patient-specific treatment for artery disease for the patient. In some embodiments, the recvaluation of the determined patient-specific treatment for artery disease for the patient is based at least in part on an absolute difference in the second baseline risk of artery disease compared to one or more of the first predicted risk of artery disease and the second predicted risk of artery disease. In some embodiments, the reevaluation of the determined patient-specific treatment for artery disease for the patient is based at least in part on a percentage difference in the second baseline risk of artery disease compared to one or more of the first predicted risk of artery disease and the second predicted risk of artery disease. In some embodiments, the reevaluation of the determined patient-specific treatment for artery disease for the patient is based at least in part on a rate of change in the second baseline risk of artery disease against one or more of the first predicted risk of artery disease and the second predicted risk of artery disease. In some embodiments, the method further comprises: accessing, by the computer system, a second baseline risk of artery disease derived at the second point in time; and generating, by the computer system, a comparison of the second baseline risk of artery disease and the first baseline risk of artery disease, wherein the comparison is configured to facilitate reevaluation of the determined patient-specific treatment for artery disease for the patient. In some embodiments, the reevaluation of the determined patient-specific treatment for artery disease for the patient is based at least in part on an absolute difference in the second baseline risk of artery disease compared to the first baseline risk of artery disease. In some embodiments, the reevaluation of the determined patient-specific treatment for artery disease for the patient is based at least in part on a rate of change in the second baseline risk of artery disease against the first baseline risk of artery disease. In some embodiments, the reevaluation of the determined patient-specific treatment for artery disease for the patient is based at least in part on a percentage difference in the second baseline risk of artery disease compared to the first baseline risk of artery disease. In some embodiments, the one or more medical images comprises a Computed Tomography (CT) image. In some embodiments, the one or more medical images is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS). In some embodiments, the density of the one or more pixels comprises absolute density. In some embodiments, the density of the one or more pixels comprises radiodensity. In some embodiments, the one or more regions of plaque are classified as low density non-calcified plaque when a radiodensity value is between about −189 and about 30 Hounsfield units. In some embodiments, the one or more regions of plaque are classified as non-calcified plaque when a radiodensity value is between about 31 and about 350 Hounsfield units. In some embodiments, the one or more regions of plaque are classified as calcified plaque when a radiodensity value is between about 351 and 2500 Hounsfield units.

Various embodiments described herein relate to systems, devices, and methods for patient-specific atherosclerosis treatment based on computational modeling. In some embodiments, the systems, devices, and methods utilize an image-based analysis, wherein an image of the patient (e.g., a CT scan or other non-invasive medical image) is analyzed and modified to determine a patient's risk of a risk of coronary artery disease (CAD), such as for example myocardial infarction (MI), and to evaluate the outcome of potential treatment options. For example, a medical image of the patient can be analyzed by a computer system that identifies vessels and regions of plaque in the image. The computer system can further determine vascular morphology parameters associated with the vessels and atherosclerosis parameters associated with the regions of plaque. A baseline risk based on the analysis of the image can be established. One or more computer models can be generated and applied to the image to (i) computationally reduce one or more of the regions of plaque (e.g., as a possible outcome of treatment) and/or (ii) computationally transform one or more of the regions of plaque from one type of plaque to another type of plaque (e.g., as another possible outcome of treatment). One or more predicted risks can be generated from the computer models and the systems, devices, and methods can be configured to generate a graphical representation that illustrates the baseline risk and predicted risk as a way to visualize and evaluate the effects of the proposed treatments.

In some embodiments, the systems, methods, and devices for patient-specific atherosclerosis treatment based on computational modeling. In particular, in some embodiments, the systems, devices, and methods described herein are related to analysis of one or more regions of plaque, such as for example coronary plaque, based on one or more distances, volumes, shapes, morphologies, embeddedness, and/or axes measurements. For example, in some embodiments, the systems, devices, and methods described herein are related to plaque analysis based on one or more of distance between plaque and vessel wall, distance between plaque and lumen wall, length along longitudinal axis, length along latitudinal axis, volume of low density non-calcified plaque, volume of total plaque, a ratio(s) between volume of low density non-calcified plaque and volume of total plaque, embeddedness of low density non-calcified plaque, and/or the like. In some embodiments, the systems, devices, and methods described herein are configured to determine a risk of coronary artery disease (CAD), such as for example myocardial infarction (MI), based on one or more plaque analyses described herein. In some embodiments, the systems, devices, and methods described herein are configured to generate a graphical representation based on the first baseline determined risk of CAD and/or one or more plaque analyses described herein.

In some embodiments, the systems, devices, and methods described herein are configured to generate a first computational model of the one or more regions of plaque, such as for example coronary plaque, in which one or more regions of plaque, such as for example coronary plaque, is computationally reduced. In some embodiments, the systems, devices, and methods described herein are configured to determine a first predicted risk of coronary artery disease (CAD), such as for example myocardial infarction (MI), based on one or more plaque analyses described herein of the first computational model. In some embodiments, the systems, devices, and methods described herein are configured to generate a graphical representation based on the first predicted risk of CAD and/or one or more plaque analyses described herein.

In some embodiments, the systems, devices, and methods described herein are configured to generate a second computational model of the one or more regions of plaque, such as for example coronary plaque, in which one or more regions of plaque, such as for example coronary plaque, is computationally transformed such that one or more regions of low density non-calcified plaque is transformed to non-calcified plaque or calcified plaque. In some embodiments, the systems, devices, and methods described herein are configured to generate a second computational model of the one or more regions of plaque, such as for example coronary plaque, in which one or more regions of plaque, such as for example coronary plaque, is computationally transformed such that one or more regions of non-calcified plaque is transformed to calcified plaque. In some embodiments, the systems, devices, and methods described herein are configured to determine a second predicted risk of coronary artery disease (CAD), such as for example myocardial infarction (MI), based on one or more plaque analyses described herein of the second computational model. In some embodiments, the systems, devices, and methods described herein are configured to generate a graphical representation based on the second predicted risk of CAD and/or one or more plaque analyses described herein.

In some embodiments, the systems, devices, and methods described herein are configured to generate a graphical representation based on the first baseline risk, the first predicted risk, and the second predicted risk of coronary artery disease (CAD), such as for example myocardial infarction (MI). In some embodiments, the systems, devices, and methods described herein are configured to facilitate determination of a patient-specific treatment for coronary artery disease (CAD), such as for example myocardial infarction (MI), for the patient based on the first baseline risk, the first predicted risk, and the second predicted risk of coronary artery disease (CAD), such as for example myocardial infarction (MI). In some embodiments, this treatment comprises stent implantation. In some embodiments, this treatment comprises medication or lifestyle treatment.

Current technology does not allow for predictive modeling of arteries, thus leaving patients vulnerable to unpredictable cardiac events and diseases. In some embodiments, the systems, devices, and methods described herein will improve a patient's ability to foresee what could happen to their cardiac health if they make certain choices. In some embodiments, subtracting plaque can simulate using a stent because a stent pushes the plaque against the wall of the artery. In some embodiments, computationally making plaque more calcified can simulate medication or lifestyle treatment because they can cause plaque to become more calcified.

Figure 14:
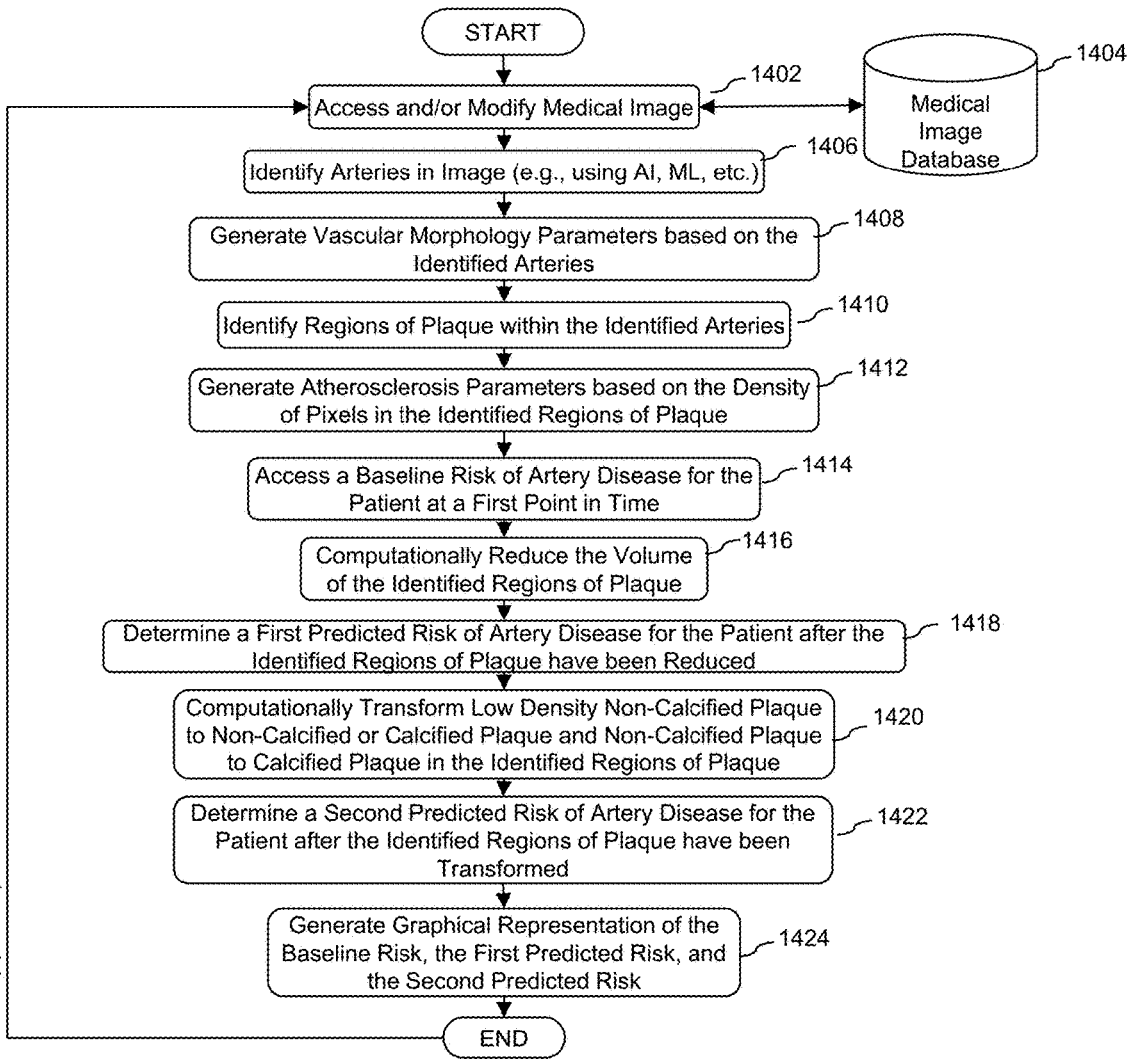
FIG. 14 is a flowchart illustrating an example embodiment(s) of systems, devices, and methods for non-invasive image-based plaque analysis and risk determination and patient-specific atherosclerosis treatment based on computational modeling, wherein the second computational model is calculated by transforming low-density non-calcified plaque into non-calcified or calcified plaque and non-calcified plaque into calcified plaque.

FIG. 14 is a flowchart illustrating an example embodiment(s) of systems, devices, and methods for patient-specific atherosclerosis treatment based on computational modeling. As illustrated in FIG. 14, in some embodiments, the system can be configured to access and/or modify one or more medical images at block 1402. In some embodiments, the medical image can include one or more arteries, such as coronary, carotid, and/or other arteries of a subject. In some embodiments, the medical image can be stored in a medical image database 1404. In some embodiments, the medical image database 1404 can be locally accessible by the system and/or can be located remotely and accessible through a network connection. The medical image can comprise an image obtained using one or more modalities such as for example, CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the medical image comprises one or more of a contrast-enhanced CT image, non-contrast CT image, MR image, and/or an image obtained using any of the modalities described above.

In some embodiments, the system can be configured to automatically and/or dynamically perform one or more analyses of the medical image as discussed herein. For example, in some embodiments, at block 1406, the system can be configured to identify one or more vessels, such as of one or more arteries. The one or more arteries can include coronary arteries, carotid arteries, aorta, renal artery, lower extremity artery, upper extremity artery, and/or cerebral artery, amongst others. In some embodiments, the system can be configured to utilize one or more AI and/or ML algorithms to automatically and/or dynamically identify one or more arteries or coronary arteries using image processing. For example, in some embodiments, the one or more AI and/or ML algorithms can be trained using a Convolutional Neural Network (CNN) on a set of medical images on which arteries or coronary arteries have been identified, thereby allowing the AI and/or ML algorithm automatically identify arteries or coronary arteries directly from a medical image. In some embodiments, the arteries or coronary arteries are identified by size and/or location.

In some embodiments, at block 1408, the system can be configured to generate vascular morphology parameters based on the identified arteries. In some embodiments, the vascular morphology parameters can include the size, shape, location, or texture of the identified arteries.

In some embodiments, at block 1410, the system can be configured to identify one or more regions of plaque in the medical image. In some embodiments, the system can be configured to utilize one or more AI and/or ML algorithms to automatically and/or dynamically identify one or more regions of plaque using image processing. For example, in some embodiments, the one or more AI and/or ML algorithms can be trained using a Convolutional Neural Network (CNN) on a set of medical images on which regions of plaque have been identified, thereby allowing the AI and/or ML algorithm automatically identify regions of plaque directly from a medical image. In some embodiments, the system is configured to identify vessel and lumen walls and classify everything in between the vessel and lumen walls as plaque.

In some embodiments, at block 1412, the system can be configured to generate atherosclerosis parameters based on the density of pixels in the identified regions of plaque. In some embodiments, the atherosclerosis parameters comprise volume of the one or more regions of plaque. In some embodiments, the atherosclerosis parameters comprise classification of the one or more regions of plaque as one or more of low density non-calcified plaque, non-calcified plaque, or calcified plaque based at least in part on density of one or more pixels corresponding to the one or more regions of plaque. In some embodiments, the system can be configured to analyze and/or characterize one or more regions of plaque based on density. For example, in some embodiments, the system can be configured to analyze and/or characterize one or more regions of plaque based on absolute density and/or relative density and/or radiodensity.

In some embodiments, at block 1412, the system can be configured to analyze and/or characterize one or more regions of plaque based on one or more distances. For example, as described herein, in some embodiments, the system can be configured to determine a distance between a low density non-calcified plaque and lumen wall and/or vessel wall. In some embodiments, proximity of a low density non-calcified plaque to the lumen wall can be indicative of a high-risk plaque and/or CAD. Conversely, in some embodiments, a position of a low density non-calcified plaque far from the lumen wall can be indicative of less risk. In some embodiments, the system can be configured to utilize one or more predetermined thresholds in determining the risk factor associated with the proximity of low density non-calcified plaque with the vessel wall and/or lumen wall. In some embodiments, the system can be configured to utilize one or more image processing algorithms to automatically and/or dynamically determine one or more distances to and/or from one or more regions of plaque.

In some embodiments, at block 1412, the system can be configured to analyze and/or characterize one or more regions of plaque based on morphology or shape and/or one or more axes measurements of low density non-calcified plaque. As described herein, in some embodiments, the system can be configured to determine the length of one or more axes of a low density non-calcified plaque, such as for example a major axis of a longitudinal cross section and/or a major and/or minor axis of a latitudinal cross section of a low density non-calcified plaque. In some embodiments, the system can be configured to utilize the one more axes measurements to determine a morphology and/or shape of a low density non-calcified plaque. In some embodiments, the system can be configured to utilize one or more image processing algorithms to automatically and/or dynamically determine one or more axes measurements of one or more regions of plaque.

In some embodiments, the system can be configured to utilize one or more AI and/or ML algorithms to automatically and/or dynamically classify the shape of one or more regions of plaque using image processing. For example, in some embodiments, the one or more AI and/or ML algorithms can be trained using a Convolutional Neural Network (CNN) on a set of medical images on which the shape of regions of plaque have been identified, thereby allowing the AI and/or ML algorithm automatically identify the shape or morphology of a region of plaque directly from a medical image. In some embodiments, the system can be configured to classify the shape or morphology of a region of plaque as one or more of crescent, lobular, round, or bean-shaped. In some embodiments, round and/or bean-shaped plaques can be associated with high risk, while crescent and/or lobular-shaped plaques can be associated with low risk of CAD.

In some embodiments, at block 1412, the system can be configured to analyze and/or characterize one or more regions of plaque based on one or more sizes and/or volumes. For example, in some embodiments, the system can be configured to determine a size and/or volume of plaque based at least in part on one or more axes measurements described herein. In some embodiments, the system can be configured to determine the size and/or volume of a region of plaque directly from analysis of a three-dimensional image scan. In some embodiments, the system can be configured to determine the size and/or volume of total plaque, low-density non-calcified plaque, non-calcified plaque, calcified plaque, and/or a ratio between two of the aforementioned volumes or sizes. In some embodiments, a high total plaque volume and/or high low-density non-calcified plaque and/or non-calcified plaque volume can be associated with high baseline risk of CAD. In some embodiments, a high ratio of low-density non-calcified plaque volume to total plaque volume and/or a high ratio of non-calcified plaque volume to total plaque volume can be associated with high baseline risk of CAD. In some embodiments, a high calcified plaque volume and/or high ratio of calcified plaque volume to total plaque volume can be associated with low risk of CAD. In some embodiments, the system can be configured to utilize one or more predetermined threshold values for determining the baseline risk of CAD based on plaque volume, size, or one or more ratios thereof. In some embodiments, the system can be configured to utilize one or more image processing algorithms to automatically and/or dynamically determine the size and/or volume of one or more regions of plaque.

In some embodiments, at block 1412, the system can be configured to analyze and/or characterize plaque based on embeddedness. For example, in some embodiments, the system can be configured to determined how embedded or surrounded a low density non-calcified plaque is by non-calcified plaque or calcified plaque. In some embodiments, the system can be configured to analyze the embeddedness of low density non-calcified plaque based on the degree by which it is surrounded by other types of plaque. In some embodiments, a higher embeddedness of a low density non-calcified plaque can be indicative of high baseline risk of CAD. For example, in some embodiments, a low density non-calcified plaque that is surrounded by 270 degrees or more by non-calcified plaque can be associated with high baseline risk of CAD. In some embodiments, the system can be configured to utilize one or more image processing algorithms to automatically and/or dynamically determine the embeddedness of one or more regions of plaque.

In some embodiments, at block 1414, the system can be configured to determine a first baseline risk of CAD or MI based on one or more plaque analyses described herein, for example in relation to one or more of blocks 1402-1414. In some embodiments, at block 1414, the system can be configured to determine a second or further baseline risk of CAD or MI based on one or more plaque analyses described herein, for example in relation to one or more of blocks 1402-1414. In some embodiments, the system can be configured to utilize some or all of the plaque analyses results. In some embodiments, the system can be configured to generate a weighted measure of some or all of the plaque analyses described herein in determining a risk of CAD. In some embodiments, the system can be configured to refer to one or more reference values of one or more plaque analyses results in determining risk of CAD. For example, in some embodiments, the one or more reference values can comprise one or more values derived from a population with varying states of risks of CAD, wherein the one or more values can comprise one or more of one or more distances to and/or from a low density non-calcified plaque, one or more axes measurements, morphology classification, size and/or volume, and/or embeddedness of low density non-calcified plaque. In some embodiments, the one or more reference values can be stored on a reference values database 222, which can be locally accessible by the system and/or can be located remotely and accessible through a network connection.

In some embodiments, at block 1416, the system can be configured to generate a first computational model of the one or more arteries based at least in part on the identified one or more vascular morphology parameters and the one or more atherosclerosis parameters, wherein the first computational model is configured to computationally reduce the volume of the one or more regions of plaque. In some embodiments, the first computational model is configured to computationally increase the volume of the one or more regions of plaque.

In some embodiments, at block 1418, the system can be configured to determine a first predicted risk of artery disease for the patient at a second point in time based on the first computational model, wherein the first predicted risk of artery disease is determined using a machine learning algorithm trained from a plurality of medical images comprising one or more portions of arteries derived from a plurality of reference subjects with varying states of artery disease.

In some embodiments, at block 1420, the system can be configured to generate a second computational model of the one or more arteries based at least in part on the identified one or more vascular morphology parameters and the one or more atherosclerosis parameters, wherein the second computational model is configured to computationally transform one or more regions of low density non-calcified plaque to non-calcified plaque or calcified plaque, and wherein the second computational model is further configured to computationally transform one or more regions of non-calcified plaque to calcified plaque.

In some embodiments, at block 1422, the system can be configured to determine a second predicted risk of artery disease for the patient at the second point in time based on the second computational model, wherein the second predicted risk of artery disease is determined using the machine learning algorithm.

In some embodiments, at block 1424, the system can be configured to generate a graphical representation of the first baseline risk of artery disease, the first predicted risk of artery disease, and the second predicted risk of artery disease to facilitate determination of a patient-specific treatment for artery disease for the patient, wherein a difference between the first baseline risk of artery disease and the first predicted risk of artery disease represents a decrease in risk of artery disease for the patient based on stent implantation, and wherein a difference between the first baseline risk of artery disease and the first predicted risk of artery disease represents a decrease in risk of artery disease for the patient based on medication or lifestyle treatment. In some embodiments, the difference between the first baseline risk of artery disease and the first predicted risk of artery disease represents an increase in risk of artery disease for the patient based on an increase in plaque. In some embodiments, the computer system comprises a computer processor and an electronic storage medium. In some embodiments, the analyses results can be displayed on a vessel, lesion, and/or subject basis. In some embodiments, the proposed treatment can include, for example, medical treatment such as statins, interventional treatment such as stent implantation, and/or lifestyle treatment such as exercise or diet. In some embodiments, at block 1424, the system can be configured to generate a graphical representation of the second or further baseline risk of artery disease, the first predicted risk of artery disease, and the second predicted risk of artery disease to determine whether a treatment or lack thereof affected the progression of the plaque in a similar or dissimilar manner to the prediction. In some embodiments, the reevaluation of the determined patient-specific treatment for artery disease for the patient is based at least in part on an absolute difference in the second or further baseline risk of artery disease compared to one or more of the first predicted risk of artery disease and the second predicted risk of artery disease. In some embodiments, the reevaluation of the determined patient-specific treatment for artery disease for the patient is based at least in part on a percentage difference in the second baseline risk of artery disease compared to one or more of the first predicted risk of artery disease and the second predicted risk of artery disease. In some embodiments, at block 1424, the system can be configured to compare the second baseline risk of artery disease to the first baseline risk of artery disease, wherein the comparison is configured to facilitate reevaluation of the determined patient-specific treatment for artery disease for the patient. In some embodiments, the reevaluation of the determined patient-specific treatment for artery disease for the patient is based at least in part on an absolute difference in the second baseline risk of artery disease compared to the first baseline risk of artery disease. In some embodiments, the reevaluation of the determined patient-specific treatment for artery disease for the patient is based at least in part on a rate of change in the second baseline risk of artery disease against the first baseline risk of artery disease. In some embodiments, the reevaluation of the determined patient-specific treatment for artery disease for the patient is based at least in part on a percentage difference in the second baseline risk of artery disease compared to the first baseline risk of artery disease.

In some embodiments, the system can be configured to repeat one or more processes described in relation to blocks 1402-1424, for example for one or more other vessels, segment, regions of plaque, different subjects, and/or for the same subject at a different time. As such, in some embodiments, the system can provide for longitudinal disease tracking and/or personalized treatment for a subject.

The computer system 902 of FIG. 9, and in some instances, the analysis and/or risk assessment module 940, can be configured to carry out the functions, methods, acts, and/or processes for patient-specific atherosclerosis treatment based on computational modeling described herein, such as those described above with reference to FIG. 14.

The following are non-limiting examples of certain embodiments of systems and methods for patient-specific atherosclerosis treatment based on computational modeling. Other embodiments may include one or more other features, or different features, that are discussed herein.

Embodiment 1: A computer-implemented method of facilitating determination of a patient-specific treatment for atherosclerosis using computational modeling based at least in part on parameters generated from medical image analysis, the method comprising: accessing, by a computer system, one or more medical images of a patient, the one or more medical images comprising a representation of a portion of one or more arteries; automatically identifying, by the computer system, one or more arteries in the one or more medical images based at least in part on image segmentation; generating, by the computer system, one or more vascular morphology parameters based on the identified one or more arteries; automatically identifying, by the computer system, one or more regions of plaque within the identified one or more arteries; generating, by the computer system, one or more atherosclerosis parameters based on the identified one or more regions of plaque, wherein the one or more atherosclerosis parameters comprises volume of the one or more regions of plaque and classification of the one or more regions of plaque as one or more of low density non-calcified plaque, non-calcified plaque, or calcified plaque based at least in part on density of one or more pixels corresponding to the one or more regions of plaque; accessing, by the computer system, a first baseline risk of artery disease for the patient at a first point in time; generating, by the computer system, a first computational model of the one or more arteries based at least in part on the identified one or more vascular morphology parameters and the one or more atherosclerosis parameters, wherein the first computational model is configured to computationally reduce the volume of the one or more regions of plaque; determining, by the computer system, a first predicted risk of artery disease for the patient at a second point in time based on the first computational model, wherein the first predicted risk of artery disease is determined using a machine learning algorithm trained from a plurality of medical images comprising one or more portions of arteries derived from a plurality of reference subjects with varying states of artery disease; generating, by the computer system, a second computational model of the one or more arteries based at least in part on the identified one or more vascular morphology parameters and the one or more atherosclerosis parameters, wherein the second computational model is configured to computationally transform one or more regions of low density non-calcified plaque to non-calcified plaque or calcified plaque, and wherein the second computational model is further configured to computationally transform one or more regions of non-calcified plaque to calcified plaque; determining, by the computer system, a second predicted risk of artery disease for the patient at the second point in time based on the second computational model, wherein the second predicted risk of artery disease is determined using the machine learning algorithm; and generating, by the computer system, a graphical representation of the first baseline risk of artery disease, the first predicted risk of artery disease, and the second predicted risk of artery disease to facilitate determination of a patient-specific treatment for artery disease for the patient, wherein a difference between the first baseline risk of artery disease and the first predicted risk of artery disease represents a decrease in risk of artery disease for the patient based on stent implantation, and wherein a difference between the first baseline risk of artery disease and the first predicted risk of artery disease represents a decrease in risk of artery disease for the patient based on medication or lifestyle treatment, wherein the computer system comprises a computer processor and an electronic storage medium.

Embodiment 2: The computer-implemented method of Embodiment 1, wherein the one or more arteries comprise one or more coronary arteries.

Embodiment 3: The computer-implemented method of Embodiment 1, wherein the one or more arteries comprise one or more coronary arteries, carotid arteries, aorta, upper extremity arteries, or lower extremity arteries.

Embodiment 4: The computer-implemented method of Embodiment 1, wherein the artery disease comprises coronary artery disease (CAD).

Embodiment 5: The computer-implemented method of Embodiment 1, wherein the artery disease comprises one or more major adverse cardiovascular events (MACE) or myocardial infarction.

Embodiment 6: The computer-implemented method of Embodiment 5, wherein the first baseline risk of artery disease is generated based at least in part on the machine learning algorithm.

Embodiment 7: The computer-implemented method of Embodiment 1, wherein the artery disease comprises ischemia.

Embodiment 8: The computer-implemented method of Embodiment 7, wherein the first baseline risk of artery disease is generated based at least in part on the machine learning algorithm.

Embodiment 9: The computer-implemented method of Embodiment 7, wherein the first baseline risk of artery disease is generated based at least in part on one or more of invasive fractional flow reserve, CT fractional flow reserve, computational fractional flow reserve, virtual fractional flow reserve, vessel fractional flow reserve, or quantitative flow ratio.

Embodiment 10: The computer-implemented method of Embodiment 1, further comprising: accessing, by the computer system, a second baseline risk of artery disease derived at the second point in time; and generating, by the computer system, a comparison of the second baseline risk of artery disease and one or more of the first predicted risk of artery disease and the second predicted risk of artery disease, wherein the comparison is configured to facilitate reevaluation of the determined patient-specific treatment for artery disease for the patient.

Embodiment 11: The computer-implemented method of Embodiment 10, wherein the reevaluation of the determined patient-specific treatment for artery disease for the patient is based at least in part on an absolute difference in the second baseline risk of artery disease compared to one or more of the first predicted risk of artery disease and the second predicted risk of artery disease.

Embodiment 12: The computer-implemented method of Embodiment 10, wherein the reevaluation of the determined patient-specific treatment for artery disease for the patient is based at least in part on a percentage difference in the second baseline risk of artery disease compared to one or more of the first predicted risk of artery disease and the second predicted risk of artery disease.

Embodiment 13: The computer-implemented method of Embodiment 10, wherein the reevaluation of the determined patient-specific treatment for artery disease for the patient is based at least in part on a rate of change in the second baseline risk of artery disease against one or more of the first predicted risk of artery disease and the second predicted risk of artery disease.

Embodiment 14: The computer-implemented method of Embodiment 1, further comprising: accessing, by the computer system, a second baseline risk of artery disease derived at the second point in time; and generating, by the computer system, a comparison of the second baseline risk of artery disease and the first baseline risk of artery disease, wherein the comparison is configured to facilitate reevaluation of the determined patient-specific treatment for artery disease for the patient.

Embodiment 15: The computer-implemented method of Embodiment 14, wherein the reevaluation of the determined patient-specific treatment for artery disease for the patient is based at least in part on an absolute difference in the second baseline risk of artery disease compared to the first baseline risk of artery disease.

Embodiment 16: The computer-implemented method of Embodiment 14, wherein the reevaluation of the determined patient-specific treatment for artery disease for the patient is based at least in part on a rate of change in the second baseline risk of artery disease against the first baseline risk of artery disease.

Embodiment 17: The computer-implemented method of Embodiment 14, wherein the reevaluation of the determined patient-specific treatment for artery disease for the patient is based at least in part on a percentage difference in the second baseline risk of artery disease compared to the first baseline risk of artery disease.

Embodiment 18: The computer-implemented method of Embodiment 1, wherein the one or more medical images comprises a Computed Tomography (CT) image.

Embodiment 19: The computer-implemented method of Embodiment 1, wherein the one or more medical images is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 20: The computer-implemented method of Embodiment 1, wherein the density of the one or more pixels comprises absolute density.

Embodiment 21: The computer-implemented method of Embodiment 1, wherein the density of the one or more pixels comprises radiodensity.

Embodiment 22: The computer-implemented method of Embodiment 21, wherein the one or more regions of plaque are classified as low density non-calcified plaque when a radiodensity value is between about −189 and about 30 Hounsfield units.

Embodiment 23: The computer-implemented method of Embodiment 21, wherein the one or more regions of plaque are classified as non-calcified plaque when a radiodensity value is between about 31 and about 350 Hounsfield units.

Embodiment 24: The computer-implemented method of Embodiment 21, wherein the one or more regions of plaque are classified as calcified plaque when a radiodensity value is between about 351 and 2500 Hounsfield units.

Embodiment 25: A non-transitory computer readable medium configured for facilitating determination of a patient-specific treatment for atherosclerosis using computational modeling based at least in part on parameters generated from medical image analysis, the computer readable medium having program instructions for causing a hardware processor to perform a method of: accessing one or more medical images of a patient, the one or more medical images comprising a representation of a portion of one or more arteries; automatically identifying one or more arteries in the one or more medical images based at least in part on image segmentation; generating one or more vascular morphology parameters based on the identified one or more arteries; automatically identifying one or more regions of plaque within the identified one or more arteries; generating one or more atherosclerosis parameters based on the identified one or more regions of plaque, wherein the one or more atherosclerosis parameters comprises volume of the one or more regions of plaque and classification of the one or more regions of plaque as one or more of low density non-calcified plaque, non-calcified plaque, or calcified plaque based at least in part on density of one or more pixels corresponding to the one or more regions of plaque; accessing a first baseline risk of artery disease for the patient at a first point in time; generating a first computational model of the one or more arteries based at least in part on the identified one or more vascular morphology parameters and the one or more atherosclerosis parameters, wherein the first computational model is configured to computationally reduce the volume of the one or more regions of plaque; determining a first predicted risk of artery disease for the patient at a second point in time based on the first computational model, wherein the first predicted risk of artery disease is determined using a machine learning algorithm trained from a plurality of medical images comprising one or more portions of arteries derived from a plurality of reference subjects with varying states of artery disease; generating a second computational model of the one or more arteries based at least in part on the identified one or more vascular morphology parameters and the one or more atherosclerosis parameters, wherein the second computational model is configured to computationally transform one or more regions of low density non-calcified plaque to noncalcified plaque or calcified plaque, and wherein the second computational model is further configured to computationally transform one or more regions of non-calcified plaque to calcified plaque; determining a second predicted risk of artery disease for the patient at the second point in time based on the second computational model, wherein the second predicted risk of artery disease is determined using the machine learning algorithm; and generating a graphical representation of the first baseline risk of artery disease, the first predicted risk of artery disease, and the second predicted risk of artery disease to facilitate determination of a patient-specific treatment for artery disease for the patient, wherein a difference between the first baseline risk of artery disease and the first predicted risk of artery disease represents a decrease in risk of artery disease for the patient based on stent implantation, and wherein a difference between the first baseline risk of artery disease and the first predicted risk of artery disease represents a decrease in risk of artery disease for the patient based on medication or lifestyle treatment.

Embodiment 26: The non-transitory computer readable medium configured as in Embodiment 25, wherein the one or more arteries comprise one or more coronary arteries.

Embodiment 27: The non-transitory computer readable medium configured as in Embodiment 25, wherein the one or more arteries comprise one or more coronary arteries, carotid arteries, aorta, upper extremity arteries, or lower extremity arteries.

Embodiment 28: The non-transitory computer readable medium configured as in Embodiment 25, wherein the artery disease comprises coronary artery disease (CAD).

Embodiment 29: The non-transitory computer readable medium configured as in Embodiment 25, wherein the artery disease comprises one or more major adverse cardiovascular events (MACE) or myocardial infarction.

Embodiment 30: The non-transitory computer readable medium configured as in Embodiment 29, wherein the first baseline risk of artery disease is generated based at least in part on the machine learning algorithm.

Embodiment 31: The non-transitory computer readable medium configured as in Embodiment 25, wherein the artery disease comprises ischemia.

Embodiment 32: The non-transitory computer readable medium configured as in Embodiment 31, wherein the first baseline risk of artery disease is generated based at least in part on the machine learning algorithm.

Embodiment 33: The non-transitory computer readable medium configured as in Embodiment 31, wherein the first baseline risk of artery disease is generated based at least in part on one or more of invasive fractional flow reserve, CT fractional flow reserve, computational fractional flow reserve, virtual fractional flow reserve, vessel fractional flow reserve, or quantitative flow ratio.

Embodiment 34: The non-transitory computer readable medium configured as in Embodiment 25, the computer readable medium having program instructions for causing a hardware processor to perform a method of: accessing a second baseline risk of artery disease derived at the second point in time; and comparing the second baseline risk of artery disease to one or more of the first predicted risk of artery disease and the second predicted risk of artery disease, wherein the comparison is configured to facilitate reevaluation of the determined patient-specific treatment for artery disease for the patient.

Embodiment 35: The non-transitory computer readable medium configured as in Embodiment 34, wherein the reevaluation of the determined patient-specific treatment for artery disease for the patient is based at least in part on an absolute difference in the second baseline risk of artery disease compared to one or more of the first predicted risk of artery disease and the second predicted risk of artery disease.

Embodiment 36: The non-transitory computer readable medium configured as in Embodiment 34, wherein the reevaluation of the determined patient-specific treatment for artery disease for the patient is based at least in part on a percentage difference in the second baseline risk of artery disease compared to one or more of the first predicted risk of artery disease and the second predicted risk of artery disease.

Embodiment 37: The non-transitory computer readable medium configured as in Embodiment 34, wherein the reevaluation of the determined patient-specific treatment for artery disease for the patient is based at least in part on a rate of change in the second baseline risk of artery disease against one or more of the first predicted risk of artery disease and the second predicted risk of artery disease.

Embodiment 38: The non-transitory computer readable medium configured as in Embodiment 25, the computer readable medium having program instructions for causing the hardware processor to perform a method of: accessing a second baseline risk of artery disease derived at the second point in time; and comparing the second baseline risk of artery disease to the first baseline risk of artery disease, wherein the comparison is configured to facilitate reevaluation of the determined patient-specific treatment for artery disease for the patient.

Embodiment 39: The non-transitory computer readable medium configured as in Embodiment 38, wherein the reevaluation of the determined patient-specific treatment for artery disease for the patient is based at least in part on an absolute difference in the second baseline risk of artery disease compared to the first baseline risk of artery disease.

Embodiment 40: The non-transitory computer readable medium configured as in Embodiment 38, wherein the reevaluation of the determined patient-specific treatment for artery disease for the patient is based at least in part on a rate of change in the second baseline risk of artery disease against the first baseline risk of artery disease.

Embodiment 41: The non-transitory computer readable medium configured as in Embodiment 38, wherein the reevaluation of the determined patient-specific treatment for artery disease for the patient is based at least in part on a percentage difference in the second baseline risk of artery disease compared to the first baseline risk of artery disease.

Embodiment 42: The non-transitory computer readable medium configured as in Embodiment 25, wherein the one or more medical images comprises a Computed Tomography (CT) image.

Embodiment 43: The non-transitory computer readable medium configured as in Embodiment 25, wherein the one or more medical images is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 44: The non-transitory computer readable medium configured as in Embodiment 25, wherein the density of the one or more pixels comprises absolute density.

Embodiment 45: The non-transitory computer readable medium configured as in Embodiment 25, wherein the density of the one or more pixels comprises radiodensity.

Embodiment 46: The non-transitory computer readable medium configured as in Embodiment 45, wherein the one or more regions of plaque are classified as low density non-calcified plaque when a radiodensity value is between about −189 and about 30 Hounsfield units.

Embodiment 47: The non-transitory computer readable medium configured as in Embodiment 45, wherein the one or more regions of plaque are classified as non-calcified plaque when a radiodensity value is between about 31 and about 350 Hounsfield units.

Embodiment 48: The non-transitory computer readable medium configured as in Embodiment 45, wherein the one or more regions of plaque are classified as calcified plaque when a radiodensity value is between about 351 and 2500 Hounsfield units.

Embodiment 49: A system comprising: a non-transitory computer storage medium configured to at least store computer-executable instructions; and one or more computer hardware processors in communication with the non-transitory computer storage medium, the one or more computer hardware processors configured to execute the computer-executable instructions to at least: access one or more medical images of a patient, the one or more medical images comprising a representation of a portion of one or more arteries; automatically identify one or more arteries in the one or more medical images based at least in part on image segmentation; generate one or more vascular morphology parameters based on the identified one or more arteries; automatically identify or more regions of plaque within the identified one or more arteries; generate one or more atherosclerosis parameters based on the identified one or more regions of plaque, wherein the one or more atherosclerosis parameters comprises volume of the one or more regions of plaque and classification of the one or more regions of plaque as one or more of low density non-calcified plaque, non-calcified plaque, or calcified plaque based at least in part on density of one or more pixels corresponding to the one or more regions of plaque; access a first baseline risk of artery disease for the patient at a first point in time; generate a first computational model of the one or more arteries based at least in part on the identified one or more vascular morphology parameters and the one or more atherosclerosis parameters, wherein the first computational model is configured to computationally reduce the volume of the one or more regions of plaque; determine a first predicted risk of artery disease for the patient at a second point in time based on the first computational model, wherein the first predicted risk of artery disease is determined using a machine learning algorithm trained from a plurality of medical images comprising one or more portions of arteries derived from a plurality of reference subjects with varying states of artery disease; generate a second computational model of the one or more arteries based at least in part on the identified one or more vascular morphology parameters and the one or more atherosclerosis parameters, wherein the second computational model is configured to computationally transform one or more regions of low density non-calcified plaque to non-calcified plaque or calcified plaque, and wherein the second computational model is further configured to computationally transform one or more regions of non-calcified plaque to calcified plaque; determine a second predicted risk of artery disease for the patient at the second point in time based on the second computational model, wherein the second predicted risk of artery disease is determined using the machine learning algorithm; and generate a graphical representation of the first baseline risk of artery disease, the first predicted risk of artery disease, and the second predicted risk of artery disease to facilitate determination of a patient-specific treatment for artery disease for the patient, wherein a difference between the first baseline risk of artery disease and the first predicted risk of artery disease represents a decrease in risk of artery disease for the patient based on stent implantation, and wherein a difference between the first baseline risk of artery disease and the first predicted risk of artery disease represents a decrease in risk of artery disease for the patient based on medication or lifestyle treatment.

Embodiment 50: The system of Embodiment 49, wherein the one or more arteries comprise one or more coronary arteries.

Embodiment 51: The system of Embodiment 49, wherein the one or more arteries comprise one or more coronary arteries, carotid arteries, aorta, upper extremity arteries, or lower extremity arteries.

Embodiment 52: The system of Embodiment 49, wherein the artery disease comprises coronary artery disease (CAD).

Embodiment 53: The system of Embodiment 49, wherein the artery disease comprises one or more major adverse cardiovascular events (MACE) or myocardial infarction.

Embodiment 54: The system of Embodiment 53, wherein the first baseline risk of artery disease is generated based at least in part on the machine learning algorithm.

Embodiment 55: The system of Embodiment 49, wherein the artery disease comprises ischemia.

Embodiment 56: The system of Embodiment 55, wherein the first baseline risk of artery disease is generated based at least in part on the machine learning algorithm.

Embodiment 57: The system of Embodiment 55, wherein the first baseline risk of artery disease is generated based at least in part on one or more of invasive fractional flow reserve, CT fractional flow reserve, computational fractional flow reserve, virtual fractional flow reserve, vessel fractional flow reserve, or quantitative flow ratio.

Embodiment 58: The system of Embodiment 49, wherein the processors are further configured to: access a second baseline risk of artery disease derived at the second point in time; and generate a comparison of the second baseline risk of artery disease and one or more of the first predicted risk of artery disease and the second predicted risk of artery disease, wherein the comparison is configured to facilitate reevaluation of the determined patient-specific treatment for artery disease for the patient.

Embodiment 59: The system of Embodiment 58, wherein the reevaluation of the determined patient-specific treatment for artery disease for the patient is based at least in part on an absolute difference in the second baseline risk of artery disease compared to one or more of the first predicted risk of artery disease and the second predicted risk of artery disease.

Embodiment 60: The system of Embodiment 58, wherein the reevaluation of the determined patient-specific treatment for artery disease for the patient is based at least in part on a percentage difference in the second baseline risk of artery disease compared to one or more of the first predicted risk of artery disease and the second predicted risk of artery disease.

Embodiment 61: The system of Embodiment 58, wherein the reevaluation of the determined patient-specific treatment for artery disease for the patient is based at least in part on a rate of change in the second baseline risk of artery disease against one or more of the first predicted risk of artery disease and the second predicted risk of artery disease.

Embodiment 62: The system of Embodiment 49, wherein the processors are further configured to: access a second baseline risk of artery disease derived at the second point in time; and generate a comparison of the second baseline risk of artery disease and the first baseline risk of artery disease, wherein the comparison is configured to facilitate reevaluation of the determined patient-specific treatment for artery disease for the patient.

Embodiment 63: The system of Embodiment 62, wherein the reevaluation of the determined patient-specific treatment for artery disease for the patient is based at least in part on an absolute difference in the second baseline risk of artery disease compared to the first baseline risk of artery disease.

Embodiment 64: The system of Embodiment 62, wherein the reevaluation of the determined patient-specific treatment for artery disease for the patient is based at least in part on a rate of change in the second baseline risk of artery disease against the first baseline risk of artery disease.

Embodiment 65: The system of Embodiment 62, wherein the reevaluation of the determined patient-specific treatment for artery disease for the patient is based at least in part on a percentage difference in the second baseline risk of artery disease compared to the first baseline risk of artery disease.

Embodiment 66: The system of Embodiment 49, wherein the one or more medical images comprises a Computed Tomography (CT) image.

Embodiment 67: The system of Embodiment 49, wherein the one or more medical images is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 68: The system of Embodiment 49, wherein the density of the one or more pixels comprises absolute density.

Embodiment 69: The system of Embodiment 49, wherein the density of the one or more pixels comprises radiodensity.

Embodiment 70: The system of Embodiment 69, wherein the one or more regions of plaque are classified as low density non-calcified plaque when a radiodensity value is between about −189 and about 30 Hounsfield units.

Embodiment 71: The system of Embodiment 69, wherein the one or more regions of plaque are classified as non-calcified plaque when a radiodensity value is between about 31 and about 350 Hounsfield units.

Embodiment 72: The system of Embodiment 69, wherein the one or more regions of plaque are classified as calcified plaque when a radiodensity value is between about 351 and 2500 Hounsfield units.

Conversion of a Medical Image Based on Plaque and/or Vascular Parameters

Disclosed herein are systems, devices, and methods for conversion of a medical image based on plaque and/or vascular parameters. In some embodiments, the systems, devices, and methods described herein are configured to allow for conversion of a low- (or lower-) resolution medical image to a high- (or higher-resolution medical image. In particular, some embodiments may be configured to input a low-resolution medical image, analyze the medical image to identify vessels and regions of plaque within the image, and generate one or more plaque parameters based on the image, the identified vessels, and/or the identified one or more regions of plaque. In some embodiments, the one or more plaque parameters can include one or more of volume of low-density non-calcified plaque, volume of non-calcified plaque, volume of calcified plaque, total plaque volume, plaque morphology, or embeddedness of a low density non-calcified plaque by non-calcified plaque or calcified plaque. In some embodiments, the systems, devices, and methods, can further be configured to generate one or more vascular parameters based on the image and the identified vessels. The one or more vascular parameters can include, in some embodiments, one or more of remodeling index, stenosis area percentage, stenosis diameter percentage, lumen volume, number of chronic total occlusion (CTO), or distance between plaque and lumen wall or vessel wall. In some embodiments, the systems, devices, and methods described herein can then allow for converting the low-resolution medical image into a high-resolution medical image based on the one or more plaque parameters and the one or more vascular parameters. For example, the low-resolution image, the plaque parameters, and the vascular parameters can be input into a machine learning algorithm that is configured to convert the image to a higher-resolution image. For example, in some embodiments, the machine learning algorithm has been trained based at least in part on the one or more plaque parameters and the one or more vascular parameters generated from a plurality of low-resolution medical images and the one or more plaque parameters and the one or more vascular parameters generated from a plurality of high-resolution medical images.

In some embodiments, the systems, devices, and methods described herein are configured to determine a risk of coronary artery disease (CAD), such as for example myocardial infarction (MI), based on one or more plaque analyses described herein. In some embodiments, the systems, devices, and methods described herein are configured to generate a proposed treatment and/or graphical representation based on the determined risk of CAD and/or one or more plaque analyses described herein.

In some embodiments, the systems, devices, and methods, can further be configured to generate one or more vascular parameters based on the image and the identified vessels. The one or more vascular parameters can include, in some embodiments, one or more of remodeling index, stenosis area percentage, stenosis diameter percentage, lumen volume, number of chronic total occlusion (CTO), or distance between plaque and lumen wall or vessel wall.

In some embodiments, the systems, devices, and methods described herein can then allow for converting the low-resolution medical image into a high-resolution medical image based on the one or more plaque parameters and the one or more vascular parameters. For example, the low-resolution image, the plaque parameters, and the vascular parameters can be input into a machine learning algorithm that is configured to convert the image to a higher-resolution image. For example, in some embodiments, the machine learning algorithm has been trained based at least in part on the one or more plaque parameters and the one or more vascular parameters generated from a plurality of low-resolution medical images and the one or more plaque parameters and the one or more vascular parameters generated from a plurality of high-resolution medical images.

In some embodiments, the systems, devices, and methods described herein are configured to determine a risk of coronary artery disease (CAD), such as for example myocardial infarction (MI), based on one or more plaque analyses described herein. In some embodiments, the systems, devices, and methods described herein are configured to generate a proposed treatment and/or graphical representation based on the determined risk of CAD and/or one or more plaque analyses described herein. For example, the converted medical image can be used in analysis that allows for determination of a risk of CAD or MI and in the generation of a proposed treatment and/or graphical representation.

In some embodiments, the medical images can be CT images and the systems, methods, and devices described herein can be configured to convert the CT images into higher quality optical coherence tomography (OCT) images. This can be used to increase or enhance the resolution of the original image. For example, in some instances, a CT image can have a lower spatial resolution (e.g., 10 µm) and this can be converted or enhanced to increase the resolution in an OCT image (e.g., 500 µm). Other resolutions can also be obtained.

In some embodiments, lower-resolution images may exhibit calcium blooming. Calcium blooming can occur when calcium present within in image appears as a large, bright, and/or indistinct blur due to the low resolution of the image. Calcium blooming can cause the appearance of plaque within an image to be indistinct which can cause diagnosing or characterizing the plaque to be difficult or impossible. By converting the image to a higher resolution image, the effects of calcium blooming can be diminished or eliminated. For example, in some instances the higher-resolution image contains less or no calcium blooming.

To achieve this conversion, an artificial intelligence or machine learning algorithm can be trained using a dataset that contains both CT and OCT or intravascular ultrasound (IVUS) images contained from a plurality (e.g., hundreds or thousands of patients). Each image can be analyzed, for example, as described herein to determine various image-derived parameters associated therewith. The image-derived parameters can include plaque parameters associated with plaques in the images and/or vascular parameters associated with vessels in the images. Since the parameters can be determined with respect to both the lower resolution CT images and the higher resolution OCT or IVUS images, a mapping can be generated between the two. This mapping can allow conversion of a lower resolution image into a higher resolution image.

The improved or enhanced resolution images can then further be used to diagnose and or treat a patient.

Figure 15:
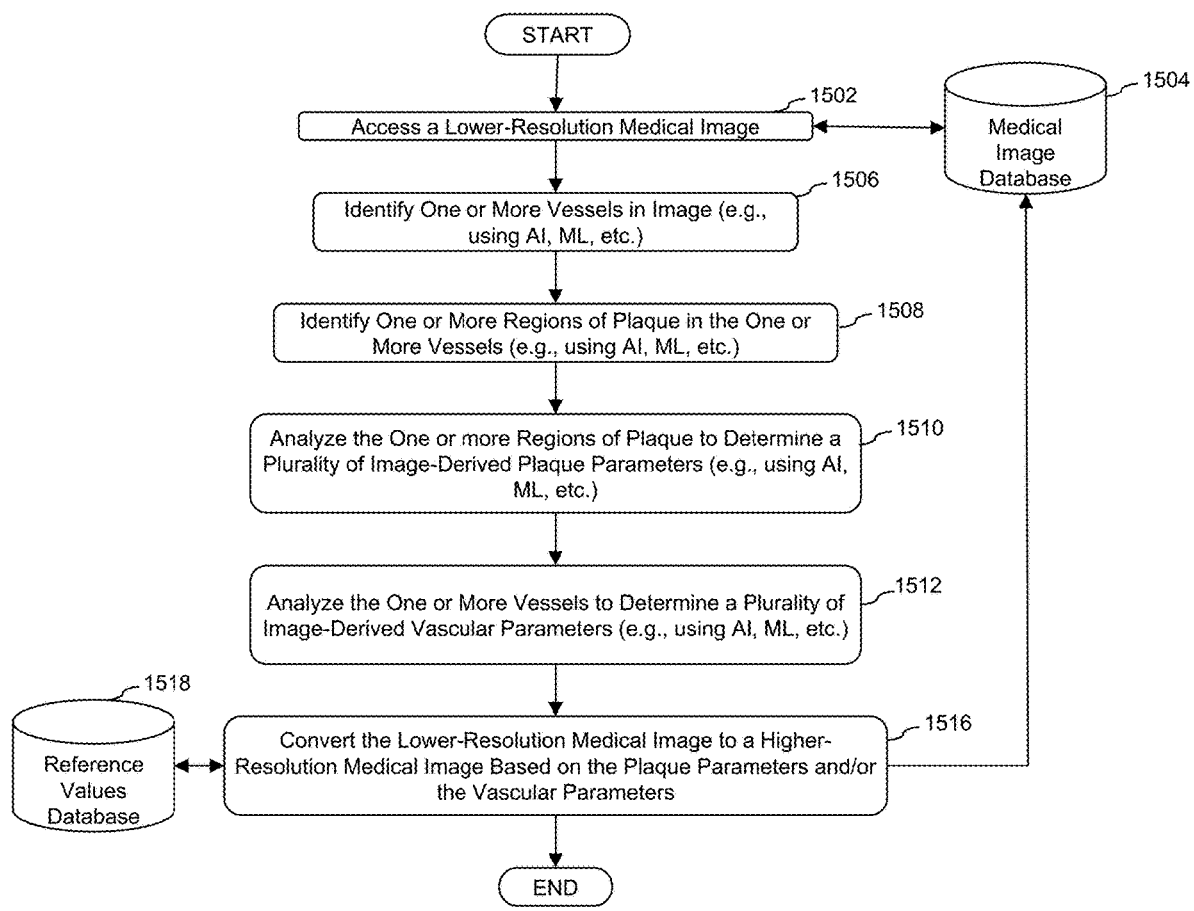
FIG. 15 is a flowchart illustrating an example embodiment(s) of systems, devices, and methods for conversion of medical images based on plaque and/or vascular parameters.

FIG. 15 is a flowchart illustrating an example embodiment(s) of systems, devices, and methods for conversion of a medical image based on plaque and/or vascular parameters. As illustrated in FIG. 15, in some embodiments, the system can be configured to access one or more medical images at block 1502. In some embodiments, the medical image can be a lower-resolution or lower-quality medical image. For example, the medical image can include calcium blooming effects, etc. In some embodiments, the medical image can include one or more arteries, such as coronary, carotid, and/or other arteries of a subject. In some embodiments, the medical image can be stored in a medical image database 1504.

In some embodiments, the medical image database 1504 can be locally accessible by the system and/or can be located remotely and accessible through a network connection. The medical image can comprise an image obtain using one or more modalities such as for example, CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the medical image comprises one or more of a contrast-enhanced CT image, non-contrast CT image, MR image, and/or an image obtained using any of the modalities described above.

In some embodiments, the system can be configured to automatically and/or dynamically perform one or more analyses of the medical image as discussed herein. For example, in some embodiments, at block 1506, the system can be configured to identify one or more vessels, such as of one or more arteries. The one or more arteries can include coronary arteries, carotid arteries, aorta, renal artery, lower extremity artery, upper extremity artery, and/or cerebral artery, amongst others. In some embodiments, the system can be configured to utilize one or more AI and/or ML algorithms to automatically and/or dynamically identify one or more arteries or coronary arteries using image processing. For example, in some embodiments, the one or more AI and/or ML algorithms can be trained using a Convolutional Neural Network (CNN) on a set of medical images on which arteries or coronary arteries have been identified, thereby allowing the AI and/or ML algorithm automatically identify arteries or coronary arteries directly from a medical image. In some embodiments, the arteries or coronary arteries are identified by size and/or location.

In some embodiments, at block 1508, the system can be configured to identify one or more regions of plaque in the medical image. In some embodiments, the system can be configured to utilize one or more AI and/or ML algorithms to automatically and/or dynamically identify one or more regions of plaque using image processing. For example, in some embodiments, the one or more AI and/or ML algorithms can be trained using a Convolutional Neural Network (CNN) on a set of medical images on which regions of plaque have been identified, thereby allowing the AI and/or ML algorithm automatically identify regions of plaque directly from a medical image. In some embodiments, the system is configured to identify vessel and lumen walls and classify everything in between the vessel and lumen walls as plaque.

In some embodiments, at block 1508, the system can be configured to analyze the identified one or more regions of plaque to generate one or more plaque parameters associated therewith. For example, using an image-based analysis, the system can generate one or more of the following plaque parameters based on the image: volume of low-density non-calcified plaque, volume of non-calcified plaque, volume of calcified plaque, total plaque volume, plaque morphology, or embeddedness of a low density non-calcified plaque by non-calcified plaque or calcified plaque. In some embodiments, the plaque parameters may also include one or more of plaque slice percentage, eccentricity of plaque, presence of low-density non-calcified plaque, presence of non-calcified plaque, or presence of calcified plaque. In some embodiments, the plaque parameters may further include one or more of one or more of plaque area, plaque burden, necrotic core percentage, necrotic core volume, fatty fibrous volume, fatty fibrous percentage, dense calcium percentage, low-density calcium percentage, medium-density calcified percentage, high-density calcified percentage, presence of two-feature positive plaques, or number of two-feature positive plaques.

In some embodiments, to generate the plaque parameters, the system may be configured analyze and/or characterize the one or more regions of plaque. For example, the system can be configured to characterize the one or more regions of plaque based on density. For example, in some embodiments, the system can be configured to analyze and/or characterize one or more regions of plaque based on absolute density and/or relative density and/or radiodensity. In some embodiments, the system can be configured to classify a region of plaque as one of low density non-calcified plaque, non-calcified plaque, and calcified plaque, using any one or more processes and/or features described herein.

For example, in some embodiments, the system can be configured to characterize a region of plaque as one or more of low density non-calcified plaque, non-calcified plaque, or calcified plaque. In some embodiments, calcified plaque can correspond to plaque having a highest density range, low density non-calcified plaque can correspond to plaque having a lowest density range, and non-calcified plaque can correspond to plaque having a density range between calcified plaque and low density non-calcified plaque. For example, in some embodiments, the system can be configured to characterize a particular region of plaque as low density non-calcified plaque when the radiodensity of an image pixel or voxel corresponding to that region of plaque is between about −189 and about 30 Hounsfield units (HU). In some embodiments, the system can be configured to characterize a particular region of plaque as non-calcified plaque when the radiodensity of an image pixel or voxel corresponding to that region of plaque is between about 31 and about 350 HU. In some embodiments, the system can be configured to characterize a particular region of plaque as calcified plaque when the radiodensity of an image pixel or voxel corresponding to that region of plaque is between about 351 and about 2500 HU.

In some embodiments, the lower and/or upper Hounsfield unit boundary threshold for determining whether a plaque corresponds to one or more of low density non-calcified plaque, non-calcified plaque, and/or calcified plaque can be about −1000 HU, about −900 HU, about −800 HU, about −700 HU, about −600 HU, about −500 HU, about −400 HU, about −300 HU, about −200 HU, about −190 HU, about −180 HU, about −170 HU, about −160 HU, about −150 HU, about −140 HU, about −130 HU, about −120 HU, about −110 HU, about −100 HU, about −90 HU, about −80 HU, about −70 HU, about −60 HU, about −50 HU, about −40 HU, about −30 HU, about −20 HU, about −10 HU, about 0 HU, about 10 HU, about 20 HU, about 30 HU, about 40 HU, about 50 HU, about 60 HU, about 70 HU, about 80 HU, about 90 HU, about 100 HU, about 110 HU, about 120 HU, about 130 HU, about 140 HU, about 150 HU, about 160 HU, about 170 HU, about 180 HU, about 190 HU, about 200 HU, about 210 HU, about 220 HU, about 230 HU, about 240 HU, about 250 HU, about 260 HU, about 270 HU, about 280 HU, about 290 HU, about 300 HU, about 310 HU, about 320 HU, about 330 HU, about 340 HU, about 350 HU, about 360 HU, about 370 HU, about 380 HU, about 390 HU, about 400 HU, about 410 HU, about 420 HU, about 430 HU, about 440 HU, about 450 HU, about 460 HU, about 470 HU, about 480 HU, about 490 HU, about 500 HU, about 510 HU, about 520 HU, about 530 HU, about 540 HU, about 550 HU, about 560 HU, about 570 HU, about 580 HU, about 590 HU, about 600 HU, about 700 HU, about 800 HU, about 900 HU, about 1000 HU, about 1100 HU, about 1200 HU, about 1300 HU, about 1400 HU, about 1500 HU, about 1600 HU, about 1700 HU, about 1800 HU, about 1900 HU, about 2000 HU, about 2100 HU, about 2200 HU, about 2300 HU, about 2400 HU, about 2500 HU, about 2600 HU, about 2700 HU, about 2800 HU, about 2900 HU, about 3000 HU, about 3100 HU, about 3200 HU, about 3300 HU, about 3400 HU, about 3500 HU, and/or about 4000 HU.

In some embodiments, at block 1510, the system can be configured to analyze and/or characterize one or more regions of plaque based on one or more distances. For example, as described herein, in some embodiments, the system can be configured to determine a distance between a low density non-calcified plaque and lumen wall and/or vessel wall. In some embodiments, proximity of a low density non-calcified plaque to the lumen wall can be indicative of a high-risk plaque and/or CAD. Conversely, in some embodiments, a position of a low density non-calcified plaque far from the lumen wall can be indicative of less risk. In some embodiments, the system can be configured to utilize one or more predetermined thresholds in determining the risk factor associated with the proximity of low density non-calcified plaque with the vessel wall and/or lumen wall. In some embodiments, the system can be configured to utilize one or more image processing algorithms to automatically and/or dynamically determine one or more distances to and/or from one or more regions of plaque.

In some embodiments, at block 1510, the system can be configured to analyze and/or characterize one or more regions of plaque based on morphology or shape and/or one or more axes measurements of low density non-calcified plaque. As described herein, in some embodiments, the system can be configured to determine the length of one or more axes of a low density non-calcified plaque, such as for example a major axis of a longitudinal cross section and/or a major and/or minor axis of a latitudinal cross section of a low density non-calcified plaque. In some embodiments, the system can be configured to utilize the one more axes measurements to determine a morphology and/or shape of a low density non-calcified plaque. In some embodiments, the system can be configured to utilize one or more image processing algorithms to automatically and/or dynamically determine one or more axes measurements of one or more regions of plaque.

In some embodiments, the system can be configured to utilize one or more AI and/or ML algorithms to automatically and/or dynamically classify the shape of one or more regions of plaque using image processing. For example, in some embodiments, the one or more AI and/or ML algorithms can be trained using a Convolutional Neural Network (CNN) on a set of medical images on which the shape of regions of plaque have been identified, thereby allowing the AI and/or ML algorithm automatically identify the shape or morphology of a region of plaque directly from a medical image. In some embodiments, the system can be configured to classify the shape or morphology of a region of plaque as one or more of crescent, lobular, round, or bean-shaped. In some embodiments, round and/or bean-shaped plaques can be associated with high risk, while crescent and/or lobular-shaped plaques can be associated with low risk of CAD.

In some embodiments, at block 1510, the system can be configured to analyze and/or characterize one or more regions of plaque based on one or more sizes and/or volumes. For example, in some embodiments, the system can be configured to determine a size and/or volume of plaque based at least in part on one or more axes measurements described herein. In some embodiments, the system can be configured to determine the size and/or volume of a region of plaque directly from analysis of a three-dimensional image scan. In some embodiments, the system can be configured to determine the size and/or volume of total plaque, low-density non-calcified plaque, non-calcified plaque, calcified plaque, and/or a ratio between two of the aforementioned volumes or sizes. In some embodiments, a high total plaque volume and/or high low-density non-calcified plaque and/or non-calcified plaque volume can be associated with high risk of CAD. In some embodiments, a high ratio of low-density non-calcified plaque volume to total plaque volume and/or a high ratio of non-calcified plaque volume to total plaque volume can be associated with high risk of CAD. In some embodiments, a high calcified plaque volume and/or high ratio of calcified plaque volume to total plaque volume can be associated with low risk of CAD. In some embodiments, the system can be configured to utilize one or more predetermined threshold values for determining the risk of CAD based on plaque volume, size, or one or more ratios thereof. In some embodiments, the system can be configured to utilize one or more image processing algorithms to automatically and/or dynamically determine the size and/or volume of one or more regions of plaque.

In some embodiments, at block 1510, the system can be configured to analyze and/or characterize plaque based on embeddedness. For example, in some embodiments, the system can be configured to determined how embedded or surrounded a low density non-calcified plaque is by non-calcified plaque or calcified plaque. In some embodiments, the system can be configured to analyze the embeddedness of low density non-calcified plaque based on the degree by which it is surrounded by other types of plaque. In some embodiments, a higher embeddedness of a low density non-calcified plaque can be indicative of high risk of CAD. For example, in some embodiments, a low density non-calcified plaque that is surrounded by 270 degrees or more by non-calcified plaque can be associated with high risk of CAD. In some embodiments, the system can be configured to utilize one or more image processing algorithms to automatically and/or dynamically determine the embeddedness of one or more regions of plaque.

In some embodiments, at block 1510, the system can be configured to analyze the one or more identified vessels (e.g., identified at block 1506) to determine one or more image-derived vascular parameters. In some embodiments, the one or more vascular parameters can include one or more of remodeling index, stenosis area percentage, stenosis diameter percentage, lumen volume, number of chronic total occlusion (CTO), or distance between plaque and lumen wall or vessel wall. In some embodiments, the one or more vascular parameters can include one or more of lesion length, presence of positive remodeling, reference diameter after stenosis, reference diameter before stenosis, vessel length, vessel volume, number of stenosis, or number of mild stenosis. In some embodiments, the one more vascular parameters can include one or more of percent atheroma volume of total plaque, percent atheroma volume of low-density non-calcified plaque, percent atheroma volume of non-calcified plaque, percent atheroma volume of calcified plaque, number of high-risk plaque regions, number of segments with calcified plaque, number of segments with non-calcified plaque, segment length, severity of stenosis, minimum lumen diameter, maximum lumen diameter, mean lumen diameter, number of moderate stenosis, number of zero stenosis, number of severe stenosis, presence of high-risk anatomy, number of severe stenosis excluding CTO, vessel area, lumen area, diameter stenosis percentage, presence of ischemia, number of stents, reference lumen diameter before stenosis, perivascular fat attenuation, or reference lumen diameter after stenosis.

In some embodiments, the system can be configured to utilize one or more AI and/or ML algorithms to automatically and/or dynamically generate the vascular parameters. For example, in some embodiments, the one or more AI and/or ML algorithms can be trained using a Convolutional Neural Network (CNN) on a set of medical images on which the vascular parameters have been identified, thereby allowing the AI and/or ML algorithm automatically identify the vascular parameters directly from a medical image.

At block 1516, the system can be configured to convert the lower-resolution medical image to a higher-resolution medical image based on the plaque parameters and/or the vascular parameters. For example, in some embodiments, the system is configured to convert the medical image by inputting the generated one or more plaque parameters and the generated one or more vascular parameters into a machine learning algorithm. The machine learning algorithm can be trained based at least in part on the one or more plaque parameters and the one or more vascular parameters generated from a plurality of low-resolution medical images and the one or more plaque parameters and the one or more vascular parameters generated from a plurality of high-resolution medical images. In some embodiments, the plurality of low-resolution medical images and the plurality of high-resolution medical images obtained from a plurality of other subjects. In some embodiments, plurality of high-resolution medical images obtained from the plurality of other subjects comprises images obtained using intravascular ultrasound (IVUS). In some embodiments, the plurality of high-resolution medical images obtained from the plurality of other subjects comprises images obtained using optical coherence tomography (OCT) intravascular imaging. In some embodiments, parameters derived from the plurality of higher resolution images are stored in a reference values database 1518.

In some embodiments, the higher image resolution image comprises lesser calcium blooming artifacts than the low-resolution medical image.

In some embodiments, the higher resolution image can be stored in the medical image database 1504.

The computer system 902 of FIG. 9, and in some instances, the analysis and/or risk assessment module 940, can be configured to carry out the functions, methods, acts, and/or processes for conversion of a medical image based on plaque and/or vascular parameters described herein, such as those described above with reference to FIG. 15.

The following are non-limiting examples of certain embodiments of systems and methods for conversion of a medical image based on plaque and/or vascular parameters. Other embodiments may include one or more other features, or different features, that are discussed herein.

Embodiment 1: A computer-implemented method of converting a low-resolution medical image of a subject to a high-resolution medical image based on one or more plaque parameters or vascular parameters, the method comprising: accessing, by a computer system, a low-resolution medical image of a subject, the low-resolution medical image comprising a portion of one or more arteries; analyzing, by the computer system, the medical image of the subject to identify one or more artery vessels and one or more regions of plaque within the one or more artery vessels; generating, by the computer system, one or more plaque parameters based at least in part on analyzing the one or more regions of plaque, the one or more plaque parameters comprising one or more of volume of low-density non-calcified plaque, volume of non-calcified plaque, volume of calcified plaque, total plaque volume, plaque morphology, or embeddedness of a low density non-calcified plaque by non-calcified plaque or calcified plaque; generating, by the computer system, one or more vascular parameters based at least in part on analyzing the one or more artery vessels, the one or more vascular parameters comprising one or more of remodeling index, stenosis area percentage, stenosis diameter percentage, lumen volume, number of chronic total occlusion (CTO), or distance between plaque and lumen wall or vessel wall; and converting, by the computer system, the low-resolution medical image into a high-resolution medical image by inputting the generated one or more plaque parameters and the generated one or more vascular parameters into a machine learning algorithm, the machine learning algorithm trained based at least in part on the one or more plaque parameters and the one or more vascular parameters generated from a plurality of low-resolution medical images and the one or more plaque parameters and the one or more vascular parameters generated from a plurality of high-resolution medical images, the plurality of low-resolution medical images and the plurality of high-resolution medical images obtained from a plurality of other subjects, wherein the high-resolution medical image comprises a higher image resolution than the low-resolution medical image, and wherein the high-resolution medical image comprises lesser calcium blooming artifacts than the low-resolution medical image, wherein the computer system comprises a computer processor and an electronic storage medium.

Embodiment 2: The computer-implemented method of Embodiment 1, further comprising generating, by the computer system, a weighted measure of the generated one or more plaque parameters and the generated one or more vascular parameters, wherein the weighted measure is inputted into the machine learning algorithm to convert the low-resolution medical image into the high-resolution medical image.

Embodiment 3: The computer-implemented method of Embodiment 1, wherein the plurality of high-resolution medical images obtained from the plurality of other subjects comprises images obtained using intravascular ultrasound (IVUS).

Embodiment 4: The computer-implemented method of Embodiment 1, wherein the plurality of high-resolution medical images obtained from the plurality of other subjects comprises images obtained using optical coherence tomography (OCT) intravascular imaging.

Embodiment 5: The computer-implemented method of Embodiment 1, wherein the one or more artery vessels comprises one or more coronary arteries.

Embodiment 6: The computer-implemented method of Embodiment 1, wherein the one or more artery vessels comprises one or more carotid arteries, aorta, upper extremity arteries, or lower extremity arteries.

Embodiment 7: The computer-implemented method of Embodiment 1, wherein the low-resolution medical image comprises a coronary computed tomography angiography (CCTA) image.

Embodiment 8: The computer-implemented method of Embodiment 1, wherein the low-resolution medical image comprises a computed tomography (CT) image.

Embodiment 9: The computer-implemented method of Embodiment 1, wherein the low-resolution medical image comprises a medical image obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 10: The computer-implemented method of Embodiment 1, wherein the one or more plaque parameters further comprises one or more of plaque slice percentage, eccentricity of plaque, presence of low-density non-calcified plaque, presence of non-calcified plaque, or presence of calcified plaque.

Embodiment 11: The computer-implemented method of Embodiment 1, wherein the one or more vascular parameters further comprises one or more of lesion length, presence of positive remodeling, reference diameter after stenosis, reference diameter before stenosis, vessel length, vessel volume, number of stenosis, or number of mild stenosis.

Embodiment 12: The computer-implemented method of Embodiment 1, wherein the one or more plaque parameters further comprises one or more of plaque area, plaque burden, necrotic core percentage, necrotic core volume, fatty fibrous volume, fatty fibrous percentage, dense calcium percentage, low-density calcium percentage, medium-density calcified percentage, high-density calcified percentage, presence of two-feature positive plaques, or number of two-feature positive plaques.

Embodiment 13: The computer-implemented method of Embodiment 1, wherein the one or more vascular parameters further comprises one or more of percent atheroma volume of total plaque, percent atheroma volume of low-density non-calcified plaque, percent atheroma volume of non-calcified plaque, percent atheroma volume of calcified plaque, number of high-risk plaque regions, number of segments with calcified plaque, number of segments with non-calcified plaque, segment length, severity of stenosis, minimum lumen diameter, maximum lumen diameter, mean lumen diameter, number of moderate stenosis, number of zero stenosis, number of severe stenosis, presence of high-risk anatomy, number of severe stenosis excluding CTO, vessel area, lumen area, diameter stenosis percentage, presence of ischemia, number of stents, reference lumen diameter before stenosis, perivascular fat attenuation, or reference lumen diameter after stenosis.

Embodiment 14: The computer-implemented method of Embodiment 1, wherein low density non-calcified plaque comprises a region of plaque with a radiodensity value between about −189 and about 30 Hounsfield units.

Embodiment 15: The computer-implemented method of Embodiment 1, wherein non-calcified plaque comprises a region of plaque with a radiodensity value between about 30 and about 350 Hounsfield units.

Embodiment 16: The computer-implemented method of Embodiment 1, wherein calcified plaque comprises a region of plaque with a radiodensity value between about 351 and 2500 Hounsfield units.

Embodiment 17: A system for converting a low-resolution medical image of a subject to a high-resolution medical image based on one or more plaque parameters or vascular parameters, the system comprising: a non-transitory computer storage medium configured to at least store computer-executable instructions; and one or more computer hardware processors in communication with the first non-transitory computer storage medium, the one or more computer hardware processors configured to execute the computer-executable instructions to at least: access a low-resolution medical image of a subject, the low-resolution medical image comprising a portion of one or more arteries; analyze the medical image of the subject to identify one or more artery vessels and one or more regions of plaque within the one or more artery vessels; generate one or more plaque parameters based at least in part on analyzing the one or more regions of plaque, the one or more plaque parameters comprising one or more of volume of low-density non-calcified plaque, volume of non-calcified plaque, volume of calcified plaque, total plaque volume, plaque morphology, or embeddedness of a low density non-calcified plaque by non-calcified plaque or calcified plaque; generate one or more vascular parameters based at least in part on analyzing the one or more artery vessels, the one or more vascular parameters comprising one or more of remodeling index, stenosis area percentage, stenosis diameter percentage, lumen volume, number of chronic total occlusion (CTO), or distance between plaque and lumen wall or vessel wall; and convert the low-resolution medical image into a high-resolution medical image by inputting the generated one or more plaque parameters and the generated one or more vascular parameters into a machine learning algorithm, the machine learning algorithm trained based at least in part on the one or more plaque parameters and the one or more vascular parameters generated from a plurality of low-resolution medical images and the one or more plaque parameters and the one or more vascular parameters generated from a plurality of high-resolution medical images, the plurality of low-resolution medical images and the plurality of high-resolution medical images obtained from a plurality of other subjects, wherein the high-resolution medical image comprises a higher image resolution than the low-resolution medical image, and wherein the high-resolution medical image comprises lesser calcium blooming artifacts than the low-resolution medical image.

Embodiment 18: The system of Embodiment 17, wherein the one or more processors are further configured to generate a weighted measure of the generated one or more plaque parameters and the generated one or more vascular parameters, wherein the weighted measure is inputted into the machine learning algorithm to convert the low-resolution medical image into the high-resolution medical image.

Embodiment 19: The system of Embodiment 17, wherein the plurality of high-resolution medical images obtained from the plurality of other subjects comprises images obtained using intravascular ultrasound (IVUS).

Embodiment 20: The system of Embodiment 17, wherein the plurality of high-resolution medical images obtained from the plurality of other subjects comprises images obtained using optical coherence tomography (OCT) intravascular imaging.

Embodiment 21: The system of Embodiment 17, wherein the one or more artery vessels comprises one or more coronary arteries.

Embodiment 22: The system of Embodiment 17, wherein the one or more artery vessels comprises one or more carotid arteries, aorta, upper extremity arteries, or lower extremity arteries.

Embodiment 23: The system of Embodiment 17, wherein the low-resolution medical image comprises a coronary computed tomography angiography (CCTA) image.

Embodiment 24: The system of Embodiment 17, wherein the low-resolution medical image comprises a computed tomography (CT) image.

Embodiment 25: The system of Embodiment 17, wherein the low-resolution medical image comprises a medical image obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 26: The system of Embodiment 17, wherein the one or more plaque parameters further comprises one or more of plaque slice percentage, eccentricity of plaque, presence of low-density non-calcified plaque, presence of non-calcified plaque, or presence of calcified plaque.

Embodiment 27: The system of Embodiment 17, wherein the one or more vascular parameters further comprises one or more of lesion length, presence of positive remodeling, reference diameter after stenosis, reference diameter before stenosis, vessel length, vessel volume, number of stenosis, or number of mild stenosis.

Embodiment 28: The system of Embodiment 17, wherein the one or more plaque parameters further comprises one or more of plaque area, plaque burden, necrotic core percentage, necrotic core volume, fatty fibrous volume, fatty fibrous percentage, dense calcium percentage, low-density calcium percentage, medium-density calcified percentage, high-density calcified percentage, presence of two-feature positive plaques, or number of two-feature positive plaques.

Embodiment 29: The system of Embodiment 17, wherein the one or more vascular parameters further comprises one or more of percent atheroma volume of total plaque, percent atheroma volume of low-density non-calcified plaque, percent atheroma volume of non-calcified plaque, percent atheroma volume of calcified plaque, number of high-risk plaque regions, number of segments with calcified plaque, number of segments with non-calcified plaque, segment length, severity of stenosis, minimum lumen diameter, maximum lumen diameter, mean lumen diameter, number of moderate stenosis, number of zero stenosis, number of severe stenosis, presence of high-risk anatomy, number of severe stenosis excluding CTO, vessel area, lumen area, diameter stenosis percentage, presence of ischemia, number of stents, reference lumen diameter before stenosis, perivascular fat attenuation, or reference lumen diameter after stenosis.

Embodiment 30: The system of Embodiment 17, wherein low density non-calcified plaque comprises a region of plaque with a radiodensity value between about −189 and about 30 Hounsfield units.

Embodiment 31: The system of Embodiment 17, wherein non-calcified plaque comprises a region of plaque with a radiodensity value between about 30 and about 350 Hounsfield units.

Embodiment 32: The system of Embodiment 17, wherein calcified plaque comprises a region of plaque with a radiodensity value between about 351 and 2500 Hounsfield units.

Embodiment 33: A non-transitory computer readable medium configured for converting a low-resolution medical image of a subject to a high-resolution medical image based on one or more plaque parameters or vascular parameters, the computer readable medium having program instructions for causing a hardware processor to perform a method of: accessing a low-resolution medical image of a subject, the low-resolution medical image comprising a portion of one or more arteries; analyzing the medical image of the subject to identify one or more artery vessels and one or more regions of plaque within the one or more artery vessels; generating one or more plaque parameters based at least in part on analyzing the one or more regions of plaque, the one or more plaque parameters comprising one or more of volume of low-density non-calcified plaque, volume of non-calcified plaque, volume of calcified plaque, total plaque volume, plaque morphology, or embeddedness of a low density non-calcified plaque by non-calcified plaque or calcified plaque; generating one or more vascular parameters based at least in part on analyzing the one or more artery vessels, the one or more vascular parameters comprising one or more of remodeling index, stenosis area percentage, stenosis diameter percentage, lumen volume, number of chronic total occlusion (CTO), or distance between plaque and lumen wall or vessel wall; and converting the low-resolution medical image into a high-resolution medical image by inputting the generated one or more plaque parameters and the generated one or more vascular parameters into a machine learning algorithm, the machine learning algorithm trained based at least in part on the one or more plaque parameters and the one or more vascular parameters generated from a plurality of low-resolution medical images and the one or more plaque parameters and the one or more vascular parameters generated from a plurality of high-resolution medical images, the plurality of low-resolution medical images and the plurality of high-resolution medical images obtained from a plurality of other subjects, wherein the high-resolution medical image comprises a higher image resolution than the low-resolution medical image, and wherein the high-resolution medical image comprises lesser calcium blooming artifacts than the low-resolution medical image.

Embodiment 34: The computer readable medium of Embodiment 33, wherein the method further comprises a weighted measure of the generated one or more plaque parameters and the generated one or more vascular parameters, wherein the weighted measure is inputted into the machine learning algorithm to convert the low-resolution medical image into the high-resolution medical image.

Embodiment 35: The computer readable medium of Embodiment 33, wherein the plurality of high-resolution medical images obtained from the plurality of other subjects comprises images obtained using intravascular ultrasound (IVUS).

Embodiment 36: The computer readable medium of Embodiment 33, wherein the plurality of high-resolution medical images obtained from the plurality of other subjects comprises images obtained using optical coherence tomography (OCT) intravascular imaging.

Embodiment 37: The computer readable medium of Embodiment 33, wherein the one or more artery vessels comprises one or more coronary arteries.

Embodiment 38: The computer readable medium of Embodiment 33, wherein the one or more artery vessels comprises one or more carotid arteries, aorta, upper extremity arteries, or lower extremity arteries.

Embodiment 39: The computer readable medium of Embodiment 33, wherein the low-resolution medical image comprises a coronary computed tomography angiography (CCTA) image.

Embodiment 40: The computer readable medium of Embodiment 33, wherein the low-resolution medical image comprises a computed tomography (CT) image.

Embodiment 41: The computer readable medium of Embodiment 33, wherein the low-resolution medical image comprises a medical image obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 42: The computer readable medium of Embodiment 33, wherein the one or more plaque parameters further comprises one or more of plaque slice percentage, eccentricity of plaque, presence of low-density non-calcified plaque, presence of non-calcified plaque, or presence of calcified plaque.

Embodiment 43: The computer readable medium of Embodiment 33, wherein the one or more vascular parameters further comprises one or more of lesion length, presence of positive remodeling, reference diameter after stenosis, reference diameter before stenosis, vessel length, vessel volume, number of stenosis, or number of mild stenosis.

Embodiment 44: The computer readable medium of Embodiment 33, wherein the one or more plaque parameters further comprises one or more of plaque area, plaque burden, necrotic core percentage, necrotic core volume, fatty fibrous volume, fatty fibrous percentage, dense calcium percentage, low-density calcium percentage, medium-density calcified percentage, high-density calcified percentage, presence of two-feature positive plaques, or number of two-feature positive plaques.

Embodiment 45: The computer readable medium of Embodiment 33, wherein the one or more vascular parameters further comprises one or more of percent atheroma volume of total plaque, percent atheroma volume of low-density non-calcified plaque, percent atheroma volume of non-calcified plaque, percent atheroma volume of calcified plaque, number of high-risk plaque regions, number of segments with calcified plaque, number of segments with non-calcified plaque, segment length, severity of stenosis, minimum lumen diameter, maximum lumen diameter, mean lumen diameter, number of moderate stenosis, number of zero stenosis, number of severe stenosis, presence of high-risk anatomy, number of severe stenosis excluding CTO, vessel area, lumen area, diameter stenosis percentage, presence of ischemia, number of stents, reference lumen diameter before stenosis, perivascular fat attenuation, or reference lumen diameter after stenosis.

Embodiment 46: The computer readable medium of Embodiment 33, wherein low density non-calcified plaque comprises a region of plaque with a radiodensity value between about −189 and about 30 Hounsfield units.

Embodiment 47: The computer readable medium of Embodiment 33, wherein non-calcified plaque comprises a region of plaque with a radiodensity value between about 30 and about 350 Hounsfield units.

Embodiment 48: The computer readable medium of Embodiment 33, wherein calcified plaque comprises a region of plaque with a radiodensity value between about 351 and 2500 Hounsfield units.

Image-Based Analysis and/or Tracking of Plaque Progression

Disclosed herein are systems, devices, and methods for image-based analysis and/or tracking of plaque progression. In particular, in some embodiments, the systems, devices, and methods can be configured to generate a representation of plaque progression within a vessel or vessels in order to facilitate tracking of progression of a disease, such as coronary artery disease. This can allow medical providers and patients a way to visualize the progression of a disease in order to facilitate treatment and/or determine treatment efficacy. For example, a first medical image of a patient taken at a first point in time can provide a baseline. The first medical image can show, for example, one or more vessels of the patient as well as one or more regions of plaque associated with the vessels. In some embodiments, the first medical image may have been analyzed using an image-based analysis to identify and/or quantify plaque or other factors associated with arterial disease. A second medical image of the patient taken at a second point in time, later than the first point in time, can be obtained and analyzed to identify and/or quantify plaque or other factors associated with arterial disease in the second image.

The systems, devices, and methods can then be configured to determine differences in the plaque or other disease parameters between the two medical images. For example, plaque only present in the second image (e.g., plaque that has developed since the first image was captured) can be identified and/or plaque only identified in the first image (e.g., representing plaque that has been reduced since the first image was obtained) can be identified. A graphical representation of the change can be generated and/or displayed as a way to visually represent the plaque progression of the patient. In some embodiments, one or more colors may be assigned to the changes in order to visually depict them.

In some embodiments, the systems, devices, and methods can be configured to classify the type of plaque in the first and second images, such as, for example, low-density non-calcified plaque, non-calcified plaque, or calcified plaque. The systems, devices, and methods can be configured to determine changes in the classification of plaque between the first and second medical images and to generate and/or display a visual representation of the changes.

Such systems, devices, and methods can be useful in allowing doctors and/or patients to better understand the progression of coronary artery disease, for example, by allowing for visualization of an increasing severity of the disease and/or allowing visualization of the efficacy of a treatment of the disease.

Various embodiments described herein relate to systems, devices, and methods for image-based analysis and/or tracking of plaque progression to facilitate training a user to identify arterial plaque on a medical image. In particular, some embodiments, of the systems, devices, and methods described herein can be used to train and/or evaluate the efficacy of a user in visually analyzing a medical image to identify arterial plaque therein. This can be an aid to doctors or other medical professionals who regularly review medical images to identify plaque therein. For example, in some embodiments of the systems, devices, and methods described herein, a user may annotate a medical image of a subject by, for example, indicating which portions of the image represent plaque. A prestored annotated version of the medical can then be compared with the user-annotated version. Differences between the user-annotated can be identified and graphical representations of the differences can be generated and/or displayed. For example, plaque that was not identified by the user can be highlighted or otherwise indicated and/or portions of the image that the user identified as plaque that do not represent plaque can be highlighted or otherwise indicated.

Such systems, devices, and methods can be useful in training users in correctly identifying plaque in medical images and/or evaluating the efficacy of users that regularly identify plaque in medical images.

As discussed herein, disclosed herein are systems, devices, and methods for image-based analysis and/or tracking of plaque progression. In particular, in some embodiments, the systems, devices, and methods can be configured to generate a representation of plaque progression within a vessel or vessels in order to facilitate tracking of progression of a disease, such as coronary artery disease. This can allow medical providers and patients a way to visualize the progression of a disease in order to facilitate treatment and/or determine treatment efficacy. For example, a first medical image of a patient taken at a first point in time can provide a baseline. The first medical image can show, for example, one or more vessels of the patient as well as one or more regions of plaque associated with the vessels. In some embodiments, the first medical image may have been analyzed using an image-based analysis to identify and/or quantify plaque or other factors associated with arterial disease. A second medical image of the patient taken at a second point in time, later than the first point in time, can be obtained and analyzed to identify and/or quantify plaque or other factors associated with arterial disease in the second image.

The systems, devices, and methods can then be configured to determine differences in the plaque or other disease parameters between the two medical images. For example, plaque only present in the second image (e.g., plaque that has developed since the first image was captured) can be identified and/or plaque only identified in the first image (e.g., representing plaque that has been reduced since the first image was obtained) can be identified. A graphical representation of the change can be generated and/or displayed as a way to visually represent the plaque progression of the patient. In some embodiments, one or more colors may be assigned to the changes in order to visually depict them.

In some embodiments, the systems, devices, and methods can be configured to classify the type of plaque in the first and second images, such as, for example, low-density non-calcified plaque, non-calcified plaque, or calcified plaque. The systems, devices, and methods can be configured to determine changes in the classification of plaque between the first and second medical images and to generate and/or display a visual representation of the changes.

Such systems, devices, and methods can be useful in allowing doctors and/or patients to better understand the progression of coronary artery disease, for example, by allowing for visualization of an increasing severity of the disease and/or allowing visualization of the efficacy of a treatment of the disease.

In some embodiments, the systems, devices, and methods can determine, based on a mapping between first and second medical images, a first subset of one or more regions of plaque that are present only in the second image. These can represent new or developing plaque. The systems, devices, and methods can, in the graphical representation, assign a first color to this first subset to visually distinguish it from other portions of the image. For example, this can be used to highlight new and/or worsening plaque. While color is described other graphical methods for annotating the first subset can also be used.

In some embodiments, the systems, devices, and methods can determine, based on a mapping between first and second medical images, a second subset of one or more regions of plaque that are present in both the first and in the second image. These can represent plaque that is unchanged between the two images. The systems, devices, and methods can, in the graphical representation, assign a second color to this second subset to visually distinguish it from other portions of the image. While color is described other graphical methods for annotating the second subset can also be used. In some embodiments, the second subset of plaque can be graphically removed in the first and/or second image.

In some embodiments, the systems, devices, and methods can be configured to classify regions of plaque in the first and/or second medical images. In some embodiments, the systems, devices, and methods can determine, based on a mapping between first and second medical images and the classifications, a third subset of one or more regions of plaque that are different between the first and second images. These can represent new or developing plaque. The systems, devices, and methods can, in the graphical representation, assign a third color to this third subset to visually distinguish it from other portions of the image. For example, this can be used to highlight changing plaque (e.g., plaque changing from a good plaque to a bad plaque or plaque changing from a bad plaque to a good plaque). While color is described other graphical methods for annotating the third subset can also be used.

In some embodiments, the systems, devices, and methods can determine, based on a mapping between first and second medical images and the classifications, a fourth subset of one or more regions of plaque that are the same in the first and second images. These can represent new or developing plaque. The systems, devices, and methods can, in the graphical representation, assign a fourth color to this fourth subset to visually distinguish it from other portions of the image. For example, this can be used to highlight unchanged plaque. While color is described other graphical methods for annotating the fourth subset can also be used. In some embodiments, the systems, devices, and methods can be configured to graphically remove the fourth subset from the first and/or second images.

Figure 16:
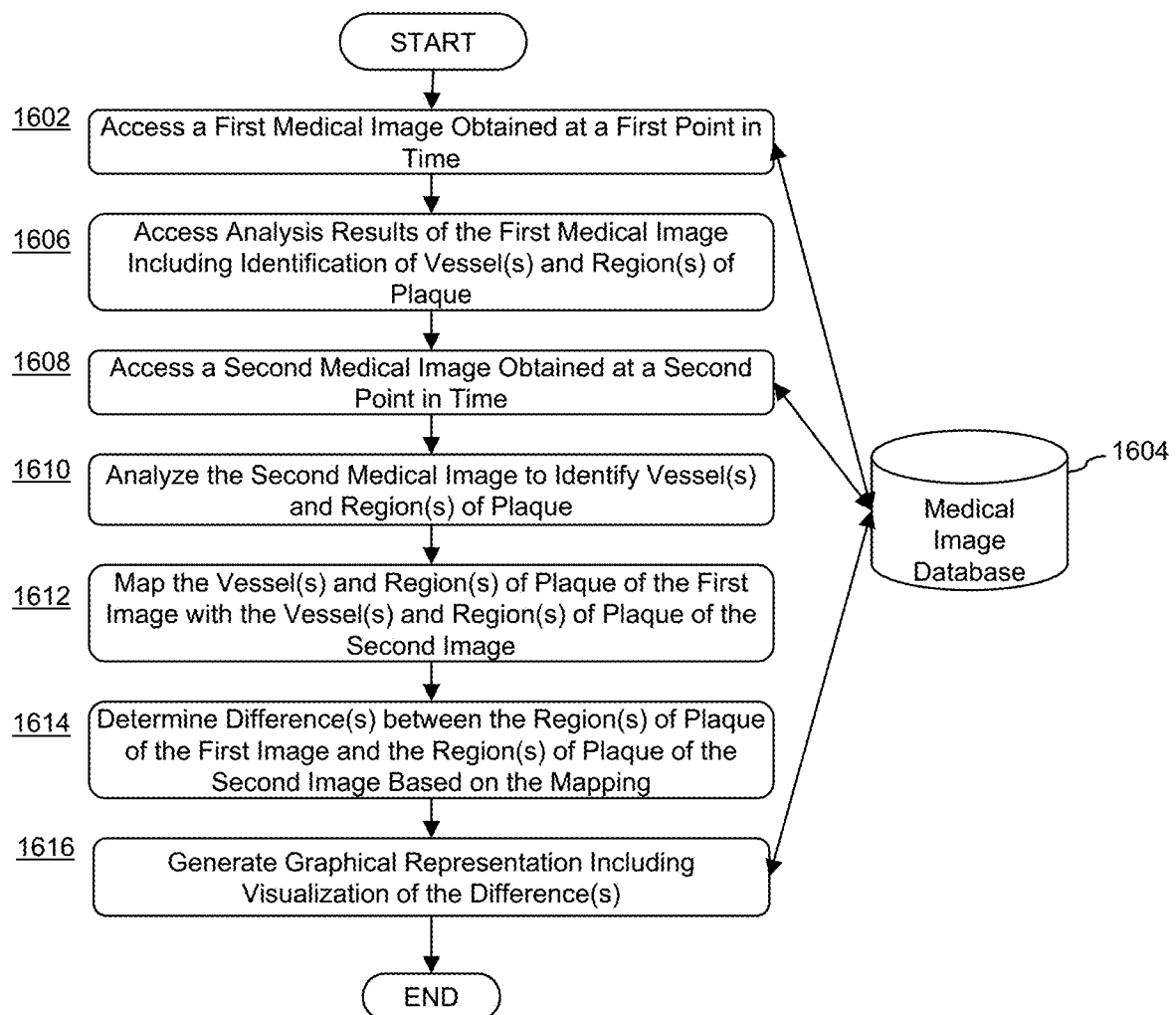
FIG. 16 is a flowchart illustrating an example embodiment(s) of systems, devices, and methods for image-based analysis and/or tracking of plaque progression.

FIG. 16 is a flowchart illustrating an example embodiment(s) of systems, devices, and methods for image-based analysis and tracking of plaque progression. As illustrated in FIG. 16, at block 1602, the system can be configured to access a first medical image obtained at a first point in time. For example, in some embodiments, the first medical image can be an image of a subject and can include a region of one or more vessels (e.g., arteries) of the subject and one or more regions of plaque captured at the first point in time. In some embodiments, the first medical image can include one or more arteries, such as coronary, carotid, and/or other arteries of a subject. In some embodiments, the medical image can be stored in a medical image database 1604. In some embodiments, the medical image database 1604 can be locally accessible by the system and/or can be located remotely and accessible through a network connection. The medical image can comprise an image obtain using one or more modalities such as for example, CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the medical image comprises one or more of a contrast-enhanced CT image, non-contrast CT image, MR image, and/or an image obtained using any of the modalities described above.

At block 1606, the system can be configured to access analysis results of the first medical image, including identification of vessels and regions of plaque in the first medical image. In some embodiments, the analysis has been performed previously. In some embodiments, the system can be configured to perform the analysis on the first medical image to identify vessels and regions of plaque in the first medical image.

In some embodiments, the analysis results of the first medical image further includes classification of the one or more regions of plaque identified in the first medical image. The classification of the one or more regions of plaque identified in the first medical image can be based at least in part on density. In some embodiments, the density comprises material density. In some embodiments, the density comprises radiodensity. The classification of the one or more regions of plaque in the first medical image can include classification of the one or more regions of plaque as one or more of low-density non-calcified plaque, non-calcified plaque, or calcified plaque. In some embodiments, low density non-calcified plaque corresponds to one or more regions of plaque comprising one or more pixels with a radiodensity value between about −189 and about 30 Hounsfield units, wherein non-calcified plaque corresponds to one or more regions of plaque comprising one or more pixels with a radiodensity value between about 190 and about 350 Hounsfield units, and wherein calcified plaque corresponds to one or more regions of plaque comprising one or more pixels with a radiodensity value between about 351 and 2500 Hounsfield units.

At block 1608, the system can be configured to access a second medical image obtained at a second point in time. For example, the second medical image can be an image of the subject obtained at a second point in time and can include the region of the one or more arteries of the subject and the one or more regions of plaque captured at the second point in time. The second point in time can be later in time than the first point in time. In some embodiments, the second medical image can include one or more arteries, such as coronary, carotid, and/or other arteries of a subject. In some embodiments, the medical image can be stored in a medical image database 1604. In some embodiments, the medical image database 1604 can be locally accessible by the system and/or can be located remotely and accessible through a network connection. The medical image can comprise an image obtain using one or more modalities such as for example, CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the medical image comprises one or more of a contrast-enhanced CT image, non-contrast CT image, MR image, and/or an image obtained using any of the modalities described above.

At block 1610, the system can be configured to analyze the second medical image to identify vessels and regions of plaque therein. In some embodiments, the analysis of the second medical image further includes classification of the one or more regions of plaque identified in the first medical image. The classification of the one or more regions of plaque identified in the first medical image can be based at least in part on density. In some embodiments, the density comprises material density. In some embodiments, the density comprises radiodensity. The classification of the one or more regions of plaque in the first medical image can include classification of the one or more regions of plaque as one or more of low-density non-calcified plaque, non-calcified plaque, or calcified plaque. In some embodiments, low density non-calcified plaque corresponds to one or more regions of plaque comprising one or more pixels with a radiodensity value between about −189 and about 30 Hounsfield units, wherein non-calcified plaque corresponds to one or more regions of plaque comprising one or more pixels with a radiodensity value between about 190 and about 350 Hounsfield units, and wherein calcified plaque corresponds to one or more regions of plaque comprising one or more pixels with a radiodensity value between about 351 and 2500 Hounsfield units.

In some embodiments, the system can be configured to automatically and/or dynamically perform one or more analyses of the medical image as discussed herein. For example, in some embodiments, at block 1610, the system can be configured to identify one or more vessels, such as of one or more arteries. The one or more arteries can include coronary arteries, carotid arteries, aorta, renal artery, lower extremity artery, upper extremity artery, and/or cerebral artery, amongst others. In some embodiments, the system can be configured to utilize one or more AI and/or ML algorithms to automatically and/or dynamically identify one or more arteries or coronary arteries using image processing. For example, in some embodiments, the one or more AI and/or ML algorithms can be trained using a Convolutional Neural Network (CNN) on a set of medical images on which arteries or coronary arteries have been identified, thereby allowing the AI and/or ML algorithm automatically identify arteries or coronary arteries directly from a medical image. In some embodiments, the arteries or coronary arteries are identified by size and/or location.

In some embodiments, at block 1610, the system can be configured to identify one or more regions of plaque in the medical image. In some embodiments, the system can be configured to utilize one or more AI and/or ML algorithms to automatically and/or dynamically identify one or more regions of plaque using image processing. For example, in some embodiments, the one or more AI and/or ML algorithms can be trained using a Convolutional Neural Network (CNN) on a set of medical images on which regions of plaque have been identified, thereby allowing the AI and/or ML algorithm automatically identify regions of plaque directly from a medical image. In some embodiments, the system is configured to identify vessel and lumen walls and classify everything in between the vessel and lumen walls as plaque.

In some embodiments, at block 1610, the system can be configured to analyze and/or characterize one or more regions of plaque based on density. For example, in some embodiments, the system can be configured to analyze and/or characterize one or more regions of plaque based on absolute density and/or relative density and/or radiodensity. In some embodiments, the system can be configured to classify a region of plaque as one of low density non-calcified plaque, non-calcified plaque, and calcified plaque, using any one or more processes and/or features described herein.

In some embodiments, at block 1610, the system can be configured to analyze and/or characterize one or more regions of plaque based on one or more distances. For example, as described herein, in some embodiments, the system can be configured to determine a distance between a low density non-calcified plaque and lumen wall and/or vessel wall. In some embodiments, proximity of a low density non-calcified plaque to the lumen wall can be indicative of a high-risk plaque and/or CAD. Conversely, in some embodiments, a position of a low density non-calcified plaque far from the lumen wall can be indicative of less risk. In some embodiments, the system can be configured to utilize one or more predetermined thresholds in determining the risk factor associated with the proximity of low density non-calcified plaque with the vessel wall and/or lumen wall. In some embodiments, the system can be configured to utilize one or more image processing algorithms to automatically and/or dynamically determine one or more distances to and/or from one or more regions of plaque.

In some embodiments, at block 1610, the system can be configured to analyze and/or characterize one or more regions of plaque based on morphology or shape and/or one or more axes measurements of low density non-calcified plaque. As described herein, in some embodiments, the system can be configured to determine the length of one or more axes of a low density non-calcified plaque, such as for example a major axis of a longitudinal cross section and/or a major and/or minor axis of a latitudinal cross section of a low density non-calcified plaque. In some embodiments, the system can be configured to utilize the one more axes measurements to determine a morphology and/or shape of a low density non-calcified plaque. In some embodiments, the system can be configured to utilize one or more image processing algorithms to automatically and/or dynamically determine one or more axes measurements of one or more regions of plaque.

In some embodiments, the system can be configured to utilize one or more AI and/or ML algorithms to automatically and/or dynamically classify the shape of one or more regions of plaque using image processing. For example, in some embodiments, the one or more AI and/or ML algorithms can be trained using a Convolutional Neural Network (CNN) on a set of medical images on which the shape of regions of plaque have been identified, thereby allowing the AI and/or ML algorithm automatically identify the shape or morphology of a region of plaque directly from a medical image. In some embodiments, the system can be configured to classify the shape or morphology of a region of plaque as one or more of crescent, lobular, round, or bean-shaped.

In some embodiments, at block 1610, the system can be configured to analyze and/or characterize one or more regions of plaque based on one or more sizes and/or volumes. For example, in some embodiments, the system can be configured to determine a size and/or volume of plaque based at least in part on one or more axes measurements described herein. In some embodiments, the system can be configured to determine the size and/or volume of a region of plaque directly from analysis of a three-dimensional image scan. In some embodiments, the system can be configured to determine the size and/or volume of total plaque, low-density non-calcified plaque, non-calcified plaque, calcified plaque, and/or a ratio between two of the aforementioned volumes or sizes. In some embodiments, a high total plaque volume and/or high low-density non-calcified plaque and/or non-calcified plaque volume can be associated with high risk of CAD. In some embodiments, a high ratio of low-density non-calcified plaque volume to total plaque volume and/or a high ratio of non-calcified plaque volume to total plaque volume can be associated with high risk of CAD. In some embodiments, a high calcified plaque volume and/or high ratio of calcified plaque volume to total plaque volume can be associated with low risk of CAD. In some embodiments, the system can be configured to utilize one or more predetermined threshold values for determining the risk of CAD based on plaque volume, size, or one or more ratios thereof. In some embodiments, the system can be configured to utilize one or more image processing algorithms to automatically and/or dynamically determine the size and/or volume of one or more regions of plaque.

In some embodiments, at block 1610, the system can be configured to analyze and/or characterize plaque based on embeddedness. For example, in some embodiments, the system can be configured to determined how embedded or surrounded a low density non-calcified plaque is by non-calcified plaque or calcified plaque. In some embodiments, the system can be configured to analyze the embeddedness of low density non-calcified plaque based on the degree by which it is surrounded by other types of plaque. In some embodiments, a higher embeddedness of a low density non-calcified plaque can be indicative of high risk of CAD. For example, in some embodiments, a low density non-calcified plaque that is surrounded by 270 degrees or more by non-calcified plaque can be associated with high risk of CAD. In some embodiments, the system can be configured to utilize one or more image processing algorithms to automatically and/or dynamically determine the embeddedness of one or more regions of plaque.

At block 1612, the system can be configured to map the vessels and regions of plaque of the first medical image with the vessels and regions of plaque with the second medical image. For example, the mapping can include overlaying the first medical image on the second medical image or overlaying the second medical image on the first medical image.

In some embodiments that include classification of the plaque in the first and second medical image, the system can further be configured to analyze the second medical image to classify the one or more regions of plaque identified in the second medical image, and map the classification of the one or more regions of plaque in the first medical image with the classification of the one or more regions of plaque identified in the second medical image.

At block 1614, the system can be configured to determine differences between the regions of plaque of the first medical image and the regions of plaque of the second medical image. In some embodiments, the differences can be determined based on the mapping of block 1612.

For example, in some embodiments, the system can be configured to determine first subset of the one or more regions of plaque in the second medical image, wherein the first subset of the one or more regions of plaque are present only in the second medical image and not in the first medical image based at least in part on the mapping.

In some embodiments, the system can be configured to determine a second subset of the one or more regions of plaque in the second medical image, the second subset of the one or more regions of plaque present in both the first medical image and the second medical image based at least in part on the mapping.

In some embodiments, the system can further be configured to determine a third subset of the one or more regions of plaque in the second medical image, the third subset of the one or more regions of plaque comprising a different classification between the first medical image and the second medical image, In some embodiments, the system can be configured to determine a fourth subset of the one or more regions of plaque in the second medical image, the fourth subset of the one or more regions of plaque comprising a same classification between the first medical image and the second medical image.

At block 1616, the system can be configured to generate a graphical representation including a visualization of the differences determined at block 1614. For example, the system can be configured to generate a graphical representation of arterial plaque progression of the subject, wherein generating the graphical representation comprises assigning a first color to the first subset of the one or more regions of plaque, and wherein the graphical representation of arterial plaque progression in the subject is configured to facilitate tracking of progression of arterial disease for the subject.

In some embodiments, the system can be configured to generate the graphical representation of arterial plaque progression of the subject by further assigning a second color to the second subset of the one or more regions of plaque in the second medical image. In some embodiments, the system can be configured to graphically remove the second subset of the one or more regions of plaque in the second medical image.

In some embodiments, the system can be configured to generate the graphical representation of arterial plaque progression of the subject further by assigning a third color to the third subject of the one or more regions of plaque.

In some embodiments, the system can be configured to generate the graphical representation of arterial plaque progression of the subject further by assigning a fourth color to the third subject of the one or more regions of plaque. In some embodiments, the system can be configured to graphically remove the fourth subset of the one or more regions of plaque in the second medical image.

In some embodiments, the system can be configured to repeat one or more processes described in relation to blocks 1602-1616, for example for one or more other vessels, segments, regions of plaque, different subjects, and/or for the same subject at a different time. As such, in some embodiments, the system can provide for longitudinal disease tracking and/or personalized treatment for a subject.

As discussed herein, disclosed herein are systems, devices, and methods for image-based analysis and/or tracking of plaque progression to facilitate training a user to identify arterial plaque on a medical image. In particular, some embodiments, of the systems, devices, and methods described herein can be used to train and/or evaluate the efficacy of a user in visually analyzing a medical image to identify arterial plaque therein. This can be an aid to doctors or other medical professionals who regularly review medical images to identify plaque therein. For example, in some embodiments of the systems, devices, and methods described herein, a user may annotate a medical image of a subject by, for example, indicating which portions of the image represent plaque. A prestored annotated version of the medical can then be compared with the user-annotated version. Differences between the user-annotated can be identified and graphical representations of the differences can be generated and/or displayed. For example, plaque that was not identified by the user can be highlighted or otherwise indicated and/or portions of the image that the user identified as plaque that do not represent plaque can be highlighted or otherwise indicated.

Such systems, devices, and methods can be useful in training users in correctly identifying plaque in medical images and/or evaluating the efficacy of users that regularly identify plaque in medical images.

In some embodiments, the user-annotated medical image can be graphically overlayed onto the prestored annotated medical image. A first subset of the one or more user annotations absent in the prestored medical image can be identified. A first color can be assigned to the first subset. This can visually depict plaques that the user failed to identify in the image. While color is described, other mechanisms for visually distinguishing the first subset can be used.

In some embodiments, a second subset of the user annotations present in the prestored image can be identified. A second color can be assigned to the second subset. This can visually depict plaques that the user correctly identified in the image. While color is described, other mechanisms for visually distinguishing the second subset can be used.

In some embodiments, the prestored annotated medical image can be graphically overlayed onto the user-annotated medical image. A first subset of the one or more user annotations absent in the user-annotated medical image can be identified. A first color can be assigned to the first subset. This can visually depict plaques that the user identified in the image that are not actually plaque. While color is described, other mechanisms for visually distinguishing the first subset can be used.

In some embodiments, a second subset of the user annotations present in the user-annotated image can be identified.

A second color can be assigned to the second subset. This can visually depict plaques that the user correctly identified in the image. While color is described, other mechanisms for visually distinguishing the second subset can be used.

In some embodiments, a read score for the user can be generated representative of how well the user correctly visually analyzed plaques in the medical image.

Figure 17:
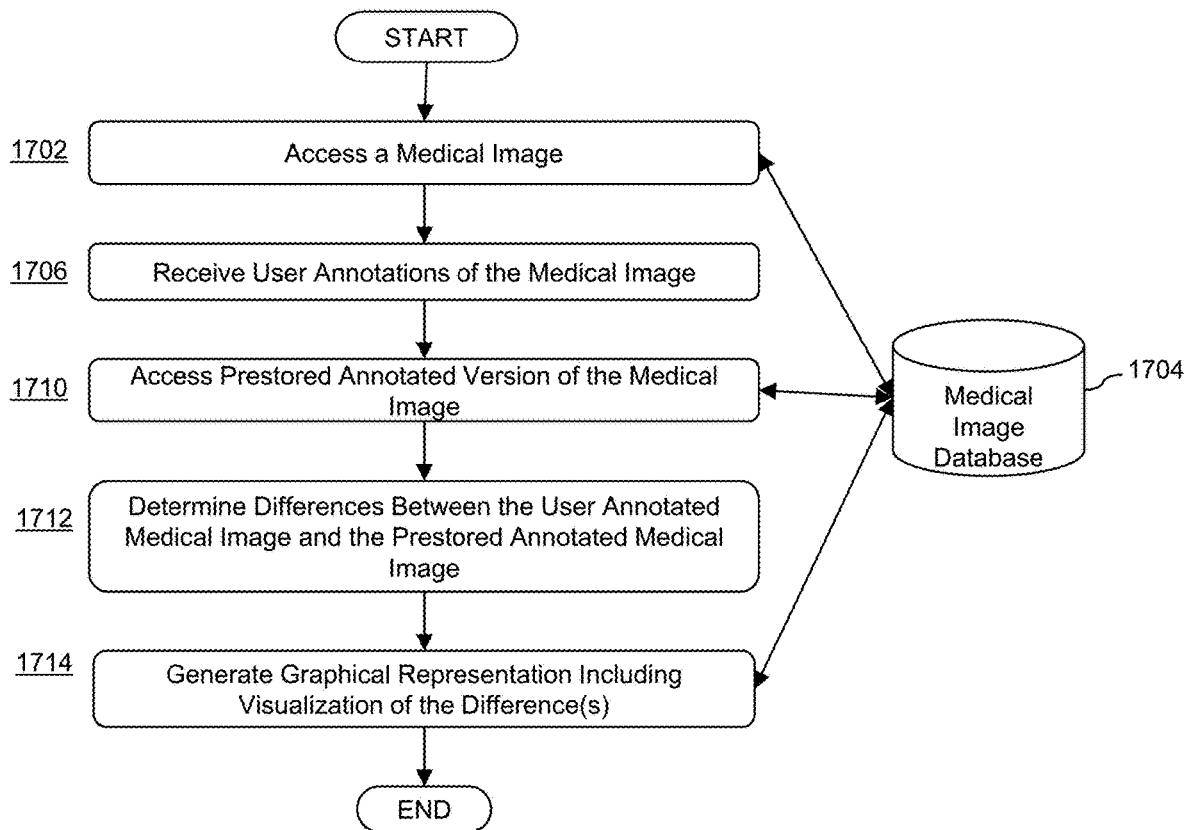
FIG. 17 is a flowchart illustrating an example embodiment(s) of systems, devices, and methods for image-based analysis and/or plaque identification user training.

As discussed herein, systems, methods, and devise for plaque identification user training are described herein. An example of a system is shown in FIG. 17. At block 1702, the system can be configured to access a medical image from a medical image database 1704. For example, the medical image can be a medical image of the subject and can include one or more regions of arterial plaque.

At block 1706, the system can be configured to receive user annotations of the medical image (i.e., a user-annotated medical image). The user annotations can comprise identifications of the one or more regions of plaque.

At block 1710, the system can be configured to access a prestored annotated version of the medical image. The prestored annotated version of the medical image may previously have been annotated by an expert or by a computer system.

At block 1712, the system can be configured to determine differences between the user annotated medical image (block 1706) and the prestored annotated medical image (block 1710). For example, the system can overlay the user annotated medical image onto the prestored annotated medical image and determine differences therebetween. Alternatively, the system can overlay the prestored annotated medical image onto the user annotated medical image and determine differences therebetween.

In some embodiments, the system can be configured to determine a first subset of the one or more user annotations of the medical image, the first subset of the one or more user annotations being absent in the prestored annotated version of the medical image. In some embodiments, the system can be configured to identify a second subset of the one or more user annotations of the medical image, the second subset of the one or more user annotations present in the prestored annotated version of the medical image At block 1714, the system can be configured to generate a graphical representation including visualization of the differences. For example, the system can be configured to graphically assign a first color to the first subset of the one or more user annotations of the medical image, wherein the graphically assigned first color is configured to facilitate training of the user to identify arterial plaque. In some embodiments, the system can be configured to graphically assign a second color to the second subset of the one or more user annotations of the medical image.

The computer system 902 of FIG. 9, and in some instances, the analysis and/or risk assessment module 940, can be configured to carry out the functions, methods, acts, and/or processes for image-based analysis and/or tracking of plaque progression described herein, such as those described above with reference to FIGS. 15 and 16.

The following are non-limiting examples of certain embodiments of systems and methods for image-based analysis and/or tracking of plaque progression. Other embodiments may include one or more other features, or different features, that are discussed herein.

Embodiment 1: A computer-implemented method of generating a graphical representation of arterial plaque progression to facilitate tracking of progression of arterial disease for a subject, the method comprising: accessing, by a computer system, a first medical image of a subject obtained at a first point in time, the first medical image comprising a region of one or more arteries of the subject and one or more regions of plaque captured at the first point in time; accessing, by the computer system, analysis results of the first medical image, the analysis results comprising identification of the region of the one or more arteries and the one or more regions of plaque in the first medical image; accessing, by the computer system, a second medical image of the subject obtained at a second point in time, the second medical image comprising the region of the one or more arteries of the subject and the one or more regions of plaque captured at the second point in time; analyzing, by the computer system, the second medical image to identify the region of the one or more arteries and the one or more regions of plaque; mapping, by the computer system, the region of the one or more arteries and the one or more regions of plaque in the first medical image with the region of the one or more arteries and the one or more regions of plaque in the second medical image; determining, by the computer system, a first subset of the one or more regions of plaque in the second medical image, the first subset of the one or more regions of plaque present only in the second medical image and not in the first medical image based at least in part on the mapping; and generating, by the computer system, a graphical representation of arterial plaque progression of the subject, wherein generating the graphical representation comprises assigning a first color to the first subset of the one or more regions of plaque, wherein the graphical representation of arterial plaque progression in the subject is configured to facilitate tracking of progression of arterial disease for the subject, wherein the computer system comprises a computer processor and an electronic storage medium.

Embodiment 2: The computer-implemented method of Embodiment 1, further comprising: determining, by the computer system, a second subset of the one or more regions of plaque in the second medical image, the second subset of the one or more regions of plaque present in both the first medical image and the second medical image based at least in part on the mapping.

Embodiment 3: The computer-implemented method of Embodiment 2, wherein generating the graphical representation of arterial plaque progression of the subject further comprises assigning a second color to the second subset of the one or more regions of plaque in the second medical image.

Embodiment 4: The computer-implemented method of Embodiment 2, further comprising: graphically removing, by the computer system, the second subset of the one or more regions of plaque in the second medical image.

Embodiment 5: The computer-implemented method of Embodiment 1, wherein the analysis results of the first medical image further comprises classification of the one or more regions of plaque identified in the first medical image.

Embodiment 6: The computer-implemented method of Embodiment 5, wherein classification of the one or more regions of plaque identified in the first medical image is based at least in part on density.

Embodiment 7: The computer-implemented method of Embodiment 6, wherein the density comprises material density.

Embodiment 8: The computer-implemented method of Embodiment 6, wherein the density comprises radiodensity.

Embodiment 9: The computer-implemented method of Embodiment 5, wherein the classification of the one or more regions of plaque in the first medical image comprises classification of the one or more regions of plaque as one or more of low-density non-calcified plaque, non-calcified plaque, or calcified plaque.

Embodiment 10: The computer-implemented method of Embodiment 9, wherein low density non-calcified plaque corresponds to one or more regions of plaque comprising one or more pixels with a radiodensity value between about −189 and about 30 Hounsfield units, wherein non-calcified plaque corresponds to one or more regions of plaque comprising one or more pixels with a radiodensity value between about 190 and about 350 Hounsfield units, and wherein calcified plaque corresponds to one or more regions of plaque comprising one or more pixels with a radiodensity value between about 351 and 2500 Hounsfield units.

Embodiment 11: The computer-implemented method of Embodiment 5, further comprising: analyzing, by the computer system, the second medical image to classify the one or more regions of plaque identified in the second medical image; and mapping, by the computer system, the classification of the one or more regions of plaque in the first medical image with the classification of the one or more regions of plaque identified in the second medical image.

Embodiment 12: The computer-implemented method of Embodiment 11, wherein classification of the one or more regions of plaque identified in the second medical image is based at least in part on density.

Embodiment 13: The computer-implemented method of Embodiment 12, wherein the density comprises material density.

Embodiment 14: The computer-implemented method of Embodiment 12, wherein the density comprises radiodensity.

Embodiment 15: The computer-implemented method of Embodiment 11, wherein the classification of the one or more regions of plaque in the second medical image comprises classification of the one or more regions of plaque as one or more of low-density non-calcified plaque, non-calcified plaque, or calcified plaque.

Embodiment 16: The computer-implemented method of Embodiment 15, wherein low density non-calcified plaque corresponds to one or more regions of plaque comprising one or more pixels with a radiodensity value between about −189 and about 30 Hounsfield units, wherein non-calcified plaque corresponds to one or more regions of plaque comprising one or more pixels with a radiodensity value between about 190 and about 350 Hounsfield units, and wherein calcified plaque corresponds to one or more regions of plaque comprising one or more pixels with a radiodensity value between about 351 and 2500 Hounsfield units.

Embodiment 17: The computer-implemented method of Embodiment 11, further comprising: determining, by the computer system, a third subset of the one or more regions of plaque in the second medical image, the third subset of the one or more regions of plaque comprising a different classification between the first medical image and the second medical image, wherein generating the graphical representation of arterial plaque progression of the subject further comprises assigning a third color to the third subject of the one or more regions of plaque.

Embodiment 18: The computer-implemented method of Embodiment 11, further comprising: determining, by the computer system, a fourth subset of the one or more regions of plaque in the second medical image, the fourth subset of the one or more regions of plaque comprising a same classification between the first medical image and the second medical image.

Embodiment 19: The computer-implemented method of Embodiment 18, wherein generating the graphical representation of arterial plaque progression of the subject further comprises assigning a fourth color to the third subject of the one or more regions of plaque.

Embodiment 20: The computer-implemented method of Embodiment 18, further comprising: graphically removing, by the computer system, the fourth subset of the one or more regions of plaque in the second medical image.

Embodiment 21: The computer-implemented method of Embodiment 1, wherein the one or more arteries comprises one or more coronary arteries.

Embodiment 22: The computer-implemented method of Embodiment 1, wherein the one or more arteries comprises one or more coronary arteries, carotid arteries, aorta, upper extremity arteries, or lower extremity arteries.

Embodiment 23: The computer-implemented method of Embodiment 1, wherein one or more of the first medical image or the second medical image is obtained using coronary computed tomography angiography (CCTA).

Embodiment 24: The computer-implemented method of Embodiment 1, wherein one or more of the first medical image or the second medical image is obtained using computed tomography (CT).

Embodiment 25: The computer-implemented method of Embodiment 1, wherein one or more of the first medical image or the second medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 26: A computer-implemented method of generating a graphical representation of arterial plaque progression to facilitate tracking of progression of arterial disease for a subject, the method comprising: accessing, by a computer system, a first medical image of a subject obtained at a first point in time, the first medical image comprising a region of one or more arteries of the subject and one or more regions of plaque captured at the first point in time; accessing, by the computer system, analysis results of the first medical image, the analysis results comprising identification of the region of the one or more arteries and the one or more regions of plaque in the first medical image; accessing, by the computer system, a second medical image of the subject obtained at a second point in time, the second medical image comprising the region of the one or more arteries of the subject and the one or more regions of plaque captured at the second point in time; analyzing, by the computer system, the second medical image to identify the region of the one or more arteries and the one or more regions of plaque; mapping, by the computer system, the region of the one or more arteries and the one or more regions of plaque in the first medical image with the region of the one or more arteries and the one or more regions of plaque in the second medical image; and generating, by the computer system, a graphical representation of arterial plaque progression of the subject, wherein generating the graphical representation comprises: generating an annotated version of the second medical image by graphically indicating the one or more regions of plaque identified in the second medical image; and graphically overlaying the one or more regions of plaque identified in the first medical image on the annotated version of the second medical image based at least in part on the mapping, wherein the graphical representation of arterial plaque progression in the subject is configured to facilitate tracking of progression of arterial disease for the subject, wherein the computer system comprises a computer processor and an electronic storage medium.

Embodiment 27: The computer-implemented method of Embodiment 26, wherein generating the graphical representation of arterial plaque progression of the subject further comprises: determining, by the computer system, a first subset of the one or more regions of plaque identified in the second medical image, the first subset of the one or more regions of plaque identified only in the second medical image and not in the first medical image; and graphically identifying, by the computer system, the first subset of the one or more regions of the plaque identified in the second medical image.

Embodiment 28: The computer-implemented method of Embodiment 27, further comprising assigning a first color to the first subset of the one or more regions of plaque identified in the second medical image.

Embodiment 29: The computer-implemented method of Embodiment 27, wherein generating the graphical representation of arterial plaque progression of the subject further comprises: determining, by the computer system, a second subset of the one or more regions of plaque identified in the second medical image, the second subset of the one or more regions of plaque identified in both the first medical image and the second medical image; and graphically identifying, by the computer system, the second subset of the one or more regions of the plaque identified in the second medical image.

Embodiment 30: The computer-implemented method of Embodiment 29, further comprising assigning a second color to the second subset of the one or more regions of plaque identified in the second medical image.

Embodiment 31: The computer-implemented method of Embodiment 29, further comprising graphically removing, by the computer system, the second subset of the one or more regions of plaque in the second medical image.

Embodiment 32: The computer-implemented method of Embodiment 26, wherein the analysis results of the first medical image further comprises classification of the one or more regions of plaque identified in the first medical image.

Embodiment 33: The computer-implemented method of Embodiment 32, wherein classification of the one or more regions of plaque identified in the first medical image is based at least in part on density.

Embodiment 34: The computer-implemented method of Embodiment 33, wherein the density comprises material density.

Embodiment 35: The computer-implemented method of Embodiment 33, wherein the density comprises radiodensity.

Embodiment 36: The computer-implemented method of Embodiment 32, wherein the classification of the one or more regions of plaque in the first medical image comprises classification of the one or more regions of plaque as one or more of low-density non-calcified plaque, non-calcified plaque, or calcified plaque.

Embodiment 37: The computer-implemented method of Embodiment 36, wherein low density non-calcified plaque corresponds to one or more regions of plaque comprising one or more pixels with a radiodensity value between about −189 and about 30 Hounsfield units, wherein non-calcified plaque corresponds to one or more regions of plaque comprising one or more pixels with a radiodensity value between about 190 and about 350 Hounsfield units, and wherein calcified plaque corresponds to one or more regions of plaque comprising one or more pixels with a radiodensity value between about 351 and 2500 Hounsfield units.

Embodiment 38: The computer-implemented method of Embodiment 32, further comprising: analyzing, by the computer system, the second medical image to classify the one or more regions of plaque identified in the second medical image; and mapping, by the computer system, the classification of the one or more regions of plaque in the first medical image with the classification of the one or more regions of plaque identified in the second medical image.

Embodiment 39: The computer-implemented method of Embodiment 38, wherein classification of the one or more regions of plaque identified in the second medical image is based at least in part on density.

Embodiment 40: The computer-implemented method of Embodiment 39, wherein the density comprises material density.

Embodiment 41: The computer-implemented method of Embodiment 39, wherein the density comprises radiodensity.

Embodiment 42: The computer-implemented method of Embodiment 38, wherein the classification of the one or more regions of plaque in the second medical image comprises classification of the one or more regions of plaque as one or more of low-density non-calcified plaque, non-calcified plaque, or calcified plaque.

Embodiment 43: The computer-implemented method of Embodiment 42, wherein low density non-calcified plaque corresponds to one or more regions of plaque comprising one or more pixels with a radiodensity value between about −189 and about 30 Hounsfield units, wherein non-calcified plaque corresponds to one or more regions of plaque comprising one or more pixels with a radiodensity value between about 190 and about 350 Hounsfield units, and wherein calcified plaque corresponds to one or more regions of plaque comprising one or more pixels with a radiodensity value between about 351 and 2500 Hounsfield units.

Embodiment 44: The computer-implemented method of Embodiment 38, further comprising: determining, by the computer system, a third subset of the one or more regions of plaque in the second medical image, the third subset of the one or more regions of plaque comprising a different classification between the first medical image and the second medical image, wherein generating the graphical representation of arterial plaque progression of the subject further comprises assigning a third color to the third subject of the one or more regions of plaque.

Embodiment 45: The computer-implemented method of Embodiment 38, further comprising: determining, by the computer system, a fourth subset of the one or more regions of plaque in the second medical image, the fourth subset of the one or more regions of plaque comprising a same classification between the first medical image and the second medical image.

Embodiment 46: The computer-implemented method of Embodiment 45, wherein generating the graphical representation of arterial plaque progression of the subject further comprises assigning a fourth color to the third subject of the one or more regions of plaque.

Embodiment 47: The computer-implemented method of Embodiment 45, further comprising: graphically removing, by the computer system, the fourth subset of the one or more regions of plaque in the second medical image.

Embodiment 48: The computer-implemented method of Embodiment 26, wherein the one or more arteries comprises one or more coronary arteries.

Embodiment 49: The computer-implemented method of Embodiment 26, wherein the one or more arteries comprises one or more coronary arteries, carotid arteries, aorta, upper extremity arteries, or lower extremity arteries.

Embodiment 50: The computer-implemented method of Embodiment 26, wherein one or more of the first medical image or the second medical image is obtained using coronary computed tomography angiography (CCTA).

Embodiment 51: The computer-implemented method of Embodiment 26, wherein one or more of the first medical image or the second medical image is obtained using computed tomography (CT).

Embodiment 52: The computer-implemented method of Embodiment 26, wherein one or more of the first medical image or the second medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 53: A system for generating a graphical representation of arterial plaque progression to facilitate tracking of progression of arterial disease for a subject, the system comprising: a non-transitory computer storage medium configured to at least store computer-executable instructions; and one or more computer hardware processors in communication with the first non-transitory computer storage medium, the one or more computer hardware processors configured to execute the computer-executable instructions to at least: access a first medical image of a subject obtained at a first point in time, the first medical image comprising a region of one or more arteries of the subject and one or more regions of plaque captured at the first point in time; access analysis results of the first medical image, the analysis results comprising identification of the region of the one or more arteries and the one or more regions of plaque in the first medical image; access a second medical image of the subject obtained at a second point in time, the second medical image comprising the region of the one or more arteries of the subject and the one or more regions of plaque captured at the second point in time; analyze the second medical image to identify the region of the one or more arteries and the one or more regions of plaque; map the region of the one or more arteries and the one or more regions of plaque in the first medical image with the region of the one or more arteries and the one or more regions of plaque in the second medical image; determine a first subset of the one or more regions of plaque in the second medical image, the first subset of the one or more regions of plaque present only in the second medical image and not in the first medical image based at least in part on the mapping; and generate a graphical representation of arterial plaque progression of the subject, wherein generating the graphical representation comprises assigning a first color to the first subset of the one or more regions of plaque, wherein the graphical representation of arterial plaque progression in the subject is configured to facilitate tracking of progression of arterial disease for the subject.

Embodiment 54: The system of Embodiment 53, wherein the processors are further configured to: determine a second subset of the one or more regions of plaque in the second medical image, the second subset of the one or more regions of plaque present in both the first medical image and the second medical image based at least in part on the mapping.

Embodiment 55: The system of Embodiment 54, wherein generating the graphical representation of arterial plaque progression of the subject further comprises assigning a second color to the second subset of the one or more regions of plaque in the second medical image.

Embodiment 56: The system of Embodiment 54, wherein the processors are further configured to: graphically remove the second subset of the one or more regions of plaque in the second medical image.

Embodiment 57: The system of Embodiment 53, wherein the analysis results of the first medical image further comprises classification of the one or more regions of plaque identified in the first medical image.

Embodiment 58: The system of Embodiment 57, wherein classification of the one or more regions of plaque identified in the first medical image is based at least in part on density.

Embodiment 59: The system of Embodiment 58, wherein the density comprises material density.

Embodiment 60: The system of Embodiment 58, wherein the density comprises radiodensity.

Embodiment 61: The system of Embodiment 57, wherein the classification of the one or more regions of plaque in the first medical image comprises classification of the one or more regions of plaque as one or more of low-density non-calcified plaque, non-calcified plaque, or calcified plaque.

Embodiment 62: The system of Embodiment 61, wherein low density non-calcified plaque corresponds to one or more regions of plaque comprising one or more pixels with a radiodensity value between about −189 and about 30 Hounsfield units, wherein non-calcified plaque corresponds to one or more regions of plaque comprising one or more pixels with a radiodensity value between about 190 and about 350 Hounsfield units, and wherein calcified plaque corresponds to one or more regions of plaque comprising one or more pixels with a radiodensity value between about 351 and 2500 Hounsfield units.

Embodiment 63: The system of Embodiment 57, wherein the processors are further configured to: analyze the second medical image to classify the one or more regions of plaque identified in the second medical image; and map the classification of the one or more regions of plaque in the first medical image with the classification of the one or more regions of plaque identified in the second medical image.

Embodiment 64: The system of Embodiment 63, wherein classification of the one or more regions of plaque identified in the second medical image is based at least in part on density.

Embodiment 65: The system of Embodiment 64, wherein the density comprises material density.

Embodiment 66: The system of Embodiment 64, wherein the density comprises radiodensity.

Embodiment 67: The system of Embodiment 63, wherein the classification of the one or more regions of plaque in the second medical image comprises classification of the one or more regions of plaque as one or more of low-density non-calcified plaque, non-calcified plaque, or calcified plaque.

Embodiment 68: The system of Embodiment 67, wherein low density non-calcified plaque corresponds to one or more regions of plaque comprising one or more pixels with a radiodensity value between about −189 and about 30 Hounsfield units, wherein non-calcified plaque corresponds to one or more regions of plaque comprising one or more pixels with a radiodensity value between about 190 and about 350 Hounsfield units, and wherein calcified plaque corresponds to one or more regions of plaque comprising one or more pixels with a radiodensity value between about 351 and 2500 Hounsfield units.

Embodiment 69: The system of Embodiment 63, wherein the processors are further configured to: determine a third subset of the one or more regions of plaque in the second medical image, the third subset of the one or more regions of plaque comprising a different classification between the first medical image and the second medical image, wherein generating the graphical representation of arterial plaque progression of the subject further comprises assigning a third color to the third subject of the one or more regions of plaque.

Embodiment 70: The system of Embodiment 63, wherein the processors are further configured to: determine a fourth subset of the one or more regions of plaque in the second medical image, the fourth subset of the one or more regions of plaque comprising a same classification between the first medical image and the second medical image.

Embodiment 71: The system of Embodiment 70, wherein generating the graphical representation of arterial plaque progression of the subject further comprises assigning a fourth color to the third subject of the one or more regions of plaque.

Embodiment 72: The system of Embodiment 70, wherein the processors are further configured to: graphically remove the fourth subset of the one or more regions of plaque in the second medical image.

Embodiment 73: The system of Embodiment 53, wherein the one or more arteries comprises one or more coronary arteries.

Embodiment 74: The system of Embodiment 53, wherein the one or more arteries comprises one or more coronary arteries, carotid arteries, aorta, upper extremity arteries, or lower extremity arteries.

Embodiment 75: The system of Embodiment 53, wherein one or more of the first medical image or the second medical image is obtained using coronary computed tomography angiography (CCTA).

Embodiment 76: The system of Embodiment 53, wherein one or more of the first medical image or the second medical image is obtained using computed tomography (CT).

Embodiment 77: The system of Embodiment 53, wherein one or more of the first medical image or the second medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 78: A system for generating a graphical representation of arterial plaque progression to facilitate tracking of progression of arterial disease for a subject, the system comprising: a non-transitory computer storage medium configured to at least store computer-executable instructions; and one or more computer hardware processors in communication with the first non-transitory computer storage medium, the one or more computer hardware processors configured to execute the computer-executable instructions to at least: access a first medical image of a subject obtained at a first point in time, the first medical image comprising a region of one or more arteries of the subject and one or more regions of plaque captured at the first point in time; access analysis results of the first medical image, the analysis results comprising identification of the region of the one or more arteries and the one or more regions of plaque in the first medical image; access a second medical image of the subject obtained at a second point in time, the second medical image comprising the region of the one or more arteries of the subject and the one or more regions of plaque captured at the second point in time; analyze the second medical image to identify the region of the one or more arteries and the one or more regions of plaque; map the region of the one or more arteries and the one or more regions of plaque in the first medical image with the region of the one or more arteries and the one or more regions of plaque in the second medical image; and generate a graphical representation of arterial plaque progression of the subject, wherein generating the graphical representation comprises: generating an annotated version of the second medical image by graphically indicating the one or more regions of plaque identified in the second medical image; and graphically overlaying the one or more regions of plaque identified in the first medical image on the annotated version of the second medical image based at least in part on the mapping, wherein the graphical representation of arterial plaque progression in the subject is configured to facilitate tracking of progression of arterial disease for the subject.

Embodiment 79: The system of Embodiment 78, wherein generating the graphical representation of arterial plaque progression of the subject further comprises: determining, by the computer system, a first subset of the one or more regions of plaque identified in the second medical image, the first subset of the one or more regions of plaque identified only in the second medical image and not in the first medical image; and graphically identifying, by the computer system, the first subset of the one or more regions of the plaque identified in the second medical image.

Embodiment 80: The system of Embodiment 79, wherein the processors are further configured to assign a first color to the first subset of the one or more regions of plaque identified in the second medical image.

Embodiment 81: The system of Embodiment 79, wherein generating the graphical representation of arterial plaque progression of the subject further comprises:
determining, by the computer system, a second subset of the one or more regions of plaque identified in the second medical image, the second subset of the one or more regions of plaque identified in both the first medical image and the second medical image; and
graphically identifying, by the computer system, the second subset of the one or more regions of the plaque identified in the second medical image.

Embodiment 82: The system of Embodiment 81, wherein the processors are further configured to assign a second color to the second subset of the one or more regions of plaque identified in the second medical image.

Embodiment 83: The system of Embodiment 81, wherein the processors are further configured to remove the second subset of the one or more regions of plaque in the second medical image.

Embodiment 84: The system of Embodiment 78, wherein the analysis results of the first medical image further comprises classification of the one or more regions of plaque identified in the first medical image.

Embodiment 85: The system of Embodiment 84, wherein classification of the one or more regions of plaque identified in the first medical image is based at least in part on density.

Embodiment 86: The system of Embodiment 85, wherein the density comprises material density.

Embodiment 87: The system of Embodiment 85, wherein the density comprises radiodensity.

Embodiment 88: The system of Embodiment 84, wherein the classification of the one or more regions of plaque in the first medical image comprises classification of the one or more regions of plaque as one or more of low-density non-calcified plaque, non-calcified plaque, or calcified plaque.

Embodiment 89: The system of Embodiment 88, wherein low density non-calcified plaque corresponds to one or more regions of plaque comprising one or more pixels with a radiodensity value between about −189 and about 30 Hounsfield units, wherein non-calcified plaque corresponds to one or more regions of plaque comprising one or more pixels with a radiodensity value between about 190 and about 350 Hounsfield units, and wherein calcified plaque corresponds to one or more regions of plaque comprising one or more pixels with a radiodensity value between about 351 and 2500 Hounsfield units.

Embodiment 90: The system of Embodiment 84, wherein the processors are further configured to: analyze the second medical image to classify the one or more regions of plaque identified in the second medical image; and map the classification of the one or more regions of plaque in the first medical image with the classification of the one or more regions of plaque identified in the second medical image.

Embodiment 91: The system of Embodiment 90, wherein classification of the one or more regions of plaque identified in the second medical image is based at least in part on density.

Embodiment 92: The system of Embodiment 91, wherein the density comprises material density.

Embodiment 93: The system of Embodiment 91, wherein the density comprises radiodensity.

Embodiment 94: The system of Embodiment 90, wherein the classification of the one or more regions of plaque in the second medical image comprises classification of the one or more regions of plaque as one or more of low-density non-calcified plaque, non-calcified plaque, or calcified plaque.

Embodiment 95: The system of Embodiment 94, wherein low density non-calcified plaque corresponds to one or more regions of plaque comprising one or more pixels with a radiodensity value between about −189 and about 30 Hounsfield units, wherein non-calcified plaque corresponds to one or more regions of plaque comprising one or more pixels with a radiodensity value between about 190 and about 350 Hounsfield units, and wherein calcified plaque corresponds to one or more regions of plaque comprising one or more pixels with a radiodensity value between about 351 and 2500 Hounsfield units.

Embodiment 96: The system of Embodiment 90, wherein the processors are further configured to: determine a third subset of the one or more regions of plaque in the second medical image, the third subset of the one or more regions of plaque comprising a different classification between the first medical image and the second medical image, wherein generating the graphical representation of arterial plaque progression of the subject further comprises assigning a third color to the third subset of the one or more regions of plaque.

Embodiment 97: The system of Embodiment 90, wherein the processors are further configured to: determine a fourth subset of the one or more regions of plaque in the second medical image, the fourth subset of the one or more regions of plaque comprising a same classification between the first medical image and the second medical image.

Embodiment 98: The system of Embodiment 97, wherein generating the graphical representation of arterial plaque progression of the subject further comprises assigning a fourth color to the third subset of the one or more regions of plaque.

Embodiment 99: The computer-implemented method of Embodiment 45, wherein the processors are further configured to: graphically remove the fourth subset of the one or more regions of plaque in the second medical image.

Embodiment 100: The computer-implemented method of Embodiment 78, wherein the one or more arteries comprises one or more coronary arteries.

Embodiment 101: The computer-implemented method of Embodiment 78, wherein the one or more arteries comprises one or more coronary arteries, carotid arteries, aorta, upper extremity arteries, or lower extremity arteries.

Embodiment 102: The computer-implemented method of Embodiment 78, wherein one or more of the first medical image or the second medical image is obtained using coronary computed tomography angiography (CCTA).

Embodiment 103: The computer-implemented method of Embodiment 78, wherein one or more of the first medical image or the second medical image is obtained using computed tomography (CT).

Embodiment 104: The computer-implemented method of Embodiment 78, wherein one or more of the first medical image or the second medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 105: A non-transitory computer readable medium configured for generating a graphical representation of arterial plaque progression to facilitate tracking of progression of arterial disease for a subject, the computer readable medium having program instructions for causing a hardware processor to perform a method of: accessing first medical image of a subject obtained at a first point in time, the first medical image comprising a region of one or more arteries of the subject and one or more regions of plaque captured at the first point in time; accessing analysis results of the first medical image, the analysis results comprising identification of the region of the one or more arteries and the one or more regions of plaque in the first medical image; accessing a second medical image of the subject obtained at a second point in time, the second medical image comprising the region of the one or more arteries of the subject and the one or more regions of plaque captured at the second point in time; analyzing the second medical image to identify the region of the one or more arteries and the one or more regions of plaque; mapping the region of the one or more arteries and the one or more regions of plaque in the first medical image with the region of the one or more arteries and the one or more regions of plaque in the second medical image; determining a first subset of the one or more regions of plaque in the second medical image, the first subset of the one or more regions of plaque present only in the second medical image and not in the first medical image based at least in part on the mapping; and generating a graphical representation of arterial plaque progression of the subject, wherein generating the graphical representation comprises assigning a first color to the first subset of the one or more regions of plaque, wherein the graphical representation of arterial plaque progression in the subject is configured to facilitate tracking of progression of arterial disease for the subject.

Embodiment 106: The computer readable medium of Embodiment 105, wherein the method further comprises: determining a second subset of the one or more regions of plaque in the second medical image, the second subset of the one or more regions of plaque present in both the first medical image and the second medical image based at least in part on the mapping.

Embodiment 107: The computer readable medium of Embodiment 106, wherein generating the graphical representation of arterial plaque progression of the subject further comprises assigning a second color to the second subset of the one or more regions of plaque in the second medical image.

Embodiment 108: The computer readable medium of Embodiment 106, wherein the method further comprises: graphically removing the second subset of the one or more regions of plaque in the second medical image.

Embodiment 109: The computer readable medium of Embodiment 105, wherein the analysis results of the first medical image further comprises classification of the one or more regions of plaque identified in the first medical image.

Embodiment 110: The computer readable medium of Embodiment 109, wherein classification of the one or more regions of plaque identified in the first medical image is based at least in part on density.

Embodiment 111: The computer readable medium of Embodiment 110, wherein the density comprises material density.

Embodiment 112: The computer readable medium of Embodiment 110, wherein the density comprises radiodensity.

Embodiment 113: The computer readable medium of Embodiment 109, wherein the classification of the one or more regions of plaque in the first medical image comprises classification of the one or more regions of plaque as one or more of low-density non-calcified plaque, non-calcified plaque, or calcified plaque.

Embodiment 114: The computer readable medium of Embodiment 113, wherein low density non-calcified plaque corresponds to one or more regions of plaque comprising one or more pixels with a radiodensity value between about −189 and about 30 Hounsfield units, wherein non-calcified plaque corresponds to one or more regions of plaque comprising one or more pixels with a radiodensity value between about 190 and about 350 Hounsfield units, and wherein calcified plaque corresponds to one or more regions of plaque comprising one or more pixels with a radiodensity value between about 351 and 2500 Hounsfield units.

Embodiment 115: The computer readable medium of Embodiment 109, wherein the method further comprises: analyzing the second medical image to classify the one or more regions of plaque identified in the second medical image; and mapping the classification of the one or more regions of plaque in the first medical image with the classification of the one or more regions of plaque identified in the second medical image.

Embodiment 116: The computer readable medium of Embodiment 115, wherein classification of the one or more regions of plaque identified in the second medical image is based at least in part on density.

Embodiment 117: The computer readable medium of Embodiment 116, wherein the density comprises material density.

Embodiment 118: The computer readable medium of Embodiment 116, wherein the density comprises radiodensity.

Embodiment 119: The computer readable medium of Embodiment 115, wherein the classification of the one or more regions of plaque in the second medical image comprises classification of the one or more regions of plaque as one or more of low-density non-calcified plaque, non-calcified plaque, or calcified plaque.

Embodiment 120: The computer readable medium of Embodiment 119, wherein low density non-calcified plaque corresponds to one or more regions of plaque comprising one or more pixels with a radiodensity value between about −189 and about 30 Hounsfield units, wherein non-calcified plaque corresponds to one or more regions of plaque comprising one or more pixels with a radiodensity value between about 190 and about 350 Hounsfield units, and wherein calcified plaque corresponds to one or more regions of plaque comprising one or more pixels with a radiodensity value between about 351 and 2500 Hounsfield units.

Embodiment 121: The computer readable medium of Embodiment 115, wherein the method further comprises: determining a third subset of the one or more regions of plaque in the second medical image, the third subset of the one or more regions of plaque comprising a different classification between the first medical image and the second medical image, wherein generating the graphical representation of arterial plaque progression of the subject further comprises assigning a third color to the third subject of the one or more regions of plaque.

Embodiment 122: The computer readable medium of Embodiment 115, wherein the method further comprises: determining a fourth subset of the one or more regions of plaque in the second medical image, the fourth subset of the one or more regions of plaque comprising a same classification between the first medical image and the second medical image.

Embodiment 123: The computer readable medium of Embodiment 122, wherein generating the graphical representation of arterial plaque progression of the subject further comprises assigning a fourth color to the third subject of the one or more regions of plaque.

Embodiment 124: The computer readable medium of Embodiment 122, wherein the method further comprises: graphically removing the fourth subset of the one or more regions of plaque in the second medical image.

Embodiment 125: The computer readable medium of Embodiment 105, wherein the one or more arteries comprises one or more coronary arteries.

Embodiment 126: The computer readable medium of Embodiment 105, wherein the one or more arteries comprises one or more coronary arteries, carotid arteries, aorta, upper extremity arteries, or lower extremity arteries.

Embodiment 127: The computer readable medium of Embodiment 105, wherein one or more of the first medical image or the second medical image is obtained using coronary computed tomography angiography (CCTA).

Embodiment 128: The computer readable medium of Embodiment 105, wherein one or more of the first medical image or the second medical image is obtained using computed tomography (CT).

Embodiment 129: The computer readable medium of Embodiment 105, wherein one or more of the first medical image or the second medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 130: A non-transitory computer readable medium configured for generating a graphical representation of arterial plaque progression to facilitate tracking of progression of arterial disease for a subject, the computer readable medium having program instructions for causing a hardware processor to perform a method of: accessing a first medical image of a subject obtained at a first point in time, the first medical image comprising a region of one or more arteries of the subject and one or more regions of plaque captured at the first point in time; accessing analysis results of the first medical image, the analysis results comprising identification of the region of the one or more arteries and the one or more regions of plaque in the first medical image; accessing a second medical image of the subject obtained at a second point in time, the second medical image comprising the region of the one or more arteries of the subject and the one or more regions of plaque captured at the second point in time; analyzing the second medical image to identify the region of the one or more arteries and the one or more regions of plaque; mapping the region of the one or more arteries and the one or more regions of plaque in the first medical image with the region of the one or more arteries and the one or more regions of plaque in the second medical image; and generating a graphical representation of arterial plaque progression of the subject, wherein generating the graphical representation comprises: generating an annotated version of the second medical image by graphically indicating the one or more regions of plaque identified in the second medical image; and graphically overlaying the one or more regions of plaque identified in the first medical image on the annotated version of the second medical image based at least in part on the mapping, wherein the graphical representation of arterial plaque progression in the subject is configured to facilitate tracking of progression of arterial disease for the subject.

Embodiment 131: The computer readable medium of Embodiment 130, wherein generating the graphical representation of arterial plaque progression of the subject further comprises: determining a first subset of the one or more regions of plaque identified in the second medical image, the first subset of the one or more regions of plaque identified only in the second medical image and not in the first medical image; and graphically identifying the first subset of the one or more regions of the plaque identified in the second medical image.

Embodiment 132: The computer readable medium of Embodiment 131, wherein the method further comprises assigning a first color to the first subset of the one or more regions of plaque identified in the second medical image.

Embodiment 133: The computer readable medium of Embodiment 131, wherein generating the graphical representation of arterial plaque progression of the subject further comprises: determining a second subset of the one or more regions of plaque identified in the second medical image, the second subset of the one or more regions of plaque identified in both the first medical image and the second medical image; and graphically identifying, by the computer system, the second subset of the one or more regions of the plaque identified in the second medical image.

Embodiment 134: The computer readable medium of Embodiment 133, wherein the method further comprises assigning a second color to the second subset of the one or more regions of plaque identified in the second medical image.

Embodiment 135: The computer readable medium of Embodiment 133, wherein the method further comprises graphically removing, by the computer system, the second subset of the one or more regions of plaque in the second medical image.

Embodiment 136: The computer readable medium of Embodiment 130, wherein the analysis results of the first medical image further comprises classification of the one or more regions of plaque identified in the first medical image.

Embodiment 137: The computer readable medium of Embodiment 136, wherein classification of the one or more regions of plaque identified in the first medical image is based at least in part on density.

Embodiment 138: The computer readable medium of Embodiment 136, wherein the density comprises material density.

Embodiment 139: The computer readable medium of Embodiment 137, wherein the density comprises radiodensity.

Embodiment 140: The computer readable medium of Embodiment 136, wherein the classification of the one or more regions of plaque in the first medical image comprises classification of the one or more regions of plaque as one or more of low-density non-calcified plaque, non-calcified plaque, or calcified plaque.

Embodiment 141: The computer readable medium of Embodiment 140, wherein low density non-calcified plaque corresponds to one or more regions of plaque comprising one or more pixels with a radiodensity value between about −189 and about 30 Hounsfield units, wherein non-calcified plaque corresponds to one or more regions of plaque comprising one or more pixels with a radiodensity value between about 190 and about 350 Hounsfield units, and wherein calcified plaque corresponds to one or more regions of plaque comprising one or more pixels with a radiodensity value between about 351 and 2500 Hounsfield units.

Embodiment 142: The computer readable medium of Embodiment 136, wherein the method further comprises: analyzing the second medical image to classify the one or more regions of plaque identified in the second medical image; and mapping the classification of the one or more regions of plaque in the first medical image with the classification of the one or more regions of plaque identified in the second medical image.

Embodiment 143: The computer readable medium of Embodiment 142, wherein classification of the one or more regions of plaque identified in the second medical image is based at least in part on density.

Embodiment 144: The computer readable medium of Embodiment 143, wherein the density comprises material density.

Embodiment 145: The computer readable medium of Embodiment 143, wherein the density comprises radiodensity.

Embodiment 146: The computer readable medium of Embodiment 142, wherein the classification of the one or more regions of plaque in the second medical image comprises classification of the one or more regions of plaque as one or more of low-density non-calcified plaque, non-calcified plaque, or calcified plaque.

Embodiment 147: The computer readable medium of Embodiment 146, wherein low density non-calcified plaque corresponds to one or more regions of plaque comprising one or more pixels with a radiodensity value between about −189 and about 30 Hounsfield units, wherein non-calcified plaque corresponds to one or more regions of plaque comprising one or more pixels with a radiodensity value between about 190 and about 350 Hounsfield units, and wherein calcified plaque corresponds to one or more regions of plaque comprising one or more pixels with a radiodensity value between about 351 and 2500 Hounsfield units.

Embodiment 148: The computer readable medium of Embodiment 142, wherein the method further comprises: determining a third subset of the one or more regions of plaque in the second medical image, the third subset of the one or more regions of plaque comprising a different classification between the first medical image and the second medical image, wherein generating the graphical representation of arterial plaque progression of the subject further comprises assigning a third color to the third subject of the one or more regions of plaque.

Embodiment 149: The computer readable medium of Embodiment 142, wherein the method further comprises: determining a fourth subset of the one or more regions of plaque in the second medical image, the fourth subset of the one or more regions of plaque comprising a same classification between the first medical image and the second medical image.

Embodiment 150: The computer readable medium of Embodiment 149, wherein generating the graphical representation of arterial plaque progression of the subject further comprises assigning a fourth color to the third subject of the one or more regions of plaque.

Embodiment 151: The computer readable medium of Embodiment 149, wherein the method further comprises: graphically removing the fourth subset of the one or more regions of plaque in the second medical image.

Embodiment 152: The computer readable medium of Embodiment 130, wherein the one or more arteries comprises one or more coronary arteries.

Embodiment 153: The computer readable medium of Embodiment 130, wherein the one or more arteries comprises one or more coronary arteries, carotid arteries, aorta, upper extremity arteries, or lower extremity arteries.

Embodiment 154: The computer readable medium of Embodiment 130, wherein one or more of the first medical image or the second medical image is obtained using coronary computed tomography angiography (CCTA).

Embodiment 155: The computer readable medium of Embodiment 130, wherein one or more of the first medical image or the second medical image is obtained using computed tomography (CT).

Embodiment 156: The computer readable medium of Embodiment 130, wherein one or more of the first medical image or the second medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 157: A computer-implemented method of generating a graphical training tool configured to facilitate training a user to identify arterial plaque on a medical image, the method comprising: accessing, by a computer system, a medical image of a subject, the medical image comprising one or more regions of arterial plaque; receiving, by the computer system, one or more user annotations of the medical image from a user, the one or more user annotations comprising identification of the one or more regions of arterial plaque; accessing, by the computer system, a prestored annotated version of the medical image, the prestored version of the medical image comprising one or more prestored annotations comprising identification of the one or more regions of arterial plaque; graphically overlaying, by the computer system, the one or more user annotations of the medical image on the prestored annotated version of the medical image; identifying, by the computer system, a first subset of the one or more user annotations of the medical image, the first subset of the one or more user annotations absent in the prestored annotated version of the medical image; and graphically assigning, by the computer system, a first color to the first subset of the one or more user annotations of the medical image, wherein the graphically assigned first color is configured to facilitate training of the user to identify arterial plaque, wherein the computer system comprises a computer processor and an electronic storage medium.

Embodiment 158: The computer-implemented method of Embodiment 157, further comprising: identifying, by the computer system, a second subset of the one or more user annotations of the medical image, the second subset of the one or more user annotations present in the prestored annotated version of the medical image; and graphically assigning, by the computer system, a second color to the second subset of the one or more user annotations of the medical image.

Embodiment 159: The computer-implemented method of Embodiment 157, further comprising: identifying, by the computer system, a first subset of the prestored annotations, the first subset of the prestored annotations absent in the one or more user annotations; and graphically assigning, by the computer system, a third color to the first subset of the prestored annotations.

Embodiment 160: The computer-implemented method of Embodiment 159, wherein the first color and the third color are the same.

Embodiment 161: The computer-implemented method of Embodiment 159, wherein the first color and the third color are different.

Embodiment 162: The computer-implemented method of Embodiment 159, further comprising: identifying, by the computer system, a second subset of the prestored annotations, the second subset of the prestored annotations present in the one or more user annotations; and graphically assigning, by the computer system, a fourth color to the second subset of the prestored annotations.

Embodiment 163: The computer-implemented method of Embodiment 157, further comprising generating, by the computer system, a read score for the user based at least in part on the first subset of the one or more user annotations of the medical image.

Embodiment 164: The computer-implemented method of Embodiment 157, wherein one or more of the prestored annotations are received from an expert reader.

Embodiment 165: The computer-implemented method of Embodiment 157, wherein one or more of the prestored annotations are generated by a machine learning algorithm.

Embodiment 166: The computer-implemented method of Embodiment 157, wherein the one or more user annotations and the prestored annotations further comprise classification of one or more regions of plaque.

Embodiment 167: The computer-implemented method of Embodiment 166, wherein classification of the one or more regions of plaque in the prestored annotations is based at least in part on density.

Embodiment 168: The computer-implemented method of Embodiment 167, wherein the density comprises material density.

Embodiment 169: The computer-implemented method of Embodiment 167, wherein the density comprises radiodensity.

Embodiment 170: The computer-implemented method of Embodiment 169, wherein the classification of the one or more regions of plaque in the prestored annotations comprises classification of the one or more regions of plaque as one or more of low-density non-calcified plaque, non-calcified plaque, or calcified plaque.

Embodiment 171: The computer-implemented method of Embodiment 170, wherein low density non-calcified plaque corresponds to one or more regions of plaque comprising one or more pixels with a radiodensity value between about −189 and about 30 Hounsfield units, wherein non-calcified plaque corresponds to one or more regions of plaque comprising one or more pixels with a radiodensity value between about 190 and about 350 Hounsfield units, and wherein calcified plaque corresponds to one or more regions of plaque comprising one or more pixels with a radiodensity value between about 351 and 2500 Hounsfield units.

Embodiment 172: The computer-implemented method of Embodiment 157, wherein the arterial plaque comprises coronary arterial plaque.

Embodiment 173: The computer-implemented method of Embodiment 157, wherein the arterial plaque comprises plaque in one or more coronary arteries, carotid arteries, aorta, upper extremity arteries, or lower extremity arteries.

Embodiment 174: The computer-implemented method of Embodiment 157, wherein the medical image is obtained using coronary computed tomography angiography (CCTA).

Embodiment 175: The computer-implemented method of Embodiment 157, wherein the medical image is obtained using computed tomography (CT).

Embodiment 176: The computer-implemented method of Embodiment 157, wherein the medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 177: A computer-implemented method of generating a graphical training tool configured to facilitate training a user to identify arterial plaque on a medical image, the method comprising: accessing, by a computer system, a medical image of a subject, the medical image comprising one or more regions of arterial plaque; receiving, by the computer system, one or more user annotations of the medical image from a user to generate a user-annotated version of the medical image, the one or more user annotations comprising identification of the one or more regions of arterial plaque; accessing, by the computer system, one or more prestored annotations of the medical image, the one or more prestored annotations of the medical image comprising identification of the one or more regions of arterial plaque; graphically overlaying, by the computer system, the one or more prestored annotations of the medical image on the user-annotated version of the medical image; identifying, by the computer system, a first subset of the one or more user annotations of the medical image, the first subset of the one or more user annotations absent in the prestored annotations of the medical image; and graphically assigning, by the computer system, a first color to the first subset of the one or more user annotations of the medical image, wherein the graphically assigned first color is configured to facilitate training of the user to identify arterial plaque, wherein the computer system comprises a computer processor and an electronic storage medium.

Embodiment 178: The computer-implemented method of Embodiment 177, further comprising: identifying, by the computer system, a second subset of the one or more user annotations of the medical image, the second subset of the one or more user annotations present in the prestored annotations of the medical image; and graphically assigning, by the computer system, a second color to the second subset of the one or more user annotations of the medical image.

Embodiment 179: The computer-implemented method of Embodiment 177, further comprising: identifying, by the computer system, a first subset of the prestored annotations, the first subset of the prestored annotations absent in the one or more user annotations; and graphically assigning, by the computer system, a third color to the first subset of the prestored annotations.

Embodiment 180: The computer-implemented method of Embodiment 179, wherein the first color and the third color are the same.

Embodiment 181: The computer-implemented method of Embodiment 179, wherein the first color and the third color are different.

Embodiment 182: The computer-implemented method of Embodiment 179, further comprising: identifying, by the computer system, a second subset of the prestored annotations, the second subset of the prestored annotations present in the one or more user annotations; and graphically assigning, by the computer system, a fourth color to the second subset of the prestored annotations.

Embodiment 183: The computer-implemented method of Embodiment 177, further comprising generating, by the computer system, a read score for the user based at least in part on the first subset of the one or more user annotations of the medical image.

Embodiment 184: The computer-implemented method of Embodiment 177, wherein one or more of the prestored annotations are received from an expert reader.

Embodiment 185: The computer-implemented method of Embodiment 177, wherein one or more of the prestored annotations are generated by a machine learning algorithm.

Embodiment 186: The computer-implemented method of Embodiment 177, wherein the one or more user annotations and the prestored annotations further comprise classification of one or more regions of plaque.

Embodiment 187: The computer-implemented method of Embodiment 186, wherein classification of the one or more regions of plaque in the prestored annotations is based at least in part on density.

Embodiment 188: The computer-implemented method of Embodiment 187, wherein the density comprises material density.

Embodiment 189: The computer-implemented method of Embodiment 187, wherein the density comprises radiodensity.

Embodiment 190: The computer-implemented method of Embodiment 189, wherein the classification of the one or more regions of plaque in the prestored annotations comprises classification of the one or more regions of plaque as one or more of low-density non-calcified plaque, non-calcified plaque, or calcified plaque.

Embodiment 191: The computer-implemented method of Embodiment 190, wherein low density non-calcified plaque corresponds to one or more regions of plaque comprising one or more pixels with a radiodensity value between about −189 and about 30 Hounsfield units, wherein non-calcified plaque corresponds to one or more regions of plaque comprising one or more pixels with a radiodensity value between about 190 and about 350 Hounsfield units, and wherein calcified plaque corresponds to one or more regions of plaque comprising one or more pixels with a radiodensity value between about 351 and 2500 Hounsfield units.

Embodiment 192: The computer-implemented method of Embodiment 177, wherein the arterial plaque comprises coronary arterial plaque.

Embodiment 193: The computer-implemented method of Embodiment 177, wherein the arterial plaque comprises plaque in one or more coronary arteries, carotid arteries, aorta, upper extremity arteries, or lower extremity arteries.

Embodiment 194: The computer-implemented method of Embodiment 177, wherein the medical image is obtained using coronary computed tomography angiography (CCTA).

Embodiment 195: The computer-implemented method of Embodiment 177, wherein the medical image is obtained using computed tomography (CT).

Embodiment 196: The computer-implemented method of Embodiment 177, wherein the medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 197: A system for generating a graphical training tool configured to facilitate training a user to identify arterial plaque on a medical image, the system comprising: a non-transitory computer storage medium configured to at least store computer-executable instructions; and one or more computer hardware processors in communication with the first non-transitory computer storage medium, the one or more computer hardware processors configured to execute the computer-executable instructions to at least: access a medical image of a subject, the medical image comprising one or more regions of arterial plaque; receive one or more user annotations of the medical image from a user, the one or more user annotations comprising identification of the one or more regions of arterial plaque; access a prestored annotated version of the medical image, the prestored version of the medical image comprising one or more prestored annotations comprising identification of the one or more regions of arterial plaque; graphically overlay the one or more user annotations of the medical image on the prestored annotated version of the medical image; identify a first subset of the one or more user annotations of the medical image, the first subset of the one or more user annotations absent in the prestored annotated version of the medical image; and graphically assign a first color to the first subset of the one or more user annotations of the medical image, wherein the graphically assigned first color is configured to facilitate training of the user to identify arterial plaque.

Embodiment 198: The system of Embodiment 197, wherein the processors are further configured to: identify a second subset of the one or more user annotations of the medical image, the second subset of the one or more user annotations present in the prestored annotated version of the medical image; and graphically assign a second color to the second subset of the one or more user annotations of the medical image.

Embodiment 199: The system of Embodiment 197, wherein the processors are further configured to: identify a first subset of the prestored annotations, the first subset of the prestored annotations absent in the one or more user annotations; and graphically assign a third color to the first subset of the prestored annotations.

Embodiment 200: The system of Embodiment 199, wherein the first color and the third color are the same.

Embodiment 201: The system of Embodiment 199, wherein the first color and the third color are different.

Embodiment 202: The system of Embodiment 199, wherein the processors are further configured to: identify a second subset of the prestored annotations, the second subset of the prestored annotations present in the one or more user annotations; and graphically assign a fourth color to the second subset of the prestored annotations.

Embodiment 203: The system of Embodiment 197, wherein the processors are further configured to generate a read score for the user based at least in part on the first subset of the one or more user annotations of the medical image.

Embodiment 204: The system of Embodiment 197, wherein one or more of the prestored annotations are received from an expert reader.

Embodiment 205: The system of Embodiment 197, wherein one or more of the prestored annotations are generated by a machine learning algorithm.

Embodiment 206: The system of Embodiment 197, wherein the one or more user annotations and the prestored annotations further comprise classification of one or more regions of plaque.

Embodiment 207: The system of Embodiment 206, wherein classification of the one or more regions of plaque in the prestored annotations is based at least in part on density.

Embodiment 208: The system of Embodiment 207, wherein the density comprises material density.

Embodiment 209: The system of Embodiment 207, wherein the density comprises radiodensity.

Embodiment 210: The system of Embodiment 209, wherein the classification of the one or more regions of plaque in the prestored annotations comprises classification of the one or more regions of plaque as one or more of low-density non-calcified plaque, non-calcified plaque, or calcified plaque.

Embodiment 211: The system of Embodiment 210, wherein low density non-calcified plaque corresponds to one or more regions of plaque comprising one or more pixels with a radiodensity value between about −189 and about 30 Hounsfield units, wherein non-calcified plaque corresponds to one or more regions of plaque comprising one or more pixels with a radiodensity value between about 190 and about 350 Hounsfield units, and wherein calcified plaque corresponds to one or more regions of plaque comprising one or more pixels with a radiodensity value between about 351 and 2500 Hounsfield units.

Embodiment 212: The system of Embodiment 197, wherein the arterial plaque comprises coronary arterial plaque.

Embodiment 213: The system of Embodiment 197, wherein the arterial plaque comprises plaque in one or more coronary arteries, carotid arteries, aorta, upper extremity arteries, or lower extremity arteries.

Embodiment 214: The system of Embodiment 197, wherein the medical image is obtained using coronary computed tomography angiography (CCTA).

Embodiment 215: The system of Embodiment 197, wherein the medical image is obtained using computed tomography (CT).

Embodiment 216: The system of Embodiment 197, wherein the medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 217: A system for generating a graphical training tool configured to facilitate training a user to identify arterial plaque on a medical image, the system comprising: a non-transitory computer storage medium configured to at least store computer-executable instructions;

and one or more computer hardware processors in communication with the first non-transitory computer storage medium, the one or more computer hardware processors configured to execute the computer-executable instructions to at least: access a medical image of a subject, the medical image comprising one or more regions of arterial plaque; receive one or more user annotations of the medical image from a user to generate a user-annotated version of the medical image, the one or more user annotations comprising identification of the one or more regions of arterial plaque; access one or more prestored annotations of the medical image, the one or more prestored annotations of the medical image comprising identification of the one or more regions of arterial plaque; graphically overlay the one or more prestored annotations of the medical image on the user-annotated version of the medical image; identify a first subset of the one or more user annotations of the medical image, the first subset of the one or more user annotations absent in the prestored annotations of the medical image; and graphically assign a first color to the first subset of the one or more user annotations of the medical image, wherein the graphically assigned first color is configured to facilitate training of the user to identify arterial plaque.

Embodiment 218: The system of Embodiment 217, wherein the processors are configured to: identify a second subset of the one or more user annotations of the medical image, the second subset of the one or more user annotations present in the prestored annotations of the medical image; and graphically assign a second color to the second subset of the one or more user annotations of the medical image.

Embodiment 219: The system of Embodiment 217, wherein the processors are configured to: identify a first subset of the prestored annotations, the first subset of the prestored annotations absent in the one or more user annotations; and graphically assign a third color to the first subset of the prestored annotations.

Embodiment 220: The system of Embodiment 219, wherein the first color and the third color are the same.

Embodiment 221: The system of Embodiment 219, wherein the first color and the third color are different.

Embodiment 222: The system of Embodiment 219, wherein the processors are configured to: identify, a second subset of the prestored annotations, the second subset of the prestored annotations present in the one or more user annotations; and graphically assign a fourth color to the second subset of the prestored annotations.

Embodiment 223: The system of Embodiment 217, wherein the processors are configured to generate a read score for the user based at least in part on the first subset of the one or more user annotations of the medical image.

Embodiment 224: The system of Embodiment 217, wherein one or more of the prestored annotations are received from an expert reader.

Embodiment 225: The system of Embodiment 217, wherein one or more of the prestored annotations are generated by a machine learning algorithm.

Embodiment 226: The system of Embodiment 217, wherein the one or more user annotations and the prestored annotations further comprise classification of one or more regions of plaque.

Embodiment 227: The system method of Embodiment 226, wherein classification of the one or more regions of plaque in the prestored annotations is based at least in part on density.

Embodiment 228: The system of Embodiment 227, wherein the density comprises material density.

Embodiment 229: The system of Embodiment 227, wherein the density comprises radiodensity.

Embodiment 230: The system of Embodiment 229, wherein the classification of the one or more regions of plaque in the prestored annotations comprises classification of the one or more regions of plaque as one or more of low-density non-calcified plaque, non-calcified plaque, or calcified plaque.

Embodiment 231: The system of Embodiment 230, wherein low density non-calcified plaque corresponds to one or more regions of plaque comprising one or more pixels with a radiodensity value between about −189 and about 30 Hounsfield units, wherein non-calcified plaque corresponds to one or more regions of plaque comprising one or more pixels with a radiodensity value between about 190 and about 350 Hounsfield units, and wherein calcified plaque corresponds to one or more regions of plaque comprising one or more pixels with a radiodensity value between about 351 and 2500 Hounsfield units.

Embodiment 232: The system of Embodiment 217, wherein the arterial plaque comprises coronary arterial plaque.

Embodiment 233: The system of Embodiment 217, wherein the arterial plaque comprises plaque in one or more coronary arteries, carotid arteries, aorta, upper extremity arteries, or lower extremity arteries.

Embodiment 234: The system of Embodiment 217, wherein the medical image is obtained using coronary computed tomography angiography (CCTA).

Embodiment 235: The system of Embodiment 217, wherein the medical image is obtained using computed tomography (CT).

Embodiment 236: The system of Embodiment 217, wherein the medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 237: A non-transitory computer readable medium configured for generating a graphical training tool configured to facilitate training a user to identify arterial plaque on a medical image, the computer readable medium having program instructions for causing a hardware processor to perform a method of: accessing a medical image of a subject, the medical image comprising one or more regions of arterial plaque; receiving one or more user annotations of the medical image from a user, the one or more user annotations comprising identification of the one or more regions of arterial plaque; accessing a prestored annotated version of the medical image, the prestored version of the medical image comprising one or more prestored annotations comprising identification of the one or more regions of arterial plaque; graphically overlaying the one or more user annotations of the medical image on the prestored annotated version of the medical image; identifying a first subset of the one or more user annotations of the medical image, the first subset of the one or more user annotations absent in the prestored annotated version of the medical image; and graphically assign a first color to the first subset of the one or more user annotations of the medical image, wherein the graphically assigned first color is configured to facilitate training of the user to identify arterial plaque.

Embodiment 238: The computer readable medium of Embodiment 237, further comprising: identifying, by the computer system, a second subset of the one or more user annotations of the medical image, the second subset of the one or more user annotations present in the prestored annotated version of the medical image; and graphically assigning, by the computer system, a second color to the second subset of the one or more user annotations of the medical image.

Embodiment 239: The computer readable medium of Embodiment 237, wherein the method further comprises: identifying a first subset of the prestored annotations, the first subset of the prestored annotations absent in the one or more user annotations; and graphically assigning a third color to the first subset of the prestored annotations.

Embodiment 240: The computer readable medium of Embodiment 239, wherein the first color and the third color are the same.

Embodiment 241: The computer readable medium of Embodiment 239, wherein the first color and the third color are different.

Embodiment 242: The computer readable medium of Embodiment 239, wherein the method further comprises: identifying a second subset of the prestored annotations, the second subset of the prestored annotations present in the one or more user annotations; and graphically assigning a fourth color to the second subset of the prestored annotations.

Embodiment 243: The computer readable medium of Embodiment 237, wherein the method further comprises generating a read score for the user based at least in part on the first subset of the one or more user annotations of the medical image.

Embodiment 244: The computer readable medium of Embodiment 237, wherein one or more of the prestored annotations are received from an expert reader.

Embodiment 245: The computer readable medium of Embodiment 237, wherein one or more of the prestored annotations are generated by a machine learning algorithm.

Embodiment 246: The computer readable medium of Embodiment 237, wherein the one or more user annotations and the prestored annotations further comprise classification of one or more regions of plaque.

Embodiment 247: The computer readable medium of Embodiment 246, wherein classification of the one or more regions of plaque in the prestored annotations is based at least in part on density.

Embodiment 248: The computer readable medium of Embodiment 247, wherein the density comprises material density.

Embodiment 249: The computer readable medium of Embodiment 247, wherein the density comprises radiodensity.

Embodiment 250: The computer readable medium of Embodiment 249, wherein the classification of the one or more regions of plaque in the prestored annotations comprises classification of the one or more regions of plaque as one or more of low-density non-calcified plaque, non-calcified plaque, or calcified plaque.

Embodiment 251: The computer readable medium of Embodiment 250, wherein low density non-calcified plaque corresponds to one or more regions of plaque comprising one or more pixels with a radiodensity value between about −189 and about 30 Hounsfield units, wherein non-calcified plaque corresponds to one or more regions of plaque comprising one or more pixels with a radiodensity value between about 190 and about 350 Hounsfield units, and wherein calcified plaque corresponds to one or more regions of plaque comprising one or more pixels with a radiodensity value between about 351 and 2500 Hounsfield units.

Embodiment 252: The computer readable medium method of Embodiment 237, wherein the arterial plaque comprises coronary arterial plaque.

Embodiment 253: The computer readable medium of Embodiment 237, wherein the arterial plaque comprises plaque in one or more coronary arteries, carotid arteries, aorta, upper extremity arteries, or lower extremity arteries.

Embodiment 254: The computer readable medium of Embodiment 237, wherein the medical image is obtained using coronary computed tomography angiography (CCTA).

Embodiment 255: The computer readable medium of Embodiment 237, wherein the medical image is obtained using computed tomography (CT).

Embodiment 256: The computer readable medium of Embodiment 237, wherein the medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 257: A non-transitory computer readable medium configured for generating a graphical training tool configured to facilitate training a user to identify arterial plaque on a medical image, the computer readable medium having program instructions for causing a hardware processor to perform a method of: accessing a medical image of a subject, the medical image comprising one or more regions of arterial plaque; receiving one or more user annotations of the medical image from a user to generate a user-annotated version of the medical image, the one or more user annotations comprising identification of the one or more regions of arterial plaque; accessing one or more prestored annotations of the medical image, the one or more prestored annotations of the medical image comprising identification of the one or more regions of arterial plaque; graphically overlaying the one or more prestored annotations of the medical image on the user-annotated version of the medical image; identifying first subset of the one or more user annotations of the medical image, the first subset of the one or more user annotations absent in the prestored annotations of the medical image; and graphically assigning a first color to the first subset of the one or more user annotations of the medical image, wherein the graphically assigned first color is configured to facilitate training of the user to identify arterial plaque.

Embodiment 258: The computer readable medium of Embodiment 257, wherein the method further comprises: identifying a second subset of the one or more user annotations of the medical image, the second subset of the one or more user annotations present in the prestored annotations of the medical image; and graphically assigning a second color to the second subset of the one or more user annotations of the medical image.

Embodiment 259: The computer readable medium of Embodiment 257, wherein the method further comprises: identifying a first subset of the prestored annotations, the first subset of the prestored annotations absent in the one or more user annotations; and graphically assigning a third color to the first subset of the prestored annotations.

Embodiment 260: The computer readable medium of Embodiment 259, wherein the first color and the third color are the same.

Embodiment 261: The computer readable medium of Embodiment 259, wherein the first color and the third color are different.

Embodiment 262: The computer readable medium of Embodiment 259, wherein the method further comprises: identifying a second subset of the prestored annotations, the second subset of the prestored annotations present in the one or more user annotations; and graphically assigning a fourth color to the second subset of the prestored annotations.

Embodiment 263: The computer readable medium of Embodiment 257, wherein the method further comprises generating a read score for the user based at least in part on the first subset of the one or more user annotations of the medical image.

Embodiment 264: The computer readable medium of Embodiment 257, wherein one or more of the prestored annotations are received from an expert reader.

Embodiment 265: The computer readable medium of Embodiment 257, wherein one or more of the prestored annotations are generated by a machine learning algorithm.

Embodiment 266: The computer readable medium of Embodiment 257, wherein the one or more user annotations and the prestored annotations further comprise classification of one or more regions of plaque.

Embodiment 267: The computer readable medium of Embodiment 266, wherein classification of the one or more regions of plaque in the prestored annotations is based at least in part on density.

Embodiment 268: The computer readable medium of Embodiment 267, wherein the density comprises material density.

Embodiment 269: The computer readable medium of Embodiment 267, wherein the density comprises radiodensity.

Embodiment 270: The computer readable medium of Embodiment 269, wherein the classification of the one or more regions of plaque in the prestored annotations comprises classification of the one or more regions of plaque as one or more of low-density non-calcified plaque, non-calcified plaque, or calcified plaque.

Embodiment 271: The computer readable medium of Embodiment 270, wherein low density non-calcified plaque corresponds to one or more regions of plaque comprising one or more pixels with a radiodensity value between about −189 and about 30 Hounsfield units, wherein non-calcified plaque corresponds to one or more regions of plaque comprising one or more pixels with a radiodensity value between about 190 and about 350 Hounsfield units, and wherein calcified plaque corresponds to one or more regions of plaque comprising one or more pixels with a radiodensity value between about 351 and 2500 Hounsfield units.

Embodiment 272: The computer readable medium of Embodiment 257, wherein the arterial plaque comprises coronary arterial plaque.

Embodiment 273: The computer readable medium of Embodiment 257, wherein the arterial plaque comprises plaque in one or more coronary arteries, carotid arteries, aorta, upper extremity arteries, or lower extremity arteries.

Embodiment 274: The computer readable medium of Embodiment 257, wherein the medical image is obtained using coronary computed tomography angiography (CCTA).

Embodiment 275: The computer readable medium of Embodiment 257, wherein the medical image is obtained using computed tomography (CT).

Embodiment 276: The computer readable medium Embodiment 257, wherein the medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Automated Medical Image Segmentation and/or Analysis for Hospital Admission Determination As discussed herein, disclosed herein are systems, methods, and devices for automated medical image segmentation analysis for hospital admission determination. In some embodiments, the systems, methods, and devices herein relate to clinical decision-making as to discharge or admit an individual to the hospital from the emergency room. For a patient who comes to the emergency room with chest pains or shortness of breath, there can be at least four potentially fatal conditions that are typically screened individually. As such, it can be advantageous to combine this procedure in an automated system, method, and device that screens for each fatal condition, generates a decision on whether any of the fatal conditions are present, and/or outputs a decision and/or rubric to facilitate determination of whether to admit or discharge the patient. More specifically, in some embodiments, the systems, methods, and devices can be configured to perform automated image segmentation, characterization, and/or quantification of medical images of a patient in the emergency room in determining the risk assessment of one or more of coronary artery disease, aortic disease, pneumonia, pulmonary embolism, and/or the like. In some embodiments, the findings from the images can be used to automatically determine, for example by comparison to a database, whether the risk is low, intermediate, or high risk. In some embodiments, the systems, methods, and devices are configured to rank patients based on the risk assessment of disease, need for case compared to other patients, and/or even hospital resource utilization. In some embodiments, the systems, methods, and devices are configured on a visual platform that can display the decision results.

For a patient who comes to the emergency room with chest pain or shortness of breath, there are enumerated risks, such as a heart attack, aortic disease, or death. In typical emergency room practice, an individual with chest pain may be ordered a pulmonary embolism evaluation with a chest CT scan but without a coronary CT angiogram. This may lead to the patient being admitted to a hospital and later requiring another scan to search for a different coronary risk that could have been evaluated with the initial scan. As such, it can be advantageous to combine this process into a streamlined system, method, and device to rule out certain risks from a single scan.

The systems, methods, and devices as described herein relate to clinical decision-making as to whether to discharge or admit an individual to the hospital from the emergency room. In some embodiments, the systems, methods, and devices relate to taking a CT image of a patient in the ER and then performing automated image segmentation, characterization, and/or quantification of one or more of coronary artery disease, pulmonary embolism, aortic disease, and/or pneumonia. In some embodiments, those findings may then be then used to automatically determine, for example based at least in part on accessing a database of reference values, whether the findings are low, intermediate, or high risk. From there, in some embodiments, the system, methods, and devices may be configured to automatically generate a decision per each finding, decision based on all findings combined, generate next steps, and/or at the patient level, a decision of whether to discharge or admit the patient. In some embodiments, the systems, methods, and devices as described herein relate to a fully automated clinical decision support with the advantage of outputting a decision as to whether to admit or discharge a patient.

In some embodiments, the systems, methods, and device seek to screen potentially fatal chest condition risk and/or automate the entire process through a clinical physician's support pathway using automated image segmentation, automated analytics platform for risk assessment, and/or a criteria database coupled to a decision-making node that outputs a decision to admit or discharge a patient. In some embodiments, the output decision may include a notification that states a low likelihood of events upon discharge.

In some embodiments, the systems, methods, and devices are configured to rank patients based on the comparative seriousness of a patient's detected risk. In some embodiments, the system, methods, and devices are configured to rank patients based on resource utilization, such as the available equipment or available hospital personnel. In some embodiments, the systems, methods, and devices are configured on a visual platform that can display the decision results.

Figure 18:
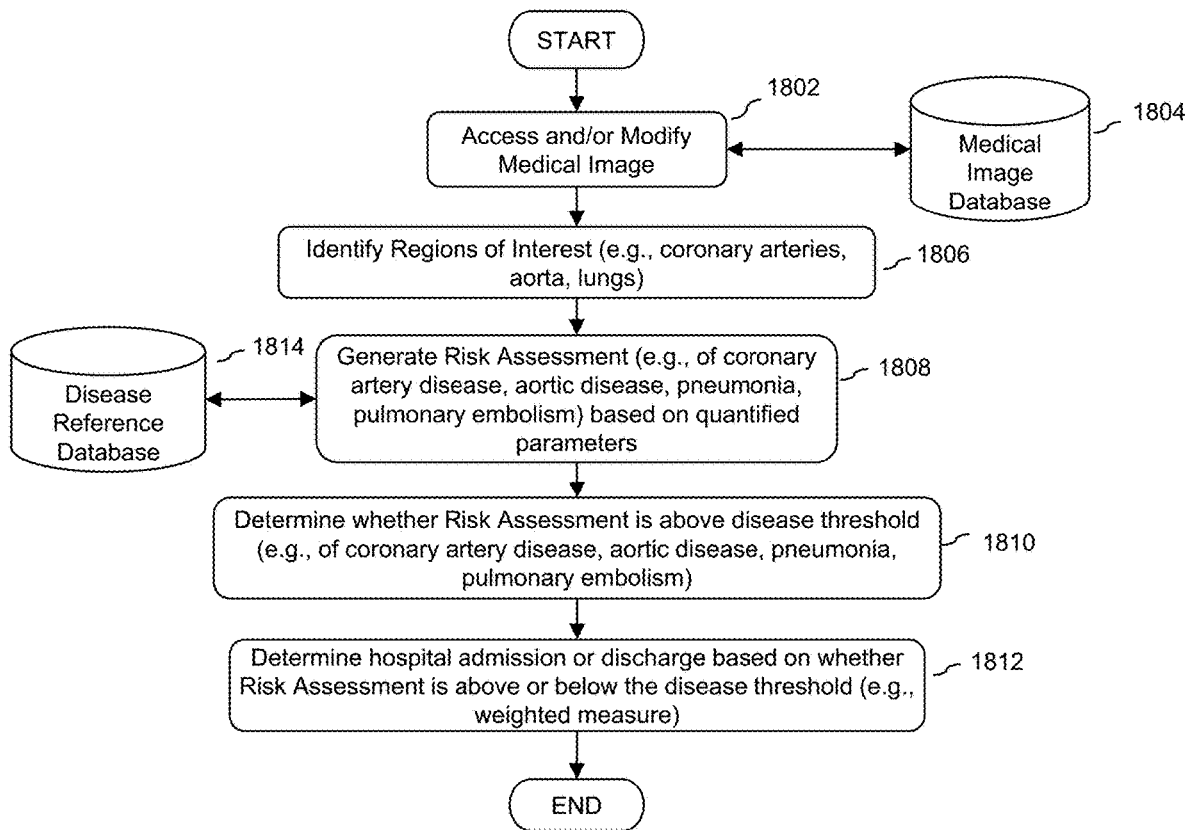
FIG. 18 is a flowchart illustrating an example embodiment(s) of systems, devices, and methods for automated medical image segmentation and/or analysis for hospital admission.

FIG. 18 is a flowchart illustrating an example embodiment(s) of systems, devices, and methods for guiding therapeutic decision-making to determine hospital admission or discharge for a patient based at least in part on automated segmentation and/or analysis of one or more medical images.

In some embodiments, at block 1802, the method can include accessing, by the computer system, one or more medical images of a chest of a patient, the one or more medical images comprising a representation of a portion of one or more coronary arteries, a portion of aorta, and a portion of lungs. In some embodiments, the medical image can be stored in a medical image database 1804. In some embodiments, the medical image database 1804 can be locally accessible by the system and/or can be located remotely and accessible through a network connection.

In some embodiments, the one or more medical images comprises a single medical image comprising the portion of one or more coronary arteries, the portion of aorta, and/or the portion of lungs. In some embodiments, the single medical image is obtained using computed tomography (CT). In some embodiments, the one or more of the one or more medical images is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS). In some embodiments, the one or more medical images comprises a Computed Tomography (CT) image. In some embodiments, the single medical image comprises results from a coronary computed tomography angiography (CCTA), chest CT angiography (CTA), and CT pulmonary angiography. In some embodiments, the one or more medical images comprises a plurality of medical images comprising one or more of the portion of one or more coronary arteries, the portion of aorta, and/or the portion of lungs.

In some embodiments, at block 1806, the method can include automatically performing, by the computer system, image segmentation on the one or more medical images to identify a plurality of regions of interest, the plurality of regions comprising the portion of the one or more coronary arteries, the portion of aorta, and/or the portion of lungs. In some embodiments, the image segmentation is performed based at least in part on utilizing an artificial intelligence algorithm trained on a plurality of medical images comprising the plurality of regions from a plurality of subjects. In some embodiments, the system can be configured to utilize one or more AI and/or ML algorithms to automatically and/or dynamically identify one or more regions of interest using image processing. For example, in some embodiments, the one or more AI and/or ML algorithms can be trained using a Convolutional Neural Network (CNN) on a set of medical images on which coronary arteries, the portion of aorta, and/or the portion of lungs have been identified, thereby allowing the AI and/or ML algorithm automatically identify coronary arteries, the portion of aorta, and/or the portion of lungs directly from a medical image. In some embodiments, the coronary arteries, the portion of aorta, and/or the portion of lungs are identified by size and/or location.

In some embodiments, the method can be configured to repeat one or more processes described in relation to block 1808. For example, to generate a risk assessment for coronary artery disease, for aortic disease, for pneumonia, and/or for pulmonary embolism. As such, in some embodiments, the method can provide for longitudinal disease tracking and/or personalized treatment for a subject. In some embodiments, at block 1808, the method can include analyzing, by the computer system, the portion of the one or more coronary arteries in the one or more medical images to generate a risk assessment of coronary artery disease for the patient, wherein the risk assessment of coronary artery disease can be generated based at least in part on generating one or more quantified parameters from the portion of the one or more coronary arteries in the one or more medical images and comparing the generated one or more quantified parameters to a Disease reference database 1814. The Disease reference database 1814 may store one or more quantified parameters related to coronary artery disease. In some embodiments, the risk assessment of coronary artery disease for the patient is generated based at least in part on utilizing an artificial intelligence algorithm trained on a plurality of longitudinal medical images comprising the portion of one or more coronary arteries from a plurality of subjects.

In some embodiments, at block 1808, the method can include analyzing, by the computer system, the portion of the aorta in the one or more medical images to generate a risk assessment of aortic disease for the patient, wherein the risk assessment of aortic disease is generated based at least in part on generating one or more quantified parameters from the portion of the aorta in the one or more medical images and comparing the generated one or more quantified parameters to a Disease reference database 1814. The Disease reference database 1814 may store one or more quantified parameters related to aortic disease. In some embodiments, the risk assessment of aortic disease for the patient is generated based at least in part on utilizing an artificial intelligence algorithm trained on a plurality of longitudinal medical images comprising the portion of aorta from a plurality of subjects.

In some embodiments, at block 1808, the method can include analyzing, by the computer system, the portion of the lungs in the one or more medical images to generate a risk assessment of pneumonia, wherein the risk assessment of pneumonia is generated based at least in part on generating one or more quantified parameters from the portion of the lungs in the one or more medical images and comparing the generated one or more quantified parameters to a Disease reference database 1814. The Disease reference database 1814 may store one or more quantified parameters related to pneumonia. In some embodiments, the risk assessment of pneumonia for the patient is generated based at least in part on utilizing an artificial intelligence algorithm trained on a plurality of longitudinal medical images comprising the portion of lungs from a plurality of subjects.

In some embodiments, at block 1808, the method can include analyzing, by the computer system, the portion of the lungs in the one or more medical images to generate a risk assessment of pulmonary embolism, wherein the risk assessment of pulmonary embolism is generated based at least in part on generating one or more quantified parameters from the portion of the lungs in the one or more medical images and comparing the generated one or more quantified parameters to a Disease reference database 1814. The Disease reference database 1814 may store one or more quantified parameters related to pulmonary embolism. In some embodiments, the risk assessment of pulmonary embolism for the patient is generated based at least in part on utilizing an artificial intelligence algorithm trained on a plurality of longitudinal medical images comprising the portion of lungs from a plurality of subjects.

In some embodiments, the generated risk assessment of one or more of coronary artery disease, aortic disease, pneumonia, and/or pulmonary embolism for the patient is categorized as one of low, intermediate, or high risk.

In some embodiments, the method can provide for personalized treatment for a subject. For example, the method can include generating, by the computer system, one or more recommended treatments for the patient based at least in part on the generated risk assessment of coronary artery disease, generated risk assessment of aortic disease, generated risk assessment of pneumonia, and/or the generated risk assessment of pulmonary embolism when the patient is determined to be admitted.

In some embodiments, the method can be configured to utilize one or more predetermined threshold values for determining the risk assessment of a coronary disease. In some embodiments, at block 1810, the method can include determining, by the computer system, whether the generated risk assessment of coronary artery disease for the patient is above a coronary artery disease risk threshold. In some embodiments, at block 1810, the method can include determining, by the computer system, whether the generated risk assessment of aortic disease for the patient is above an aortic disease risk threshold. In some embodiments, at block 1810, the method can include determining, by the computer system, whether the generated risk assessment of pneumonia for the patient is above a pneumonia risk threshold. In some embodiments, at block 1810, the method can include determining, by the computer system, whether the generated risk assessment of pulmonary embolism for the patient is above a pulmonary embolism risk threshold.

In some embodiments, the method can include generating a ranking of need for care for the patient based at least in part on the determination of whether the generated risk assessment of coronary artery disease for the patient is above the coronary artery disease risk threshold, determination of whether the generated risk assessment of aortic disease for the patient is above the aortic disease risk threshold, determination of whether the generated risk assessment of pneumonia for the patient is above the pneumonia risk threshold, and/or determination of whether the generated risk assessment of pulmonary embolism for the patient is above a pulmonary embolism risk threshold.

In some embodiments, a resource utilization for the patient is determined based at least in part on the generated ranking of need for care for the patient compared to other patients.

In some embodiments, the method can include generating, by the computer system, a weighted measure of the determination of whether the generated risk assessment of coronary artery disease for the patient is above the coronary artery disease risk threshold, determination of whether the generated risk assessment of aortic disease for the patient is above the aortic disease risk threshold, determination of whether the generated risk assessment of pneumonia for the patient is above the pneumonia risk threshold, and/or determination of whether the generated risk assessment of pulmonary embolism for the patient is above a pulmonary embolism risk threshold, wherein determining hospital admission or discharge for the patient is based at least in part on the generated weighted measure.

In some embodiments, at block 1812, the method can include determining, by the computer system, hospital admission or discharge for the patient based at least in part on the determination of whether the generated risk assessment of coronary artery disease for the patient is above the coronary artery disease risk threshold, determination of whether the generated risk assessment of aortic disease for the patient is above the aortic disease risk threshold, determination of whether the generated risk assessment of pneumonia for the patient is above the pneumonia risk threshold, and/or determination of whether the generated risk assessment of pulmonary embolism for the patient is above a pulmonary embolism risk threshold, wherein the computer system comprises a computer processor and an electronic storage medium. In some embodiments, the patient is determined to be admitted when at least one of the generated risk assessment of coronary artery disease for the patient is above the coronary artery disease risk threshold, the generated risk assessment of aortic disease for the patient is above the aortic disease risk threshold, the generated risk assessment of pneumonia for the patient is above the pneumonia risk threshold, and/or the generated risk assessment of pulmonary embolism for the patient is above a pulmonary embolism risk threshold. In some embodiments, the patient is determined to be discharged when a low likelihood of adverse events is determined based at least in part on the determination of whether the generated risk assessment of coronary artery disease for the patient is above the coronary artery disease risk threshold, determination of whether the generated risk assessment of aortic disease for the patient is above the aortic disease risk threshold, determination of whether the generated risk assessment of pneumonia for the patient is above the pneumonia risk threshold, and/or determination of whether the generated risk assessment of pulmonary embolism for the patient is above a pulmonary embolism risk threshold.

In some embodiments, the method can include causing, by the computer system, generation of a graphical representation of the determination of hospital admission or discharge for the patient.

In some embodiments, the risk assessment of coronary artery disease is generated based at least in part on one or more quantified atherosclerosis parameters. In some embodiments, the one or more parameters include one or more of percent atheroma volume of total plaque, total plaque volume, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, presence of two-feature positive plaques, number of two-feature positive plaques, vessel length, segment length, lesion length, lumen volume, number of chronic total occlusion (CTO), vessel volume, number of stenosis, severity of stenosis, remodeling index, minimum lumen diameter, maximum lumen diameter, mean lumen diameter, stenosis area percentage, stenosis diameter percentage, number of mild stenosis, number of moderate stenosis, number of zero stenosis, number of severe stenosis, presence of high-risk anatomy, presence of positive remodeling, number of severe stenosis excluding CTO, vessel area, lumen area, diameter stenosis percentage, presence of ischemia, number of stents, reference lumen diameter before stenosis, perivascular fat attenuation, or reference lumen diameter after stenosis. In some embodiments, low-density non-calcified plaque can be defined as a region of plaque with a radiodensity value less than or equal to about 30 Hounsfield units, non-calcified plaque can be defined as a region of plaque with a radiodensity value greater than about 30 Hounsfield units and/or less than or equal to about 350 Hounsfield units, calcified plaque can be defined as a region of plaque with a radiodensity value greater than about 350 Hounsfield units, low-density calcified plaque can be defined as a region of plaque with a radiodensity value greater than about 350 Hounsfield units and/or less than or equal to about 700 Hounsfield units, medium-density calcified plaque can be defined as a region of plaque with a radiodensity value greater than about 700 Hounsfield units and/or less than or equal to about 1000 Hounsfield units, and/or high-density calcified plaque can be defined as a region of plaque with a radiodensity value greater than about 1000 Hounsfield units.

In some embodiments, hospital admission or discharge for the patient is determined in an emergency department.

The computer system 902 of FIG. 9, and in some instances, the analysis and/or risk assessment module 940, can be configured to carry out the functions, methods, acts, and/or processes for automated medical image segmentation and/or analysis for hospital admission determination described herein, such as those described above with reference to FIG. 18.

The following are non-limiting examples of certain embodiments of systems and methods for automated medical image segmentation and/or analysis for hospital admission determination. Other embodiments may include one or more other features, or different features, that are discussed herein.

Embodiment 1: A computer-implemented method of guiding therapeutic decision-making to determine hospital admission or discharge for a patient based at least in part on automated segmentation and analysis of one or more medical images, the method comprising: accessing, by the computer system, one or more medical images of a chest of a patient, the one or more medical images comprising a representation of a portion of one or more coronary arteries, a portion of aorta, and a portion of lungs; automatically performing, by the computer system, image segmentation on the one or more medical images to identify a plurality of regions of interest, the plurality of regions comprising the portion of the one or more coronary arteries, the portion of aorta, and the portion of lungs; analyzing, by the computer system, the portion of the one or more coronary arteries in the one or more medical images to generate a risk assessment of coronary artery disease for the patient, wherein the risk assessment of coronary artery disease is generated based at least in part on generating one or more quantified parameters from the portion of the one or more coronary arteries in the one or more medical images and comparing the generated one or more quantified parameters to a coronary artery disease reference database; determining, by the computer system, whether the generated risk assessment of coronary artery disease for the patient is above a coronary artery disease risk threshold; analyzing, by the computer system, the portion of the aorta in the one or more medical images to generate a risk assessment of aortic disease for the patient, wherein the risk assessment of aortic disease is generated based at least in part on generating one or more quantified parameters from the portion of the aorta in the one or more medical images and comparing the generated one or more quantified parameters to an aortic disease reference database; determining, by the computer system, whether the generated risk assessment of aortic disease for the patient is above an aortic disease risk threshold; analyzing, by the computer system, the portion of the lungs in the one or more medical images to generate a risk assessment of pneumonia, wherein the risk assessment of pneumonia is generated based at least in part on generating one or more quantified parameters from the portion of the lungs in the one or more medical images and comparing the generated one or more quantified parameters to a pneumonia disease reference database; determining, by the computer system, whether the generated risk assessment of pneumonia for the patient is above a pneumonia risk threshold; analyzing, by the computer system, the portion of the lungs in the one or more medical images to generate a risk assessment of pulmonary embolism, wherein the risk assessment of pulmonary embolism is generated based at least in part on generating one or more quantified parameters from the portion of the lungs in the one or more medical images and comparing the generated one or more quantified parameters to a pulmonary embolism reference database; determining, by the computer system, whether the generated risk assessment of pulmonary embolism for the patient is above a pulmonary embolism risk threshold; determining, by the computer system, hospital admission or discharge for the patient based at least in part on the determination of whether the generated risk assessment of coronary artery disease for the patient is above the coronary artery disease risk threshold, determination of whether the generated risk assessment of aortic disease for the patient is above the aortic disease risk threshold, determination of whether the generated risk assessment of pneumonia for the patient is above the pneumonia risk threshold, and determination of whether the generated risk assessment of pulmonary embolism for the patient is above a pulmonary embolism risk threshold, wherein the computer system comprises a computer processor and an electronic storage medium.

Embodiment 2: The computer-implemented method of Embodiment 1, further comprising generating a ranking of need for care for the patient based at least in part on the determination of whether the generated risk assessment of coronary artery disease for the patient is above the coronary artery disease risk threshold, determination of whether the generated risk assessment of aortic disease for the patient is above the aortic disease risk threshold, determination of whether the generated risk assessment of pneumonia for the patient is above the pneumonia risk threshold, and determination of whether the generated risk assessment of pulmonary embolism for the patient is above a pulmonary embolism risk threshold.

Embodiment 3: The computer-implemented method of Embodiment 2, wherein a resource utilization for the patient is determined based at least in part on the generated ranking of need for care for the patient compared to other patients.

Embodiment 4: The computer-implemented method of Embodiment 1, wherein the one or more medical images comprises a single medical image comprising the portion of one or more coronary arteries, the portion of aorta, and the portion of lungs.

Embodiment 5: The computer-implemented method of Embodiment 4, wherein the single medical image is obtained using computed tomography (CT).

Embodiment 6: The computer-implemented method of Embodiment 4, wherein the single medical image comprises results from a coronary computed tomography angiography (CCTA), chest CT angiography (CTA), and CT pulmonary angiography.

Embodiment 7: The computer-implemented method of Embodiment 1, wherein the one or more medical images comprises a plurality of medical images comprising one or more of the portion of one or more coronary arteries, the portion of aorta, or the portion of lungs.

Embodiment 8: The computer-implemented method of Embodiment 1, wherein the image segmentation is performed based at least in part on utilizing an artificial intelligence algorithm trained on a plurality of medical images comprising the plurality of regions from a plurality of subjects.

Embodiment 9: The computer-implemented method of Embodiment 1, wherein the risk assessment of coronary artery disease for the patient is generated based at least in part on utilizing an artificial intelligence algorithm trained on a plurality of longitudinal medical images comprising the portion of one or more coronary arteries from a plurality of subjects.

Embodiment 10: The computer-implemented method of Embodiment 1, wherein the risk assessment of aortic disease for the patient is generated based at least in part on utilizing an artificial intelligence algorithm trained on a plurality of longitudinal medical images comprising the portion of aorta from a plurality of subjects.

Embodiment 11: The computer-implemented method of Embodiment 1, wherein the risk assessment of pneumonia for the patient is generated based at least in part on utilizing an artificial intelligence algorithm trained on a plurality of longitudinal medical images comprising the portion of lungs from a plurality of subjects.

Embodiment 12: The computer-implemented method of Embodiment 1, wherein the risk assessment of pulmonary embolism for the patient is generated based at least in part on utilizing an artificial intelligence algorithm trained on a plurality of longitudinal medical images comprising the portion of lungs from a plurality of subjects.

Embodiment 13: The computer-implemented method of Embodiment 1, wherein the generated risk assessment of one or more of coronary artery disease, aortic disease, pneumonia, or pulmonary embolism for the patient is categorized as one of low, intermediate, or high risk.

Embodiment 14: The computer-implemented method of Embodiment 1, further comprising: generating, by the computer system, a weighted measure of the determination of whether the generated risk assessment of coronary artery disease for the patient is above the coronary artery disease risk threshold, determination of whether the generated risk assessment of aortic disease for the patient is above the aortic disease risk threshold, determination of whether the generated risk assessment of pneumonia for the patient is above the pneumonia risk threshold, and determination of whether the generated risk assessment of pulmonary embolism for the patient is above a pulmonary embolism risk threshold, wherein determining hospital admission or discharge for the patient is based at least in part on the generated weighted measure.

Embodiment 15: The computer-implemented method of Embodiment 1, wherein the patient is determined to be admitted when at least one of the generated risk assessment of coronary artery disease for the patient is above the coronary artery disease risk threshold, the generated risk assessment of aortic disease for the patient is above the aortic disease risk threshold, the generated risk assessment of pneumonia for the patient is above the pneumonia risk threshold, or the generated risk assessment of pulmonary embolism for the patient is above a pulmonary embolism risk threshold.

Embodiment 16: The computer-implemented method of Embodiment 1, wherein the patient is determined to be discharged when a low likelihood of adverse events is determined based at least in part on the determination of whether the generated risk assessment of coronary artery disease for the patient is above the coronary artery disease risk threshold, determination of whether the generated risk assessment of aortic disease for the patient is above the aortic disease risk threshold, determination of whether the generated risk assessment of pneumonia for the patient is above the pneumonia risk threshold, and determination of whether the generated risk assessment of pulmonary embolism for the patient is above a pulmonary embolism risk threshold.

Embodiment 17: The computer-implemented method of Embodiment 1, wherein the one or more medical images comprises a Computed Tomography (CT) image.

Embodiment 18: The computer-implemented method of Embodiment 1, wherein one or more of the one or more medical images is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 19: The computer-implemented method of Embodiment 1, further comprising generating, by the computer system, one or more recommended treatments for the patient based at least in part on the generated risk assessment of coronary artery disease, generated risk assessment of aortic disease, generated risk assessment of pneumonia, and the generated risk assessment of pulmonary embolism when the patient is determined to be admitted.

Embodiment 20: The computer-implemented method of Embodiment 1, further comprising causing, by the computer system, generation of a graphical representation of the determination of hospital admission or discharge for the patient.

Embodiment 21: The computer-implemented method of Embodiment 1, wherein the risk assessment of coronary artery disease is generated based at least in part on one or more quantified atherosclerosis parameters.

Embodiment 22: The computer-implemented method of Embodiment 1, wherein hospital admission or discharge for the patient is determined in an emergency department.

Embodiment 23: A computer-implemented method of guiding therapeutic decision-making to facilitate determination of hospital admission or discharge for a patient based at least in part on automated segmentation and analysis of one or more medical images, the method comprising: accessing, by the computer system, one or more medical images of a chest of a patient, the one or more medical images comprising a representation of a portion of one or more coronary arteries, a portion of aorta, and a portion of lungs; automatically performing, by the computer system, image segmentation on the one or more medical images to identify a plurality of regions of interest, the plurality of regions comprising the portion of the one or more coronary arteries, the portion of aorta, and the portion of lungs; analyzing, by the computer system, the portion of the one or more coronary arteries in the one or more medical images to generate a risk assessment of coronary artery disease for the patient, wherein the risk assessment of coronary artery disease is generated based at least in part on generating one or more quantified parameters from the portion of the one or more coronary arteries in the one or more medical images and comparing the generated one or more quantified parameters to a coronary artery disease reference database; determining, by the computer system, whether the generated risk assessment of coronary artery disease for the patient is above a coronary artery disease risk threshold; analyzing, by the computer system, the portion of the aorta in the one or more medical images to generate a risk assessment of aortic disease for the patient, wherein the risk assessment of aortic disease is generated based at least in part on generating one or more quantified parameters from the portion of the aorta in the one or more medical images and comparing the generated one or more quantified parameters to an aortic disease reference database; determining, by the computer system, whether the generated risk assessment of aortic disease for the patient is above an aortic disease risk threshold; analyzing, by the computer system, the portion of the lungs in the one or more medical images to generate a risk assessment of pneumonia, wherein the risk assessment of pneumonia is generated based at least in part on generating one or more quantified parameters from the portion of the lungs in the one or more medical images and comparing the generated one or more quantified parameters to a pneumonia disease reference database; determining, by the computer system, whether the generated risk assessment of pneumonia for the patient is above a pneumonia risk threshold; analyzing, by the computer system, the portion of the lungs in the one or more medical images to generate a risk assessment of pulmonary embolism, wherein the risk assessment of pulmonary embolism is generated based at least in part on generating one or more quantified parameters from the portion of the lungs in the one or more medical images and comparing the generated one or more quantified parameters to a pulmonary embolism reference database; determining, by the computer system, whether the generated risk assessment of pulmonary embolism for the patient is above a pulmonary embolism risk threshold; and generating, by the computer system, a graphical representation of the determination of whether the generated risk assessment of coronary artery disease for the patient is above the coronary artery disease risk threshold, determination of whether the generated risk assessment of aortic disease for the patient is above the aortic disease risk threshold, determination of whether the generated risk assessment of pneumonia for the patient is above the pneumonia risk threshold, and determination of whether the generated risk assessment of pulmonary embolism for the patient is above a pulmonary embolism risk threshold, wherein the generated graphical representation is configured to be used to facilitate determination of hospital admission or discharge for a patient, wherein the computer system comprises a computer processor and an electronic storage medium.

Embodiment 24: The computer-implemented method of Embodiment 23, further comprising generating a ranking of need for care for the patient based at least in part on the determination of whether the generated risk assessment of coronary artery disease for the patient is above the coronary artery disease risk threshold, determination of whether the generated risk assessment of aortic disease for the patient is above the aortic disease risk threshold, determination of whether the generated risk assessment of pneumonia for the patient is above the pneumonia risk threshold, and determination of whether the generated risk assessment of pulmonary embolism for the patient is above a pulmonary embolism risk threshold.

Embodiment 25: The computer-implemented method of Embodiment 24, wherein a resource utilization for the patient is determined based at least in part on the generated ranking of need for care for the patient compared to other patients.

Embodiment 26: The computer-implemented method of Embodiment 23, wherein the one or more medical images comprises a single medical image comprising the portion of one or more coronary arteries, the portion of aorta, and the portion of lungs.

Embodiment 27: The computer-implemented method of Embodiment 26, wherein the single medical image is obtained using computed tomography (CT).

Embodiment 28: The computer-implemented method of Embodiment 26, wherein the single medical image comprises results from a coronary computed tomography angiography (CCTA), chest CT angiography (CTA), and CT pulmonary angiography.

Embodiment 29: The computer-implemented method of Embodiment 23, wherein the one or more medical images comprises a plurality of medical images comprising one or more of the portion of one or more coronary arteries, the portion of aorta, or the portion of lungs.

Embodiment 30: The computer-implemented method of Embodiment 23, wherein the image segmentation is performed based at least in part on utilizing an artificial intelligence algorithm trained on a plurality of medical images comprising the plurality of regions from a plurality of subjects.

Embodiment 31: The computer-implemented method of Embodiment 23, wherein the risk assessment of coronary artery disease for the patient is generated based at least in part on utilizing an artificial intelligence algorithm trained on a plurality of longitudinal medical images comprising the portion of one or more coronary arteries from a plurality of subjects.

Embodiment 32: The computer-implemented method of Embodiment 23, wherein the risk assessment of aortic disease for the patient is generated based at least in part on utilizing an artificial intelligence algorithm trained on a plurality of longitudinal medical images comprising the portion of aorta from a plurality of subjects.

Embodiment 33: The computer-implemented method of Embodiment 23, wherein the risk assessment of pneumonia for the patient is generated based at least in part on utilizing an artificial intelligence algorithm trained on a plurality of longitudinal medical images comprising the portion of lungs from a plurality of subjects.

Embodiment 34: The computer-implemented method of Embodiment 23, wherein the risk assessment of pulmonary embolism for the patient is generated based at least in part on utilizing an artificial intelligence algorithm trained on a plurality of longitudinal medical images comprising the portion of lungs from a plurality of subjects.

Embodiment 35: The computer-implemented method of Embodiment 23, wherein the generated risk assessment of one or more of coronary artery disease, aortic disease, pneumonia, or pulmonary embolism for the patient is categorized as one of low, intermediate, or high risk.

Embodiment 36: The computer-implemented method of Embodiment 23, further comprising: generating, by the computer system, a weighted measure of the determination of whether the generated risk assessment of coronary artery disease for the patient is above the coronary artery disease risk threshold, determination of whether the generated risk assessment of aortic disease for the patient is above the aortic disease risk threshold, determination of whether the generated risk assessment of pneumonia for the patient is above the pneumonia risk threshold, and determination of whether the generated risk assessment of pulmonary embolism for the patient is above a pulmonary embolism risk threshold, wherein the generated weighted measure is configured to be used to facilitate determination of hospital admission or discharge for a patient.

Embodiment 37: The computer-implemented method of Embodiment 1, wherein the one or more medical images comprises a Computed Tomography (CT) image.

Embodiment 38: The computer-implemented method of Embodiment 1, wherein one or more of the one or more medical images is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 39: The computer-implemented method of Embodiment 1, wherein the risk assessment of coronary artery disease is generated based at least in part on one or more quantified atherosclerosis parameters.

Embodiment 40: The computer-implemented method of Embodiment 1, wherein the computer system is part of an emergency department computer network.

Embodiment 41: A system comprising: a non-transitory computer storage medium configured to at least store computer-executable instructions; and one or more computer hardware processors in communication with the first non-transitory computer storage medium, the one or more computer hardware processors configured to execute the computer-executable instructions to at least: access one or more medical images of a chest of a patient, the one or more medical images comprising a representation of a portion of one or more coronary arteries, a portion of aorta, and a portion of lungs; automatically perform image segmentation on the one or more medical images to identify a plurality of regions of interest, the plurality of regions comprising the portion of the one or more coronary arteries, the portion of aorta, and the portion of lungs; analyze the portion of the one or more coronary arteries in the one or more medical images to generate a risk assessment of coronary artery disease for the patient, wherein the risk assessment of coronary artery disease is generated based at least in part on generating one or more quantified parameters from the portion of the one or more coronary arteries in the one or more medical images and comparing the generated one or more quantified parameters to a coronary artery disease reference database; determine whether the generated risk assessment of coronary artery disease for the patient is above a coronary artery disease risk threshold; analyze the portion of the aorta in the one or more medical images to generate a risk assessment of aortic disease for the patient, wherein the risk assessment of aortic disease is generated based at least in part on generating one or more quantified parameters from the portion of the aorta in the one or more medical images and comparing the generated one or more quantified parameters to an aortic disease reference database; determine whether the generated risk assessment of aortic disease for the patient is above an aortic disease risk threshold; analyze the portion of the lungs in the one or more medical images to generate a risk assessment of pneumonia, wherein the risk assessment of pneumonia is generated based at least in part on generating one or more quantified parameters from the portion of the lungs in the one or more medical images and comparing the generated one or more quantified parameters to a pneumonia disease reference database; determine whether the generated risk assessment of pneumonia for the patient is above a pneumonia risk threshold; analyze the portion of the lungs in the one or more medical images to generate a risk assessment of pulmonary embolism, wherein the risk assessment of pulmonary embolism is generated based at least in part on generating one or more quantified parameters from the portion of the lungs in the one or more medical images and comparing the generated one or more quantified parameters to a pulmonary embolism reference database; determine whether the generated risk assessment of pulmonary embolism for the patient is above a pulmonary embolism risk threshold; determine hospital admission or discharge for the patient based at least in part on the determination of whether the generated risk assessment of coronary artery disease for the patient is above the coronary artery disease risk threshold, determination of whether the generated risk assessment of aortic disease for the patient is above the aortic disease risk threshold, determination of whether the generated risk assessment of pneumonia for the patient is above the pneumonia risk threshold, and determination of whether the generated risk assessment of pulmonary embolism for the patient is above a pulmonary embolism risk threshold.

Embodiment 42: The system of Embodiment 41, wherein the one or more computer hardware processors are further configured to execute the computer-executable instructions to at least generate a ranking of need for care for the patient based at least in part on the determination of whether the generated risk assessment of coronary artery disease for the patient is above the coronary artery disease risk threshold, determination of whether the generated risk assessment of aortic disease for the patient is above the aortic disease risk threshold, determination of whether the generated risk assessment of pneumonia for the patient is above the pneumonia risk threshold, and determination of whether the generated risk assessment of pulmonary embolism for the patient is above a pulmonary embolism risk threshold.

Embodiment 43: The system of Embodiment 42, wherein the one or more computer hardware processors are further configured to execute the computer-executable instructions to at least determine a resource utilization for the patient based at least in part on the generated ranking of need for care for the patient compared to other patients.

Embodiment 44: The system of Embodiment 41, wherein the one or more medical images comprises a single medical image comprising the portion of one or more coronary arteries, the portion of aorta, and the portion of lungs.

Embodiment 45: The system of Embodiment 44, wherein the single medical image is obtained using computed tomography (CT).

Embodiment 46: The system of Embodiment 44, wherein the single medical image comprises results from a coronary computed tomography angiography (CCTA), chest CT angiography (CTA), and CT pulmonary angiography.

Embodiment 47: The system of Embodiment 41, wherein the one or more medical images comprises a plurality of medical images comprising one or more of the portion of one or more coronary arteries, the portion of aorta, or the portion of lungs.

Embodiment 48: The system of Embodiment 41, wherein the one or more computer hardware processors are further configured to execute the computer-executable instructions to at least perform image segmentation based at least in part on utilizing an artificial intelligence algorithm trained on a plurality of medical images comprising the plurality of regions from a plurality of subjects.

Embodiment 49: The system of Embodiment 41, wherein the one or more computer hardware processors are further configured to execute the computer-executable instructions to at least generate the risk assessment of coronary artery disease for the patient based at least in part on utilizing an artificial intelligence algorithm trained on a plurality of longitudinal medical images comprising the portion of one or more coronary arteries from a plurality of subjects.

Embodiment 50: The system of Embodiment 41, wherein the one or more computer hardware processors are further configured to execute the computer-executable instructions to at least generate the risk assessment of aortic disease for the patient based at least in part on utilizing an artificial intelligence algorithm trained on a plurality of longitudinal medical images comprising the portion of aorta from a plurality of subjects.

Embodiment 51: The system of Embodiment 41, wherein the one or more computer hardware processors are further configured to execute the computer-executable instructions to at least generate the risk assessment of pneumonia for the patient based at least in part on utilizing an artificial intelligence algorithm trained on a plurality of longitudinal medical images comprising the portion of lungs from a plurality of subjects.

Embodiment 52: The system of Embodiment 41, wherein the one or more computer hardware processors are further configured to execute the computer-executable instructions to at least generate the risk assessment of pulmonary embolism for the patient based at least in part on utilizing an artificial intelligence algorithm trained on a plurality of longitudinal medical images comprising the portion of lungs from a plurality of subjects.

Embodiment 53: The system of Embodiment 41, wherein the one or more computer hardware processors are further configured to execute the computer-executable instructions to at least categorize the generated risk assessment of one or more of coronary artery disease, aortic disease, pneumonia, or pulmonary embolism for the patient as one of low, intermediate, or high risk.

Embodiment 54: The system of Embodiment 1, wherein the one or more computer hardware processors are further configured to execute the computer-executable instructions to at least generate: a weighted measure of the determination of whether the generated risk assessment of coronary artery disease for the patient is above the coronary artery disease risk threshold, determination of whether the generated risk assessment of aortic disease for the patient is above the aortic disease risk threshold, determination of whether the generated risk assessment of pneumonia for the patient is above the pneumonia risk threshold, and determination of whether the generated risk assessment of pulmonary embolism for the patient is above a pulmonary embolism risk threshold, wherein determining hospital admission or discharge for the patient is based at least in part on the generated weighted measure.

Embodiment 55: The system of Embodiment 41, wherein the one or more computer hardware processors are further configured to execute the computer-executable instructions to at least determine admission of a patient when at least one of the generated risk assessment of coronary artery disease for the patient is above the coronary artery disease risk threshold, the generated risk assessment of aortic disease for the patient is above the aortic disease risk threshold, the generated risk assessment of pneumonia for the patient is above the pneumonia risk threshold, or the generated risk assessment of pulmonary embolism for the patient is above a pulmonary embolism risk threshold.

Embodiment 56: The system of Embodiment 41, wherein the one or more computer hardware processors are further configured to execute the computer-executable instructions to at least determine discharge of a patient when a low likelihood of adverse events is determined based at least in part on the determination of whether the generated risk assessment of coronary artery disease for the patient is above the coronary artery disease risk threshold, determination of whether the generated risk assessment of aortic disease for the patient is above the aortic disease risk threshold, determination of whether the generated risk assessment of pneumonia for the patient is above the pneumonia risk threshold, and determination of whether the generated risk assessment of pulmonary embolism for the patient is above a pulmonary embolism risk threshold.

Embodiment 57: The system of Embodiment 41, wherein the one or more medical images comprises a Computed Tomography (CT) image.

Embodiment 58: The system of Embodiment 41, wherein one or more of the one or more medical images is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 59: The system of Embodiment 1, wherein the one or more computer hardware processors are further configured to execute the computer-executable instructions to at least generate one or more recommended treatments for the patient based at least in part on the generated risk assessment of coronary artery disease, generated risk assessment of aortic disease, generated risk assessment of pneumonia, and the generated risk assessment of pulmonary embolism when the patient is determined to be admitted.

Embodiment 60: The system of Embodiment 41, wherein the one or more computer hardware processors are further configured to execute the computer-executable instructions to at least generate a graphical representation of the determination of hospital admission or discharge for the patient.

Embodiment 61: The system of Embodiment 41, wherein the one or more computer hardware processors are further configured to execute the computer-executable instructions to at least generate the risk assessment of coronary artery disease based at least in part on one or more quantified atherosclerosis parameters.

Embodiment 62: The system of Embodiment 41, wherein hospital admission or discharge for the patient is determined in an emergency department.

Embodiment 63: A system comprising: a non-transitory computer storage medium configured to at least store computer-executable instructions; and one or more computer hardware processors in communication with the first non-transitory computer storage medium, the one or more computer hardware processors configured to execute the computer-executable instructions to at least: access one or more medical images of a chest of a patient, the one or more medical images comprising a representation of a portion of one or more coronary arteries, a portion of aorta, and a portion of lungs; automatically perform image segmentation on the one or more medical images to identify a plurality of regions of interest, the plurality of regions comprising the portion of the one or more coronary arteries, the portion of aorta, and the portion of lungs; analyze the portion of the one or more coronary arteries in the one or more medical images to generate a risk assessment of coronary artery disease for the patient, wherein the risk assessment of coronary artery disease is generated based at least in part on generating one or more quantified parameters from the portion of the one or more coronary arteries in the one or more medical images and comparing the generated one or more quantified parameters to a coronary artery disease reference database; determine whether the generated risk assessment of coronary artery disease for the patient is above a coronary artery disease risk threshold; analyze the portion of the aorta in the one or more medical images to generate a risk assessment of aortic disease for the patient, wherein the risk assessment of aortic disease is generated based at least in part on generating one or more quantified parameters from the portion of the aorta in the one or more medical images and comparing the generated one or more quantified parameters to an aortic disease reference database; determine whether the generated risk assessment of aortic disease for the patient is above an aortic disease risk threshold; analyze the portion of the lungs in the one or more medical images to generate a risk assessment of pneumonia, wherein the risk assessment of pneumonia is generated based at least in part on generating one or more quantified parameters from the portion of the lungs in the one or more medical images and comparing the generated one or more quantified parameters to a pneumonia disease reference database; determine whether the generated risk assessment of pneumonia for the patient is above a pneumonia risk threshold; analyze the portion of the lungs in the one or more medical images to generate a risk assessment of pulmonary embolism, wherein the risk assessment of pulmonary embolism is generated based at least in part on generating one or more quantified parameters from the portion of the lungs in the one or more medical images and comparing the generated one or more quantified parameters to a pulmonary embolism reference database; determine whether the generated risk assessment of pulmonary embolism for the patient is above a pulmonary embolism risk threshold; and generate a graphical representation of the determination of whether the generated risk assessment of coronary artery disease for the patient is above the coronary artery disease risk threshold, determination of whether the generated risk assessment of aortic disease for the patient is above the aortic disease risk threshold, determination of whether the generated risk assessment of pneumonia for the patient is above the pneumonia risk threshold, and determination of whether the generated risk assessment of pulmonary embolism for the patient is above a pulmonary embolism risk threshold, wherein the generated graphical representation is configured to be used to facilitate determination of hospital admission or discharge for a patient, wherein the computer system comprises a computer processor and an electronic storage medium.

Embodiment 64: The system of Embodiment 63, wherein the one or more computer hardware processors are further configured to execute the computer-executable instructions to at least generate a ranking of need for care for the patient based at least in part on the determination of whether the generated risk assessment of coronary artery disease for the patient is above the coronary artery disease risk threshold, determination of whether the generated risk assessment of aortic disease for the patient is above the aortic disease risk threshold, determination of whether the generated risk assessment of pneumonia for the patient is above the pneumonia risk threshold, and determination of whether the generated risk assessment of pulmonary embolism for the patient is above a pulmonary embolism risk threshold.

Embodiment 65: The system of Embodiment 64, wherein the one or more computer hardware processors are further configured to execute the computer-executable instructions to at least determine a resource utilization for the patient based at least in part on the generated ranking of need for care for the patient compared to other patients.

Embodiment 66: The system of Embodiment 63, wherein the one or more medical images comprises a single medical image comprising the portion of one or more coronary arteries, the portion of aorta, and the portion of lungs.

Embodiment 67: The system of Embodiment 63, wherein the single medical image is obtained using computed tomography (CT).

Embodiment 68: The system of Embodiment 63, wherein the single medical image comprises results from a coronary computed tomography angiography (CCTA), chest CT angiography (CTA), and CT pulmonary angiography.

Embodiment 69: The system of Embodiment 63, wherein the one or more medical images comprises a plurality of medical images comprising one or more of the portion of one or more coronary arteries, the portion of aorta, or the portion of lungs.

Embodiment 70: The system of Embodiment 63, wherein the one or more computer hardware processors are further configured to execute the computer-executable instructions to at least perform image segmentation based at least in part on utilizing an artificial intelligence algorithm trained on a plurality of medical images comprising the plurality of regions from a plurality of subjects.

Embodiment 71: The system of Embodiment 63, wherein the one or more computer hardware processors are further configured to execute the computer-executable instructions to at least generate the risk assessment of coronary artery disease for the patient based at least in part on utilizing an artificial intelligence algorithm trained on a plurality of longitudinal medical images comprising the portion of one or more coronary arteries from a plurality of subjects.

Embodiment 72: The system of Embodiment 63, wherein the one or more computer hardware processors are further configured to execute the computer-executable instructions to at least generate the risk assessment of aortic disease for the patient based at least in part on utilizing an artificial intelligence algorithm trained on a plurality of longitudinal medical images comprising the portion of aorta from a plurality of subjects.

Embodiment 73: The system of Embodiment 63, wherein the one or more computer hardware processors are further configured to execute the computer-executable instructions to at least generate the risk assessment of pneumonia for the patient based at least in part on utilizing an artificial intelligence algorithm trained on a plurality of longitudinal medical images comprising the portion of lungs from a plurality of subjects.

Embodiment 74: The system of Embodiment 63, wherein the one or more computer hardware processors are further configured to execute the computer-executable instructions to at least generate the risk assessment of pulmonary embolism for the patient based at least in part on utilizing an artificial intelligence algorithm trained on a plurality of longitudinal medical images comprising the portion of lungs from a plurality of subjects.

Embodiment 75: The system of Embodiment 63, wherein the one or more computer hardware processors are further configured to execute the computer-executable instructions to at least categorize the generated risk assessment of one or more of coronary artery disease, aortic disease, pneumonia, or pulmonary embolism for the patient as one of low, intermediate, or high risk.

Embodiment 76: The system of Embodiment 63, wherein the one or more computer hardware processors are further configured to execute the computer-executable instructions to at least: generate a weighted measure of the determination of whether the generated risk assessment of coronary artery disease for the patient is above the coronary artery disease risk threshold, determination of whether the generated risk assessment of aortic disease for the patient is above the aortic disease risk threshold, determination of whether the generated risk assessment of pneumonia for the patient is above the pneumonia risk threshold, and determination of whether the generated risk assessment of pulmonary embolism for the patient is above a pulmonary embolism risk threshold, wherein the generated weighted measure is configured to be used to facilitate determination of hospital admission or discharge for a patient.

Embodiment 77: The system of Embodiment 41, wherein the one or more medical images comprises a Computed Tomography (CT) image.

Embodiment 78: The system of Embodiment 41, wherein one or more of the one or more medical images is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 79: The system of Embodiment 41, wherein the one or more computer hardware processors are further configured to execute the computer-executable instructions to at least generate the risk assessment of coronary artery disease based at least in part on one or more quantified atherosclerosis parameters.

Embodiment 80: The system of Embodiment 41, wherein the computer system is part of an emergency department computer network.

Embodiment 81: A non-transitory computer readable medium configured for guiding therapeutic decision-making to facilitate determination of hospital admission or discharge for a patient based at least in part on automated segmentation and analysis of one or more medical images, the computer readable medium having program instructions for causing a hardware processor to perform a method of: accessing one or more medical images of a chest of a patient, the one or more medical images comprising a representation of a portion of one or more coronary arteries, a portion of aorta, and a portion of lungs; automatically performing image segmentation on the one or more medical images to identify a plurality of regions of interest, the plurality of regions comprising the portion of the one or more coronary arteries, the portion of aorta, and the portion of lungs; analyzing the portion of the one or more coronary arteries in the one or more medical images to generate a risk assessment of coronary artery disease for the patient, wherein the risk assessment of coronary artery disease is generated based at least in part on generating one or more quantified parameters from the portion of the one or more coronary arteries in the one or more medical images and comparing the generated one or more quantified parameters to a coronary artery disease reference database; determining whether the generated risk assessment of coronary artery disease for the patient is above a coronary artery disease risk threshold; analyzing the portion of the aorta in the one or more medical images to generate a risk assessment of aortic disease for the patient, wherein the risk assessment of aortic disease is generated based at least in part on generating one or more quantified parameters from the portion of the aorta in the one or more medical images and comparing the generated one or more quantified parameters to an aortic disease reference database; determining whether the generated risk assessment of aortic disease for the patient is above an aortic disease risk threshold; analyzing the portion of the lungs in the one or more medical images to generate a risk assessment of pneumonia, wherein the risk assessment of pneumonia is generated based at least in part on generating one or more quantified parameters from the portion of the lungs in the one or more medical images and comparing the generated one or more quantified parameters to a pneumonia disease reference database; determining whether the generated risk assessment of pneumonia for the patient is above a pneumonia risk threshold; analyzing the portion of the lungs in the one or more medical images to generate a risk assessment of pulmonary embolism, wherein the risk assessment of pulmonary embolism is generated based at least in part on generating one or more quantified parameters from the portion of the lungs in the one or more medical images and comparing the generated one or more quantified parameters to a pulmonary embolism reference database; determining whether the generated risk assessment of pulmonary embolism for the patient is above a pulmonary embolism risk threshold; and generating and displaying a graphical representation of the determination of whether the generated risk assessment of coronary artery disease for the patient is above the coronary artery disease risk threshold, determination of whether the generated risk assessment of aortic disease for the patient is above the aortic disease risk threshold, determination of whether the generated risk assessment of pneumonia for the patient is above the pneumonia risk threshold, and determination of whether the generated risk assessment of pulmonary embolism for the patient is above a pulmonary embolism risk threshold, wherein the generated graphical representation is configured to be used to facilitate determination of hospital admission or discharge for a patient.

Embodiment 82: The non-transitory computer readable medium of Embodiment 81, wherein the hardware processor is further configured to generate a ranking of need for care for the patient based at least in part on the determination of whether the generated risk assessment of coronary artery disease for the patient is above the coronary artery disease risk threshold, determination of whether the generated risk assessment of aortic disease for the patient is above the aortic disease risk threshold, determination of whether the generated risk assessment of pneumonia for the patient is above the pneumonia risk threshold, and determination of whether the generated risk assessment of pulmonary embolism for the patient is above a pulmonary embolism risk threshold.

Embodiment 83: The non-transitory computer readable medium of Embodiment 82, wherein the hardware processor is further configured to determine a resource utilization for the patient based at least in part on the generated ranking of need for care for the patient compared to other patients.

Embodiment 84: The non-transitory computer readable medium of Embodiment 81, wherein the one or more medical images comprises a single medical image comprising the portion of one or more coronary arteries, the portion of aorta, and the portion of lungs.

Embodiment 85: The non-transitory computer readable medium of Embodiment 84, wherein the single medical image is obtained using computed tomography (CT).

Embodiment 86: The non-transitory computer readable medium of Embodiment 84, wherein the single medical image comprises results from a coronary computed tomography angiography (CCTA), chest CT angiography (CTA), and CT pulmonary angiography.

Embodiment 87: The non-transitory computer readable medium of Embodiment 81, wherein the one or more medical images comprises a plurality of medical images comprising one or more of the portion of one or more coronary arteries, the portion of aorta, or the portion of lungs.

Embodiment 88: The non-transitory computer readable medium of Embodiment 81, wherein the hardware processor is further configured to perform image segmentation is performed based at least in part on utilizing an artificial intelligence algorithm trained on a plurality of medical images comprising the plurality of regions from a plurality of subjects.

Embodiment 89: The non-transitory computer readable medium of Embodiment 81, wherein the hardware processor is further configured to generate the risk assessment of coronary artery disease for the patient based at least in part on utilizing an artificial intelligence algorithm trained on a plurality of longitudinal medical images comprising the portion of one or more coronary arteries from a plurality of subjects.

Embodiment 90: The non-transitory computer readable medium of Embodiment 81, wherein the hardware processor is further configured to generate the risk assessment of aortic disease for the patient based at least in part on utilizing an artificial intelligence algorithm trained on a plurality of longitudinal medical images comprising the portion of aorta from a plurality of subjects.

Embodiment 91: The non-transitory computer readable medium of Embodiment 81, wherein the hardware processor is further configured to generate the risk assessment of pneumonia for the patient based at least in part on utilizing an artificial intelligence algorithm trained on a plurality of longitudinal medical images comprising the portion of lungs from a plurality of subjects.

Embodiment 92: The non-transitory computer readable medium of Embodiment 81, wherein the hardware processor is further configured to generate the risk assessment of pulmonary embolism for the patient based at least in part on utilizing an artificial intelligence algorithm trained on a plurality of longitudinal medical images comprising the portion of lungs from a plurality of subjects.

Embodiment 93: The non-transitory computer readable medium of Embodiment 81, wherein the hardware processor is further configured to categorize the generated risk assessment of one or more of coronary artery disease, aortic disease, pneumonia, or pulmonary embolism for the patient as one of low, intermediate, or high risk.

Embodiment 94: The non-transitory computer readable medium of Embodiment 81, wherein the hardware processor is further configured to further: generate a weighted measure of the determination of whether the generated risk assessment of coronary artery disease for the patient is above the coronary artery disease risk threshold, determination of whether the generated risk assessment of aortic disease for the patient is above the aortic disease risk threshold, determination of whether the generated risk assessment of pneumonia for the patient is above the pneumonia risk threshold, and determination of whether the generated risk assessment of pulmonary embolism for the patient is above a pulmonary embolism risk threshold, wherein determining hospital admission or discharge for the patient is based at least in part on the generated weighted measure.

Embodiment 95: The non-transitory computer readable medium of Embodiment 81, wherein the hardware processor is further configured to determine admission of the patient when at least one of the generated risk assessment of coronary artery disease for the patient is above the coronary artery disease risk threshold, the generated risk assessment of aortic disease for the patient is above the aortic disease risk threshold, the generated risk assessment of pneumonia for the patient is above the pneumonia risk threshold, or the generated risk assessment of pulmonary embolism for the patient is above a pulmonary embolism risk threshold.

Embodiment 96: The non-transitory computer readable medium of Embodiment 81, wherein the hardware processor is further configured to determine discharge of the patient when a low likelihood of adverse events is determined based at least in part on the determination of whether the generated risk assessment of coronary artery disease for the patient is above the coronary artery disease risk threshold, determination of whether the generated risk assessment of aortic disease for the patient is above the aortic disease risk threshold, determination of whether the generated risk assessment of pneumonia for the patient is above the pneumonia risk threshold, and determination of whether the generated risk assessment of pulmonary embolism for the patient is above a pulmonary embolism risk threshold.

Embodiment 97: The non-transitory computer readable medium of Embodiment 81, wherein the one or more medical images comprises a Computed Tomography (CT) image.

Embodiment 98: The non-transitory computer readable medium of Embodiment 81, wherein one or more of the one or more medical images is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 99: The non-transitory computer readable medium of Embodiment 81, wherein the hardware processor is further configured to generate one or more recommended treatments for the patient based at least in part on the generated risk assessment of coronary artery disease, generated risk assessment of aortic disease, generated risk assessment of pneumonia, and the generated risk assessment of pulmonary embolism when the patient is determined to be admitted.

Embodiment 100: The non-transitory computer readable medium of Embodiment 81, wherein the hardware processor is further configured to generate a graphical representation of the determination of hospital admission or discharge for the patient.

Embodiment 101: The non-transitory computer readable medium of Embodiment 81, wherein the hardware processor is further configured to generate the risk assessment of coronary artery disease based at least in part on one or more quantified atherosclerosis parameters.

Embodiment 102: The non-transitory computer readable medium of Embodiment 81, wherein hospital admission or discharge for the patient is determined in an emergency department.

Embodiment 103: A non-transitory computer readable medium configured for guiding therapeutic decision-making to facilitate determination of hospital admission or discharge for a patient based at least in part on automated segmentation and analysis of one or more medical images, the computer readable medium having program instructions for causing a hardware processor to perform a method of: accessing, by the computer system, one or more medical images of a chest of a patient, the one or more medical images comprising a representation of a portion of one or more coronary arteries, a portion of aorta, and a portion of lungs; automatically performing, by the computer system, image segmentation on the one or more medical images to identify a plurality of regions of interest, the plurality of regions comprising the portion of the one or more coronary arteries, the portion of aorta, and the portion of lungs; analyzing, by the computer system, the portion of the one or more coronary arteries in the one or more medical images to generate a risk assessment of coronary artery disease for the patient, wherein the risk assessment of coronary artery disease is generated based at least in part on generating one or more quantified parameters from the portion of the one or more coronary arteries in the one or more medical images and comparing the generated one or more quantified parameters to a coronary artery disease reference database; determining, by the computer system, whether the generated risk assessment of coronary artery disease for the patient is above a coronary artery disease risk threshold; analyzing, by the computer system, the portion of the aorta in the one or more medical images to generate a risk assessment of aortic disease for the patient, wherein the risk assessment of aortic disease is generated based at least in part on generating one or more quantified parameters from the portion of the aorta in the one or more medical images and comparing the generated one or more quantified parameters to an aortic disease reference database; determining, by the computer system, whether the generated risk assessment of aortic disease for the patient is above an aortic disease risk threshold; analyzing, by the computer system, the portion of the lungs in the one or more medical images to generate a risk assessment of pneumonia, wherein the risk assessment of pneumonia is generated based at least in part on generating one or more quantified parameters from the portion of the lungs in the one or more medical images and comparing the generated one or more quantified parameters to a pneumonia disease reference database; determining, by the computer system, whether the generated risk assessment of pneumonia for the patient is above a pneumonia risk threshold; analyzing, by the computer system, the portion of the lungs in the one or more medical images to generate a risk assessment of pulmonary embolism, wherein the risk assessment of pulmonary embolism is generated based at least in part on generating one or more quantified parameters from the portion of the lungs in the one or more medical images and comparing the generated one or more quantified parameters to a pulmonary embolism reference database; determining, by the computer system, whether the generated risk assessment of pulmonary embolism for the patient is above a pulmonary embolism risk threshold; and generating, by the computer system, a graphical representation of the determination of whether the generated risk assessment of coronary artery disease for the patient is above the coronary artery disease risk threshold, determination of whether the generated risk assessment of aortic disease for the patient is above the aortic disease risk threshold, determination of whether the generated risk assessment of pneumonia for the patient is above the pneumonia risk threshold, and determination of whether the generated risk assessment of pulmonary embolism for the patient is above a pulmonary embolism risk threshold, wherein the generated graphical representation is configured to be used to facilitate determination of hospital admission or discharge for a patient, wherein the computer system comprises a computer processor and an electronic storage medium.

Embodiment 104: The non-transitory computer readable medium of Embodiment 103, wherein the hardware processor is further configured to generate a ranking of need for care for the patient based at least in part on the determination of whether the generated risk assessment of coronary artery disease for the patient is above the coronary artery disease risk threshold, determination of whether the generated risk assessment of aortic disease for the patient is above the aortic disease risk threshold, determination of whether the generated risk assessment of pneumonia for the patient is above the pneumonia risk threshold, and determination of whether the generated risk assessment of pulmonary embolism for the patient is above a pulmonary embolism risk threshold.

Embodiment 105: The non-transitory computer readable medium of Embodiment 104, wherein the hardware processor is further configured to determine a resource utilization for the patient based at least in part on the generated ranking of need for care for the patient compared to other patients.

Embodiment 106: The non-transitory computer readable medium of Embodiment 103, wherein the one or more medical images comprises a single medical image comprising the portion of one or more coronary arteries, the portion of aorta, and the portion of lungs.

Embodiment 107: The non-transitory computer readable medium of Embodiment 106, wherein the single medical image is obtained using computed tomography (CT).

Embodiment 108: The non-transitory computer readable medium of Embodiment 26, wherein the single medical image comprises results from a coronary computed tomography angiography (CCTA), chest CT angiography (CTA), and CT pulmonary angiography.

Embodiment 109: The non-transitory computer readable medium of Embodiment 103, wherein the one or more medical images comprises a plurality of medical images comprising one or more of the portion of one or more coronary arteries, the portion of aorta, or the portion of lungs.

Embodiment 110: The non-transitory computer readable medium of Embodiment 103, wherein the hardware processor is further configured to perform image segmentation is performed based at least in part on utilizing an artificial intelligence algorithm trained on a plurality of medical images comprising the plurality of regions from a plurality of subjects.

Embodiment 111: The non-transitory computer readable medium of Embodiment 103, wherein the hardware processor is further configured to generate the risk assessment of coronary artery disease for the patient based at least in part on utilizing an artificial intelligence algorithm trained on a plurality of longitudinal medical images comprising the portion of one or more coronary arteries from a plurality of subjects.

Embodiment 112: The non-transitory computer readable medium of Embodiment 103, wherein the hardware processor is further configured to generate the risk assessment of aortic disease for the patient based at least in part on utilizing an artificial intelligence algorithm trained on a plurality of longitudinal medical images comprising the portion of aorta from a plurality of subjects.

Embodiment 113: The non-transitory computer readable medium of Embodiment 103, wherein the hardware processor is further configured to generate the risk assessment of pneumonia for the patient based at least in part on utilizing an artificial intelligence algorithm trained on a plurality of longitudinal medical images comprising the portion of lungs from a plurality of subjects.

Embodiment 114: The non-transitory computer readable medium of Embodiment 103, wherein the hardware processor is further configured to generate the risk assessment of pulmonary embolism for the patient based at least in part on utilizing an artificial intelligence algorithm trained on a plurality of longitudinal medical images comprising the portion of lungs from a plurality of subjects.

Embodiment 115: The non-transitory computer readable medium of Embodiment 103, wherein the hardware processor is further configured to categorize the generated risk assessment of one or more of coronary artery disease, aortic disease, pneumonia, or pulmonary embolism for the patient as one of low, intermediate, or high risk.

Embodiment 116: The non-transitory computer readable medium of Embodiment 103, wherein the hardware processor is further configured to: generate a weighted measure of the determination of whether the generated risk assessment of coronary artery disease for the patient is above the coronary artery disease risk threshold, determination of whether the generated risk assessment of aortic disease for the patient is above the aortic disease risk threshold, determination of whether the generated risk assessment of pneumonia for the patient is above the pneumonia risk threshold, and determination of whether the generated risk assessment of pulmonary embolism for the patient is above a pulmonary embolism risk threshold, wherein the generated weighted measure is configured to be used to facilitate determination of hospital admission or discharge for a patient.

Embodiment 117: The non-transitory computer readable medium of Embodiment 81, wherein the one or more medical images comprises a Computed Tomography (CT) image.

Embodiment 118: The non-transitory computer readable medium of Embodiment 81, wherein one or more of the one or more medical images is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 119: The non-transitory computer readable medium of Embodiment 81, wherein the hardware processor is further configured to generate the risk assessment of coronary artery disease based at least in part on one or more quantified atherosclerosis parameters.

Embodiment 120: The non-transitory computer readable medium of Embodiment 81, wherein the computer system is part of an emergency department computer network.

Image-Based Analysis and Risk Assessment of Type of Myocardial Infarction

Disclosed herein are systems, devices, and methods for image-based analysis and risk assessment of type of myocardial infarction.

In particular, in some embodiments, the systems, devices, and methods described herein are related to a method of peri-operative risk assessment of type of myocardial infarction for a patient based at least in part on automated analysis of one or more medical images. For example, in some embodiments, the systems, methods, and devices described herein are related to analysis of identified coronary arteries and one or more regions of plaque to generate a plurality of image-derived variables, the plurality of image-derived variables comprising one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, or low-density plaque volume. In some embodiments, the systems, devices, and methods described herein are configured to apply a machine learning algorithm to determine risk of a type of post-operative myocardial infarction subsequent to a vascular operation for the patient based at least in part on the plurality of image-derived variables. In some embodiments, the systems, devices, and methods described herein are determine a need for peri-operative treatment or planning for the patient based on the determined risk of type of post-operative myocardial infarction.

MI, also known as a "heart attack," can occur when one or more areas of the heart muscle do not get enough oxygen, such as when blood flow to the heart muscle is blocked. MI can be further classified into types, which can be helpful in guiding therapeutic recommendations. In some embodiments, the systems, devices, and methods described herein relate to guiding patient therapy based on the predicted type of MI in a peri-operative setting.

As noted above, MI can occur when one or more areas of the heart muscle do not get enough oxygen, such as when blood flow to the heart muscle is blocked. MI can further be broken down into two types: Type 1 and Type 2. Type 1 MI can be characterized by coronary plaque rupture, plaque erosion, blood clots, and/or calcified nodules. The majority of patients exhibiting spontaneous myocardial infarction tend to have Type 1. Type 2 MI can be characterized by an imbalance between the myocardial oxygen supply and demand. This can occur when the oxygen demand is greater than the current supply, as precipitated by extracardiac stressors such as tachycardia, hypotension, hypertension, etc. For example, patients who are severely stenotic are generally categorized as Type 2.

It can be clinically important to differentiate between the risk of Type 1 MI and Type 2 MI because the therapeutic focus may differ. For Type 1 MI patients, the focus of treatment can be centered around consideration of urgent coronary angiography and revascularization. For Type 2 MI patients, the focus can be on treating extracardiac stressors that precipitate the supply and demand imbalance. For example, if a patient is found to be at a higher risk of Type 2 MI, as opposed to Type 1, a physician may accordingly prescribe beta blockers to slow down the heart rate. Further, it can be advantageous to be able to understand a predicted etiology of myocardial infarction to specify a patient-specific treatment. For example, Type 1 MI can arise due to one or more of plaque rupture, plaque erosion, and/or calcified nodules. Therefore, it can be advantageous for a system to differentiate between the types of MI and guide therapy based on the type of MI predicted. In some embodiments, the systems, devices, and methods described herein relate to predicting the type and/or etiology of MI and/or guiding patient therapy based on the predicted type of MI. For example, in some embodiments, the systems, devices, and methods described herein are configured to generate and/or derive one or more features from one or more medical images, for example from regions of plaque, compare such features to known sample features with known risk and/or occurrence of a type and/or etiology of MI, and/or use the results of such comparison to predict the likelihood or risk of a subject experiencing a particular type and/or etiology of MI.

In some embodiments, the systems, devices, and methods are configured to determine risk of myocardial infarction in a peri-operative setting. The term "peri-operative" is generally understood as meaning the time around surgery and can expansively refer to the time that a patient goes into a hospital or doctor's office for surgery until the time the patient goes home.

Figure 19:
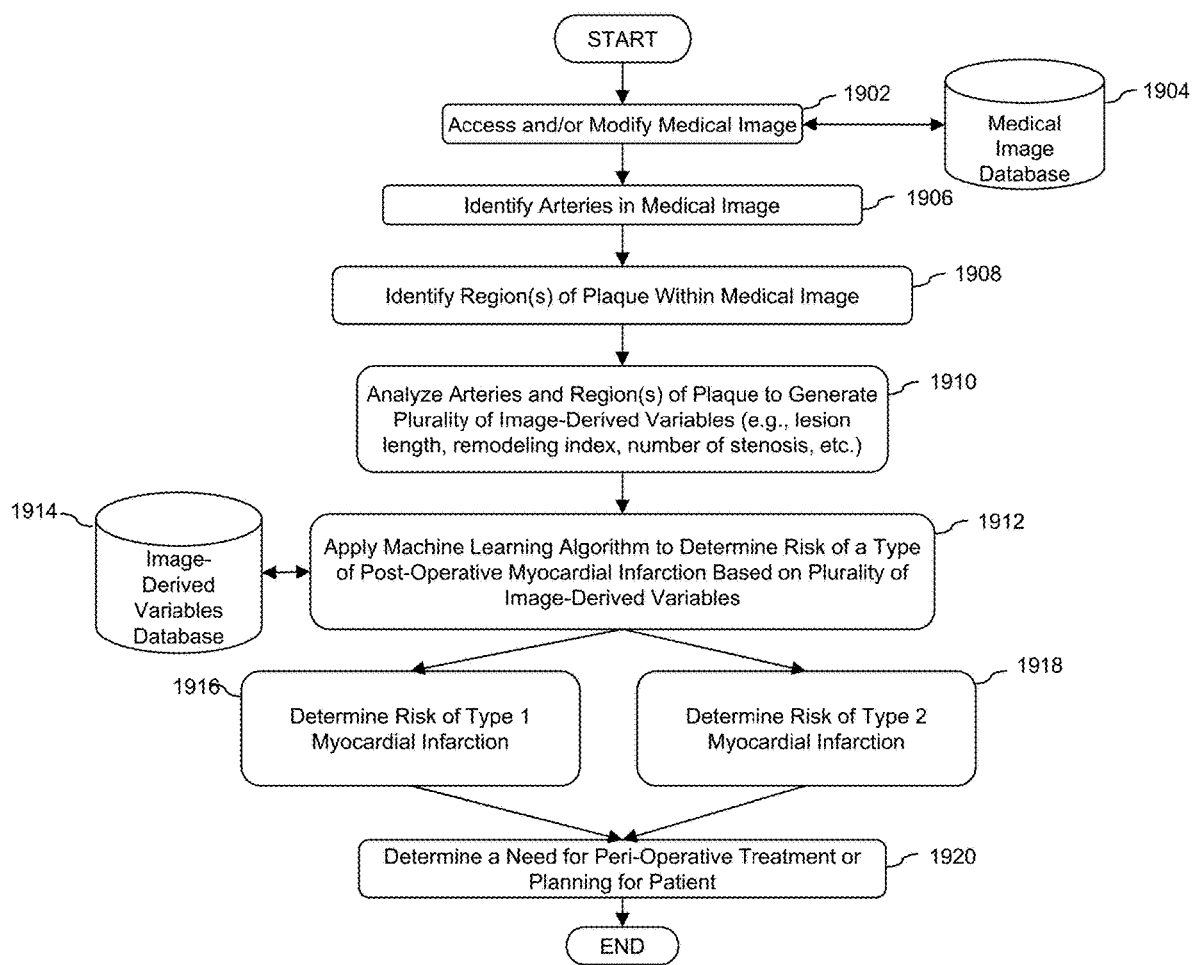
FIG. 19 is a flowchart illustrating an example embodiment(s) of systems, devices, and methods for image-based analysis and risk assessment of type of myocardial infarction.

FIG. 19 is a flowchart illustrating an example embodiment(s) of systems, devices, and methods for peri-operative risk assessment of type of myocardial infarction for a patient based at least in part on automated analysis of one or more medical images.

In some embodiments, at block 1902, the method can include accessing, by a computer system, one or more medical images of a patient, the one or more medical images comprising a representation of a portion of one or more coronary arteries. In some embodiments, the medical image can be stored in a medical image database 1904. In some embodiments, the medical image database 1904 can be locally accessible by the system and/or can be located remotely and accessible through a network connection.

In some embodiments, the one or more medical images comprises a Computed Tomography (CT) image. In some embodiments, the one or more of the one or more medical images is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

In some embodiments, at block 1906, the method can include analyzing, by the computer system, the one or more medical images to identify one or more coronary arteries. Additionally, in some embodiments, at block 1908, the method can include analyzing, by the computer system, the one or more medical images to identify the one or more coronary arteries comprising one or more regions of plaque.

In some embodiments, at block 1910, the method can include analyzing, by the computer system, the identified one or more coronary arteries and the one or more regions of plaque to generate a plurality of image-derived variables, the plurality of image-derived variables comprising one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, or low-density plaque volume. In some embodiments, the one or more variables can include one or more of percent atheroma volume of total plaque, total plaque volume, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, presence of two-feature positive plaques, number of two-feature positive plaques, vessel length, segment length, lesion length, lumen volume, number of chronic total occlusion (CTO), vessel volume, number of stenosis, severity of stenosis, remodeling index, minimum lumen diameter, maximum lumen diameter, mean lumen diameter, stenosis area percentage, stenosis diameter percentage, number of mild stenosis, number of moderate stenosis, number of zero stenosis, number of severe stenosis, presence of high-risk anatomy, presence of positive remodeling, number of severe stenosis excluding CTO, vessel area, lumen area, diameter stenosis percentage, presence of ischemia, number of stents, reference lumen diameter before stenosis, perivascular fat attenuation, or reference lumen diameter after stenosis. In some embodiments, low-density non-calcified plaque can be defined as a region of plaque with a radiodensity value less than or equal to about 30 Hounsfield units, non-calcified plaque can be defined as a region of plaque with a radiodensity value greater than about 30 Hounsfield units and/or less than or equal to about 350 Hounsfield units, calcified plaque can be defined as a region of plaque with a radiodensity value greater than about 350 Hounsfield units, low-density calcified plaque can be defined as a region of plaque with a radiodensity value greater than about 350 Hounsfield units and/or less than or equal to about 700 Hounsfield units, medium-density calcified plaque can be defined as a region of plaque with a radiodensity value greater than about 700 Hounsfield units and/or less than or equal to about 1000 Hounsfield units, and/or high-density calcified plaque can be defined as a region of plaque with a radiodensity value greater than about 1000 Hounsfield units.

In some embodiments, at block 1912, the method can include applying, by the computer system, a machine learning algorithm to determine risk of a type of post-operative myocardial infarction subsequent to a vascular operation for the patient based at least in part on the plurality of image-derived variables 1914. In some embodiments, the machine learning algorithm is trained based at least in part on the plurality of image-derived variables derived from medical images of other subjects with known risk and type of myocardial infarction. In some embodiments, the method can include generating a weighted measure of the plurality of image-derived variables, wherein the risk of type of post-operative myocardial infarction is determined based at least in part on the weighted measure of the plurality of image-derived variables.

In some embodiments, the type of post-operative myocardial infarction comprises one of type 1 myocardial infarction or type 2 myocardial infarction, wherein type 1 myocardial infarction is caused by plaque rupture, and wherein type 2 myocardial infarction is caused by mismatch in supply and demand of oxygen. In some embodiments, stenosis area percentage above a predetermined threshold is indicative of a high risk of post-operative type 2 myocardial infarction. In some embodiments, number of stenosis above a predetermined threshold is indicative of a high risk of post-operative type 2 myocardial infarction. In some embodiments, the risk of post-operative type 1 myocardial infarction or the risk of post-operative type 2 myocardial infarction for the patient comprises one of low, medium, or high risk.

In some embodiments, at block 1916, the method can include determining a risk of Type 1 myocardial infarction. In some embodiments, at block 1918, the method can include determining a risk of Type 2 myocardial infarction.

In some embodiments, at block 1920, the method can include determining, by the computer system, a need for peri-operative treatment or planning for the patient based on the determined risk of type of post-operative myocardial infarction. In some embodiments, the peri-operative treatment comprises one or more of prescription of beta blockers or stenting.

In some embodiments, a determination of high risk of post-operative type 2 myocardial infarction for the patient is indicative of a need for peri-operative use of beta blockers for the patient. In some embodiments, a determination of high risk of post-operative type 2 myocardial infarction for the patient is indicative of a need for stenting for the patient.

In some embodiments, the method can include determining, by the computer system, a need for cardiac catheterization for the patient prior to the vascular operation based at least in part on the determined risk of type of post-operative myocardial infarction. In some embodiments, the method can include determining, by the computer system, a type of cardiac catheterization for the patient based at least in part on the plurality of image-derived variables, the type of cardiac catheterization comprising one or more of coronary angiography, right heart catheterization, coronary catheterization, placement of a pacemaker or defibrillator, valve assessment, pulmonary angiography, shunt evaluation, ventriculography, percutaneous aortic valve replacement, balloon septostomy, stenting, or alcohol septal ablation. In some embodiments, the type of cardiac catheterization for the patient is determined using a machine learning algorithm trained based at least in part on the plurality of image-derived variables derived from medical images of other subjects with known types of cardiac catheterization.

In some embodiments, the method includes causing generation of a graphical representation of the determined type of cardiac catheterization for the patient. In some embodiments, the method includes causing, by the computer system, generation of a graphical representation of the determined need for cardiac catheterization for the patient. In some embodiments, the method includes causing, by the computer system, generation of a graphical representation of the determined risk of type of post-operative myocardial infarction.

The computer system 902 of FIG. 9, and in some instances, the analysis and/or risk assessment module 940, can be configured to carry out the functions, methods, acts, and/or processes for image-based analysis and risk assessment of type of myocardial infarction described herein, such as those described above with reference to FIG. 19.

The following are non-limiting examples of certain embodiments of systems and methods for image-based analysis and risk assessment of type of myocardial infarction. Other embodiments may include one or more other features, or different features, that are discussed herein.

Embodiment 1: A computer-implemented method of peri-operative risk assessment of type of myocardial infarction for a patient based at least in part on automated analysis of one or more medical images, the method comprising: accessing, by a computer system, one or more medical images of a patient, the one or more medical images comprising a representation of a portion of one or more coronary arteries; analyzing, by the computer system, the one or more medical images to identify one or more coronary arteries, the one or more coronary arteries comprising one or more regions of plaque; analyzing, by the computer system, the identified one or more coronary arteries and the one or more regions of plaque to generate a plurality of image-derived variables, the plurality of image-derived variables comprising one or more of percent atheroma volume of total plaque, total plaque volume, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, vessel length, segment length, lesion length, lumen volume, number of chronic total occlusion (CTO), vessel volume, number of stenosis, severity of stenosis, remodeling index, minimum lumen diameter, maximum lumen diameter, mean lumen diameter, stenosis area percentage, stenosis diameter percentage, number of mild stenosis, number of moderate stenosis, number of zero stenosis, number of severe stenosis, presence of high-risk anatomy, presence of positive remodeling, number of severe stenosis excluding CTO, vessel area, lumen area, diameter stenosis percentage, reference lumen diameter before stenosis, perivascular fat attenuation, or reference lumen diameter after stenosis; and applying, by the computer system, a machine learning algorithm to determine risk of a type of post-operative myocardial infarction subsequent to a vascular operation for the patient based at least in part on the plurality of image-derived variables, the type of post-operative myocardial infarction comprising one of type 1 myocardial infarction or type 2 myocardial infarction, wherein type 1 myocardial infarction is caused by plaque rupture, and wherein type 2 myocardial infarction is caused by mismatch in supply and demand of oxygen, wherein the machine learning algorithm is trained based at least in part on the plurality of image-derived variables derived from medical images of other subjects with known risk and type of myocardial infarction, wherein the determined risk of type of post-operative myocardial infarction is configured to be utilized to determine a need for peri-operative treatment or planning for the patient, wherein the computer system comprises a computer processor and an electronic storage medium.

Embodiment 2: The computer-implemented method of Embodiment 1, wherein the peri-operative treatment comprises one or more of prescription of beta blockers or stenting.

Embodiment 3: The computer-implemented method of Embodiment 1, wherein a determination of high risk of post-operative type 2 myocardial infarction for the patient is indicative of a need for peri-operative use of beta blockers for the patient.

Embodiment 4: The computer-implemented method of Embodiment 1, wherein stenosis area percentage above a predetermined threshold is indicative of a high risk of post-operative type 2 myocardial infarction.

Embodiment 5: The computer-implemented method of Embodiment 1, wherein number of stenosis above a predetermined threshold is indicative of a high risk of post-operative type 2 myocardial infarction.

Embodiment 6: The computer-implemented method of Embodiment 1, wherein a determination of high risk of post-operative type 2 myocardial infarction for the patient is indicative of a need for stenting for the patient.

Embodiment 7: The computer-implemented method of Embodiment 1, wherein the risk of post-operative type 1 myocardial infarction or the risk of post-operative type 2 myocardial infarction for the patient comprises one of low, medium, or high risk.

Embodiment 8: The computer-implemented method of Embodiment 1, further comprising determining, by the computer system, a need for cardiac catheterization for the patient prior to the vascular operation based at least in part on the determined risk of type of post-operative myocardial infarction.

Embodiment 9: The computer-implemented method of Embodiment 8, further comprising determining, by the computer system, a type of cardiac catheterization for the patient based at least in part on the plurality of image-derived variables, the type of cardiac catheterization comprising one or more of coronary angiography, right heart catheterization, coronary catheterization, placement of a pacemaker or defibrillator, valve assessment, pulmonary angiography, shunt evaluation, ventriculography, percutaneous aortic valve replacement, balloon septostomy, stenting, or alcohol septal ablation.

Embodiment 10: The computer-implemented method of Embodiment 9, wherein the type of cardiac catheterization for the patient is determined using a machine learning algorithm trained based at least in part on the plurality of image-derived variables derived from medical images of other subjects with known types of cardiac catheterization.

Embodiment 11: The computer-implemented method of Embodiment 9, further comprising causing, by the computer system, generation of a graphical representation of the determined type of cardiac catheterization for the patient.

Embodiment 12: The computer-implemented method of Embodiment 8, further comprising causing, by the computer system, generation of a graphical representation of the determined need for cardiac catheterization for the patient.

Embodiment 13: The computer-implemented method of Embodiment 1, further comprising causing, by the computer system, generation of a graphical representation of the determined risk of type of post-operative myocardial infarction.

Embodiment 14: The computer-implemented method of Embodiment 1, wherein the machine learning algorithm is trained based at least in part on the plurality of image-derived variables derived from medical images of other subjects with known event rates of post-operative type 1 myocardial infarction and post-operative type 2 myocardial infarction subsequent to vascular operations.

Embodiment 15: The computer-implemented method of Embodiment 1, further comprising generating, by the computer system, a weighted measure of the plurality of image-derived variables, wherein the risk of type of post-operative myocardial infarction is determined based at least in part on the weighted measure of the plurality of image-derived variables.

Embodiment 16: The computer-implemented method of Embodiment 1, wherein the one or more medical images comprises a Computed Tomography (CT) image.

Embodiment 17: The computer-implemented method of Embodiment 1, wherein one or more of the one or more medical images is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 18: The computer-implemented method of Embodiment 1, further comprising determining, by the computer system, likelihood of an etiology of type 1 myocardial infarction for the subject based at least in part on the plurality of image-derived variables, the etiology of type 1 myocardial infarction comprising one or more of plaque rupture, plaque erosion, or calcified nodules.

Embodiment 19: A system comprising: a non-transitory computer storage medium configured to at least store computer-executable instructions; and one or more computer hardware processors in communication with the first non-transitory computer storage medium, the one or more computer hardware processors configured to execute the computer-executable instructions to at least: access one or more medical images of a patient, the one or more medical images comprising a representation of a portion of one or more coronary arteries; analyze the one or more medical images to identify one or more coronary arteries, the one or more coronary arteries comprising one or more regions of plaque; analyze the identified one or more coronary arteries and the one or more regions of plaque to generate a plurality of image-derived variables, the plurality of image-derived variables comprising one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, or low-density plaque volume; and apply a machine learning algorithm to determine risk of a type of post-operative myocardial infarction subsequent to a vascular operation for the patient based at least in part on the plurality of image-derived variables, the type of post-operative myocardial infarction comprising one of type 1 myocardial infarction or type 2 myocardial infarction, wherein type 1 myocardial infarction is caused by plaque rupture, and wherein type 2 myocardial infarction is caused by mismatch in supply and demand of oxygen, wherein the machine learning algorithm is trained based at least in part on the plurality of image-derived variables derived from medical images of other subjects with known risk and type of myocardial infarction, wherein the determined risk of type of post-operative myocardial infarction is configured to be utilized to determine a need for peri-operative treatment or planning for the patient.

Embodiment 20: The system of Embodiment 19, wherein the peri-operative treatment comprises one or more of prescription of beta blockers or stenting.

Embodiment 21: The system of Embodiment 19, wherein a determination of high risk of post-operative type 2 myocardial infarction for the patient is indicative of a need for peri-operative use of beta blockers for the patient.

Embodiment 22: The system of Embodiment 19, wherein stenosis area percentage above a predetermined threshold is indicative of a high risk of post-operative type 2 myocardial infarction.

Embodiment 23: The system of Embodiment 19, wherein number of stenosis above a predetermined threshold is indicative of a high risk of post-operative type 2 myocardial infarction.

Embodiment 24: The system of Embodiment 19, wherein a determination of high risk of post-operative type 2 myocardial infarction for the patient is indicative of a need for stenting for the patient.

Embodiment 25: The system of Embodiment 19, wherein the risk of post-operative type 1 myocardial infarction or the risk of post-operative type 2 myocardial infarction for the patient comprises one of low, medium, or high risk.

Embodiment 26: The system of Embodiment 19, wherein the one or more computer hardware processors are further configured to determine a need for cardiac catheterization for the patient prior to the vascular operation based at least in part on the determined risk of type of post-operative myocardial infarction.

Embodiment 27: The system of Embodiment 26, wherein the one or more computer hardware processors are further configured to determine a type of cardiac catheterization for the patient based at least in part on the plurality of image-derived variables, the type of cardiac catheterization comprising one or more of coronary angiography, right heart catheterization, coronary catheterization, placement of a pacemaker or defibrillator, valve assessment, pulmonary angiography, shunt evaluation, ventriculography, percutaneous aortic valve replacement, balloon septostomy, stenting, or alcohol septal ablation.

Embodiment 28: The system of Embodiment 27, wherein the type of cardiac catheterization for the patient is determined using a machine learning algorithm trained based at least in part on the plurality of image-derived variables derived from medical images of other subjects with known types of cardiac catheterization.

Embodiment 29: The system of Embodiment 27, wherein the one or more computer hardware processors are further configured to cause generation of a graphical representation of the determined type of cardiac catheterization for the patient.

Embodiment 30: The system of Embodiment 26, wherein the one or more computer hardware processors are further configured to cause generation of a graphical representation of the determined need for cardiac catheterization for the patient.

Embodiment 31: The system of Embodiment 19, wherein the one or more computer hardware processors are further configured to cause generation of a graphical representation of the determined risk of type of post-operative myocardial infarction.

Embodiment 32: The system of Embodiment 19, wherein the machine learning algorithm is trained based at least in part on the plurality of image-derived variables derived from medical images of other subjects with known event rates of post-operative type 1 myocardial infarction and post-operative type 2 myocardial infarction subsequent to vascular operations.

Embodiment 33: The system of Embodiment 19, wherein the one or more computer hardware processors are further configured to generate a weighted measure of the plurality of image-derived variables, wherein the risk of type of post-operative myocardial infarction is determined based at least in part on the weighted measure of the plurality of image-derived variables.

Embodiment 34: The system of Embodiment 19, wherein the one or more medical images comprises a Computed Tomography (CT) image.

Embodiment 35: The system of Embodiment 19, wherein one or more of the one or more medical images is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 36: The system of Embodiment 19, wherein the one or more computer hardware processors are further configured to determine a likelihood of an etiology of type 1 myocardial infarction for the subject based at least in part on the plurality of image-derived variables, the etiology of type 1 myocardial infarction comprising one or more of plaque rupture, plaque erosion, or calcified nodules.

Embodiment 37: A non-transitory computer readable medium configured for peri-operative risk assessment of type of myocardial infarction for a patient based at least in part on automated analysis of one or more medical images, the computer readable medium having program instructions for causing a hardware processor to perform the method of: accessing one or more medical images of a patient, the one or more medical images comprising a representation of a portion of one or more coronary arteries; analyzing the one or more medical images to identify one or more coronary arteries, the one or more coronary arteries comprising one or more regions of plaque; analyzing the identified one or more coronary arteries and the one or more regions of plaque to generate a plurality of image-derived variables, the plurality of image-derived variables comprising one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, or low-density plaque volume; and applying a machine learning algorithm to determine risk of a type of post-operative myocardial infarction subsequent to a vascular operation for the patient based at least in part on the plurality of image-derived variables, the type of post-operative myocardial infarction comprising one of type 1 myocardial infarction or type 2 myocardial infarction, wherein type 1 myocardial infarction is caused by plaque rupture, and wherein type 2 myocardial infarction is caused by mismatch in supply and demand of oxygen, wherein the machine learning algorithm is trained based at least in part on the plurality of image-derived variables derived from medical images of other subjects with known risk and type of myocardial infarction, wherein the determined risk of type of post-operative myocardial infarction is configured to be utilized to determine a need for peri-operative treatment or planning for the patient.

Embodiment 38: The non-transitory computer readable medium of Embodiment 37, wherein the peri-operative treatment comprises one or more of prescription of beta blockers or stenting.

Embodiment 39: The non-transitory computer readable medium of Embodiment 37, wherein a determination of high risk of post-operative type 2 myocardial infarction for the patient is indicative of a need for peri-operative use of beta blockers for the patient.

Embodiment 40: The non-transitory computer readable medium of Embodiment 37, wherein stenosis area percentage above a predetermined threshold is indicative of a high risk of post-operative type 2 myocardial infarction.

Embodiment 41: The non-transitory computer readable medium of Embodiment 37, wherein number of stenosis above a predetermined threshold is indicative of a high risk of post-operative type 2 myocardial infarction.

Embodiment 42: The non-transitory computer readable medium of Embodiment 37, wherein a determination of high risk of post-operative type 2 myocardial infarction for the patient is indicative of a need for stenting for the patient.

Embodiment 43: The non-transitory computer readable medium of Embodiment 37, wherein the risk of post-operative type 1 myocardial infarction or the risk of post-operative type 2 myocardial infarction for the patient comprises one of low, medium, or high risk.

Embodiment 44: The non-transitory computer readable medium of Embodiment 37, wherein the hardware processor is further configured to determine a need for cardiac catheterization for the patient prior to the vascular operation based at least in part on the determined risk of type of post-operative myocardial infarction.

Embodiment 45: The non-transitory computer readable medium of Embodiment 44, wherein the hardware processor is further configured to determine a type of cardiac catheterization for the patient based at least in part on the plurality of image-derived variables, the type of cardiac catheterization comprising one or more of coronary angiography, right heart catheterization, coronary catheterization, placement of a pacemaker or defibrillator, valve assessment, pulmonary angiography, shunt evaluation, ventriculography, percutaneous aortic valve replacement, balloon septostomy, stenting, or alcohol septal ablation.

Embodiment 46: The non-transitory computer readable medium of Embodiment 45, wherein the type of cardiac catheterization for the patient is determined using a machine learning algorithm trained based at least in part on the plurality of image-derived variables derived from medical images of other subjects with known types of cardiac catheterization.

Embodiment 47: The non-transitory computer readable medium of Embodiment 45, wherein the hardware processor is further configured to cause generation of a graphical representation of the determined type of cardiac catheterization for the patient.

Embodiment 48: The non-transitory computer readable medium of Embodiment 44, wherein the hardware processor is further configured to cause generation of a graphical representation of the determined need for cardiac catheterization for the patient.

Embodiment 49: The non-transitory computer readable medium of Embodiment 37, wherein the hardware processor is further configured to cause generation of a graphical representation of the determined risk of type of post-operative myocardial infarction.

Embodiment 50: The non-transitory computer readable medium of Embodiment 37, wherein the machine learning algorithm is trained based at least in part on the plurality of image-derived variables derived from medical images of other subjects with known event rates of post-operative type 1 myocardial infarction and post-operative type 2 myocardial infarction subsequent to vascular operations.

Embodiment 51: The non-transitory computer readable medium of Embodiment 37, wherein the hardware processor is further configured to generate a weighted measure of the plurality of image-derived variables, wherein the risk of type of post-operative myocardial infarction is determined based at least in part on the weighted measure of the plurality of image-derived variables.

Embodiment 52: The non-transitory computer readable medium of Embodiment 37, wherein the one or more medical images comprises a Computed Tomography (CT) image.

Embodiment 53: The non-transitory computer readable medium of Embodiment 37, wherein one or more of the one or more medical images is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 54: The non-transitory computer readable medium of Embodiment 37, wherein the hardware processor is further configured to determine a likelihood of an etiology of type 1 myocardial infarction for the subject based at least in part on the plurality of image-derived variables, the etiology of type 1 myocardial infarction comprising one or more of plaque rupture, plaque erosion, or calcified nodules.

Image-Based Analysis and Risk Assessment of Post-Operative Myocardial Infarction Various embodiments described herein relate to systems, devices, and methods for image-based analysis and risk assessment of post-operative myocardial infarction. For example, in some embodiments, they systems, devices, and methods described herein are related to risk analysis based on one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, low-density plaque volume, and/or the like. In some embodiments, the systems, devices, and methods described herein are configured to determine a risk of coronary artery disease (CAD), such as for example myocardial infarction (MI), based on one or more plaque analyses described herein. In some embodiments, the systems, devices, and methods described herein are configured to determine the risk of myocardial infarction to occur following a medical procedure. In some embodiments, the systems, devices, and methods described herein are configured to generate a proposed treatment and/or graphical representation based on the determined risk of post-operative myocardial infarction and/or one or more plaque analyses described herein.

More specifically, in some embodiments, the systems, methods, and devices can be configured to analyze a medical image to perform one or more analyses of plaque and/or types of plaque, such as for example low density non-calcified plaque, calcified plaque, non-calcified plaque, and/or the like. In particular, in some embodiments, low density non-calcified plaque can be a focus due to the high-risk generally associated with low density non-calcified plaque. For example, low density non-calcified plaque can have a higher risk of potential rupture compared to other types of plaque, such as regular non-calcified plaque or calcified plaque. A plaque rupture can, in some instances, clog or block a vessel, thereby causing a heart attack or MI. As such, it can be advantageous to analyze one or more features of low density non-calcified plaque, and/or non-calcified plaque and/or calcified plaque, which may correspond to high or low risk of CAD and/or stability or instability of plaque. In some embodiments, the systems, devices, and methods are configured to analyze a medical image, such as a CT or CCTA image, to derive one or more features, measures, and/or characterizations of plaque, such as low density non-calcified plaque, non-calcified plaque, and/or calcified plaque, and use the same to facilitate an assessment or and/or generate an assessment of risk of CAD and/or stability or instability of plaque. Thus, in some embodiments, the systems, devices, and methods can provide an efficient and/or non-invasive method of assessing risk of CAD and/or plaque.

In some embodiments, the systems, methods, and devices can be configured to assess risk of a post-operative myocardial infarction and provide, from a risk/treatment database, a treatment option or plan for the physician to advise to the patient. In particular, surgical treatment, such as for example stent implantation, other cardiac surgery, and/or any other non-cardiac surgery, can be more risky for a patient that is considered to have a higher risk of myocardial infarction due to the presence of one or more factors associated with risk of MI or CAD. As such, in some embodiments described herein, the systems, methods, and devices are configured to analyze one or more medical images of a patient, such as a CCTA scan, prior to surgery to determine risk of MI or CAD for the patient, the results of which can be used to help determine whether or not to proceed with the surgical procedure. For example, in some embodiments, if the pre-operative analysis shows that a patient has high risk of MI or CAD based on one or more image-derived features, then it may be determined not to proceed with a surgical intervention for the patient in lieu of other treatment. In contrast, if the pre-operative analysis shows that a patient has low risk of MI or CAD based on one or more image-derived features, then it may be determined to proceed with a particular surgical intervention for the patient.

Figure 20:
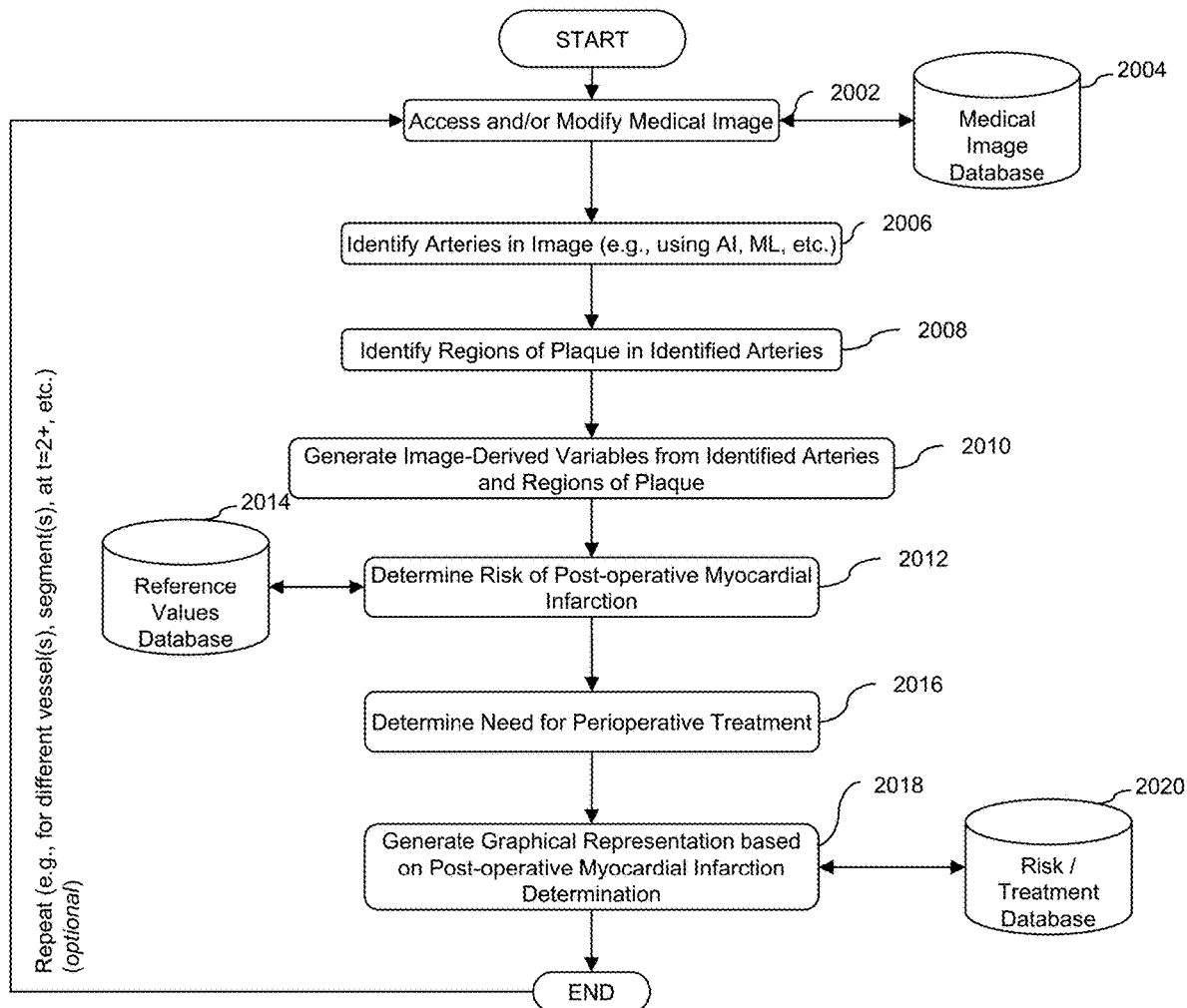
FIG. 20 is a flowchart illustrating an example embodiment(s) of systems, devices, and methods for image-based analysis and risk assessment of post-operative myocardial infarction.

FIG. 20 is a flowchart illustrating an example embodiment(s) of systems, devices, and methods for image-based analysis and risk assessment of post-operative myocardial infarction. As illustrated in FIG. 20, in some embodiments, the system can be configured to access and/or modify one or more medical images at block 2002. In some embodiments, the medical image can include one or more arteries, such as coronary, carotid, and/or other arteries of a subject. In some embodiments, the medical image can be stored in a medical image database 2004. In some embodiments, the medical image database 2004 can be locally accessible by the system and/or can be located remotely and accessible through a network connection. The medical image can comprise an image obtain using one or more modalities such as for example, CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the medical image comprises one or more of a contrast-enhanced CT image, non-contrast CT image, MR image, and/or an image obtained using any of the modalities described above.

In some embodiments, the system can be configured to automatically and/or dynamically perform one or more analyses of the medical image as discussed herein. For example, in some embodiments, at block 2006, the system can be configured to identify one or more vessels, such as of one or more arteries. In some embodiments, the analysis of one or more medical images is automated. The one or more arteries can include coronary arteries, carotid arteries, aorta, renal artery, lower extremity artery, upper extremity artery, and/or cerebral artery, amongst others. In some embodiments, the system can be configured to utilize one or more AI and/or ML algorithms to automatically and/or dynamically identify one or more arteries or coronary arteries using image processing. For example, in some embodiments, the one or more AI and/or ML algorithms can be trained using a Convolutional Neural Network (CNN) on a set of medical images on which arteries or coronary arteries have been identified, thereby allowing the AI and/or ML algorithm automatically identify arteries or coronary arteries directly from a medical image. In some embodiments, the arteries or coronary arteries are identified by size and/or location.

In some embodiments, at block 2008, the system can be configured to identify one or more regions of plaque in the medical image. In some embodiments, the system can be configured to utilize one or more AI and/or ML algorithms to automatically and/or dynamically identify one or more regions of plaque using image processing. For example, in some embodiments, the one or more AI and/or ML algorithms can be trained using a Convolutional Neural Network (CNN) on a set of medical images on which regions of plaque have been identified, thereby allowing the AI and/or ML algorithm automatically identify regions of plaque directly from a medical image. In some embodiments, the system is configured to identify vessel and lumen walls and classify everything in between the vessel and lumen walls as plaque.

In some embodiments, at block 2010, the system can be configured to generate image-derived variables from the identified arteries and regions of plaque. In some embodiments, these image-derived variables can include lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, low-density plaque volume, and/or the like. In some embodiments, the system can be configured to analyze and/or characterize one or more regions of plaque based on density. For example, in some embodiments, the system can be configured to analyze and/or characterize one or more regions of plaque based on absolute density and/or relative density and/or radiodensity. In some embodiments, the system can be configured to classify a region of plaque as one of low density noncalcified plaque, non-calcified plaque, and calcified plaque, using any one or more processes and/or features described herein.

In some embodiments, at block 2010, the system can be configured to analyze and/or characterize one or more regions of plaque based on one or more distances. For example, as described herein, in some embodiments, the system can be configured to determine a distance between a low density non-calcified plaque and lumen wall and/or vessel wall. In some embodiments, proximity of a low density non-calcified plaque to the lumen wall can be indicative of a high-risk plaque and/or CAD. Conversely, in some embodiments, a position of a low density non-calcified plaque far from the lumen wall can be indicative of less risk. In some embodiments, the system can be configured to utilize one or more predetermined thresholds in determining the risk factor associated with the proximity of low density non-calcified plaque with the vessel wall and/or lumen wall. In some embodiments, the system can be configured to utilize one or more image processing algorithms to automatically and/or dynamically determine one or more distances to and/or from one or more regions of plaque.

In some embodiments, at block 2010, the system can be configured to analyze and/or characterize one or more regions of plaque based on morphology or shape and/or one or more axes measurements of low density non-calcified plaque. As described herein, in some embodiments, the system can be configured to determine the length of one or more axes of a low density non-calcified plaque, such as for example a major axis of a longitudinal cross section and/or a major and/or minor axis of a latitudinal cross section of a low density non-calcified plaque. In some embodiments, the system can be configured to utilize the one more axes measurements to determine a morphology and/or shape of a low density non-calcified plaque. In some embodiments, the system can be configured to utilize one or more image processing algorithms to automatically and/or dynamically determine one or more axes measurements of one or more regions of plaque.

In some embodiments, the system can be configured to utilize one or more AI and/or ML algorithms to automatically and/or dynamically classify the shape of one or more regions of plaque using image processing. For example, in some embodiments, the one or more AI and/or ML algorithms can be trained using a Convolutional Neural Network (CNN) on a set of medical images on which the shape of regions of plaque have been identified, thereby allowing the AI and/or ML algorithm automatically identify the shape or morphology of a region of plaque directly from a medical image. In some embodiments, the system can be configured to classify the shape or morphology of a region of plaque as one or more of crescent, lobular, round, or bean-shaped. In some embodiments, round and/or bean-shaped plaques can be associated with high risk, while crescent and/or lobular-shaped plaques can be associated with low risk of CAD.

In some embodiments, at block 2010, the system can be configured to analyze and/or characterize one or more regions of plaque based on one or more sizes and/or volumes. For example, in some embodiments, the system can be configured to determine a size and/or volume of plaque based at least in part on one or more axes measurements described herein. In some embodiments, the system can be configured to determine the size and/or volume of a region of plaque directly from analysis of a three-dimensional image scan. In some embodiments, the system can be configured to determine the size and/or volume of total plaque, low-density non-calcified plaque, non-calcified plaque, calcified plaque, and/or a ratio between two of the aforementioned volumes or sizes. In some embodiments, a high total plaque volume and/or high low-density non-calcified plaque and/or non-calcified plaque volume can be associated with high risk of CAD. In some embodiments, a high ratio of low-density non-calcified plaque volume to total plaque volume and/or a high ratio of non-calcified plaque volume to total plaque volume can be associated with high risk of CAD. In some embodiments, a high calcified plaque volume and/or high ratio of calcified plaque volume to total plaque volume can be associated with low risk of CAD. In some embodiments, the system can be configured to utilize one or more predetermined threshold values for determining the risk of CAD based on plaque volume, size, or one or more ratios thereof. In some embodiments, the system can be configured to utilize one or more image processing algorithms to automatically and/or dynamically determine the size and/or volume of one or more regions of plaque.

In some embodiments, at block 2010, the system can be configured to analyze and/or characterize plaque based on embeddedness. For example, in some embodiments, the system can be configured to determined how embedded or surrounded a low density non-calcified plaque is by non-calcified plaque or calcified plaque. In some embodiments, the system can be configured to analyze the embeddedness of low density non-calcified plaque based on the degree by which it is surrounded by other types of plaque. In some embodiments, a higher embeddedness of a low density non-calcified plaque can be indicative of high risk of CAD. For example, in some embodiments, a low density non-calcified plaque that is surrounded by 270 degrees, or more, by non-calcified plaque can be associated with high risk of CAD. In some embodiments, the system can be configured to utilize one or more image processing algorithms to automatically and/or dynamically determine the embeddedness of one or more regions of plaque.

In some embodiments, at block 2012, the system can be configured to determine a risk of post-operative myocardial infarction based on one or more plaque analyses described herein, for example in relation to one or more of blocks 2002-2010. In some embodiments, a machine learning algorithm determines the risk of MI subsequent to a surgical operation. In some embodiments, the surgical operation is a vascular operation. In some embodiments, the risk of post-operative myocardial infarction for the patient comprises one of low, medium, or high risk. In some embodiments, the machine learning algorithm determines the risk of MI based at least in part on the plurality of image-derived variables. In some embodiments, the machine learning algorithm is trained on the plurality of image-derived variables derived from medical images of other subjects with known risk of myocardial infarction. In some embodiments, the system can be configured to determine a risk of CAD based on one or more plaque analyses described herein, for example in relation to one or more of blocks 2002-2010. In some embodiments, the system can be configured to utilize some or all of the artery and plaque analyses results. In some embodiments, the system can be configured to generate a weighted measure of some or all of the plaque analyses described herein in determining a risk of CAD or MI. In some embodiments, the system can be configured to refer to one or more reference values of one or more plaque analyses results in determining risk of CAD or MI. For example, in some embodiments, the one or more reference values can comprise one or more values derived from a population with varying states of risks of CAD or MI, wherein the one or more values can comprise one or more of one or more distances to and/or from a low density non-calcified plaque, one or more axes measurements, morphology classification, size and/or volume, and/or embeddedness of low density non-calcified plaque. In some embodiments, the one or more reference values can be stored on a reference values database 2014, which can be locally accessible by the system and/or can be located remotely and accessible through a network connection. In some embodiments, the system can be configured to generate a weighted measure of the plurality of image-derived variables, wherein the risk of post-operative myocardial infarction is determined based at least in part on the weighted measure of the plurality of image-derived variables.

In some embodiments, at block 2016, the system can be configured to determine whether perioperative treatment is necessary. In some embodiments, the need for perioperative treatment is determined using the risk of post-operative myocardial infarction. In some embodiments, the peri-operative treatment comprises one or more of a prescription of beta blockers or stenting. In some embodiments, a determination of high risk of post-operative myocardial infarction for the patient is indicative of a need for peri-operative use of beta blockers or stenting for the patient. In some embodiments, the system can be configured to determine whether cardiac catheterization is necessary for the patient prior to the surgical operation based on the determined risk of post-operative myocardial infarction and the plurality of image-derived variables. In some embodiments, the type of cardiac catheterization comprises one or more of coronary angiography, right heart catheterization, coronary catheterization, placement of a pacemaker or defibrillator, valve assessment, pulmonary angiography, shunt evaluation, ventriculography, percutaneous aortic valve replacement, balloon septostomy, stenting, or alcohol septal ablation. In some embodiments, the type of cardiac catheterization for the patient is determined using a machine learning algorithm trained based at least in part on the plurality of image-derived variables derived from medical images of other subjects with known types of cardiac catheterization. In some embodiments, the machine learning algorithm is trained based at least in part on the plurality of image-derived variables derived from medical images of other subjects with known event rates of post-operative myocardial infarction subsequent to surgical operations. In some embodiments, the surgical operation is a vascular operation.

In some embodiments, at block 2018, the system can be configured to generate a graphical representation of the analyses results, determined risk of CAD, and/or proposed treatment for the subject. In some embodiments, the analyses results can be displayed on a vessel, lesion, and/or subject basis. In some embodiments, the proposed treatment can include, for example, medical treatment such as statins, interventional treatment such as stent implantation, and/or lifestyle treatment such as exercise or diet. In some embodiments, in determining the risk or state of cardiovascular disease or health and/or treatment, the system can access a risk/treatment database 2020, which can be locally accessible by the system and/or can be located remotely and accessible through a network connection. In some embodiments, the risk/treatment database 2020 can include reference points or data that relate one or more treatment to cardiovascular disease risk or state determined based on one or more reference plaque analyses values. In some embodiments, the system can be configured to generate a graphical representation of the determined type of cardiac catheterization for the patient. In some embodiments, the system can be configured to generate a graphical representation of the determined need for cardiac catheterization for the patient. In some embodiments, the system can be configured to generate a graphical representation of the determined risk of post-operative myocardial infarction.

In some embodiments, the system can be configured to repeat one or more processes described in relation to blocks 2002-2020, for example for one or more other vessels, segment, regions of plaque, different subjects, and/or for the same subject at a different time. As such, in some embodiments, the system can provide for longitudinal disease tracking and/or personalized treatment for a subject.

The computer system 902 of FIG. 9, and in some instances, the analysis and/or risk assessment module 940, can be configured to carry out the functions, methods, acts, and/or processes for multivariable image-based analysis of post-operative myocardial infarction described herein, such as those described above with reference to FIG. 20.

The following are non-limiting examples of certain embodiments of systems and methods for multivariable image-based analysis of post-operative myocardial infarction. Other embodiments may include one or more other features, or different features, that are discussed herein.

Embodiment 1: A computer-implemented method of perioperative assessment of risk of postoperative myocardial infarction for a patient based at least in part on automated analysis of one or more medical images, the computer-implemented method comprising: accessing, by a computer system, one or more medical images of a patient, the one or more medical images comprising a representation of a portion of one or more coronary arteries; analyzing, by the computer system, the one or more medical images to identify one or more coronary arteries, the one or more coronary arteries comprising one or more regions of plaque; analyzing, by the computer system, the identified one or more coronary arteries and the one or more regions of plaque to generate a plurality of image-derived variables, the plurality of image-derived variables comprising one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, or low-density plaque volume; and applying, by the computer system, a machine learning algorithm to determine risk of postoperative myocardial infarction subsequent to a surgical operation for the patient based at least in part on the plurality of image-derived variables, wherein the machine learning algorithm is trained based at least in part on the plurality of image-derived variables derived from medical images of other subjects with known risk of myocardial infarction, wherein the determined risk of postoperative myocardial infarction is configured to be utilized to determine a need for perioperative treatment or planning for the patient, wherein the computer system comprises a computer processor and an electronic storage medium.

Embodiment 2: The computer-implemented method of Embodiment 1, wherein the surgical operation comprises a vascular operation.

Embodiment 3: The computer-implemented method of Embodiment 1, wherein the perioperative treatment comprises one or more of a prescription of beta blockers or stenting.

Embodiment 4: The computer-implemented method of Embodiment 1, wherein a determination of high risk of postoperative myocardial infarction for the patient is indicative of a need for perioperative use of beta blockers or stenting for the patient.

Embodiment 5: The computer-implemented method of Embodiment 1, wherein the risk of postoperative myocardial infarction for the patient comprises one of low, medium, or high risk.

Embodiment 6: The computer-implemented method of Embodiment 1, further comprising determining, by the computer system, a need for cardiac catheterization for the patient prior to the surgical operation based at least in part on the determined risk of postoperative myocardial infarction.

Embodiment 7: The computer-implemented method of Embodiment 6, further comprising determining, by the computer system, a type of cardiac catheterization for the patient based at least in part on the determined risk of postoperative myocardial infarction and the plurality of image-derived variables, the type of cardiac catheterization comprising one or more of coronary angiography, right heart catheterization, coronary catheterization, placement of a pacemaker or defibrillator, valve assessment, pulmonary angiography, shunt evaluation, ventriculography, percutaneous aortic valve replacement, balloon septostomy, stenting, or alcohol septal ablation.

Embodiment 8: The computer-implemented method of Embodiment 7, wherein the type of cardiac catheterization for the patient is determined using a machine learning algorithm trained based at least in part on the plurality of image-derived variables derived from medical images of other subjects with known types of cardiac catheterization.

Embodiment 9: The computer-implemented method of Embodiment 7, further comprising causing, by the computer system, generation of a graphical representation of the determined type of cardiac catheterization for the patient.

Embodiment 10: The computer-implemented method of Embodiment 6, further comprising causing, by the computer system, generation of a graphical representation of the determined need for cardiac catheterization for the patient.

Embodiment 11: The computer-implemented method of Embodiment 1, further comprising causing, by the computer system, generation of a graphical representation of the determined risk of postoperative myocardial infarction.

Embodiment 12: The computer-implemented method of Embodiment 1, wherein the machine learning algorithm is trained based at least in part on the plurality of image-derived variables derived from medical images of other subjects with known event rates of postoperative myocardial infarction subsequent to vascular operations.

Embodiment 13: The computer-implemented method of Embodiment 1, further comprising generating, by the computer system, a weighted measure of the plurality of image-derived variables, wherein the risk of postoperative myocardial infarction is determined based at least in part on the weighted measure of the plurality of image-derived variables.

Embodiment 14: The computer-implemented method of Embodiment 1, wherein the one or more medical images comprises a Computed Tomography (CT) image.

Embodiment 15: The computer-implemented method of Embodiment 1, wherein one or more of the one or more medical images is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 16: A system for determining perioperative assessment of risk of post-operative myocardial infarction for a patient based at least in part on automated analysis of one or more medical images, the system comprising: a non-transitory computer storage medium configured to at least store computer executable instructions; and one or more computer hardware processors in communication with the non-transitory computer storage medium, the one or more computer hardware processors configured to execute the computer-executable instructions to at least: accessing one or more medical images of a patient, the one or more medical images comprising a representation of a portion of one or more coronary arteries; analyzing the one or more medical images to identify one or more coronary arteries, the one or more coronary arteries comprising one or more regions of plaque; analyzing the identified one or more coronary arteries and the one or more regions of plaque to generate a plurality of image-derived variables, the plurality of image-derived variables comprising one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, or low-density plaque volume; and applying a machine learning algorithm to determine risk of post-operative myocardial infarction subsequent to a surgical operation for the patient based at least in part on the plurality of image-derived variables, wherein the machine learning algorithm is trained based at least in part on the plurality of image-derived variables derived from medical images of other subjects with known risk of myocardial infarction, wherein the determined risk of post-operative myocardial infarction is configured to be utilized to determine a need for perioperative treatment or planning for the patient.

Embodiment 17: The system of Embodiment 16, wherein the surgical operation comprises a vascular operation.

Embodiment 18: The system of Embodiment 16, wherein the perioperative treatment comprises one or more of a prescription of beta blockers or stenting.

Embodiment 19: The system of Embodiment 16, wherein a determination of high risk of post-operative myocardial infarction for the patient is indicative of a need for perioperative use of beta blockers or stenting for the patient.

Embodiment 20: The system of Embodiment 16, wherein the risk of post-operative myocardial infarction for the patient comprises one of low, medium, or high risk.

Embodiment 21: The system of Embodiment 16, further comprising determining, by the one or more computer hardware processors, a need for cardiac catheterization for the patient prior to the surgical operation based at least in part on the determined risk of post-operative myocardial infarction.

Embodiment 22: The system of Embodiment 21, further comprising determining, by the one or more computer hardware processors, a type of cardiac catheterization for the patient based at least in part on the determined risk of post-operative myocardial infarction and the plurality of image-derived variables, the type of cardiac catheterization comprising one or more of coronary angiography, right heart catheterization, coronary catheterization, placement of a pacemaker or defibrillator, valve assessment, pulmonary angiography, shunt evaluation, ventriculography, percutaneous aortic valve replacement, balloon septostomy, stenting, or alcohol septal ablation.

Embodiment 23: The system of Embodiment 22, wherein the type of cardiac catheterization for the patient is determined using a machine learning algorithm is trained based at least in part on the plurality of image-derived variables derived from medical images of other subjects with known types of cardiac catheterization.

Embodiment 24: The system of Embodiment 22, further comprising causing, by the one or more computer hardware processors, generation of a graphical representation of the determined type of cardiac catheterization for the patient.

Embodiment 25: The system of Embodiment 21, further comprising causing, by the one or more computer hardware processors, generation of a graphical representation of the determined need for cardiac catheterization for the patient.

Embodiment 26: The system of Embodiment 16, further comprising causing, by the one or more computer hardware processors, generation of a graphical representation of the determined risk of post-operative myocardial infarction.

Embodiment 27: The system of Embodiment 16, wherein the machine learning algorithm is trained based at least in part on the plurality of image-derived variables derived from medical images of other subjects with known event rates of post-operative myocardial infarction subsequent to surgical operations.

Embodiment 28: The system of Embodiment 16, further comprising generating, by the one or more computer hardware processors, a weighted measure of the plurality of image-derived variables, wherein the risk of post-operative myocardial infarction is determined based at least in part on the weighted measure of the plurality of image-derived variables.

Embodiment 29: The system of Embodiment 16, wherein the one or more medical images comprises a Computed Tomography (CT) image.

Embodiment 30: The system of Embodiment 16, wherein one or more of the one or more medical images is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 31: A non-transitory computer readable medium configured for perioperative assessment of risk of post-operative myocardial infarction for a patient based at least in part on automated analysis of one or more medical images, the computer readable medium having program instructions for causing a hardware processor to perform a method of: accessing one or more medical images of a patient, the one or more medical images comprising a representation of a portion of one or more coronary arteries; analyzing the one or more medical images to identify one or more coronary arteries, the one or more coronary arteries comprising one or more regions of plaque; analyzing the identified one or more coronary arteries and the one or more regions of plaque to generate a plurality of image-derived variables, the plurality of image-derived variables comprising one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, or low-density plaque volume; and applying a machine learning algorithm to determine risk of post-operative myocardial infarction subsequent to a surgical operation for the patient based at least in part on the plurality of image-derived variables, wherein the machine learning algorithm is trained based at least in part on the plurality of image-derived variables derived from medical images of other subjects with known risk of myocardial infarction, wherein the determined risk of post-operative myocardial infarction is configured to be utilized to determine a need for perioperative treatment or planning for the patient.

Embodiment 32: The non-transitory computer readable medium of Embodiment 31, wherein the surgical operation comprises a vascular operation.

Embodiment 33: The non-transitory computer readable medium of Embodiment 31, wherein the perioperative treatment comprises one or more of a prescription of beta blockers or stenting.

Embodiment 34: The non-transitory computer readable medium of Embodiment 31, wherein a determination of high risk of post-operative myocardial infarction for the patient is indicative of a need for perioperative use of beta blockers or stenting for the patient.

Embodiment 35: The non-transitory computer readable medium of Embodiment 31, wherein the risk of post-operative myocardial infarction for the patient comprises one of low, medium, or high risk.

Embodiment 36: The non-transitory computer readable medium of Embodiment 31, the method further comprising determining a need for cardiac catheterization for the patient prior to the surgical operation based at least in part on the determined risk of post-operative myocardial infarction.

Embodiment 37: The non-transitory computer readable medium of Embodiment 36, the method further comprising determining a type of cardiac catheterization for the patient based at least in part on the determined risk of post-operative myocardial infarction and the plurality of image-derived variables, the type of cardiac catheterization comprising one or more of coronary angiography, right heart catheterization, coronary catheterization, placement of a pacemaker or defibrillator, valve assessment, pulmonary angiography, shunt evaluation, ventriculography, percutaneous aortic valve replacement, balloon septostomy, stenting, or alcohol septal ablation.

Embodiment 38: The non-transitory computer readable medium of Embodiment 37, wherein the type of cardiac catheterization for the patient is determined using a machine learning algorithm trained based at least in part on the plurality of image-derived variables derived from medical images of other subjects with known types of cardiac catheterization.

Embodiment 39: The non-transitory computer readable medium of Embodiment 37, the method further comprising causing generation of a graphical representation of the determined type of cardiac catheterization for the patient.

Embodiment 40: The non-transitory computer readable medium of Embodiment 36, the method further comprising causing generation of a graphical representation of the determined need for cardiac catheterization for the patient.

Embodiment 41: The non-transitory computer readable medium of Embodiment 31, the method further comprising causing generation of a graphical representation of the determined risk of post-operative myocardial infarction.

Embodiment 42: The non-transitory computer readable medium of Embodiment 31, wherein the machine learning algorithm is trained based at least in part on the plurality of image-derived variables derived from medical images of other subjects with known event rates of post-operative myocardial infarction subsequent to surgical operations.

Embodiment 43: The non-transitory computer readable medium of Embodiment 31, the method further comprising generating a weighted measure of the plurality of image-derived variables, wherein the risk of post-operative myocardial infarction is determined based at least in part on the weighted measure of the plurality of image-derived variables.

Embodiment 44: The non-transitory computer readable medium of Embodiment 31, wherein the one or more medical images comprises a Computed Tomography (CT) image.

Embodiment 45: The non-transitory computer readable medium of Embodiment 31, wherein one or more of the one or more medical images is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Determination of Prescribed Flow Reserve for Treating Cardiovascular Disease

Disclosed herein are systems, devices, and methods for determination of prescribed flow reserve for treating cardiovascular disease. In particular, in some embodiments, the systems, devices, and methods described herein are related to determining the effectiveness of treatments for patients based on an individually prescribed blood flow reserve. In some embodiments, a patient's prescribed blood flow reserve is determined based on their blood flow at the maximum physical activity they engage in. Currently, flow reserve is typically determined for most patients using a common maximal hyperemia point, the maximum level of physical activity, or as the patient is sprinting. For patients who do not engage in such high degrees of physical activity, they may not benefit from the same treatments as those who engage in activities like sprinting. For example, stenting may be beneficial for a patient who engages in high degrees of physical activity by allowing higher amounts of blood flow, but it may be less beneficial for a more sedentary patient who does not engage in activities that require such increased blood flow. In some embodiments, the systems, devices, and methods described herein allow the blood flow reserve of a patient to be measured according to a state of sprinting, running, jogging, walking, or rest. In some embodiments, the systems, devices, and methods described herein are configured to recommend a treatment that will be tailored to a patient with their lifestyle.

Figure 21A:
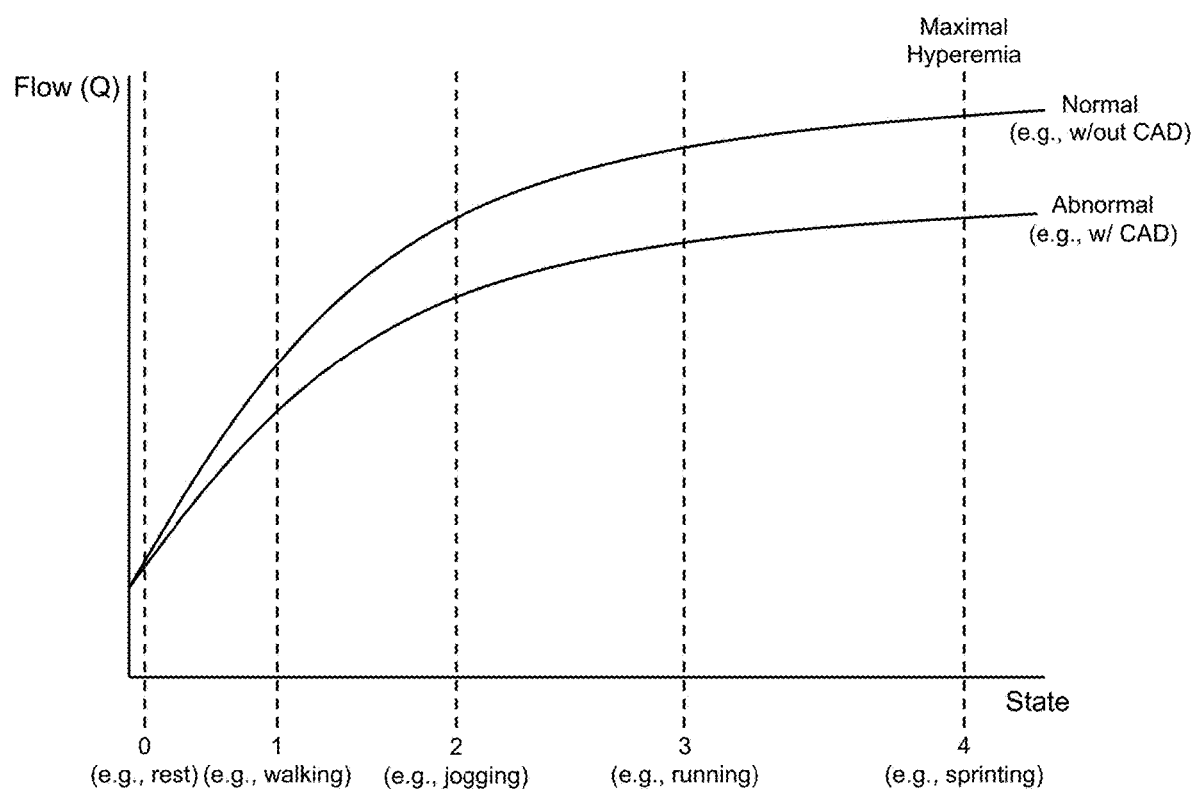
FIG. 21A is an example graph of blood flow at different levels of physical exertion for a patient with, and without, coronary artery disease.

FIG. 21A is an example graph of blood flow at different levels of physical exertion for a patient with coronary artery disease (CAD) and without CAD. The x axis of the graph in FIG. 21A may represent a state of the patient. In some embodiments, the x axis of the graph may represent the level of physical exertion a patient is undergoing. In some embodiments, at state 0 on the x axis, the patient is in a state of rest. In some embodiments, at state 1 on the x axis, the patient is walking. In some embodiments, at state 2 on the x axis, the patient is jogging. In some embodiments, at state 3 on the x axis, the patient is running. In some embodiments, at state 4 on the x axis, the patient is sprinting (i.e., at a high, or the highest, state of physical exertion). In some embodiments, the y axis of the graph represents the patient's blood flow. In some embodiments, a line on the graph represents the blood flow of a patient without coronary artery disease (normal blood flow). In some embodiments, a line on the graph represents the blood flow of a patient with coronary artery disease (abnormal blood flow). In some embodiments, state 4 on the x axis of the graph is considered maximal hyperemia. In some embodiments, taking the difference between normal blood flow at the point of maximal hyperemia and a patient's blood flow at the point of maximal hyperemia can determine the fractional flow reserve (FFR) of the patient. In some embodiments, patients who are more sedentary or less healthy may have higher FFR. In some embodiments, patients who are more active or healthy may have lower FFR. In some embodiments, a patient with an FFR lower than 0.75 is determined to have myocardial infarction (MI). In some embodiments, a patient with an FFR lower than 0.8 is determined to have MI. In some embodiments, a patient with an FFR of approximately 1 is considered healthy.

Figure 21B:
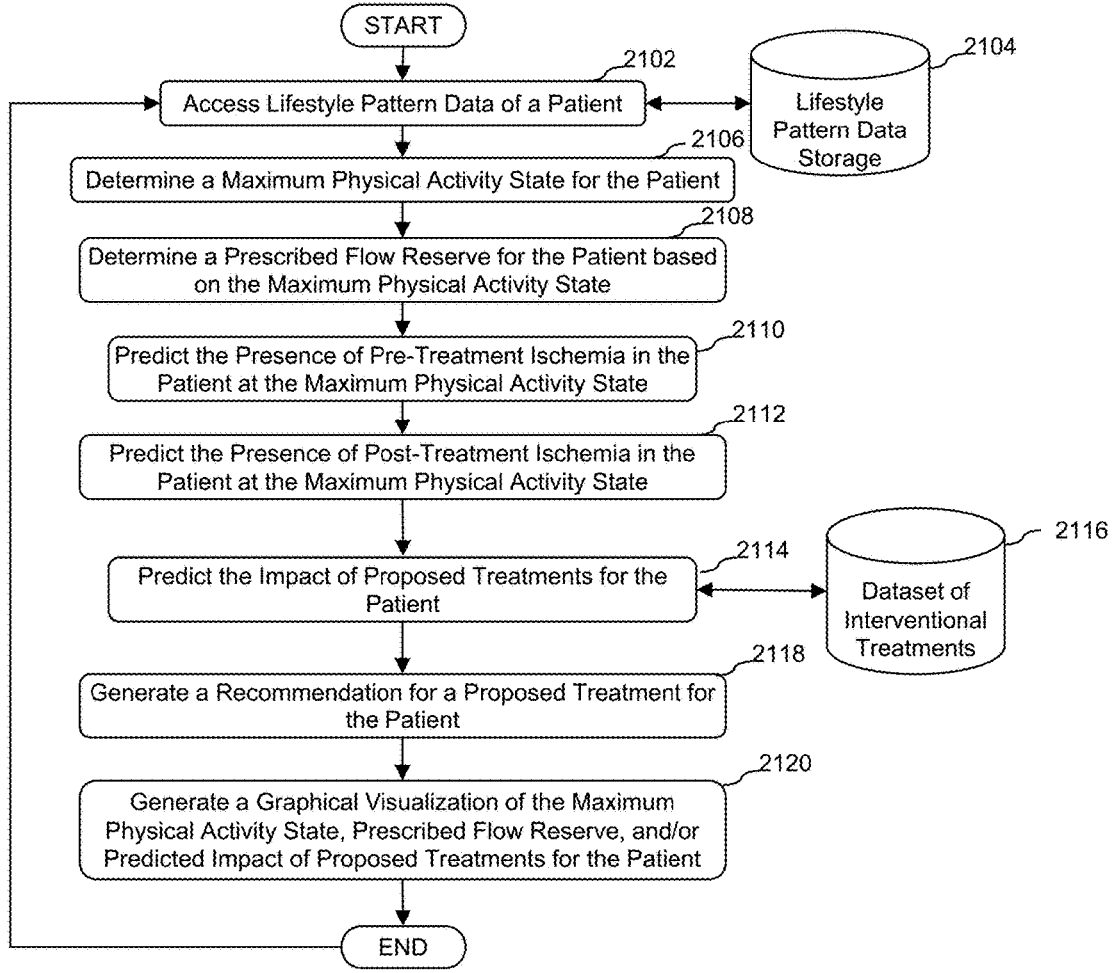
FIG. 21B is a flowchart illustrating an example embodiment(s) of systems, devices, and methods for determination of prescribed flow reserve for treating cardiovascular disease.

FIG. 21B is a flowchart illustrating an example embodiment(s) of systems, devices, and methods for determination of prescribed flow reserve for treating cardiovascular disease. As illustrated in FIG. 21B, in some embodiments, the system can be configured to access and/or modify lifestyle pattern data of a patient at block 2102. In some embodiments, the lifestyle pattern data can include the level of physical activity they engage in. In some embodiments, the lifestyle pattern data comprises one or more of heart rate, blood oxygen level, respiratory rate, or survey data. In some embodiments, the survey data comprises data related to physical activity levels of the subject. In some embodiments, one or more of heart rate, blood oxygen level, or respiratory rate of the patient is collected via a wearable device over a period of time. In some embodiments, the lifestyle pattern data can be stored in a lifestyle pattern data storage 2104. In some embodiments, the lifestyle pattern data storage 2104 can be locally accessible by the system and/or can be located remotely and accessed through a network connection.

In some embodiments, at block 2106, the system can be configured to determine a maximum physical activity state for the patient. In some embodiments, the maximum physical activity state comprises one or more of rest, walking, jogging, running, or sprinting. In some embodiments, the maximum physical activity state is determined on a continuous scale. In some embodiments, the maximum physical activity state for the patient meets a predetermined confidence threshold. In some embodiments, the predetermined confidence threshold comprises about 90%. In some embodiments, the maximum physical activity state for the patient is determined based at least in part on the data indicative of the lifestyle pattern of the patient. In some embodiments, the system can be configured to utilize one or more AI and/or ML algorithms to automatically and/or dynamically determine the patient's maximum physical activity state. In some embodiments, the data used to determine maximum physical activity state for a patient can also include medications, self-reported activity, Bruce treadmill stress test, blood pressure, and/or the like.

In some embodiments, at block 2108, the system can be configured to determine a prescribed flow reserve for the patient based on the maximum physical activity state. In some embodiments, the prescribed flow reserve comprises a ratio or percentage of coronary blood flow rate of the patient at the maximum physical activity state against a reference coronary blood flow rate at the maximum physical activity state. In some embodiments, the prescribed flow reserve of the patient at the maximum physical activity state is determined based at least in part on one or more parameters derived from analyzing a medical image of the patient, the medical image of the patient comprising a portion of coronary arteries, wherein the one or more parameters comprise one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, or low-density plaque volume. In some embodiments, the one or more parameters further comprise one or more of percent atheroma volume of total plaque, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, presence of two-feature positive plaques, number of two-feature positive plaques, segment length, severity of stenosis, minimum lumen diameter, maximum lumen diameter, mean lumen diameter, number of moderate stenosis, number of zero stenosis, number of severe stenosis, presence of high-risk anatomy, number of severe stenosis excluding CTO, vessel area, lumen area, diameter stenosis percentage, presence of ischemia, number of stents, reference lumen diameter before stenosis, perivascular fat attenuation, or reference lumen diameter after stenosis. In some embodiments, the medical image is obtained using computed tomography (CT). In some embodiments, the medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS). In some embodiments, low-density non-calcified plaque comprises a region of plaque with a radiodensity value less than or equal to about 30 Hounsfield units on a computed tomography (CT) image, non-calcified plaque comprises a region of plaque with a radiodensity value greater than about 30 Hounsfield units and less than or equal to about 350 Hounsfield units on a CT image, calcified plaque comprises a region of plaque with a radiodensity value greater than about 350 Hounsfield units on a CT image, low-density calcified plaque comprises a region of plaque with a radiodensity value greater than about 350 Hounsfield units and less than or equal to about 700 Hounsfield units on a CT image, medium-density calcified plaque comprises a region of plaque with a radiodensity value greater than about 700 Hounsfield units and less than or equal to about 1000 Hounsfield units on a CT image, and high-density calcified plaque comprises a region of plaque with a radiodensity value greater than about 1000 Hounsfield units on a CT image. In some embodiments, the prescribed flow reserve of the patient at the maximum physical activity state is determined using one or more of an artificial intelligence (AI) or machine learning (ML) algorithm. In some embodiments, the system can be configured to utilize one or more AI and/or ML algorithms to automatically and/or dynamically determine the patient's prescribed blood flow. In some embodiments, the prescribed flow reserve of the patient at the maximum physical activity state is determined based at least in part on fractional flow reserve derived from computed tomography. In some embodiments, the prescribed flow reserve of the patient at the maximum physical activity state is determined based at least in part on fractional flow reserve derived from computed tomography, computational fractional flow reserve, virtual fractional flow reserve, vessel fractional flow reserve, quantitative flow ratio, or invasive fractional flow reserve. In some embodiments, the prescribed flow reserve can be computationally determined. In some embodiments, the prescribed flow reserve can be used to determine one or more thresholds for determining if a patient and/or a lesion and/or vessel of the patient is ischemic.

In some embodiments, at block 2110, the system can be configured to predict the presence of pre-treatment ischemia in the patient at the maximum physical activity state. In some embodiments, the presence of pre-treatment ischemia is predicted using an artificial intelligence (AI), or machine learning (ML) algorithm, applied to the one or more parameters derived from analyzing the medical image of the patient, wherein prediction of presence of pre-treatment ischemia at the determined maximum physical activity state can be suggestive of treating the patient with the proposed treatment.

In some embodiments, at block 2112, the system can be configured to predict the presence of post-treatment ischemia in the patient at the maximum physical activity state. In some embodiments, the presence of post-treatment ischemia is predicted using an artificial intelligence (AI) or machine learning (ML) algorithm applied to the one or more parameters derived from analyzing a post-treatment medical image of the patient, the post-treatment medical image of the patient comprising a portion of coronary arteries, wherein prediction of presence of post-treatment ischemia at the determined maximum physical activity state can be suggestive of treating the patient with additional treatment.

In some embodiments, at block 2114, the system can be configured to predict the impact of proposed treatments for the patient. In some embodiments, the impact of the proposed treatment on the prescribed flow reserve of the patient is predicted based at least in part on a plurality of reference data derived from a plurality of subjects treated with the proposed treatment with varying prescribed flow reserves. In some embodiments, the proposed treatment can include, for example, medical treatment such as statins, interventional treatment such as stent implantation, and/or lifestyle treatment such as exercise or diet. In some embodiments, in determining the risk or state of cardiovascular disease or health and/or treatment, the system can access an interventional treatment database 2116, which can be locally accessible by the system and/or can be located remotely and accessible through a network connection. In some embodiments, the interventional treatment database 2116 can include reference points or data that relate one or more treatments to cardiovascular disease risk or state determined based on one or more reference values. In some embodiments, the impact of the proposed treatment on the prescribed flow reserve of the patient at the maximum physical activity state prescribed flow reserve is determined using one or more of an artificial intelligence (AI) or machine learning (ML) algorithm.

In some embodiments, at block 2118, the system can be configured to generate a recommendation of a proposed treatment for the patient. In some embodiments, the predicted impact of the proposed treatment on the prescribed flow reserve of the patient at the maximum physical activity state is used to determine whether to treat the patient with the proposed treatment. In some embodiments, the proposed treatment comprises stenting. In some embodiments, the proposed treatment comprises one or more of lifestyle change, exercise, diet, medication, stenting, or surgical procedure.

In some embodiments, at block 2120, the system can be configured to generate a graphical visualization of one or more of the determined maximum physical activity states for the patient, the prescribed flow reserve of the patient at the determined maximum physical activity state, or the predicted impact of the proposed treatment on the prescribed flow reserve of the patient at the maximum physical activity state. In some embodiments, the analyses results can be displayed on a vessel, lesion, and/or subject basis. In some embodiments, the proposed treatment can include, for example, medical treatment such as statins, interventional treatment such as stent implantation, and/or lifestyle treatment such as exercise or diet In some embodiments, the system can be configured to repeat one or more processes described in relation to blocks 2102-2120, for example for one or more other vessels, segments, regions of plaque, different subjects, and/or for the same subject at a different time. As such, in some embodiments, the system can provide for longitudinal disease tracking and/or personalized treatment for a subject.

The computer system 902 of FIG. 9, and in some instances, the analysis and/or risk assessment module 940, can be configured to carry out the functions, methods, acts, and/or processes for determination of prescribed flow reserve for treating cardiovascular disease described herein, such as those described above with reference to FIG. 21A-21B.

The following are non-limiting examples of certain embodiments of systems and methods for determination of prescribed flow reserve for treating cardiovascular disease. Other embodiments may include one or more other features, or different features, that are discussed herein.

Embodiment 1: A computer-implemented method of determining a prescribed flow reserve of a patient based on a patient-specific maximum physical activity state to facilitate determination of a cardiovascular disease treatment for the patient, the method comprising: accessing, by a computer system, data indicative of a lifestyle pattern of a patient, the data comprising one or more of heart rate, blood oxygen level, respiratory rate, or survey data; determining, by the computer system, a maximum physical activity state for the patient that meets a predetermined confidence threshold, the maximum physical activity state for the patient determined based at least in part on the data indicative of the lifestyle pattern of the patient; determining, by the computer system, a prescribed flow reserve of the patient at the maximum physical activity state, wherein prescribed flow reserve comprises a ratio or percentage of coronary blood flow rate of the patient at the maximum physical activity state against a reference coronary blood flow rate at the maximum physical activity state; and predicting, by the computer system, an impact of a proposed treatment on the prescribed flow reserve of the patient at the maximum physical activity state, wherein the impact of the proposed treatment on the prescribed flow reserve of the patient is predicted based at least in part on a plurality of reference data derived from a plurality of subjects treated with the proposed treatment with varying prescribed flow reserves, wherein the predicted impact of the proposed treatment on the prescribed flow reserve of the patient at the maximum physical activity state is used to determine whether to treat the patient with the proposed treatment, wherein the computer system comprises a computer processor and an electronic storage medium.

Embodiment 2: The computer-implemented method of Embodiment 1, wherein the prescribed flow reserve of the patient at the maximum physical activity state is determined based at least in part on one or more parameters derived from analyzing a medical image of the patient, the medical image of the patient comprising a portion of coronary arteries, wherein the one or more parameters comprise one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, or low-density plaque volume.

Embodiment 3: The computer-implemented method of Embodiment 2, wherein the prescribed flow reserve of the patient at the maximum physical activity state is determined using one or more of an artificial intelligence (AI) or machine learning (ML) algorithm.

Embodiment 4: The computer-implemented method of Embodiment 2, wherein the one or more parameters further comprise one or more of percent atheroma volume of total plaque, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, presence of two-feature positive plaques, number of two-feature positive plaques, segment length, severity of stenosis, minimum lumen diameter, maximum lumen diameter, mean lumen diameter, number of moderate stenosis, number of zero stenosis, number of severe stenosis, presence of high-risk anatomy, number of severe stenosis excluding CTO, vessel area, lumen area, diameter stenosis percentage, presence of ischemia, number of stents, reference lumen diameter before stenosis, perivascular fat attenuation, or reference lumen diameter after stenosis.

Embodiment 5: The computer-implemented method of Embodiment 4, wherein low-density non-calcified plaque comprises a region of plaque with a radiodensity value less than or equal to about 30 Hounsfield units on a computed tomography (CT) image, non-calcified plaque comprises a region of plaque with a radiodensity value greater than about 30 Hounsfield units and less than or equal to about 350 Hounsfield units on a CT image, calcified plaque comprises a region of plaque with a radiodensity value greater than about 350 Hounsfield units on a CT image, low-density calcified plaque comprises a region of plaque with a radiodensity value greater than about 350 Hounsfield units and less than or equal to about 700 Hounsfield units on a CT image, medium-density calcified plaque comprises a region of plaque with a radiodensity value greater than about 700 Hounsfield units and less than or equal to about 1000 Hounsfield units on a CT image, and high-density calcified plaque comprises a region of plaque with a radiodensity value greater than about 1000 Hounsfield units on a CT image.

Embodiment 6: The computer-implemented method of Embodiment 1, wherein the prescribed flow reserve of the patient at the maximum physical activity state is determined based at least in part on fractional flow reserve derived from computed tomography.

Embodiment 7: The computer-implemented method of Embodiment 1, wherein the prescribed flow reserve of the patient at the maximum physical activity state is determined based at least in part on fractional flow reserve derived from computed tomography, computational fractional flow reserve, virtual fractional flow reserve, vessel fractional flow reserve, quantitative flow ratio, or invasive fractional flow reserve.

Embodiment 8: The computer-implemented method of Embodiment 1, wherein the impact of the proposed treatment on the prescribed flow reserve of the patient at the maximum physical activity state prescribed flow reserve is determined using one or more of an artificial intelligence (AI) or machine learning (ML) algorithm.

Embodiment 9: The computer-implemented method of Embodiment 2, further comprising predicting, by the computer system, presence of pre-treatment ischemia in the patient at the determined maximum physical activity state when the patient is determined not to be treated with the proposed treatment, wherein presence of pre-treatment ischemia is predicted using an artificial intelligence (AI) or machine learning (ML) algorithm applied to the one or more parameters derived from analyzing the medical image of the patient, wherein prediction of presence of pre-treatment ischemia at the determined maximum physical activity state is suggestive of treating the patient with the proposed treatment.

Embodiment 10: The computer-implemented method of Embodiment 2, further comprising predicting, by the computer system, presence of post-treatment ischemia in the patient at the determined maximum physical activity state when the patient is determined to be treated with the proposed treatment, wherein presence of post-treatment ischemia is predicted using an artificial intelligence (AI) or machine learning (ML) algorithm applied to the one or more parameters derived from analyzing a post-treatment medical image of the patient, the post-treatment medical image of the patient comprising a portion of coronary arteries, wherein prediction of presence of post-treatment ischemia at the determined maximum physical activity state is suggestive of treating the patient with additional treatment.

Embodiment 11: The computer-implemented method of Embodiment 1, further comprising generating, by the computer system, a graphical visualization of one or more of the determined maximum physical activity state for the patient, the prescribed flow reserve of the patient at the determined maximum physical activity state, or the predicted impact of the proposed treatment on the prescribed flow reserve of the patient at the maximum physical activity state.

Embodiment 12: The computer-implemented method of Embodiment 1, wherein the survey data comprises data related to physical activity levels of the subject.

Embodiment 13: The computer-implemented method of Embodiment 1, wherein one or more of heart rate, blood oxygen level, or respiratory rate of the patient is collected via a wearable device over a period of time.

Embodiment 14: The computer-implemented method of Embodiment 1, wherein the maximum physical activity state comprises one or more of rest, walking, jogging, running, or sprinting.

Embodiment 15: The computer-implemented method of Embodiment 1, wherein the maximum physical activity state is determined on a continuous scale.

Embodiment 16: The computer-implemented method of Embodiment 1, wherein the proposed treatment comprises stenting.

Embodiment 17: The computer-implemented method of Embodiment 1, wherein the proposed treatment comprises one or more of lifestyle change, exercise, diet, medication, stenting, or surgical procedure.

Embodiment 18: The computer-implemented method of Embodiment 1, wherein the predetermined confidence threshold comprises about 90%.

Embodiment 19: The computer-implemented method of Embodiment 2, wherein the medical image is obtained using computed tomography (CT).

Embodiment 20: The computer-implemented method of Embodiment 2, wherein the medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 21: A non-transitory computer readable medium configured for determining a prescribed flow reserve of a patient based on a patient-specific maximum physical activity state to facilitate determination of a cardiovascular disease treatment for the patient, the computer readable medium having program instructions for causing a hardware processor to perform a method of: accessing data indicative of a lifestyle pattern of a patient, the data comprising one or more of heart rate, blood oxygen level, respiratory rate, or survey data; determining a maximum physical activity state for the patient that meets a predetermined confidence threshold, the maximum physical activity state for the patient determined based at least in part on the data indicative of the lifestyle pattern of the patient; determining a prescribed flow reserve of the patient at the maximum physical activity state, wherein prescribed flow reserve comprises a ratio or percentage of coronary blood flow rate of the patient at the maximum physical activity state against a reference coronary blood flow rate at the maximum physical activity state; and predicting an impact of a proposed treatment on the prescribed flow reserve of the patient at the maximum physical activity state, wherein the impact of the proposed treatment on the prescribed flow reserve of the patient is predicted based at least in part on a plurality of reference data derived from a plurality of subjects treated with the proposed treatment with varying prescribed flow reserves, wherein the predicted impact of the proposed treatment on the prescribed flow reserve of the patient at the maximum physical activity state is used to determine whether to treat the patient with the proposed treatment.

Embodiment 22: The non-transitory computer readable medium configured as in Embodiment 21, wherein the prescribed flow reserve of the patient at the maximum physical activity state is determined based at least in part on one or more parameters derived from analyzing a medical image of the patient, the medical image of the patient comprising a portion of coronary arteries, wherein the one or more parameters comprise one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, or low-density plaque volume.

Embodiment 23: The non-transitory computer readable medium configured as in Embodiment 22, wherein the prescribed flow reserve of the patient at the maximum physical activity state is determined using one or more of an artificial intelligence (AI) or machine learning (ML) algorithm.

Embodiment 24: The non-transitory computer readable medium configured as in Embodiment 22, wherein the one or more parameters further comprise one or more of percent atheroma volume of total plaque, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, presence of two-feature positive plaques, number of two-feature positive plaques, segment length, severity of stenosis, minimum lumen diameter, maximum lumen diameter, mean lumen diameter, number of moderate stenosis, number of zero stenosis, number of severe stenosis, presence of high-risk anatomy, number of severe stenosis excluding CTO, vessel area, lumen area, diameter stenosis percentage, presence of ischemia, number of stents, reference lumen diameter before stenosis, perivascular fat attenuation, or reference lumen diameter after stenosis.

Embodiment 25: The non-transitory computer readable medium configured as in Embodiment 24, wherein low-density non-calcified plaque comprises a region of plaque with a radiodensity value less than or equal to about 30 Hounsfield units on a computed tomography (CT) image, non-calcified plaque comprises a region of plaque with a radiodensity value greater than about 30 Hounsfield units and less than or equal to about 350 Hounsfield units on a CT image, calcified plaque comprises a region of plaque with a radiodensity value greater than about 350 Hounsfield units on a CT image, low-density calcified plaque comprises a region of plaque with a radiodensity value greater than about 350 Hounsfield units and less than or equal to about 700 Hounsfield units on a CT image, medium-density calcified plaque comprises a region of plaque with a radiodensity value greater than about 700 Hounsfield units and less than or equal to about 1000 Hounsfield units on a CT image, and high-density calcified plaque comprises a region of plaque with a radiodensity value greater than about 1000 Hounsfield units on a CT image.

Embodiment 26: The non-transitory computer readable medium configured as in Embodiment 21, wherein the prescribed flow reserve of the patient at the maximum physical activity state is determined based at least in part on fractional flow reserve derived from computed tomography.

Embodiment 27: The non-transitory computer readable medium configured as in Embodiment 21, wherein the prescribed flow reserve of the patient at the maximum physical activity state is determined based at least in part on fractional flow reserve derived from computed tomography, computational fractional flow reserve, virtual fractional flow reserve, vessel fractional flow reserve, quantitative flow ratio, or invasive fractional flow reserve.

Embodiment 28: The non-transitory computer readable medium configured as in Embodiment 21, wherein the impact of the proposed treatment on the prescribed flow reserve of the patient at the maximum physical activity state prescribed flow reserve is determined using one or more of an artificial intelligence (AI) or machine learning (ML) algorithm.

Embodiment 29: The non-transitory computer readable medium configured as in Embodiment 22, further comprising: predicting presence of pre-treatment ischemia in the patient at the determined maximum physical activity state when the patient is determined not to be treated with the proposed treatment, wherein presence of pre-treatment ischemia is predicted using an artificial intelligence (AI) or machine learning (ML) algorithm applied to the one or more parameters derived from analyzing the medical image of the patient, wherein prediction of presence of pre-treatment ischemia at the determined maximum physical activity state is suggestive of treating the patient with the proposed treatment.

Embodiment 30: The non-transitory computer readable medium configured as in Embodiment 22, further comprising: predicting presence of post-treatment ischemia in the patient at the determined maximum physical activity state when the patient is determined to be treated with the proposed treatment, wherein presence of post-treatment ischemia is predicted using an artificial intelligence (AI) or machine learning (ML) algorithm applied to the one or more parameters derived from analyzing a post-treatment medical image of the patient, the post-treatment medical image of the patient comprising a portion of coronary arteries, wherein prediction of presence of post-treatment ischemia at the determined maximum physical activity state is suggestive of treating the patient with additional treatment.

Embodiment 31: The non-transitory computer readable medium configured as in Embodiment 21, further comprising: generating a graphical visualization of one or more of the determined maximum physical activity state for the patient, the prescribed flow reserve of the patient at the determined maximum physical activity state, or the predicted impact of the proposed treatment on the prescribed flow reserve of the patient at the maximum physical activity state.

Embodiment 32: The non-transitory computer readable medium configured as in Embodiment 21, wherein the survey data comprises data related to physical activity levels of the subject.

Embodiment 33: The non-transitory computer readable medium configured as in Embodiment 21, wherein one or more of heart rate, blood oxygen level, or respiratory rate of the patient is collected via a wearable device over a period of time.

Embodiment 34: The non-transitory computer readable medium configured as in Embodiment 21, wherein the maximum physical activity state comprises one or more of rest, walking, jogging, running, or sprinting.

Embodiment 35: The non-transitory computer readable medium configured as in Embodiment 21, wherein the maximum physical activity state is determined on a continuous scale.

Embodiment 36: The non-transitory computer readable medium configured as in Embodiment 21, wherein the proposed treatment comprises stenting.

Embodiment 37: The non-transitory computer readable medium configured as in Embodiment 21, wherein the proposed treatment comprises one or more of lifestyle change, exercise, diet, medication, stenting, or surgical procedure.

Embodiment 38: The non-transitory computer readable medium configured as in Embodiment 21, wherein the predetermined confidence threshold comprises about 90%.

Embodiment 39: The non-transitory computer readable medium configured as in Embodiment 22, wherein the medical image is obtained using computed tomography (CT).

Embodiment 40: The non-transitory computer readable medium configured as in Embodiment 22, wherein the medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 41: A system comprising: accessing, by a computer system, data indicative of a lifestyle pattern of a patient, the data comprising one or more of heart rate, blood oxygen level, respiratory rate, or survey data; determining, by the computer system, a maximum physical activity state for the patient that meets a predetermined confidence threshold, the maximum physical activity state for the patient determined based at least in part on the data indicative of the lifestyle pattern of the patient; determining, by the computer system, a prescribed flow reserve of the patient at the maximum physical activity state, wherein prescribed flow reserve comprises a ratio or percentage of coronary blood flow rate of the patient at the maximum physical activity state against a reference coronary blood flow rate at the maximum physical activity state; and predicting, by the computer system, an impact of a proposed treatment on the prescribed flow reserve of the patient at the maximum physical activity state, wherein the impact of the proposed treatment on the prescribed flow reserve of the patient is predicted based at least in part on a plurality of reference data derived from a plurality of subjects treated with the proposed treatment with varying prescribed flow reserves, wherein the predicted impact of the proposed treatment on the prescribed flow reserve of the patient at the maximum physical activity state is used to determine whether to treat the patient with the proposed treatment, wherein the computer system comprises a computer processor and an electronic storage medium.

Embodiment 42: The system of Embodiment 41, wherein the prescribed flow reserve of the patient at the maximum physical activity state is determined based at least in part on one or more parameters derived from analyzing a medical image of the patient, the medical image of the patient comprising a portion of coronary arteries, wherein the one or more parameters comprise one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, or low-density plaque volume.

Embodiment 43: The system of Embodiment 42, wherein the prescribed flow reserve of the patient at the maximum physical activity state is determined using one or more of an artificial intelligence (AI) or machine learning (ML) algorithm.

Embodiment 44: The system of Embodiment 42, wherein the one or more parameters further comprise one or more of percent atheroma volume of total plaque, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, presence of two-feature positive plaques, number of two-feature positive plaques, segment length, severity of stenosis, minimum lumen diameter, maximum lumen diameter, mean lumen diameter, number of moderate stenosis, number of zero stenosis, number of severe stenosis, presence of high-risk anatomy, number of severe stenosis excluding CTO, vessel area, lumen area, diameter stenosis percentage, presence of ischemia, number of stents, reference lumen diameter before stenosis, perivascular fat attenuation, or reference lumen diameter after stenosis.

Embodiment 45: The system of Embodiment 44, wherein low-density non-calcified plaque comprises a region of plaque with a radiodensity value less than or equal to about 30 Hounsfield units on a computed tomography (CT) image, non-calcified plaque comprises a region of plaque with a radiodensity value greater than about 30 Hounsfield units and less than or equal to about 350 Hounsfield units on a CT image, calcified plaque comprises a region of plaque with a radiodensity value greater than about 350 Hounsfield units on a CT image, low-density calcified plaque comprises a region of plaque with a radiodensity value greater than about 350 Hounsfield units and less than or equal to about 700

Hounsfield units on a CT image, medium-density calcified plaque comprises a region of plaque with a radiodensity value greater than about 700 Hounsfield units and less than or equal to about 1000 Hounsfield units on a CT image, and high-density calcified plaque comprises a region of plaque with a radiodensity value greater than about 1000 Hounsfield units on a CT image.

Embodiment 46: The system of Embodiment 41, wherein the prescribed flow reserve of the patient at the maximum physical activity state is determined based at least in part on fractional flow reserve derived from computed tomography.

Embodiment 47: The system of Embodiment 41, wherein the prescribed flow reserve of the patient at the maximum physical activity state is determined based at least in part on fractional flow reserve derived from computed tomography, computational fractional flow reserve, virtual fractional flow reserve, vessel fractional flow reserve, quantitative flow ratio, or invasive fractional flow reserve.

Embodiment 48: The system of Embodiment 41, wherein the impact of the proposed treatment on the prescribed flow reserve of the patient at the maximum physical activity state prescribed flow reserve is determined using one or more of an artificial intelligence (AI) or machine learning (ML) algorithm.

Embodiment 49: The system of Embodiment 42, further comprising predicting, by the computer system, presence of pre-treatment ischemia in the patient at the determined maximum physical activity state when the patient is determined not to be treated with the proposed treatment, wherein presence of pre-treatment ischemia is predicted using an artificial intelligence (AI) or machine learning (ML) algorithm applied to the one or more parameters derived from analyzing the medical image of the patient, wherein prediction of presence of pre-treatment ischemia at the determined maximum physical activity state is suggestive of treating the patient with the proposed treatment.

Embodiment 50: The system of Embodiment 42, further comprising predicting, by the computer system, presence of post-treatment ischemia in the patient at the determined maximum physical activity state when the patient is determined to be treated with the proposed treatment, wherein presence of post-treatment ischemia is predicted using an artificial intelligence (AI) or machine learning (ML) algorithm applied to the one or more parameters derived from analyzing a post-treatment medical image of the patient, the post-treatment medical image of the patient comprising a portion of coronary arteries, wherein prediction of presence of post-treatment ischemia at the determined maximum physical activity state is suggestive of treating the patient with additional treatment.

Embodiment 51: The system of Embodiment 41, further comprising generating, by the computer system, a graphical visualization of one or more of the determined maximum physical activity state for the patient, the prescribed flow reserve of the patient at the determined maximum physical activity state, or the predicted impact of the proposed treatment on the prescribed flow reserve of the patient at the maximum physical activity state.

Embodiment 52: The system of Embodiment 41, wherein the survey data comprises data related to physical activity levels of the subject.

Embodiment 53: The system of Embodiment 41, wherein one or more of heart rate, blood oxygen level, or respiratory rate of the patient is collected via a wearable device over a period of time.

Embodiment 54: The system of Embodiment 41, wherein the maximum physical activity state comprises one or more of rest, walking, jogging, running, or sprinting.

Embodiment 55: The system of Embodiment 41, wherein the maximum physical activity state is determined on a continuous scale.

Embodiment 56: The system of Embodiment 41, wherein the proposed treatment comprises stenting.

Embodiment 57: The system of Embodiment 41, wherein the proposed treatment comprises one or more of lifestyle change, exercise, diet, medication, stenting, or surgical procedure.

Embodiment 58: The system of Embodiment 41, wherein the predetermined confidence threshold comprises about 90%.

Embodiment 59: The system of Embodiment 42, wherein the medical image is obtained using computed tomography (CT).

Embodiment 60: The system of Embodiment 42, wherein the medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Three-Dimensional Topological Mapping of Plaque

Disclosed herein are systems, devices, and methods for three-dimensional topological mapping of plaque. In particular, in some embodiments, the systems, devices, and methods described herein are related to transforming a two-dimensional medical image of an artery with plaque into a three-dimensional image. In some embodiments, creating a three-dimensional map of plaque by pixel can be used to guide stenting, orbital atherectomy, rotational atherectomy, or shockwave lithotripsy. In some embodiments, the systems, devices, and methods described herein are related to facilitating determination of an interventional treatment of plaque based at least in part on a three-dimensional topological mapping of plaque generated from medical image analysis. In some embodiments, the systems, devices, and methods described herein include accessing, by a computer system, a plurality of two-dimensional medical images of a patient, the plurality of two-dimensional medical images comprising a representation of a portion of one or more arteries. In some embodiments, the systems, devices, and methods described herein include automatically identifying one or more arteries in the plurality of two-dimensional medical images based at least in part on image segmentation. In some embodiments, the systems, devices, and methods described herein include automatically identifying one or more regions of plaque within the one or more arteries identified in the plurality of two-dimensional medical images. In some embodiments, the systems, devices, and methods described herein include analyzing the plurality of two-dimensional medical images to generate one or more plaque parameters for the one or more regions of plaque. In some embodiments, the one or more plaque parameters comprise volume, shape, density, and exterior contour of the one or more regions of plaque. In some embodiments, the systems, devices, and methods described herein include generating a graphical representation of a three-dimensional topological mapping of the one or more regions of plaque based at least in part on the one or more plaque parameters generated from analyzing the plurality of two-dimensional medical images. In some embodiments, the three-dimensional topological mapping of the one or more regions of plaque comprises a three-dimensional topological mapping of densities. In some embodiments, the systems, devices, and methods described herein include generating a prediction of efficacy of one or more interventional treatments for the one or more regions of plaque, the prediction of efficacy of one or more interventional treatments generated by a machine learning algorithm trained on a dataset comprising a plurality of interventional treatments performed on a plurality of patients with varying three-dimensional topological mappings of plaque derived from serial medical image analyses. In some embodiments, the one or more interventional treatments comprise one of stenting, orbital atherectomy, rotational atherectomy, shockwave lithotripsy, or no intervention. In some embodiments, the computer system comprises a computer processor and an electronic storage medium.

In some embodiments, the systems, devices, and methods described herein are related to analysis of whether a patient should undergo orbital, rotational, or shockwave atherectomy. In some embodiments, the systems, devices, and methods described herein generate a three-dimensional map of densities that comprises a topological map of calcium by pixel. In some embodiments, the systems, devices, and methods described herein predict the success of multiple routes of treatment. In some embodiments, the systems, devices, and methods described herein will allow physicians to visualize a patient's plaque in a way that current technology does not allow.

Figure 22:
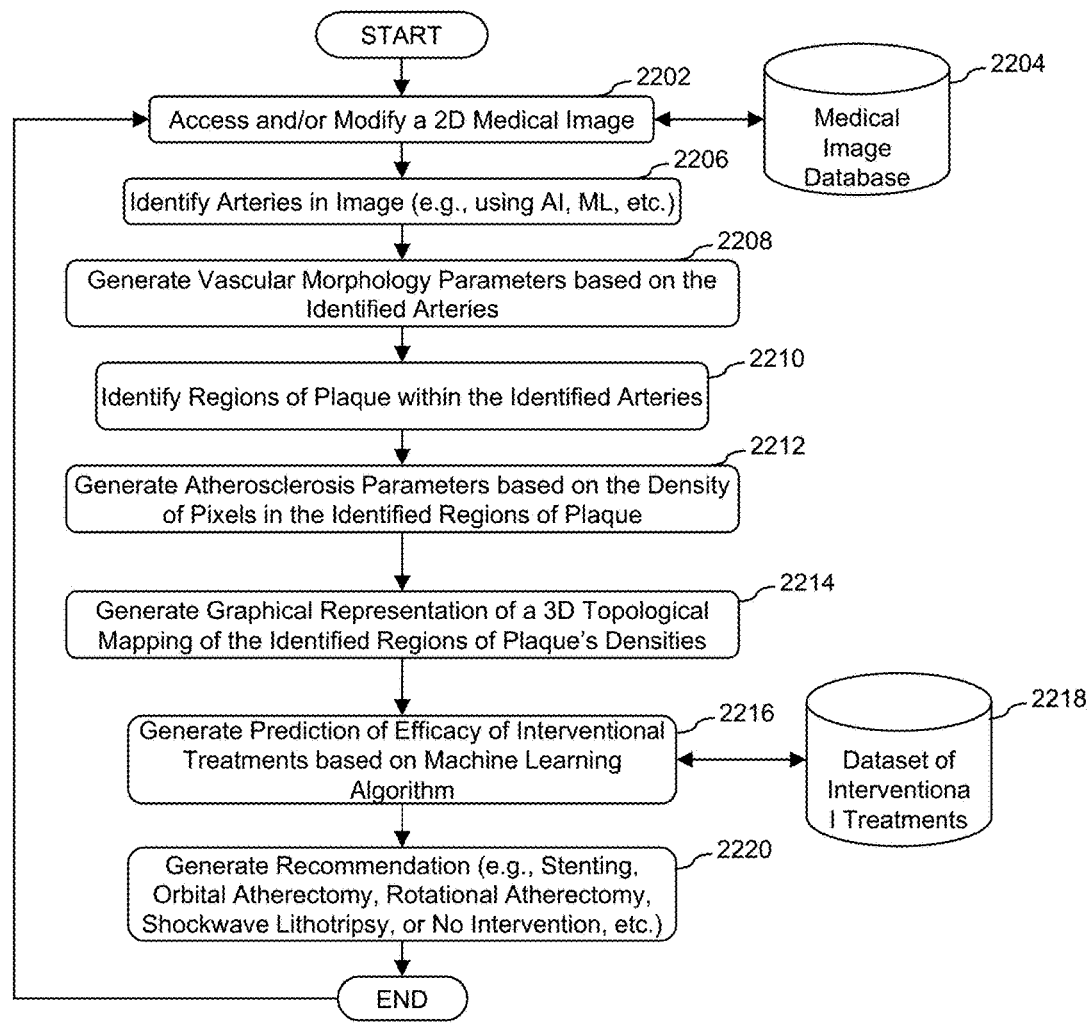
FIG. 22 is a flowchart illustrating an example embodiment(s) of systems, devices, and methods for three-dimensional topological mapping of plaque.

FIG. 22 is a flowchart illustrating an example embodiment(s) of systems, devices, and methods for three-dimensional topological mapping of plaque. As illustrated in FIG. 22, in some embodiments, the system can be configured to access and/or modify one or more medical images at block 2202. In some embodiments, the medical image is two-dimensional. In some embodiments, the medical image can include one or more arteries, such as coronary, carotid, and/or other arteries of a subject. In some embodiments, the medical image can be stored in a medical image database 2204. In some embodiments, the medical image database 2204 can be locally accessible by the system and/or can be located remotely and accessible through a network connection. The medical image can comprise an image obtained using one or more modalities such as for example, CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the medical image comprises one or more of a contrast-enhanced CT image, non-contrast CT image, MR image, and/or an image obtained using any of the modalities described above.

In some embodiments, the system can be configured to automatically and/or dynamically perform one or more analyses of the medical image as discussed herein. For example, in some embodiments, at block 2206, the system can be configured to identify one or more vessels, such as of one or more arteries. The one or more arteries can include coronary arteries, carotid arteries, aorta, renal artery, lower extremity artery, upper extremity artery, and/or cerebral artery, amongst others. In some embodiments, the system can be configured to utilize one or more AI and/or ML algorithms to automatically and/or dynamically identify one or more arteries or coronary arteries using image processing. For example, in some embodiments, the one or more AI and/or ML algorithms can be trained using a Convolutional Neural Network (CNN) on a set of medical images on which arteries or coronary arteries have been identified, thereby allowing the AI and/or ML algorithm automatically identify arteries or coronary arteries directly from a medical image. In some embodiments, the arteries or coronary arteries are identified by size and/or location.

In some embodiments, at block 2208, the system can be configured to identify one or more regions of plaque in the medical image. In some embodiments, the system can be configured to utilize one or more AI and/or ML algorithms to automatically and/or dynamically identify one or more regions of plaque using image processing. For example, in some embodiments, the one or more AI and/or ML algorithms can be trained using a Convolutional Neural Network (CNN) on a set of medical images on which regions of plaque have been identified, thereby allowing the AI and/or ML algorithm automatically identify regions of plaque directly from a medical image. In some embodiments, the system is configured to identify vessel and lumen walls and classify everything in between the vessel and lumen walls as plaque.

In some embodiments, at block 2210, the system can be configured to analyze and/or characterize one or more regions of plaque based on density. For example, in some embodiments, the system can be configured to analyze and/or characterize one or more regions of plaque based on absolute density and/or relative density and/or radiodensity. In some embodiments, the system can be configured to classify a region of plaque as one of low density non-calcified plaque, non-calcified plaque, and calcified plaque, using any one or more processes and/or features described herein.

In some embodiments, at block 2212, the system can be configured to analyze and/or characterize one or more regions of plaque based on one or more distances. For example, as described herein, in some embodiments, the system can be configured to determine a distance between a low density non-calcified plaque and lumen wall and/or vessel wall. In some embodiments, proximity of a low density non-calcified plaque to the lumen wall can be indicative of a high-risk plaque and/or CAD. Conversely, in some embodiments, a position of a low density non-calcified plaque far from the lumen wall can be indicative of less risk. In some embodiments, the system can be configured to utilize one or more predetermined thresholds in determining the risk factor associated with the proximity of low density non-calcified plaque with the vessel wall and/or lumen wall. In some embodiments, the system can be configured to utilize one or more image processing algorithms to automatically and/or dynamically determine one or more distances to and/or from one or more regions of plaque.

In some embodiments, at block 2212, the system can be configured to analyze and/or characterize one or more regions of plaque based on morphology or shape and/or one or more axes measurements of low density non-calcified plaque. As described herein, in some embodiments, the system can be configured to determine the length of one or more axes of a low density non-calcified plaque, such as for example a major axis of a longitudinal cross section and/or a major and/or minor axis of a latitudinal cross section of a low density non-calcified plaque. In some embodiments, the system can be configured to utilize the one or more axes measurements to determine a morphology and/or shape of a low density non-calcified plaque. In some embodiments, the system can be configured to utilize one or more image processing algorithms to automatically and/or dynamically determine one or more axes measurements of one or more regions of plaque.

In some embodiments, the system can be configured to utilize one or more AI and/or ML algorithms to automatically and/or dynamically classify the shape of one or more regions of plaque using image processing. For example, in some embodiments, the one or more AI and/or ML algorithms can be trained using a Convolutional Neural Network (CNN) on a set of medical images on which the shape of regions of plaque have been identified, thereby allowing the AI and/or ML algorithm automatically identify the shape or morphology of a region of plaque directly from a medical image. In some embodiments, the system can be configured to classify the shape or morphology of a region of plaque as one or more of crescent, lobular, round, or bean-shaped. In some embodiments, round and/or bean-shaped plaques can be associated with high risk, while crescent and/or lobular-shaped plaques can be associated with low risk of CAD.

In some embodiments, at block 2212, the system can be configured to analyze and/or characterize one or more regions of plaque based on one or more sizes and/or volumes. For example, in some embodiments, the system can be configured to determine a size and/or volume of plaque based at least in part on one or more axes measurements described herein. In some embodiments, the system can be configured to determine the size and/or volume of a region of plaque directly from analysis of a three-dimensional image scan. In some embodiments, the system can be configured to determine the size and/or volume of total plaque, low-density non-calcified plaque, non-calcified plaque, calcified plaque, and/or a ratio between two of the aforementioned volumes or sizes. In some embodiments, a high total plaque volume and/or high low-density non-calcified plaque and/or non-calcified plaque volume can be associated with high risk of CAD. In some embodiments, a high ratio of low-density non-calcified plaque volume to total plaque volume and/or a high ratio of non-calcified plaque volume to total plaque volume can be associated with high risk of CAD. In some embodiments, a high calcified plaque volume and/or high ratio of calcified plaque volume to total plaque volume can be associated with low risk of CAD. In some embodiments, the system can be configured to utilize one or more predetermined threshold values for determining the risk of CAD based on plaque volume, size, or one or more ratios thereof. In some embodiments, the system can be configured to utilize one or more image processing algorithms to automatically and/or dynamically determine the size and/or volume of one or more regions of plaque.

In some embodiments, at block 2212, the system can be configured to analyze and/or characterize plaque based on embeddedness. For example, in some embodiments, the system can be configured to determined how embedded or surrounded a low density non-calcified plaque is by non-calcified plaque or calcified plaque. In some embodiments, the system can be configured to analyze the embeddedness of low density non-calcified plaque based on the degree by which it is surrounded by other types of plaque. In some embodiments, a higher embeddedness of a low density non-calcified plaque can be indicative of high risk of CAD. For example, in some embodiments, a low density non-calcified plaque that is surrounded by 270 degrees or more by non-calcified plaque can be associated with high risk of CAD. In some embodiments, the system can be configured to utilize one or more image processing algorithms to automatically and/or dynamically determine the embeddedness of one or more regions of plaque.

In some embodiments, at block 2214, the system can be configured to generate a graphical representation of a three-dimensional topological mapping of the one or more regions of plaque based at least in part on the one or more plaque parameters generated from analyzing the plurality of two-dimensional medical images. In some embodiments, the three-dimensional topological mapping of the one or more regions of plaque comprises a three-dimensional topological mapping of densities.

In some embodiments, at block 2216, the system can be configured to generate a prediction of efficacy of one or more interventional treatments for the one or more regions of plaque. In some embodiments, the prediction of efficacy of one or more interventional treatments generated by a machine learning algorithm trained on a treatment dataset 2218. In some embodiments, the treatment dataset 2218 comprises a plurality of interventional treatments performed on a plurality of patients with varying three-dimensional topological mappings of plaque derived from serial medical image analyses. In some embodiments, the treatment dataset 2218 can be locally accessible by the system and/or can be located remotely and accessible through a network connection. In some embodiments, the one or more interventional treatments comprise one of stenting, orbital atherectomy, rotational atherectomy, shockwave lithotripsy, or no intervention.

In some embodiments, at block 2216, the system can be configured to generate a graphical simulation of performing the one or more interventional treatments for the one or more regions of plaque. In some embodiments, the generated graphical simulation comprises one or more of an angle or position of performing the one or more interventional treatments.

In some embodiments, at block 2220, the system can be configured to generate a recommendation for one or more interventional treatments for the one or more regions of plaque. In some embodiments, the one or more interventional treatments comprise one of stenting, orbital atherectomy, rotational atherectomy, shockwave lithotripsy, or no intervention. In some embodiments, the system can be configured to receive a user selection of one of the one or more interventional treatments for the one or more regions of plaque. In some embodiments, the system can be configured to generate surgical planning for the user-selected interventional treatment.

In some embodiments, the system can be configured to repeat one or more processes described in relation to blocks 2202-2220, for example for one or more other vessels, segment, regions of plaque, different subjects, and/or for the same subject at a different time. As such, in some embodiments, the system can provide for longitudinal disease tracking and/or personalized treatment for a subject.

The computer system 902 of FIG. 9, and in some instances, the analysis and/or risk assessment module 940, can be configured to carry out the functions, methods, acts, and/or processes for three-dimensional topological mapping of plaque described herein, such as those described above with reference to FIG. 22.

The following are non-limiting examples of certain embodiments of systems and methods for three-dimensional topological mapping of plaque. Other embodiments may include one or more other features, or different features, that are discussed herein Embodiment 1: A computer-implemented method of facilitating determination of an interventional treatment of plaque based at least in part on a three-dimensional topological mapping of plaque generated from medical image analysis, the method comprising: accessing, by a computer system, a plurality of two-dimensional medical images of a patient, the plurality of two-dimensional medical images comprising a representation of a portion of one or more arteries; automatically identifying, by the computer system, one or more arteries in the plurality of two-dimensional medical images based at least in part on image segmentation; automatically identifying, by the computer system, one or more regions of plaque within the one or more arteries identified in the plurality of two-dimensional medical images; analyzing, by the computer system, the plurality of two-dimensional medical images to generate one or more plaque parameters for the one or more regions of plaque, the one or more plaque parameters comprising volume, shape, density, and exterior contour of the one or more regions of plaque; generating, by the computer system, a graphical representation of a three-dimensional topological mapping of the one or more regions of plaque based at least in part on the one or more plaque parameters generated from analyzing the plurality of two-dimensional medical images, wherein the three-dimensional topological mapping of the one or more regions of plaque comprises a three-dimensional topological mapping of densities; and generating, by the computer system, a prediction of efficacy of one or more interventional treatments for the one or more regions of plaque, the prediction of efficacy of one or more interventional treatments generated by a machine learning algorithm trained on a dataset comprising a plurality of interventional treatments performed on a plurality of patients with varying three-dimensional topological mappings of plaque derived from serial medical image analyses, the one or more interventional treatments comprising one of stenting, orbital atherectomy, rotational atherectomy, shockwave lithotripsy, or no intervention, wherein the computer system comprises a computer processor and an electronic storage medium.

Embodiment 2: The computer-implemented method of Embodiment 1, further comprising generating, by the computer system, a graphical simulation of performing the one or more interventional treatments for the one or more regions of plaque.

Embodiment 3: The computer-implemented method of Embodiment 2, wherein the generated graphical simulation comprises one or more of an angle or position of performing the one or more interventional treatments.

Embodiment 4: The computer-implemented method of Embodiment 1, further comprising: receiving, by the computer system, user selection of one of the one or more interventional treatments for the one or more regions of plaque; and generating, by the computer system, surgical planning for the user-selected interventional treatment.

Embodiment 5: The computer-implemented method of Embodiment 1, wherein the density comprises material density.

Embodiment 6: The computer-implemented method of Embodiment 1, wherein the density comprises radiodensity.

Embodiment 7: The computer-implemented method of Embodiment 1, wherein the one or more plaque parameters comprises classification of the one or more regions of plaque.

Embodiment 8: The computer-implemented method of Embodiment 7, wherein the classification of the one or more regions of plaque comprises classifying the one or more regions of plaque as one or more of low density non-calcified plaque, non-calcified plaque, and calcified plaque.

Embodiment 9: The computer-implemented method of Embodiment 1, wherein the one or more arteries comprise one or more coronary arteries.

Embodiment 10: The computer-implemented method of Embodiment 1, wherein the one or more arteries comprise one or more coronary arteries, carotid arteries, aorta, upper extremity arteries, or lower extremity arteries.

Embodiment 11: The computer-implemented method of Embodiment 1, wherein the one or more medical images comprises a Computed Tomography (CT) image.

Embodiment 12: The computer-implemented method of Embodiment 1, wherein the one or more medical images is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 13: A computer-implemented method of facilitating determination of an interventional treatment of plaque based at least in part on a three-dimensional topological mapping of plaque generated from medical image analysis, the method comprising: accessing, by a computer system, a plurality of two-dimensional medical images of a patient, the plurality of two-dimensional medical images comprising a representation of a portion of one or more arteries; automatically identifying, by the computer system, one or more arteries in the plurality of two-dimensional medical images based at least in part on image segmentation; automatically identifying, by the computer system, one or more regions of plaque within the one or more arteries identified in the plurality of two-dimensional medical images; analyzing, by the computer system, the plurality of two-dimensional medical images to generate one or more plaque parameters for the one or more regions of plaque, the one or more plaque parameters comprising volume, shape, density, and exterior contour of the one or more regions of plaque; generating, by the computer system, a graphical representation of a three-dimensional topological mapping of the one or more regions of plaque based at least in part on the one or more plaque parameters generated from analyzing the plurality of two-dimensional medical images, wherein the three-dimensional topological mapping of the one or more regions of plaque comprises a three-dimensional topological mapping of densities; and wherein the generated graphical representation of the three-dimensional topological mapping of the one or more regions of plaque is configured to be utilized to facilitate determination of an interventional treatment of the one or more regions of plaque, the interventional treatment comprising one of stenting, orbital atherectomy, rotational atherectomy, shockwave lithotripsy, or no intervention, wherein the computer system comprises a computer processor and an electronic storage medium.

Embodiment 14: The computer-implemented method of Embodiment 13, further comprising generating, by the computer system, a graphical simulation of performing the one or more interventional treatments for the one or more regions of plaque.

Embodiment 15: The computer-implemented method of Embodiment 14, wherein the generated graphical simulation comprises one or more of an angle or position of performing the one or more interventional treatments.

Embodiment 16: The computer-implemented method of Embodiment 13, further comprising: receiving, by the computer system, user selection of one of the one or more interventional treatments for the one or more regions of plaque; and generating, by the computer system, surgical planning for the user-selected interventional treatment.

Embodiment 17: The computer-implemented method of Embodiment 13, wherein the density comprises material density.

Embodiment 18: The computer-implemented method of Embodiment 13, wherein the density comprises radiodensity.

Embodiment 19: The computer-implemented method of Embodiment 13, wherein the one or more plaque parameters comprises classification of the one or more regions of plaque.

Embodiment 20: The computer-implemented method of Embodiment 19, wherein the classification of the one or more regions of plaque comprises classifying the one or more regions of plaque as one or more of low density non-calcified plaque, non-calcified plaque, and calcified plaque.

Embodiment 21: The computer-implemented method of Embodiment 13, wherein the one or more arteries comprise one or more coronary arteries.

Embodiment 22: The computer-implemented method of Embodiment 13, wherein the one or more arteries comprise one or more coronary arteries, carotid arteries, aorta, upper extremity arteries, or lower extremity arteries.

Embodiment 23: The computer-implemented method of Embodiment 13, wherein the one or more medical images comprises a Computed Tomography (CT) image.

Embodiment 24: The computer-implemented method of Embodiment 13, wherein the one or more medical images is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 25: A non-transitory computer readable medium configured for facilitating determination of an interventional treatment of plaque based at least in part on a three-dimensional topological mapping of plaque generated from medical image analysis, the computer readable medium having program instructions for causing a hardware processor to perform a method of: accessing, by a computer system, a plurality of two-dimensional medical images of a patient, the plurality of two-dimensional medical images comprising a representation of a portion of one or more arteries; automatically identifying, by the computer system, one or more arteries in the plurality of two-dimensional medical images based at least in part on image segmentation; automatically identifying, by the computer system, one or more regions of plaque within the one or more arteries identified in the plurality of two-dimensional medical images; analyzing, by the computer system, the plurality of two-dimensional medical images to generate one or more plaque parameters for the one or more regions of plaque, the one or more plaque parameters comprising volume, shape, density, and exterior contour of the one or more regions of plaque; generating, by the computer system, a graphical representation of a three-dimensional topological mapping of the one or more regions of plaque based at least in part on the one or more plaque parameters generated from analyzing the plurality of two-dimensional medical images, wherein the three-dimensional topological mapping of the one or more regions of plaque comprises a three-dimensional topological mapping of densities; and generating, by the computer system, a prediction of efficacy of one or more interventional treatments for the one or more regions of plaque, the prediction of efficacy of one or more interventional treatments generated by a machine learning algorithm trained on a dataset comprising a plurality of interventional treatments performed on a plurality of patients with varying three-dimensional topological mappings of plaque derived from serial medical image analyses, the one or more interventional treatments comprising one of stenting, orbital atherectomy, rotational atherectomy, shockwave lithotripsy, or no intervention, wherein the computer system comprises a computer processor and an electronic storage medium.

Embodiment 26: The non-transitory computer readable medium configured as in Embodiment 25, the computer readable medium having program instructions for causing the hardware processor to perform a method of generating a graphical simulation of performing the one or more interventional treatments for the one or more regions of plaque.

Embodiment 27: The non-transitory computer readable medium configured as in Embodiment 26, wherein the generated graphical simulation comprises one or more of an angle or position of performing the one or more interventional treatments.

Embodiment 28: The non-transitory computer readable medium configured as in Embodiment 25, the computer readable medium having program instructions for causing the hardware processor to perform a method of: receiving, by the computer system, user selection of one of the one or more interventional treatments for the one or more regions of plaque; and generating, by the computer system, surgical planning for the user-selected interventional treatment.

Embodiment 29: The non-transitory computer readable medium configured as in Embodiment 25, wherein the density comprises material density.

Embodiment 30: The non-transitory computer readable medium configured as in Embodiment 25, wherein the density comprises radiodensity.

Embodiment 31: The non-transitory computer readable medium configured as in Embodiment 25, wherein the one or more plaque parameters comprises classification of the one or more regions of plaque.

Embodiment 32: The non-transitory computer readable medium configured as in Embodiment 31, wherein the classification of the one or more regions of plaque comprises classifying the one or more regions of plaque as one or more of low density non-calcified plaque, non-calcified plaque, and calcified plaque.

Embodiment 33: The non-transitory computer readable medium configured as in Embodiment 25, wherein the one or more arteries comprise one or more coronary arteries.

Embodiment 34: The non-transitory computer readable medium configured as in Embodiment 25, wherein the one or more arteries comprise one or more coronary arteries, carotid arteries, aorta, upper extremity arteries, or lower extremity arteries.

Embodiment 35: The non-transitory computer readable medium configured as in Embodiment 25, wherein the one or more medical images comprises a Computed Tomography (CT) image.

Embodiment 36: The non-transitory computer readable medium configured as in Embodiment 25, wherein the one or more medical images is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 37: A non-transitory computer readable medium configured for facilitating determination of an interventional treatment of plaque based at least in part on a three-dimensional topological mapping of plaque generated from medical image analysis, the computer readable medium having program instructions for causing a hardware processor to perform a method of: accessing, by a computer system, a plurality of two-dimensional medical images of a patient, the plurality of two-dimensional medical images comprising a representation of a portion of one or more arteries; automatically identifying, by the computer system, one or more arteries in the plurality of two-dimensional medical images based at least in part on image segmentation; automatically identifying, by the computer system, one or more regions of plaque within the one or more arteries identified in the plurality of two-dimensional medical images; analyzing, by the computer system, the plurality of two-dimensional medical images to generate one or more plaque parameters for the one or more regions of plaque, the one or more plaque parameters comprising volume, shape, density, and exterior contour of the one or more regions of plaque; generating, by the computer system, a graphical representation of a three-dimensional topological mapping of the one or more regions of plaque based at least in part on the one or more plaque parameters generated from analyzing the plurality of two-dimensional medical images, wherein the three-dimensional topological mapping of the one or more regions of plaque comprises a three-dimensional topological mapping of densities; and wherein the generated graphical representation of the three-dimensional topological mapping of the one or more regions of plaque is configured to be utilized to facilitate determination of an interventional treatment of the one or more regions of plaque, the interventional treatment comprising one of stenting, orbital atherectomy, rotational atherectomy, shockwave lithotripsy, or no intervention, wherein the computer system comprises a computer processor and an electronic storage medium.

Embodiment 38: The non-transitory computer readable medium configured as in Embodiment 37, the computer readable medium having program instructions for causing the hardware processor to perform a method of generating a graphical simulation of performing the one or more interventional treatments for the one or more regions of plaque.

Embodiment 39: The non-transitory computer readable medium configured as in Embodiment 38, wherein the generated graphical simulation comprises one or more of an angle or position of performing the one or more interventional treatments.

Embodiment 40: The non-transitory computer readable medium configured as in Embodiment 37, the computer readable medium having program instructions for causing the hardware processor to perform a method of: receiving, by the computer system, user selection of one of the one or more interventional treatments for the one or more regions of plaque; and generating, by the computer system, surgical planning for the user-selected interventional treatment.

Embodiment 41: The non-transitory computer readable medium configured as in Embodiment 37, wherein the density comprises material density.

Embodiment 42: The non-transitory computer readable medium configured as in Embodiment 37, wherein the density comprises radiodensity.

Embodiment 43: The non-transitory computer readable medium configured as in Embodiment 37, wherein the one or more plaque parameters comprises classification of the one or more regions of plaque.

Embodiment 44: The non-transitory computer readable medium configured as in Embodiment 43, wherein the classification of the one or more regions of plaque comprises classifying the one or more regions of plaque as one or more of low density non-calcified plaque, non-calcified plaque, and calcified plaque.

Embodiment 45: The non-transitory computer readable medium configured as in Embodiment 37, wherein the one or more arteries comprise one or more coronary arteries.

Embodiment 46: The non-transitory computer readable medium configured as in Embodiment 37, wherein the one or more arteries comprise one or more coronary arteries, carotid arteries, aorta, upper extremity arteries, or lower extremity arteries.

Embodiment 47: The non-transitory computer readable medium configured as in Embodiment 37, wherein the one or more medical images comprises a Computed Tomography (CT) image.

Embodiment 48: The non-transitory computer readable medium configured as in Embodiment 37, wherein the one or more medical images is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 49: A system comprising: accessing, by a computer system, a plurality of two-dimensional medical images of a patient, the plurality of two-dimensional medical images comprising a representation of a portion of one or more arteries; automatically identifying, by the computer system, one or more arteries in the plurality of two-dimensional medical images based at least in part on image segmentation; automatically identifying, by the computer system, one or more regions of plaque within the one or more arteries identified in the plurality of two-dimensional medical images; analyzing, by the computer system, the plurality of two-dimensional medical images to generate one or more plaque parameters for the one or more regions of plaque, the one or more plaque parameters comprising volume, shape, density, and exterior contour of the one or more regions of plaque; generating, by the computer system, a graphical representation of a three-dimensional topological mapping of the one or more regions of plaque based at least in part on the one or more plaque parameters generated from analyzing the plurality of two-dimensional medical images, wherein the three-dimensional topological mapping of the one or more regions of plaque comprises a three-dimensional topological mapping of densities; and generating, by the computer system, a prediction of efficacy of one or more interventional treatments for the one or more regions of plaque, the prediction of efficacy of one or more interventional treatments generated by a machine learning algorithm trained on a dataset comprising a plurality of interventional treatments performed on a plurality of patients with varying three-dimensional topological mappings of plaque derived from serial medical image analyses, the one or more interventional treatments comprising one of stenting, orbital atherectomy, rotational atherectomy, shockwave lithotripsy, or no intervention, wherein the computer system comprises a computer processor and an electronic storage medium.

Embodiment 50: The system of Embodiment 49, further comprising generating, by the computer system, a graphical simulation of performing the one or more interventional treatments for the one or more regions of plaque.

Embodiment 51: The system of Embodiment 50, wherein the generated graphical simulation comprises one or more of an angle or position of performing the one or more interventional treatments.

Embodiment 52: The system of Embodiment 49, further comprising: receiving, by the computer system, user selection of one of the one or more interventional treatments for the one or more regions of plaque; and generating, by the computer system, surgical planning for the user-selected interventional treatment.

Embodiment 53: The system of Embodiment 49, wherein the density comprises material density.

Embodiment 54: The system of Embodiment 49, wherein the density comprises radiodensity.

Embodiment 55: The system of Embodiment 49, wherein the one or more plaque parameters comprises classification of the one or more regions of plaque.

Embodiment 56: The system of Embodiment 55, wherein the classification of the one or more regions of plaque comprises classifying the one or more regions of plaque as one or more of low density non-calcified plaque, non-calcified plaque, and calcified plaque.

Embodiment 57: The system of Embodiment 49, wherein the one or more arteries comprise one or more coronary arteries.

Embodiment 58: The system of Embodiment 49, wherein the one or more arteries comprise one or more coronary arteries, carotid arteries, aorta, upper extremity arteries, or lower extremity arteries.

Embodiment 59: The system of Embodiment 49, wherein the one or more medical images comprises a Computed Tomography (CT) image.

Embodiment 60: The system of Embodiment 49, wherein the one or more medical images is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 61: A system comprising: accessing, by a computer system, a plurality of two-dimensional medical images of a patient, the plurality of two-dimensional medical images comprising a representation of a portion of one or more arteries; automatically identifying, by the computer system, one or more arteries in the plurality of two-dimensional medical images based at least in part on image segmentation; automatically identifying, by the computer system, one or more regions of plaque within the one or more arteries identified in the plurality of two-dimensional medical images; analyzing, by the computer system, the plurality of two-dimensional medical images to generate one or more plaque parameters for the one or more regions of plaque, the one or more plaque parameters comprising volume, shape, density, and exterior contour of the one or more regions of plaque; generating, by the computer system, a graphical representation of a three-dimensional topological mapping of the one or more regions of plaque based at least in part on the one or more plaque parameters generated from analyzing the plurality of two-dimensional medical images, wherein the three-dimensional topological mapping of the one or more regions of plaque comprises a three-dimensional topological mapping of densities; and wherein the generated graphical representation of the three-dimensional topological mapping of the one or more regions of plaque is configured to be utilized to facilitate determination of an interventional treatment of the one or more regions of plaque, the interventional treatment comprising one of stenting, orbital atherectomy, rotational atherectomy, shockwave lithotripsy, or no intervention, wherein the computer system comprises a computer processor and an electronic storage medium.

Embodiment 62: The system of Embodiment 61, further comprising generating, by the computer system, a graphical simulation of performing the one or more interventional treatments for the one or more regions of plaque.

Embodiment 63: The system of Embodiment 62, wherein the generated graphical simulation comprises one or more of an angle or position of performing the one or more interventional treatments.

Embodiment 64: The system of Embodiment 61, further comprising: receiving, by the computer system, user selection of one of the one or more interventional treatments for the one or more regions of plaque; and generating, by the computer system, surgical planning for the user-selected interventional treatment.

Embodiment 65: The system of Embodiment 61, wherein the density comprises material density.

Embodiment 66: The system of Embodiment 61, wherein the density comprises radiodensity.

Embodiment 67: The system of Embodiment 61, wherein the one or more plaque parameters comprises classification of the one or more regions of plaque.

Embodiment 68: The system of Embodiment 67, wherein the classification of the one or more regions of plaque comprises classifying the one or more regions of plaque as one or more of low density non-calcified plaque, non-calcified plaque, and calcified plaque.

Embodiment 69: The system of Embodiment 61, wherein the one or more arteries comprise one or more coronary arteries.

Embodiment 70: The system of Embodiment 61, wherein the one or more arteries comprise one or more coronary arteries, carotid arteries, aorta, upper extremity arteries, or lower extremity arteries.

Embodiment 71: The system of Embodiment 61, wherein the one or more medical images comprises a Computed Tomography (CT) image.

Embodiment 72: The system of Embodiment 61, wherein the one or more medical images is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Automated Searching and/or Curation of Data Based on Image-Derived Variables

Disclosed herein are systems, devices, and methods for automated searching and/or curation of data based on image-derived variables. In particular, in some embodiments, the systems, devices, and methods described herein are related to automatically searching and curating data related to a medical condition of a subject based at least in part on one or more variables derived from image-based analysis of the subject. For example, in some embodiments, the systems, devices, and methods described herein relate to accessing a medical image of a subject, the medical image comprising a representation of a portion of one or more coronary arteries to identify one or more regions of plaque. In some embodiments, the systems, devices, and methods described herein further relate to generating a plurality of image-derived variables and one or more syntaxes descriptive of the medical image based on said image-derived variables. In some embodiments, the systems, devices, and methods described herein further relate to automatically searching a database of medical literature for data related to a medical condition of the subject based at least in part on the generated one or more syntaxes causing generation of a display of the data related to the medical condition of the subject. In some embodiments, the systems can search the internet or other databases generally based on the image and generate data for display relating to the image using generative artificial intelligence (AI).

In some embodiments, the systems, devices, and methods described herein are related to automatically searching and curating data related to a medical condition of a subject based at least in part on one or more variables derived from image-based analysis of the subject. For example, in some embodiments, the systems, devices, and methods described herein relate to accessing a medical image of a subject, the medical image comprising a representation of a portion of one or more coronary arteries to identify one or more regions of plaque. In some embodiments, the systems, devices, and methods described herein further relate to generating a plurality of image-derived variables and one or more syntaxes descriptive of the medical image based on said image-derived variables. In some embodiments, the systems, devices, and methods described herein further relate to automatically searching a database of medical literature for data related to a medical condition of the subject based at least in part on the generated one or more syntaxes causing generation of a display of the data related to the medical condition of the subject. In some embodiments, the systems can search the internet or other databases generally based on the image and generate data for display relating to the image using generative AI. For example, generative AI can prepare a customized report for the user based on the image.

As discussed herein, disclosed herein are systems, methods, and devices for automated searching and/or curation of data based on image-derived variables. In other words, this process may "transpose" an image into keyword search syntaxes. For example, given an image with identified regions of plaque, the systems, methods, and devices described herein may generate image-derived variables based on the identified regions. This process may be known as an "autodiagnosis." Based on the image-derived variables, the systems, methods, and devices may generate keyword search syntaxes descriptive of the image analysis for use in a public medical database search, such as PubMed®. PubMed® is an online search engine with access to over 35 million citations for biomedical literature, life science journals, and online books. PubMed® contains a search functionality that takes keyword inputs and pulls resources relevant to the search query. In some embodiments, the systems, methods, and devices may input the generated syntax "autodiagnosis" into a PubMed® search. PubMed® and other publicly available medical libraries are valuable resources that may be used to supplement image-based diagnoses of diseases. Given a medical image taken from a patient, it would be advantageous to search databases for similar images that may aid medical professionals in diagnoses and treatment. In some instances, the systems and methods can search databases for similar images and generate customized and personalized display data for the user using generative AI. For example, the systems and methods can synthesize a custom report, which may include, for example, a treatment plan based on the image and comparison to image and data obtained from the database.

In some embodiments, the systems, methods, and devices may utilize natural language processing (NLP) or other artificial intelligence processing on the PubMed® search results, or other databases, including the internet generally. For example, the system, methods, and devices may be configured to process the search results and output a summary of risk and treatment recommendations.

Figure 23:
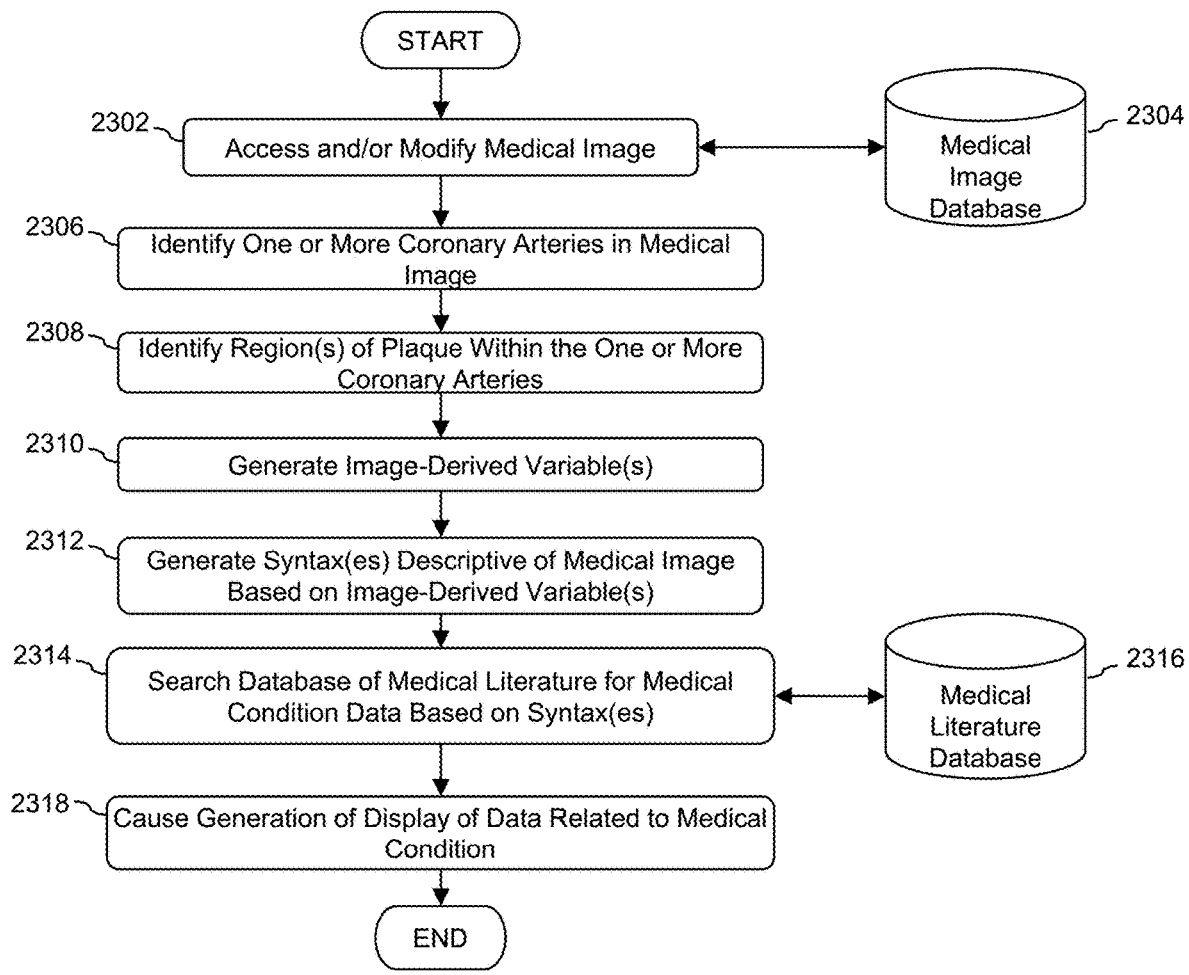
FIG. 23 is a flowchart illustrating an example embodiment(s) of systems, devices, and methods for automated searching and/or curation of data based on image-derived variables.

FIG. 23 is a flowchart illustrating an example embodiment(s) of systems, devices, and methods for automatically searching and curating data related to a medical condition of a subject based at least in part on one or more variables derived from image-based analysis of the subject. As illustrated in FIG. 23, in some embodiments, at block 2302, the system can be configured to access a medical image of a subject, the medical image comprising a representation of a portion of one or more coronary arteries. In some embodiments, the medical image can be stored in a medical image database 2304. In some embodiments, the medical image database 2304 can be locally accessible by the system and/or can be located remotely and accessible through a network connection.

In some embodiments, the medical image is obtained using computed tomography (CT). In some embodiments, the medical image is obtained using coronary CT angiography (CCTA). In some embodiments, the medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

In some embodiments, at block 2306, the system can be configured to analyze the medical image to identify one or more coronary arteries. In some embodiments, at block 2308, the system can be further configured to identify one or more regions of plaque. In some embodiments, the medical image comprises a CT image, and wherein low-density non-calcified plaque comprises a region of plaque comprising a radiodensity value between about −189 and about 30 Hounsfield units. In some embodiments, the Hounsfield units in this range are, or between, two of about −189 HU, about −180 HU, about −170 HU, about −160 HU, about −150 HU, about −140 HU, about −130 HU, about −120 HU, about −110 HU, about −100 HU, about −90 HU, about −80 HU, about −70 HU, about −60 HU, about −50 HU, about −40 HU, about −30, about −20, about −10, about 0, about 10, about 20, and about 30 HU.

In some embodiments, non-calcified plaque comprises a region of plaque comprising a radiodensity value between about 31 and about 350 Hounsfield units. In some embodiments, the Hounsfield units in this range are, or between, two of about 31 HU, about 40 HU, about 50 HU, about 60 HU, about 70 HU, about 80 HU, about 90 HU, about 100 HU, about 110 HU, about 120 HU, about 130 HU, about 140 HU, about 150 HU, about 160 HU, about 170 HU, about 180 HU, about 190 HU, about 200 HU, about 210 HU, about 220 HU, about 230 HU, about 240 HU, about 250 HU, about 260 HU, about 270 HU, about 280 HU, about 290 HU, about 300 HU, about 310 HU, about 320 HU, about 330 HU, about 340 HU, and about 350 HU.

In some embodiments, calcified plaque comprises a region of plaque comprising a radiodensity value between about 351 and 2500 Hounsfield units. In some embodiments, the Hounsfield units in this range are, or between, two of about 351 HU, about 400 HU, about 500 HU, about 600 HU, about 700 HU, about 800 HU, about 900 HU, about 1000 HU, about 1100 HU, about 1200 HU, about 1300 HU, about 1400 HU, about 1500 HU, about 1600 HU, about 1700 HU, about 1800 HU, about 1900 HU, about 2000 HU, about 2100 HU, about 2200 HU, about 2300 HU, about 2400 HU, and about 2500 HU.

In some embodiments, at block 2310, the system can be configured to analyze the identified one or more coronary arteries and the one or more regions of plaque to generate a plurality of image-derived variables, the plurality of image-derived variables comprising one or more of percent atheroma volume of total plaque, total plaque volume, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, vessel length, segment length, lesion length, lumen volume, number of chronic total occlusion (CTO), vessel volume, number of stenosis, severity of stenosis, remodeling index, minimum lumen diameter, maximum lumen diameter, mean lumen diameter, stenosis area percentage, stenosis diameter percentage, number of mild stenosis, number of moderate stenosis, number of zero stenosis, number of severe stenosis, presence of high-risk anatomy, presence of positive remodeling, number of severe stenosis excluding CTO, vessel area, lumen area, diameter stenosis percentage, reference lumen diameter before stenosis, perivascular fat attenuation, or reference lumen diameter after stenosis.

In some embodiments, the plurality of image-derived variables is generated using one or more of an artificial intelligence (AI) or machine learning (ML) algorithm trained on a dataset comprising a plurality of medical images with known image-derived variables from a plurality of other subjects.

In some embodiments, at block 2312, the system can be configured to generate one or more syntaxes descriptive of the medical image based at least in part on the plurality of image-derived variables. In some embodiments, the one or more syntaxes descriptive of the medical image are generated based at least in part on a database comprising a plurality of predetermined syntaxes generated from a plurality of medical images with known image-derived variables from a plurality of other subjects.

In some embodiments, at block 2314, the system can be configured to automatically search a Medical Literature Database 2314 of medical literature for data related to a medical condition of the subject based at least in part on the generated one or more syntaxes. Medical Literature Database 2314 may be any available research library or online database, such as PubMed®. In other instances, the system can search other databases, including the internet generally.

In some embodiments, at block 2318, the system can be configured to cause generation of a display of the data related to the medical condition of the subject.

In some embodiments, the data related to the medical condition of the subject comprises one or more images of other subjects with similar medical conditions to the subject. In some embodiments, the data related to the medical condition of the subject comprises one or more scientific articles. In some embodiments, the system may be further configured to generate a listing of the one or more scientific articles by one or more of relevance or date. In some embodiments, relevance of the one or more scientific articles is determined by: deriving, by the computer system, one or more syntaxes from the one or more scientific articles; determining, by the computer system, an overlap between the one or more syntaxes derived from the one or more scientific articles and the generated one or more syntaxes descriptive of the medical image; and determining, by the computer system, relevance of the one or more scientific articles based at least in part on the determined overlap. In some embodiments, rather than displaying the retrieved articles, the system can generative customized data based on the articles. For example, generative AI can generate a custom report based on the articles or other information retrieved from or stored in the database.

In some embodiments, the one or more syntaxes from the one or more scientific articles is derived using natural language processing (NLP). In some embodiments, the system may be further configured to generate summary of the one or more scientific articles using NLP. In some embodiments, the system may be further configured to extract from the one or more scientific articles one or more recommended treatments for the medical condition of the subject using NLP.

The computer system 902 of FIG. 9, and in some instances, the analysis and/or risk assessment module 940, can be configured to carry out the functions, methods, acts, and/or processes for automated searching and/or curation of data based on image-derived variables described herein, such as those described above with reference to FIG. 23.

The following are non-limiting examples of certain embodiments of systems and methods for automated searching and/or curation of data based on image-derived variables. Other embodiments may include one or more other features, or different features, that are discussed herein.

Embodiment 1: A computer-implemented method of automatically searching and curating data related to a medical condition of a subject based at least in part on one or more variables derived from image-based analysis of the subject, the method comprising: accessing, by a computer system, a medical image of a subject, the medical image comprising a representation of a portion of one or more coronary arteries; analyzing, by the computer system, the medical image to identify one or more coronary arteries, the one or more coronary arteries comprising one or more regions of plaque; analyzing, by the computer system, the identified one or more coronary arteries and the one or more regions of plaque to generate a plurality of image-derived variables, the plurality of image-derived variables comprising one or more of percent atheroma volume of total plaque, total plaque volume, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, vessel length, segment length, lesion length, lumen volume, number of chronic total occlusion (CTO), vessel volume, number of stenosis, severity of stenosis, remodeling index, minimum lumen diameter, maximum lumen diameter, mean lumen diameter, stenosis area percentage, stenosis diameter percentage, number of mild stenosis, number of moderate stenosis, number of zero stenosis, number of severe stenosis, presence of high-risk anatomy, presence of positive remodeling, number of severe stenosis excluding CTO, vessel area, lumen area, diameter stenosis percentage, reference lumen diameter before stenosis, perivascular fat attenuation, or reference lumen diameter after stenosis; generating, by the computer system, one or more syntaxes descriptive of the medical image based at least in part on the plurality of image-derived variables; automatically searching, by the computer system, a database of medical literature for data related to a medical condition of the subject based at least in part on the generated one or more syntaxes; and causing, by the computer system, generation of a display of the data related to the medical condition of the subject, wherein the computer system comprises a computer processor and an electronic storage medium.

Embodiment 2: The computer-implemented method of Embodiment 1, wherein the data related to the medical condition of the subject comprises one or more images of other subjects with similar medical conditions to the subject.

Embodiment 3: The computer-implemented method of Embodiment 1, wherein the data related to the medical condition of the subject comprises one or more scientific articles.

Embodiment 4: The computer-implemented method of Embodiment 3, further comprising generating, by the computer system, a listing of the one or more scientific articles by one or more of relevance or date.

Embodiment 5: The computer-implemented method of Embodiment 4, wherein relevance of the one or more scientific articles is determined by: deriving, by the computer system, one or more syntaxes from the one or more scientific articles; determining, by the computer system, an overlap between the one or more syntaxes derived from the one or more scientific articles and the generated one or more syntaxes descriptive of the medical image; and determining, by the computer system, relevance of the one or more scientific articles based at least in part on the determined overlap.

Embodiment 6: The computer-implemented method of Embodiment 5, wherein the one or more syntaxes from the one or more scientific articles is derived using natural language processing (NLP).

Embodiment 7: The computer-implemented method of Embodiment 3, further comprising generating, by the computer system, a summary of the one or more scientific articles using NLP.

Embodiment 8: The computer-implemented method of Embodiment 3, further comprising extracting, by the computer system, from the one or more scientific articles one or more recommended treatments for the medical condition of the subject using NLP.

Embodiment 9: The computer-implemented method of Embodiment 1, wherein the plurality of image-derived variables is generated using one or more of an artificial intelligence (AI) or machine learning (ML) algorithm trained on a dataset comprising a plurality of medical images with known image-derived variables from a plurality of other subjects.

Embodiment 10: The computer-implemented method of Embodiment 1, wherein the one or more syntaxes descriptive of the medical image are generated based at least in part on a database comprising a plurality of predetermined syntaxes generated from a plurality of medical images with known image-derived variables from a plurality of other subjects.

Embodiment 11: The computer-implemented method of Embodiment 1, wherein the medical image is obtained using computed tomography (CT).

Embodiment 12: The computer-implemented method of Embodiment 1, wherein the medical image is obtained using coronary CT angiography (CCTA).

Embodiment 13: The computer-implemented method of Embodiment 1, wherein the medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 14: The computer-implemented method of Embodiment 1, wherein the medical image comprises a CT image, and wherein low-density non-calcified plaque comprises a region of plaque comprising a radiodensity value between about −189 and about 30 Hounsfield units, wherein non-calcified plaque comprises a region of plaque comprising a radiodensity value between about 31 and about 350 Hounsfield units, and wherein calcified plaque comprises a region of plaque comprising a radiodensity value between about 351 and 2500 Hounsfield units.

Embodiment 15: A computer-implemented method of automatically searching and curating data related to a medical condition of a subject based at least in part on one or more variables derived from image-based analysis of the subject, the method comprising: accessing, by a computer system, a medical image of a subject; analyzing, by the computer system, the medical image to identify one or more areas of interest, the one or more areas of interest comprising one or more regions of disease; analyzing, by the computer system, the identified one or more areas of interest and the one or more regions of disease to generate a plurality of image-derived variables; generating, by the computer system, one or more syntaxes descriptive of the medical image based at least in part on the plurality of image-derived variables; automatically searching, by the computer system, a database of medical literature for data related to a medical condition of the subject based at least in part on the generated one or more syntaxes, wherein the database comprises one or more scientific articles and one or more syntaxes generated from the one or more scientific articles, wherein the searching of the database of medical literature related to the medical condition of the subject is based at least in part on determining an overlap in the one or more syntaxes generated from the medical image and the one or more syntaxes generated from the one or more scientific articles; and causing, by the computer system, generation of a display of the data related to the medical condition of the subject, wherein the computer system comprises a computer processor and an electronic storage medium.

Embodiment 16: The computer-implemented method of Embodiment 15, wherein the data related to the medical condition of the subject comprises one or more images of other subjects with similar medical conditions to the subject.

Embodiment 17: The computer-implemented method of Embodiment 15, further comprising generating, by the computer system, a listing of the one or more scientific articles by one or more of relevance or date.

Embodiment 18: The computer-implemented method of Embodiment 17, wherein relevance of the one or more scientific articles is determined based at least in part on a degree of overlap in the one or more syntaxes generated from the medical image and the one or more syntaxes generated from the one or more scientific articles.

Embodiment 19: The computer-implemented method of Embodiment 15, wherein the one or more syntaxes from the one or more scientific articles is derived using natural language processing (NLP).

Embodiment 20: The computer-implemented method of Embodiment 15, further comprising generating, by the computer system, a summary of the one or more scientific articles using NLP.

Embodiment 21: The computer-implemented method of Embodiment 15, further comprising extracting, by the computer system, from the one or more scientific articles one or more recommended treatments for the medical condition of the subject using NLP.

Embodiment 22: The computer-implemented method of Embodiment 15, wherein the plurality of image-derived variables is generated using one or more of an artificial intelligence (AI) or machine learning (ML) algorithm trained on a dataset comprising a plurality of medical images with known image-derived variables from a plurality of other subjects.

Embodiment 23: The computer-implemented method of Embodiment 15, wherein the one or more syntaxes descriptive of the medical image are generated based at least in part on a database comprising a plurality of predetermined syntaxes generated from a plurality of medical images with known image-derived variables from a plurality of other subjects.

Embodiment 24: The computer-implemented method of Embodiment 15, wherein the medical image is obtained using computed tomography (CT).

Embodiment 25: The computer-implemented method of Embodiment 24, wherein the medical image is obtained using coronary CT angiography (CCTA).

Embodiment 26: The computer-implemented method of Embodiment 15, wherein the medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 27: The computer-implemented method of Embodiment 15, wherein the medical image comprises a CT image, and wherein low-density non-calcified plaque comprises a region of plaque comprising a radiodensity value between about −189 and about 30 Hounsfield units, wherein non-calcified plaque comprises a region of plaque comprising a radiodensity value between about 31 and about 350 Hounsfield units, and wherein calcified plaque comprises a region of plaque comprising a radiodensity value between about 351 and 2500 Hounsfield units.

Embodiment 28: A system comprising: a non-transitory computer storage medium configured to at least store computer-executable instructions; and one or more computer hardware processors in communication with the first non-transitory computer storage medium, the one or more computer hardware processors configured to execute the computer-executable instructions to at least: access a medical image of a subject, the medical image comprising a representation of a portion of one or more coronary arteries; analyze the medical image to identify one or more coronary arteries, the one or more coronary arteries comprising one or more regions of plaque; analyze the identified one or more coronary arteries and the one or more regions of plaque to generate a plurality of image-derived variables, the plurality of image-derived variables comprising one or more of percent atheroma volume of total plaque, total plaque volume, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, vessel length, segment length, lesion length, lumen volume, number of chronic total occlusion (CTO), vessel volume, number of stenosis, severity of stenosis, remodeling index, minimum lumen diameter, maximum lumen diameter, mean lumen diameter, stenosis area percentage, stenosis diameter percentage, number of mild stenosis, number of moderate stenosis, number of zero stenosis, number of severe stenosis, presence of high-risk anatomy, presence of positive remodeling, number of severe stenosis excluding CTO, vessel area, lumen area, diameter stenosis percentage, reference lumen diameter before stenosis, perivascular fat attenuation, or reference lumen diameter after stenosis; generate one or more syntaxes descriptive of the medical image based at least in part on the plurality of image-derived variables; automatically search a database of medical literature for data related to a medical condition of the subject based at least in part on the generated one or more syntaxes; and cause generation of a display of the data related to the medical condition of the subject.

Embodiment 29: The system of Embodiment 28, wherein the data related to the medical condition of the subject comprises one or more images of other subjects with similar medical conditions to the subject.

Embodiment 30: The system of Embodiment 28, wherein the data related to the medical condition of the subject comprises one or more scientific articles.

Embodiment 31: The system of Embodiment 30, wherein the one or more hardware processors are further configured to generate a listing of the one or more scientific articles by one or more of relevance or date.

Embodiment 32: The system of Embodiment 31, wherein relevance of the one or more scientific articles is determined by: deriving one or more syntaxes from the one or more scientific articles; determining an overlap between the one or more syntaxes derived from the one or more scientific articles and the generated one or more syntaxes descriptive of the medical image; and determining relevance of the one or more scientific articles based at least in part on the determined overlap.

Embodiment 33: The system of Embodiment 32, wherein the one or more syntaxes from the one or more scientific articles is derived using natural language processing (NLP).

Embodiment 34: The system of Embodiment 30, wherein the one or more hardware processors are further configured to generate a summary of the one or more scientific articles using NLP.

Embodiment 35: The system of Embodiment 30, wherein the one or more hardware processors are further configured to extract from the one or more scientific articles one or more recommended treatments for the medical condition of the subject using NLP.

Embodiment 36: The system of Embodiment 28, wherein the plurality of image-derived variables is generated using one or more of an artificial intelligence (AI) or machine learning (ML) algorithm trained on a dataset comprising a plurality of medical images with known image-derived variables from a plurality of other subjects.

Embodiment 37: The system of Embodiment 28, wherein the one or more syntaxes descriptive of the medical image are generated based at least in part on a database comprising a plurality of predetermined syntaxes generated from a plurality of medical images with known image-derived variables from a plurality of other subjects.

Embodiment 38: The system of Embodiment 28, wherein the medical image is obtained using computed tomography (CT).

Embodiment 39: The system of Embodiment 28, wherein the medical image is obtained using coronary CT angiography (CCTA).

Embodiment 40: The system of Embodiment 28, wherein the medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 41: The system of Embodiment 28, wherein the medical image comprises a CT image, and wherein low-density non-calcified plaque comprises a region of plaque comprising a radiodensity value between about −189 and about 30 Hounsfield units, wherein non-calcified plaque comprises a region of plaque comprising a radiodensity value between about 31 and about 350 Hounsfield units, and wherein calcified plaque comprises a region of plaque comprising a radiodensity value between about 351 and 2500 Hounsfield units.

Embodiment 42: A system comprising: a non-transitory computer storage medium configured to at least store computer-executable instructions; and one or more computer hardware processors in communication with the first non-transitory computer storage medium, the one or more computer hardware processors configured to execute the computer-executable instructions to at least: access a medical image of a subject; analyze the medical image to identify one or more areas of interest, the one or more areas of interest comprising one or more regions of disease; analyze the identified one or more areas of interest and the one or more regions of disease to generate a plurality of image-derived variables; generate one or more syntaxes descriptive of the medical image based at least in part on the plurality of image-derived variables; automatically search a database of medical literature for data related to a medical condition of the subject based at least in part on the generated one or more syntaxes, wherein the database comprises one or more scientific articles and one or more syntaxes generated from the one or more scientific articles, wherein the searching of the database of medical literature related to the medical condition of the subject is based at least in part on determining an overlap in the one or more syntaxes generated from the medical image and the one or more syntaxes generated from the one or more scientific articles; and cause generation of a display of the data related to the medical condition of the subject.

Embodiment 43: The system of Embodiment 42, wherein the data related to the medical condition of the subject comprises one or more images of other subjects with similar medical conditions to the subject.

Embodiment 44: The system of Embodiment 42, wherein the one or more computer hardware processors are further configured to generate a listing of the one or more scientific articles by one or more of relevance or date.

Embodiment 45: The system of Embodiment 44, wherein relevance of the one or more scientific articles is determined based at least in part on a degree of overlap in the one or more syntaxes generated from the medical image and the one or more syntaxes generated from the one or more scientific articles.

Embodiment 46: The system of Embodiment 42, wherein the one or more syntaxes from the one or more scientific articles is derived using natural language processing (NLP).

Embodiment 47: The system of Embodiment 42, wherein the one or more computer hardware processors are further configured to generate a summary of the one or more scientific articles using NLP.

Embodiment 48: The system of Embodiment 42, wherein the one or more computer hardware processors are further configured to extract from the one or more scientific articles one or more recommended treatments for the medical condition of the subject using NLP.

Embodiment 49: The system of Embodiment 42, wherein the plurality of image-derived variables is generated using one or more of an artificial intelligence (AI) or machine learning (ML) algorithm trained on a dataset comprising a plurality of medical images with known image-derived variables from a plurality of other subjects.

Embodiment 50: The system of Embodiment 42, wherein the one or more syntaxes descriptive of the medical image are generated based at least in part on a database comprising a plurality of predetermined syntaxes generated from a plurality of medical images with known image-derived variables from a plurality of other subjects.

Embodiment 51: The system of Embodiment 42, wherein the medical image is obtained using computed tomography (CT).

Embodiment 52: The system of Embodiment 42, wherein the medical image is obtained using coronary CT angiography (CCTA).

Embodiment 53: The system of Embodiment 42, wherein the medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 54: The system of Embodiment 42, wherein the medical image comprises a CT image, and wherein low-density non-calcified plaque comprises a region of plaque comprising a radiodensity value between about −189 and about 30 Hounsfield units, wherein non-calcified plaque comprises a region of plaque comprising a radiodensity value between about 31 and about 350 Hounsfield units, and wherein calcified plaque comprises a region of plaque comprising a radiodensity value between about 351 and 2500 Hounsfield units.

Embodiment 55: A non-transitory computer-readable medium configured for automatically searching and curating data related to a medical condition of a subject based at least in part on one or more variables derived from image-based analysis of the subject, the computer-readable medium having program instructions for causing a hardware processor to perform a method of: accessing a medical image of a subject, the medical image comprising a representation of a portion of one or more coronary arteries; analyzing the medical image to identify one or more coronary arteries, the one or more coronary arteries comprising one or more regions of plaque; analyzing the identified one or more coronary arteries and the one or more regions of plaque to generate a plurality of image-derived variables, the plurality of image-derived variables comprising one or more of percent atheroma volume of total plaque, total plaque volume, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, vessel length, segment length, lesion length, lumen volume, number of chronic total occlusion (CTO), vessel volume, number of stenosis, severity of stenosis, remodeling index, minimum lumen diameter, maximum lumen diameter, mean lumen diameter, stenosis area percentage, stenosis diameter percentage, number of mild stenosis, number of moderate stenosis, number of zero stenosis, number of severe stenosis, presence of high-risk anatomy, presence of positive remodeling, number of severe stenosis excluding CTO, vessel area, lumen area, diameter stenosis percentage, reference lumen diameter before stenosis, perivascular fat attenuation, or reference lumen diameter after stenosis; generating one or more syntaxes descriptive of the medical image based at least in part on the plurality of image-derived variables; automatically searching a database of medical literature for data related to a medical condition of the subject based at least in part on the generated one or more syntaxes; and causing generation of a display of the data related to the medical condition of the subject.

Embodiment 56: The non-transitory computer readable medium of Embodiment 55, wherein the data related to the medical condition of the subject comprises one or more images of other subjects with similar medical conditions to the subject.

Embodiment 57: The non-transitory computer readable medium of Embodiment 55, wherein the data related to the medical condition of the subject comprises one or more scientific articles.

Embodiment 58: The non-transitory computer readable medium of Embodiment 57, wherein the method performed by the hardware processor further comprises generating a listing of the one or more scientific articles by one or more of relevance or date.

Embodiment 59: The non-transitory computer readable medium of Embodiment 58, wherein relevance of the one or more scientific articles is determined by: deriving one or more syntaxes from the one or more scientific articles; determining an overlap between the one or more syntaxes derived from the one or more scientific articles and the generated one or more syntaxes descriptive of the medical image; and determining relevance of the one or more scientific articles based at least in part on the determined overlap.

Embodiment 60: The non-transitory computer readable medium of Embodiment 59, wherein the one or more syntaxes from the one or more scientific articles is derived using natural language processing (NLP).

Embodiment 61: The non-transitory computer readable medium of Embodiment 57, wherein the method performed by the hardware processor further comprises generating a summary of the one or more scientific articles using NLP.

Embodiment 62: The non-transitory computer readable medium of Embodiment 57, wherein the method performed by the hardware processor further comprises extracting from the one or more scientific articles one or more recommended treatments for the medical condition of the subject using NLP.

Embodiment 63: The non-transitory computer readable medium of Embodiment 55, wherein the plurality of image-derived variables is generated using one or more of an artificial intelligence (AI) or machine learning (ML) algorithm trained on a dataset comprising a plurality of medical images with known image-derived variables from a plurality of other subjects.

Embodiment 64: The non-transitory computer readable medium of Embodiment 55, wherein the one or more syntaxes descriptive of the medical image are generated based at least in part on a database comprising a plurality of predetermined syntaxes generated from a plurality of medical images with known image-derived variables from a plurality of other subjects.

Embodiment 65: The non-transitory computer readable medium of Embodiment 55, wherein the medical image is obtained using computed tomography (CT).

Embodiment 66: The non-transitory computer readable medium of Embodiment 55, wherein the medical image is obtained using coronary CT angiography (CCTA).

Embodiment 67: The non-transitory computer readable medium of Embodiment 55, wherein the medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 68: The non-transitory computer readable medium of Embodiment 55, wherein the medical image comprises a CT image, and wherein low-density non-calcified plaque comprises a region of plaque comprising a radiodensity value between about −189 and about 30 Hounsfield units, wherein non-calcified plaque comprises a region of plaque comprising a radiodensity value between about 31 and about 350 Hounsfield units, and wherein calcified plaque comprises a region of plaque comprising a radiodensity value between about 351 and 2500 Hounsfield units.

Embodiment 69: A non-transitory computer readable medium configured for automatically searching and curating data related to a medical condition of a subject based at least in part on one or more variables derived from image-based analysis of the subject, the computer readable medium having program instructions for causing a hardware processor to perform a method of: accessing a medical image of a subject; analyzing the medical image to identify one or more areas of interest, the one or more areas of interest comprising one or more regions of disease; analyzing the identified one or more areas of interest and the one or more regions of disease to generate a plurality of image-derived variables; generating one or more syntaxes descriptive of the medical image based at least in part on the plurality of image-derived variables; automatically searching a database of medical literature for data related to a medical condition of the subject based at least in part on the generated one or more syntaxes, wherein the database comprises one or more scientific articles and one or more syntaxes generated from the one or more scientific articles, wherein the searching of the database of medical literature related to the medical condition of the subject is based at least in part on determining an overlap in the one or more syntaxes generated from the medical image and the one or more syntaxes generated from the one or more scientific articles; and causing generation of a display of the data related to the medical condition of the subject.

Embodiment 70: The non-transitory computer readable medium of Embodiment 69, wherein the data related to the medical condition of the subject comprises one or more images of other subjects with similar medical conditions to the subject.

Embodiment 71: The non-transitory computer readable medium of Embodiment 69, further comprising generating a listing of the one or more scientific articles by one or more of relevance or date.

Embodiment 72: The non-transitory computer readable medium of Embodiment 71, wherein relevance of the one or more scientific articles is determined based at least in part on a degree of overlap in the one or more syntaxes generated from the medical image and the one or more syntaxes generated from the one or more scientific articles.

Embodiment 73: The non-transitory computer readable medium of Embodiment 69, wherein the one or more syntaxes from the one or more scientific articles is derived using natural language processing (NLP).

Embodiment 74: The non-transitory computer readable medium of Embodiment 69, further comprising generating a summary of the one or more scientific articles using NLP.

Embodiment 75: The non-transitory computer readable medium of Embodiment 69, further comprising extracting from the one or more scientific articles one or more recommended treatments for the medical condition of the subject using NLP.

Embodiment 76: The non-transitory computer readable medium of Embodiment 69, wherein the plurality of image-derived variables is generated using one or more of an artificial intelligence (AI) or machine learning (ML) algorithm trained on a dataset comprising a plurality of medical images with known image-derived variables from a plurality of other subjects.

Embodiment 77: The non-transitory computer readable medium of Embodiment 69, wherein the one or more syntaxes descriptive of the medical image are generated based at least in part on a database comprising a plurality of predetermined syntaxes generated from a plurality of medical images with known image-derived variables from a plurality of other subjects.

Embodiment 78: The non-transitory computer readable medium of Embodiment 69, wherein the medical image is obtained using computed tomography (CT).

Embodiment 79: The non-transitory computer readable medium of Embodiment 69, wherein the medical image is obtained using coronary CT angiography (CCTA).

Embodiment 80: The non-transitory computer readable medium of Embodiment 69, wherein the medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 81: The non-transitory computer readable medium of Embodiment 69, wherein the medical image comprises a CT image, and wherein low-density non-calcified plaque comprises a region of plaque comprising a radiodensity value between about −189 and about 30 Hounsfield units, wherein non-calcified plaque comprises a region of plaque comprising a radiodensity value between about 31 and about 350 Hounsfield units, and wherein calcified plaque comprises a region of plaque comprising a radiodensity value between about 351 and 2500 Hounsfield units.

Quantitative Volumetric Assessment of a Medical Image for Identification

Disclosed herein are systems, devices, and methods for quantitative volumetric assessment of a medical image for identification. For example, in some embodiments, the systems, devices, and methods described herein are related to identifying each pixel or voxel within a volume of interest of a medical image, determining a density of each identified pixel or voxel, and further mapping a distribution of density of each pixel or voxel within the volume of interest. In some embodiments, the systems, devices, and methods described herein are related to comparing a quantitative volumetric assessment with quantitative volumetric assessments of pre-existing medical images and determining a match, and based on the match, identifying the medical image to be identical to a pre-existing medical image.

In some embodiments, the systems, methods, and devices herein relate to quantifying each pixel or voxel within a volume of interest of a medical image. In some embodiments, the quantification can be related to the distribution of radiodensity values of pixels with respect to a particular volume of interest, such as an organ. In some embodiments, the systems, methods, and devices herein relate to analyzing the radiodensity and/or absolute density of pixels relative to the other pixels for a volume of interest. In some embodiments, the systems, methods, and devices herein are configured to utilize radiomic type and/or other pixel and/or voxel evaluation and relationship thereof for identification purposes. In some embodiments, the systems, methods, and devices herein relate to normalizing the medical image based on known materials in the image to a homogenous result and tracking variability. For example, in some embodiments, the systems, methods, and devices herein can be configured to utilize a normalization device, such as one or more normalization devices described in U.S. Pat. Nos.

11,113,811 and/or 11,302,001, both of which are incorporated herein by reference in their entirety. In particular, in some embodiments, the system can be configured to utilize a normalization device to identify a subject and/or medical image and/or evaluate longitudinal change in a quantifiable manner independent of differences in the acquisition protocol used to obtain the image.

As discussed herein, disclosed herein are systems, methods, and devices for quantitative and/or qualitative volumetric assessment of a medical image for identification, which can also be referred to as a "CT Fingerprint." A regular CT scan provides an interior view of a patient. Much like a fingerprint, a CT Fingerprint is unique to each patient and can enable a patient to be recognized. Certain processes, including certain artificial intelligence (AI) processes have the capability to evaluate a scan and quantify each pixel. For example, pixel quantification of an image can be used to determine a length of vessels, a number of vessels, and/or a volume of a heart muscle, which may be unique for each patient. However, by eye, one cannot quantify the different pixels of a CT scan and differentiate one patient from another based on the scan. As such, it would be advantageous to quantitatively evaluate each pixel of a scan to identify the patient.

In some embodiments, the systems, methods, and devices herein relate to quantifying each pixel or voxel within a volume of interest of a medical image. More specifically, in some embodiments, the quantification can be related to the radiodensity of each pixel, in Hounsfield units. In some embodiments, the quantification can be related to the distribution of radiodensity values of pixels with respect to a particular volume of interest, such as an organ. In some embodiments, the systems, methods, and devices herein relate to analyzing the radiodensity and/or absolute density of pixels relative to the other pixels for a volume of interest. In some embodiments, the radiodensity and/or absolute density of pixels can be analyzed relative to different reference points.

A CT Fingerprint may also be used to distinguish between scans by quantitative and/or qualitative evaluation of pixels that renders each scan unique. For example, distinguishing between two scans taken of the same patient a year apart. Because each CT Fingerprint taken is different, a CT Fingerprint may identify a specific exam of a specific patient in a specific point in time. For example, in some embodiments, a first CT Fingerprint of a patient can be taken with respect to a particular volume of interest. In some embodiments, a second CT Fingerprint of the patient can be taken at a later time with respect to the same particular volume of interest. In some embodiments, the CT Fingerprint can be normalized to the levels of the first CT Fingerprint, therefore allowing a comparison between scans of a particular volume of interest over a period of time. Additionally, because a CT Fingerprint may identify a specific exam of a specific patient, a CT Fingerprint may also be advantageous to correct typos in a patient file. For example, if the second CT Fingerprint was placed in the incorrect patient's medical file, an assessment of the CT Fingerprint would reveal a quantitative volumetric assessment unique to the correct patient. In some embodiments, a CT Fingerprint may also be used to determine whether two similar-looking scans are identical. In some embodiments, a CT Fingerprint may be used to automatically locate duplicate scans. In some embodiments, the systems, methods, and devices herein relate to normalizing the medical image based on known materials in the image to a homogenous result and tracking variability.

In some embodiments, the system can be configured to identify a subject of a CT scan by comparing to a previous CT scan of the same and/or similar anatomic area, for example using quantitative and/or qualitative analysis and/or techniques. In some embodiments, the system can be configured to identify a CT image of a subject as a pre-existing CT image in a database even if the CT image and/or the pre-existing CT image is from an incomplete volume and/or not from a full exam, for example using quantitative and/or qualitative analysis and/or techniques. In some embodiments, the system is configured to utilize one or more anatomic structure comparisons and/or pixel and/or voxel evaluation for comparing two or more CT scans. In some embodiments, the anatomic structure can include a distance to ostium of vessel bifurcations and/or bronchi bifurcations, spatial relationship between two or three or more structures, such as for example the aortic annulus to pulmonary annulus to fifth dorsal vertebra. In some embodiments, the system is configured to identify and/or differentiate a subject and/or a medical image of a subject by utilizing spatial triangulation.

In some embodiments, the system can be configured to utilize quantitative and/or qualitative techniques and/or analyses and/or radiomic type features. In some embodiments, the system can be configured to utilize one or more techniques described herein to compare two or more medical images obtained using any modality, such as for example CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the medical image comprises one or more of a contrast-enhanced CT image, non-contrast CT image, MR image, and/or an image obtained using any of the modalities described above. In some embodiments, the system can be configured to be applied to any anatomic area for evaluation, such as for example the chest, abdomen, neck, and/or the like.

Figure 24:
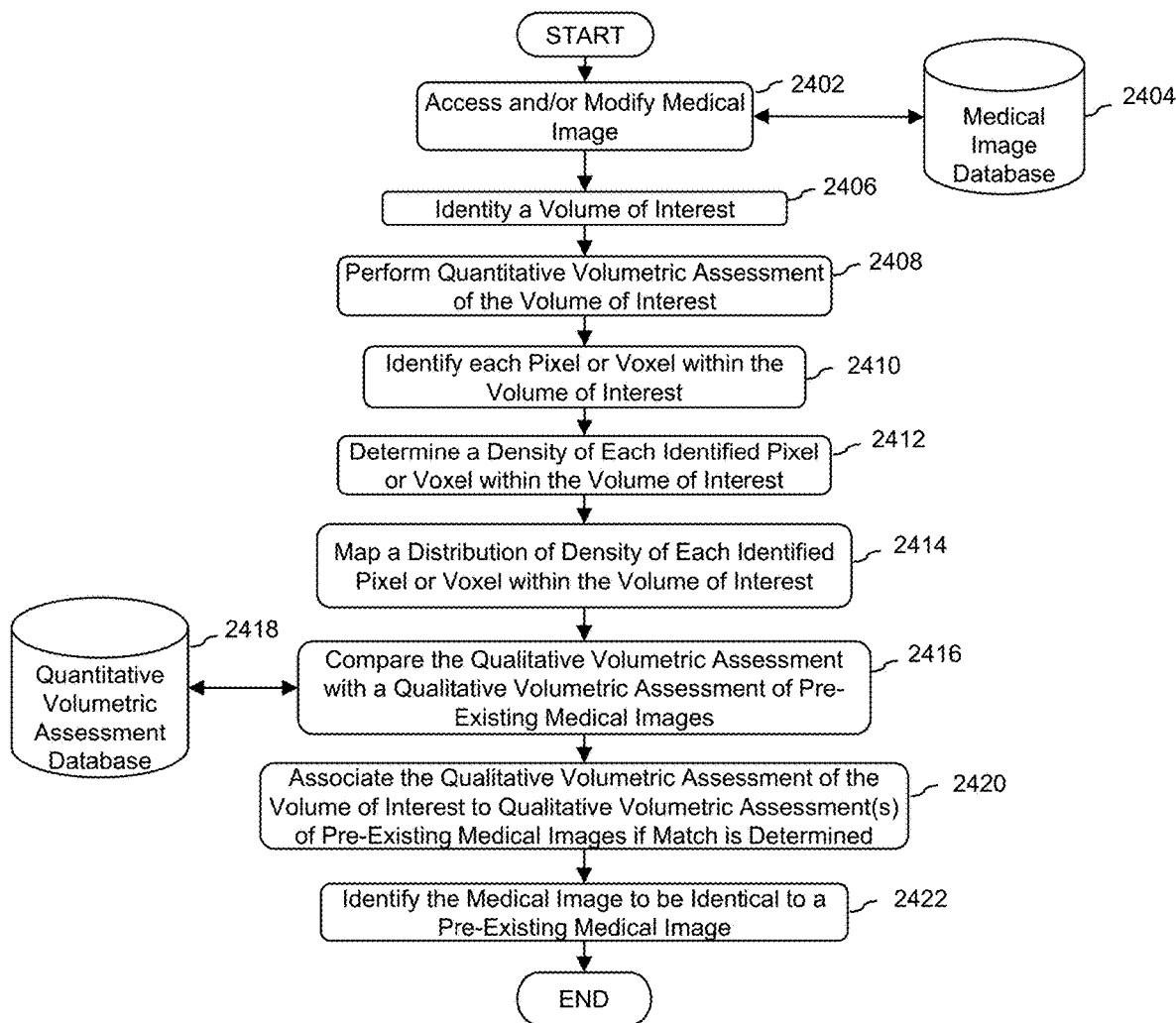
FIG. 24 is a flowchart illustrating an example embodiment(s) of systems, devices, and methods for non-invasive image-based plaque analysis and risk determination.

FIG. 24 is a flowchart illustrating an example embodiment(s) of systems, devices, and methods for quantitative volumetric assessment of a medical image for identification.

At block 2402, the system can be configured to access a medical image of a subject, wherein the medical image of the subject is obtained non-invasively. In some embodiments, the medical image can be stored in a medical image database 2404. In some embodiments, the medical image database 2404 can be locally accessible by the system and/or can be located remotely and accessible through a network connection. In some embodiments, the medical image comprises a Computed Tomography (CT) image. In some embodiments, the medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

At block 2406, the system can be configured to analyze the medical image of the subject to identify a volume of interest. For example, in some embodiments, the volume of interest comprises a portion of a heart of the subject. In some embodiments, the volume of interest comprises a portion of lungs of the subject. In some embodiments, wherein the volume of interest comprises an organ of the subject. In some embodiments, the volume of interest comprises one or more coronary arteries. In some embodiments, the system is configured to identify an organ from the medical image(s) of a subject, and then identify the volume of interest as a portion of the identified organ (e.g., a portion of a heart or lung of the subject). In some embodiments, the system is configured to identify the volume of interest based at least in part, or only using, predetermined criteria. In some embodiments, the system is configured to identify the volume of interest based at least in part on one or more user inputs, for example, an input indicating an area of the medical image to identify the volume of interest.

At block 2408, the system can be configured to perform quantitative volumetric assessment of the volume of interest. In some embodiments, performing quantitative volumetric assessment of the volume of interest further comprises normalizing the medical image. In some embodiments, the system can be configured to compare, by the computer system, the quantitative volumetric assessment of the volume of interest to one or more quantitative volumetric assessments of pre-existing medical images to determine whether an overlap between the quantitative volumetric assessment of the volume of interest and one or more quantitative volumetric assessments of pre-existing medical images is above a predetermined threshold. For example, in some embodiments, quantitative volumetric analysis may include the determination of a volume of pixels within a volume of interest, such as a lung, heart, etc. An overlap between the quantitative volumetric assessments may depend on a similarity in the respective volumes of pixels of a volume of interest between the assessments, for example, in overlap in location, size, and/or shape. In some embodiments, the system can be configured to associate, by the computer system, the one or more quantitative volumetric assessments of pre-existing medical images to the subject when the overlap is determined to be above the predetermined threshold.

The quantitative volumetric assessment of the volume of interest can include the steps outlined in blocks 2410-2414. At block 2410, the system can be configured to identify each pixel or voxel within the volume of interest. At block 2412, the system can be configured to determine a density of each identified pixel or voxel within the volume of interest. In some embodiments, the density comprises material density. In some embodiments, the density comprises radiodensity. At block 2414, the system can be configured to map a distribution of the density of each identified pixel or voxel within the volume of interest. In some embodiments, mapping the distribution of the density comprises a mapping of one or more of low density non-calcified plaque, non-calcified plaque, or calcified plaque. In some embodiments, calcified plaque can correspond to plaque having a highest density range, low density non-calcified plaque can correspond to plaque having a lowest density range, and non-calcified plaque can correspond to plaque having a density range between calcified plaque and low density non-calcified plaque. For example, in some embodiments, the system can be configured to characterize a particular region of plaque as low density non-calcified plaque when the radiodensity of an image pixel or voxel corresponding to that region of plaque is between about −189 and about 30 Hounsfield units (HU). In some embodiments, the Hounsfield units in this range are, or between, two of about −189 HU, about −180 HU, about −170 HU, about −160 HU, about −150 HU, about −140 HU, about −130 HU, about −120 HU, about −110 HU, about −100 HU, about −90 HU, about −80 HU, about −70 HU, about −60 HU, about −50 HU, about −40 HU, about −30, about −20, about −10, about 0, about 10, about 20, and about 30 HU. In some embodiments, the system can be configured to characterize a particular region of plaque as non-calcified plaque when the radiodensity of an image pixel or voxel corresponding to that region of plaque is between about 31 and about 350 HU. In some embodiments, the Hounsfield units in this range are, or between, two of about 31 HU, about 40 HU, about 50 HU, about 60 HU, about 70 HU, about 80 HU, about 90 HU, about 100 HU, about 110 HU, about 120 HU, about 130 HU, about 140 HU, about 150 HU, about 160 HU, about 170 HU, about 180 HU, about 190 HU, about 200 HU, about 210 HU, about 220 HU, about 230 HU, about 240 HU, about 250 HU, about 260 HU, about 270 HU, about 280 HU, about 290 HU, about 300 HU, about 310 HU, about 320 HU, about 330 HU, about 340 HU, and about 350 HU. In some embodiments, the system can be configured to characterize a particular region of plaque as calcified plaque when the radiodensity of an image pixel or voxel corresponding to that region of plaque is between about 351 and about 2500 HU. In some embodiments, the Hounsfield units in this range are, or between, two of about 351 HU, about 400 HU, about 500 HU, about 600 HU, about 700 HU, about 800 HU, about 900 HU, about 1000 HU, about 1100 HU, about 1200 HU, about 1300 HU, about 1400 HU, about 1500 HU, about 1600 HU, about 1700 HU, about 1800 HU, about 1900 HU, about 2000 HU, about 2100 HU, about 2200 HU, about 2300 HU, about 2400 HU, and about 2500 HU.

At block 2416, the system can be configured to compare the quantitative volumetric assessment of the volume of interest to one or more quantitative volumetric assessments of pre-existing medical images to determine whether the quantitative volumetric assessment of the volume of interest matches one or more quantitative volumetric assessments of pre-existing medical images. In some embodiments, in determining whether the quantitative volumetric assessment of the volume of interest matches one or more quantitative volumetric assessments of pre-existing medical images, the system can access a quantitative volumetric assessment database 2418, which can be locally accessible by the system and/or can be located remotely and accessible through a network connection. In some embodiments, the system can be configured to track progression of disease of the subject based at least in part on comparison of the quantitative volumetric assessment of the volume of interest and the one or more quantitative volumetric assessments of pre-existing medical images. In some embodiments, the disease comprises a plaque-based disease. In some embodiments, the quantitative volumetric assessment of the volume of interest is compared to one or more quantitative volumetric assessments of pre-existing medical images using an artificial intelligence algorithm.

At block 2420, the system can be configured to associate the quantitative volumetric assessment of the volume of interest to one or more quantitative volumetric assessments of pre-existing medical images when a match is determined. In some embodiments, the system can be configured to identify, by the computer system, one or more vessels within the medical image when a match is not determined, determine, by the computer system, one or more regions of plaque within the one or more vessels, perform, by the computer system, one or more quantified plaque analyses of the one or more regions of plaque, and determine, by the computer system, a risk of plaque-based disease of the subject based at least in part on the one or more quantified plaque analyses.

At block 2422, the system can be configured to identify the medical image to be identical to the one or more pre-existing medical images when a match is determined. In some embodiments, the system can be configured to retrieve, by the computer system, a medical report of a subject associated with the one or more pre-existing medical images when a match is determined. In some embodiments, the system can be further configured to associate, by the computer system, the retrieved medical report of the subject with the medical image. In some embodiments, the retrieved medical report of the subject comprises an analysis of plaque-based disease of the subject.

Figure 25:
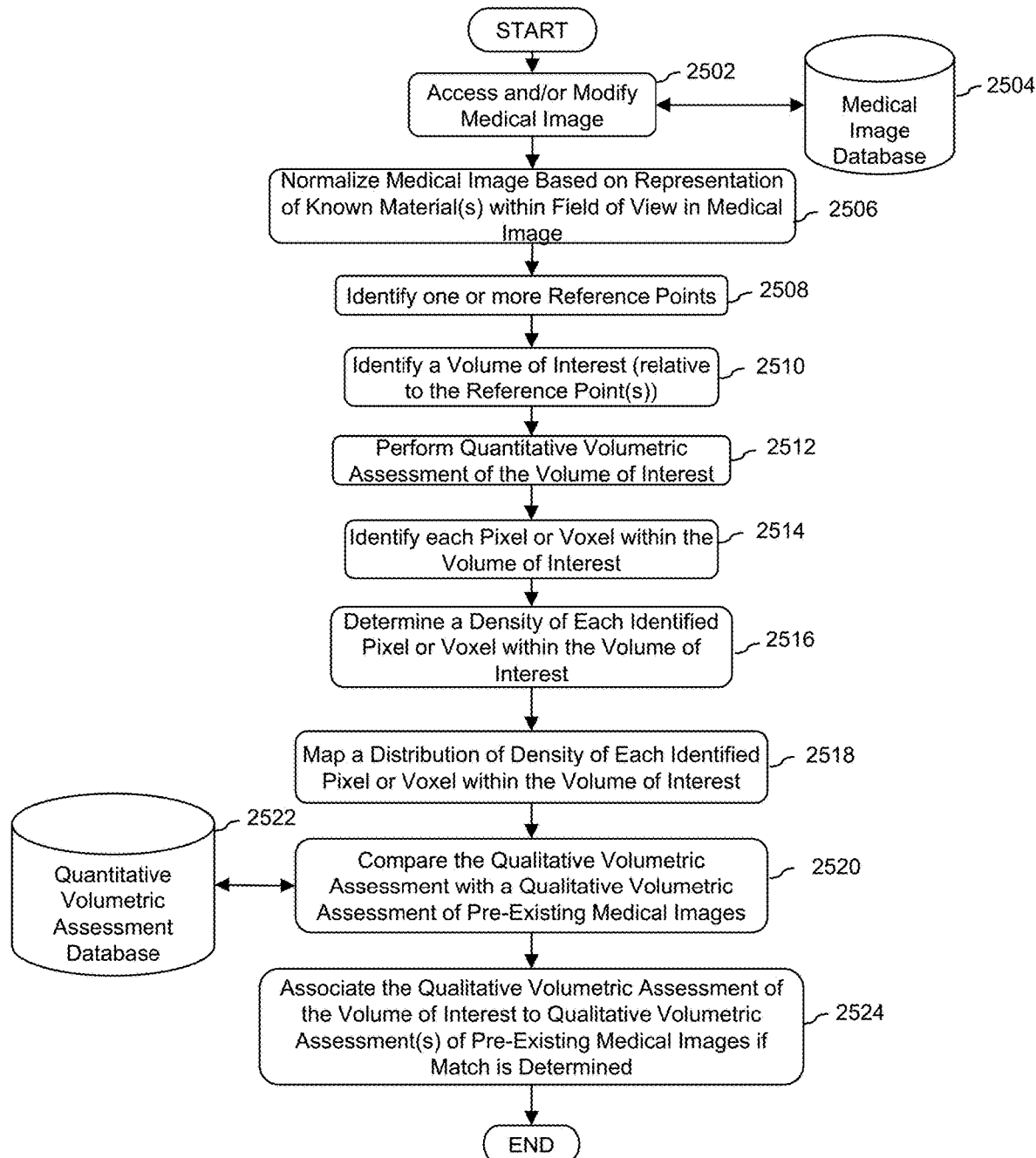
FIG. 25 is a flowchart illustrating an additional example embodiment(s) of systems, devices, and methods for non-invasive image-based plaque analysis and risk determination.

FIG. 25 is a flowchart illustrating an example embodiment(s) of systems, devices, and methods for identifying a subject of a medical image based at least in part on quantitative volumetric assessment of a medical image.

At block 2502, the system can be configured to access a medical image of a subject, wherein the medical image of the subject is obtained non-invasively. In some embodiments, the medical image can be stored in a medical image database 2504. In some embodiments, the medical image database 2504 can be locally accessible by the system and/or can be located remotely and accessible through a network connection. In some embodiments, the medical image comprises a Computed Tomography (CT) image. In some embodiments, the medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

At block 2506, the system can be configured to normalize the medical image of the subject based at least in part on a representation of one or more known materials in the medical image, wherein the one or more known materials are within a field of view in the medical image with the subject.

At block 2508, the system can be configured to analyze the medical image of the subject to identify one or more reference points. In some embodiments, the one or more reference points comprises the ostium.

At block 2510, the system can be configured to analyze the medical image of the subject to identify a volume of interest, wherein the volume of interest is defined relative to the one or more reference points. In some embodiments, the volume of interest comprises a portion of a heart of the subject. In some embodiments, the volume of interest comprises a portion of lungs of the subject. In some embodiments, the volume of interest comprises an organ of the subject. In some embodiments, the volume of interest comprises one or more coronary arteries.

At block 2512, the system can be configured to perform quantitative volumetric assessment of the volume of interest.

The quantitative volumetric assessment of the volume of interest can include the steps outlined in blocks 2514-2518. At block 2514, the system can be configured to identify each pixel or voxel within the volume of interest. At block 2516, the system can be configured to determine a density of each identified pixel or voxel within the volume of interest. In some embodiments, the density comprises material density. In some embodiments, the density comprises radiodensity.

At block 2518, the system can be configured to map a distribution of the density of each identified pixel or voxel within the volume of interest. In some embodiments, mapping the distribution of the density comprises a mapping of one or more of low density non-calcified plaque, non-calcified plaque, or calcified plaque. In some embodiments, one or more regions of plaque are identified as low density non-calcified plaque when a radiodensity value is between about −189 and about 30 Hounsfield units. In some embodiments, the Hounsfield units in this range are, or between, two of about −189 HU, about −180 HU, about −170 HU, about −160 HU, about −150 HU, about −140 HU, about −130 HU, about −120 HU, about −110 HU, about −100 HU, about −90 HU, about −80 HU, about −70 HU, about −60 HU, about −50 HU, about −40 HU, about −30, about −20, about −10, about 0, about 10, about 20, and about 30 HU. In some embodiments, one or more regions of plaque are identified as non-calcified plaque when a radiodensity value is between about 31 and about 350 Hounsfield units. In some embodiments, the Hounsfield units in this range are, or between, two of about 31 HU, about 40 HU, about 50 HU, about 60 HU, about 70 HU, about 80 HU, about 90 HU, about 100 HU, about 110 HU, about 120 HU, about 130 HU, about 140 HU, about 150 HU, about 160 HU, about 170 HU, about 180 HU, about 190 HU, about 200 HU, about 210 HU, about 220 HU, about 230 HU, about 240 HU, about 250 HU, about 260 HU, about 270 HU, about 280 HU, about 290 HU, about 300 HU, about 310 HU, about 320 HU, about 330 HU, about 340 HU, and about 350 HU. In some embodiments, one or more regions of plaque are identified as calcified plaque when a radiodensity value is between about 351 and 2500 Hounsfield units. In some embodiments, the Hounsfield units in this range are, or between, two of about 351 HU, about 400 HU, about 500 HU, about 600 HU, about 700 HU, about 800 HU, about 900 HU, about 1000 HU, about 1100 HU, about 1200 HU, about 1300 HU, about 1400 HU, about 1500 HU, about 1600 HU, about 1700 HU, about 1800 HU, about 1900 HU, about 2000 HU, about 2100 HU, about 2200 HU, about 2300 HU, about 2400 HU, and about 2500 HU.

At block 2520, the system can be configured to compare the quantitative volumetric assessment of the volume of interest to quantitative volumetric assessments of pre-existing medical images of known subjects to determine whether the quantitative volumetric assessment of the volume of interest matches one or more quantitative volumetric assessments of pre-existing medical images of known subjects. In some embodiments, in determining whether the quantitative volumetric assessment of the volume of interest matches one or more quantitative volumetric assessments of pre-existing medical images, the system can access a quantitative volumetric assessment database 2522, which can be locally accessible by the system and/or can be located remotely and accessible through a network connection. In some embodiments, the quantitative volumetric assessment of the volume of interest is compared to one or more quantitative volumetric assessments of pre-existing medical images using an artificial intelligence algorithm.

At block 2524, the system can be configured to associate the medical image to a known subject associated with one or more quantitative volumetric assessments of pre-existing medical images when a match is determined.

In some embodiments, the system can be configured to retrieve a quantified plaque analysis performed on the one or more pre-existing medical images, perform plaque analysis performed on the medical image, compare results of the quantified plaque analysis performed on the one or more pre-existing medical images and the quantified plaque analysis performed on the medical image and determine, by the computer system, progression of a plaque-based disease based on the comparison.

The computer system 902 of FIG. 9, and in some instances, the analysis and/or risk assessment module 940, can be configured to carry out the functions, methods, acts, and/or processes for quantitative volumetric assessment of a medical image for identification described herein, such as those described above with reference to FIGS. 24-25.

The following are non-limiting examples of certain embodiments of systems and methods for quantitative volumetric assessment of a medical image for identification. Other embodiments may include one or more other features, or different features, that are discussed herein.

Embodiment 1: A computer-implemented method of identifying a medical image based at least in part on quantitative volumetric assessment of the medical image, the method comprising: accessing, by a computer system, a medical image of a subject, wherein the medical image of the subject is obtained non-invasively; analyzing, by the computer system, the medical image of the subject to identify a volume of interest; performing, by the computer system, quantitative volumetric assessment of the volume of interest, wherein the quantitative volumetric assessment comprises: identifying each pixel or voxel within the volume of interest; determining a density of each identified pixel or voxel within the volume of interest; and mapping a distribution of the density of each identified pixel or voxel within the volume of interest; comparing, by the computer system, the quantitative volumetric assessment of the volume of interest to one or more quantitative volumetric assessments of pre-existing medical images to determine whether the quantitative volumetric assessment of the volume of interest matches one or more quantitative volumetric assessments of pre-existing medical images; associating, by the computer system, the quantitative volumetric assessment of the volume of interest to one or more quantitative volumetric assessments of pre-existing medical images when a match is determined; and identifying, by the computer system, the medical image to be identical to the one or more pre-existing medical images when a match is determined, wherein the computer system comprises a computer processor and an electronic storage medium.

Embodiment 2: The computer-implemented method of Embodiment 1, further comprising: retrieving, by the computer system, a medical report of a subject associated with the one or more pre-existing medical images when a match is determined; and associating, by the computer system, the retrieved medical report of the subject with the medical image.

Embodiment 3: The computer-implemented method of Embodiment 2, wherein the retrieved medical report of the subject comprises an analysis of plaque-based disease of the subject.

Embodiment 4: The computer-implemented method of Embodiment 1, wherein performing quantitative volumetric assessment of the volume of interest further comprises normalizing the medical image.

Embodiment 5: The computer-implemented method of Embodiment 4, further comprising: comparing, by the computer system, the quantitative volumetric assessment of the volume of interest to one or more quantitative volumetric assessments of pre-existing medical images to determine whether an overlap between the quantitative volumetric assessment of the volume of interest and one or more quantitative volumetric assessments of pre-existing medical images is above a predetermined threshold; and associating, by the computer system, the one or more quantitative volumetric assessments of pre-existing medical images to the subject when the overlap is determined to be above the predetermined threshold.

Embodiment 6: The computer-implemented method of Embodiment 4, further comprising tracking progression of disease of the subject based at least in part on comparison of the quantitative volumetric assessment of the volume of interest and the one or more quantitative volumetric assessments of pre-existing medical images.

Embodiment 7: The computer-implemented method of Embodiment 6, wherein the disease comprises a plaque-based disease.

Embodiment 8: The computer-implemented method of Embodiment 1, further comprising: identifying, by the computer system, one or more vessels within the medical image when a match is not determined; determining, by the computer system, one or more regions of plaque within the one or more vessels; performing, by the computer system, one or more quantified plaque analyses of the one or more regions of plaque; and determining, by the computer system, a risk of plaque-based disease of the subject based at least in part on the one or more quantified plaque analyses.

Embodiment 9: The computer-implemented method of Embodiment 1, wherein the volume of interest comprises a portion of a heart of the subject.

Embodiment 10: The computer-implemented method of Embodiment 1, wherein the volume of interest comprises a portion of lungs of the subject.

Embodiment 11: The computer-implemented method of Embodiment 1, wherein the volume of interest comprises an organ of the subject.

Embodiment 12: The computer-implemented method of Embodiment 1, wherein the volume of interest comprises one or more coronary arteries.

Embodiment 13: The computer-implemented method of Embodiment 1, wherein the quantitative volumetric assessment of the volume of interest is compared to one or more quantitative volumetric assessments of pre-existing medical images using an artificial intelligence algorithm.

Embodiment 14: The computer-implemented method of Embodiment 1, wherein the density comprises material density.

Embodiment 15: The computer-implemented method of Embodiment 1, wherein the density comprises radiodensity.

Embodiment 16: The computer-implemented method of Embodiment 1, wherein mapping the distribution of the density comprises a mapping of one or more of low density non-calcified plaque, non-calcified plaque, or calcified plaque.

Embodiment 17: The computer-implemented method of Embodiment 16, wherein one or more regions of plaque are identified as low density non-calcified plaque when a radiodensity value is between about −189 and about 30 Hounsfield units.

Embodiment 18: The computer-implemented method of Embodiment 16, wherein one or more regions of plaque are identified as non-calcified plaque when a radiodensity value is between about 31 and about 350 Hounsfield units.

Embodiment 19: The computer-implemented method of Embodiment 16, wherein one or more regions of plaque are identified as calcified plaque when a radiodensity value is between about 351 and 2500 Hounsfield units.

Embodiment 20: The computer-implemented method of Embodiment 1, wherein the medical image comprises a Computed Tomography (CT) image.

Embodiment 21: The computer-implemented method of Embodiment 1, wherein the medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 22: A computer-implemented method of identifying a subject of a medical image based at least in part on quantitative volumetric assessment of the medical image, the method comprising: accessing, by a computer system, a medical image of a subject, wherein the medical image of the subject is obtained non-invasively; normalizing, by the computer system, the medical image of the subject based at least in part on a representation of one or more known materials in the medical image, wherein the one or more known materials are within a field of view in the medical image with the subject; analyzing, by the computer system, the medical image of the subject to identify one or more reference points; analyzing, by the computer system, the medical image of the subject to identify a volume of interest, wherein the volume of interest is defined relative to the one or more reference points; performing, by the computer system, quantitative volumetric assessment of the volume of interest, wherein the quantitative volumetric assessment comprises: identifying each pixel or voxel within the volume of interest; determining a density of each identified pixel or voxel within the volume of interest; and mapping a distribution of the density of each identified pixel or voxel within the volume of interest; comparing, by the computer system, the quantitative volumetric assessment of the volume of interest to quantitative volumetric assessments of pre-existing medical images of known subjects to determine whether the quantitative volumetric assessment of the volume of interest matches one or more quantitative volumetric assessments of pre-existing medical images of known subjects; and associating, by the computer system, the medical image to a known subject associated with one or more quantitative volumetric assessments of pre-existing medical images when a match is determined, wherein the computer system comprises a computer processor and an electronic storage medium.

Embodiment 23: The computer-implemented method of Embodiment 22, further comprising: retrieving, by the computer system, a quantified plaque analysis performed on the one or more pre-existing medical images; performing, by the computer system, quantified plaque analysis performed on the medical image; comparing, by the computer system, results of the quantified plaque analysis performed on the one or more pre-existing medical images and the quantified plaque analysis performed on the medical image; and determining, by the computer system, progression of a plaque-based disease based on the comparison.

Embodiment 24: The computer-implemented method of Embodiment 22, wherein the one or more reference points comprises the ostium.

Embodiment 25: The computer-implemented method of Embodiment 22, wherein the volume of interest comprises a portion of a heart of the subject.

Embodiment 26: The computer-implemented method of Embodiment 22, wherein the volume of interest comprises a portion of lungs of the subject.

Embodiment 27: The computer-implemented method of Embodiment 22, wherein the volume of interest comprises an organ of the subject.

Embodiment 28: The computer-implemented method of Embodiment 22, wherein the volume of interest comprises one or more coronary arteries.

Embodiment 29: The computer-implemented method of Embodiment 22, wherein the quantitative volumetric assessment of the volume of interest is compared to one or more quantitative volumetric assessments of pre-existing medical images using an artificial intelligence algorithm.

Embodiment 30: The computer-implemented method of Embodiment 22, wherein the density comprises material density.

Embodiment 31: The computer-implemented method of Embodiment 22, wherein the density comprises radiodensity.

Embodiment 32: The computer-implemented method of Embodiment 22, wherein mapping the distribution of the density comprises a mapping of one or more of low density non-calcified plaque, non-calcified plaque, or calcified plaque.

Embodiment 33: The computer-implemented method of Embodiment 32, wherein one or more regions of plaque are identified as low density non-calcified plaque when a radiodensity value is between about −189 and about 30 Hounsfield units.

Embodiment 34: The computer-implemented method of Embodiment 32, wherein one or more regions of plaque are identified as non-calcified plaque when a radiodensity value is between about 31 and about 350 Hounsfield units.

Embodiment 35: The computer-implemented method of Embodiment 32, wherein one or more regions of plaque are identified as calcified plaque when a radiodensity value is between about 351 and 2500 Hounsfield units.

Embodiment 36: The computer-implemented method of Embodiment 22, wherein the medical image comprises a Computed Tomography (CT) image.

Embodiment 37: The computer-implemented method of Embodiment 22, wherein the medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 38: A system comprising: a non-transitory computer storage medium configured to at least store computer-executable instructions; and one or more computer hardware processors in communication with the first non-transitory computer storage medium, the one or more computer hardware processors configured to execute the computer-executable instructions to at least: access a medical image of a subject, wherein the medical image of the subject is obtained non-invasively; analyze the medical image of the subject to identify a volume of interest; perform quantitative volumetric assessment of the volume of interest, wherein the quantitative volumetric assessment comprises: identifying each pixel or voxel within the volume of interest; determining a density of each identified pixel or voxel within the volume of interest; and mapping a distribution of the density of each identified pixel or voxel within the volume of interest; compare the quantitative volumetric assessment of the volume of interest to one or more quantitative volumetric assessments of pre-existing medical images to determine whether the quantitative volumetric assessment of the volume of interest matches one or more quantitative volumetric assessments of pre-existing medical images; associate the quantitative volumetric assessment of the volume of interest to one or more quantitative volumetric assessments of pre-existing medical images when a match is determined; and identify the medical image to be identical to the one or more pre-existing medical images when a match is determined.

Embodiment 39: The system of Embodiment 38, wherein the one or more computer hardware processors are further configured to execute the computer-executable instructions to at least retrieve a medical report of a subject associated with the one or more pre-existing medical images when a match is determined; and associate the retrieved medical report of the subject with the medical image.

Embodiment 40: The system of Embodiment 39, wherein the retrieved medical report of the subject comprises an analysis of plaque-based disease of the subject.

Embodiment 41: The system of Embodiment 38, wherein performing quantitative volumetric assessment of the volume of interest further comprises normalizing the medical image.

Embodiment 42: The system of Embodiment 41, wherein the one or more computer hardware processors are further configured to execute the computer-executable instructions to at least compare the quantitative volumetric assessment of the volume of interest to one or more quantitative volumetric assessments of pre-existing medical images to determine whether an overlap between the quantitative volumetric assessment of the volume of interest and one or more quantitative volumetric assessments of pre-existing medical images is above a predetermined threshold; and associate the one or more quantitative volumetric assessments of pre-existing medical images to the subject when the overlap is determined to be above the predetermined threshold.

Embodiment 43: The system of Embodiment 41, wherein the one or more computer hardware processors are further configured to execute the computer-executable instructions to at least track progression of disease of the subject based at least in part on comparison of the quantitative volumetric assessment of the volume of interest and the one or more quantitative volumetric assessments of pre-existing medical images.

Embodiment 44: The system of Embodiment 43, wherein the disease comprises a plaque-based disease.

Embodiment 45: The system of Embodiment 38, wherein the one or more computer hardware processors are further configured to execute the computer-executable instructions to at least identify one or more vessels within the medical image when a match is not determined; determine one or more regions of plaque within the one or more vessels; perform one or more quantified plaque analyses of the one or more regions of plaque; and determine a risk of plaque-based disease of the subject based at least in part on the one or more quantified plaque analyses.

Embodiment 46: The system of Embodiment 38, wherein the volume of interest comprises a portion of a heart of the subject.

Embodiment 47: The system of Embodiment 38, wherein the volume of interest comprises a portion of lungs of the subject.

Embodiment 48: The system of Embodiment 38, wherein the volume of interest comprises an organ of the subject.

Embodiment 49: The system of Embodiment 38, wherein the volume of interest comprises one or more coronary arteries.

Embodiment 50: The system of Embodiment 38, wherein the quantitative volumetric assessment of the volume of interest is compared to one or more quantitative volumetric assessments of pre-existing medical images using an artificial intelligence algorithm.

Embodiment 51: The system of Embodiment 38, wherein the density comprises material density.

Embodiment 52: The system of Embodiment 38, wherein the density comprises radiodensity.

Embodiment 53: The system of Embodiment 38, wherein mapping the distribution of the density comprises a mapping of one or more of low density non-calcified plaque, non-calcified plaque, or calcified plaque.

Embodiment 54: The system of Embodiment 53, wherein one or more regions of plaque are identified as low density non-calcified plaque when a radiodensity value is between about −189 and about 30 Hounsfield units.

Embodiment 55: The system of Embodiment 53, wherein one or more regions of plaque are identified as non-calcified plaque when a radiodensity value is between about 31 and about 350 Hounsfield units.

Embodiment 56: The system of Embodiment 53, wherein one or more regions of plaque are identified as calcified plaque when a radiodensity value is between about 351 and 2500 Hounsfield units.

Embodiment 57: The system of Embodiment 38, wherein the medical image comprises a Computed Tomography (CT) image.

Embodiment 58: The system of Embodiment 38, wherein the medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 59: A system comprising: a non-transitory computer storage medium configured to at least store computer-executable instructions; and one or more computer hardware processors in communication with the first non-transitory computer storage medium, the one or more computer hardware processors configured to execute the computer-executable instructions to at least: access a medical image of a subject, wherein the medical image of the subject is obtained non-invasively; normalize the medical image of the subject based at least in part on a representation of one or more known materials in the medical image, wherein the one or more known materials are within a field of view in the medical image with the subject; analyzing the medical image of the subject to identify one or more reference points; analyzing, by the computer system, the medical image of the subject to identify a volume of interest, wherein the volume of interest is defined relative to the one or more reference points; perform quantitative volumetric assessment of the volume of interest, wherein the quantitative volumetric assessment comprises: identifying each pixel or voxel within the volume of interest; determining a density of each identified pixel or voxel within the volume of interest; and mapping a distribution of the density of each identified pixel or voxel within the volume of interest; compare the quantitative volumetric assessment of the volume of interest to quantitative volumetric assessments of pre-existing medical images of known subjects to determine whether the quantitative volumetric assessment of the volume of interest matches one or more quantitative volumetric assessments of pre-existing medical images of known subjects; and associate the medical image to a known subject associated with one or more quantitative volumetric assessments of pre-existing medical images when a match is determined.

Embodiment 60: The system of Embodiment 59, wherein the one or more computer hardware processors are further configured to execute the computer-executable instructions to at least retrieve a quantified plaque analysis performed on the one or more pre-existing medical images; perform quantified plaque analysis performed on the medical image; compare results of the quantified plaque analysis performed on the one or more pre-existing medical images and the quantified plaque analysis performed on the medical image; and determine progression of a plaque-based disease based on the comparison.

Embodiment 61: The system of Embodiment 59, wherein the one or more reference points comprises the ostium.

Embodiment 62: The system of Embodiment 59, wherein the volume of interest comprises a portion of a heart of the subject.

Embodiment 63: The system of Embodiment 59, wherein the volume of interest comprises a portion of lungs of the subject.

Embodiment 64: The system of Embodiment 59, wherein the volume of interest comprises an organ of the subject.

Embodiment 65: The system of Embodiment 59, wherein the volume of interest comprises one or more coronary arteries.

Embodiment 66: The system of Embodiment 59, wherein the quantitative volumetric assessment of the volume of interest is compared to one or more quantitative volumetric assessments of pre-existing medical images using an artificial intelligence algorithm.

Embodiment 67: The system of Embodiment 59, wherein the density comprises material density.

Embodiment 68: The system of Embodiment 59, wherein the density comprises radiodensity.

Embodiment 69: The system of Embodiment 59 wherein mapping the distribution of the density comprises a mapping of one or more of low density non-calcified plaque, non-calcified plaque, or calcified plaque.

Embodiment 70: The system of Embodiment 69, wherein one or more regions of plaque are identified as low density non-calcified plaque when a radiodensity value is between about −189 and about 30 Hounsfield units.

Embodiment 71: The system of Embodiment 69, wherein one or more regions of plaque are identified as non-calcified plaque when a radiodensity value is between about 31 and about 350 Hounsfield units.

Embodiment 72: The system of Embodiment 69, wherein one or more regions of plaque are identified as calcified plaque when a radiodensity value is between about 351 and 2500 Hounsfield units.

Embodiment 73: The system of Embodiment 59, wherein the medical image comprises a Computed Tomography (CT) image.

Embodiment 74: The system of Embodiment 59, wherein the medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 75: A non-transitory computer readable medium configured for identifying a medical image based at least in part on quantitative volumetric assessment of the medical image, the computer readable medium having program instructions for causing a hardware processor to perform a method of: accessing, by a computer system, a medical image of a subject, wherein the medical image of the subject is obtained non-invasively; analyzing, by the computer system, the medical image of the subject to identify a volume of interest; performing, by the computer system, quantitative volumetric assessment of the volume of interest, wherein the quantitative volumetric assessment comprises: identifying each pixel or voxel within the volume of interest; determining a density of each identified pixel or voxel within the volume of interest; and mapping a distribution of the density of each identified pixel or voxel within the volume of interest; comparing, by the computer system, the quantitative volumetric assessment of the volume of interest to one or more quantitative volumetric assessments of pre-existing medical images to determine whether the quantitative volumetric assessment of the volume of interest matches one or more quantitative volumetric assessments of pre-existing medical images; associating, by the computer system, the quantitative volumetric assessment of the volume of interest to one or more quantitative volumetric assessments of pre-existing medical images when a match is determined; and identifying, by the computer system, the medical image to be identical to the one or more pre-existing medical images when a match is determined.

Embodiment 76: The non-transitory computer readable medium of Embodiment 75, wherein the hardware processor is further configured to: retrieve a medical report of a subject associated with the one or more pre-existing medical images when a match is determined; and associate the retrieved medical report of the subject with the medical image.

Embodiment 77: The non-transitory computer readable medium of Embodiment 76, wherein the retrieved medical report of the subject comprises an analysis of plaque-based disease of the subject.

Embodiment 78: The computer-implemented method of Embodiment 75, wherein performing quantitative volumetric assessment of the volume of interest further comprises normalizing the medical image.

Embodiment 79: The non-transitory computer readable medium of Embodiment 78, wherein the hardware processor is further configured to: compare the quantitative volumetric assessment of the volume of interest to one or more quantitative volumetric assessments of pre-existing medical images to determine whether an overlap between the quantitative volumetric assessment of the volume of interest and one or more quantitative volumetric assessments of pre-existing medical images is above a predetermined threshold; and associate the one or more quantitative volumetric assessments of pre-existing medical images to the subject when the overlap is determined to be above the predetermined threshold.

Embodiment 80: The non-transitory computer readable medium of Embodiment 78, wherein the hardware processor is further configured to track progression of disease of the subject based at least in part on comparison of the quantitative volumetric assessment of the volume of interest and the one or more quantitative volumetric assessments of pre-existing medical images.

Embodiment 81: The non-transitory computer readable medium of Embodiment 80, wherein the disease comprises a plaque-based disease.

Embodiment 82: The non-transitory computer readable medium of Embodiment 75, wherein the hardware processor is further configured to: identify one or more vessels within the medical image when a match is not determined; determine one or more regions of plaque within the one or more vessels; perform one or more quantified plaque analyses of the one or more regions of plaque; and determine a risk of plaque-based disease of the subject based at least in part on the one or more quantified plaque analyses.

Embodiment 83: The non-transitory computer readable medium of Embodiment 75, wherein the volume of interest comprises a portion of a heart of the subject.

Embodiment 84: The non-transitory computer readable medium of Embodiment 75, wherein the volume of interest comprises a portion of lungs of the subject.

Embodiment 85: The non-transitory computer readable medium of Embodiment 75, wherein the volume of interest comprises an organ of the subject.

Embodiment 86: The non-transitory computer readable medium of Embodiment 75, wherein the volume of interest comprises one or more coronary arteries.

Embodiment 87: The non-transitory computer readable medium of Embodiment 75, wherein the quantitative volumetric assessment of the volume of interest is compared to one or more quantitative volumetric assessments of pre-existing medical images using an artificial intelligence algorithm.

Embodiment 88: The non-transitory computer readable medium of Embodiment 75, wherein the density comprises material density.

Embodiment 89: The non-transitory computer readable medium of Embodiment 75, wherein the density comprises radiodensity.

Embodiment 90: The non-transitory computer readable medium of Embodiment 75, wherein mapping the distribution of the density comprises a mapping of one or more of low density non-calcified plaque, non-calcified plaque, or calcified plaque.

Embodiment 91: The non-transitory computer readable medium of Embodiment 90, wherein one or more regions of plaque are identified as low density non-calcified plaque when a radiodensity value is between about −189 and about 30 Hounsfield units.

Embodiment 92: The non-transitory computer readable medium of Embodiment 90, wherein one or more regions of plaque are identified as non-calcified plaque when a radiodensity value is between about 31 and about 350 Hounsfield units.

Embodiment 93: The non-transitory computer readable medium of Embodiment 90, wherein one or more regions of plaque are identified as calcified plaque when a radiodensity value is between about 351 and 2500 Hounsfield units.

Embodiment 94: The non-transitory computer readable medium of Embodiment 75, wherein the medical image comprises a Computed Tomography (CT) image.

Embodiment 95: 4The non-transitory computer readable medium of Embodiment 75, wherein the medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 96: A non-transitory computer readable medium configured for identifying a medical image based at least in part on quantitative volumetric assessment of the medical image, the computer readable medium having program instructions for causing a hardware processor to perform a method of: accessing, by a computer system, a medical image of a subject, wherein the medical image of the subject is obtained non-invasively; normalizing, by the computer system, the medical image of the subject based at least in part on a representation of one or more known materials in the medical image, wherein the one or more known materials are within a field of view in the medical image with the subject; analyzing, by the computer system, the medical image of the subject to identify one or more reference points; analyzing, by the computer system, the medical image of the subject to identify a volume of interest, wherein the volume of interest is defined relative to the one or more reference points; performing, by the computer system, quantitative volumetric assessment of the volume of interest, wherein the quantitative volumetric assessment comprises: identifying each pixel or voxel within the volume of interest; determining a density of each identified pixel or voxel within the volume of interest; and mapping a distribution of the density of each identified pixel or voxel within the volume of interest; comparing, by the computer system, the quantitative volumetric assessment of the volume of interest to quantitative volumetric assessments of pre-existing medical images of known subjects to determine whether the quantitative volumetric assessment of the volume of interest matches one or more quantitative volumetric assessments of pre-existing medical images of known subjects; and associating, by the computer system, the medical image to a known subject associated with one or more quantitative volumetric assessments of pre-existing medical images when a match is determined.

Embodiment 97: The computer-implemented method of Embodiment 96, wherein the hardware processor is further configured to: retrieve a quantified plaque analysis performed on the one or more pre-existing medical images; perform quantified plaque analysis performed on the medical image; compare results of the quantified plaque analysis performed on the one or more pre-existing medical images and the quantified plaque analysis performed on the medical image; and determine progression of a plaque-based disease based on the comparison.

Embodiment 98: The non-transitory computer readable medium of Embodiment 96, wherein the one or more reference points comprises the ostium.

Embodiment 99: The non-transitory computer readable medium of Embodiment 96, wherein the volume of interest comprises a portion of a heart of the subject.

Embodiment 100: The non-transitory computer readable medium of Embodiment 96, wherein the volume of interest comprises a portion of lungs of the subject.

Embodiment 101: The non-transitory computer readable medium of Embodiment 96, wherein the volume of interest comprises an organ of the subject.

Embodiment 102: The non-transitory computer readable medium of Embodiment 96, wherein the volume of interest comprises one or more coronary arteries.

Embodiment 103: The non-transitory computer readable medium of Embodiment 96, wherein the quantitative volumetric assessment of the volume of interest is compared to one or more quantitative volumetric assessments of pre-existing medical images using an artificial intelligence algorithm.

Embodiment 104: The non-transitory computer readable medium of Embodiment 96, wherein the density comprises material density.

Embodiment 105: The non-transitory computer readable medium of Embodiment 96, wherein the density comprises radiodensity.

Embodiment 106: The non-transitory computer readable medium of Embodiment 96, wherein mapping the distribution of the density comprises a mapping of one or more of low density non-calcified plaque, non-calcified plaque, or calcified plaque.

Embodiment 107: The non-transitory computer readable medium of Embodiment 106, wherein one or more regions of plaque are identified as low density non-calcified plaque when a radiodensity value is between about −189 and about 30 Hounsfield units.

Embodiment 108: The non-transitory computer readable medium of Embodiment 106, wherein one or more regions of plaque are identified as non-calcified plaque when a radiodensity value is between about 31 and about 350 Hounsfield units.

Embodiment 109: The non-transitory computer readable medium of Embodiment 106, wherein one or more regions of plaque are identified as calcified plaque when a radiodensity value is between about 351 and 2500 Hounsfield units.

Embodiment 110: The non-transitory computer readable medium of Embodiment 96, wherein the medical image comprises a Computed Tomography (CT) image.

Embodiment 111: The non-transitory computer readable medium of Embodiment 96, wherein the medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Multivariable Image-Based Analysis of Thin-Cap Fibroatheroma

Disclosed herein are systems, devices, and methods for multivariable image-based analysis of thin-cap fibroatheroma (TCFA). In particular, in some embodiments, the systems, devices, and methods described herein are related to analysis (e.g., image-based analysis) of a medical image or medical images to determine one or more CAD-related variables or plaque parameters from which the presence of TCFA, which itself may not be easily recognizable within the image, can be determined or estimated. For example, in some embodiments, the variable can include one or more of distance between plaque and vessel wall, distance between plaque and lumen wall, length along longitudinal axis, length along latitudinal axis, volume of low density non-calcified plaque, volume of total plaque, a ratio(s) between volume of low density non-calcified plaque and volume of total plaque, embeddedness of low density non-calcified plaque, and/or the like. In some embodiments, the plaque analyses are based on plaque parameters generated by medical imaging and are compared to known TCFA indicators to determine or estimate the presence of TCFA and risk of CAD. For example, a machine learning algorithm can be trained to determine or estimate the presence of TCFA based on the CAD-related variables and/or plaque parameters determined from an image-based analysis. In some embodiments, the systems, devices, and methods described herein are configured to determine a risk of coronary artery disease (CAD), such as for example, myocardial infarction (MI), based on one or more plaque or TCFA analyses described herein. In some embodiments, the systems, devices, and methods described herein are configured to generate a proposed treatment and/or graphical representation based on the determined risk of CAD and/or one or more plaque analyses described herein Disclosed herein are systems, methods, and devices for determining a likelihood of thin-cap fibroatheroma (TCFA) based at least in part on a plurality of variables derived from non-invasive medical image analysis, such as for example a CT image. In some embodiments, the system devices, and methods described herein are configured to determine a risk of CAD based on TCFA as determined by one or more plaque and/or vascular analyses described herein. In some embodiments, the plaque and/or vascular analyses are based on plaque and/or vascular parameters generated by medical imaging and are compared to plaque and/or vascular parameters derived from known cases with or without TCFA to determine TCFA risk of CAD. In some embodiments, the systems, devices, and methods are configured to generate a proposed treatment based on the determined risk of TCFA and/or one or more plaque and/or vascular analyses described herein.

In some instances, plaque can be considered "vulnerable plaque," which can be plaque that is more likely to cause heart attacks. Such plaque can have a necrotic core, non-calcified plaque, and thin-cap fibroatheroma (TCFA). TCFA can be a fibrous, thin layer that stretches across a lipid pool. The lipid pool can be filled with a necrotic core and/or noncalcified plaque. If the layer of TCFA breaks, the lipid pool escapes into the vessel potentially causing a cardiac event. The presence of TCFA indicates that a patient is more at risk of cardiac events such as MI.

If TCFA were detectable, patients and physicians could better analyze a patient's CAD and more accurately prescribe a course of treatment. While certain invasive imaging capabilities, such as integrated intravascular ultrasound (IVUS), and/or high-resolution imaging capabilities, such as optical coherence tomography (OCT), may allow for visualization of some TCFA, more commonly available imaging capabilities, such as CT, have limitations on spatial resolution, with the resolution being around 500 microns. TCFA can have a spatial resolution at around 10 microns and can be essentially undetectable by the limits of CT imaging.

Without more readily adequate imaging existing to detect TCFA, there is a need for TCFA to be discovered through other methods, systems, and devices. Vulnerable plaque and TCFA can be associated with indicators that suggest the presence of TCFA. Because TCFA is undetectable by imaging methods such as CT, additional methods are needed to identify TCFA to aid in detecting at-risk patients.

Some embodiments of the systems, devices, and methods described herein address this technical shortcoming by providing a way to diagnose, detect, and/or determine the presence or likelihood of presence of TCFA by utilizing one or more variables that can derived from a medical image without directly identifying TCFA from the medical image. That is, in some embodiments, an analysis can generate an estimate or determination of TCFA indirectly by analyzing one or more other variables or plaque parameters determined from an image-based analysis, even when TCFA itself is not directly determinable within the medical image.

The one or more variables derived from the medical image can be one or more of around 60 variables of which some or all can be used to determine the presence or likelihood of TCFA. Some embodiments may include a machine learning algorithm that can compare the variables with a database of variables derived from known cases with or without TCFA, for example verified through IVUS and/or OCT and/or other techniques. A database can be created by using a collection of cases and for each case in the collection, determining through IVUS and/or OCT if there is TCFA in the case. The database, after each case has been checked for TCFA, can be used as a training set for a machine learning algorithm. In some embodiments, the algorithm can provide a physician the percent chance of having TCFA based on the variables and the database. In some examples, the variables include percent atheroma volume of total plaque, total plaque volume, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, presence of two-feature positive plaques, number of two-feature positive plaques, vessel length, segment length, lesion length, lumen volume, number of chronic total occlusion (CTO), vessel volume, number of stenosis, severity of stenosis, remodeling index, minimum lumen diameter, maximum lumen diameter, mean lumen diameter, stenosis area percentage, stenosis diameter percentage, number of mild stenosis, number of moderate stenosis, number of zero stenosis, number of severe stenosis, presence of high-risk anatomy, presence of positive remodeling, number of severe stenosis excluding CTO, vessel area, lumen area, diameter stenosis percentage, presence of ischemia, number of stents, reference lumen diameter before stenosis, perivascular fat attenuation, or reference lumen diameter after stenosis. In some embodiments, low-density non-calcified plaque can be defined as a region of plaque with a radiodensity value less than or equal to about 30 Hounsfield units, non-calcified plaque can be defined as a region of plaque with a radiodensity value greater than about 30 Hounsfield units and/or less than or equal to about 350 Hounsfield units, calcified plaque can be defined as a region of plaque with a radiodensity value greater than about 350 Hounsfield units, low-density calcified plaque can be defined as a region of plaque with a radiodensity value greater than about 350 Hounsfield units and/or less than or equal to about 700 Hounsfield units, medium-density calcified plaque can be defined as a region of plaque with a radiodensity value greater than about 700 Hounsfield units and/or less than or equal to about 1000 Hounsfield units, and/or high-density calcified plaque can be defined as a region of plaque with a radiodensity value greater than about 1000 Hounsfield units.

As an example, a medical image can be obtained and analyzed to determine one or more vascular parameters or variable and/or one or more plaque parameters or variables based on an image-based analysis of the image. A machine learning algorithm can be applied to these variables in conjunction with a database of TCFA indicators to determine the presence of TCFA or to estimate a percent chance of TCFA. In some embodiments, the machine learning algorithm, using testing and imaging outputs, can provide an analysis that determines a likelihood of the presence or absence of TCFA or a binary yes or no which could include data that indicates if it is more or less probable there is TCFA.

In some embodiments, the systems, methods, and devices can be configured to analyze a medical image to perform one or more analyses of plaque and/or types of plaque, such as for example low density non-calcified plaque, calcified plaque, non-calcified plaque, and/or the like. In particular, in some embodiments, low density non-calcified plaque can be a focus due to the high-risk generally associated with low density non-calcified plaque. For example, low density non-calcified plaque can have a higher risk of potential rupture compared to other types of plaque, such as regular non-calcified plaque or calcified plaque. A plaque rupture can, in some instances, clog or block a vessel, thereby causing a heart attack or MI. As such, it can be advantageous to analyze one or more features of low density non-calcified plaque, and/or non-calcified plaque and/or calcified plaque, which may correspond to high or low risk of CAD and/or stability or instability of plaque. In some embodiments, the systems, devices, and methods are configured to analyze a medical image, such as a CT or CCTA image, to derive one or more features, measures, and/or characterizations of plaque, such as low density non-calcified plaque, non-calcified plaque, and/or calcified plaque, and use the same to facilitate an assessment or and/or generate an assessment of risk of CAD and/or stability or instability of plaque. Thus, in some embodiments, the systems, devices, and methods can provide an efficient and/or non-invasive method of assessing risk of CAD and/or plaque.

Additionally, to prevent a rupture or to assess risk of CAD, in some embodiments, the systems, methods, and devices can be configured to use the analysis of plaque and other variables provided by the CT to create a risk assessment of TCFA. In some embodiments, the risk assessment is created by comparing the variables to a database of known TCFA indicators. TCFA indicators can include but are not limited to total plaque, total plaque volume, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, presence of two-feature positive plaques, number of two-feature positive plaques, vessel length, segment length, lesion length, lumen volume, number of chronic total occlusion (CTO), vessel volume, number of stenosis, severity of stenosis, remodeling index, minimum lumen diameter, maximum lumen diameter, mean lumen diameter, stenosis area percentage, stenosis diameter percentage, number of mild stenosis, number of moderate stenosis, number of zero stenosis, number of severe stenosis, presence of high-risk anatomy, presence of positive remodeling, number of severe stenosis excluding CTO, vessel area, lumen area, diameter stenosis percentage, presence of ischemia, number of stents, reference lumen diameter before stenosis, perivascular fat attenuation, or reference lumen diameter after stenosis. In some embodiments, low-density non-calcified plaque can be defined as a region of plaque with a radiodensity value less than or equal to about 30 Hounsfield units, non-calcified plaque can be defined as a region of plaque with a radiodensity value greater than about 30 Hounsfield units and/or less than or equal to about 350 Hounsfield units, calcified plaque can be defined as a region of plaque with a radiodensity value greater than about 350 Hounsfield units, low-density calcified plaque can be defined as a region of plaque with a radiodensity value greater than about 350 Hounsfield units and/or less than or equal to about 700 Hounsfield units, medium-density calcified plaque can be defined as a region of plaque with a radiodensity value greater than about 700 Hounsfield units and/or less than or equal to about 1000 Hounsfield units, and/or high-density calcified plaque can be defined as a region of plaque with a radiodensity value greater than about 1000 Hounsfield units.

In some embodiments, the systems, methods, and devices can be configured to identify TCFA indicators and calculate a percentage risk of having TCFA. The percentage risk of TCFA, in some embodiments, could be included in an overall diagnosis for CAD and can be included in a general risk assessment for CAD and MI. In some embodiments, the systems, methods, and devices can be configured to indicate positively or negatively of a diagnosis of TCFA.

In some embodiments, the systems, methods, and devices can be configured to assess risk of TCFA and provide, from a risk/treatment database, a treatment option or plan for the physician to advise to the patient. In some embodiments, a diagnostic plan may include aiding the medical provider in step-by-step treatment options and provide analysis at different stages of the treatment.

Figure 26:
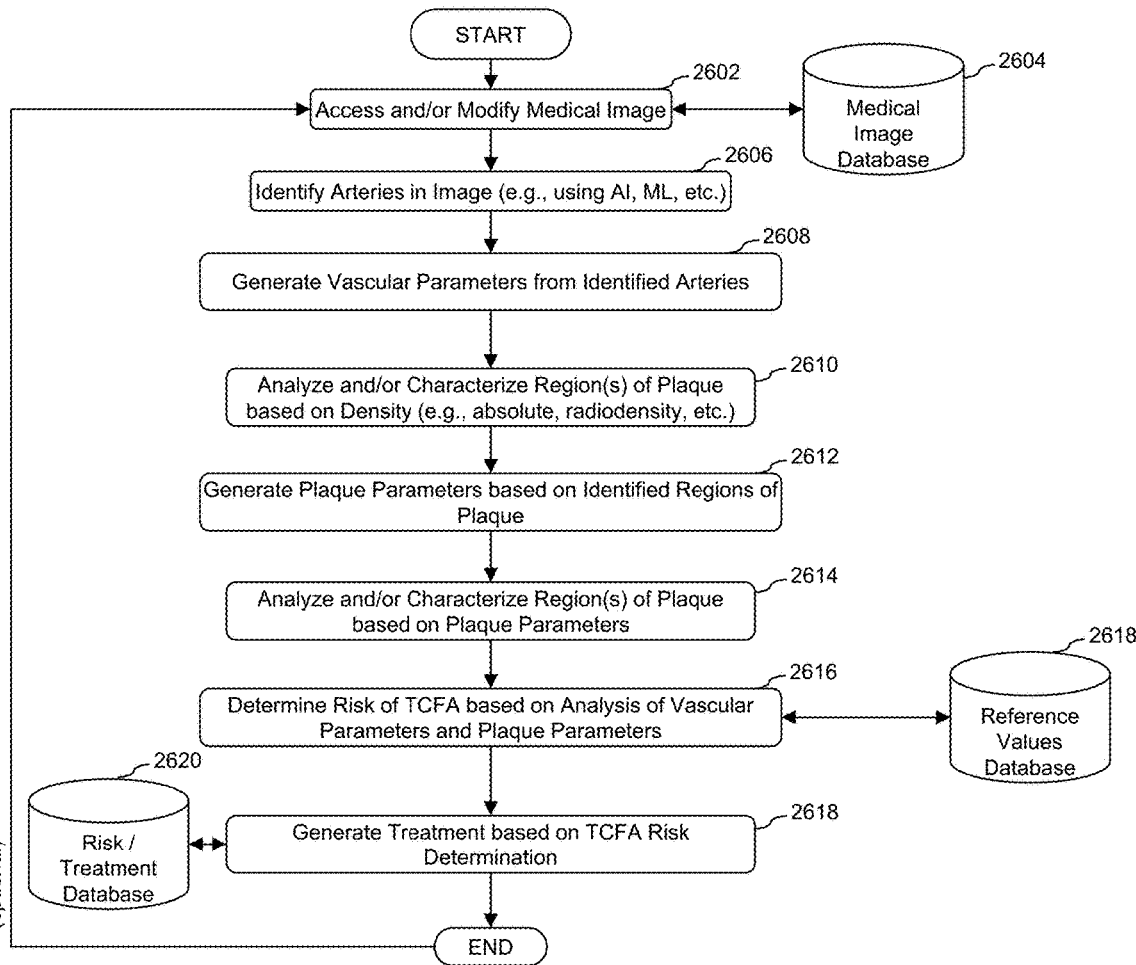
FIG. 26 is a flowchart illustrating an example embodiment(s) of systems, devices, and methods for multivariable image-based analysis of thin-cap fibroatheroma (TCFA).

FIG. 26 is a flowchart illustrating an example embodiment(s) of systems, devices, and methods for multivariable image-based analysis of thin-cap fibroatheroma. As illustrated in FIG. 26, in some embodiments, the system can be configured to access and/or modify one or more medical images at block 2602. In some embodiments, the medical image can include one or more arteries, such as coronary, carotid, and/or other arteries of a subject. In some embodiments, the medical image can be stored in a medical image database 2604. In some embodiments, the medical image database 2604 can be locally accessible by the system and/or can be located remotely and accessible through a network connection. The medical image can comprise an image obtain using one or more modalities such as for example, Computed Tomography (CT), Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the medical image comprises one or more of a contrast-enhanced CT image, non-contrast CT image, MR image, and/or an image obtained using any of the modalities described above.

In some embodiments, the system can be configured to automatically and/or dynamically perform one or more analyses of the medical image as discussed herein. For example, in some embodiments, at block 2606, the system can be configured to identify one or more vessels, such as of one or more arteries. The one or more arteries can include coronary arteries, carotid arteries, aorta, renal artery, lower extremity artery, upper extremity artery, and/or cerebral artery, amongst others. In some embodiments, the system can be configured to utilize one or more AI and/or ML algorithms to automatically and/or dynamically identify one or more arteries or coronary arteries using image processing. For example, in some embodiments, the one or more AI and/or ML algorithms can be trained using a Convolutional Neural Network (CNN) on a set of medical images on which arteries or coronary arteries have been identified, thereby allowing the AI and/or ML algorithm automatically identify arteries or coronary arteries directly from a medical image. In some embodiments, the arteries or coronary arteries are identified by size and/or location.

In some embodiments, at block 2608, the system can be configured to identify one or more regions of plaque in the medical image and collect one or more quantified vascular parameters. In some embodiments, the system can be configured to utilize one or more AI and/or ML algorithms to automatically and/or dynamically identify one or more regions of plaque using image processing. For example, in some embodiments, the one or more AI and/or ML algorithms can be trained using a Convolutional Neural Network (CNN) on a set of medical images on which regions of plaque have been identified, thereby allowing the AI and/or ML algorithm automatically identify regions of plaque directly from a medical image. In some embodiments, the system is configured to identify vessel and lumen walls and classify everything in between the vessel and lumen walls as plaque. In some embodiments, quantified vascular parameters can be one or more of vessel length, segment length, lesion length, lumen volume, number of chronic total occlusion (CTO), vessel volume, number of stenosis, severity of stenosis, remodeling index, minimum lumen diameter, maximum lumen diameter, mean lumen diameter, stenosis area percentage, stenosis diameter percentage, number of mild stenosis, number of moderate stenosis, number of zero stenosis, number of severe stenosis, presence of high-risk anatomy, presence of positive remodeling, number of severe stenosis excluding CTO, vessel area, lumen area, diameter stenosis percentage, presence of ischemia, number of stents, reference lumen diameter before stenosis, or reference lumen diameter after stenosis.

In some embodiments, at block 2610, the system can be configured to analyze and/or characterize one or more regions of plaque based on density. For example, in some embodiments, the system can be configured to analyze and/or characterize one or more regions of plaque based on absolute density and/or relative density and/or radiodensity. In some embodiments, the system can be configured to classify a region of plaque as one of low density non-calcified plaque, non-calcified plaque, and calcified plaque, using any one or more processes and/or features described herein.

In some embodiments, at block 2612, the system can be configured to analyze and/or characterize one or more regions of plaque based on one or more distances. For example, as described herein, in some embodiments, the system can be configured to determine a distance between a low density non-calcified plaque and lumen wall and/or vessel wall. In some embodiments, proximity of a low density non-calcified plaque to the lumen wall can be indicative of a high-risk plaque and/or CAD. Conversely, in some embodiments, a position of a low density non-calcified plaque far from the lumen wall can be indicative of less risk. In some embodiments, the system can be configured to utilize one or more predetermined thresholds in determining the risk factor associated with the proximity of low density non-calcified plaque with the vessel wall and/or lumen wall. In some embodiments, the system can be configured to utilize one or more image processing algorithms to automatically and/or dynamically determine one or more distances to and/or from one or more regions of plaque. In some embodiments, the one or more regions of plaque can include a necrotic core and/or non-calcified plaque. In some embodiments, the one or more regions of plaque can include one or more low density non-calcified plaque and/or non-calcified plaque. In some embodiments, the regions of plaque can be identified as low density non-calcified plaque when it has a radiodensity value between about −189 and about 30 Hounsfield units. In some embodiments, the regions of plaque can be identified as non-calcified plaque when it has a radiodensity value between about 31 and about 350 Hounsfield units. In some embodiments, the regions of plaque can be identified as calcified plaque when it has a radiodensity value between about 351 and about 2500 Hounsfield units. In some embodiments, the lower and/or upper Hounsfield unit boundary threshold for determining whether a plaque corresponds to one or more of low density non-calcified plaque, non-calcified plaque, and/or calcified plaque can be about −1000 HU, about −900 HU, about −800 HU, about −700 HU, about −600 HU, about −500 HU, about −400 HU, about −300 HU, about −200 HU, about −190 HU, about −180 HU, about −170 HU, about −160 HU, about −150 HU, about −140 HU, about −130 HU, about −120 HU, about −110 HU, about −100 HU, about −90 HU, about −80 HU, about −70 HU, about −60 HU, about −50 HU, about −40 HU, about −30 HU, about −20 HU, about −10 HU, about 0 HU, about 10 HU, about 20 HU, about 30 HU, about 40 HU, about 50 HU, about 60 HU, about 70 HU, about 80 HU, about 90 HU, about 100 HU, about 110 HU, about 120 HU, about 130 HU, about 140 HU, about 150 HU, about 160 HU, about 170 HU, about 180 HU, about 190 HU, about 200 HU, about 210 HU, about 220 HU, about 230 HU, about 240 HU, about 250 HU, about 260 HU, about 270 HU, about 280 HU, about 290 HU, about 300 HU, about 310 HU, about 320 HU, about 330 HU, about 340 HU, about 350 HU, about 360 HU, about 370 HU, about 380 HU, about 390 HU, about 400 HU, about 410 HU, about 420 HU, about 430 HU, about 440 HU, about 450 HU, about 460 HU, about 470 HU, about 480 HU, about 490 HU, about 500 HU, about 510 HU, about 520 HU, about 530 HU, about 540 HU, about 550 HU, about 560 HU, about 570 HU, about 580 HU, about 590 HU, about 600 HU, about 700 HU, about 800 HU, about 900 HU, about 1000 HU, about 1100 HU, about 1200 HU, about 1300 HU, about 1400 HU, about 1500 HU, about 1600 HU, about 1700 HU, about 1800 HU, about 1900 HU, about 2000 HU, about 2100 HU, about 2200 HU, about 2300 HU, about 2400 HU, about 2500 HU, about 2600 HU, about 2700 HU, about 2800 HU, about 2900 HU, about 3000 HU, about 3100 HU, about 3200 HU, about 3300 HU, about 3400 HU, about 3500 HU, and/or about 4000 HU.

Based on the analysis or characterization of the regions of plaque, in some embodiments, at block 2612, the system can generate plaque parameters. In some embodiments, the system can be configured to collect and store data collected from the medical image from the identified regions of plaque. In some embodiments, the system can identify, from the medical image of block 2602, additional parameters related to plaque, coronary artery disease, and/or artery anatomy that are located in the identified regions of plaque of block 2610. In some embodiments, the system can be configured to provide quantified plaque parameters based on one or more of percent atheroma volume of total plaque, total plaque volume, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, presence of two-feature positive plaques, or number of two-feature positive plaques.

In some embodiments, the system can be configured to analyze and/or characterize regions of plaque based on TCFA variables. In some embodiments, for example, at block 2614, the system can be configured to use the quantified plaque parameters of block 2612 compared with known TCFA variables analyze and/or characterize regions of plaque based on the TCFA variables. In some examples, the variables include percent atheroma volume of total plaque, total plaque volume, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, presence of two-feature positive plaques, number of two-feature positive plaques, vessel length, segment length, lesion length, lumen volume, number of chronic total occlusion (CTO), vessel volume, number of stenosis, severity of stenosis, remodeling index, minimum lumen diameter, maximum lumen diameter, mean lumen diameter, stenosis area percentage, stenosis diameter percentage, number of mild stenosis, number of moderate stenosis, number of zero stenosis, number of severe stenosis, presence of high-risk anatomy, presence of positive remodeling, number of severe stenosis excluding CTO, vessel area, lumen area, diameter stenosis percentage, presence of ischemia, number of stents, reference lumen diameter before stenosis, perivascular fat attenuation, or reference lumen diameter after stenosis.

In some embodiments, the system can be configured to determine risk of TCFA based on a TCFA variable analysis. For example, in some embodiments, at block 2616, the system can be configured to determine the risk of TCFA. In some embodiments, based on the analysis and/or characterization of the regions of plaque of block 2614, the system can use the reference values found in the reference values database of block 2618 to determine the risk and/or likelihood of TCFA found in the identified regions of plaque. In some embodiments, the likelihood of the presence of TCFA is determined on a subject basis. In some embodiments, the determined likelihood of the presence of TCFA provides a percentage of likelihood of the presence of TCFA. In some embodiments, the system provides a binary output, for example "yes" or "no," to identify if there is TCFA detected and/or suspected by the system.

In some embodiments, for example, at block 2618, the system is configured to generate treatment based on the TCFA risk determination of block 2616. In some embodiments, the system uses a risk/treatment database as depicted in block 2620, in conjunction with the determined risk of block 2616 to provide a treatment for the suspected and/or detected TCFA. In some embodiments, the treatment can include advising a known regiment, crafting a personalized plan for the individual, and/or providing treatment plan options. In some embodiments, the treatment may include follow up scans at designated points which can allow the system to make changes to the treatment plan based on the scans.

In some embodiments, the system can be further configured to determine a risk of artery disease for the subject, based at least in part on the determined likelihood of the presence of TCFA. In such embodiments, the artery disease may be coronary artery disease and/or peripheral artery disease. In some embodiments, the determination of artery disease is determined, in part, by comparing the determined likelihood of TCFA against a dataset of various risks of artery disease from a reference population. In such embodiments, the system can use the determined likelihood of TCFA and the TCFA variables to determine, using a dataset from a reference population, what variables are most often found with artery disease and/or which carry the most risk associated with artery disease.

In some embodiments, the system can further be configured to propose a treatment for the subject based, at least in part, on the determined risk of artery disease. In some embodiments, the system uses a risk/treatment database to provide a treatment for the suspected and/or detected artery disease determine by the likelihood of TCFA. In some embodiments, the treatment can include advising a known regiment, crafting a personalized plan for the individual, and/or providing treatment plan options. In some embodiments, the treatment may include follow up scans at designated points which can allow the system to make changes to the treatment plan based on the scans.

The computer system 902 of FIG. 9, and in some instances, the analysis and/or risk assessment module 940, can be configured to carry out the functions, methods, acts, and/or processes for Multivariable image-based analysis of thin-cap fibroatheroma described herein, such as those described above with reference to FIG. 26.

The following are non-limiting examples of certain embodiments of systems and methods for multivariable image-based analysis of thin-cap fibroatheroma. Other embodiments may include one or more other features, or different features, that are discussed herein.

Embodiment 1: A computer-implemented method of determining a likelihood of thin-cap fibroatheroma (TCFA) based at least in part on a plurality of variables derived from non-invasive medical image analysis, the method comprising: accessing, by a computer system, a medical image of a subject, wherein the medical image of the subject is obtained non-invasively; analyzing, by the computer system, the medical image of the subject to identify one or more arteries; generating, by the computer system, one or more quantified vascular parameters based at least in part on the identified one or more arteries; analyzing, by the computer system, the identified one or more arteries to identify one or more regions of plaque based at least in part on density; generating, by the computer system, one or more quantified plaque parameters based at least in part on the identified one or more regions of plaque; determining, by the computer system, a likelihood of presence of TCFA for the one or more regions of plaque without direct identification of TCFA from the medical image, wherein the likelihood of presence of TCFA is determined by applying a machine learning algorithm to the one or more quantified vascular parameters and the one or more quantified plaque parameters, wherein the machine learning algorithm is trained by a dataset comprising one or more quantified vascular parameters and one or more quantified plaque parameters derived from a plurality of other medical images with known presence or absence of TCFA for a region of plaque, wherein the computer system comprises a computer processor and an electronic storage medium.

Embodiment 2: The computer-implemented method of Embodiment 1, wherein the one or more quantified plaque parameters comprises one or more of percent atheroma volume of total plaque, total plaque volume, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, presence of two-feature positive plaques, or number of two-feature positive plaques.

Embodiment 3: The computer-implemented method of Embodiment 1, wherein the one or more quantified vascular parameters comprises one or more of vessel length, segment length, lesion length, lumen volume, number of chronic total occlusion (CTO), vessel volume, number of stenosis, severity of stenosis, remodeling index, minimum lumen diameter, maximum lumen diameter, mean lumen diameter, stenosis area percentage, stenosis diameter percentage, number of mild stenosis, number of moderate stenosis, number of zero stenosis, number of severe stenosis, presence of high-risk anatomy, presence of positive remodeling, number of severe stenosis excluding CTO, vessel area, lumen area, diameter stenosis percentage, presence of ischemia, number of stents, reference lumen diameter before stenosis, perivascular fat attenuation, or reference lumen diameter after stenosis. The computer-implemented method of Embodiment 1, wherein the likelihood of presence of TCFA is determined on a subject basis.

Embodiment 4: The computer-implemented method of Embodiment 1, wherein the determined likelihood of presence of TCFA comprises a percentage of likelihood of presence of TCFA.

Embodiment 5: The computer-implemented method of Embodiment 1, wherein the determined likelihood of presence of TCFA comprises a binary output of likelihood or unlikelihood of presence of TCFA.

Embodiment 6: The computer-implemented method of Embodiment 1, further comprising determining a risk of artery disease for the subject based at least in part on the determined likelihood of presence of TCFA.

Embodiment 7: The computer-implemented method of Embodiment 6, wherein the artery disease comprises coronary artery disease (CAD).

Embodiment 8: The computer-implemented method of Embodiment 6, wherein the artery disease comprises peripheral artery disease (PAD).

Embodiment 9: The computer-implemented method of Embodiment 6, wherein the risk of artery disease for the subject is determined based at least in part on comparing the determined likelihood of presence of TCFA against dataset comprising varying risks of artery disease and known presence or absence of TCFA derived from a reference population.

Embodiment 10: The computer-implemented method of Embodiment 6, further comprising determining a proposed treatment for the subject based at least in part on the determined risk of artery disease.

Embodiment 11: The computer-implemented method of Embodiment 10, wherein the proposed treatment comprises one or more of a lifestyle treatment, interventive treatment, or medication treatment.

Embodiment 12: The computer-implemented method of Embodiment 1, wherein the one or more regions of plaque comprises a necrotic core and non-calcified plaque.

Embodiment 13: The computer-implemented method of Embodiment 1, wherein the one or more regions of plaque comprises one or more of low density non-calcified plaque or non-calcified plaque.

Embodiment 14: The computer-implemented method of Embodiment 1, wherein the one or more arteries comprises one or more coronary arteries.

Embodiment 15: The computer-implemented method of Embodiment 1, wherein the one or more arteries comprises one or more coronary arteries, carotid arteries, lower extremity arteries, upper extremity arteries, or aorta.

Embodiment 16: The computer-implemented method of Embodiment 1, wherein the density comprises absolute density.

Embodiment 17: The computer-implemented method of Embodiment 1, wherein the density comprises radiodensity.

Embodiment 18: The computer-implemented method of Embodiment 1, wherein the one or more regions of plaque are identified as low density non-calcified plaque when a radiodensity value is between about −189 and about 30 Hounsfield units.

Embodiment 19: The computer-implemented method of Embodiment 1, wherein the one or more regions of plaque are identified as non-calcified plaque when a radiodensity value is between about 31 and about 350 Hounsfield units.

Embodiment 20: The computer-implemented method of Embodiment 1, wherein the one or more regions of plaque are identified as calcified plaque when a radiodensity value is between about 351 and 2500 Hounsfield units.

Embodiment 21: The computer-implemented method of Embodiment 1, wherein the medical image comprises a Computed Tomography (CT) image.

Embodiment 22: The computer-implemented method of Embodiment 1, wherein the medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 23: A system for determining a likelihood of thin-cap fibroatheroma (TCFA) based at least in part on a plurality of variables derived from non-invasive medical image analysis, the system comprising: a non-transitory computer storage medium configured to at least store computer executable instructions; and one or more computer hardware processors in communication with the first non-transitory computer storage medium, the one or more computer hardware processors configured to execute the computer-executable instructions to at least: access a medical image of a subject, wherein the medical image of the subject is obtained non-invasively; analyze the medical image of the subject to identify one or more arteries; generate one or more quantified vascular parameters based at least in part on the identified one or more arteries; analyze the identified one or more arteries to identify one or more regions of plaque based at least in part on density; generate one or more quantified plaque parameters based at least in part on the identified one or more regions of plaque; determine a likelihood of presence of TCFA for the one or more regions of plaque without direct identification of TCFA from the medical image, wherein the likelihood of presence of TCFA is determined by applying a machine learning algorithm to the one or more quantified vascular parameters and the one or more quantified plaque parameters, wherein the machine learning algorithm is trained by a dataset comprising one or more quantified vascular parameters and one or more quantified plaque parameters derived from a plurality of other medical images with known presence or absence of TCFA for a region of plaque.

Embodiment 24: The system of Embodiment 23, wherein the one or more quantified plaque parameters comprising one or more of percent atheroma volume of total plaque, total plaque volume, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, or medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, presence of two-feature positive plaques, or number of two-feature positive plaques.

Embodiment 25: The system of Embodiment 23, wherein the one or more quantified vascular parameters comprising one or more of vessel length, segment length, lesion length, lumen volume, number of chronic total occlusion (CTO), vessel volume, number of stenosis, severity of stenosis, remodeling index, minimum lumen diameter, maximum lumen diameter, mean lumen diameter, stenosis area percentage, stenosis diameter percentage, number of mild stenosis, number of moderate stenosis, number of zero stenosis, number of severe stenosis, presence of high-risk anatomy, presence of positive remodeling, number of severe stenosis excluding CTO, vessel area, lumen area, diameter stenosis percentage, presence of ischemia, number of stents, reference lumen diameter before stenosis, perivascular fat attenuation, or reference lumen diameter after stenosis.

Embodiment 26: The system of Embodiment 23, wherein the one or more computer hardware processors are further configured to execute the computer-executable instructions to at least determine the likelihood of presence of TCFA on a subject basis.

Embodiment 27: The system of Embodiment 23, wherein the determined likelihood of presence of TCFA comprises a percentage of likelihood of presence of TCFA.

Embodiment 28: The system of Embodiment 23, wherein the determined likelihood of presence of TCFA comprises a binary output of likelihood or unlikelihood of presence of TCFA.

Embodiment 29: The system of Embodiment 23, wherein the one or more computer hardware processors are further configured to execute the computer-executable instructions to at least determine a risk of artery disease for the subject based at least in part on the determined likelihood of presence of TCFA.

Embodiment 30: The system of Embodiment 29, wherein at least the artery disease comprises coronary artery disease (CAD).

Embodiment 31: The system of Embodiment 29, wherein the artery disease comprises peripheral artery disease (PAD).

Embodiment 32: The system of Embodiment 29, wherein the risk of artery disease for the subject is determined based at least in part on comparing the determined likelihood of presence of TCFA against dataset comprising varying risks of artery disease and known presence or absence of TCFA derived from a reference population.

Embodiment 33: The system of Embodiment 29, wherein the one or more computer hardware processors are further configured to execute the computer-executable instructions to at least determine a proposed treatment for the subject based at least in part on the determined risk of artery disease.

Embodiment 34: The system of Embodiment 33, wherein the proposed treatment comprises one or more of a lifestyle treatment, interventive treatment, or medication treatment.

Embodiment 35: The system of Embodiment 29, wherein the one or more regions of plaque comprises a necrotic core and non-calcified plaque.

Embodiment 36: The system of Embodiment 29, wherein the one or more regions of plaque comprises one or more of low density non-calcified plaque or non-calcified plaque.

Embodiment 37: The system method of Embodiment 29, wherein the one or more arteries comprises one or more coronary arteries.

Embodiment 38: The system of Embodiment 29, wherein the one or more arteries comprises one or more coronary arteries, carotid arteries, lower extremity arteries, upper extremity arteries, or aorta.

Embodiment 39: The system of Embodiment 29, wherein the density comprises absolute density.

Embodiment 40: The system of Embodiment 29, wherein the density comprises radiodensity.

Embodiment 41: The system of Embodiment 23, wherein the one or more regions of plaque are identified as low density non-calcified plaque when a radiodensity value is between about −189 and about 30 Hounsfield units.

Embodiment 42: The system of Embodiment 23, wherein the one or more regions of plaque are identified as non-calcified plaque when a radiodensity value is between about 31 and about 350 Hounsfield units.

Embodiment 43: The system of Embodiment 23, wherein the one or more regions of plaque are identified as calcified plaque when a radiodensity value is between about 351 and 2500 Hounsfield units.

Embodiment 44: The system of Embodiment 29, wherein the medical image comprises a Computed Tomography (CT) image.

Embodiment 45: The system of Embodiment 29, wherein the medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 46: A non-transitory computer readable medium configured for determining a likelihood of thin-cap fibroatheroma (TCFA) based at least in part on a plurality of variables derived from non-invasive medical image analysis, the computer readable medium having program instructions for causing a hardware processor to perform a method of: accessing a medical image of a subject, wherein the medical image of the subject is obtained non-invasively; analyzing the medical image of the subject to identify one or more arteries; generating one or more quantified vascular parameters based at least in part on the identified one or more arteries; analyzing the identified one or more arteries to identify one or more regions of plaque based at least in part on density; generating one or more quantified plaque parameters based at least in part on the identified one or more regions of plaque; determining a likelihood of presence of TCFA for the one or more regions of plaque without direct identification of TCFA from the medical image, wherein the likelihood of presence of TCFA is determined by applying a machine learning algorithm to the one or more quantified vascular parameters and the one or more quantified plaque parameters, wherein the machine learning algorithm is trained by a dataset comprising one or more quantified vascular parameters and one or more quantified plaque parameters derived from a plurality of other medical images with known presence or absence of TCFA for a region of plaque.

Embodiment 47: The non-transitory computer readable medium of Embodiment 46, wherein the one or more quantified plaque parameters comprises one or more of percent atheroma volume of total plaque, total plaque volume, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, or medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, presence of two-feature positive plaques, or number of two-feature positive plaques.

Embodiment 48: The non-transitory computer readable medium of Embodiment 46, wherein the one or more quantified vascular parameters comprises one or more of vessel length, segment length, lesion length, lumen volume, number of chronic total occlusion (CTO), vessel volume, number of stenosis, severity of stenosis, remodeling index, minimum lumen diameter, maximum lumen diameter, mean lumen diameter, stenosis area percentage, stenosis diameter percentage, number of mild stenosis, number of moderate stenosis, number of zero stenosis, number of severe stenosis, presence of high-risk anatomy, presence of positive remodeling, number of severe stenosis excluding CTO, vessel area, lumen area, diameter stenosis percentage, presence of ischemia, number of stents, reference lumen diameter before stenosis, perivascular fat attenuation, or reference lumen diameter after stenosis.

Embodiment 49: The non-transitory computer readable medium of Embodiment 46, wherein the likelihood of presence of TCFA is determined on a subject basis.

Embodiment 50: The non-transitory computer readable medium Embodiment 46, wherein the determined likelihood of presence of TCFA comprises a percentage of likelihood of presence of TCFA.

Embodiment 51: The non-transitory computer readable medium of Embodiment 46, wherein the determined likelihood of presence of TCFA comprises a binary output of likelihood or unlikelihood of presence of TCFA.

Embodiment 52: The non-transitory computer readable medium of Embodiment 46, the method further comprising determining a risk of artery disease for the subject based at least in part on the determined likelihood of presence of TCFA.

Embodiment 53: The non-transitory computer readable medium of Embodiment 52, wherein the artery disease comprises coronary artery disease (CAD).

Embodiment 54: The non-transitory computer readable medium of Embodiment 52, wherein the artery disease comprises peripheral artery disease (PAD).

Embodiment 55: The computer-implemented method of Embodiment 52, wherein the risk of artery disease for the subject is determined based at least in part on comparing the determined likelihood of presence of TCFA against dataset comprising varying risks of artery disease and known presence or absence of TCFA derived from a reference population.

Embodiment 56: The non-transitory computer readable medium of Embodiment 52, the method further comprising determining a proposed treatment for the subject based at least in part on the determined risk of artery disease.

Embodiment 57: The non-transitory computer readable medium of Embodiment 56, wherein the proposed treatment comprises one or more of a lifestyle treatment, interventive treatment, or medication treatment.

Embodiment 58: The non-transitory computer readable medium of Embodiment 46, wherein the one or more regions of plaque comprises a necrotic core and non-calcified plaque.

Embodiment 59: The non-transitory computer readable medium of Embodiment 46, wherein the one or more regions of plaque comprises one or more of low density non-calcified plaque or non-calcified plaque.

Embodiment 60: The non-transitory computer readable medium of Embodiment 46, wherein the one or more arteries comprises one or more coronary arteries.

Embodiment 61: The non-transitory computer readable medium of Embodiment 46, wherein the one or more arteries comprises one or more coronary arteries, carotid arteries, lower extremity arteries, upper extremity arteries, or aorta.

Embodiment 62: The non-transitory computer readable medium of Embodiment 46, wherein the density comprises absolute density.

Embodiment 63: The non-transitory computer readable medium of Embodiment 46, wherein the density comprises radiodensity.

Embodiment 64: The non-transitory computer readable medium of Embodiment 46, wherein the one or more regions of plaque are identified as low density non-calcified plaque when a radiodensity value is between about −189 and about 30 Hounsfield units.

Embodiment 65: The non-transitory computer readable medium of Embodiment 46, wherein the one or more regions of plaque are identified as non-calcified plaque when a radiodensity value is between about 31 and about 350 Hounsfield units.

Embodiment 66: The non-transitory computer readable medium of Embodiment 46, wherein the one or more regions of plaque are identified as calcified plaque when a radiodensity value is between about 351 and 2500 Hounsfield units.

Embodiment 67: The non-transitory computer readable medium of Embodiment 46, wherein the medical image comprises a Computed Tomography (CT) image.

Embodiment 68: The non-transitory computer readable medium of Embodiment 46, wherein the medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Other Embodiment(s)

Although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Any methods disclosed herein need not be performed in the order recited. Thus, it is intended that the scope of the invention herein disclosed should not be limited by the particular embodiments described above.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the inventions or claims.

Further, while the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various implementations described and the appended claims. Further, the disclosure hereinof any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 3.5 mm" includes "3.5 mm." Phrases preceded by a term such as "substantially" include the recited phrase and should be interpreted based on the circumstances (e.g., as much as reasonably possible under the circumstances). For example, "substantially constant" includes "constant." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y, and at least one of Z to each be present.

The invention claimed is:

1. A computer-implemented method of determining presence of ischemia based at least in part on a plurality of variables derived from non-invasive medical image analysis, the method comprising:
    accessing, by a computer system, a medical image of a subject, wherein the medical image of the subject is obtained non-invasively;
    analyzing, by the computer system, the medical image of the subject to identify a plurality of vessels, the plurality of vessels comprising at least a first vessel;
    identifying, by the computer system, one or more lesions in the first vessel;
    identifying, by the computer system, one or more regions of plaque within the one or more lesions in the first vessel;
    determining, by the computer system using at least in part a first machine learning algorithm, a plurality of variables associated with the one or more lesions in the first vessel and the one or more regions of plaque within the one or more lesions in the first vessel, wherein the plurality of variables comprise stenosis, total plaque volume, non-calcified plaque volume, calcified plaque volume, lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, and number of mild stenosis; and
    applying, by the computer system, a second machine learning algorithm to determine a presence of ischemia in the first vessel based at least in part on the plurality of variables,
    wherein the computer system comprises a computer processor and an electronic storage medium.

2. The computer-implemented method of claim 1, further comprising generating, by the computer system, a graphical display comprising:
    a visualization of the plurality of vessels including the first vessel,
    an indication associated with the visualization of the first vessel indicating a likelihood of the presence of ischemia in the first vessel,
    an indication of stenosis in the first vessel, and
    an indication of atherosclerosis based at least in part on the total plaque volume, the non-calcified plaque volume, and the calcified plaque volume of the first vessel,
    wherein the indication of the presence of ischemia, the indication of stenosis, and the indication of atherosclerosis are configured to aid a clinician in diagnosing coronary artery disease of the subject.

3. The computer-implemented method of claim 1, wherein the total plaque volume, the non-calcified plaque volume, and the calcified plaque volume are determined based at least in part on analyzing density of one or more pixels corresponding to plaque in the medical image.

4. The computer-implemented method of claim 3, wherein the density comprises material density.

5. The computer-implemented method of claim 3, wherein the density comprises radiodensity.

6. The computer-implemented method of claim 5, wherein low density non-calcified plaque corresponds to one or more pixels with a radiodensity value between about −189 and about 30 Hounsfield units.

7. The computer-implemented method of claim 5, wherein non-calcified plaque corresponds to one or more pixels with a radiodensity value between about 31 and about 189 Hounsfield units.

8. The computer-implemented method of claim 5, wherein non-calcified plaque corresponds to one or more pixels with a radiodensity value between about 190 and about 350 Hounsfield units.

9. The computer-implemented method of claim 5, wherein calcified plaque corresponds to one or more pixels with a radiodensity value between about 351 and 2500 Hounsfield units.

10. The computer-implemented method of claim 1, wherein the medical image comprises a Computed Tomography (CT) image.

11. The computer-implemented method of claim 1, wherein the medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

12. The computer-implemented method of claim 1, wherein the plurality of vessels comprises one or more coronary arteries.

13. The computer-implemented method of claim 12, wherein the one or more coronary arteries comprise one or more of left main (LM), ramus intermedius (RI), left anterior descending (LAD), diagonal 1 (D1), diagonal 2 (D2), left circumflex (Cx), obtuse marginal 1 (OM1), obtuse marginal 2 (OM2), left posterior descending artery (L-PDA), left posterolateral branch (L-PLB), right coronary artery (RCA), right posterior descending artery (R-PDA), or right posterolateral branch (R-PLB).

14. The computer-implemented method of claim 1, wherein at least one of the first machine learning algorithm or the second machine learning algorithm is trained based at least in part on a dataset comprising the plurality of variables and presence of ischemia derived using invasive fractional flow reserve.

15. The computer-implemented method of claim 1, wherein at least one of the first machine learning algorithm or the second machine learning algorithm is trained based at least in part on a dataset comprising the plurality of variables and presence of ischemia derived using one or more of CT fractional flow reserve, computational fractional flow reserve, virtual fractional flow reserve, vessel fractional flow reserve, or quantitative flow ratio.

16. The computer-implemented method of claim 1, further comprising generating, by the computer system, an assessment of risk of coronary artery disease (CAD) or major adverse cardiovascular event (MACE) of the subject based at least in part on the determination of presence of ischemia in the first vessel.

17. The computer-implemented method of claim 16, further comprising generating, by the computer system, a recommended treatment for the subject based at least in part on the generated assessment of risk of CAD or MACE.

18. A system for determining presence of ischemia based at least in part on a plurality of variables derived from non-invasive medical image analysis, the system comprising:
  a non-transitory computer storage medium configured to at least store computer-executable instructions; and
  one or more computer hardware processors in communication with the non-transitory computer storage medium, the one or more computer hardware processors configured to execute the computer-executable instructions to at least:
    access a medical image of a subject, wherein the medical image of the subject is obtained non-invasively;
    analyze the medical image of the subject to identify a plurality of vessels, the plurality of vessels comprising at least a first vessel;
    identify one or more lesions in the first vessel;
    identify one or more regions of plaque within the one or more lesions in the first vessel;
    determine, at least in part, with a first machine learning algorithm, a plurality of variables associated with the one or more lesions in the first vessel and the one or more regions of plaque within the one or more lesions in the first vessel, wherein the plurality of variables comprise stenosis, total plaque volume, non-calcified plaque volume, calcified plaque volume, lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, and number of mild stenosis; and
    apply a second machine learning algorithm to determine a presence of ischemia in the first vessel based at least in part on the plurality of variables.

* * * * *